(12) United States Patent
Mounir et al.

(10) Patent No.: US 10,479,997 B2
(45) Date of Patent: Nov. 19, 2019

(54) COMPOSITIONS AND METHODS FOR DIAGNOSIS AND TREATMENT OF PROSTATE CANCER

(71) Applicants: Zineb Mounir, Cambridge, MA (US); Raymond Pal Pagliarini, Arlington, MA (US)

(72) Inventors: Zineb Mounir, Cambridge, MA (US); Raymond Pal Pagliarini, Arlington, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/532,087

(22) PCT Filed: Dec. 1, 2015

(86) PCT No.: PCT/US2015/063206
§ 371 (c)(1),
(2) Date: May 31, 2017

(87) PCT Pub. No.: WO2016/089883
PCT Pub. Date: Jun. 9, 2016

(65) Prior Publication Data
US 2017/0283807 A1    Oct. 5, 2017

Related U.S. Application Data

(60) Provisional application No. 62/085,937, filed on Dec. 1, 2014.

(51) Int. Cl.
| | | |
|---|---|---|
| *C12N 15/113* | (2010.01) | |
| *A61K 31/713* | (2006.01) | |
| *A61K 47/68* | (2017.01) | |
| *A61K 39/00* | (2006.01) | |

(52) U.S. Cl.
CPC ........ *C12N 15/1137* (2013.01); *A61K 31/713* (2013.01); *A61K 47/6807* (2017.08); *A61K 2039/5158* (2013.01); *C12N 2310/10* (2013.01); *C12N 2310/14* (2013.01); *C12N 2310/20* (2017.05); *C12N 2320/10* (2013.01); *C12N 2320/31* (2013.01)

(58) Field of Classification Search
None
See application file for complete search history.

(56) References Cited

U.S. PATENT DOCUMENTS

| | | | | |
|---|---|---|---|---|
| 2010/0215638 | A1* | 8/2010 | Iljin | C12Q 1/6886 424/130.1 |
| 2013/0011497 | A1* | 1/2013 | Lathangue | C07K 14/4705 424/649 |
| 2013/0142875 | A1 | 6/2013 | Shemi et al. | |
| 2014/0068797 | A1 | 3/2014 | Doudna et al. | |
| 2014/0221345 | A1 | 8/2014 | Duncan et al. | |
| 2015/0191432 | A1 | 7/2015 | Duncan et al. | |
| 2015/0196648 | A1 | 7/2015 | Shemi et al. | |
| 2015/0344433 | A1 | 12/2015 | Dunvan et al. | |
| 2016/0046961 | A1 | 2/2016 | Jinek et al. | |
| 2016/0060653 | A1 | 3/2016 | Doudna et al. | |
| 2016/0060654 | A1 | 3/2016 | Doudna et al. | |
| 2016/0068864 | A1 | 3/2016 | Doudna et al. | |

FOREIGN PATENT DOCUMENTS

| | | |
|---|---|---|
| EP | 2 592 146 A2 | 5/2013 |
| WO | 208023087 A2 | 2/2008 |
| WO | 2011077133 A2 | 6/2011 |
| WO | 2013176772 A1 | 11/2013 |
| WO | 2014100730 A1 | 6/2014 |

OTHER PUBLICATIONS

Baylin et al., DNA methylation and gene silencing in cancer, Nature Clinical Practice, Oncology, vol. 2, supplement 1 2005.*
Fitzgerald, et al. "Association of TMPRSS2-ERG gene fusion with clinical characteristics and outcomes: results from a population-based study of prostate cancer", BMC Cancer, 8(1):230-240. (2008).
Kumar-Sinha, et al., "Recurrent gene fusions in prostate cancer", Nature Reviews Cancer, 8:497-511. (2008).
Mounir, et al., "TMPRSS2:ERG blocks neuroendocrine and luminal cell differentiation to maintain prostate cancer proliferation", Oncogene, 34:3815-3825. (2015).
Zhang et al., "Transcriptional activation of PRMT5 by NF-Y is required for cell growth and negatively regulated by the PKC/c-Fos signaling in prostate cancer cells", BBA—Gene Regulatory Mechanisms, 1839:1330-1340. (2014).
International Search Report and Written Opinion for International Application No. PCT/US2015/063206 dated May 13, 2016. 19 pages.
Mounir, et al., "ERG signaling in prostate cancer is driven through PRMT5-dependent methylation of the Androgen Receptor", eLife, 5:1-19. 2016.
Gu, et al., "Protein Arginine Methyltransferase 5 Funcitons in Opposite Ways in the Cytoplasm and Nucleus of Prostate Cancer Cells", PLOS One, 7(8):1-13. 2012.
Hermans, et al., "TMPRSS2:ERG Fusion by Translocation or Interstitial Deletion Is Highly Relevant in Androgen-Prostate Cancer, But is Bypassed in Late-Stage Androgen Receptor-Negative Prostate Cancer", Cancer Research, 66(22):10658-10663. 2006.

* cited by examiner

*Primary Examiner* — Addison D Ault
(74) *Attorney, Agent, or Firm* — Tommy J. Noh

(57) ABSTRACT

The invention provides novel personalized therapies, kits, transmittable forms of information and methods for use in treating subjects having TMPRSS2:ERG positive prostate cancer, which we show is amenable to therapeutic treatment with a PRMT5 inhibitor. Kits, methods of screening for candidate PRMT5 inhibitors, and associated methods of treatment are also provided.

10 Claims, 9 Drawing Sheets
Specification includes a Sequence Listing.

**Identification of ERG interactors necessary for *TMPRSS2:ERG*-positive prostate cancer proliferation**

Figs. 2A-2D
**PRMT5 interacts with ERG and is necessary for *TMPRSS2:ERG*- positive prostate cancer proliferation**
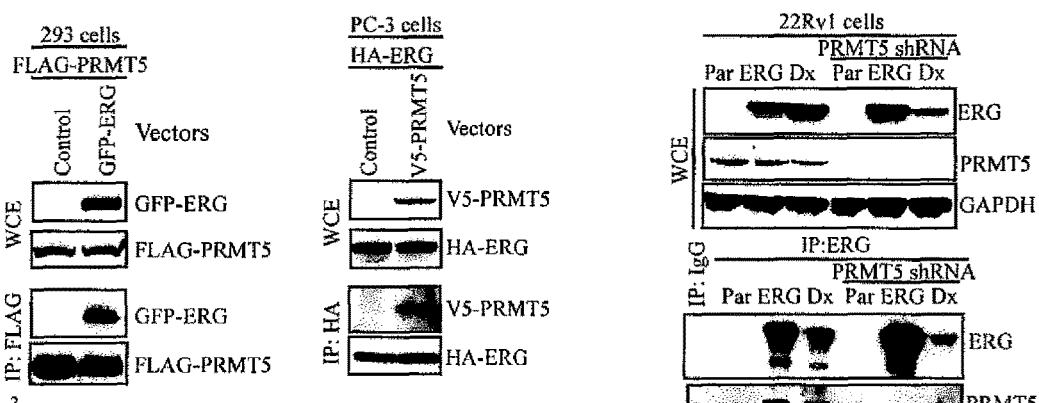
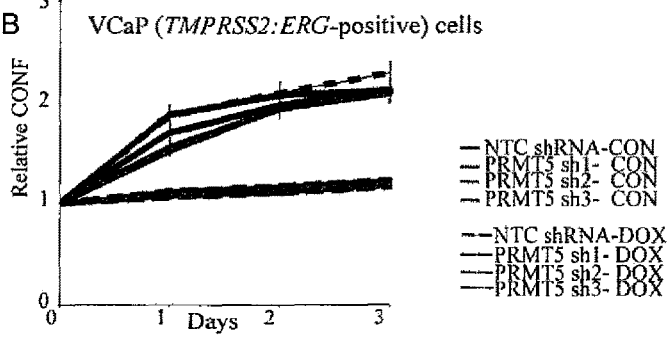
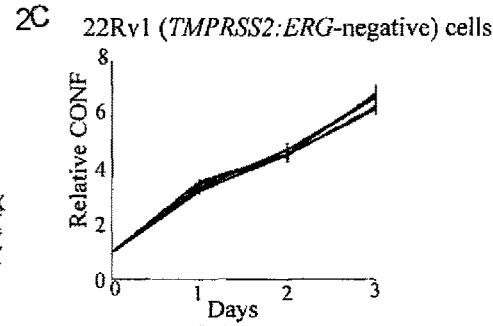
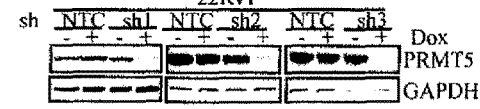
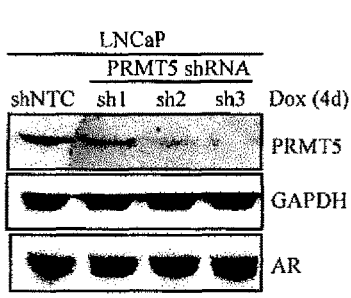
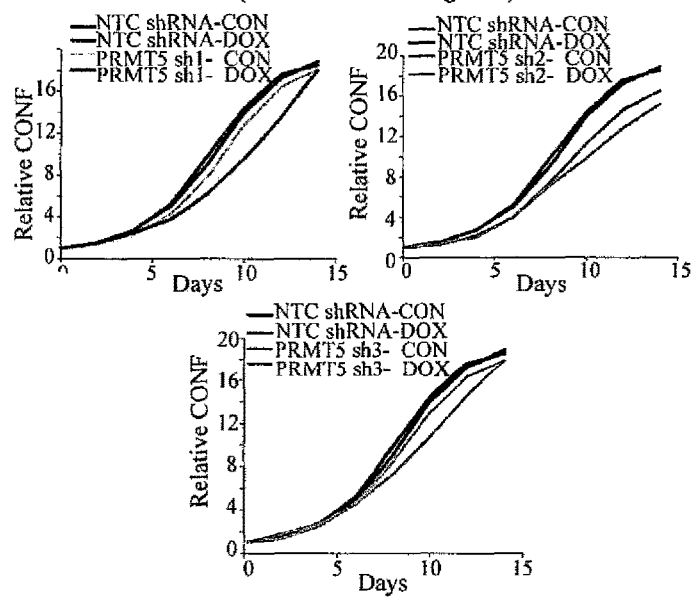

PRMT5 is an ERG-dependent inhibitor of AR signaling

PRMT5 is an ERG-dependent inhibitor of AR signaling

4A

4B

PRMT5 is an ERG corepressor recruited to block AR transcriptional functions

5A

5B

PRMT5 mediates its ERG-dependent corepressor functions through its methyltransferase activity

6A

6B

PRMT5 methylates AR on its ligand binding domain

Figs. 8A-8D

PRMT5 methylates AR on its ligand binding domain

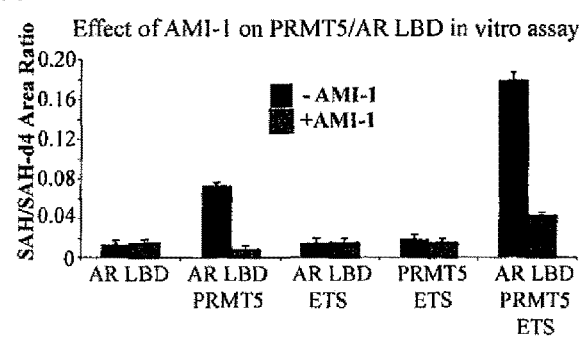
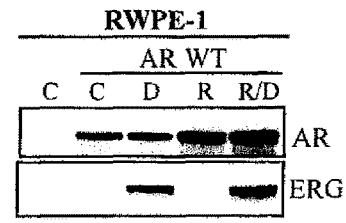
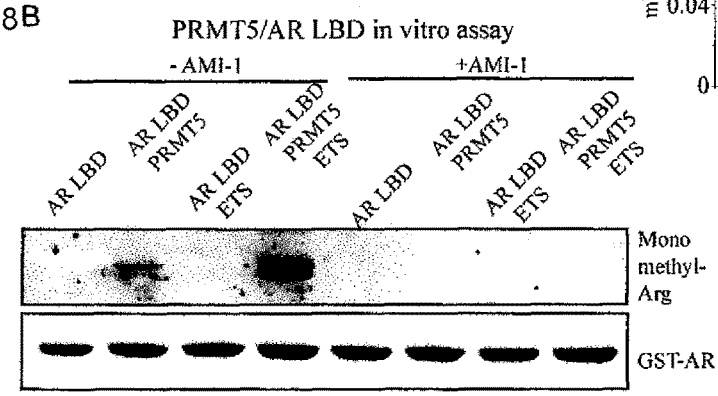
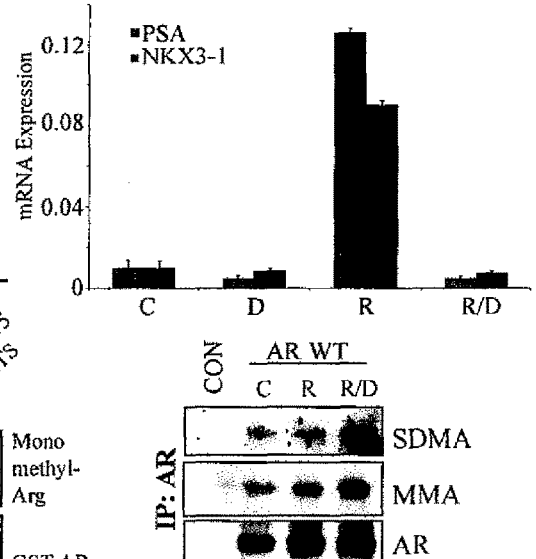

AR- Ligand Binding Domain (LBD)

IFLNVLEAIEPGVVCAGHDNNQPDSFAALLSSLNEL
GER(711)QLVHVVKWAKALPGFR(727)NLHVDDQM
AVIQYSWMGLMVFAMGWR(753)SFTNVNSR(761)M
LYFAPDLVFNEYR(775)MHKSR(780)MYSQCVR(787)
MR(789)HLSQEFGWLQITPQEFLCMKALLLFSIIPVD
GLKNQKFFDELR(832)MNYIKELDR(841)HACK
R(847)KNPTSCSR(855)R(856)FYQLTKLLDSVQPIA
R(872)ELHQFTFDLLIKSHMVSVDFPEMMAEIISVQ
VPKILSGKVKPIYFH

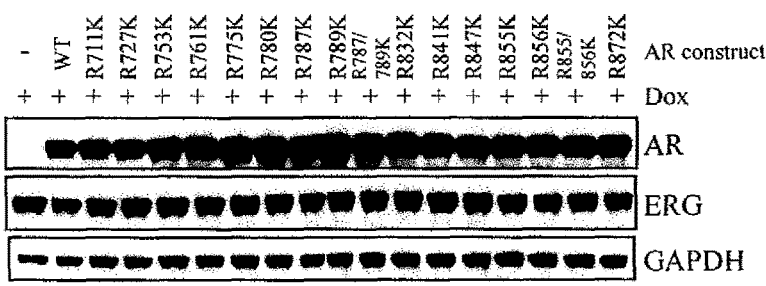

COMPOSITIONS AND METHODS FOR DIAGNOSIS AND TREATMENT OF PROSTATE CANCER

RELATED APPLICATIONS

This application is a U.S. National Stage of the International Patent Application PCT/US2015/063206 with the International Filing Date of Dec. 1, 2015, which claims priority to and the benefit of U.S. Provisional Patent Application No. 62/085,937, filed on Dec. 1, 2014, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 23, 2015, is named PAT056560-WO-PCT SL.txt and is 404,564 bytes in size.

TECHNICAL FIELD

The present invention provides novel diagnostic and treatment methods for the TMPRSS2:ERG positive prostate cancer.

BACKGROUND

The ERG (ETS-related gene) proto-oncogene is overexpressed in a majority of prostate tumors as a result of a gene fusion involving TMPRSS2 and ERG. Petrovics et al. 2005 Oncogene 24: 3847-3852; Tomlins et al. 2005 Science 310: 644-647; Kumar-Sinha et al. 2008 Nat. Rev. Cancer 8: 497-511. The TMPRSS2/ERG fusion results in the overexpression of N-terminally truncated or full-length forms of ERG. Klezovitch et al. 2008 Proc. Natl. Acad. Sci. USA 105: 2105-2110; and Sun et al. 2008 Oncogene 27: 5348-5353. Various studies have underscored the causative oncogenic function of ERG in prostate cancer. Klezovitch et al. 2008 Proc. Natl. Acad. Sci. USA 105: 2105-2110; Tomlins et al. 2008 Neoplasia 10: 177-188; Sun et al. 2008 Oncogene 27: 5348-5353; Wang et al. 2008 Cancer Res. 68: 8516-24.

Poor disease outcome for subjects with tumors harboring duplications of TMPRSS2/ERG fusions or chromosomal losses (Edel) associated with the fusion event has been highlighted. Attard et al. 2008 Oncogene 27: 253-263; FitzGerald et al. 2008 BMC Cancer 8: 230; Mehra et al. 2008 Cancer Res 68: 3584-3590.

An unmet medical need thus exists for new treatments for TMPRSS2:ERG positive prostate cancer.

SUMMARY OF THE INVENTION

The present invention provides methods of treating a TMPRSS2:ERG-positive prostate cancer comprising administering to a subject in need thereof a composition comprising a PRMT5 inhibitor. The present invention further provides methods of patient selection, treatment response evaluation, and screening assays. The present invention is based, in part, on the discovery that the arginine methyltransferase PRMT5 is an ERG protein interactor necessary for TMPRSS2:ERG-positive prostate cancer cell proliferation. Functional analysis of ERG-dependent PRMT5 function in prostate cancer demonstrates that ERG binds and recruits PRMT5 to methylate AR on arginine 761 (R761), which then blocks AR binding to its target genes and transcriptional activity. This inhibitory function of PRMT5 on AR is dependent on ERG expression and DNA binding function, and is selective to TMPRSS2:ERG-positive prostate cancer cells. These effects are mediated through PRMT5 catalytic activity.

Accordingly, the TMPRSS2:ERG gene fusion is a biomarker that can be used to predict a patient's sensitivity to PRMT5 inhibition treatment in prostate cancer. AR arginine methylation on 761 can be used as a diagnostic tool to differentiate among TMPRSS2:ERG-positive prostate cancers; where prostate cancers with "active" ERG would have elevated AR arginine methylation levels (e.g., methylation at R761 of AR) while those with "inactive" ERG would show lower to undetectable AR arginine methylation. Such stratification based on ERG activity can show diagnostic value in prostate cancer.

According to a first aspect, the invention provides a method for inhibiting the proliferation of TMPRSS2:ERG positive prostate cancer cells in a subject in need thereof is provided, the method comprising the step of administering to the subject a PRMT5 inhibitor in an amount that is effective to inhibit the proliferation of the TMPRSS2:ERG positive prostate cancer cells. Such a method can selectively inhibit the proliferation of TMPRSS2:ERG positive prostate cancer cells (e.g., the method can inhibit proliferation of TMPRSS2:ERG positive prostate cancer cells with a 5-fold, 10-fold, 20-fold, 30-fold, 40-fold, 50-fold, 100-fold or more efficacy or efficiency than it can inhibit cells which are not TMPRSS2:ERG positive prostate cancer cells).

Prostate cancer cells are determined to be TMPRSS2:ERG-positive by techniques described herein or known in the art, for example, detection of methylation of R761 of AR, immunohistochemistry utilizing an anti-TMPRSS2:ERG antibody or derivative thereof, and/or genomic sequencing, and/or nucleic acid hybridization or amplification utilizing at least one probe or primer comprising a sequence of at least 12 contiguous nucleotides (nt) of a sequence of a TMPRSS2:ERG fusion (as known in the art, e.g., Perner et al. 2006 Cancer Res. 66: 8337-8341; Demichelis et al. 2007 Oncogene 26: 4596-4599), wherein the primer is no longer than about 30 nt, about 50 nt, or about 100 nt in length.

In one embodiment, the invention provides use of a molecule that inhibits the cellular function of the PRMT5 protein for the treatment of TMPRSS2:ERG positive prostate cancer.

Also provided is a use of a molecule that inhibits the cellular function of the PRMT5 protein for the manufacture of a medicament for treating TMPRSS2:ERG positive prostate cancer.

The PRMT5 inhibitor may be selected from the group consisting of: a RNA inhibitor (e.g., a RNAi agent), a CRISPR, a TALEN, a zinc finger nuclease, an mRNA, an antibody or derivative thereof, a chimeric antigen receptor T cell (CART) or a low molecular weight (LMW) compound.

The PRMT5 inhibitor may be selected from the group consisting of: an antibody or derivative thereof, or a low molecular weight compound.

According to an embodiment, the method according to the first aspect comprises administering to a subject in need thereof, a PRMT5 inhibitor in combination with a second therapeutic agent.

In an embodiment, the second therapeutic agent is an anti-cancer agent, anti-allergic agent, anti-nausea agent (or anti-emetic), pain reliever, or cytoprotective agent.

According to one embodiment, the second therapeutic agent is an anti-cancer agent selected from the list consisting of: an Androgen Receptor antagonist, abiraterone, enzalutamide, bicalutamide, flutamide, HDAC inhibitor, fluorouracil (5-FU) and irinotecan, a HDM2 inhibitor, a purine analogue, 6-thioguanine, 6-mercaptopurine, and CDK4 inhibitors, including, but not limited to, LEE011, and inhibitors of HDM2i, PI3K/mTOR-I, MAPKi, RTKi, EGFRi, FGFRi, METi, IGFiRi, JAKi, and WNTi. In various embodiments, the anti-cancer agent is known in the art, and/or known to be effective against prostate cancer cells.

According to a second aspect, the invention provides a method of determining if a subject afflicted with prostate cancer will respond to therapeutic treatment with a PRMT5 inhibitor is provided, the method comprising the steps: a) evaluating a test sample obtained from said subject for TMPRSS2:ERG positivity, wherein TMPRSS2:ERG positivity indicates that the subject will respond to therapeutic treatment with a PRMT5 inhibitor; wherein the method comprises any one or more of the following optional steps: b) determining the level and/or activity of PRMT5 in the subject, wherein steps a) and b) can be performed in any order; c) administering a therapeutically effective amount of a PRMT5 inhibitor to the subject; and d) determining the level and/or activity of PRMT5 in the subject following step c), wherein a decrease in the level and/or activity of PRMT5 is correlated with the inhibition of the proliferation of the cancer, and wherein steps c) and d), if performed, are performed after steps a) and b).

According to another aspect, the invention provides a method of determining if a subject afflicted with prostate cancer will respond to therapeutic treatment with a PRMT5 inhibitor is provided. The method comprises the steps: a) evaluating a test sample obtained from said subject for TMPRSS2:ERG positivity, wherein TMPRSS2:ERG positivity indicates that the subject will respond to therapeutic treatment with a PRMT5 inhibitor; wherein the method comprises two or more of the following steps: b) determining the level and/or activity of PRMT5 in the subject, wherein steps a) and b) can be performed in any order; c) administering a therapeutically effective amount of a PRMT5 inhibitor to the subject; and d) determining the level and/or activity of PRMT5 in the subject following step c), wherein a decrease in the level and/or activity of PRMT5 is correlated with the inhibition of the proliferation of the cancer, and wherein steps c) and d), if performed, are performed after steps a) and b).

According to another aspect, the invention provides a method of determining if a subject afflicted with prostate cancer will respond to therapeutic treatment with a PRMT5 inhibitor is provided. The method comprises the steps: a) evaluating a test sample obtained from said subject for TMPRSS2:ERG positivity, wherein TMPRSS2:ERG positivity indicates that the subject will respond to therapeutic treatment with a PRMT5 inhibitor; wherein the method comprises the following steps: b) determining the level and/or activity of PRMT5 in the subject, wherein steps a) and b) can be performed in any order; c) administering a therapeutically effective amount of a PRMT5 inhibitor to the subject; and d) determining the level and/or activity and/or activity of PRMT5 in the subject following step c), wherein a decrease in the level and/or activity of PRMT5 is correlated with the inhibition of the proliferation of the cancer, and wherein steps c) and d) are performed after steps a) and b).

In some embodiments, the TMPRSS2:ERG positive prostate cancer cells are identified by any technique described herein or known in the art, for example, immunohistochemistry utilizing an antibody or derivative thereof, and/or genomic sequencing, or nucleic acid hybridization or amplification utilizing at least one probe or primer comprising a sequence of at least 12 contiguous nucleotides (nt) of a sequence of TMPRSS2:ERG, as are known in the art, wherein the primer is no longer than about 30 nt.

In another embodiment, the invention provides a method of determining if a subject afflicted with prostate cancer will respond to therapeutic treatment with a PRMT5 inhibitor, comprising the steps of: a) evaluating a test sample obtained from said subject for methylation of R761 of Androgen Receptor, wherein methylation of R761 of Androgen Receptor indicates that the subject will respond to therapeutic treatment with a PRMT5 inhibitor; wherein the method comprises any one or more of the following optional steps: b) determining the level and/or activity of PRMT5 in the subject, wherein steps a) and b) can be performed in any order; c) administering a therapeutically effective amount of a PRMT5 inhibitor to the subject; and d) determining the level and/or activity of PRMT5 in the subject following step c), wherein a decrease in the level and/or activity of PRMT5 is correlated with the inhibition of the proliferation of the cancer, and wherein steps c) and d), if performed, are performed after steps a) and b).

The PRMT5 inhibitor may be selected from the group consisting of a RNA inhibitor (e.g., a RNAi agent), a CRISPR, a TALEN, a zinc finger nuclease, an mRNA, an antibody or derivative thereof, a chimeric antigen receptor T cell (CART) or a low molecular weight compound.

In some embodiments, the PRMT5 inhibitor is a short hairpin RNA (shRNA) or a short inhibitory RNA (siRNA) or other molecule capable of mediating RNA interference against PRMT5.

In some embodiments, the PRMT5 inhibitor is a molecule capable of mediating RNA interference against PRMT5 and comprising a sequence selected from the group consisting of SEQ ID NO: 1 to SEQ ID NO: 18, 41-49, 52-79, and 84-97, and complementary sequences thereof.

In some embodiments, the PRMT5 inhibitor is a CRISPR comprising a PRMT5-targeting domain comprising any one of SEQ ID NOs: 105-1477.

According to a third aspect, the invention provides a method of determining if a prostate cancer cell is TMPRSS2:ERG positive and therefore sensitive to PRMT5 inhibition, is provided. The method comprises the steps of: a) determining the positivity or negativity of TMPRSS2:ERG in said cancer cell; and b) wherein TMPRSS2:ERG positivity indicates said cell is sensitive to a PRMT5 inhibitor.

According to a fourth aspect, the invention provides a method of determining the sensitivity of a prostate cancer cell to a PRMT5 inhibitor is provided. The method comprises: determining the positivity or negativity of TMPRSS2:ERG in said cancer cell, wherein TMPRSS2:ERG positivity indicates that said cell is sensitive to a PRMT5 inhibitor.

In some embodiments, the PRMT5 inhibitor is a short hairpin RNA (shRNA) or a short inhibitory RNA (siRNA) or other molecule capable of mediating RNA interference against PRMT5.

In some embodiments, the PRMT5 inhibitor is molecule capable of mediating RNA interference against PRMT5 and comprising a sequence selected from the group consisting of SEQ ID NO: 1 to SEQ ID NO: 18, 41-49, 52-79, 84-97, and 98-103, and the complementary sequence thereof.

The PRMT5 inhibitor may be a low molecular weight compound, a cyclic peptide, an aptamers or CRISPRs.

In some embodiments, the PRMT5 inhibitor is a CRISPR comprising a PRMT5-targeting domain comprising any one of SEQ ID NOs: 105-1477.

According to a fifth aspect, the invention provides a method of screening for PRMT5 inhibitors is provided. An example method comprises contacting a first sample containing one or more TMPRSS2:ERG positive prostate cancer cells with a candidate PRMT5 inhibitor and measuring the reduction in viability of said cells; contacting a second sample containing the same type of cells with a known PRMT5 inhibitor and measuring the reduction in viability of said cells; comparing the reduction in viability of the cells in the first sample with that of the second sample, to determine the potency of the candidate PRMT5 inhibitor. Another example method comprises contacting a first and a second sample containing an AR or an AR fragment comprising R761 with PRMT5, wherein the first sample further comprises a candidate PRMT5 inhibitor and the second does not; measuring the methylation of R761 in the two samples, wherein a reduction in methylation in the first sample compared to the second indicates that the candidate PRMT5 inhibitor inhibits PRMT5. In some embodiments, the AR fragment comprising R761 comprises the LBD (ligand binding domain). In some embodiments, the LBD is that shown in FIG. 8D (SEQ ID NO: 104).

According to a sixth aspect, the invention provides a kit for predicting the sensitivity of a subject afflicted with a TMPRSS2:ERG-positive prostate cancer for treatment with a PRMT5 inhibitor is provided. The method comprises: i) reagents capable of detecting TMPRSS2:ERG-positivity in prostate cancer cells; and ii) instructions for how to use said kit.

According to a seventh aspect, the invention provides a composition comprising a PRMT5 inhibitor for use in treatment of prostate cancer in a selected patient (subject) population is provided, wherein the patient population is selected on the basis of being afflicted with a TMPRSS2:ERG positive prostate cancer.

According to an eighth aspect, the invention provides a therapeutic method of treating a subject afflicted with TMPRSS2:ERG positive prostate cancer is provided, comprising the steps of: contacting a test sample obtained from said subject with a reagent capable of detecting TMPRSS2:ERG positive prostate cancer cells, wherein TMPRSS2:ERG positivity in said test sample indicates said afflicted subject will respond to therapeutic treatment with a PRMT5 inhibitor; and administering a therapeutically effective amount of PRMT5 inhibitor to those subjects identified in step b).

According to a ninth aspect, the invention provides a therapeutic method of treating a subject afflicted with TMPRSS2:ERG positive prostate cancer is provided comprising the steps of: contacting a test sample obtained from said subject with a reagent capable of detecting TMPRSS2:ERG positive prostate cancer cells, wherein TMPRSS2:ERG positivity in said test sample indicates said afflicted subject will respond to therapeutic treatment with a PRMT5 inhibitor; and administering a therapeutically effective amount of the composition according to the seventh aspect of the invention.

According to a tenth aspect, the invention provides a method of determining if a subject afflicted with TMPRSS2:ERG positive prostate cancer will respond to therapeutic treatment with a PRMT5 inhibitor is provided, comprising the steps of: contacting a test sample obtained from said subject with a reagent capable of detecting a TMPRSS2:ERG positive prostate cancer cell, wherein TMPRSS2:ERG positivity indicates said afflicted subject will respond to therapeutic treatment with a PRMT5 inhibitor. In some embodiments, the method further comprises the step of determining the level and/or activity of PRMT5 in the cancer cells. In many cancers, PRMT5 is over-expressed. The level and/or activity of expression of PRMT5 can be taken into account when determining the therapeutically effective dosage of a PRMT5 inhibitor. In addition, during treatment, the level and/or activities of PRMT5 can be monitored to assess disease or treatment progression.

According to an eleventh aspect, the invention provides a method of determining if a subject afflicted with TMPRSS2:ERG positive prostate cancer will respond to therapeutic treatment with a PRMT5 inhibitor is provided, comprising the steps of: contacting a test sample obtained from said subject with a reagent capable of detecting a TMPRSS2:ERG positive prostate cancer cell, wherein TMPRSS2:ERG positivity indicates said afflicted subject will respond to therapeutic treatment with a PRMT5 inhibitor. In some embodiments, the method further comprises the step of determining the level and/or activity of PRMT5 in the cancer cells. In many cancers, PRMT5 is over-expressed. The level of expression of PRMT5 can be taken into account when determining the therapeutically effective dosage of a PRMT5 inhibitor. In addition, during treatment, the level and/or activities of PRMT5 can be monitored to assess disease or treatment progression.

According to an eleventh aspect, the invention provides a method of determining if a subject afflicted with TMPRSS2:ERG positive prostate cancer will respond to therapeutic treatment with a PRMT5 inhibitor is provided, comprising the steps of: contacting a test sample obtained from said subject with a reagent capable of detecting methylation of R761 of Androgen Receptor, wherein TMPRSS2:ERG positivity indicates said afflicted subject will respond to therapeutic treatment with a PRMT5 inhibitor. In some embodiments, the method further comprises the step of determining the level and/or activity of PRMT5 in the cancer cells. In many cancers, PRMT5 is over-expressed. The level of expression of PRMT5 can be taken into account when determining the therapeutically effective dosage of a PRMT5 inhibitor. In addition, during treatment, the level and/or activities of PRMT5 can be monitored to assess disease or treatment progression.

In a further aspect, the disclosure provides a method of determining if a subject afflicted with prostate cancer will respond to therapeutic treatment with a PRMT5 inhibitor, comprising the steps of: a) evaluating a test sample obtained from said subject for monomethylation of R761 of Androgen Receptor, wherein monomethylation of R761 of Androgen Receptor indicates that the subject will respond to therapeutic treatment with a PRMT5 inhibitor; wherein the method comprises any one or more of the following optional steps: b) determining the level and/or activity of PRMT5 in the subject, wherein steps a) and b) can be performed in any order; c) administering a therapeutically effective amount of a PRMT5 inhibitor to the subject; and d) determining the level and/or activity of PRMT5 in the subject following step c), wherein a decrease in the level and/or activity of PRMT5 is correlated with the inhibition of the proliferation of the cancer, and wherein steps c) and d) are performed after steps a) and b).

In one embodiment of this method, the PRMT5 inhibitor is selected from the group consisting of: a RNAi agent, a CRISPR, a TALEN, a zinc finger nuclease, an mRNA, an antibody or derivative thereof, an antibody-drug conjugate, a chimeric antigen receptor T cell (CART) or a low molecular weight compound.

In one embodiment of this method, the PRMT5 inhibitor is a low molecular weight compound.

In one embodiment of this method, the PRMT5 inhibitor is a RNAi agent.

In one embodiment of this method, the PRMT5 inhibitor is an antibody or derivative thereof.

In one embodiment of this method, the PRMT5 inhibitor is a CRISPR comprising a PRMT5-targeting domain comprising any one of SEQ ID NOs: 105-1477.

In one embodiment of this method, the method further comprises the step of administering to a subject a second therapeutic agent.

In one embodiment of this method, the second therapeutic agent is an anti-cancer agent, anti-allergic agent, anti-nausea agent or anti-emetic agent, pain reliever, cytoprotective agent.

In one embodiment of this method, the second therapeutic agent is an anti-cancer agent selected from the list consisting of: an Androgen Receptor antagonist, abiraterone, enzalutamide, bicalutamide, flutamide, HDAC inhibitor, fluorouracil (5-FU) irinotecan, a HDM2 inhibitor, a purine analogue, 6-thioguanine, 6-mercaptopurine, a CDK4 inhibitor, and LEE011, and inhibitors of HDM2i, PI3K/mTOR-I, MAPKi, RTKi, EGFRi, FGFRi, METi, IGFiRi, JAKi, and WNTi.

In a further aspect, the disclosure provides a method of determining if a subject afflicted with prostate cancer will respond to therapeutic treatment with a PRMT5 inhibitor, comprising the steps of: a) evaluating a test sample obtained from said subject for dimethylation of R761 of Androgen Receptor, wherein dimethylation of R761 of Androgen Receptor indicates that the subject will respond to therapeutic treatment with a PRMT5 inhibitor; wherein the method comprises any one or more of the following optional steps: b) determining the level and/or activity of PRMT5 in the subject, wherein steps a) and b) can be performed in any order; c) administering a therapeutically effective amount of a PRMT5 inhibitor to the subject; and d) determining the level and/or activity of PRMT5 in the subject following step c), wherein a decrease in the level and/or activity of PRMT5 is correlated with the inhibition of the proliferation of the cancer, and wherein steps c) and d) are performed after steps a) and b).

In one embodiment of this method, the PRMT5 inhibitor is selected from the group consisting of: a RNAi agent, a CRISPR, a TALEN, a zinc finger nuclease, an mRNA, an antibody or derivative thereof, an antibody-drug conjugate, a chimeric antigen receptor T cell (CART) or a low molecular weight compound.

In one embodiment of this method, the PRMT5 inhibitor is a low molecular weight compound.

In one embodiment of this method, the PRMT5 inhibitor is a RNAi agent.

In one embodiment of this method, the PRMT5 inhibitor is an antibody or derivative thereof.

In one embodiment of this method, the PRMT5 inhibitor is a CRISPR comprising a PRMT5-targeting domain comprising any one of SEQ ID NOs: 105-1477.

In one embodiment of this method, the method further comprises the step of administering to a subject a second therapeutic agent.

In one embodiment of this method, the second therapeutic agent is an anti-cancer agent, anti-allergic agent, anti-nausea agent or anti-emetic agent, pain reliever, cytoprotective agent.

In one embodiment of this method, the second therapeutic agent is an anti-cancer agent selected from the list consisting of: an Androgen Receptor antagonist, abiraterone, enzalutamide, bicalutamide, flutamide, HDAC inhibitor, fluorouracil (5-FU) irinotecan, a HDM2 inhibitor, a purine analogue, 6-thioguanine, 6-mercaptopurine, a CDK4 inhibitor, and LEE011, and inhibitors of HDM2i, PI3K/mTOR-I, MAPKi, RTKi, EGFRi, FGFRi, METi, IGFiRi, JAKi, and WNTi.

BRIEF DESCRIPTION OF THE DRAWINGS

FIG. 1A shows identification of ERG interactors necessary for TMPRSS2:ERG-positive prostate cancer proliferation. FIG. 1B shows VCaP vs (versus) 22Rv1 differential gene level calls.

FIGS. 2A to 2D show that PRMT5 interacts with ERG and is necessary for TMPRSS2:ERG-positive prostate cancer proliferation.

FIGS. 8A to 8D also show that PRMT5 methylates AR on its ligand binding domain. The sequence of LBD of AR shown in FIG. 8D is SEQ ID NO: 104.

Figure 1A:
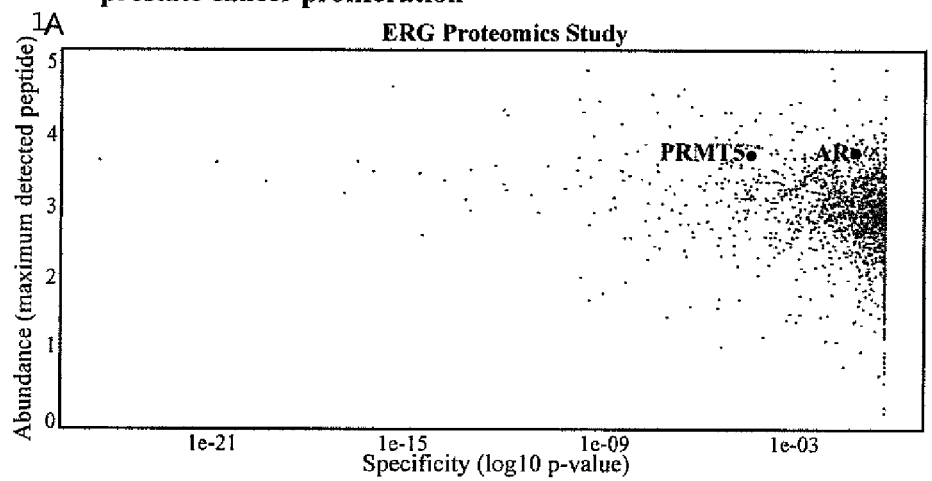
FIGS. 1A and 1B describe the strategy used to identify ERG interactors necessary for prostate cancer proliferation and which led to the identification of PRMT5.

Abbreviations used in Figures: AR: Androgen Receptor. AR FL: full-length AR. AR TR: truncated AR. ChIP: chromatin immunoprecipitation. CTD: C-terminal domain of ERG. d: day. Δ: Deletion. DBD: DNA-binding domain of AR. FL: full-length ERG. IP: Immunoprecipitation. LBD: ligand binding domain of AR. mCherry: vector. MMA: Monomethylarginine. NTC: non-targeting control. NTD: N-terminal domain of AR. Par: Parent. PNT: Pointed domain of ERG. RSA: redundant siRNA activity. SDMA: Symmetrical dimethylarginine. sh1, sh2, and sh3: shRNA1, shRNA2, shRNA3. TSS: Transcriptional start site. WCE: whole cell extract. WT, wild-type.

DETAILED DESCRIPTION OF THE INVENTION

Provided herein are novel diagnostic and treatment methods for a subject with TMPRSS2:ERG positive prostate cancer. The present invention is based, in part, on the discovery that TMPRSS2:ERG positive prostate cancer lines are sensitive to inhibition of the PRMT5 gene. Accordingly, provided herein are methods of inhibiting PRMT5 to treat TMPRSS2:ERG-positive prostate cancer. The methods, inter alia, comprise the step of administering, to a subject in need thereof, a PRMT5 inhibitor in an amount that is effective to inhibit the proliferation of the TMPRSS2:ERG positive prostate cancer cells. TMPRSS2:ERG fusion activity can be evaluated by assaying for methylation of R761 of Androgen Receptor.

According to the present invention, methylation of R761 of Androgen Receptor (AR) can comprise: monomethylation (resulting in AR with a monomethylated R761, or AR R761me1) or dimethylation (resulting in AR with a dimethylated R761, or AR R761me2). Provided herein are also antibodies that bind specifically to AR R761me1 (e.g., which bind to AR R761me1 with a higher affinity, e.g., 5-fold, 10-fold, 20-fold, 30-fold, 40-fold, 50-fold, or 100-fold or more, than to unmethylated AR R761 or AR R761me2). Also provided herein are antibodies that bind specifically to AR R761me2 (e.g., which bind to AR R761me2 with a higher affinity, e.g., 5-fold, 10-fold, 20-fold, 30-fold, 40-fold, 50-fold, or 100-fold or more, than to unmethylated AR R761 or AR R761me1). Antibodies specific to AR R761me1 or AR R761me2 are useful in methods of diagnosis or treatment described herein. For example, such antibodies can be used to determine activity of a TMPRSS2:ERG fusion (e.g., to detect TMPRSS2:ERG-positive prostate cancer cells).

A method of determining the level of PRMT5 activity can comprise the step of determining (e.g., quantifying) the level of methylation, monomethylation and/or dimethylation of AR R761 (or a fragment thereof comprising R761), wherein an increase in the methylation, monomethylation and/or dimethylation of R761 indicates the presence of PRMT5 activity. AR R761 (or a fragment thereof comprising R761), if not methylated, can be used in a method for determining the efficacy of an inhibitor to PRMT5. In a non-limiting example, a method of determining the efficacy of a candidate inhibitor of PRMT5 comprises the steps of: (a) contacting AR R761 (or a fragment thereof comprising R761) with PRMT5 in the absence of the candidate inhibitor under conditions which allow methylation, monomethylation or dimethylation of R761; and (b) contacting AR R761 (or a fragment thereof comprising R761) with PRMT5 in the presence of the candidate inhibitor under conditions which allow methylation, monomethylation or dimethylation of R761; wherein steps (a) and (b) can be performed simultaneously or in any order, and measuring the relative presence or generation of methylated, monomethylated and/or dimethylated R761 in (a) and (b), wherein a greater presence or generation of methylated, monomethylated and/or dimethylated R761 in (b) than in (a) indicates that the candidate inhibitor inhibits methylation, monomethylation or dimethylation of R761. One embodiment of this method comprises measuring methylation of R761. One embodiment of this method comprises measuring monomethylation of R761. One embodiment of this method comprises measuring dimethylation of R761.

Without being bound by any particular theory, this disclosure indicates that a key mechanism used by ERG to repress Androgen Receptor (AR) transcriptional functions in TMPRSS2:ERG-positive prostate cancer is the recruitment of PRMT5 to AR transcriptional complexes. ERG-mediated PRMT5 recruitment leads to mono- and/or symmetric dimethylation of AR at arginine 761 (R761), which then blocks AR binding to its target genes and transcriptional activity. This inhibitory function of PRMT5 on AR is dependent on ERG expression and DNA binding function, and is highly selective to TMPRSS2:ERG-positive prostate cancers. ERG promotes the proliferation of prostate cancer, but the nature of this protein makes it a challenging target for therapeutics development. As PRMT5 enzymatic function is required for ERG-dependent AR inhibition and cell proliferation in prostate cancer, TMPRSS2:ERG can be used as a biomarker that predicts sensitivity to PRMT5 inhibition. In addition, detection of AR arginine 761 methylation may provide a biomarker tool to assess ERG activity in prostate cancer samples, rather than solely looking and relying on ERG mRNA or protein expression levels. AR methylation on arginine 761 can be used as a diagnostic tool to differentiate among all TMPRSS2:ERG-positive prostate cancers. This tool can be used to stratify ERG-positive prostate cancers with "active" ERG from those with "inactive" ERG based on the level and/or activity of AR arginine methylation, which would be high or low, respectively. This stratification based on ERG activity provides a more accurate analysis of AR activity status and transcriptional functions which can have both diagnostic and predictive value of tumor response to anti-androgen therapy.

Definitions

Prostate and Prostate Cancer

By "prostate" is meant the muscular, glandular organ that surrounds the urethra of males at the base of the bladder. The prostate is a non-essential organ. The prostate helps make and store seminal fluid. In adult men, the typical prostate is about three centimeters long and weighs about twenty grams. It is located in the pelvis, under the urinary bladder and in front of the rectum. The prostate surrounds part of the urethra, the tube that carries urine from the bladder during urination and semen during ejaculation. The prostate contains many small glands which make about twenty percent of the fluid constituting semen.

By "prostate cancer", "PC" or "PCa" and the like is meant a form of cancer that develops in and/or exists in the prostate. By "cancer" is meant the abnormal presence of cells which exhibit relatively autonomous growth and/or proliferation, so that they exhibit an aberrant growth and/or proliferation phenotype characterized by a significant loss of cell proliferation control. One type of PCa is castration-resistant PCa (CRPC).

Most prostate cancers are slow growing, though some cases are aggressive. The cancer cells may metastasize from the prostate to other parts of the body, such as the bones or lymph nodes. Prostate cancer may cause pain, difficulty in urinating, problems during sexual intercourse, and/or erectile dysfunction.

The presence of prostate cancer may be indicated by symptoms, physical examination, prostate specific antigen (PSA), or biopsy.

Prostate cancer is an adenocarcinoma or glandular cancer, that begins when normal semen-secreting prostate gland cells mutated into cancer cells. The region of the prostate gland where the adenocarcinoma is most common is the peripheral zone. Initially, small clumps of cancer cells remain confined to otherwise normal prostate glands, a condition known as carcinoma in situ or prostatic intraepithelial neoplasia (PIN). Over time, these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer is considered a malignant tumor because it is a mass of cells that can invade other parts of the body. This invasion of the organs is called metastasis. Prostate cancer most commonly metastasizes to the bones, lymph nodes, and may invade the rectum, bladder and lower ureters.

Many different genes have been implicated in prostate cancer, including the TMPRSS2-ERG fusion, the Androgen Receptor (AR), BRCA1 and BRCA2, HPC1, Vitamin D receptor, and TMPRSS2-ETV1/4.

TMPRSS2:ERG Positive Prostate Cancer

By "TMPRSS2:ERG", "TMPRSS2-ERG", "TMPRSS2: ERG fusion" and the like, as used herein, is meant the fusion gene or its gene product, which is a fusion of TMPRSS2 and ERG, and which is commonly found in human prostate cancer, especially in hormone-refractory prostate cancer. One study showed that, in 90% of prostate cancers overexpressing ERG, they also possess a fusion TMPRSS2-ERG protein, suggesting that this fusion is the predominant subtype in prostate cancer. A common mechanism for the gene fusion is the loss of 2.8 Mb of genomic DNA between TMPRSS2 and ERG. See, for example: Perner et al. 2006 Cancer Res. 66: 8337-8341; Yu et al. 2010 Cancer Cell 17: 443-54; Tomlins et al. 2008 Neoplasia 177: 188; Soller et al. 2006 Genes Chrom. Cancer. 45: 717-9; Yoshimoto et al. 2006 Neoplasia 8: 465-9; Cerveira et al. 2006 Neoplasia 8: 826-32; Winnes et al. 2007 Oncol. Rep. 17: 1033-6; and Tu et al. 2007 Mod. Pathol. 20: 921-8.

By a "fusion" or "fusion gene" and the like is meant a hybrid gene formed from two or more previously separate genes. A fusion can occur as a result of, as non-limiting examples, translocation, deletion, or chromosomal inversion.

By "TMPRSS2" as used herein, is meant the gene or its product, also known as Transmembrane protease, serine 2; Identifiers: Symbols TMPRSS2; PP9284; PRSS10; External IDs OMIM: 602060 MGI: 1354381 HomoloGene: 4136 ChEMBL: 1795140 GeneCards: TMPRSS2 Gene EC number 3.4.21.-; Orthologs: Human 7113 ENSG00000184012 015393 NM_001135099 NP_001128571 Chr 21: 42.84-42.9 Mb; Mouse 50528 ENSMUSG00000000385 Q9JIQ8 NM_015775 NP_056590 Chr 16: 97.56-97.61 Mb.

TMPRSS2 belongs to the serine protease family; the protein contains a Type II transmembrane domain, a receptor class A domain, a scavenger receptor cysteine-rich domain and a protease domain. TMPRSS2 is up-regulated by androgenic hormones in prostate cancer cells and down-regulated in androgen-independent prostate cancer tissues. See, for example: Paolini-Giacobino et al. 1997 Genomics 44: 309-20; Yu et al. 2010 Cancer Cell 17: 443-54; Lin et al. 1999 Cancer Res. 59: 4180-4; Vaarala et al. 2001 J. Pathol. 193: 134-140; Afar et al. 2001 cancer Res. 61: 1686-92; Wilson et al. 2005 Biochem. J. 388 (Pt. 3): 967-72; Soller et al. 2006 Genes Chrom. Cancer. 45: 717-9; Yoshimoto et al. 2006 Neoplasia 8: 465-9; Cerveira et al. 2006 Neoplasia 8: 826-32; Winnes et al. 2007 Oncol. Rep. 17: 1033-6; and Tu et al. 2007 Mod. Pathol. 20: 921-8.

By "ERG", as used herein, is meant the gene or the gene product also known as ETS (erythroblast transformation-specific)-related gene or V-ets avian erythroblastosis virus E26 oncogene homolog; Symbols ERG; erg-3; p55; External IDs OMIM: 165080 MGI: 95415 HomoloGene: 15848 ChEMBL: 1293191 GeneCards: ERG Gene Orthologs: Human: 2078 ENSG00000157554 P11308 NM_001136154 NP_001129626 Chr 21: 39.75-40.03 Mb; Mouse: 13876 ENSMUSG00000040732 P81270 NM_133659 NP_598420 Chr 16: 95.36-95.59 Mb.

ERG is an oncogene and a member of the ETS family of transcription factors. Genes in the ETS family regulate embryonic development, cell proliferation, differentiation, angiogenesis, inflammation and apoptosis. ERG comprises a PNT (pointed) domain and a DNA binding domain (DBD); it binds to purine-rich sequences of DNA.

ERG is a proto-oncogene that participates in chromosomal translocations; this can result in a fusion gene product such as TMPRSS2-ERG or NDRG1-ERG in prostate cancer, EWS-ERG in Ewing's Sarcoma, or FUS-ERG in acute myeloid leukemia.

See, for example: Reddy et al. 1987 Proc. Natl. Acad. Sci. USA 84: 6131-5; Rao et al. 1987 Science 237: 635-9; Rao et al. 188 Oncogene 3: 497-500; Reddy et al. 1991 Oncogene 6: 2285-9; Siddique et al. 1993 Oncogene 8: 1751-5; Murakami et al. 1993 Oncogene 8: 1559-66; Loughran et al. 2008 Nat. Immunol. 9: 810-9; Taoudi et al. 2011 Genes Rev. 825: 251-262; Soller et al. 2006 Genes Chrom. Cancer. 45: 717-9; Yoshimoto et al. 2006 Neoplasia 8: 465-9; Cerveira et al. 2006 Neoplasia 8: 826-32; Winnes et al. 2007 Oncol. Rep. 17: 1033-6; and Tu et al. 2007 Mod. Pathol. 20: 921-8.

By "TMPRSS2:ERG positive" or "TMPRSS2:ERG-positive" prostate cancer, cancer cell, tissue, subject, etc., as used herein, is meant a prostate cancer, cancer cell, tissue, subject, etc., which comprises or expresses (or is detected to comprise or express) the TMPRSS2:ERG fusion gene and/or its gene product. By "TMPRSS2:ERG negative" or "TMPRSS2:ERG-negative" prostate cancer, cancer cell, tissue, subject, etc., as used herein, is meant a prostate cancer, cancer cell, tissue, subject, etc., which does not comprise or express (or does not comprise or express detected or detectable levels of) the TMPRSS2:ERG fusion gene and/or its gene product. Methods of detecting the presence of the TMPRSS2:ERG gene and/or the gene product include various methods known in the art, such as FISH, QCPCR, RACE, and various other techniques known and described in the art. See, for example, Perner et al. 2006 Cancer Res. 66: 8337-8341; Demichelis et al. 2007 Oncogene 26: 4596-4599. The TMPRSS2:ERG activity of a TMPRSS2:ERG positive cell can be detected, as shown herein, by detecting of the methylation of R761 of AR.

By "TMPRSS2:ERG positivity", as used herein, is meant that a cell, cancer, prostate cancer, tissue, subject, etc., is positive for TMPRSS2:ERG; e.g., it comprises the gene for and/or the protein product for the gene for TMPRSS2:ERG. By "determining the TMPRSS2:ERG positivity or negativity" of a cell, cancer, prostate cancer, tissue, subject, etc., and similar phrases, as used herein, is meant analyzing and/or assaying a cell, cancer, prostate cancer, tissue, subject, etc., for the presence of the gene and/or the gene product of TMPRSS2:ERG. A cell, cancer, prostate cancer, tissue, subject, etc., which is TMPRSS2:ERG "positive" comprises the gene and/or gene product TMPRSS2:ERG; e.g., TMPRSS2:ERG is present. A cell, cancer, prostate cancer, tissue, subject, etc., which is TMPRSS2:ERG "negative" does not comprise the gene and/or gene product TMPRSS2: ERG; e.g., TMPRSS2:ERG is absent.

Determining the TMPRSS2:ERG positivity or negativity of a prostate cancer cell can be performed using any reagent or technique described herein or known in the art, for example: detection of methylated R761 of AR, immunohistochemistry utilizing an antibody to TMPRSS2:ERG, and/or genomic sequencing, and/or nucleic acid hybridization and/or amplification utilizing at least one probe or primer comprising a sequence of at least 12 contiguous nucleotides (nt) of the sequence of a TMPRSS2:ERG fusion gene, wherein the primer is no longer than about 30 nt.

The present disclosure encompasses methods of treatment involving TMPRSS2:ERG positive prostate cancer, which can be inhibited by administration of a PRMT5 inhibitor.

As described further herein, a cell, cancer, prostate cancer, tissue, subject, etc., is "PRMT5 inhibitor sensitive," "sensitive to treatment with PRMT5 inhibitors," "sensitive to PRMT5 therapeutic inhibition," or described in similar terms, if it is amenable to treatment with a PRMT5 inhibitor, e.g., due to its status as TMPRSS2:ERG positive.

PRMT5

By "PRMT5", as used herein, is meant the gene or protein of Protein Arginine Methyltransferase 5, also known as HRMT1L5; IBP72; JBP1; SKB1; or SKB1Hs External IDs: OMIM: 604045, MGI: 1351645, HomoloGene: 4454, ChEMBL: 1795116, GeneCards: PRMT5 Gene; EC number 2.1.1.125. Ensembl ENSG00000100462; UniProt 014744; Entrez Gene ID: 10419; RefSeq (mRNA): NM_001039619. The mouse homolog is NM_013768.

Methyltransferases such as PRMT5 catalyse the transfer of one to three methyl groups from the co-factor S-adenosylmethionine (also known as SAM or AdoMet) to lysine or arginine residues of histone proteins. Arginine methylation is carried out by 9 different protein arginine methyltransferases (PRMT) in humans. Three types of methylarginine species exist: (1) Monomethylarginine (MMA); (2) Asymmetric dimethyl arginine (ADMA), which is produced by Type I methyl transferases (PRMT1, PRMT2, PRMT3, CARM1, PRMT6 and PRMT8); and (3) Symmetrical dimethylarginine (SDMA), which is produced by Type II methyl transferases (PRMT5 and PRMT7).

PRMT1 and PRMT5 are the major asymmetric and symmetric arginine methyltransferases, respectively. Loss results in embryonic lethality.

PRMT5 promotes symmetric dimethylation on histones at H3R8 and H4R3 (H4R3me2). Symmetric methylation of H4R3 is associated with transcriptional repression and can act as a binding site for DNMT3A. Loss of PRMT5 results in reduced DNMT3A binding and gene activation. Tumor suppressor gene ST7 and chemokines RNATES, IP10, CXCL11 are targeted and silenced by PRMT5. WO 2011/079236. Additional substrates include E2F1, p53, EGFR and CRAF.

PRMT5 is part of a multi-protein complex comprising the co-regulatory factor WDR77 (also known as MEP50, a CDK4 substrate) during G1/S transition. Phosphorylation increases PRMT5/WDR77 activity. WDR77 is the non-catalytic component of the complex and mediates interactions with binding partners and substrates.

PRMT5 can also interact with pICln or RioK1 adaptor proteins in a mutually exclusive fashion to modulate complex composition and substrate specificity.

PRMT5 has either a positive or negative effect on its substrates by arginine methylation when interacting with a number of complexes and is involved in a variety of cellular processes, including RNA processing, signal transduction, transcriptional regulation, and germ cell development. PRMT5 is a major pro-survival factor regulating eIF4E expression and p53 translation. PRMT5 triggers p53-dependent apoptosis and sensitized various cancer cells to Tumor necrosis factor (TNF)-related apoptosis-inducing ligand (TRAIL) without affecting TRAIL resistance in non-transformed cells.

PRMT5 mutations are embryonic lethal. PRMT5+/− mice are viable, but produce no viable homozygous PRMT5−/− offspring. Tee et al. 2010 Genes Dev. 24: 2772-7.

The term "PRMT5 inhibitor" refers to any compound capable of inhibiting the production, level, activity, expression or presence of PRMT5. These include, as non-limiting examples, any compound inhibiting the transcription of the gene, the maturation of RNA, the translation of mRNA, the posttranslational modification of the protein, the enzymatic activity of the protein, the interaction of same with a substrate, etc. The term also refers to any agent that inhibits the cellular function of the PRMT5 protein, either by ATP-competitive inhibition of the active site, allosteric modulation of the protein structure, disruption of protein-protein interactions, or by inhibiting the transcription, translation, post-translational modification, or stability of PRMT5 protein.

A PRMT5 inhibitor can target any of the various domains of PRMT5. For example, PRMT5 is known to comprise a TIM barrel, a Rossman fold, a dimerization domain and a beta barrel. The catalytic domain consists of a SAM binding domain containing the nucleotide binding Rossman fold, followed by a beta-sandwich domain (involved in substrate binding) The TIM barrel is required for binding of adaptor proteins (RIOK1 and pICIn). A PRMT5 inhibitor can contact or attack any of these domains or any portion of PRMT5.

In some embodiments, a PRMT5 inhibitor competes with another compound, protein or other molecule which interacts with PRMT5 and is necessary for PRMT5 function.

As a non-limiting example, a PRMT5 inhibitor can compete with the co-factor S-adenosylmethionine (also known as SAM or AdoMet).

As another non-limiting example, a PRMT5 inhibitor can be a protein-protein interaction (PPI) inhibitor. For example, a PPI inhibitor may inhibit the ability of PRMT5 to proper interact with another protein.

Instead of interacting with PRMT5, a PRMT5 inhibitor can interact with a component necessary or important for PRMT5 function.

For example:

A PRMT5 inhibitor can act indirectly by interacting with and/or inhibiting WDR77. By "WDR77", as used herein, is meant the gene or its product, also known as MEP-50; MEP50; Nbla10071; RP11-552M11.3; p44; p44/Mep50; or OMIM: 611734 MGI: 1917715 HomoloGene: 11466 GeneCards: WDR77 Gene. Friesen et al. 2002 J. Biol. Chem. 277:8243-7; Licciardo et al. 2003 Nucl. Acids Res. 31:999-1005; Furuno et al. 2006 Biochem. Biophys. Res. Comm. 345: 1051-8.

PRMT5 inhibitors include those compositions which inhibit WDR77 or inhibit the interaction (e.g., the protein-protein interaction) between WDR77 and PRMT5.

WDR77 inhibitors can include, without limitation: a RNA inhibitor (e.g., a RNAi agent), a CRISPR, a TALEN, a zinc finger nuclease, an mRNA, an antibody or derivative thereof, a chimeric antigen receptor T cell (CART) or a low molecular weight (LMW) compound.

WDR77 inhibitors include, but are not limited to, those known in the art.

For example, siRNAs to WDR77 are known in the art.

For example, Aggarwal et al. 2010 Cancer Cell 18: 329-340 shows a MEP50 (WDR77) siRNA with the sequence CUCCUUACCAUUAAACUG (SEQ ID NO: 36).

Additional RNAi agents to WDR77 are disclosed in:
Gu et al. 2013 Oncogene 31: 1888-1900; and
Ligr et al. 2011 PLoS One 6: 10.1371.

As another non-limiting example, a PRMT5 inhibitor can inhibit RIOK1. By "RIOK1", as used herein, is meant RioK1, RIO Kinase 1, bA288G3.1, Serine/Threonine-Protein Kinase RIO1, EC 2.7.11.1; External Ids: HGNC: 18656; Entrez Gene: 83732; Ensembl: ENSG00000124784; UniProtKB: Q9BRS2.

RIOK1 inhibitors can include, without limitation: a RNA inhibitor (e.g., a RNAi agent), a CRISPR, a TALEN, a zinc finger nuclease, an mRNA, an antibody or derivative thereof, a chimeric antigen receptor T cell (CART) or a low molecular weight (LMW) compound.

RIOK1 inhibitors include, but are not limited to, those known in the art.

For example, siRNAs to RioK1 are known in the art. For example, Guderian et al. 2011 J. Biol. Chem. 286: 1976-1986 shows RioK1 siRNAs with the sequences GAGAAGGAUGACAUUCUGUTT (SEQ ID NO: 37) and ACAGAAUGUCAUCCUUCUCTT (SEQ ID NO: 38).

Additional RIOK1 RNAi agents are disclosed in: Read et al. 2013 PLoS Genetics 10.1371.

As another non-limiting example, a PRMT5 inhibitor can act indirectly by inhibiting pICIN.

pICln is an essential, highly conserved 26-kDa protein whose functions include binding to Sm proteins in the cytoplasm of human cells and mediating the ordered and regulated assembly of the cell's RNA-splicing machinery by the survival motor neurons complex. pICln also interacts with PRMT5, the enzyme responsible for generating symmetric dimethylarginine modifications on the carboxyl-terminal regions of three of the canonical Sm proteins. Pesiridis et al. 2009. J. Biol. Chem. 284: 21347-21359.

pICIN inhibitors can include, without limitation: a RNA inhibitor (e.g., a RNAi agent), a CRISPR, a TALEN, a zinc finger nuclease, an mRNA, an antibody or derivative thereof, a chimeric antigen receptor T cell (CART) or a low molecular weight (LMW) compound.

The present disclosure also notes that PRMT5 is normally found in both the nucleus and cytoplasm. A PRMT5 inhibitor may inhibit PRMT5 function by reducing the post-translational modification, production, expression, level, stability and/or activity of PRTMS in the nucleus, in the cytoplasm, or both the nucleus and cytoplasm. An inhibitor could, for example, reduce PRMT5 in the cytoplasm, but not the nucleus, or vice versa.

According to the present invention, an PRMT5 inhibitor includes, as non-limiting examples: an antibody or derivative thereof, a RNA inhibitor (e.g., a RNAi agent), a therapeutic modality, including but not limited to, a low molecular weight compound, a CRISPR, a TALEN, a zinc finger nuclease, an mRNA, or a chimeric antigen receptor T cell (CART).

In any method described herein, the PRMT5 inhibitor can inhibit PRMT5 indirectly by inhibiting WDR77, RIOK1, and/or pICIN.

Antibody

The term "antibody" or "antibody to PRMT5" and the like as used herein refers to a whole antibody or a fragment thereof that interacts with (e.g., by binding, steric hindrance, stabilizing/destabilizing, spatial distribution) a PRMT5 epitope. A naturally occurring IgG "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelised antibodies, or chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively. In particular, the term "antibody" specifically includes an IgG-scFv format.

The term "epitope binding domain" or "EBD" refers to portions of a binding molecule (e.g., an antibody or epitope-binding fragment or derivative thereof), that specifically interacts with (e.g., by binding, steric hindrance, stabilizing/destabilizing, spatial distribution) a binding site on a target epitope. EBD also refers to one or more fragments of an antibody that retain the ability to specifically interact with (e.g., by binding, steric hindrance, stabilizing/destabilizing, spatial distribution) a PRMT5 epitope and inhibit signal transduction. Examples of antibody fragments include, but are not limited to, an scFv, a Fab fragment, a monovalent fragment consisting of the VL, VH, CL and CH1 domains; a F(ab).sub.2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR).

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883).

Such single chain antibodies are also intended to be encompassed within the terms "fragment", "epitope-binding fragment" or "antibody fragment". These fragments are obtained using conventional techniques known to those of skill in the art, and the fragments are screened for utility in the same manner as are intact antibodies.

Antibody fragments can be incorporated into single chain molecules comprising a pair of tandem Fv segments (VH-CH1-VH-CH1) which, together with complementary light chain polypeptides, form a pair of antigen binding regions (Zapata et al., (1995) Protein Eng. 8:1057-1062; and U.S. Pat. No. 5,641,870), and also include Fab fragments, F(ab') fragments, and anti-idiotypic (anti-Id) antibodies (including, e.g., anti-Id antibodies to antibodies of the invention), and epitope-binding fragments of any of the above.

EBDs also include single domain antibodies, maxibodies, unibodies, minibodies, triabodies, tetrabodies, v-NAR and bis-scFv, as is known in the art (see, e.g., Hollinger and Hudson, (2005) Nature Biotechnology 23: 1126-1136), bispecific single chain diabodies, or single chain diabodies designed to bind two distinct epitopes. EBDs also include antibody-like molecules or antibody mimetics, which include, but not limited to minibodies, maxybodies, Fn3 based protein scaffolds, Ankrin repeats (also known as DARpins), VASP polypeptides, Avian pancreatic polypeptide (aPP), Tetranectin, Affililin, Knottins, SH3 domains, PDZ domains, Tendamistat, Neocarzinostatin, Protein A domains, Lipocalins, Transferrin, and Kunitz domains that specifically bind epitopes, which are within the scope of the invention. Antibody fragments can be grafted into scaffolds based on polypeptides such as Fibronectin type III (Fn3) (see U.S. Pat. No. 6,703,199, which describes fibronectin polypeptide monobodies).

The present invention also encompasses an antibody to PRMT5, which is an isolated antibody, monovalent antibody, bivalent antibody, multivalent antibody, bivalent antibody, biparatopic antibody, bispecific antibody, monoclonal antibody, human antibody, recombinant human antibody, or any other type of antibody or epitope-binding fragment or derivative thereof.

The phrase "isolated antibody", as used herein, refers to antibody that is substantially free of other antibodies having different antigenic specificities (e.g., an isolated antibody that specifically binds PRMT5 is substantially free of antibodies that specifically bind antigens other than PRMT5). An isolated antibody that specifically binds PRMT5 may, however, have cross-reactivity to other antigens, such as PRMT5 molecules from other species. Moreover, an isolated antibody may be substantially free of other cellular material and/or chemicals.

The term "monovalent antibody" as used herein, refers to an antibody that binds to a single epitope on a target molecule such as PRMT5.

The term "bivalent antibody" as used herein, refers to an antibody that binds to two epitopes on at least two identical PRMT5 target molecules. The bivalent antibody may also crosslink the target PRMT5 molecules to one another. A "bivalent antibody" also refers to an antibody that binds to two different epitopes on at least two identical PRMT5 target molecules.

The term "multivalent antibody" refers to a single binding molecule with more than one valency, where "valency" is described as the number of antigen-binding moieties present per molecule of an antibody construct. As such, the single binding molecule can bind to more than one binding site on a target molecule. Examples of multivalent antibodies include, but are not limited to bivalent antibodies, trivalent antibodies, tetravalent antibodies, pentavalent antibodies, and the like, as well as bispecific antibodies and biparatopic antibodies. For example, for the PRMT5, the mutivalent antibody (e.g., a PRMT5 biparatopic antibody) has a binding moiety for two domains of PRMT5, respectively.

The multivalent antibody mediates biological effect or which modulates a disease or disorder in a subject (e.g., by mediating or promoting cell killing, or by modulating the amount of a substance which is bioavailable.

The term "multivalent antibody" also refers to a single binding molecule that has more than one antigen-binding moieties for two separate WRM target molecules. For example, an antibody that binds to both a PRMT5 target molecule and a second target molecule that is not PRMT5. In one embodiment, a multivalent antibody is a tetravalent antibody that has four epitope binding domains. A tetravalent molecule may be bispecific and bivalent for each binding site on that target molecule.

The term "biparatopic antibody" as used herein, refers to an antibody that binds to two different epitopes on a single PRMT5 target. The term also includes an antibody, which binds to two domains of at least two PRMT5 targets, e.g., a tetravalent biparatopic antibody.

The term "bispecific antibody" as used herein, refers to an antibody that binds to two or more different epitopes on at least two different targets (e.g., a PRMT5 and a target that is not PRMT5).

The phrases "monoclonal antibody" or "monoclonal antibody composition" as used herein refers to polypeptides, including antibodies, bispecific antibodies, etc. that have substantially identical to amino acid sequence or are derived from the same genetic source. This term also includes preparations of antibody molecules of single molecular composition. A monoclonal antibody composition displays a single binding specificity and affinity for a particular epitope.

The phrase "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86). The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S. Department of Health and Human Services (1991), eds. Kabat et al.; Al Lazikani et al., (1997) J. Mol. Bio. 273:927 948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mal. Biol. 273:927-948.

The human antibodies of the invention may include amino acid residues not encoded by human sequences (e.g., mutations introduced by random or site-specific mutagenesis in vitro or by somatic mutation in vivo, or a conservative substitution to promote stability or manufacturing). However, the term "human antibody" as used herein, is not intended to include antibodies in which CDR sequences derived from the germline of another mammalian species, such as a mouse, have been grafted onto human framework sequences.

The phrase "recombinant human antibody" as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "Fc region" as used herein refers to a polypeptide comprising the CH3, CH2 and at least a portion of the hinge region of a constant domain of an antibody. Optionally, an Fc region may include a CH4 domain, present in some antibody classes. An Fc region, may comprise the entire hinge region of a constant domain of an antibody. In one embodiment, the invention comprises an Fc region and a CH1 region of an antibody. In one embodiment, the invention comprises an Fc region CH3 region of an antibody. In another embodiment, the invention comprises an Fc region, a CH1 region and a Ckappa/lambda region from the constant domain of an antibody. In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Example modifications include additions, deletions or substitutions of one or more amino acids in one or more domains. Such changes may be included to optimize effector function, half-life, etc.

The term "binding site" as used herein comprises an area on a PRMT5 target molecule to which an antibody or antigen binding fragment selectively binds.

The term "epitope" as used herein refers to any determinant capable of binding with high affinity to an immunoglobulin. An epitope is a region of an antigen that is bound by an antibody that specifically targets that antigen, and when the antigen is a protein, includes specific amino acids that directly contact the antibody. Most often, epitopes reside on proteins, but in some instances, may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics.

Generally, antibodies specific for a particular target antigen will bind to an epitope on the target antigen in a complex mixture of proteins and/or macromolecules.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity. As used herein, the term "high affinity" for an IgG antibody or fragment thereof (e.g., a Fab fragment) refers to an antibody having a $K_D$ of $10^{-8}$ M or less, $10^{-9}$M or less, or $10^{-10}$ M, or $10^{-11}$ M or less, or $10^{-12}$ M or less, or $10^{-13}$ M or less for a target antigen. However, high affinity binding can 10 vary for other antibody isotypes. For example, high affinity binding for an IgM isotype refers to an antibody having a $K_D$ of $10^{-7}$ M or less, or $10^{-8}$ M or less.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids such as by, e.g., x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. MoI. Biol. 157:105-132; for hydropathy plots.

A PRMT5 inhibitor which is an antibody can be prepared; alternatively, many PRMT5 antibodies are known in the art.

Any inhibitory anti-PRMT5 antibody or fragment thereof can be used with any method disclosed herein.

RNAi Agent

As used herein, the term "RNAi agent," "RNAi agent to PRMT5", "siRNA to PRMT5", "PRMT5 siRNA" and the like refer to an siRNA (short inhibitory RNA), shRNA (short or small hairpin RNA), iRNA (interference RNA) agent, RNAi (RNA interference) agent, dsRNA (double-stranded RNA), microRNA, and the like, which specifically binds to the PRMT5 mRNA and which mediates the targeted cleavage of the RNA transcript via an RNA-induced silencing complex (RISC) pathway. In one embodiment, the RNAi agent is an oligonucleotide composition that activates the RISC complex/pathway. In another embodiment, the RNAi agent comprises an antisense strand sequence (antisense oligonucleotide). In one embodiment, the RNAi comprises a single strand. This single-stranded RNAi agent oligonucleotide or polynucleotide can comprise the sense or antisense strand, as described by Sioud 2005 J. Mol. Bioi. 348:1079-1090, and references therein. Thus the disclosure encompasses RNAi agents with a single strand comprising either the sense or antisense strand of an RNAi agent described herein. The use of the RNAi agent to PRMT5 results in a decrease of PRMT5 post-translational modification, production, expression, level, stability and/or activity, e.g., a "knock-down" or "knock-out" of the PRMT5 target gene or target sequence. In some embodiments, the PRMT5 inhibitor is molecule capable of mediating RNA interference against PRMT5 and comprising a sequence selected from the group consisting of SEQ ID NO: 1 to SEQ ID NO: 18, 41-49, 52-79, 84-97, and 98-103, and the complementary sequence thereof.

RNA interference is a post-transcriptional, targeted gene-silencing technique that, usually, uses double-stranded RNA (dsRNA) to degrade messenger RNA (mRNA) containing the same sequence as the dsRNA. The process of RNAi occurs naturally when ribonuclease III (Dicer) cleaves longer dsRNA into shorter fragments called siRNAs. Naturally-occurring siRNAs (small interfering RNAs) are typically about 21 to 23 nucleotides long and comprise about 19 base pair duplexes. The smaller RNA segments then mediate the degradation of the target mRNA. Dicer has also been implicated in the excision of 21- and 22-nucleotide small temporal RNAs (stRNAs) from precursor RNA of conserved structure that are implicated in translational control. Hutvagner et al. 2001, Science, 293, 834. The RNAi response also features an endonuclease complex, commonly referred to as an RNA-induced silencing complex (RISC), which mediates cleavage of single-stranded mRNA complementary to the antisense strand of the siRNA. Cleavage of the target RNA takes place in the middle of the region complementary to the antisense strand of the siRNA duplex.

"RNAi" (RNA interference) has been studied in a variety of systems. Early work in *Drosophila* embryonic lysates (Elbashir et al. 2001 EMBO J. 20: 6877 and Tuschl et al. International PCT Publication No. WO 01/75164) revealed certain parameters for siRNA length, structure, chemical composition, and sequence that are beneficial to mediate efficient RNAi activity. These studies have shown that 21-nucleotide siRNA duplexes are most active when containing 3'-terminal dinucleotide overhangs. Substitution of the 3'-terminal siRNA overhang nucleotides with 2'-deoxy nucleotides (2'-H) was tolerated. In addition, a 5'-phosphate on the target-complementary strand of an siRNA duplex is usually required for siRNA activity. Later work showed that a 3'-terminal dinucleotide overhang can be replaced by a 3' end cap, provided that the 3' end cap still allows the molecule to mediate RNA interference; the 3' end cap also reduces sensitivity of the molecule to nucleases. See, for example, U.S. Pat. Nos. 8,097,716; 8,084,600; 8,404,831; 8,404,832; and 8,344,128, and International Patent Application PCT/US14/58705. Additional later work on artificial RNAi agents showed that the strand length could be shortened, or a single-stranded nick could be introduced into a strand. International Patent Applications PCT/US14/58703 and PCT/US14/59301. In addition, mismatches can be introduced between the sense and anti-sense strands and a variety of modifications can be used. Any of the these and various other formats for RNAi agents known in the art can be used to produce RNAi agents to PRMT5.

In various embodiments, the RNAi agent can comprise nucleotides (e.g., RNA or DNA), modified nucleotides, and/or nucleotide substitutes. In some embodiments, the RNAi agent can comprise RNA. In some embodiments, the RNAi agent can comprise RNA, with several of the RNA nucleotides replaced with DNA or a modified nucleotide. In various embodiments, the nucleotide (consisting of a phosphate, sugar and base) can be modified and/or substituted at the phosphate, sugar and/or base. For example, the sugar can be modified at the 2' carbon, as is known in the art. In another non-limiting example, the phosphate can be modified or replaced, e.g., substituted with a modified internucleoside linker.

In various embodiments, the modified internucleoside linker is selected from phosphorothioate, phosphorodithioate, phosphoramidate, boranophosphonate, an amide linker, and a compound of formula (I):

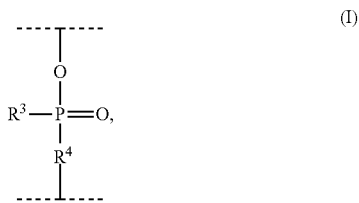

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$.

In some embodiments, the RNAi agent comprises an 18-mer strand terminating in a 3' phosphate or modified internucleoside linker, and further comprising a spacer (but no phosphate or modified internucleoside linker, or 3' end cap). Thus: In some embodiments, the RNAi agent comprises an 18-mer strand terminating in a 3' phosphate or modified internucleoside linker, and further comprising a spacer (e.g., ribitol). In some embodiments, the RNAi comprises an 18-mer strand terminating in a 3' phosphate or modified internucleoside linker, and further comprising a spacer (e.g., a ribitol). In some embodiments, the RNAi comprises an 18-mer strand terminating in a 3' phosphate or modified internucleoside linker, and further comprising, in 5' to 3' order, a spacer (e.g., a ribitol), a second phosphate or modified internucleoside linker, and a second spacer (e.g., ribitol).

In various embodiments, one or both strands can comprise ribonucleotide subunits, or one or more nucleotide can optionally be modified or substituted. Thus, in various embodiments, the RNAi agent can either contain only naturally-occurring ribonucleotide subunits, or one or more modifications to the sugar, phosphate or base of one or more of nucleotide subunits. In one embodiment, the modifications improve efficacy, stability and/or reduce immunogenicity of the RNAi agent.

One aspect of the present disclosure relates to a RNAi agent comprising at least one non-natural nucleobase. In certain embodiments, the non-natural nucleobase is difluorotolyl, nitroindolyl, nitropyrrolyl, or nitroimidazolyl. In a particular embodiment, the non-natural nucleobase is difluorotolyl. In certain embodiments, only one of the two strands contains a non-natural nucleobase. In certain embodiments, both of the strands contain a non-natural nucleobase.

In one embodiment, the first two base-pairing nucleotides on the 3' end of the sense and/or anti-sense strand are modified. In one embodiment, the first two base-pairing nucleotides on the 3' end of the sense and/or anti-sense strand are 2'-MOE (a 2' MOE clamp).

In one embodiment, the 3' terminal phosphate of the sense and/or anti-sense strands is replaced by a modified internucleoside linker.

In one embodiment, at least one nucleotide of the RNAi agent is modified.

In one embodiment, said at least one modified nucleotide is selected from among 2' alkoxyribonucleotide, 2' alkoxyalkoxy ribonucleotide, or 2'-fluoro ribonucleotide. In another embodiment, said at least one modified nucleotide is selected from 2'-OMe, 2'-MOE and 2'-H. In various aspects, the nucleotide subunit is chemically modified at the 2' position of the sugar. In one aspect, the 2' chemical modification is selected from a halo, a C1-10 alkyl, a C1-10 alkoxy, a halo, and the like. In specific aspects, the 2' chemical modification is a C1-10 alkoxy selected from —OCH$_3$ (i.e., "OMe"), —OCH$_2$CH$_3$ (i.e., "OEt") or —CH$_2$OCH$_2$CH$_3$ (i.e., methoxyethyl or "MOE"); or is a halo selected from F.

In various embodiments, one or more nucleotides is modified or is DNA or is replaced by a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA); and/or at least one nucleotide comprises a modified internucleoside linker (e.g., wherein at least one phosphate of a nucleotide is replaced by a modified internucleoside linker), wherein the modified internucleoside linker is selected from phosphorothioate, phosphorodithioate, phosphoramidate, boranophosphonoate, an amide linker, and a compound of formula (I) (as described elsewhere herein).

In some embodiments, the RNAi agent to PRMT5 is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

Kits for RNAi synthesis are commercially available, e.g., from New England Biolabs and Ambion.

A suitable RNAi agent can be selected by any process known in the art or conceivable by one of ordinary skill in the art. For example, the selection criteria can include one or more of the following steps: initial analysis of the PRMT5 gene sequence and design of RNAi agents; this design can take into consideration sequence similarity across species (human, cynomolgus, mouse, etc.) and dissimilarity to other (non-PRMT5) genes; screening of RNAi agents in vitro (e.g., at 10 nM in cells); determination of EC50 in HeLa cells; determination of viability of various cells treated with RNAi agents, wherein it is desired that the RNAi agent to PRMT5 not inhibit the viability of these cells; testing with human PBMC (peripheral blood mononuclear cells), e.g., to test levels of TNF-alpha to estimate immunogenicity, wherein immunostimulatory sequences are less desired; testing in human whole blood assay, wherein fresh human blood is treated with an RNAi agent and cytokine/chemokine levels are determined [e.g., TNF-alpha (tumor necrosis factor-alpha) and/or MCP1 (monocyte chemotactic protein 1)], wherein Immunostimulatory sequences are less desired; determination of gene knockdown in vivo using subcutaneous tumors in test animals; PRMT5 target gene modulation analysis, e.g., using a pharmacodynamic (PD) marker, and optimization of specific modifications of the RNAi agents.

Specific RNAi agents include: the shRNAs to PRMT5 disclosed herein (particularly those having a target sequence of any of SEQ ID NOs: 1 to 18, 41-49, 52-79, 84-97, and 98-103, and the complementary sequence thereof, or a target sequence comprising 15 contiguous nt of a PRMT5 target sequence thereof). Additional RNAi agents to PRMT5 can be prepared, or are known in the art. It is noted that in the present disclosure a RNAi agent to PRMT5 may be recited to target a particular PRMT5 sequence, indicating that the recited sequence may be comprised in the sequence of the sense or anti-sense strand of the RNAi agent; or, in some cases, a sequence of at least 15 contiguous nt of this sequence may be comprised in the sequence of the sense or anti-sense strand. It is also understood that some of the target sequences are presented as DNA, but the RNAi agents targeting these sequences can be RNA, or any nucleotide, modified nucleotide or substitute disclosed herein.

Androgen Receptor

As shown herein (see Examples), AR is a direct substrate of PRMT5.

Without being bound by any particular theory, this disclosure is based on a discovery that a key mechanism used by ERG to repress Androgen Receptor (AR) transcriptional functions in TMPRSS2:ERG-positive prostate cancer is the recruitment of PRMT5 to AR transcriptional complexes. ERG-mediated PRMT5 recruitment leads to mono- and symmetric di-methylation of AR at arginine 761, which then blocks AR binding to its target genes and transcriptional activity. This inhibitory function of PRMT5 on AR is dependent on ERG expression and DNA binding function, and is highly selective to TMPRSS2:ERG-positive prostate cancers.

By "Androgen receptor" or "AR" is meant the gene or gene product (e.g., a polypeptide) also known as NR3C4 (nuclear receptor subfamily 3, group C, member 4) and also known by the symbols AR; AIS; DHTR; HUMARA; HYSP1; KD; NR3C4; SBMA; SMAX1; and TFM; and External IDs OMIM: 313700 MGI: 88064 HomoloGene: 28 IUPHAR: NR3C4 ChEMBL: 1871. A polypeptide of an example AR are shown below.

Androgen receptor is a type of nuclear receptor [Lu et al. 2006 Pharmacol. Rev. 58: 782-97] that is activated by binding of either of the androgenic hormones testosterone or dihydrotestosterone [Roy et al. Vitam. Horm. 55: 309-52] in the cytoplasm and then translocating into the nucleus. The androgen receptor is most closely related to the progesterone receptor, and progestins in higher dosages can block the androgen receptor. Bardin et al. 1983 Pharm. Ther. 23: 443-59; and Raudrant et al. 2003 Drugs 63: 463-92. The main function of the androgen receptor is as a DNA-binding transcription factor that regulates gene expression [Mooradian et al. 1987 Endocr. Rev. 8: 1-28]; however, the androgen receptor has other functions as well [Heinlein et al.

2002. Mol. Endocrinol. 16: 2181-7]. Androgen regulated genes are critical for the development and maintenance of the male sexual phenotype.

The binding of androgen to the androgen receptor induces a conformational change to the receptor, resulting in a dissociation of heat shock proteins, dimerization and transport from the cytosol to the cell nucleus where the androgen receptor dimer binds to specific DNA sequences—referred to as hormone response elements or androgen response elements (ARE). Depending on the interaction with other nuclear proteins, the AR controls gene expression, either increasing or decreasing transcription of specific genes, such as insulin-like growth factor I (IGF-1).

Androgen receptors can also have cytoplasmic activities though with signal transduction proteins in the cytoplasm. Androgen binding to cytoplasmic androgen receptors, can cause rapid changes in cell function independent of gene transcription, for example ion transport, as well as indirect influence of gene transcription, for example via mediating other signal transduction pathways, thereby influencing the activity of other transcription factors.

The amino acid sequence of an example AR is shown below:

```
Androgen Receptor isoform 1 [Homo sapiens]
NCBI Reference Sequence: NP_000035.2
gi|21322252|ref|NP_000035.2| androgen receptor
isoform 1 [Homo sapiens]
                                        (SEQ ID NO: 1478)
MEVQLGLGRVYPRPPSKTYRGAFQNLFQSVREVIQNPGPRHPEAASAAPP

GASLLLLQQQQQQQQQQQQQQQQQQQQQQQQETSPRQQQQQQGEDGSPQAH

RRGPTGYLVLDEEQQPSQPQSALECHPERGCVPEPGAAVAASKGLPQQLP

APPDEDDSAAPSTLSLLGPTFPGLSSCSADLKDILSEASTMQLLQQQQQE

AVSEGSSSGRAREASGAPTSSKDNYLGGTSTISDNAKELCKAVSVSMGLG

VEALEHLSPGEQLRGDCMYAPLLGVPPAVRPTPCAPLAECKGSLLDDSAG

KSTEDTAEYSPFKGGYTKGLEGESLGCSGSAAAGSSGTLELPSTLSLYKS

GALDEAAAYQSRDYYNFPLALAGPPPPPPPPHPHARIKLENPLDYGSAWA

AAAAQCRYGDLASLHGAGAAGPGSGSPSAAASSSWHTLFTAEEGQLYGPC

GGGGGGGGGGGGGGGGGGGGGGEAGAVAPYGYTRPPQGLAGQESDFTAP

DVWYPGGMVSRVPYPSPTCVKSEMGPWMDSYSGPYGDMRLETARDHVLPI

DYYFPPQKTCLICGDEASGCHYGALTCGSCKVFFKRAAEGKQKYLCASRN

DCTIDKFRRKNCPSCRLRKCYEAGMTLGARKLKKLGNLKLQEEGEASSTT

SPTEETTQKLTVSHIEGYECQPIFLNVLEAIEPGVVCAGHDNNQPDSFAA

LLSSLNELGERQLVHVVKWAKALPGFRNLHVDDQMAVIQYSWMGLMVFAM

GWRSFTNVNSRMLYFAPDLVFNEYRMHKSRMYSQCVRMRHLSQEFGWLQI

TPQEFLCMKALLLFSIIPVDGLKNQKFFDELRMNYIKELDRIIACKRKNP

TSCSRRFYQLTKLLDSVQPIARELHQFTFDLLIKSHMVSVDFPEMMAEII

SVQVPKILSGKVKPIYFHTQ
```

R761 is underlined. Please note that some references, due to a slightly different numbering scheme for AR, reference this amino acid as R760.

By "methylation of R761 of AR", "methylation of R761 of Androgen Receptor" and the like is meant that the Arg at position 761 (as provided in SEQ ID NO: 1478) is methylated by PRMT5. Detection of methylation of R761 of AR indicates a determination if this amino acid is methylated. Such a determination can be performed by various assays described herein, including, for example, the use of an antibody specific to methylated R761 of AR. Alternatively, as described herein, a proximity ligation assay can be used, wherein a pair of antibodies is used, one of which binds to AR (whether or not R761 is methylated), and one binds to methylated Arg (including R761), wherein binding of the two antibodies to AR with a methylated 761 can be detected (e.g., by a compound by detects the proximity of the two bound antibodies).

As shown herein (see Examples), AR is a direct substrate of PRMT5. Using a symmetric dimethyl arginine antibody, we observed that AR is methylated at basal levels and that methylation is reduced following either ERG or PRMT5 knockdown. AR mono-methylation is also reduced by ERG or PRMT5 knockdown. R761 is the primary arginine residue in AR methylated by PRMT5 in an ERG-dependent fashion.

Additional Definitions

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely examples and that equivalents of such are known in the art.

As used herein the term "amino acid" refers to either natural and/or unnatural or synthetic amino acids, and both the D and L optical isomers, amino acid analogs, and peptidomimetics. A peptide of three or more amino acids is commonly called an oligopeptide if the peptide chain is short. If the peptide chain is long, the peptide is commonly called a polypeptide or a protein.

The terms "biomarker" or "marker" are used interchangeably herein. A biomarker is a nucleic acid or polypeptide and the presence (positivity) or absence (negativity) of a mutation or differential expression of the polypeptide is used to determine sensitivity to any PRMT5 inhibitor. For example, TMPRSS2:ERG positivity is a biomarker in a prostate cancer cell which indicates that the cell is sensitive to a PRMT5 inhibitor.

The term "cDNA" refers to complementary DNA, i.e. mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Example vectors for libraries include bacteriophage (also known as "phage"), viruses that infect bacteria, for example, lambda phage. The library can then be probed for the specific cDNA (and thus mRNA) of interest.

The term "cell proliferative disorders" shall include dysregulation of normal physiological function characterized by abnormal cell growth, proliferation and/or division or loss of function. Examples of "cell proliferative disorders" includes but is not limited to hyperplasia, neoplasia, metaplasia, and various autoimmune disorders, e.g., those characterized by the dysregulation of T cell apoptosis.

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the present invention and a combination partner, are both administered to a subject simultaneously in the form of a single entity or dosage. The term "non-fixed combination" means that the active ingredients, e.g. a compound of the present invention and a combination partner, are both administered to a subject as separate entities either simultaneously, concurrently or sequentially with no specific time limits, wherein such administration provides therapeutically effective levels of the two compounds in the body of the subject. The latter also applies to cocktail therapy, e.g. the administration of three or more active ingredients.

A "gene" refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

"Gene expression" or alternatively a "gene product" refers to the nucleic acids or amino acids (e.g., peptide or polypeptide) generated when a gene is transcribed and translated.

As used herein, "expression" refers to the process by which DNA is transcribed into mRNA and/or the process by which the transcribed mRNA is subsequently translated into peptides, polypeptides or proteins. If the polynucleotide is derived from genomic DNA, expression may include splicing of the mRNA in a eukaryotic cell.

"Differentially expressed" as applied to a gene, refers to the differential production of the mRNA transcribed and/or translated from the gene or the protein product encoded by the gene. A differentially expressed gene may be overexpressed or underexpressed as compared to the expression level of a normal or control cell. However, as used herein, overexpression is an increase in gene expression and generally is at least 1.25 fold or, alternatively, at least 1.5 fold or, alternatively, at least 2 fold, or alternatively, at least 3 fold or alternatively, at least 4 fold expression over that detected in a normal or control counterpart cell or tissue. As used herein, underexpression, is a reduction of gene expression and generally is at least 1.25 fold, or alternatively, at least 1.5 fold, or alternatively, at least 2 fold or alternatively, at least 3 fold or alternatively, at least 4 fold expression under that detected in a normal or control counterpart cell or tissue. The term "differentially expressed" also refers to where expression in a cancer cell or cancerous tissue is detected but expression in a control cell or normal tissue (e.g. non cancerous cell or tissue) is undetectable.

A high expression level of the gene can occur because of over expression of the gene or an increase in gene copy number. The gene can also be translated into increased protein levels because of deregulation or absence of a negative regulator. Lastly, high expression of the gene can occur due to increased stabilization or reduced degradation of the protein, resulting in accumulation of the protein.

A "gene expression profile" or "gene signature" refers to a pattern of expression of at least one biomarker that recurs in multiple samples and reflects a property shared by those samples, such as mutation, response to a particular treatment, or activation of a particular biological process or pathway in the cells. A gene expression profile differentiates between samples that share that common property and those that do not with better accuracy than would likely be achieved by assigning the samples to the two groups at random. A gene expression profile may be used to predict whether samples of unknown status share that common property or not. Some variation between the biomarker(s) and the typical profile is to be expected, but the overall similarity of biomarker(s) to the typical profile is such that it is statistically unlikely that the similarity would be observed by chance in samples not sharing the common property that the biomarker(s) reflects.

As used herein, the term "inhibit", "inhibiting", or "inhibit the proliferation" of a cancer cell refers to slowing, interrupting, arresting or stopping the growth and/or proliferation of the cancer cell, and does not necessarily indicate a total elimination of the cancer cell growth and/or proliferation. The terms "inhibit" and "inhibiting", or the like, denote quantitative differences between two states, refer to at least statistically significant differences between the two states. For example, "an amount effective to inhibit growth and/or proliferation of cancer cells" means that the rate of growth and/or proliferation of the cells will be at least statistically significantly different from the untreated cells. Such terms are applied herein to, for example, rates of cell proliferation.

This disclosure shows that presence of a TMPRSS2:ERG positive prostate cancer predicts response of cancer cells to PRMT5 inhibition.

A "wild-type," "normal," or "non-mutant" human PRMT5 refers to sequence of PRMT5 of Entrez Gene ID: 10419. A "wild-type," "normal," or "non-mutant" does not comprise a TMPRSS2:ERG gene or its gene product.

A "mutant," or "mutation" is any change in DNA or protein sequence that deviates from wild type gene or protein product sequence. This includes, inter alia, the presence of a TMPRSS2:ERG fusion (TMPRSS2:ERG positivity), which is not normally found in normal (non-cancerous) prostate cells.

The term "isolated" means separated from constituents, cellular and otherwise, in which the polynucleotide, peptide, polypeptide, protein, antibody or fragment(s) thereof, are normally associated with in nature. For example, an isolated polynucleotide is separated from the 3' and 5' contiguous nucleotides with which it is normally associated within its native or natural environment, e.g., on the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated," "separated" or "diluted" polynucleotide, peptide, polypeptide, protein, antibody or fragment(s) thereof, is distinguishable from its naturally occurring counterpart in that the concentration or number of molecules per volume is greater in a "concentrated" version or less than in a "separated" version than that of its naturally occurring counterpart.

As used herein, the terms "neoplastic cells," "neoplastic disease," "neoplasia," "tumor," "tumor cells," "cancer," and "cancer cells," (used interchangeably) refer to cells which exhibit relatively autonomous growth and/or proliferation, so that they exhibit an aberrant growth and/or proliferation phenotype characterized by a significant loss of control of cell proliferation (i.e., de-regulated cell division). Neoplastic cells can be malignant or benign. A "metastatic cell or tissue" means that the cell can invade and destroy neighboring body structures.

The term "PBMC" refers to peripheral blood mononuclear cells and includes "PBL"—peripheral blood lymphocytes.

The terms "nucleic acid" and "polynucleotide" are used interchangeably and refer to a polymeric form of nucleotides of any length, either deoxyribonucleotides or ribonucleotides or analogs thereof. Polynucleotides can have any three-dimensional structure and can perform any function. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, siRNAs, shRNAs, RNAi agents, and primers. A polynucleotide can be modified or substituted at one or more base, sugar and/or phosphate, with any of various modifications or substitutions described herein or known in the art. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form. In some contexts, the terms "nucleic acid" or "polynucleotide" and the like encompass any material which conveys genetic information or performs a function of a nucleic acid or polynucleotide (e.g., it can be translated into a protein or act as an RNAi agent), even if such material is not strictly composed of nucleotides (which consist of a sugar, base and phosphate); such genetic material may comprise, as non-limiting examples, peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA).

The term "polypeptide" is used interchangeably with the term "protein" and in its broadest sense refers to a compound of two or more subunit amino acids, amino acid analogs, or peptidomimetics. The subunits can be linked by peptide bonds. In another embodiment, the subunit may be linked by other bonds, e.g., ester, ether, etc.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in PCR: A Practical Approach, M. MacPherson et al., IRL Press at Oxford University Press (1991). All processes of producing replicate copies of a polynucleotide, such as PCR or gene cloning, are collectively referred to herein as "replication." A primer can also be used as a probe in hybridization reactions, such as Southern or Northern blot analyses (Sambrook et al., Molecular Cloning: A Laboratory Manual, 2nd edition (1989)).

A polynucleotide or polynucleotide region (or a polypeptide or polypeptide region) has a certain percentage (for example, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology, Ausubel et al., eds., (1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant.

A cell is "sensitive," displays "sensitivity" for inhibition, or is "amenable to treatment" with a PRMT5 inhibitor when the cell viability is reduced and/or the rate of cell proliferation is reduced upon treatment with a PRMT5 inhibitor when compared to an untreated control.

As used herein, "solid phase support" or "solid support," used interchangeably, is not limited to a specific type of support. Rather a large number of supports are available and are known to one of ordinary skill in the art. Solid phase supports include silica gels, resins, derivatized plastic films, glass beads, plastic beads, alumina gels, microarrays, and chips. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories), polyHIPE(R)™ resin (obtained from Aminotech, Canada), polyamide resin (obtained from Peninsula Laboratories), polystyrene resin grafted with polyethylene glycol (TentaGelR™, Rapp Polymere, Tubingen, Germany), or polydimethylacrylamide resin (obtained from Milligen/Biosearch, California).

A polynucleotide also can be attached to a solid support for use in high throughput screening assays. PCT WO 97/10365, for example, discloses the construction of high density oligonucleotide chips. See also, U.S. Pat. Nos. 5,405,783; 5,412,087 and 5,445,934. Using this method, the probes are synthesized on a derivatized glass surface to form chip arrays. Photoprotected nucleoside phosphoramidites are coupled to the glass surface, selectively deprotected by photolysis through a photolithographic mask and reacted with a second protected nucleoside phosphoramidite. The coupling/deprotection process is repeated until the desired probe is complete.

As an example, transcriptional activity can be assessed by measuring levels of messenger RNA using a gene chip such as the Affymetrix® HG-U133-Plus-2 GeneChips (Affymetrix, Santa Clara, Calif.). High-throughput, real-time quantitation of RNA of a large number of genes of interest thus becomes possible in a reproducible system.

The terms "stringent hybridization conditions" refers to conditions under which a nucleic acid probe will specifically hybridize to its target subsequence, and to no other sequences. The conditions determining the stringency of hybridization include: temperature, ionic strength, and the concentration of denaturing agents such as formamide. Varying one of these factors may influence another factor and one of skill in the art will appreciate changes in the conditions to maintain the desired level of stringency. An example of a highly stringent hybridization is: 0.015M sodium chloride, 0.0015M sodium citrate at 65-68° C. or 0.015M sodium chloride, 0.0015M sodium citrate, and 50% formamide at 42° C. An example of a "moderately stringent" hybridization is the conditions of: 0.015M sodium chloride, 0.0015M sodium citrate at 50-65° C. or 0.015M sodium chloride, 0.0015M sodium citrate, and 20% formamide at 37-50° C. The moderately stringent conditions are used when a moderate amount of nucleic acid mismatch is desired. One of skill in the art will appreciate that washing is part of the hybridization conditions. For example, washing conditions can include 02.x-0.1×SSC/0.1% SDS and temperatures from 42-68° C., wherein increasing temperature increases the stringency of the wash conditions.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

"Suppressing" or "suppression" of tumor growth indicates a reduction in tumor cell growth and/or proliferation when contacted with a PRMT5 inhibitor compared to tumor growth and/or proliferation without contact with a PRMT5 inhibitor compound. Tumor cell growth and/or proliferation can be assessed by any means known in the art, including, but not limited to, measuring tumor size, determining whether tumor cells are proliferating using a 3H-thymidine incorporation assay, measuring glucose uptake by FDG-PET (fluorodeoxyglucose positron emission tomography) imaging, or counting tumor cells. "Suppressing" tumor cell growth and/or proliferation means any or all of the following states: slowing, delaying and stopping tumor growth and/or proliferation, as well as tumor shrinkage. A "subject," "individual" or "patient" is used interchangeably herein, which refers to a vertebrate, preferably a mammal, more preferably a human. Mammals include, but are not limited to, mice, simians, humans, farm animals, sport animals, and pets.

The terms "synthetic lethality," and "synthetic lethal" are used to refer to a combination of mutations in two or more genes leads to reduced cell viability and/or a reduced rate of cell proliferation, whereas a mutation in only one of these genes does not. As a non-limiting example, a reduction of the production, level, activity, expression or presence of PRMT5 via use of a PRMT5 inhibitor is an example of a synthetic lethality in cells which are TMPRSS2:ERG-positive.

A "reference" or "control," "normal" or "wild-type" tissue, cell or sample, or the like, refers to a tissue, cell or sample used, as a non-limiting example, as a reference as a tissue, cell or sample which is not TMPRSS2:ERG-positive, for comparison with a test tissue, cell or sample from a subject, in order to determine if the test tissue, cell or sample is TMPRSS2:ERG-positive or not.

A "therapeutic agent" is any agent which elicits a therapeutic or beneficial effect in a cell and/or a subject when introduced in sufficient quantity. A therapeutic agent can, as a non-limiting example, reduce a side effect of another therapeutic agent. Therapeutic agents include, as non-limiting examples, an anti-cancer agent, anti-allergic agent, anti-nausea agent or anti-emetic agent, pain reliever, cytoprotective agent.

DETAILED DESCRIPTION

Provided herein are novel diagnostic and treatment methods for a subject with TMPRSS2:ERG positive prostate cancer. The present invention is based, in part, on the discovery that TMPRSS2:ERG positive prostate cancer lines are sensitive to inhibition of the PRMT5 gene.

TMPRSS2:ERG positive prostate cancer cells express, or are detected to comprise the TMPRSS2:ERG fusion gene or gene product. This is a fusion of TMPRSS2 and ERG and is commonly found in human prostate cancer, especially in hormone-refractory prostate cancer. ERG overexpression may contribute to development of androgen-independence in prostate cancer through disruption of androgen receptor signaling. The fusion gene is important to the progression of cancer because it inhibits the androgen receptor expression and it binds and inhibits androgen receptors already present in the cell. TMPRSS2-ERG fusion disrupts the ability of the cells to differentiate into proper prostate cells creating unregulated and unorganized tissue. One study showed that, in 90% of prostate cancers overexpressing ERG, they also possess a fusion TMPRSS2-ERG protein, suggesting that this fusion is the predominant subtype in prostate cancer.

The present disclosure demonstrates that PRMT5 inhibition represents a therapeutically useful node to inhibit TMPRSS2:ERG positive prostate cancer.

In various aspects, the present disclosure provides a method for inhibiting proliferation of prostate cancer cells in a subject, the method comprising the step of administering a PRMT5 inhibitor to a subject in need thereof, in an amount that is effective to inhibit proliferation of the TMPRSS2:ERG positive prostate cancer cells. According to the present invention, a PRMT5 inhibitor includes, but is not limited to, a low molecular weight compound, a RNA inhibitor (e.g., a RNAi agent), a CRISPR, a TALEN, a zinc finger nuclease, an mRNA, an antibody or derivative thereof, an antibody-drug conjugate, or a chimeric antigen receptor T cell (CART).

The present disclosure further provides use of a PRMT5 inhibitor, such as low molecular weight compound, a RNA inhibitor (e.g., a RNAi agent), a CRISPR, a TALEN, a zinc finger nuclease, an mRNA, an antibody or derivative thereof, an antibody-drug conjugate, or a chimeric antigen receptor T cell (CART), for the treatment of a TMPRSS2:ERG positive prostate cancer. Also provided is a use of a PRMT5 inhibitor, including, but not limited to, low molecular weight compound, a RNA inhibitor (e.g., a RNAi agent), a CRISPR, a TALEN, a zinc finger nuclease, an mRNA, an antibody or derivative thereof, an antibody-drug conjugate, or a chimeric antigen receptor T cell (CART), for the manufacture of a medicament for treating a TMPRSS2:ERG positive prostate cancer.

In one embodiment, the present invention provides a method of treating TMPRSS2:ERG positive prostate cancer, by administering to a subject in need thereof a therapeutically effective amount of a pharmaceutical composition comprising a molecule that inhibits PRMT5 expression, wherein said molecule is a low molecular weight compound.

The present disclosure further provides use of a low molecular weight compound for the treatment of TMPRSS2:ERG positive prostate cancer. Also provided is a use of a low molecular weight compound for the manufacture of a medicament for treating TMPRSS2:ERG positive prostate cancer.

In another embodiment, the present invention provides a method of treating TMPRSS2:ERG positive prostate cancer, by administering to a subject in need thereof a therapeutically effective amount of a pharmaceutical composition comprising a molecule that inhibits the cellular function of the PRMT5 protein.

The present disclosure further provides use of a molecule that inhibits the cellular function of the PRMT5 protein for the treatment of TMPRSS2:ERG positive prostate cancer. Also provided is a use of a molecule that inhibits the cellular function of the PRMT5 protein for the manufacture of a medicament for treating TMPRSS2:ERG positive prostate cancer.

In another embodiments, the present invention provides a method of treating TMPRSS2:ERG positive prostate cancer, by administering to a subject in need thereof a therapeutically effective amount of a pharmaceutical composition comprising a molecule inhibits PRMT5 expression, wherein said molecule is a RNA inhibitor, including, but not limited to, a low molecular weight compound, a RNA inhibitor (e.g., a RNAi agent), a CRISPR, a TALEN, a zinc finger nuclease, an mRNA, an antibody or derivative thereof, an antibody-drug conjugate, or a chimeric antigen receptor T cell (CART). Examples of such RNA inhibitors are described herein.

In another embodiments, the present invention provides a method of treating TMPRSS2:ERG positive prostate cancer, by administering to a subject in need thereof a therapeutically effective amount of a pharmaceutical composition comprising an inhibitor that inhibits PRMT5 expression, wherein the inhibitor includes, but not limited to, a low molecular weight compound, a RNA inhibitor (e.g., a RNAi agent), a CRISPR, a TALEN, a zinc finger nuclease, an mRNA, an antibody or derivative thereof, an antibody-drug conjugate, or a chimeric antigen receptor T cell (CART). Examples of such antibodies or antibody derivatives are described herein.

The present disclosure further provides use of a RNA inhibitor (e.g., a RNAi agent), a CRISPR, a TALEN, a zinc finger nuclease, an mRNA, an antibody or derivative thereof, an antibody-drug conjugate, or a chimeric antigen receptor T cell (CART) for the treatment of TMPRSS2:ERG positive prostate cancer. Also provided is a use of a RNA inhibitor (e.g., a RNAi agent), a CRISPR, a TALEN, a zinc finger nuclease, an mRNA, an antibody or derivative thereof, an antibody-drug conjugate, or a chimeric antigen receptor T cell (CART) for the manufacture of a medicament for treating TMPRSS2:ERG positive prostate cancer.

In one embodiment, the present invention provides a method of determining if a subject afflicted with prostate cancer will respond to therapeutic treatment with a PRMT5 inhibitor, comprising the step of: a) contacting a test sample obtained from said subject with a reagent capable of detecting TMPRSS2:ERG positive prostate cancer cells, wherein TMPRSS2:ERG positivity indicates said afflicted subject will respond to therapeutic treatment with a PRMT5 inhibitor. In some embodiments, the method further comprises the step of determining the level of PRMT5 in the cancer cells. In many cancers, PRMT5 is over-expressed. Chung et al. 2013 J. Biol. Chem. 288: 35534-47. The level of expression of PRMT5 can be taken into account when determining the therapeutically effective dosage of a PRMT5 inhibitor. In addition, during treatment, the level and/or activity of PRMT5 can be monitored to assess disease or treatment progression.

In one embodiment, the present invention provides a method of determining the sensitivity of a prostate cancer cell to a PRMT5 inhibitor, comprising the steps of: a) determining the positivity or negativity of TMPRSS2:ERG in said cancer cell; and b) wherein TMPRSS2:ERG positivity indicates said cell is sensitive to a PRMT5 inhibitor.

In one embodiment, the present invention provides a method of screening for PRMT5 inhibitors, said method comprising the steps of: a) contacting a test sample containing one or more TMPRSS2:ERG positive prostate cancer cells with a candidate PRMT5 inhibitor; b) measuring the reduction in proliferation and/or viability of said cells in said sample; c) contacting a reference sample containing the same type of TMPRSS2:ERG positive prostate cancer cells with a known PRMT5 inhibitor; d) measuring the reduction in proliferation and/or viability of said cells in said test sample; e) comparing the reduction in proliferation and/or viability of said test sample with proliferation and/or viability of said reference sample, wherein a reduction in proliferation and/or viability of said test sample relative to the reference sample indicates said candidate is a PRMT5 inhibitor.

In one embodiment, the present invention provides a kit for predicting the sensitivity of a subject afflicted with prostate cancer for treatment with a PRMT5 inhibitor, comprising: i) reagents capable of detecting TMPRSS2:ERG positive prostate cancer cells; and ii) instructions for how to use said kit.

In one embodiment, the present invention provides a composition comprising a PRMT5 inhibitor for use in treatment of a selected patient (subject) population, wherein the patient population is selected on the basis of being afflicted with a TMPRSS2:ERG positive prostate cancer.

In one embodiment, the present invention provides a therapeutic method of treating a subject afflicted with a TMPRSS2:ERG positive prostate cancer is provided comprising the steps of: a) contacting a test sample obtained from said subject with a reagent capable of detecting TMPRSS2:ERG positive prostate cancer cells, wherein TMPRSS2:ERG positivity in said test sample indicates said afflicted subject will respond to therapeutic treatment with a PRMT5 inhibitor; and c) administering a therapeutically effective amount of PRMT5 inhibitor to those subjects identified in step b). In some embodiments, the method further comprises the step of determining the level and/or activity of PRMT5 in the cancer cells. In many cancers, PRMT5 is over-expressed. Chung et al. 2013 J. Biol. Chem. 288: 35534-47. The level and/or activity of expression of PRMT5 can be taken into account when determining the therapeutically effective dosage of a PRMT5 inhibitor. In addition, during treatment, the level and/or activity of PRMT5 can be monitored to assess disease or treatment progression.

In one embodiment, the present invention provides a therapeutic method of treating a subject afflicted with TMPRSS2:ERG positive prostate cancer comprising the steps of: a) contacting a test sample obtained from said subject with a reagent capable of detecting TMPRSS2:ERG positive prostate cancer cells, TMPRSS2:ERG positivity in said test sample indicates said afflicted subject will respond to therapeutic treatment with a PRMT5 inhibitor; and c) administering a therapeutically effective amount of the composition according to some embodiments. In some embodiments, the method further comprises the step of determining the level and/or activity of PRMT5 in the cancer cells. In many cancers, PRMT5 is over-expressed. The level and/or activity of expression of PRMT5 can be taken into account when determining the therapeutically effective dosage of a PRMT5 inhibitor. In addition, during treatment, the level and/or activity of PRMT5 can be monitored to assess disease or treatment progression.

In one embodiment, the present invention provides a method of determining if a subject afflicted with TMPRSS2:ERG positive prostate cancer will respond to therapeutic treatment with a PRMT5 inhibitor, comprising the steps of: a) contacting a test sample obtained from said subject with a reagent capable of detecting a TMPRSS2:ERG positive prostate cancer cell, wherein TMPRSS2:ERG positivity indicates said afflicted subject will respond to therapeutic treatment with a PRMT5 inhibitor. In some embodiments, the method of determining if a subject has a cancer comprising TMPRSS2:ERG positive prostate cancer cells further comprises the step of determining the level and/or activity of PRMT5 in the cancer cells. In many cancers, PRMT5 is over-expressed. The level and/or activity of expression of PRMT5 can be taken into account when determining the therapeutically effective dosage of a PRMT5 inhibitor. In addition, during treatment, the level of PRMT5 can be monitored to assess disease or treatment progression.

In one embodiment, the present invention provides a method of determining if a subject afflicted with TMPRSS2:ERG positive prostate cancer will respond to therapeutic treatment with a PRMT5 inhibitor, comprising the steps of: a) contacting a test sample obtained from said subject with a reagent capable of detecting a TMPRSS2:ERG positive prostate cancer cell, wherein TMPRSS2:ERG positivity indicates said afflicted subject will respond to therapeutic treatment with a PRMT5 inhibitor. In some embodiments, the method further comprises the step of determining the level and/or activity of PRMT5 in the cancer cells. In many cancers, PRMT5 is over-expressed. The level and/or activity of expression of PRMT5 can be taken into account when determining the therapeutically effective dosage of a PRMT5 inhibitor. In addition, during treatment, the level and/or activity of PRMT5 can be monitored to assess disease or treatment progression.

Identification of a Role of PRMT5 in Prostate Cancer

The present disclosure shows that TMPRSS2:ERG positive prostate cancer cell are sensitive to inhibition of PRMT5.

As detailed in the Examples, ERG is required for proliferation of TMPRSS2:ERG positive prostate cancer cells. To better understand the mechanism of ERG function in TMPRSS2:ERG-positive prostate cancer, we identified ERG protein interactors that are also necessary to maintain the proliferation of TMPRSS2:ERG-positive prostate cancer cells. PRMT5 was identified as a strong ERG interactor with proliferation effects on ERG-positive prostate cancer. PRMT5 knockdown inhibited the proliferation of TMPRSS2:ERG-positive VCaP cells, but had no effect on TMPRSS2:ERG-negative cells.

Without being bound by any particular theory, this disclosure notes that our findings suggest that a key mechanism used by ERG to repress Androgen Receptor (AR) transcriptional functions in TMPRSS2:ERG-positive prostate cancer is the recruitment of PRMT5 to AR transcriptional complexes. ERG-mediated PRMT5 recruitment leads to mono- and symmetric di-methylation of AR at arginine 761, which then blocks AR binding to its target genes and transcriptional activity. This inhibitory function of PRMT5 on AR is dependent on ERG expression and DNA binding function, and is highly selective to TMPRSS2:ERG-positive prostate cancers. ERG promotes the proliferation of prostate cancer [Mounir et al. 2014 Oncogene; Tomlins et al. 2008 Neoplasia 10: 177-188; Carmichael et al. Proc. Natl. Acad. Sci. USA 109: 15437-15442], but the nature of this protein makes it a challenging target for therapeutics development. As PRMT5 enzymatic function is required for ERG-dependent AR inhibition and cell proliferation in prostate cancer, TMPRSS2:ERG is a biomarker that predicts sensitivity to PRMT5 inhibition. In addition, detection of AR arginine 761 methylation may provide a biomarker tool to assess ERG activity in prostate cancer samples, rather than solely looking and relying on ERG mRNA or protein expression levels. AR methylation on arginine 761 could be used as a diagnostic tool to differentiate among all TMPRSS2:ERG-positive prostate cancers. This tool could be used to stratify ERG-positive prostate cancers with "active" ERG from those with "inactive" ERG based on the level and/or activity of AR arginine methylation, which would be high or low, respectively. This stratification based on ERG activity would provide a more accurate of analysis of AR activity status and transcriptional functions which can have both diagnostic and predictive value of tumor response to anti-androgen therapy.

In the use of the present invention, any method can be used to determine if prostate cancer cells are TMPRSS2:ERG positive. These include, for example, methods known in the art, including but not limited to those described in Perner et al. 2006 Cancer Res. 66: 8337-8341; and Demichelis et al. 2007 Oncogene 26: 4596-4599.

Any PRMT5 inhibitor known in the art can be used against a TMPRSS2:ERG positive prostate cancer cell.

In some embodiments, the present invention provides compositions and methods wherein the PRMT5 inhibitor is an antibody or derivative thereof, an antibody-drug conjugate, a RNA inhibitor (e.g., a RNAi agent), a CRISPR, a TALEN, a zinc finger nuclease, an mRNA, or a chimeric antigen receptor T cell (CART), or a low molecular weight compound.

Antibodies to PRMT5

In some embodiments, the present invention provides a PRMT5 inhibitor which is an antibody or epitope-binding fragment or derivative thereof, and methods of using the same to treat TMPRSS2:ERG positive prostate cancer. Various types of antibodies and epitope-binding fragments and derivatives thereof are known in the art, as are methods of producing these. Any of these, including but not limited to those described herein, can be used to produce a PRMT5 inhibitor, which can be used in various methods of inhibiting PRMT5 and treating TMPRSS2:ERG positive prostate cancer.

In certain embodiments of the invention, the antibody to PRMT5 is an intrabody.

Single chain antibodies expressed within the cell (e.g. cytoplasm or nucleus) are called intrabodies. Due to the reducing environment within the cell, disulfide bridges, believed to be critical for antibody stability, are not formed. Thus, it was initially believed that applications of intrabodies are not suitable. But several cases are described showing the feasibility of intrabodies (Beerli et al., 1994 J Biol Chem, 269, 23931-6; Biocca et al., 1994 Bio/Technology, 12, 396-9; Duan et al., 1994 Proceedings of the National Academy of Sciences of the United States of America, 91, 5075-9; Gargano and Cattaneo, 1997 FEBS Lett, 414, 537-40; Greenman et al., 1996 J Immunol Methods, 194, 169-80; Martineau et al., 1998 Journal of Molecular Biology, 280, 117-27; Mhashilkar et al., 1995 EMBO Journal, 14, 1542-51; Tavladoraki et al., 1993 Nature, 366, 469-72). In these cases, intrabodies work by, e.g., blocking the cytoplasmic antigen and therefore inhibiting its biological activity.

Such intracellular antibodies are also referred to as intrabodies and may comprise a Fab fragment, or preferably comprise a scFv fragment (see, e.g., Lecerf et al., Proc. Natl. Acad. Sci. USA 98:4764-49 (2001). The framework regions flanking the CDR regions can be modified to improve expression levels and solubility of an intrabody in an intracellular reducing environment (see, e.g., Worn et al., J. Biol. Chem. 275:2795-803 (2000). An intrabody may be directed to a particular cellular location or organelle, for example by constructing a vector that comprises a polynucleotide sequence encoding the variable regions of an intrabody that may be operatively fused to a polynucleotide sequence that encodes a particular target antigen within the cell (see, e.g., Graus-Porta et al., Mol. Cell Biol. 15:1182-91 (1995); Lener et al., Eur. J. Biochem. 267:1196-205 (2000)). An intrabody may be introduced into a cell by a variety of techniques available to the skilled artisan including via a gene therapy vector, or a lipid mixture (e.g., Provectin™ manufactured by Imgenex Corporation, San Diego, Calif.), or according to photochemical internalization methods.

Intrabodies can be derived from monoclonal antibodies which were first selected with classical techniques (e.g., phage display) and subsequently tested for their biological activity as intrabodies within the cell (Visintin et al., 1999 Proceedings of the National Academy of Sciences of the United States of America, 96, 11723-11728). For additional information, see: Cattaneo, 1998 Bratisl Lek Listy, 99, 413-8; Cattaneo and Biocca, 1999 Trends In Biotechnology, 17, 115-21. The solubility of an intrabody can be modified by either changes in the framework (Knappik and Pluckthun, 1995 Protein Engineering, 8, 81-9) or the CDRs (Kipriyanov et al., 1997; Ulrich et al., 1995 Protein Engineering, 10, 445-53). Additional methods for producing intrabodies are described in the art, e.g., U.S. Pat. Nos. 7,258,985 and 7,258,986.

In one embodiment, antigen-binding proteins, including, but not limited to, antibodies, that are able to target cytosolic/intracellular proteins, for example, the PRMT5 protein. The disclosed antibodies target a peptide/MHC complex as it would typically appear on the surface of a cell following antigen processing of PRMT5 protein and presentation by the cell. HLA class I binds to peptides approximately 9 amino acids in length and presents them on the surface of the cell to cytotoxic T lymphocytes. The presentation of these peptides is the product of cytoplasmic cleavage by enzymes and active transport by transporter proteins. Further, the binding of particular peptides after processing and localization is heavily influenced by the amino acid sequence of the particular HLA protein. Most of these steps are amenable to in vitro characterization, allowing one to predict the likelihood that a particular amino acid sequence, derived from a larger peptide or protein of interest, will be successfully processed, transported, bound by MHC class I, and presented to cytotoxic T lymphocytes. In that regard, the antibodies mimic T-cell receptors in that the antibodies have the ability to specifically recognize and bind to a peptide in an MHC-restricted fashion, that is, when the peptide is bound to an MHC antigen. The peptide/MHC complex recapitulates the antigen as it would typically appear on the surface of a cell following antigen processing and presentation of the PRMT5 protein to a T-cell.

The accurate prediction for a particular step in this process is dependent upon models informed by experimental data. The cleavage specificity of the proteasome, producing peptides often <30 amino acids in length, can be determined by in vitro assays. The affinity for the transporter complex can similarly be determined by relatively straight-forward in vitro binding assays. The MHC class I protein's affinity is highly variable, depending on the MHC allele, and generally must be determined on an allele-by-allele basis. One approach is to elute the peptides presented by the MHC protein on the cell surface to generate a consensus motif. An alternative approach entails generating cells deficient in a peptide processing step such that most or all of the MHC proteins on the cell surface are not loaded with a peptide. Many different peptides can be washed over the cells in parallel and monitored for binding. The set of peptides that do and do not bind can be used to train a classifier (including, but not limited to, an artificial neural network or support vector machine) to discriminate between the two peptide sets. This trained classifier can then be applied to novel peptides to predict their binding to the MHC allele. Alternatively, the affinity for each peptide can be used to train a regression model, which can then be used to make quantitative predictions regarding the MHC protein's affinity for an untested peptide. The collection of such datasets is laborious, so methods exist to combine data collected for one HLA allele with the knowledge of the amino acid differences between that particular allele and another unstudied MHC allele to predict its peptide binding specificity.

Additional methods for constructing antibodies to cytosolic peptides including, but not limited to, PRMT5 are described in, for example, WO 2012/135854. This document describes production of antibodies which recognize and bind to epitopes of a peptide/MHC complex, including, but not limited to, a peptide/HLA-A2 or peptide/HLA-A0201 complex. In some embodiments of the invention, the peptide is portion of PRMT5.

HLA class I binds to peptides approximately 9 amino acids in length and presents them on the surface of the cell to cytotoxic T lymphocytes. The presentation of these peptides is the product of cytoplasmic cleavage by enzymes and active transport by transporter proteins. Further, the binding of particular peptides after processing and localization is heavily influenced by the amino acid sequence of the particular HLA protein. Most of these steps are amenable to in vitro characterization, allowing one to predict the likelihood that a particular amino acid sequence, derived from a larger peptide or protein of interest, will be successfully processed, transported, bound by MHC class I, and presented to cytotoxic T lymphocytes.

The accurate prediction for a particular step in this process is dependent upon models informed by experimental data. The cleavage specificity of the proteasome, producing peptides often <30 amino acids in length, can be determined by in vitro assays. The affinity for the transporter complex can similarly be determined by relatively straight-forward in vitro binding assays. The MHC class I protein's affinity is highly variable, depending on the MHC allele, and generally must be determined on an allele-by-allele basis. One approach is to elute the peptides presented by the MHC protein on the cell surface to generate a consensus motif. An alternative approach entails generating cells deficient in a peptide processing step such that most or all of the MHC proteins on the cell surface are not loaded with a peptide. Many different peptides can be washed over the cells in parallel and monitored for binding. The set of peptides that do and do not bind can be used to train a classifier (including, but not limited to, an artificial neural network or support vector machine) to discriminate between the two peptide sets. This trained classifier can then be applied to novel peptides to predict their binding to the MHC allele. Alternatively, the affinity for each peptide can be used to train a regression model, which can then be used to make quantitative predictions regarding the MHC protein's affinity for an untested peptide. The collection of such datasets is laborious, so methods exist to combine data collected for one HLA allele with the knowledge of the amino acid differences between that particular allele and another unstudied MHC allele to predict its peptide binding specificity.

One such machine learning approach that combines prediction of likely proteasomal cleavage, transporter affinity, and MHC affinity is SMM (Stabilized Matrix Method, Tenzer S et al, 2005. PMID 15868101), which we used to scan the PRMT5 wildtype protein sequence, and generated a number of peptides predicted to be well-processed and high-affinity MHC binders (see Example 2).

This approach can be extended to mutations specific to an indication: a mutation leading to an amino acid change alters the peptide sequence and can lead to a peptide that produces a different score than the wildtype sequence. By focusing on such mutations and selecting those mutant peptide sequences that score highly, one can generate peptides that are presented solely in a diseased state because the sequence simply does not exist in a non-diseased individual. Cross-reactivity can be further minimized by also evaluating the wildtype sequence and selecting for downstream analyses only those peptides whose non-mutant sequence is not predicted to be processed and presented by MHC efficiently.

Once appropriate peptides have been identified, peptide synthesis may be done in accordance with protocols well known to those of skill in the art. Peptides may be directly synthesized in solution or on a solid support in accordance with conventional techniques (See for example, Solid Phase Peptide Synthesis by John Morrow Stewart and Martin et al. Application of Almez-mediated Amidation Reactions to Solution Phase Peptide Synthesis, Tetrahedron Letters Vol. 39, pages 1517-1520 1998.). Peptides may then be purified by high-pressure liquid chromatography and the quality assessed by high-performance liquid chromatography analysis. Purified peptides may be dissolved in DMSO diluted in PBS (pH7.4) or saline and stored at −80 C. The expected molecular weight may be confirmed using matrix-assisted laser desorption mass spectrometry.

Subsequent to peptide selection, binding of the peptide to HLA-A may be tested. In one method, binding activity is tested using the antigen-processing deficient T2 cell line, which stabilizes expression of HLA-A on its cell surface when a peptide is loaded exogenously in the antigen-presenting groove by incubating the cells with peptide for a sufficient amount of time. This stabilized expression is read out as an increase in HLA-A expression by flow cytometry using HLA-A2 specific monoclonal antibodies (for example, BB7.2) compared to control treated cells. In another method, presence of the peptide in the HLA-A2 antigen-presenting groove of T2 cells may be detected using targeted mass spectrometry. The peptides are enriched using a MHC-specific monoclonal Ab (W6/32) and then specific MRM assays monitor the peptides predicted to be presented (See for example, Kasuga, Kie. (2013) Comprehensive Analysis of MHC Ligands in Clinical material by Immunoaffinity-Mass Spectrometry, Helena Backvall and Janne Lethio, The Low Molecular Weight Proteome: Methods and Protocols (203-218), New York, N.Y.: Springer Sciences+Business Media and Kowalewski D and Stevanovic S. (2013) Biochemical Large-Scale Identification of MHC Class I Ligands, Peter van Endert, Antigen Processing: Methods and Protocols, Methods in Molecular Biology, Vol 960 (145-158), New York, N.Y.: Springer Sciences+Business Media). This strategy differs slightly than the normally applied tandem mass spectrometry based peptide sequencing. Heavy labeled internal standards are used for identification which results in a more sensitive and quantitative approach.

Once a suitable peptide has been identified the next step would be identification of specific antibodies to the peptide/HLA-A complex, the "target antigen", utilizing conventional antibody generation techniques including, but not limited to, phage display or hybridoma technology in accordance with protocols well known to those skilled in the art. The target antigen (for example, the peptide/HLA-A02-01 complex) is prepared by bringing the peptide and the HLA-A molecule together in solution to form the complex. Next, selection of Fab or scFv presenting phage that bind to the target antigen are selected by iterative binding of the phage to the target antigen, which is either in solution or bound to a solid support (for example, beads or mammalian cells), followed by removal of non-bound phage by washing and elution of specifically bound phage. The targeted antigen may be first biotinylated for immobilization, for example, to streptavidin-conjugated (for example, Dynabeads M-280).

Positive Fab or scFv clones may be then tested for binding to peptide/HLA-A2 complexes on peptide-pulsed T2 cells by flow cytometry. T2 cells pulsed with the specific peptide or a control irrelevant peptide may be incubated with phage clones. The cells are washed and bound phage are detected by binding an antibody specific for the coat protein (for example, M13 coat protein antibody) followed by a fluorescent labelled secondary antibody to detect the coat protein antibody (for example, anti-mouse Ig). Binding of the antibody clones to human tumor cells expressing both HLA-A2 and the target (for example, PRMT5) can also be assessed by incubating the tumor cells with phage as described or purified Fab or scFv flow cytometry and appropriate secondary antibody detection.

An alternative method to isolating antibodies specific to the peptide/HLA-A2 complex may be achieved through conventional hybridoma approaches in accordance with protocols well known to those of skill in the art. In this method, the target antigen is injected into mice or rabbits to elicit an immune response and monoclonal antibody producing clones are generated. In one embodiment, the host mouse may be one of the available human HLA-A2 transgenic animals which may serve to reduce the abundance of non-specific antibodies generated to HLA-A2 alone. Clones may then be screened for specific binding to the target antigen using standard ELISA methods (for example, incubating supernatant from the clonal antibody producing cells with biotinylated peptide/MHC complex captured on streptavidin coated ELISA plates and detected with anti-mouse antibodies). The positive clones can also be identified by incubating supernatant from the antibody producing clones with peptide pulsed T2 cells by flow cytometry and detection with specific secondary antibodies (for example, fluorescent labelled anti-mouse IgG antibodies). Binding of the antibody clones to human tumor cells expressing both HLA-A2 and the target (for example, PRMT5) can also be assessed by incubating the tumor cells with supernatant or purified antibody from the hybridoma clones by flow cytometry and appropriate secondary antibody detection.

Immunotherapy

Adoptive cell transfer has been shown to be a promising treatment for various types of cancer. Adoptive cell transfer in cancer therapy involves the transfer of autologous or allogeneic immune effector cells (including, but not limited to, T cells) to enhance immune response against the tumor in a subject having cancer. Recent methods of adoptive cell transfer that have shown promise in cancer therapy include the genetic modification of cells prior to delivery to the subject to express molecules that target antigens expressed on cancer cells and improve the anti-cancer immune response. Examples of such molecules include T cell receptors (TCRs) and chimeric antigen receptors (CARs), which are described in further detail below.

TCR is a disulfide-linked membrane-anchored heterodimer present on T cell lymphocytes, and normally consisting of an alpha ($\alpha$) chain and a beta ($\beta$) chain. Each chain comprises a variable (V) and a constant (C) domain, wherein the variable domain recognizes an antigen, or an MHC-presented peptide. Signaling is mediated through interaction between the antigen-bound $\alpha\beta$ heterodimer to CD3 chain molecules, e.g., CD3zeta ($\zeta$). Upon binding of a TCR to its antigen, a signal transduction cascade is initiated that can result in T cell activation, T cell expansion, and antitumor effect, e.g., increased cytolytic activity against tumor cells.

In TCR gene therapy, naturally occurring or modified TCR$\alpha$ and TCR$\beta$ chains with a known specificity and avidity for tumor antigens are introduced and expressed in a T cell. Briefly, a tumor antigen-specific T cell clone, e.g., with high affinity to the target antigen, is isolated from a donor or subject sample, e.g., a blood or PBMC sample. The tumor antigen-specific TCR $\alpha$ and $\beta$ chains are isolated using standard molecular cloning techniques known in the art, and a recombinant expression vector for delivery into a host PBMC or T cell population, or subpopulation thereof, is generated. The host cell population is transduced, and the TCR-engineered cells are expanded and/or activated ex vivo prior to administration to the subject. T cells redirected with TCRs that target tumor antigens, including, but not limited to, glycoprotein-100 (gp100) and MART-1, have shown success in recent studies. TCR-redirected T cells recognizing any antigens that are uniquely or preferentially expressed on tumor cells can be used in the present invention.

The TCR chains can be modified to improve various TCR characteristics for enhancing therapeutic efficacy. Modifications can be made to the TCR to improve TCR surface expression by any of the following: utilizing promoters that drive high level of gene expression in T cells, e.g., retroviral long terminal repeats (LTRs), CMV, MSCV, SV40 promoters (Cooper et al., J. Virol., 2004; Jones et al., Hum. Gene Ther., 2009); introducing other regulatory elements that can enhance transgene expression, e.g., woodchuck hepatitis virus posttranscriptional regulatory element which increases RNA stability (Zufferey et al., J. Virol., 1999); codon optimization (Gustafsson et al., Trends Biotechnol., 2004); or eliminating mRNA instability motifs or cryptic splice sites (Scholten et al., Clin. Immunol., 2006); or a combination thereof. To reduce TCR chain mispairing between the introduced and endogenous TCR chains, and promote the preferential pairings of the introduced TCR chains with each other, any one of the following: introducing foreign constant domains, e.g., from another organism, to the TCR$\alpha$ and TCR$\beta$ chains, e.g., murine constant domains (C$\alpha$ and C$\beta$) for human TCR chains; increasing interchain affinity by engineering a second disulfide bond in the introduced TCR, e.g., introducing additional cysteine residues in the C$\alpha$ and C$\beta$ domains (Kuball et al., Blood, 2007); or introducing mutations, e.g., point mutations, that increase the "knob in hole" interface between the TCR$\alpha$ and TCR$\beta$ chain (Voss et al., J. Immunol., 2008); or fusing signaling domains, e.g., CD3z domains, directly to the variable domains of the TCR$\alpha$ and TCR$\beta$ (Sebestyen et al., 2008); or any combination thereof. The different TCR modifications described above merely represent exemplary modifications, and do not represent an exhaustive or comprehensive list of modifications. Other modifications that increase specificity, avidity, or function of the TCRs or the engineered T cells expressing the TCRs can be readily envisioned by the ordinarily skilled artisan. Methods for introducing the TCRs into host cells and administration of the TCR-engineered cells are further described below.

Single-chain TCRs has been described in, e.g., Willemsen R A et al, Gene Therapy 2000; 7: 1369-1377; Zhang T et al, Cancer Gene Ther 2004; 11: 487-496; Aggen et al, Gene Ther. 2012 April; 19(4):365-74.

Chimeric antigen receptors (CARs) are based upon TCRs, and generally comprise 1) an extracellular antigen binding domain; 2) a transmembrane domain; and 3) an intracellular domain comprising one or more intracellular signaling domains. Similar to TCR gene therapy, CAR gene therapy generally comprises isolating a host cell population from a donor or subject, e.g., PBMCs, T cells, or a subpopulation thereof, and introducing the CAR molecule to the host cells such that the host cells express the CAR. The CAR-redirected T cells are then expanded and activated ex vivo using methods known in the art, including, but not limited to, stimulation by anti-CD3 and anti-CD28 antibodies prior to delivery to the subject.

The antigen binding domain of a CAR refers to a molecule that has affinity for an antigen that is expressed on a target cell, e.g., a cancer cell. The antigen binding domain can be a ligand, a counterligand, or an antibody or antigen-binding fragment thereof, e.g., an Fab, Fab', F(ab')$_2$, or Fv fragment, an scFv antibody fragment, a linear antibody, single domain antibody including, but not limited to, an sdAb (either VL or VH), a camelid VHH domain, a nanobody, and multi-specific antibodies formed from antibody fragments. The antibody or fragment thereof can be humanized. Any antibodies or fragments thereof that recognize and bind to tumor antigens known in the art can be utilized in a CAR.

The transmembrane domain of a CAR refers to a polypeptide that spans the plasma membrane, linking the extracellular antigen binding domain to the intracellular domain. A transmembrane domain can include one or more additional amino acids adjacent to the transmembrane region, e.g., one or more amino acid associated with the extracellular or intracellular region of the protein from which the transmembrane was derived (e.g., 1, 2, 3, 4, 5, 6, 7, 8, 9, 10 up to 15 amino acids of the extracellular or intracellular region). Examples of transmembrane domains can be derived from any one or more of the following: the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp. Additional sequences, e.g., hinge or spacer sequence, can be disposed between a transmembrane domain and another sequence or domain to which it is fused.

The intracellular domain of a CAR includes at least one primary signaling domain and, optionally, one or more co-stimulatory signaling domains, which are responsible for activation of at least one of the normal effector functions of the immune cell in which the CAR has been introduced. Examples of primary signaling domains include TCR zeta, FcR gamma, FcR beta, CD3 gamma, CD3 delta, CD3 epsilon, CD5, CD22, CD32, CD79a, CD79b, CD66d, DAP10, and DAP12. Examples of costimulatory signaling domains include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, and PAG/Cbp. The intracellular signaling sequences may be linked to each other in random or specified order, and may be separated by a short oligo or polypeptide linker.

Introduction of the TCR and CAR molecules described above to a host cell can be accomplished using any methods known in the art. The host cells are isolated from a subject, or optionally, a donor, and can be immune effector cells, preferably T cells. In some embodiments, specific subpopulations of the immune effector cells may be preferred, for example, tumor infiltrating lymphocytes (TIL), CD4+ T cells, CD8+ T cells, helper T cells (Th cells), or NK cells. Subpopulations of immune effector cells can be identified or isolated from a subject or a donor by the expression of surface markers, e.g., CD4, CD8. The host cells can be modified by transduction or transfection of an expression vector, e.g., a lentiviral vector, a retroviral vector, or a gamma-retroviral vector, encoding the TCR or CAR molecule for sustained or stable expression of the TCR or CAR molecule. With regard to TCR, the α and β chain may be in different expression vectors, or in a single expression vector. In other embodiments, the host cells are modified by in vitro transcribed RNA encoding the TCR or CAR molecule, to transiently express the TCR or CAR. The RNA encoding the TCR or CAR molecule can be introduced to the host cell by transfection, lipofection, or electroporation. The TCR or CAR-modified host cells are cultured under conditions sufficient for expression of the TCR or CAR molecules. In some aspects, the engineered cells are expanded and/or activated using methods known in the art, including, but not limited to, culturing in the presence of specific cytokines or factors that stimulate proliferation and activation known in the art. Examples include culturing in the presence of IL-2, and/or anti-CD3/CD28 antibodies.

The subject can receive one or more doses of a therapeutic amount of TCR or CAR-engineered cells. The therapeutic amount of TCR or CAR-engineered cells in each dosage can be determined by a physician with consideration of individual differences in age, weight, tumor size, extent of infection or metastasis, and condition of the subject. It can generally be stated that a pharmaceutical composition comprising the immune TCR or CAR-engineered cells described herein may be administered at a dosage of $10^4$ to $10^9$ cells/kg body weight, in some instances $10^5$ to $10^6$ cells/kg body weight, including all integer values within those ranges. The pharmaceutical compositions may also be administered multiple times at these dosages. The cells can be administered by using infusion techniques that are commonly known in immunotherapy (see, e.g., Rosenberg et al., New Eng. J. of Med. 319:1676, 1988), e.g., intravenous injection, or direct delivery to the site of the tumor.

Cancer vaccines generally involve inoculating a subject with a reagent designed to induce an antigen specific immune response. Preventative cancer vaccines are typically administered prior to diagnosis or development of a cancer to reduce the incidence of cancer. Preventative cancer vaccines are designed to target infectious agents, e.g., oncogenic viruses, by stimulating the immune system to recognize the infectious agents for protecting the body against future exposure. Therapeutic cancer vaccines aim to treat cancer after diagnosis by delaying or inhibiting cancer cell growth and/or proliferation, causing tumor regression, preventing cancer relapse, or eliminating cancer cells that are not killed by other forms of treatment.

Cancer vaccines may comprise peptides or proteins, antibodies, glycoproteins, recombinant vectors or other recombinant microorganisms, killed tumor cells, protein- or peptide-activated dendritic cells. The composition of the cancer vaccine depends upon multiple factors, including, but not limited to, the particular tumor antigen that is targeted, the disease and disease stage, and whether the vaccine is administered in combination with another mode of cancer therapy. Adjuvants known in the art that modify or boost the immune response can be added to the cancer vaccine composition.

Antibody cancer vaccines have been developed, including anti-idiotype vaccines which comprise antibodies that recognize the antigenic determinants of tumor antigen-specific antibodies, called idiotypes. Thus, these anti-idiotype antibodies mimic distinct tumor antigens and act as surrogate antigens for triggering humoral and/or cellular immune response in the subject against the tumor cells. The anti-idiotype antibodies can also be fragments thereof that recognize idiotopes, e.g., single chain antibodies, scFv fragments, and sdAbs. Anti-idiotype cancer vaccines have had some success in clinical trials for treating melanoma, lung cancer, colorectal carcinoma, breast cancer, and ovarian carcinomas (Ladjemi et al., Front Oncol., 2012).

Other therapies that can be used in the context of the present invention include passive immunotherapy through delivery of antibodies that target a tumor antigen to a subject. The most common form of passive immunotherapy is monoclonal antibody therapy, in which monoclonal antibodies target the tumor cell resulting in tumor cell death through antibody-dependent cell-mediated cytotoxicity (ADCC) or complement-dependent cytotoxicity.

Various anti-PRMT5 antibodies include, but are not limited to, those known in the art.

A novel PRMT5 inhibitor which is an antibody can be prepared; alternatively, many PRMT5 antibodies are known in the art.

For example, Meister et al. demonstrated an inhibitory anti-PRMT5 antibody which reduced methylation by a complex of PRMT5, pICln, and other proteins. Meister et al. 2001 Curr. Biol. 11: 1990-1994.

Additional anti-PRMT5 antibodies are known, and have been published in:

Ancelin et al. 2006. Nat. Cell. Biol. 8: 623-630;
Liu et al. 2011 Cancer Cell 19: 283-294 (which shows a PRMT5 antibody generated using the PRMT5 fragment CPPNA(pY/Y)ELFAKG(pY/Y)ED(pY/Y)LQSPL, SEQ ID NO: 39, wherein Y is tyrosine, and pY is phosphorylated tyrosine);
Sif et al. 1998 Genes Dev. 12: 2842-2851;
Sif et al. 2001 Genes Dev. 15: 603-618;
Pal et al. 2003 Mol. Cell. Biol. 23: 7475 (using a polyclonal anti-PRMT5 antibody, to GST-PRMT5, aa 4-637);
Pal et al. 2004 Mol. Cell. Biol. 24: 9630-9645;
Pal et al. 2007 EMBO J. 26: 3558-3569;
Wang et al. 2008 Mol. Cell. Biol. 28: 6262;
Boisvert et al. 2002 J. Cell Biol. 159: 957-969 (using the PRMT5 fragment KNRPGPQTRSDLLLSGRDWN, SEQ ID NO: 40, as an antigenic epitope);
Boisvert et al. 2005 Genes Dev. 19: 671-676;
Guderian et al. 2011 J. Biol. Chem. 286: 1976-1986;
Ostareck-Lederer et al. 2006 J. Biol. Chem. 281: 11115-11125

Anti-PRMT5 antibodies are also available commercially. These are available from, for example:

Abcam (3766, as used in Lacroix et al. 2008 EMBO J. 9: 452-458);
BD Biosciences (611538, as used in Dacwag et al. 2007 Mol. Cell. Biol. 27: 384)
Cell Signaling Technology, Boston, Mass. (polyclonal antibody, as used in Maloney et al. 2007 Cancer Res. 67: 3239-3253);
Chemicon, Temecula (as used in Eckert et al. 2008 BMC Dev. Biol. 8);
Santa Cruz Biotechnology, Santa Cruz, Calif. (as used in Lu et al. 2012 Oncogen. 1, e29);
Sigma-Aldrich (as used in Teng et al. 2007 Cancer Res. 67: 10491-10500);
Transduction Laboratories (as used in Fabbrizio et al. 2002 EMBO J. 3: 641-645; and Amente et al. 2005 FEBS Lett. 579: 683-689); and
Upstate Biotechnology (polyclonal antibody, as used in Zhou et al. 2010 Cell Res. 20: 1023-1033; and Gonsalvez et al. 2006 Curr. Biol. 16: 1077-1089; and Cesaro et al. 2009 J. Biol. Chem. 284: 32321-32330; 07405, as used in Lacroix et al. 2008 EMBO J. 9: 452-458; and 12-303, Le Guezennec et al. 2006 Mol. Cell. Biol. 26: 843).

All references to PRMT5 antibodies cited immediately above are hereby incorporated by reference in their entirety.

Any inhibitory anti-PRMT5 antibody or fragment thereof can be used with any method disclosed herein.

All the documents listed herein describing a PRMT5 inhibitor, including, but not limited to, an antibody, a RNAi agent, a low molecular weight compound, or any other PRMT5 inhibitor, are hereby incorporated in their entirety by reference.

Any anti-PRMT5 antibody described herein or known in the art can be used in the methods described herein. For example, any of the anti-PRMT5 antibodies described herein can be used in a method of inhibiting proliferation of TMPRSS2:ERG positive prostate cancer cells in a subject in need thereof, the method comprising the step of administering to the subject, a PRMT5 inhibitor in an amount that is effective to inhibit proliferation of the TMPRSS2:ERG positive prostate cancer cells.

PRMT5 RNAi Agents and Therapies

In some embodiments, the present invention provides a RNAi agent to PRMT5, and methods of using a RNAi agent to PRMT5 to treat TMPRSS2:ERG positive prostate cancer. RNAi agents to PRMT5 include those compositions capable of mediating RNA interference, including, inter alia, shRNAs and siRNAs. In some embodiments, the RNAi agent comprises an antisense strand and a sense strand.

In some embodiments, the RNAi agent to PRMT5 includes any shRNA used in the experiments described herein, namely PRMT5 sh1, sh2, and sh3 (shRNA1, shRNA2 and shRNA3), whose PRMT5 target sequences are presented below:

PRMT5 sh1:
[SEQ ID NO: 98]
accgAGGGACTGGAATACGCTAATTCTCGAGAATTAGCGTATTCCAGTCC
CTTT

[SEQ ID NO: 99]
CGAAAAAAGGGACTGGAATACGCTAATTCTCGAGAATTAGCGTATTCCAG
TCCCT

PRMT5 sh2:
[SEQ ID NO: 100]
accgAGGGACTGGAATACGTTAATTGTTAATATTCATAGCAATTAGCGTA
TTCCAGTCCCTttt

[SEQ ID NO: 101]
CGAAAAAGGGACTGGAATACGCTAATTGCTATGAATATTAACAATTAAC
GTATTCCAGTCCCT

PRMT5 sh3:
[SEQ ID NO: 102]
accgGCGGATAAAGTTGTATGTTGTGTTAATATTCATAGCACAGCATACA
GCTTTATCCGCttt

[SEQ ID NO: 103]
CGAAAAAGCGGATAAAGCTGTATGCTGTGCTATGAATATTAACACAACAT
ACAACTTTATCCGC

An embodiment of the invention provides a composition comprising an RNAi agent comprising a first (sense) or second (antisense) strand, wherein the sense and/or antisense strand comprises at least 15 contiguous nucleotides differing by 0, 1, 2, or 3 nucleotides from the sequence of an RNAi agent to PRMT5 selected from any sequence provided herein (e.g., in SEQ ID NOs: 1-35 or 1-18, 41-49, 52-79, 84-97, or 98-103, or the complementary sequence thereof, or RNAi agent comprising a sequence comprising 15 contiguous nt of the PRMT5 target sequence of any of these sequences capable of mediating RNA interference against PRMT5). In another embodiment, the present invention provides a composition comprising an RNAi agent comprising a sense strand and an antisense strand, wherein the antisense strand comprises at least 15 contiguous nucleotides differing by 0, 1, 2, or 3 nucleotides from the antisense strand of an RNAi agent to PRMT5 from any sequence provided herein.

In another embodiment, the present invention provides a composition comprising an RNAi agent comprising a sense strand and an antisense strand, wherein the sense strand comprises at least 15 contiguous nucleotides differing by 0, 1, 2, or 3 nucleotides from the sense strand and the antisense strand comprises at least 15 contiguous nucleotides differing by 0, 1, 2, or 3 nucleotides from the antisense strand of an RNAi agent to PRMT5 listed immediately above.

In one embodiment, the present invention provides particular compositions comprising an RNAi agent comprising an antisense strand, wherein the antisense strand comprises at least 15 contiguous nucleotides from the antisense strand of an RNAi agent to PRMT5 selected from any one or more of the provided herein (e.g., in SEQ ID NOs: 1-35 or 1-18, 41-49, 52-79, 84-97, or 98-103, or the complementary sequence thereof,). In another embodiment, the present invention provides a composition comprising an RNAi agent comprising a sense strand and an antisense strand, wherein the sequence of the antisense strand is the sequence of the strand of an RNAi agent to PRMT5 sequence provided herein (e.g., in SEQ ID NOs: 1-35 or 1-18, 41-49, 52-79, 84-97, or 98-103, or the complementary sequence thereof). In another embodiment, the present invention provides a composition comprising an RNAi agent comprising a sense strand and an antisense strand, wherein the sequence of the antisense strand comprises the sequence of the antisense strand of an RNAi agent to PRMT5 selected from any one or more of the sequences presented herein.

Additional RNAi agents to PRMT5 are known in the art. Specific RNAi agents include:

The shRNAs to PRMT5 disclosed in U.S. Patent Application No. 62/049,004, which are reproduced below:

TABLE 1

PRMT5 shRNAs

| shRNA NAME | ALTERNATIVE shRNA NAME | TARGET SEQUENCE | SEQ ID NO: |
|---|---|---|---|
| GROUP 1 | | | |
| PRMT5-1832 | sh1700 | CCCATCCTCTTCCCTATTAAG | 1 |
| PRMT5-963 | sh4734 | GTCCTCCACCTAATGCCTATG | 2 |
| PRMT5-598 | | GAATGCACCAACTACACACAC | 3 |
| PRMT5-235 | | GCGTTTCAAGAGGGAGTTCAT | 4 |
| PRMT5-2178 | | GGCTCAAGCCACCAATCTATG | 5 |
| PRMT5-1290 | | CGCTAGAGAACTGGCAGTTTG | 6 |

TABLE 1-continued

PRMT5 shRNAs

| shRNA NAME | ALTERNATIVE shRNA NAME | TARGET SEQUENCE | SEQ ID NO: |
|---|---|---|---|
| PRMT5-1952 | | GTCTGTTCTGCTATTCATAAC | 7 |
| PRMT5-1656 | sh4738 | GCCATCCCAACAGAGATCCTA | 8 |
| PRMT5-645 | | CGTGGATGTGGTGGCACAACT | 9 |
| PRMT5-1139 | | CCAGAAGAGGAGAAGGATACC | 10 |
| PRMT5-1243 | sh4736 | GCGGATAAAGCTGTATGCTGT | 11 |
| PRMT5-722 | sh4732 | GACCTCCCATCTAATCATGTC | 12 |
| PRMT5-1142 | | GAAGAGGAGAAGGATACCAAT | 13 |
| PRMT5-569 | | CCAGAGGACCTGAGAGATGAT | 14 |
| PRMT5-1323 | sh4737 | GCCAAGTGACCGTAGTCTCAT | 15 |
| PRMT5-317 | sh1699 | AGGGACTGGAATACGCTAATT | 16 |
| PRMT5-940 | | CCTGGAATACTTAAGCCAGAA | 17 |
| PRMT5-1801 | | GACTCACTCTCCTGGGATGTT | 18 |
| GROUP 2 | | | |
| PRMT5-893 | | GGCACCAACCACCACTCAGAG | 19 |
| PRMT5-1604 | | CGGCTGCACAACTTCCACCAG | 20 |
| PRMT5-1570 | | CCCTGAGGCCCAGTTTGAGAT | 21 |
| PRMT5-2246 | | CGCACTCAGCCTCAAGAACTC | 22 |
| PRMT5-522 | sh4728 | CTGGCCATCACTCTTCCATGT | 23 |
| PRMT5-1106 | sh4735 | CAGGCCATCTATAAATGTCTG | 24 |
| PRMT5-161 | sh4729 | CCCGAAATAGCTGACACACTA | 25 |
| PRMT5-1855 | | GCCCATAACGGTACGTGAAGG | 26 |
| PRMT5-234 | sh4731 | CGCGTTTCAAGAGGGAGTTCA | 27 |
| PRMT5-1240 | | CCGGCGGATAAAGCTGTATGC | 28 |
| PRMT5-2114 | | GGAGCATTTCAATCTGCTTTC | 29 |
| PRMT5-2255 | sh1166 | CCTCAAGAACTCCCTGGAATA | 30 |
| PRMT5-720 | sh4730 | CTGACCTCCCATCTAATCATG | 31 |
| PRMT5-1668 | | GAGATCCTATGATTGACAACA | 32 |
| PRMT5-1577 | sh1167 | GCCCAGTTTGAGATGCCTTAT | 33 |
| PRMT5-922 | sh4733 | CTGCTCCTACCTCCAATACCT | 34 |
| PRMT5-520 | sh4727 | CACTGGCCATCACTCTTCCAT | 35 |

Of these, sh1699, sh4736, and sh4737 were most effective. sh4732, sh4738, and sh4733 were also effective.

Additional RNAi agents to PRMT5 can be prepared, or are known in the art.

Various PRMT5 RNAi agents disclosed in the art include:
Bandyopadhyay et al. 2012 Mol. Cell. Biol. 32: 1202-1213 (which shows a PRMT5 siRNA which targets the PRMT5 sequence AAGAGGGAGUUCAUUCAGGAA, SEQ ID NO: 41);
Bao et al. 2013 J. Hist. Cyt. 61: 206 (which discloses PRMT5 RNAi agents which target the PRMT5 sequences GGGACUGGAAUACGCUAAUTT, SEQ ID NO: 42, and AUUAGCGUAUUCCAGUCCCUU, SEQ ID NO: 43; and GGACCUGAGAGAUGAUAUAUU, SEQ ID NO: 44, and UAUAUCAUCUCUCAGGUCCUU, SEQ ID NO: 45);

Bezzi et al. 2013 Genes Dev. 27: 1903-1916 (which shows a PRMT5 RNAi agent which targets the PRMT5 sequence CCTCAAGAACTCCCTGGAATA, SEQ ID NO: 46);

Cesaro et al. 2009 J. Biol. Chem. 284: 32321-32330 [which describes PRMT5 siRNAs which target the PRMT5 sequences GGACAAUCUGGAAUCUCAGACAUAU, SEQ ID NO: 47 (nt 1039-1064); GGCUCCAGA-GAAAGCAGACAUCAUU, SEQ ID NO: 48 (nt 1363-1388); and GCGGCCAUGUUACAGGAGCUGAAUU, SEQ ID NO: 49 (nt 404-429)];

Chung et al. 2013 J. Biol. Chem. 288: 35534-35547 (wherein PRMT5 snRNA plasmids were constructed using sense GATCCCGCCCAGTTTGAGATGCCTTAT-GTGTGCTGTCCATAAGGCATCTCA AACTGGGCTTTTTGGAAA, SEQ ID NO: 50, and antisense AGCTTTTCCAAAAAGCCCAGTTTGAGATGC-CTTATGGACAGCACACATAA GGCATCT-CAAACTGGGCGG, SEQ ID NO: 51, primers; or sense AAAAACACTTCATATGTCTGAGACCTGTCTC, SEQ ID NO: 52, and antisense AATCTCAGACAT-AT-GAAGTGTTTCCTGTCTC, SEQ ID NO: 53, primers);

Gonsalvez et al. 2007 J. Biol. Chem. 178: 733-740 (which describes a PRMT5 RNAi agent which targets PRMT5 sequence GGCCAUCUAUAAAUGUCUG, SEQ ID NO: 54);

Girardot et al. 2014 Nucl. Acids Res. 42: 235-248 (which shows PRMT5 shRNAs which target PRMT5 sequences GAGGGAGTTCATTCAGGAA, SEQ ID NO: 55, and GGATGTGGTGGCATAACTT, SEQ ID NO: 56);

Gkountela et al. 2014 Stem Cell Rev. Rep. 10: 230-239;

Gu et al. 2012 Biochem. J. 446: 235-241 (which used a PRMT5 shRNA targeting PRMT5 sequence GGA-TAAAGCTGTATGCTGT, SEQ ID NO: 57);

Gu et al. 2012 PLoS ONE 7: e44033 (which shows a PRMT5 shRNA which targets PRMT5 sequence GGA-TAAAGCTGTATGCTGT, SEQ ID NO: 58);

Han et al. 2013 Stem Cells 31: 953-965 (which shows a PRMT5 shRNA which targets PRMT5 sequences CTCT-TGTGAATGCGTCTCTT, SEQ ID NO: 59, and AGCTCTGAGTTCTCTTCCTA, SEQ ID NO: 60);

Harris et al. J. Biol. Chem. 289: 15328-15339 (which discloses a PRMT5 siRNA which targets the sequence GAGGGAGUUCAUUCAGGAAUU, SEQ ID NO: 61);

He et al. 2011 Nucl. Acids Res. 39: 4719-4727 (which shows two shRNAs to PRMT5 which target PRMT5 sequence nt 1016-1034, GGCCATCTATAAATGTCTG, SEQ ID NO: 62, or CAGACATTTATAGATGGCC, SEQ ID NO: 63);

Huang et al. 2011 J. Biol. Chem. 286: 44424-44432 (which describes the use of a pool of PRMT5 RNAi agents which target PRMT5 sequences GAGCACAGCACUUC-CUGAAAGAUGA, SEQ ID NO: 64, AGACGUGGUU-GUGGUGGCAUAACUU, SEQ ID NO: 65, and CCAUCCCAACCGAGAUCCUAUGAUU, SEQ ID NO: 66);

Jansson et al. 2008 Nat. Cell. Biol. 10: 1431-1439 (which discloses a PRMT5 siRNA which targets PRMT5 sequence CCGCUAUUGCACCUUGAA, SEQ ID NO: 67);

Kanade et al. 2012 J. Biol. Chem. 287: 7313-7323 (which discloses several PRMT5 RNAi agents, including those that target PRMT5 sequences CAGCCACUGAUGGA-CAAUCUGGAAU, SEQ ID NO: 68, and CCGGCUAC-UUUGAGACUGUGCUUUA, SEQ ID NO: 69);

La Thangue, WO 2011/077133 and U.S. Patent Application Pub. No. 20130011497 (application Ser. No. 13/518,200), which disclose PRMT5 RNAi agents which target the PRMT5 sequences 5' CCGCUAUUGCACCUUGGAA (SEQ ID NO: 1479), and CAACAGAGAUC-CUAUGAUU (SEQ ID NO:1480);

Liu et al. 2011 Cancer Cell 19: 283-294;

Nicholas et al. 2013 PLoS ONE (which discloses a PRMT5 RNAi agent which targets PRMT5 sequence CCGC-UAUUGCACCUUGGAA, SEQ ID NO: 70);

Paul et al. 2012 Cell Death and Diff. 19: 900-908 (which shows PRMT5 shRNAs with sequences ATTGCGTC-CCCGAAATAGCT, SEQ ID NO: 71, and GCGGATG-GAAGACAGGCAT, SEQ ID NO: 72);

Richard et al. 2005 Biochem. J. 388: 379-386 (which used a PRMT5 siRNA which targeted the sequence of accession no. XM 033433, nt 1598-1620);

Scoumanne et al. 2009 Nucl. Acids Res. 1-12 (which discloses PRMT5 shRNAs which target PRMT5 sequences ACCGCTATTGCACCTTGGA, SEQ ID NO: 73; TCCAAGGTGCAATAGCGGT, SEQ ID NO: 74; ACCGCTATTGCACCTTGGA, SEQ ID NO: 75; and TCCAAGGTGCAATAGCGGT, SEQ ID NO: 76);

Tabata et al. 2009 Genes to Cells 14: 17-28 (which shows a PRMT5 siRNA which targets PRMT5 sequence CCGC-TATTGCACCTTGGAA, SEQ ID NO: 77);

Tanaka et al. 2009 Mol. Cancer Res. 7: 557 (which shows PRMT5 siRNAs to PRMT5 sequences of nt 973-961, CAGCCACTGATGGACAATCTGGAAT, SEQ ID NO: 78, and nt 1655-1679, CCGGCTACTTTGAGACTGT-GCTTTA, SEQ ID NO: 79);

Tee et al. 2010 Genes Dev. 24: 2772-2777 (which discloses PRMT5 shRNA sequences of GATCCCCGGTTT-GATTTCCTCTGCATTTCAAGAGAATGCAGAG-GAAATCA AACCTTTTTA, SEQ ID NO: 80, and GATCCCCGGACTGGAATACGCTAATTTTCAAGA-GAAATTAGCGTATTCCA GTCCTTTTTA, SEQ ID NO: 81, and GATCCCCGGTCTTCCAGCTTTCCT-ATTTCAAGAGAATAGGAAAGCTGGAA GAC-CTTTTTA, SEQ ID NO: 82, and GATCCCCGCCAC-CACTCTTCCATGTTTTCAAGAGAAACATGGAAG AGTGG TGGCTTTTTA, SEQ ID NO: 83, wherein the PRMT5 target sequences are GGTTTGATTTCCTCTG-CAT, SEQ ID NO: 84; ATGCAGAGGAAATCAAACC, SEQ ID NO: 85; GGACTGGAATACGCTAAT, SEQ ID NO: 86; AATTAGCGTATTCCAGTCC, SEQ ID NO: 87; GGTCTTCCAGCTTTCCTAT, SEQ ID NO: 88; ATAG-GAAAGCTGGAAGACC, SEQ ID NO: 89; GCCAC-CACTCTTCCATGTT, SEQ ID NO: 90; and AACATG-GAAGAGTGGTGGC, SEQ ID NO: 91);

Wei et al. 2012 Cancer Sci 103: 1640-1650 (which presents an anti-PRMT5 shRNA which targets the PRMT5 sequence ATAAGGCATCT-CAAACTGGGC, SEQ ID NO: 92);

Yan et al. 2014 Cancer Res. 74: 1752 (which discloses PRMT5 siRNAs which target the PRMT5 sequences CCGCUAUUGCACCUUGGAAUU, SEQ ID NO: 93, ACACUUCAUAUGUCUGAGA, SEQ ID NO: 94, and UCUCAGACAUAUGAAGUGU, SEQ ID NO: 95); and Zhao et al. 2009 Nature Struct. Mol. Biol. 16: 304 (which used PRMT5 shRNAs targeting sequences GGACCT-GAGAGATGATATA, SEQ ID NO: 96, and GAGGATT-GCAGTGGCTCTT, SEQ ID NO: 97); and

WO 2011/077133.

All references to PRMT5 RNAi agents cited immediately above are hereby incorporated by reference in their entirety.

It is noted that in the present disclosure a RNAi agent to PRMT5 may be recited to target a particular PRMT5 sequence, indicating that the recited sequence may be comprised in the sequence of the sense or anti-sense strand of the RNAi agent; or, in some cases, a sequence of at least 15 contiguous nt of this sequence may be comprised in the sequence of the sense or anti-sense strand. It is also understood that some of the target sequences are presented as DNA, but the RNAi agents targeting these sequences can be RNA, or any nucleotide, modified nucleotide or nucleotide substitute disclosed herein, provided that the molecule can still mediate RNA interference.

All the documents listed herein describing a PRMT5 inhibitor, including, but not limited to, a RNAi agent, a low molecular weight compound, an antibody, or any other PRMT5 inhibitor, are hereby incorporated in their entirety by reference.

The invention contemplates any PRMT5 inhibitor described herein for used in any method described herein.

Any anti-PRMT5 RNAi agent described herein or known in the art can be used in the methods described herein. For example, any of the anti-PRMT5 RNAi agents described herein (or a RNAi agent comprising 15 contiguous nt of a PRMT5 target sequence disclosed herein capable of mediating RNA interference against PRMT5) can be used in a method of inhibiting proliferation of TMPRSS2:ERG positive prostate cancer cells in a subject in need thereof, the method comprising the step of administering to the subject, a PRMT5 inhibitor in an amount that is effective to inhibit proliferation of the TMPRSS2:ERG positive prostate cancer cells.

In some embodiments, the antisense and sense strand can be two physically separated strands, or can be components of a single strand or molecule, e.g., they are linked a loop of nucleotides or other linker. A non-limiting example of the former is a siRNA; a non-limiting example of the latter is a shRNA. The can also, optionally, exist single-stranded nicks in the sense strand, or one or more mismatches between the antisense and sense strands.

The disclosure also provides combination of paired antisense and sense strands from any two sequences provided herein (e.g., in SEQ ID NOs: 1-35 or 1-18, 41-49, 52-79, 84-97, or 98-103, or the complementary sequence thereof). Additional modified sequences (e.g., sequences comprising one or more modified base) of each of the compositions above are also contemplated as part of the disclosure.

In one embodiment, the antisense strand is about 30 or fewer nucleotides in length.

In one embodiment, the antisense strand forms a duplex region with a sense strand, wherein the duplex region is about 15 to 30 nucleotide pairs in length.

In one embodiment, the antisense strand is about 15 to about 30 nucleotides in length, including about 19 to about 23 nucleotides in length. In one embodiment, the antisense strand has at least the length selected from about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides and 30 nucleotides.

In one embodiment, the RNAi agent comprises a modification that causes the RNAi agent to have increased stability in a biological sample or environment.

In one embodiment, the RNAi agent comprises at least one sugar backbone modification (e.g., phosphorothioate linkage) or at least one 2'-modified nucleotide.

In one embodiment, the RNAi agent comprises: at least one 5'-uridine-adenine-3' (5'-ua-3') dinucleotide, wherein the uridine is a 2'-modified nucleotide; at least one 5'-uridine-5 guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide. These dinucleotide motifs are particularly prone to serum nuclease degradation (e.g. RNase A). Chemical modification at the 2'-position of the first pyrimidine nucleotide in the motif prevents or slows down such cleavage. This modification recipe is also known under the term 'endo light'.

In one embodiment, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, all pyrimidines (uridine and cytidine) are 2'-O-methyl-modified nucleosides. In some embodiments, one or more nucleotides can be modified, or substituted with DNA, or a nucleotide substitute such as a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), unlocked nucleic acid (UNA).

In some embodiments, the sense and/or antisense strand can terminate at the 3' end with a phosphate or modified internucleoside linker, and further comprise, in 5' to 3' order: a spacer, a second phosphate or modified internucleoside linker, and a 3' end cap. In some embodiments, modified internucleoside linker is selected from phosphorothioate, phosphorodithioate, phosphoramidate, boranophosphonoate, an amide linker, and a compound of formula (I):

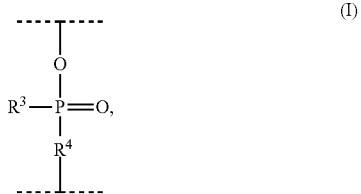

where $R^3$ is selected from O—, S—, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, and $CH_2$. In some embodiments, the spacer can be a sugar, alkyl, cycloakyl, ribitol or other type of abasic nucleotide, 2'-deoxy-ribitol, diribitol, 2'-methoxy-ethoxy-ribitol (ribitol with 2'-MOE), $C_{3-6}$ alkyl, or 4-methoxybutane-1,3-diol (5300). In some embodiments, the 3' end cap can be selected from any of various 3' end caps described herein or known in the art. In some embodiments, one or more phosphates can be replaced by a modified internucleoside linker.

In one embodiment, the RNAi agent comprises at least one blunt end.

In one embodiment, the RNAi agent comprises an overhang having 1 nt to 4 nt.

In one embodiment, the RNAi agent comprises an overhang at the 3'-end of the antisense strand of the RNAi agent.

In one embodiment, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one embodiment, the composition further comprises a second RNAi agent to PRMT5.

RNAi agents of the present invention can be delivered or introduced (e.g., to a cell in vitro or to a subject) by any means known in the art.

"Introducing into a cell," when referring to an iRNA, means facilitating or effecting uptake or absorption into the cell, as is understood by those skilled in the art. Absorption or uptake of an iRNA can occur through unaided diffusive or active cellular processes, or by auxiliary agents or devices. The meaning of this term is not limited to cells in vitro; an iRNA may also be "introduced into a cell," wherein the cell is part of a living organism. In such an instance, introduction into the cell will include the delivery to the organism. For example, for in vivo delivery, iRNA can be injected into a tissue site or administered systemically. In vivo delivery can also be by a beta-glucan delivery system, such as those described in U.S. Pat. Nos. 5,032,401 and 5,607,677, and U.S. Publication No. 2005/0281781 which are hereby incorporated by reference in their entirety. In vitro introduction into a cell includes methods known in the art including, but not limited to, electroporation and lipofection. Further approaches are described below or known in the art.

Delivery of RNAi agent to tissue is a problem both because the material must reach the target organ and must also enter the cytoplasm of target cells. RNA cannot penetrate cellular membranes, so systemic delivery of naked RNAi agent is unlikely to be successful. RNA is quickly degraded by RNAse activity in serum. For these reasons, other mechanisms to deliver RNAi agent to target cells has been devised. Methods known in the art include but are not limited to: viral delivery (retrovirus, adenovirus, lentivirus, baculovirus, AAV); liposomes (Lipofectamine, cationic DOTAP, neutral DOPC) or nanoparticles (cationic polymer, PEI), bacterial delivery (tkRNAi), and also chemical modification (LNA) of siRNA to improve stability. Xia et al. 2002 Nat. Biotechnol. 20 and Devroe et al. 2002. BMC Biotechnol. 21: 15, disclose incorporation of siRNA into a viral vector. Other systems for delivery of RNAi agents are contemplated, and the RNAi agents of the present invention can be delivered by various methods yet to be found and/or approved by the FDA or other regulatory authorities.

Liposomes have been used previously for drug delivery (e.g., delivery of a chemotherapeutic). Liposomes (e.g., cationic liposomes) are described in PCT publications W002/100435A1, W003/015757A1, and W004029213A2; U.S. Pat. Nos. 5,962,016; 5,030,453; and 6,680,068; and U.S. Patent Application 2004/0208921. A process of making liposomes is also described in W004/002453A1. Furthermore, neutral lipids have been incorporated into cationic liposomes (e.g., Farhood et al. 1995). Cationic liposomes have been used to deliver RNAi agent to various cell types (Sioud and Sorensen 2003; U.S. Patent Application 2004/0204377; Duxbury et al., 2004; Donze and Picard, 2002). Use of neutral liposomes disclosed in Miller et al. 1998, and U.S. Publ. 2003/0012812.

As used herein, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817. These applications are incorporated herein by reference in their entirety.

Chemical transfection using lipid-based, amine-based and polymer-based techniques, is disclosed in products from Ambion Inc., Austin, Tex.; and Novagen, EMD Biosciences, Inc, an Affiliate of Merck KGaA, Darmstadt, Germany); Ovcharenko D (2003) "Efficient delivery of siRNAs to human primary cells." Ambion TechNotes 10 (5): 15-16). Additionally, Song et al. (Nat Med. published online (Fete 10, 2003) doi: 10.1038/nm828) and others [Caplen et al. 2001 Proc. Natl. Acad. Sci. (USA), 98: 9742-9747; and McCaffrey et al. Nature 414: 34-39] disclose that liver cells can be efficiently transfected by injection of the siRNA into a mammal's circulatory system.

A variety of molecules have been used for cell-specific RNAi agent delivery. For example, the nucleic acid-condensing property of protamine has been combined with specific antibodies to deliver siRNAs. Song et al. 2005 Nat Biotch. 23: 709-717. The self-assembly PEGylated polycation polyethylenimine has also been used to condense and protect siRNAs. Schiffelers et al. 2004 Nucl. Acids Res. 32: 49, 141-110.

The siRNA-containing nanoparticles were then successfully delivered to integrin overexpressing tumor neovasculature. Hu-Lieskovan et al. 2005 Cancer Res. 65: 8984-8992.

The RNAi agents of the present invention can be delivered via, for example, Lipid nanoparticles (LNP); neutral liposomes (NL); polymer nanoparticles; double-stranded RNA binding motifs (dsRBMs); or via modification of the RNAi agent (e.g., covalent attachment to the dsRNA).

Lipid nanoparticles (LNP) are self-assembling cationic lipid based systems. These can comprise, for example, a neutral lipid (the liposome base); a cationic lipid (for siRNA loading); cholesterol (for stabilizing the liposomes); and PEG-lipid (for stabilizing the formulation, charge shielding and extended circulation in the bloodstream). The cationic lipid can comprise, for example, a headgroup, a linker, a tail and a cholesterol tail. The LNP can have, for example, good tumor delivery, extended circulation in the blood, small particles (e.g., less than 100 nm), and stability in the tumor microenvironment (which has low pH and is hypoxic).

Neutral liposomes (NL) are non-cationic lipid based particles.

Polymer nanoparticles are self-assembling polymer-based particles.

Double-stranded RNA binding motifs (dsRBMs) are self-assembling RNA binding proteins, which will need modifications.

Several other molecules may be suitable to inhibit PRMT5, including, but not limited to, low molecular weight compounds, RNAi agents, CRISPRs, TALENs, ZFNs, and antibodies.

Additional PRMT5 Inhibitors

In one embodiment, the disclosure comprises a low molecular weight compound inhibiting PRMT5 gene expression that inhibits PRMT5 expression.

In another embodiment, the present invention provides a molecule that inhibits the cellular function of the PRMT5 protein, such as a part of a methylation pathway.

The PRMT5 inhibitor of the present disclosure can also be, inter alia, derived from a CRISPR/Cas system, TALEN, or ZFN.

CRISPR to Inhibit PRMT5

By "CRISPR" or "CRISPR to PRMT5" or "CRISPR to inhibit PRMT5" and the like is meant a set of clustered regularly interspaced short palindromic repeats, or a system comprising such a set of repeats. By "Cas", as used herein, is meant a CRISPR-associated protein. By "CRISPR/Cas" system is meant a system derived from CRISPR and Cas which can be used to silence, enhance or mutate the PRMT5 gene.

Naturally-occurring CRISPR/Cas systems are found in approximately 40% of sequenced eubacteria genomes and 90% of sequenced archaea. Grissa et al. 2007. BMC Bioinformatics 8: 172. This system is a type of prokaryotic immune system that confers resistance to foreign genetic elements such as plasmids and phages and provides a form of acquired immunity. Barrangou et al. 2007. Science 315: 1709-1712; Marragini et al. 2008 Science 322: 1843-1845.

The CRISPR/Cas system has been modified for use in gene editing (silencing, enhancing or changing specific genes) in eukaryotes such as mice or primates. Wiedenheft et al. 2012. Nature 482: 331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the PRMT5 CRISPR/Cas system, the spacers are derived from the PRMT5 gene sequence. The repeats generally show some dyad symmetry, implying the formation of a secondary structure such as a hairpin, but they are not truly palindromic.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. 2010. Science 327: 167-170; Makarova et al. 2006 Biology Direct 1: 7. The spacers thus serve as templates for RNA molecules, analogously to siRNAs. Pennisi 2013. Science 341: 833-836.

As these naturally occur in many different types of bacteria, the exact arrangements of the CRISPR and structure, function and number of Cas genes and their product differ somewhat from species to species. Haft et al. 2005 PLoS Comput. Biol. 1: e60; Kunin et al. 2007. Genome Biol. 8: R61; Mojica et al. 2005. J. Mol. Evol. 60: 174-182; Bolotin et al. 2005. Microbiol. 151: 2551-2561; Pourcel et al. 2005. Microbiol. 151: 653-663; and Stern et al. 2010. Trends. Genet. 28: 335-340. For example, the Cse (Cas subtype, E. coli) proteins (e.g., CasA) form a functional complex, Cascade, that processes CRISPR RNA transcripts into spacer-repeat units that Cascade retains. Brouns et al. 2008. Science 321: 960-964. In other prokaryotes, Cas6 processes the CRISPR transcript. The CRISPR-based phage inactivation in E. coli requires Cascade and Cas3, but not Cas1 or Cas2. The Cmr (Cas RAMP module) proteins in Pyrococcus furiosus and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi 2013. Science 341: 833-836.

The CRISPR/Cas system can thus be used to edit the PRMT5 gene (adding or deleting a basepair), e.g., repairing a damaged PRMT5 gene (e.g., if the damage to PRMT5 results in high post-translational modification, production, expression, level, stability or activity of PRMT5), or introducing a premature stop which thus decreases expression of an over-expressed PRMT5. The CRISPR/Cas system can alternatively be used like RNA interference, turning off the PRMT5 gene in a reversible fashion. In a mammalian cell, for example, the RNA can guide the Cas protein to the PRMT5 promoter, sterically blocking RNA polymerases.

Artificial CRISPR systems can be generated which inhibit PRMT5, using technology known in the art, e.g., that described in U.S. patent application Ser. No. 13/842,859 (published as US 20140068797). Such PRMT5-inhibitory CRISPR system can include a guide RNA (gRNA) comprising a PRMT5-targeting domain, i.e., a nucleotide sequence that is complementary to a PRMT5 DNA strand, and a second domain that interacts with an RNA-directed nuclease, e.g., cpf1 or Cas molecule, e.g., Cas9 molecule. TABLE 2 lists exemplary sequences of a PRMT5-targeting domain or "PRMT5-targeting sequence."

In some embodiments, the ability of an RNA-directed nuclease, e.g., cpf1 or Cas molecule, e.g., Cas9 molecule, to interact with and cleave a target nucleic acid is Protospacer Adjacent Motif (PAM) sequence dependent. A PAM sequence is a sequence in the target nucleic acid. In some embodiments, cleavage of the target nucleic acid occurs upstream from the PAM sequence. RNA-directed nuclease molecules, e.g., cpf1 or Cas molecules, e.g., Cas9 molecules, from different bacterial species can recognize different sequence motifs (e.g., PAM sequences). In addition to recognizing different PAM sequences, RNA-directed nucleases, e.g., cpf1 or Cas molecules, e.g., Cas9 molecules, from different species may be directed to different target sequences (e.g., target sequences adjacent, e.g., immediately upstream, to the PAM sequence) by gRNA molecules comprising targeting domains capable of hybridizing to said target sequences and a tracer sequence that binds to said RNA-directed nuclease, e.g., cpf1 or Cas molecule, e.g., Cas9 molecule.

In some embodiments, the CRISPR system comprises a gRNA molecule and a Cas9 molecule from S. pyogenes. A Cas9 molecule of S. pyogenes recognizes the sequence motif NGG and directs cleavage of a target nucleic acid sequence 1 to 10, e.g., 3 to 5, base pairs upstream from that sequence. A gRNA molecule useful with S. pyogenes-based CRISPR systems may include a PRMT5-targeting sequence described in TABLE 2, e.g., any of SEQ ID NOs: 979-1449, and a tracr sequence known to interact with S. pyogenes. See, e.g., Mali el ai, SCIENCE 2013; 339(6121): 823-826.

In some embodiments, the CRISPR system comprises a gRNA molecule and a Cas9 molecule from S. thermophilus. A Cas9 molecule of S. thermophilus recognizes the sequence motif NGGNG and NNAGAAW (W=A or T) and directs cleavage of a core target nucleic acid sequence 1 to 10, e.g., 3 to 5, base pairs upstream from these sequences. A gRNA molecule useful with S. thermophilus-based CRISPR systems may include a PRMT5-targeting sequence described in TABLE 2, e.g., any of SEQ ID NOs: 1450-1477, and a tracr sequence known to interact with S. thermophilus. See, e.g., Horvath et al., SCIENCE 2010; 327(5962): 167-170, and Deveau et al., J BACTERIOL 2008; 190(4): 1390-1400.

In some embodiments, the CRISPR system comprises a gRNA molecule and a Cas9 molecule from *S. aureus*. A Cas9 molecule of *S. aureus* recognizes the sequence motif NNGRR (R=A or G) and directs cleavage of a target nucleic acid sequence 1 to 10, e.g., 3 to 5, base pairs upstream from that sequence. A gRNA molecule useful with *S. aureus*-based CRISPR systems may include a PRMT5-targeting sequence described in TABLE 2, e.g., any of SEQ ID NOs: 451-978, and a tracr sequence known to interact with *S. aureus*. See, e.g., Ran F. et al., NATURE, vol. 520, 2015, pp. 186-191.

In some embodiments, the CRISPR system comprises a gRNA molecule and a RNA-directed nuclease, e.g., cpf1 molecule, e.g., a cpf1 molecule from *L. bacterium* or a cpf1 molecule from A. sp. A cpf1 molecule, e.g., a cpf1 molecule from *L. bacterium* or a cpf1 molecule from A. sp., recognizes the sequence motive of TTN (where N=A, T, G or C) or preferably TTTN (where N=A, T, G or C), and directs cleavage of a target nucleic acid sequence 1-25 base pairs upstream of the PAM sequence, e.g., 18-19 base pairs upstream from the PAM sequence on the same strand as the PAM and 23 base pairs upstream of the PAM sequence on the opposite strand as the PAM, creating a sticky end break. A gRNA molecule useful with cpf1-based CRISPR systems (e.g., those utilizing cpf1 molecules from *L. bacterium* or A. sp.) may include a PRMT5-targeting sequence described in TABLE 2, e.g., any of SEQ ID NOs: 105-450, and a tracr sequence which interacts with cpf1. See, e.g., Zetsche B. et al., CELL, vol. 163:3, October 2015, 759-771.

TABLE 2

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22920547 | 22920550 | 10419_17_12 | 10419 | + | AUUUGUAUUCCUCUUACACAAA | 105 | cpf1 | TTT |
| chr14 | 22920548 | 22920551 | 10419_17_13 | 10419 | + | UUUGUAUUCCUCUUACACAAAA | 106 | cpf1 | TTA |
| chr14 | 22920551 | 22920554 | 10419_17_14 | 10419 | + | GUAUUCCUCUUACACAAAACCA | 107 | cpf1 | TTT |
| chr14 | 22920552 | 22920555 | 10419_17_15 | 10419 | + | UAUUCCUCUUACACAAAACCAU | 108 | cpf1 | TTG |
| chr14 | 22920557 | 22920560 | 10419_17_16 | 10419 | + | CCUCUACACAAAACCAUCAAAA | 109 | cpf1 | TTT |
| chr14 | 22920558 | 22920561 | 10419_17_17 | 10419 | + | CUCUUACACAAAACCAUCAAAAC | 110 | cpf1 | TTC |
| chr14 | 22920564 | 22920567 | 10419_17_19 | 10419 | + | CACAAAACCAUCAAAACAAGAAC | 111 | cpf1 | TTA |
| chr14 | 22920610 | 22920613 | 10419_17_28 | 10419 | + | AAACCCCAUGUUCUCAGGGAUAU | 112 | cpf1 | TTC |
| chr14 | 22920623 | 22920626 | 10419_17_34 | 10419 | + | UCAGGGAUAUUCCAGGGAGUUCU | 113 | cpf1 | TTC |
| chr14 | 22920635 | 22920638 | 10419_17_38 | 10419 | + | CAGGGAGUUCUUGAGGCUGAGUG | 114 | cpf1 | TTC |
| chr14 | 22920645 | 22920648 | 10419_17_39 | 10419 | + | UUGAGGCUGAGUGCGUAGCUUCA | 115 | cpf1 | TTG |
| chr14 | 22920648 | 22920651 | 10419_17_40 | 10419 | + | AGGCUGAGUGCGUAGCUUCAAAU | 116 | cpf1 | TTC |
| chr14 | 22920667 | 22920670 | 10419_17_41 | 10419 | + | AAAUCCAGCACUAAUUCCUCACC | 117 | cpf1 | TTC |
| chr14 | 22920684 | 22920687 | 10419_17_45 | 10419 | + | CUCACCCCCUGGCCUGAGGUCUU | 118 | cpf1 | TTC |
| chr14 | 22920708 | 22920711 | 10419_17_49 | 10419 | + | AUAGAUUGGUGGCUUGAGCCCUG | 119 | cpf1 | TTG |
| chr14 | 22920716 | 22920719 | 10419_17_50 | 10419 | + | GUGGCUUGAGCCCUGCAAUUAAU | 120 | cpf1 | TTG |
| chr14 | 22920724 | 22920727 | 10419_17_51 | 10419 | + | AGCCCUGCAAUUAAUUAUAAUCC | 121 | cpf1 | TTA |
| chr14 | 22920737 | 22920740 | 10419_17_52 | 10419 | + | AUUAUAAUCCCUUGCCCACCUUG | 122 | cpf1 | TTA |
| chr14 | 22920741 | 22920744 | 10419_17_53 | 10419 | + | UAAUCCCUUGCCCACCUUGAUGU | 123 | cpf1 | TTG |
| chr14 | 22920751 | 22920754 | 10419_17_56 | 10419 | + | CCCACCUUGAUGUAAGGCAGGAA | 124 | cpf1 | TTG |
| chr14 | 22920760 | 22920763 | 10419_17_59 | 10419 | + | AUGUAAGGCAGGAGCAGAUUG | 125 | cpf1 | TTG |
| chr14 | 22920783 | 22920786 | 10419_17_64 | 10419 | + | AAAUGCUCCUCUGAUGGGCAA | 126 | cpf1 | TTG |
| chr14 | 22920840 | 22920843 | 10419_17_76 | 10419 | + | UGUACUACAGGAGCAGAACCUGA | 127 | cpf1 | TTC |

TABLE 2-continued

| Chromosome | Start | Stop | ID | Gene_ID | PRMT5-Targeting Sequence | Strand | SEQ ID NO | System | Pam |
|---|---|---|---|---|---|---|---|---|---|
| chr14 | 22920872 | 22920875 | 10419_17_82 | 10419 | CAAGGCUCUGGACACUGGCACG | + | 128 | cpf1 | TTC |
| chr14 | 22920890 | 22920893 | 10419_17_88 | 10419 | GCACGCAGGGCUAGAGGCCAAUG | + | 129 | cpf1 | TTG |
| chr14 | 22920937 | 22920940 | 10419_17_99 | 10419 | UGAAUAGCAGAACAGACUGGUGC | + | 130 | cpf1 | TTA |
| chr14 | 22920988 | 22920991 | 10419_17_105 | 10419 | UUGGAAUUGCUGCAUCGCCAGAA | + | 131 | cpf1 | TTC |
| chr14 | 22920991 | 22920994 | 10419_17_107 | 10419 | GAAUUGCUGCAUCGCCAGAAACG | + | 132 | cpf1 | TTG |
| chr14 | 22920997 | 22921000 | 10419_17_108 | 10419 | CUGCAUCCGCCAGAAACGCACACA | + | 133 | cpf1 | TTG |
| chr14 | 22921028 | 22921031 | 10419_17_111 | 10419 | GGCCUUCACGUACCGUUAUGGGC | + | 134 | cpf1 | TTT |
| chr14 | 22921029 | 22921032 | 10419_17_113 | 10419 | GCCUUCACGUACCGUUAUGGGCU | + | 135 | cpf1 | TTG |
| chr14 | 22921035 | 22921038 | 10419_17_116 | 10419 | ACGUACCGUUAUGGGCUGCUGUA | + | 136 | cpf1 | TTC |
| chr14 | 22921046 | 22921049 | 10419_17_120 | 10419 | UGGGCUGCUGUAAGAAGAAAGAC | + | 137 | cpf1 | TTA |
| chr14 | 22920510 | 22920533 | 10419_17_123 | 10419 | CUGCACGACCAUGCUGCCCCUG | - | 138 | cpf1 | TAA |
| chr14 | 22920511 | 22920534 | 10419_17_124 | 10419 | ACUGCACGACCAUGCUGCCCCCU | - | 139 | cpf1 | AAA |
| chr14 | 22920520 | 22920543 | 10419_17_125 | 10419 | UAGCCCUUACUGCACGACCAUG | - | 140 | cpf1 | TAA |
| chr14 | 22920546 | 22920569 | 10419_17_126 | 10419 | UGUAAGAGGAAAUACAAAUAAAG | - | 141 | cpf1 | CAA |
| chr14 | 22920547 | 22920570 | 10419_17_127 | 10419 | GUGUAAGAGGAAAUACAAAUAAA | - | 142 | cpf1 | AAA |
| chr14 | 22920548 | 22920571 | 10419_17_128 | 10419 | UGUGUAAGAGGAAAUACAAAUAA | - | 143 | cpf1 | AAA |
| chr14 | 22920555 | 22920578 | 10419_17_129 | 10419 | AUGGUUUUGUGUAAGAGGAAAUA | - | 144 | cpf1 | CAA |
| chr14 | 22920556 | 22920579 | 10419_17_130 | 10419 | GAUGGUUUUGUGUAAGAGGAAAU | - | 145 | cpf1 | AAA |
| chr14 | 22920557 | 22920580 | 10419_17_131 | 10419 | UGAUGGUUUUGUGUAAGAGGAAA | - | 146 | cpf1 | AAA |
| chr14 | 22920560 | 22920583 | 10419_17_135 | 10419 | UUUUGAUGGUUUUGUGUAAGAGG | - | 147 | cpf1 | CAA |
| chr14 | 22920563 | 22920586 | 10419_17_137 | 10419 | UUGUUUUGAUGGUUUUGUGUAAG | - | 148 | cpf1 | AAA |
| chr14 | 22920568 | 22920591 | 10419_17_138 | 10419 | UGUUCUUGUUUUGAUGGUUUUGU | - | 149 | cpf1 | GAA |
| chr14 | 22920569 | 22920592 | 10419_17_139 | 10419 | CUGUUCUUGUUUUGAUGGUUUUG | - | 150 | cpf1 | GAA |
| chr14 | 22920570 | 22920593 | 10419_17_140 | 10419 | UCUGUUCUUGUUUUGAUGGUUUU | - | 151 | cpf1 | AAA |

TABLE 2-continued

PRMT5-targeting sequences

| Chromo-some | Start | Stop | ID | Gene_ID | PRMT5-Targeting Sequence | SEQ ID NO | System | Strand | Pam |
|---|---|---|---|---|---|---|---|---|---|
| chr14 | 22920571 | 22920594 | 10419_17_141 | 10419 | UUCUGUUCUUGUUUUGAUGGUUU | 152 | cpf1 | - | AAA |
| chr14 | 22920578 | 22920601 | 10419_17_143 | 10419 | AGCCUUUUCUGUUCUUGUUUG | 153 | cpf1 | - | GAA |
| chr14 | 22920579 | 22920602 | 10419_17_144 | 10419 | CAGCCUUUUCUGUUCUUGUUUU | 154 | cpf1 | - | AAA |
| chr14 | 22920580 | 22920603 | 10419_17_145 | 10419 | UCAGCCUUUUCUGUUCUUGUUU | 155 | cpf1 | - | AAA |
| chr14 | 22920589 | 22920612 | 10419_17_146 | 10419 | AACGGAUUUCAGCCUUUUCUG | 156 | cpf1 | - | CAA |
| chr14 | 22920590 | 22920613 | 10419_17_147 | 10419 | GAACGGAUUUCAGCCUUUUCU | 157 | cpf1 | - | AAA |
| chr14 | 22920646 | 22920669 | 10419_17_164 | 10419 | AAGCUACCACUCAGCCUCAAGA | 158 | cpf1 | - | CAA |
| chr14 | 22920647 | 22920670 | 10419_17_165 | 10419 | GAAGCUACGCACUCAGCCUCAAG | 159 | cpf1 | - | AAA |
| chr14 | 22920658 | 22920681 | 10419_17_166 | 10419 | GUGCUGGAUUUGAAGCUACGCAC | 160 | cpf1 | - | TAA |
| chr14 | 22920711 | 22920734 | 10419_17_183 | 10419 | CAGGGCUCAAGCCACCAAUCUAU | 161 | cpf1 | - | CAA |
| chr14 | 22920715 | 22920738 | 10419_17_184 | 10419 | AUUGCAGGGCUCAAGCCACCAAU | 162 | cpf1 | - | TAA |
| chr14 | 22920721 | 22920744 | 10419_17_185 | 10419 | UAAUUAAUUGCAGGGCUCAAGCC | 163 | cpf1 | - | TAA |
| chr14 | 22920743 | 22920766 | 10419_17_189 | 10419 | CAUCAAGGUGGGCAAGGGAUAU | 164 | cpf1 | - | TAA |
| chr14 | 22920751 | 22920774 | 10419_17_194 | 10419 | CUGCCUUACAUCAAGGUGGGCAA | 165 | cpf1 | - | GAA |
| chr14 | 22920752 | 22920775 | 10419_17_195 | 10419 | CCUGCCUUACAUCAAGGUGGGCA | 166 | cpf1 | - | AAA |
| chr14 | 22920762 | 22920785 | 10419_17_200 | 10419 | AAUCUGCUUUCCUGCCUUACAUC | 167 | cpf1 | - | GAA |
| chr14 | 22920763 | 22920786 | 10419_17_201 | 10419 | CAAUCUGCUUUCCUGCCUUACAU | 168 | cpf1 | - | AAA |
| chr14 | 22920783 | 22920806 | 10419_17_202 | 10419 | CCCAUCAGAGAGAGCAUUUCAA | 169 | cpf1 | - | CAA |
| chr14 | 22920789 | 22920812 | 10419_17_203 | 10419 | CCCUUGCCCAUCAGAGAGGAGCA | 170 | cpf1 | - | GAA |
| chr14 | 22920835 | 22920858 | 10419_17_212 | 10419 | UGCUCCUGUAGUACAGAAGGUGC | 171 | cpf1 | - | GAA |
| chr14 | 22920841 | 22920864 | 10419_17_216 | 10419 | AGGUUCUGCUCCUGUAGUACAGA | 172 | cpf1 | - | GAA |
| chr14 | 22920852 | 22920875 | 10419_17_217 | 10419 | GAAGCAGCUUCAGGUUCUGCUCC | 173 | cpf1 | - | CAA |
| chr14 | 22920888 | 22920911 | 10419_17_223 | 10419 | GCCUCUAGCCCUGCGUGCCAAGU | 174 | cpf1 | - | CAA |
| chr14 | 22920918 | 22920941 | 10419_17_225 | 10419 | AUAACCCCACAGGCCGCUCAUAU | 175 | cpf1 | - | GAA |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22920926 | 22920949 | 10419_17_226 | 10419 | - | UGCUAUUCAUAACCCCACAGGCC | 176 | cpf1 | GAA |
| chr14 | 22920971 | 22920994 | 10419_17_230 | 10419 | - | CAAGAAGGUGUGGUAUGAGUGGG | 177 | cpf1 | GAA |
| chr14 | 22920988 | 22921011 | 10419_17_236 | 10419 | - | UGGCGAUGCAGCAAUUCCAAGAA | 178 | cpf1 | GAA |
| chr14 | 22920989 | 22921012 | 10419_17_238 | 10419 | - | CUGGCGAUGCAGCAAUUCCAAGA | 179 | cpf1 | AAA |
| chr14 | 22921036 | 22921059 | 10419_17_242 | 10419 | - | CAGCAGCCCAUAACGGUACGUGA | 180 | cpf1 | TAA |
| chr14 | 22921039 | 22921062 | 10419_17_243 | 10419 | - | UUACAGCAGCCCAUAACCGUACG | 181 | cpf1 | GAA |
| chr14 | 22921042 | 22921065 | 10419_17_244 | 10419 | - | UUCUUACAGCAGCCCAUAACGGU | 182 | cpf1 | GAA |
| chr14 | 22921043 | 22921066 | 10419_17_245 | 10419 | - | CUUCUUACAGCAGCCCAUAACGG | 183 | cpf1 | AAA |
| chr14 | 22922158 | 22922161 | 10419_16_1 | 10419 | + | AAAGCAGUUCCUACCUUAAAUAGG | 184 | cpf1 | TTA |
| chr14 | 22922168 | 22922171 | 10419_16_9 | 10419 | + | CUACCUUAAAUAGGGAAGAGGAU | 185 | cpf1 | TTC |
| chr14 | 22922176 | 22922179 | 10419_16_16 | 10419 | + | AUAGGGAAGAGGAUGGGAAACCA | 186 | cpf1 | TTA |
| chr14 | 22922161 | 22922184 | 10419_16_30 | 10419 | - | CCUAUUAAGGUAGGAACUGCUUU | 187 | cpf1 | GAA |
| chr14 | 22922172 | 22922195 | 10419_16_34 | 10419 | - | CCAUCCUCUUCCCUAUUAAGGUA | 188 | cpf1 | GAA |
| chr14 | 22922173 | 22922196 | 10419_16_35 | 10419 | - | CCCAUCCUCUUCCCUAUUAAGGU | 189 | cpf1 | AAA |
| chr14 | 22922182 | 22922205 | 10419_16_37 | 10419 | - | UCAUGGUUUCCCAUCCUCUUCCC | 190 | cpf1 | GAA |
| chr14 | 22922226 | 22922249 | 10419_16_44 | 10419 | - | UCCACACAGGUAUCCGUCCAGAG | 191 | cpf1 | CAA |
| chr14 | 22922227 | 22922250 | 10419_16_45 | 10419 | - | GUCCACACAGGUAUCCGUCCAGA | 192 | cpf1 | AAA |
| chr14 | 22922228 | 22922251 | 10419_16_46 | 10419 | - | UGUCCACACAGGUAUCCGUCCAG | 193 | cpf1 | AAA |
| chr14 | 22922231 | 22922254 | 10419_16_47 | 10419 | - | UUUUGUCCACACAGGUAUCCGUC | 194 | cpf1 | TAA |
| chr14 | 22922504 | 22922507 | 10419_15_6 | 10419 | + | ACCUCCACAGGAAAUUCCAAGGU | 195 | cpf1 | TTC |
| chr14 | 22922521 | 22922524 | 10419_15_9 | 10419 | + | CAAGGUGCAAUAGCGGUUGUUGU | 196 | cpf1 | TTC |
| chr14 | 22922540 | 22922543 | 10419_15_12 | 10419 | + | UUGUCAAUCAUAGGAUCUGUCAG | 197 | cpf1 | TTG |
| chr14 | 22922543 | 22922546 | 10419_15_13 | 10419 | + | UCAAUCAUAGGAUCUGUCAGGAA | 198 | cpf1 | TTG |
| chr14 | 22922436 | 22922459 | 10419_15_18 | 10419 | - | UCAGGACAUCACUCUCUGAGUGAGU | 199 | cpf1 | TAA |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22922437 | 22922460 | 10419_15_19 | 10419 | - | AUCAGGACAUCACUCUGAGUGAG | 200 | cpf1 | AAA |
| chr14 | 22922449 | 22922472 | 10419_15_22 | 10419 | - | AGACUGCUUUAUCAGGACAUC | 201 | cpf1 | CAA |
| chr14 | 22922450 | 22922473 | 10419_15_23 | 10419 | - | GAGACUGCUUUAUCAGGACAU | 202 | cpf1 | AAA |
| chr14 | 22922461 | 22922484 | 10419_15_26 | 10419 | - | CCCGCUACUUUGAGACUGUGCUU | 203 | cpf1 | CAA |
| chr14 | 22922462 | 22922485 | 10419_15_27 | 10419 | - | GCCGGCUACUUUGAGACUGUGCU | 204 | cpf1 | AAA |
| chr14 | 22922494 | 22922517 | 10419_15_31 | 10419 | - | CUGUGGAGGUGAACACAGUACUA | 205 | cpf1 | GAA |
| chr14 | 22922495 | 22922518 | 10419_15_32 | 10419 | - | CCUGUGGAGGUGAACACAGUACU | 206 | cpf1 | AAA |
| chr14 | 22922501 | 22922524 | 10419_15_33 | 10419 | - | GAAUUCCUGUGGAGGUGAACAC | 207 | cpf1 | CAA |
| chr14 | 22922508 | 22922531 | 10419_15_35 | 10419 | - | CACCUUGGAAUUCCUGUGGAGG | 208 | cpf1 | CAA |
| chr14 | 22922524 | 22922547 | 10419_15_43 | 10419 | - | ACAACAACCGCUAUUGCACCUUG | 209 | cpf1 | GAA |
| chr14 | 22922543 | 22922566 | 10419_15_44 | 10419 | - | CUGACAGAUCCUAUGAUUGACAA | 210 | cpf1 | AAA |
| chr14 | 22922544 | 22922567 | 10419_15_45 | 10419 | - | CCUGACAGAUCCUAUGAUUGACA | 211 | cpf1 | TAA |
| chr14 | 22922547 | 22922570 | 10419_15_46 | 10419 | - | UUUCCUGACAGAUCCUAUGAUUG | 212 | cpf1 | TTG |
| chr14 | 22922746 | 22922749 | 10419_14_9 | 10419 | + | GGAUGGCUGAAGGUGAAACAGGG | 213 | cpf1 | TTG |
| chr14 | 22922797 | 22922800 | 10419_14_25 | 10419 | + | UGCAGCCGUACCACAUAAGGCAU | 214 | cpf1 | GAA |
| chr14 | 22922734 | 22922757 | 10419_14_30 | 10419 | - | AGCCAUCCCAACAGAGAGGUAGGUU | 215 | cpf1 | GAA |
| chr14 | 22922740 | 22922763 | 10419_14_33 | 10419 | - | ACCUUCAGCCAUCCCAACAGAGG | 216 | cpf1 | AAA |
| chr14 | 22922741 | 22922764 | 10419_14_35 | 10419 | - | CACCUUCAGCCAUCCCAACAGAG | 217 | cpf1 | GAA |
| chr14 | 22922770 | 22922793 | 10419_14_36 | 10419 | - | CACCAGCUCCUUGCACCCCAGCC | 218 | cpf1 | TAA |
| chr14 | 22922792 | 22922815 | 10419_14_37 | 10419 | - | UGUGGUACGGCUGCACACAUUCC | 219 | cpf1 | CAA |
| chr14 | 22922802 | 22922825 | 10419_14_38 | 10419 | - | AGAUGCCUUAUGUGGUACGGCUG | 220 | cpf1 | AAA |
| chr14 | 22922803 | 22922826 | 10419_14_39 | 10419 | - | GAGAUGCCUUAUGUGGUACGGCU | 221 | cpf1 | TTC |
| chr14 | 22923042 | 22923045 | 10419_13_5 | 10419 | + | UUUACCUCAGGGUCACGGUCCUU | 222 | cpf1 | TTT |
| chr14 | 22923045 | 22923048 | 10419_13_6 | 10419 | + | ACCUCAGGGUCACGGUCCUUCUC | 223 | cpf1 | |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22923046 | 22923049 | 10419_13_7 | 10419 | + | CCUCAGGGUCACGGUCCUUCUCC | 224 | cpf1 | TTA |
| chr14 | 22923066 | 22923069 | 10419_13_11 | 10419 | + | UCCCUACAGGCUCGGACCUCAUU | 225 | cpf1 | TTC |
| chr14 | 22923090 | 22923093 | 10419_13_19 | 10419 | + | UACAGCUUGGAGGAAGAUGGG | 226 | cpf1 | TTG |
| chr14 | 22923099 | 22923102 | 10419_13_27 | 10419 | + | GAGGAAGAGAUGGGAGCCAGAAA | 227 | cpf1 | TTG |
| chr14 | 22923082 | 22923105 | 10419_13_55 | 10419 | - | CUCCAAGCUGUACAAUGAGGUCC | 228 | cpf1 | GAA |
| chr14 | 22923098 | 22923121 | 10419_13_58 | 10419 | - | UGGCUCCCAUCUCUUCCUCCAAG | 229 | cpf1 | GAA |
| chr14 | 22923099 | 22923122 | 10419_13_59 | 10419 | - | CUGGCUCCCAUCUCUUCCUCCAA | 230 | cpf1 | AAA |
| chr14 | 22923103 | 22923126 | 10419_13_60 | 10419 | - | CUUUCUGGCUCCCAUCUCUUCCU | 231 | cpf1 | GAA |
| chr14 | 22923154 | 22923177 | 10419_13_71 | 10419 | + | ACUCUCCUGCUGUGCAGAUGAUG | 232 | cpf1 | CAA |
| chr14 | 22924008 | 22924011 | 10419_12_7 | 10419 | + | UAGGAAGUGCUGGGCUCCAUCCA | 233 | cpf1 | TTT |
| chr14 | 22924009 | 22924012 | 10419_12_8 | 10419 | + | AGGAAGUGCUGGGCUCCAUCCAG | 234 | cpf1 | TTT |
| chr14 | 22924010 | 22924013 | 10419_12_9 | 10419 | + | GGAAGUGCUGGGCUCCAUCCAGG | 235 | cpf1 | TTA |
| chr14 | 22924050 | 22924053 | 10419_12_13 | 10419 | + | AUUGUCAGCAAAUGAGCCCAGAA | 236 | cpf1 | TTC |
| chr14 | 22924054 | 22924057 | 10419_12_15 | 10419 | + | UCAGCAAAUGAGCCCAGAAGCUC | 237 | cpf1 | TTG |
| chr14 | 22924098 | 22924101 | 10419_12_19 | 10419 | + | CUCUGGAGCCACCCAUUCCCUCA | 238 | cpf1 | TTT |
| chr14 | 22924099 | 22924102 | 10419_12_20 | 10419 | + | UCUGGAGCCACCCAUUCCCUCAU | 239 | cpf1 | TTC |
| chr14 | 22924116 | 22924119 | 10419_12_22 | 10419 | + | CCUCAUGUCUGAUGAGACUACGG | 240 | cpf1 | TTG |
| chr14 | 22924146 | 22924149 | 10419_12_25 | 10419 | + | GCUUCCCAUUCUUCAAACUGCC | 241 | cpf1 | TTC |
| chr14 | 22924151 | 22924154 | 10419_12_26 | 10419 | + | CCCAUUCUUCAAACUGCCAGUUC | 242 | cpf1 | TTC |
| chr14 | 22924158 | 22924161 | 10419_12_27 | 10419 | + | UUCAAACUGCCAGUUCUCUAGCC | 243 | cpf1 | TTC |
| chr14 | 22924161 | 22924164 | 10419_12_28 | 10419 | + | AAACUGCCAGUUCUCUAGCCUGA | 244 | cpf1 | TTC |
| chr14 | 22924174 | 22924177 | 10419_12_31 | 10419 | + | UCUAGCCUGAAACAGAGACAAUA | 245 | cpf1 | TTC |
| chr14 | 22923991 | 22924014 | 10419_12_35 | 10419 | - | CUAAAAGGUGCCCCAGGUUGGG | 246 | cpf1 | GAA |
| chr14 | 22924024 | 22924047 | 10419_12_41 | 10419 | - | UCGCCUGAGUGCUGAUGGAGC | 247 | cpf1 | CAA |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22924038 | 22924061 | 10419_12_47 | 10419 | - | CUGACAAUGAAUUGUCGCCUGAG | 248 | cpf1 | CAA |
| chr14 | 22924039 | 22924062 | 10419_12_49 | 10419 | - | GCUGACAAUGAAUUGUCGCCUGA | 249 | cpf1 | AAA |
| chr14 | 22924050 | 22924073 | 10419_12_50 | 10419 | - | UGGGCUCAUUUGCUGACAAUGAA | 250 | cpf1 | GAA |
| chr14 | 22924062 | 22924085 | 10419_12_52 | 10419 | - | UCAGUGAGCUUCUGGGCUCAUUU | 251 | cpf1 | CAA |
| chr14 | 22924140 | 22924163 | 10419_12_69 | 10419 | - | AAGAAUGGGGAAGCCAAGUGACC | 252 | cpf1 | CAA |
| chr14 | 22924141 | 22924164 | 10419_12_70 | 10419 | - | GAAGAAUGGGGAAGCCAAGUGAC | 253 | cpf1 | AAA |
| chr14 | 22924162 | 22924185 | 10419_12_80 | 10419 | - | AGGCUAGAGAACUGGCAGUUUGA | 254 | cpf1 | GAA |
| chr14 | 22924163 | 22924186 | 10419_12_81 | 10419 | - | CAGGCUAGAGAACUGGCAGUUUG | 255 | cpf1 | AAA |
| chr14 | 22924172 | 22924195 | 10419_12_83 | 10419 | - | UCUCUGUUUCAGGCUAGAGAACU | 256 | cpf1 | CAA |
| chr14 | 22924175 | 22924198 | 10419_12_86 | 10419 | - | UUGUCUCUGUUUCAGGCUAGAGA | 257 | cpf1 | TAA |
| chr14 | 22924258 | 22924261 | 10419_11_2 | 10419 | + | CUACUCACGUCACCACCGGCAUUU | 258 | cpf1 | TTG |
| chr14 | 22924281 | 22924284 | 10419_11_6 | 10419 | + | GGGUUUUCUCCACAGCAUACAG | 259 | cpf1 | TTT |
| chr14 | 22924282 | 22924285 | 10419_11_7 | 10419 | + | GGUUUUCUCCACAGCAUACAGC | 260 | cpf1 | TTG |
| chr14 | 22924287 | 22924290 | 10419_11_8 | 10419 | + | UUCUCCACAGCAUACAGCUUUAU | 261 | cpf1 | TTT |
| chr14 | 22924288 | 22924291 | 10419_11_9 | 10419 | + | UCUCCACAGCAUACAGCUUUAUC | 262 | cpf1 | TTT |
| chr14 | 22924289 | 22924292 | 10419_11_10 | 10419 | + | CUCCACAGCAUACAGCUUUAUCC | 263 | cpf1 | TTT |
| chr14 | 22924290 | 22924293 | 10419_11_11 | 10419 | + | UCCACAGCAUACAGCUUUAUCCG | 264 | cpf1 | TTC |
| chr14 | 22924308 | 22924311 | 10419_11_14 | 10419 | + | AUCCGCCGGUCGGCCUGCUUGGC | 265 | cpf1 | TTT |
| chr14 | 22924309 | 22924312 | 10419_11_15 | 10419 | + | UCCGCCGGUCGGCCUGCUUGGCU | 266 | cpf1 | TTA |
| chr14 | 22924329 | 22924332 | 10419_11_22 | 10419 | + | GCUGCCCGCAGGGAAGCGUUCAC | 267 | cpf1 | TTG |
| chr14 | 22924350 | 22924353 | 10419_11_28 | 10419 | + | ACCAGGGGUCCCCGUCCUGCUCC | 268 | cpf1 | TTC |
| chr14 | 22924321 | 22924344 | 10419_11_48 | 10419 | - | CCUGCGGGCAGCCAAGCAGGCCG | 269 | cpf1 | GAA |
| chr14 | 22924370 | 22924393 | 10419_11_63 | 10419 | - | GGGUACUGAUGGUGCUGGGAGCA | 270 | cpf1 | TAA |
| chr14 | 22924373 | 22924396 | 10419_11_65 | 10419 | - | UUAGGGUACUGAUGGUGCUGGGA | 271 | cpf1 | GAA |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22924374 | 22924397 | 10419_11_69 | 10419 | - | CUUAGGGUACUGAUGGUGCUGG | 272 | cpf1 | AAA |
| chr14 | 22924377 | 22924400 | 10419_11_71 | 10419 | - | UUUCUUAGGGUACUGAUGGUGCU | 273 | cpf1 | GAA |
| chr14 | 22924378 | 22924401 | 10419_11_72 | 10419 | - | CUUUCUUAGGGUACUGAUGGUGC | 274 | cpf1 | AAA |
| chr14 | 22924383 | 22924406 | 10419_11_74 | 10419 | - | CCUUUCUUUCUUAGGGUACUGAU | 275 | cpf1 | GAA |
| chr14 | 22924459 | 22924462 | 10419_10_2 | 10419 | + | AGGGGAAAGCACUCACUGGACAU | 276 | cpf1 | TTG |
| chr14 | 22924484 | 22924487 | 10419_10_4 | 10419 | + | GUAUCCUUCUCUCUCUUCUGGUAC | 277 | cpf1 | TTG |
| chr14 | 22924493 | 22924496 | 10419_10_7 | 10419 | + | UCCUCUUCUGGUCUACUCCGUCUAG | 278 | cpf1 | TTC |
| chr14 | 22924501 | 22924504 | 10419_10_8 | 10419 | + | UGGUACUCGGUCUAGCAGACAUU | 279 | cpf1 | TTC |
| chr14 | 22924525 | 22924528 | 10419_10_20 | 10419 | + | AUAGAUGCCUGAGGGAGGAGA | 280 | cpf1 | TTA |
| chr14 | 22924526 | 22924529 | 10419_10_22 | 10419 | + | UAGAUGGCCUGAGGGAGGAGAG | 281 | cpf1 | TTA |
| chr14 | 22924551 | 22924554 | 10419_10_38 | 10419 | - | UCUCCCCUCCAGGCCAUCUAU | 282 | cpf1 | GAA |
| chr14 | 22924649 | 22924652 | 10419_9_9 | 10419 | + | GAUGGGGUCCUUUUCAAACACUU | 283 | cpf1 | TTT |
| chr14 | 22924650 | 22924653 | 10419_9_10 | 10419 | + | AUGGGGUCCUUUUCAAACACUUC | 284 | cpf1 | TTG |
| chr14 | 22924662 | 22924665 | 10419_9_11 | 10419 | + | UCAAACACUUCAUAUGUCUGAGA | 285 | cpf1 | TTT |
| chr14 | 22924663 | 22924666 | 10419_9_13 | 10419 | + | CAAACACUUCAUAUGUCUGAGAU | 286 | cpf1 | TTT |
| chr14 | 22924664 | 22924667 | 10419_9_14 | 10419 | + | AAACACUUCAUAUGUCUGAGAUU | 287 | cpf1 | TTC |
| chr14 | 22924673 | 22924676 | 10419_9_15 | 10419 | + | AUAUGUCUGAGAUUCCAGAUUGU | 288 | cpf1 | TTC |
| chr14 | 22924688 | 22924691 | 10419_9_17 | 10419 | + | CAGAUUGUCCAUCAGUGGCUGAU | 289 | cpf1 | TTC |
| chr14 | 22924695 | 22924698 | 10419_9_19 | 10419 | + | UCCAUCAGUGGCUGAUGAAUGAG | 290 | cpf1 | TTG |
| chr14 | 22924643 | 22924666 | 10419_9_31 | 10419 | - | AAAAGGACCCCAUCAAAUACUCU | 291 | cpf1 | CAA |
| chr14 | 22924644 | 22924667 | 10419_9_32 | 10419 | - | GAAAAGGACCCCAUCAAAUACUC | 292 | cpf1 | AAA |
| chr14 | 22924691 | 22924714 | 10419_9_40 | 10419 | - | AUCAGCCACUGAUGGACAAUCUG | 293 | cpf1 | GAA |
| chr14 | 22924698 | 22924721 | 10419_9_41 | 10419 | - | CUCAUUCAUCAGCCACUGAUGGA | 294 | cpf1 | GAA |
| chr14 | 22924699 | 22924722 | 10419_9_44 | 10419 | - | CCUCAUUCAUCAGCCACUGAUGG | 295 | cpf1 | AAA |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22924700 | 22924723 | 10419_9_45 | 10419 | - | UCCUCAUUCAUCAGCCACUGAUG | 296 | cpf1 | AAA |
| chr14 | 22924902 | 22924905 | 10419_8_10 | 10419 | + | AUAGCCCUUGGCAAAGAGUUCAU | 297 | cpf1 | TTC |
| chr14 | 22924912 | 22924915 | 10419_8_12 | 10419 | + | GCAAAGAGUUCAUAGGCAUUAGG | 298 | cpf1 | TTG |
| chr14 | 22924923 | 22924926 | 10419_8_19 | 10419 | + | AUAGGCAUUAGGUGGAGGACGGU | 299 | cpf1 | TTC |
| chr14 | 22924933 | 22924936 | 10419_8_22 | 10419 | + | GGUGGAGGACGGUUCUGGCUUAA | 300 | cpf1 | TTA |
| chr14 | 22924948 | 22924951 | 10419_8_24 | 10419 | + | UGGCUUAAGUAUUCCAGGUAUUG | 301 | cpf1 | TTC |
| chr14 | 22924955 | 22924958 | 10419_8_29 | 10419 | + | AGUAUUCCAGGUAUUGGAGGUAG | 302 | cpf1 | TTA |
| chr14 | 22924962 | 22924965 | 10419_8_33 | 10419 | + | CAGGUAUUGGAGGUAGGAGCAGA | 303 | cpf1 | TTC |
| chr14 | 22924971 | 22924974 | 10419_8_35 | 10419 | + | GAGGUAGGAGCAGAACUCCUUCU | 304 | cpf1 | TTG |
| chr14 | 22924993 | 22924996 | 10419_8_40 | 10419 | + | UCUGAGUGGUGGAUGAUGAACUGU | 305 | cpf1 | TTC |
| chr14 | 22925008 | 22925011 | 10419_8_42 | 10419 | + | GUGCCUGUGAUGAUGAACUGCAC | 306 | cpf1 | TTG |
| chr14 | 22924893 | 22924916 | 10419_8_53 | 10419 | - | CCAAGGGCUAUGAAGACUAUCUG | 307 | cpf1 | CAA |
| chr14 | 22924894 | 22924917 | 10419_8_54 | 10419 | - | GCCAAGGGCUAUGAAGACUAUCU | 308 | cpf1 | AAA |
| chr14 | 22924933 | 22924956 | 10419_8_60 | 10419 | - | AGCCAGAACCGUCCUCCACCUAA | 309 | cpf1 | TAA |
| chr14 | 22924963 | 22924986 | 10419_8_65 | 10419 | - | UGCUCCUACCUCCAAUACCUGGA | 310 | cpf1 | GAA |
| chr14 | 22925002 | 22925025 | 10419_8_73 | 10419 | - | AUCAUCACAGGCACCACCACCA | 311 | cpf1 | GAA |
| chr14 | 22925014 | 22925037 | 10419_8_75 | 10419 | - | GAGGUGCAGUUCAUCAUCACAGG | 312 | cpf1 | CAA |
| chr14 | 22925023 | 22925046 | 10419_8_76 | 10419 | - | UCACAGUUGGAGGUGCAGUUCAU | 313 | cpf1 | GAA |
| chr14 | 22925024 | 22925047 | 10419_8_77 | 10419 | - | CUCACAGUUGGAGGUGCAGUUCA | 314 | cpf1 | AAA |
| chr14 | 22925025 | 22925048 | 10419_8_78 | 10419 | - | UCUCACAGUUGGAGGUGCAGUUC | 315 | cpf1 | AAA |
| chr14 | 22926133 | 22926136 | 10419_7_9 | 10419 | + | AGGAGCCGGAAGAUGAGCCUCUG | 316 | cpf1 | TTG |
| chr14 | 22926166 | 22926169 | 10419_7_17 | 10419 | + | GAAAGAACAGGAAAUCCCUUCUU | 317 | cpf1 | TTA |
| chr14 | 22926187 | 22926190 | 10419_7_22 | 10419 | + | UUAUUGGUCAGGAAAAUGCUAGU | 318 | cpf1 | TTC |
| chr14 | 22926190 | 22926193 | 10419_7_23 | 10419 | + | UUGGUCAGGAAAAUGCUAGUGGG | 319 | cpf1 | TTA |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22926193 | 22926196 | 10419_7_27 | 10419 | + | GUCAGGAAAAUGCUAGUGGGGAG | 320 | cpf1 | TTG |
| chr14 | 22926228 | 22926231 | 10419_7_38 | 10419 | + | GAUGGGCUCCCCAAGCCAGCGAU | 321 | cpf1 | TTT |
| chr14 | 22926229 | 22926232 | 10419_7_39 | 10419 | + | AUGGGCUCCCCAAGCCAGCGAUC | 322 | cpf1 | TTG |
| chr14 | 22926265 | 22926268 | 10419_7_46 | 10419 | + | GAUGGGAGGUCAGCCCCAAUUUC | 323 | cpf1 | TTA |
| chr14 | 22926287 | 22926290 | 10419_7_50 | 10419 | + | CAAGAGCUACAUGAGGCAAAAGA | 324 | cpf1 | TTT |
| chr14 | 22926288 | 22926291 | 10419_7_51 | 10419 | + | AAGAGCUACAUGAGGCAAAAGAA | 325 | cpf1 | TTC |
| chr14 | 22926121 | 22926144 | 10419_7_60 | 10419 | - | CGGCUCCUCAAGUGAGUGGUAG | 326 | cpf1 | GAA |
| chr14 | 22926146 | 22926169 | 10419_7_65 | 10419 | - | UAAGAUGCACCAGAGGCUCAUCU | 327 | cpf1 | GAA |
| chr14 | 22926147 | 22926170 | 10419_7_66 | 10419 | - | CUAAGAUGCACCAGAGGCUCAUC | 328 | cpf1 | AAA |
| chr14 | 22926150 | 22926173 | 10419_7_67 | 10419 | - | UUUCUAAGAUGCACCAGAGGCUC | 329 | cpf1 | GAA |
| chr14 | 22926156 | 22926179 | 10419_7_70 | 10419 | - | CUGUUCUUUCUAAGAUGCACCAG | 330 | cpf1 | GAA |
| chr14 | 22926157 | 22926180 | 10419_7_71 | 10419 | - | CCUGUUCUUUCUAAGAUGCACCA | 331 | cpf1 | AAA |
| chr14 | 22926178 | 22926201 | 10419_7_72 | 10419 | - | CUGACCAAUAAAGAAGGAUUCC | 332 | cpf1 | GAA |
| chr14 | 22926179 | 22926202 | 10419_7_73 | 10419 | - | CCUGACCAAUAAGAAGGAUUUC | 333 | cpf1 | AAA |
| chr14 | 22926180 | 22926203 | 10419_7_74 | 10419 | - | UCCUGACCAAUAAGAAGGAUUU | 334 | cpf1 | AAA |
| chr14 | 22926195 | 22926218 | 10419_7_81 | 10419 | - | UCCCACUAGCAUUUUCCUGACC | 335 | cpf1 | GAA |
| chr14 | 22926219 | 22926242 | 10419_7_82 | 10419 | - | GGGAGCCCAUCAAAGCAGCAGCAU | 336 | cpf1 | CAA |
| chr14 | 22926231 | 22926254 | 10419_7_83 | 10419 | - | AUCGCUGGCUUGGGGAGCCCAUC | 337 | cpf1 | CAA |
| chr14 | 22926261 | 22926284 | 10419_7_92 | 10419 | - | GGGCUGACCUCCCAUCUAAUCAU | 338 | cpf1 | CAA |
| chr14 | 22926267 | 22926290 | 10419_7_93 | 10419 | - | AAAUUGGGGCUGACCUCCCAUCU | 339 | cpf1 | CAA |
| chr14 | 22926283 | 22926306 | 10419_7_98 | 10419 | - | CCUCAUGUAGCUCUUGAAAUUGG | 340 | cpf1 | CAA |
| chr14 | 22926284 | 22926307 | 10419_7_100 | 10419 | - | GCCUCAUGUAGCUCUUGAAAUUG | 341 | cpf1 | AAA |
| chr14 | 22926285 | 22926308 | 10419_7_101 | 10419 | - | UGCCUCAUGUAGCUCUUGAAAUU | 342 | cpf1 | AAA |
| chr14 | 22926288 | 22926311 | 10419_7_103 | 10419 | - | UUUUGCCUCAUGUAGCUCUUGAA | 343 | cpf1 | GAA |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22926289 | 22926312 | 10419_7_104 | 10419 | - | CUUUUGCCUCAUGUAGCUCUUGA | 344 | cpf1 | AAA |
| chr14 | 22926290 | 22926313 | 10419_7_105 | 10419 | - | UCUUUUGCCUCAUGUAGCUCUUG | 345 | cpf1 | AAA |
| chr14 | 22926490 | 22926493 | 10419_6_1 | 10419 | + | UCAUGGACUCACCCAUGCAAUC | 346 | cpf1 | TTC |
| chr14 | 22926519 | 22926522 | 10419_6_3 | 10419 | + | CUAUAGUCACACAAAGUCCGAA | 347 | cpf1 | TTA |
| chr14 | 22926546 | 22926549 | 10419_6_6 | 10419 | + | UGCCACCUGUUCAGUCAAAUACA | 348 | cpf1 | TTG |
| chr14 | 22926488 | 22926511 | 10419_6_8 | 10419 | - | CAGUGGGUGAGUCCAUGAGAAUC | 349 | cpf1 | CAA |
| chr14 | 22926510 | 22926533 | 10419_6_15 | 10419 | - | UGUGACUAUAGUAGUAAGAGGAUUG | 350 | cpf1 | CAA |
| chr14 | 22926511 | 22926534 | 10419_6_16 | 10419 | - | GUGUGACUAUAGUAGUGACUAUAGUAA | 351 | cpf1 | AAA |
| chr14 | 22926519 | 22926542 | 10419_6_20 | 10419 | - | CGGACUUUGUGUGACUAUAGUAA | 352 | cpf1 | GAA |
| chr14 | 22926541 | 22926564 | 10419_6_23 | 10419 | - | ACUGAACAGGUGGCACAACUUCC | 353 | cpf1 | CAA |
| chr14 | 22926542 | 22926565 | 10419_6_24 | 10419 | - | GACUGAACAGGUGGCACAACUUC | 354 | cpf1 | AAA |
| chr14 | 22926549 | 22926572 | 10419_6_25 | 10419 | - | UGUAUUUGACUGAACAGGUGGCA | 355 | cpf1 | GAA |
| chr14 | 22926711 | 22926714 | 10419_5_1 | 10419 | + | UCUCCCCCACUGUACUCCCUCU | 356 | cpf1 | TTT |
| chr14 | 22926712 | 22926715 | 10419_5_2 | 10419 | + | CUCCUCCCACUGUACUCCCUCUG | 357 | cpf1 | TTT |
| chr14 | 22926713 | 22926716 | 10419_5_3 | 10419 | + | UCCUCCCCACUGUACUCCCUCGU | 358 | cpf1 | TTC |
| chr14 | 22926747 | 22926750 | 10419_5_5 | 10419 | + | GUGCAUUCUCAAUUAUAUCAUCU | 359 | cpf1 | TTG |
| chr14 | 22926755 | 22926758 | 10419_5_6 | 10419 | + | UCAAUUAUAUCAUCUCUCCAGGUC | 360 | cpf1 | TTC |
| chr14 | 22926762 | 22926765 | 10419_5_8 | 10419 | + | UAUCAUCUCUCAGGUCCUCUGGU | 361 | cpf1 | TTA |
| chr14 | 22926736 | 22926759 | 10419_5_33 | 10419 | - | AGAAUGCACCAACUACACACACA | 362 | cpf1 | CAA |
| chr14 | 22926770 | 22926793 | 10419_5_36 | 10419 | - | GUGGCACCAGAGAGACCUGAGAGA | 363 | cpf1 | CAA |
| chr14 | 22926788 | 22926811 | 10419_5_42 | 10419 | - | UGGAUGCGGGUACCCUUGGUGGC | 364 | cpf1 | GAA |
| chr14 | 22926799 | 22926822 | 10419_5_45 | 10419 | - | AUGUGCAGUUCUGGAUGCGGGUA | 365 | cpf1 | GAA |
| chr14 | 22927556 | 22927559 | 10419_4_12 | 10419 | + | GUCAAAACUCUGGCCAGGUUGGU | 366 | cpf1 | TTG |
| chr14 | 22927577 | 22927580 | 10419_4_15 | 10419 | + | GUGUUAUCUUCCUGAUUAAGGGG | 367 | cpf1 | TTG |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22927583 | 22927586 | 10419_4_20 | 10419 | + | UCUUCCUGAUUAAGGGGCAGCAG | 368 | cpf1 | TTA |
| chr14 | 22927588 | 22927591 | 10419_4_24 | 10419 | + | CUGAUUAAGGGGCAGCAGGAAAG | 369 | cpf1 | TTC |
| chr14 | 22927595 | 22927598 | 10419_4_26 | 10419 | + | AGGGGCAGCAGGAAAGCUGGAAG | 370 | cpf1 | TTA |
| chr14 | 22927640 | 22927643 | 10419_4_30 | 10419 | + | AGCUCCUGUAACAUGGCCUGGAA | 371 | cpf1 | TTC |
| chr14 | 22927506 | 22927529 | 10419_4_40 | 10419 | - | CAUGGUAAGCUGAGGGGCUCCU | 372 | cpf1 | GAA |
| chr14 | 22927538 | 22927561 | 10419_4_48 | 10419 | - | ACCAACCACAUCCACACUGGCCA | 373 | cpf1 | CAA |
| chr14 | 22927539 | 22927562 | 10419_4_49 | 10419 | - | GACCAACCACCACAUCCACACUGGCC | 374 | cpf1 | AAA |
| chr14 | 22927540 | 22927563 | 10419_4_50 | 10419 | - | UGACCAACCACCACAUCCACACUGGC | 375 | cpf1 | AAA |
| chr14 | 22927573 | 22927596 | 10419_4_54 | 10419 | - | AUCAGGAAGAGAUAACACCAACCUG | 376 | cpf1 | TAA |
| chr14 | 22927586 | 22927609 | 10419_4_55 | 10419 | - | CUGCUGCCCCUUAAUCAGGAAGA | 377 | cpf1 | GAA |
| chr14 | 22927587 | 22927610 | 10419_4_56 | 10419 | - | CCUGCUGCCCCUUAAUCAGGAAG | 378 | cpf1 | AAA |
| chr14 | 22927594 | 22927617 | 10419_4_60 | 10419 | - | CAGCUUUCCUGCUGCCCCUUAAU | 379 | cpf1 | GAA |
| chr14 | 22927601 | 22927624 | 10419_4_61 | 10419 | - | GGUCUUCCAGCUUUCCUGCUGCC | 380 | cpf1 | CAA |
| chr14 | 22927602 | 22927625 | 10419_4_62 | 10419 | - | GGGUCUUCCAGCUUUCCUGCUGC | 381 | cpf1 | AAA |
| chr14 | 22927612 | 22927635 | 10419_4_63 | 10419 | - | GUGCAUAUUUGGGGUCUUCCAGCU | 382 | cpf1 | CAA |
| chr14 | 22927613 | 22927636 | 10419_4_64 | 10419 | - | GGUGCAUAUUUGGGGUCUUCCAGC | 383 | cpf1 | AAA |
| chr14 | 22927614 | 22927637 | 10419_4_65 | 10419 | - | UGGUGCAUAUUUGGGGUCUUCCAG | 384 | cpf1 | AAA |
| chr14 | 22927628 | 22927651 | 10419_4_69 | 10419 | - | CAGGAGCUGAAUUUGGUGCAUA | 385 | cpf1 | TAA |
| chr14 | 22927640 | 22927663 | 10419_4_71 | 10419 | - | CAGGCCAUGUUACAGGAGCUGAA | 386 | cpf1 | GAA |
| chr14 | 22927650 | 22927673 | 10419_4_76 | 10419 | + | AUCUCCGUUCCAGGCCAUGUUAC | 387 | cpf1 | GAA |
| chr14 | 22928121 | 22928124 | 10419_3_5 | 10419 | + | CCGCCUCGGAGUUCCUGCGAAUC | 388 | cpf1 | TTA |
| chr14 | 22928135 | 22928138 | 10419_3_6 | 10419 | + | CUGCGAAUCUUCCACACUUUGA | 389 | cpf1 | TTC |
| chr14 | 22928147 | 22928150 | 10419_3_11 | 10419 | + | UCCACUUUUGAGUCUGGACGAAU | 390 | cpf1 | TTC |
| chr14 | 22928155 | 22928158 | 10419_3_13 | 10419 | + | UGAGUCUGGACGAAUCCAUGGAG | 391 | cpf1 | TTT |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22928156 | 22928159 | 10419_3_14 | 10419 | + | GAGUCUGGACGAAUCCAUGGAGA | 392 | cpf1 | TTT |
| chr14 | 22928157 | 22928160 | 10419_3_18 | 10419 | + | AGUCUGGACGAAUCCAUGGAGAA | 393 | cpf1 | TTG |
| chr14 | 22928186 | 22928189 | 10419_3_20 | 10419 | + | CCCACAAUUAGCGUAUUCCAGUC | 394 | cpf1 | TTT |
| chr14 | 22928187 | 22928190 | 10419_3_21 | 10419 | + | CCACAAUUAGCGUAUUCCAGUCU | 395 | cpf1 | TTC |
| chr14 | 22928196 | 22928199 | 10419_3_22 | 10419 | + | GCGUAUUCCAGUCUGCCACUCCC | 396 | cpf1 | TTA |
| chr14 | 22928204 | 22928207 | 10419_3_23 | 10419 | + | CAGUCUGCCACUCCCCCACCCAAG | 397 | cpf1 | TTC |
| chr14 | 22928119 | 22928142 | 10419_3_24 | 10419 | - | GCAGGAACUCCGAGGCGGUAAGA | 398 | cpf1 | GAA |
| chr14 | 22928146 | 22928169 | 10419_3_31 | 10419 | - | GUCCAGACUCAAAAGUGGAGAAG | 399 | cpf1 | GAA |
| chr14 | 22928157 | 22928180 | 10419_3_37 | 10419 | - | UCCAUGGAUUCGUCCAGACUCA | 400 | cpf1 | GAA |
| chr14 | 22928158 | 22928181 | 10419_3_38 | 10419 | - | CUCCAUGGAUUCGUCCAGACUCA | 401 | cpf1 | AAA |
| chr14 | 22928170 | 22928193 | 10419_3_39 | 10419 | - | UGGGAAAGCUUUCUCCAUGGAU | 402 | cpf1 | CAA |
| chr14 | 22928203 | 22928226 | 10419_3_47 | 10419 | - | GGUGGGGGAGUGCAGACUGGAAU | 403 | cpf1 | CAA |
| chr14 | 22928499 | 22928502 | 10419_2_2 | 10419 | + | CUGACAGCAGUAGGUCUGAUCGU | 404 | cpf1 | TTC |
| chr14 | 22928543 | 22928546 | 10419_2_15 | 10419 | + | UUAGCAGGUUCCUGAAUGAACUC | 405 | cpf1 | TTC |
| chr14 | 22928546 | 22928549 | 10419_2_16 | 10419 | + | GCAGGUUCCUGAAUGAACUCCCU | 406 | cpf1 | TTA |
| chr14 | 22928554 | 22928557 | 10419_2_18 | 10419 | + | CUGAAUGAACUCCCCUCUUGAAAC | 407 | cpf1 | TTC |
| chr14 | 22928573 | 22928576 | 10419_2_25 | 10419 | + | AAACGCGGAUGGAAGACAGGCAU | 408 | cpf1 | TTG |
| chr14 | 22928536 | 22928559 | 10419_2_43 | 10419 | - | AGGAACCUGCUAAGAAUCGGCCC | 409 | cpf1 | GAA |
| chr14 | 22928540 | 22928563 | 10419_2_45 | 10419 | - | AUUCAGGAACCUGCUAAGAAUCG | 410 | cpf1 | GAA |
| chr14 | 22928552 | 22928575 | 10419_2_47 | 10419 | - | AAGAGGGAGUUCAUUCAGGAACC | 411 | cpf1 | GAA |
| chr14 | 22928553 | 22928576 | 10419_2_48 | 10419 | - | CAAGAGGGAGUUCAUUCAGGAAC | 412 | cpf1 | AAA |
| chr14 | 22928564 | 22928587 | 10419_2_52 | 10419 | - | CAUCCGCGUUUCAAGAGGGAGUU | 413 | cpf1 | GAA |
| chr14 | 22928582 | 22928605 | 10419_2_59 | 10419 | - | CUCUGCAUGCCUGUCUUCCAUCC | 414 | cpf1 | GAA |
| chr14 | 22928583 | 22928606 | 10419_2_60 | 10419 | - | CCUCUGCAUGCCUGUCUUCCAUC | 415 | cpf1 | AAA |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22928587 | 22928610 | 10419_2_61 | 10419 | - | AUUCCUCUGCAUGCCUGUCUUC | 416 | cpf1 | CAA |
| chr14 | 22928588 | 22928611 | 10419_2_62 | 10419 | - | GAUUUCCUCUGCAUGCCUGUCUU | 417 | cpf1 | AAA |
| chr14 | 22928595 | 22928618 | 10419_2_63 | 10419 | - | UAGGUUUGAUUUCCUCUGCAUGC | 418 | cpf1 | CAA |
| chr14 | 22929172 | 22929175 | 10419_1_5 | 10419 | + | UCCGGGAUGACUAGUCUGCCCUU | 419 | cpf1 | TTC |
| chr14 | 22929196 | 22929199 | 10419_1_9 | 10419 | + | UCCGUCCCGAGUUCGGACCCCG | 420 | cpf1 | TTC |
| chr14 | 22929211 | 22929214 | 10419_1_10 | 10419 | + | GGACCCCGCAUUCCGCUCGUGGA | 421 | cpf1 | TTC |
| chr14 | 22929224 | 22929227 | 10419_1_16 | 10419 | + | CGCUCGUGGAGGUCCGGCCCUCA | 422 | cpf1 | TTC |
| chr14 | 22929257 | 22929260 | 10419_1_18 | 10419 | + | GCCACAGCCCCUAGUGUGUCAGC | 423 | cpf1 | TTG |
| chr14 | 22929285 | 22929288 | 10419_1_26 | 10419 | + | CGGGGACGCAAUUCAGGUCCCUC | 424 | cpf1 | TTT |
| chr14 | 22929286 | 22929289 | 10419_1_27 | 10419 | + | GGGGACGCAAUUCAGGUCCCUCC | 425 | cpf1 | TTC |
| chr14 | 22929299 | 22929302 | 10419_1_30 | 10419 | + | AGUCCUCCCGCUGUCCGACGCG | 426 | cpf1 | TTT |
| chr14 | 22929362 | 22929365 | 10419_1_32 | 10419 | + | CUCCUGCGCUGUCCACGCCGGG | 427 | cpf1 | TTC |
| chr14 | 22929363 | 22929366 | 10419_1_33 | 10419 | + | UCCUGCGCUGUCCACGCCGGGA | 428 | cpf1 | TTC |
| chr14 | 22929389 | 22929392 | 10419_1_38 | 10419 | + | CUUGAUACUAGUAGCCAAUCACA | 429 | cpf1 | TTC |
| chr14 | 22929393 | 22929396 | 10419_1_39 | 10419 | + | AUACUAGUAGCCAAUCACAAAGU | 430 | cpf1 | TTG |
| chr14 | 22929453 | 22929456 | 10419_1_48 | 10419 | + | ACAACCAGAGCGUCUGCCACAGC | 431 | cpf1 | TTA |
| chr14 | 22929506 | 22929509 | 10419_1_68 | 10419 | + | UCCUGCCAAUCCGCGGGCUGCAC | 432 | cpf1 | TTT |
| chr14 | 22929507 | 22929510 | 10419_1_69 | 10419 | + | CCUGCCAAUCCGCGGGCUGCACA | 433 | cpf1 | TTT |
| chr14 | 22929508 | 22929511 | 10419_1_70 | 10419 | + | CUGCCAAUCCGCGGGCUGCACAG | 434 | cpf1 | TTC |
| chr14 | 22929571 | 22929574 | 10419_1_80 | 10419 | - | CUGACGAACUUCAAUCUCCCAGA | 435 | cpf1 | TTC |
| chr14 | 22929273 | 22929296 | 10419_1_145 | 10419 | - | CGUCCCCGAAAUAGCUGACACAC | 436 | cpf1 | CAA |
| chr14 | 22929384 | 22929407 | 10419_1_182 | 10419 | - | GCUACUAGUAUCAAGGAAUCCCG | 437 | cpf1 | CAA |
| chr14 | 22929390 | 22929413 | 10419_1_185 | 10419 | - | UGAUUGGCUACUAGUAUCAAGGA | 438 | cpf1 | CAA |
| chr14 | 22929391 | 22929414 | 10419_1_186 | 10419 | - | GUGAUUGGCUACUAGUAUCAAGG | 439 | cpf1 | AAA |

TABLE 2-continued

| Chromo-some | Start | Stop | ID | Gene_ID | PRMT5-Targeting Sequence | SEQ ID NO | System | Pam |
|---|---|---|---|---|---|---|---|---|
| chr14 | 22929396 | 22929419 | 10419_1_188 | 10419 | ACUUUGUGAUUGGCUACUAGUAU | 440 | cpf1 | CAA |
| chr14 | 22929397 | 22929420 | 10419_1_189 | 10419 | GACUUUGUGAUUGGCUACUAGUA | 441 | cpf1 | AAA |
| chr14 | 22929411 | 22929434 | 10419_1_191 | 10419 | UGGGGCACUAGUUUGACUUUGUG | 442 | cpf1 | GAA |
| chr14 | 22929431 | 22929454 | 10419_1_196 | 10419 | AGGCGACUCGUCCCGCCUUCUGG | 443 | cpf1 | TAA |
| chr14 | 22929434 | 22929457 | 10419_1_198 | 10419 | UUAAGGCGACUCGUCCCGCCUUC | 444 | cpf1 | CAA |
| chr14 | 22929460 | 22929483 | 10419_1_201 | 10419 | GGGAGCUGUGGCAGACGCUCUGG | 445 | cpf1 | GAA |
| chr14 | 22929492 | 22929515 | 10419_1_208 | 10419 | GCAGGAAAAGCCACUCCCCAUCC | 446 | cpf1 | CAA |
| chr14 | 22929532 | 22929555 | 10419_1_215 | 10419 | GUGGAUCCAUGCCGUACCGCCACU | 447 | cpf1 | CAA |
| chr14 | 22929556 | 22929579 | 10419_1_219 | 10419 | GUCAGGAACCAGACCCGAGAAUU | 448 | cpf1 | GAA |
| chr14 | 22929562 | 22929585 | 10419_1_221 | 10419 | AAGUUCGUCAGGAACCAGACCCU | 449 | cpf1 | CAA |
| chr14 | 22929572 | 22929595 | 10419_1_223 | 10419 | UGGGAGAUUGAGAGUUCGUCAGGA | 450 | cpf1 | GAA |
| chr14 | 22920490 | 22920510 | 10419_17_1 | 10419 | GAGGUGUGGGAAAAUAGUGG | 451 | S. aureus | CAGGG |
| chr14 | 22920491 | 22920511 | 10419_17_2 | 10419 | AGGUGUGGGAAAAUAGUGGC | 452 | S. aureus | AGGGG |
| chr14 | 22920492 | 22920512 | 10419_17_5 | 10419 | GGUGUGGGAAAAUAGUGGCA | 453 | S. aureus | GGGGG |
| chr14 | 22920515 | 22920535 | 10419_17_9 | 10419 | GCCAGCAUGGGUCGUGCAGUA | 454 | S. aureus | AAGGG |
| chr14 | 22920564 | 22920584 | 10419_17_18 | 10419 | UUACACAAAACCAUCAAAAC | 455 | S. aureus | AAGAA |
| chr14 | 22920569 | 22920589 | 10419_17_21 | 10419 | CAAAACCAUCAAAACAGAA | 456 | S. aureus | CAGAA |
| chr14 | 22920579 | 22920599 | 10419_17_23 | 10419 | AAAACAAGAACAGAAAAAGG | 457 | S. aureus | CTGAA |
| chr14 | 22920607 | 22920627 | 10419_17_24 | 10419 | CCGUUCAAACCCCAUGUUCU | 458 | S. aureus | CAGGG |
| chr14 | 22920608 | 22920628 | 10419_17_26 | 10419 | CGUUCAAACCCCAUGUUCUC | 459 | S. aureus | AGGGA |
| chr14 | 22920618 | 22920638 | 10419_17_29 | 10419 | CCAUGUUCUCAGGGAUAUUC | 460 | S. aureus | CAGGG |
| chr14 | 22920619 | 22920639 | 10419_17_31 | 10419 | CAUGUUCUCAGGGAUAUUCC | 461 | S. aureus | AGGGA |
| chr14 | 22920620 | 22920640 | 10419_17_32 | 10419 | AUGUUCUCAGGGAUAUUCCA | 462 | S. aureus | GGGAG |
| chr14 | 22920628 | 22920648 | 10419_17_35 | 10419 | AGGGAUAUUCCAGGGAGUUC | 463 | S. aureus | TTGAG |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22920634 | 22920654 | 10419_17_37 | 10419 | + | AUUCCAGGGAGUUCUUGAGG | 464 | S. aureus | CTGAG |
| chr14 | 22920680 | 22920700 | 10419_17_43 | 10419 | + | CUAAUUCCUCACCCCCUGGC | 465 | S. aureus | CTGAG |
| chr14 | 22920704 | 22920724 | 10419_17_48 | 10419 | + | GGUCUUCAUAGAUUGGUGGC | 466 | S. aureus | TTGAG |
| chr14 | 22920751 | 22920771 | 10419_17_55 | 10419 | + | UUGCCCACCUUGAUGUAAGG | 467 | S. aureus | CAGGA |
| chr14 | 22920752 | 22920772 | 10419_17_57 | 10419 | + | UGCCCACCUUGAUGUAAGGC | 468 | S. aureus | AGGAA |
| chr14 | 22920763 | 22920783 | 10419_17_60 | 10419 | + | AGUAAGGCAGGAAAGCAGA | 469 | S. aureus | TTGAA |
| chr14 | 22920781 | 22920801 | 10419_17_61 | 10419 | + | GAUUGAAAUGCUCCUCUCUG | 470 | S. aureus | ATGGG |
| chr14 | 22920787 | 22920807 | 10419_17_65 | 10419 | + | AAUGCUCCUCUCUGAUGGGC | 471 | S. aureus | AAGGG |
| chr14 | 22920788 | 22920808 | 10419_17_66 | 10419 | + | AUGCUCCUCUCUGAUGGGCA | 472 | S. aureus | AGGGG |
| chr14 | 22920789 | 22920809 | 10419_17_68 | 10419 | + | UGCUCCUCUCUGAUGGGCAA | 473 | S. aureus | GGGGA |
| chr14 | 22920790 | 22920810 | 10419_17_70 | 10419 | + | GCUCCUCUCUGAUGGGCAAG | 474 | S. aureus | GGGAA |
| chr14 | 22920830 | 22920850 | 10419_17_72 | 10419 | + | GUACUGCACCUUCUGUACUA | 475 | S. aureus | CAGGA |
| chr14 | 22920831 | 22920851 | 10419_17_74 | 10419 | + | UACUGCACCUUCUGUACUAC | 476 | S. aureus | AGGAG |
| chr14 | 22920836 | 22920856 | 10419_17_75 | 10419 | + | CACCUUCUGUACUACAGGAG | 477 | S. aureus | CAGAA |
| chr14 | 22920842 | 22920862 | 10419_17_77 | 10419 | + | CUGUACUACAGGAGCAGAAC | 478 | S. aureus | CTGAA |
| chr14 | 22920862 | 22920882 | 10419_17_79 | 10419 | + | CUGAAGCUGCUUCCAAGGCU | 479 | S. aureus | CTGGA |
| chr14 | 22920878 | 22920898 | 10419_17_83 | 10419 | + | GGCUCUGGACACUUGGCACG | 480 | S. aureus | CAGGG |
| chr14 | 22920884 | 22920904 | 10419_17_86 | 10419 | + | GGACACUUGGCACGCAGGGC | 481 | S. aureus | TAGAG |
| chr14 | 22920900 | 22920920 | 10419_17_90 | 10419 | + | GGGCUAGAGGCCAAUGGUAU | 482 | S. aureus | ATGAG |
| chr14 | 22920911 | 22920931 | 10419_17_92 | 10419 | + | CAAUGGUAUAUGAGCGGCCU | 483 | S. aureus | GTGGG |
| chr14 | 22920912 | 22920932 | 10419_17_93 | 10419 | + | AAUGGUAUAUGAGCGGCCUG | 484 | S. aureus | TGGGG |
| chr14 | 22920919 | 22920939 | 10419_17_97 | 10419 | + | UAUGAGCGGCCUGUGGGGUU | 485 | S. aureus | ATGAA |
| chr14 | 22920927 | 22920947 | 10419_17_98 | 10419 | + | GCCUGUGGGGUUAUGAAUAG | 486 | S. aureus | CAGAA |
| chr14 | 22920971 | 22920991 | 10419_17_101 | 10419 | + | CCCACUCAUACCACCACCUUC | 487 | S. aureus | TTGGA |

TABLE 2-continued

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22920972 | 22920992 | 10419_17_102 | 10419 | + | CCACUCAUACCACCACCUCU | 488 | S. aureus | TGGAA |
| chr14 | 22920989 | 22921009 | 10419_17_106 | 10419 | + | UCUUGGAAUUGCUGCAUCGC | 489 | S. aureus | CAGAA |
| chr14 | 22921028 | 22921048 | 10419_17_112 | 10419 | + | UUUGGCCUUCACGUACCGUU | 490 | S. aureus | ATGGG |
| chr14 | 22921040 | 22921060 | 10419_17_117 | 10419 | + | GUACCGUUAUGGGCUGCUGU | 491 | S. aureus | AAGAA |
| chr14 | 22921043 | 22921063 | 10419_17_119 | 10419 | + | CCGUUAUGGGCUGCUGUAAG | 492 | S. aureus | AAGAA |
| chr14 | 22921051 | 22921071 | 10419_17_121 | 10419 | + | GGCUGCUGUAAGAAGAAAGA | 493 | S. aureus | CAGGA |
| chr14 | 22920558 | 22920563 | 10419_17_132 | 10419 | - | UUUUGAUGGUUUUGUGUAAG | 494 | S. aureus | TTCCT |
| chr14 | 22920559 | 22920564 | 10419_17_133 | 10419 | - | GUUUUGAUGGUUUUGUGUAA | 495 | S. aureus | TCCTC |
| chr14 | 22920561 | 22920566 | 10419_17_136 | 10419 | - | UUGUUUUGAUGGUUUUGUGU | 496 | S. aureus | CTCTT |
| chr14 | 22920606 | 22920611 | 10419_17_148 | 10419 | - | CCUGAGAACAUGGGGUUUGA | 497 | S. aureus | TCCGT |
| chr14 | 22920610 | 22920615 | 10419_17_150 | 10419 | - | UAUCCCUGAGAACAUGGGGU | 498 | S. aureus | TTCAA |
| chr14 | 22920616 | 22920621 | 10419_17_151 | 10419 | - | CUGGAAUAUCCCUGAGAACA | 499 | S. aureus | CCCCA |
| chr14 | 22920617 | 22920622 | 10419_17_154 | 10419 | - | CCUGGAAUAUCCCUGAGAAC | 500 | S. aureus | CCCAT |
| chr14 | 22920623 | 22920628 | 10419_17_157 | 10419 | - | GAACUCCCUGGAAUAUCCCU | 501 | S. aureus | TTCTC |
| chr14 | 22920625 | 22920630 | 10419_17_158 | 10419 | - | AAGAACUCCCUGGAAUAUCC | 502 | S. aureus | CTCAG |
| chr14 | 22920635 | 22920640 | 10419_17_159 | 10419 | - | ACUCAGCCUCAAGAACUCCC | 503 | S. aureus | TTCCA |
| chr14 | 22920636 | 22920641 | 10419_17_160 | 10419 | - | CACUCAGCCUCAAGAACUCC | 504 | S. aureus | TCCAG |
| chr14 | 22920645 | 22920650 | 10419_17_163 | 10419 | - | GAAGCUACGCACUCAGCCUC | 505 | S. aureus | TTCTT |
| chr14 | 22920667 | 22920672 | 10419_17_167 | 10419 | - | GUGAGGAAUUAGUGCUGGAU | 506 | S. aureus | TTCAA |
| chr14 | 22920673 | 22920678 | 10419_17_168 | 10419 | - | CAGGGGUGAGGAAUUAGUG | 507 | S. aureus | TCCAG |
| chr14 | 22920684 | 22920689 | 10419_17_170 | 10419 | - | AGACCUCAGGCCAGGGGUG | 508 | S. aureus | TTCCT |
| chr14 | 22920685 | 22920690 | 10419_17_171 | 10419 | - | AAGACCUCAGGCCAGGGGU | 509 | S. aureus | TCCTC |
| chr14 | 22920687 | 22920692 | 10419_17_173 | 10419 | - | UGAAGACCUCAGGCCAGGG | 510 | S. aureus | CTCAC |
| chr14 | 22920691 | 22920696 | 10419_17_174 | 10419 | - | UCUAUGAAGACCUCAGGCCA | 511 | S. aureus | CCCCC |

TABLE 2-continued

| Chromosome | Start | Stop | ID | Gene_ID | PRMT5-Targeting Sequence | SEQ ID NO | System | Pam | Strand |
|---|---|---|---|---|---|---|---|---|---|
| chr14 | 22920692 | 22920697 | 10419_17_177 | 10419 | AUCUAUGAAGACCUCAGGCC | 512 | S. aureus | CCCCT | - |
| chr14 | 22920693 | 22920698 | 10419_17_179 | 10419 | AAUCUAUGAAGACCUCAGGC | 513 | S. aureus | CCCTG | - |
| chr14 | 22920708 | 22920713 | 10419_17_182 | 10419 | AGGGCUCAAGCCACCAAUCU | 514 | S. aureus | TTCAT | - |
| chr14 | 22920729 | 22920734 | 10419_17_186 | 10419 | CAAGGGAUUAUAAUUAAUUG | 515 | S. aureus | CCCTG | - |
| chr14 | 22920747 | 22920752 | 10419_17_190 | 10419 | GCCUUACAUCAAGGUGGGCA | 516 | S. aureus | TCCCT | - |
| chr14 | 22920748 | 22920753 | 10419_17_191 | 10419 | UGCCUUACAUCAAGGUGGGC | 517 | S. aureus | CCCTT | - |
| chr14 | 22920754 | 22920759 | 10419_17_196 | 10419 | CUUUCCUGCCCUUACAUCAAG | 518 | S. aureus | CCCAC | - |
| chr14 | 22920791 | 22920796 | 10419_17_204 | 10419 | AUUCCCCUUGCCCAUCAGAG | 519 | S. aureus | CTCCT | - |
| chr14 | 22920792 | 22920797 | 10419_17_205 | 10419 | GAUUCCCCUUGCCCAUCA | 520 | S. aureus | TCCTC | - |
| chr14 | 22920794 | 22920799 | 10419_17_207 | 10419 | GUGAUUCCCCUUGCCCAUCA | 521 | S. aureus | CTCTC | - |
| chr14 | 22920796 | 22920801 | 10419_17_208 | 10419 | CUGUGAUUCCCCUUGCCCAU | 522 | S. aureus | CTCTG | - |
| chr14 | 22920821 | 22920826 | 10419_17_210 | 10419 | ACAGAAGGUGCAGUACAUCU | 523 | S. aureus | CCCAT | - |
| chr14 | 22920840 | 22920845 | 10419_17_215 | 10419 | CAGGUUCUGCCUCCUGUAGUA | 524 | S. aureus | TTCTG | - |
| chr14 | 22920872 | 22920877 | 10419_17_219 | 10419 | GUGCCAAGUGUCCAGAGCCU | 525 | S. aureus | TTCCA | - |
| chr14 | 22920873 | 22920878 | 10419_17_220 | 10419 | CGUGCCAAGUGUCCAGAGCC | 526 | S. aureus | TCCAA | - |
| chr14 | 22920880 | 22920885 | 10419_17_222 | 10419 | AGCCCUGCGUGCCAAGUGUC | 527 | S. aureus | CTCTG | - |
| chr14 | 22920971 | 22920976 | 10419_17_229 | 10419 | UCCAAGAGGUGGGUAUGA | 528 | S. aureus | CCCAC | - |
| chr14 | 22920975 | 22920980 | 10419_17_232 | 10419 | CAAUUCCAAGAGAAGGUGGU | 529 | S. aureus | CTCAT | - |
| chr14 | 22920988 | 22920993 | 10419_17_237 | 10419 | UCUGGGCGAUGCAGCAAUUCC | 530 | S. aureus | TTCTT | - |
| chr14 | 22921035 | 22921040 | 10419_17_241 | 10419 | ACAGCAGCCCAUAACGUAC | 531 | S. aureus | TTCAC | - |
| chr14 | 22922160 | 22922180 | 10419_16_2 | 10419 | AAAAGCAGUUCCUACCUUAA | 532 | S. aureus | TAGGG | + |
| chr14 | 22922161 | 22922181 | 10419_16_4 | 10419 | AAAGCAGUUCCUACCUUAAU | 533 | S. aureus | AGGGA | + |
| chr14 | 22922162 | 22922182 | 10419_16_5 | 10419 | AAGCAGUUCCUACCUUAAUA | 534 | S. aureus | GGGAA | + |
| chr14 | 22922165 | 22922185 | 10419_16_7 | 10419 | CAGUUCCUACCUUAAUAGGG | 535 | S. aureus | AAGAG | + |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22922167 | 22922187 | 10419_16_8 | 10419 | + | GUUCCUACCUUAAUAGGGAA | 536 | S. aureus | GAGGA |
| chr14 | 22922171 | 22922191 | 10419_16_11 | 10419 | + | CUACCUUAAUAGGGAAGAGG | 537 | S. aureus | ATGGG |
| chr14 | 22922172 | 22922192 | 10419_16_12 | 10419 | + | UACCUUAAUAGGGAAGAGGA | 538 | S. aureus | TGGGA |
| chr14 | 22922173 | 22922193 | 10419_16_14 | 10419 | + | ACCUUAAUAGGGAAGAGGAU | 539 | S. aureus | GGGAA |
| chr14 | 22922181 | 22922201 | 10419_16_17 | 10419 | + | AGGGAAGAGGAUGGGAAACC | 540 | S. aureus | ATGAG |
| chr14 | 22922183 | 22922203 | 10419_16_18 | 10419 | + | GGAAGAGGAUGGGAAACCAU | 541 | S. aureus | GAGAA |
| chr14 | 22922193 | 22922213 | 10419_16_19 | 10419 | + | GGGAAACCAUGAGAACAUCC | 542 | S. aureus | CAGGA |
| chr14 | 22922194 | 22922214 | 10419_16_21 | 10419 | + | GGAAACCAUGAGAACAUCCC | 543 | S. aureus | AGGAG |
| chr14 | 22922196 | 22922216 | 10419_16_22 | 10419 | + | AAACCAUGAGAACAUCCCAG | 544 | S. aureus | GAGAG |
| chr14 | 22922200 | 22922220 | 10419_16_23 | 10419 | + | CAUGAGAACAUCCCAGGAGA | 545 | S. aureus | GTGAG |
| chr14 | 22922208 | 22922228 | 10419_16_24 | 10419 | + | CAUCCCAGGAGAGUGAGUCU | 546 | S. aureus | CTGGA |
| chr14 | 22922212 | 22922232 | 10419_16_26 | 10419 | + | CCAGGAGAGUGAGUCUCUGG | 547 | S. aureus | ACGGA |
| chr14 | 22922224 | 22922244 | 10419_16_28 | 10419 | + | GUCUCUGGACGCGAUACCUGU | 548 | S. aureus | GTGGA |
| chr14 | 22922168 | 22922173 | 10419_16_31 | 10419 | - | AUCCUCUCCCUAUUAAGGU | 549 | S. aureus | TTCCT |
| chr14 | 22922169 | 22922174 | 10419_16_32 | 10419 | - | CAUCCUCUCCCUAUUAAGG | 550 | S. aureus | TCCTA |
| chr14 | 22922210 | 22922215 | 10419_16_39 | 10419 | - | CGUCCAGAGACUCACUCUCC | 551 | S. aureus | TCCCA |
| chr14 | 22922211 | 22922216 | 10419_16_40 | 10419 | - | CCGUCCAGAGACUCACUCUC | 552 | S. aureus | CCCAG |
| chr14 | 22922226 | 22922231 | 10419_16_43 | 10419 | - | UGUCCACACAGGUAUCCGUC | 553 | S. aureus | CTCTG |
| chr14 | 22922423 | 22922443 | 10419_15_1 | 10419 | + | UACUGCCAUAGACACUCACU | 554 | S. aureus | CAGAG |
| chr14 | 22922494 | 22922514 | 10419_15_3 | 10419 | + | UAGUACUGUGUUCACCUCCA | 555 | S. aureus | CAGGA |
| chr14 | 22922495 | 22922515 | 10419_15_5 | 10419 | + | AGUACUGUGUUCACCUCCAC | 556 | S. aureus | AGGAA |
| chr14 | 22922533 | 22922553 | 10419_15_10 | 10419 | + | AUAGCGUUGUUGUCAAUCA | 557 | S. aureus | TAGGA |
| chr14 | 22922543 | 22922563 | 10419_15_14 | 10419 | + | UUGUCAAUCAUAGGAUCUGU | 558 | S. aureus | CAGGA |
| chr14 | 22922544 | 22922564 | 10419_15_15 | 10419 | + | UGUCAAUCAUAGGAUCUGUC | 559 | S. aureus | AGGAA |

TABLE 2-continued

| Chromosome | Start | Stop | ID | Gene_ID | PRMT5-Targeting Sequence | Strand | SEQ ID NO | System | Pam |
|---|---|---|---|---|---|---|---|---|---|
| chr14 | 22922437 | 22922442 | 10419_15_20 | 10419 | UUAUCAGGACAUCACUCUGA | - | 560 | S. aureus | CTCAC |
| chr14 | 22922441 | 22922446 | 10419_15_21 | 10419 | UGCUUUAUCAGGACAUCACU | - | 561 | S. aureus | CTCAG |
| chr14 | 22922453 | 22922458 | 10419_15_24 | 10419 | ACUUUGAGACUGUGCUUUAU | - | 562 | S. aureus | TCCTG |
| chr14 | 22922470 | 22922475 | 10419_15_28 | 10419 | ACAUGGCUUUGCCGGCUACU | - | 563 | S. aureus | CTCAA |
| chr14 | 22922504 | 22922509 | 10419_15_34 | 10419 | CCUUGGAAUUCCUGUGGAG | - | 564 | S. aureus | TTCAC |
| chr14 | 22922509 | 22922514 | 10419_15_37 | 10419 | UUGCACCUUGGAAUUCCUG | - | 565 | S. aureus | CTCCA |
| chr14 | 22922510 | 22922515 | 10419_15_38 | 10419 | AUUGCACCUUGGAAUUCCU | - | 566 | S. aureus | TCCAC |
| chr14 | 22922521 | 22922526 | 10419_15_40 | 10419 | CAACAACCGCUAUUGCACCU | - | 567 | S. aureus | TTCCA |
| chr14 | 22922522 | 22922527 | 10419_15_41 | 10419 | ACAACAACCGCUAUUGCACC | - | 568 | S. aureus | TCCAA |
| chr14 | 22922726 | 22922746 | 10419_14_1 | 10419 | CAUAAAAAGAACCUACCUCUG | + | 569 | S. aureus | TTGGG |
| chr14 | 22922727 | 22922747 | 10419_14_3 | 10419 | AUAAAAAGAACCUACCUCUGU | + | 570 | S. aureus | TGGGA |
| chr14 | 22922735 | 22922755 | 10419_14_6 | 10419 | ACCUACCUCUGUUGGGAUGG | + | 571 | S. aureus | CTGAA |
| chr14 | 22922741 | 22922761 | 10419_14_8 | 10419 | CUCUGUUGGGAUGGCUGAAAG | + | 572 | S. aureus | GTGAA |
| chr14 | 22922747 | 22922767 | 10419_14_10 | 10419 | UGGGAUGGCUGAAGGUGAAA | + | 573 | S. aureus | CAGGG |
| chr14 | 22922752 | 22922772 | 10419_14_13 | 10419 | UGGCUGAAGGUGAAACAGGG | + | 574 | S. aureus | CTGGG |
| chr14 | 22922753 | 22922773 | 10419_14_14 | 10419 | GGCUGAAGGUGAAACAGGGC | + | 575 | S. aureus | TGGGG |
| chr14 | 22922760 | 22922780 | 10419_14_18 | 10419 | GGUGAAACAGGGCUGGGGUG | + | 576 | S. aureus | CAGAG |
| chr14 | 22922762 | 22922782 | 10419_14_19 | 10419 | UGAAACAGGGCUGGGGUGCA | + | 577 | S. aureus | GAGAG |
| chr14 | 22922770 | 22922790 | 10419_14_21 | 10419 | GGCUGGGGUGCAGAGAGCUG | + | 578 | S. aureus | GTGGA |
| chr14 | 22922771 | 22922791 | 10419_14_22 | 10419 | GCUGGGGUGCAGAGAGCUGG | + | 579 | S. aureus | TGGAA |
| chr14 | 22922809 | 22922829 | 10419_14_26 | 10419 | ACCACAUAAGGCAUCUCAAA | + | 580 | S. aureus | CTGGG |
| chr14 | 22922741 | 22922746 | 10419_14_34 | 10419 | UUCACCUUCAGCCAUCCCAA | - | 581 | S. aureus | CTCTG |
| chr14 | 22922823 | 22922828 | 10419_14_42 | 10419 | gacagagaGACAGGCCCAGU | - | 582 | S. aureus | CTCAA |
| chr14 | 22923032 | 22923052 | 10419_13_1 | 10419 | GAGAGAGUGGUUCUUUACCU | + | 583 | S. aureus | CAGGG |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22923060 | 22923080 | 10419_13_9 | 10419 | + | CGGUCCUUCUCCCUACAGGC | 584 | S. aureus | TCGGA |
| chr14 | 22923079 | 22923099 | 10419_13_12 | 10419 | + | CUCGGACCUCAUUGUACAGC | 585 | S. aureus | TTGGA |
| chr14 | 22923080 | 22923100 | 10419_13_13 | 10419 | + | UCGGACCUCAUUGUACAGCU | 586 | S. aureus | TGGAG |
| chr14 | 22923082 | 22923102 | 10419_13_15 | 10419 | + | GGACCUCAUUGUACAGCUUG | 587 | S. aureus | GAGGA |
| chr14 | 22923083 | 22923103 | 10419_13_16 | 10419 | + | GACCUCAUUGUACAGCUUGG | 588 | S. aureus | AGGAA |
| chr14 | 22923086 | 22923106 | 10419_13_18 | 10419 | + | CUCAUUGUACAGCUUGGAGG | 589 | S. aureus | AAGGA |
| chr14 | 22923091 | 22923111 | 10419_13_20 | 10419 | + | UGUACAGCUUGGAGGAAGAG | 590 | S. aureus | ATGGG |
| chr14 | 22923092 | 22923112 | 10419_13_21 | 10419 | + | GUACAGCUUGGAGGAAGAGA | 591 | S. aureus | TGGGA |
| chr14 | 22923093 | 22923113 | 10419_13_24 | 10419 | + | UACAGCUUGGAGGAAGAGAU | 592 | S. aureus | GGGAG |
| chr14 | 22923099 | 22923119 | 10419_13_26 | 10419 | + | UUGGAGGAAGAGAUGGGAGC | 593 | S. aureus | CAGAA |
| chr14 | 22923103 | 22923123 | 10419_13_28 | 10419 | + | AGGAAGAGAUGGGAGCCAGA | 594 | S. aureus | AAGGA |
| chr14 | 22923104 | 22923124 | 10419_13_30 | 10419 | + | GGAAGAGAUGGGAGCCAGAA | 595 | S. aureus | AGGAA |
| chr14 | 22923118 | 22923138 | 10419_13_31 | 10419 | + | CCAGAAAGGAAGUGUACUCC | 596 | S. aureus | CCGGG |
| chr14 | 22923119 | 22923139 | 10419_13_32 | 10419 | + | CAGAAAGGAAGUGUACUCCC | 597 | S. aureus | CGGGG |
| chr14 | 22923120 | 22923140 | 10419_13_34 | 10419 | + | AGAAAGGAAGUGUACUCCCC | 598 | S. aureus | GGGGA |
| chr14 | 22923148 | 22923168 | 10419_13_37 | 10419 | + | UCACACCAUCAUCUGCACAG | 599 | S. aureus | CAGGA |
| chr14 | 22923149 | 22923169 | 10419_13_38 | 10419 | + | CACACCAUCAUCUGCACAGC | 600 | S. aureus | AGGAG |
| chr14 | 22923151 | 22923171 | 10419_13_40 | 10419 | + | CACCAUCAUCUGCACAGCAG | 601 | S. aureus | GAGAG |
| chr14 | 22923042 | 22923047 | 10419_13_42 | 10419 | − | AGGACCCUGACCCUGAGGUA | 602 | S. aureus | TTCTT |
| chr14 | 22923050 | 22923055 | 10419_13_44 | 10419 | − | UAGGGAGGAAGGACCGUGACC | 603 | S. aureus | CTCAG |
| chr14 | 22923063 | 22923068 | 10419_13_45 | 10419 | − | AGGUCCGAGCCUGUAGGGAG | 604 | S. aureus | TCCTT |
| chr14 | 22923066 | 22923071 | 10419_13_48 | 10419 | − | AUGAGGUCCGAGCCUGUAGG | 605 | S. aureus | TTCTC |
| chr14 | 22923068 | 22923073 | 10419_13_49 | 10419 | − | CAAUGAGGUCCGAGCCUGUA | 606 | S. aureus | CTCCC |
| chr14 | 22923069 | 22923074 | 10419_13_50 | 10419 | − | ACAAUGAGGUCCGAGCCUGU | 607 | S. aureus | TCCCT |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22923070 | 22923075 | 10419_13_51 | 10419 | - | UACAAUGAGGUCCGAGCCUG | 608 | S. aureus | CCCTA |
| chr14 | 22923079 | 22923084 | 10419_13_54 | 10419 | - | UCCAAGCUGUACAAUGAGGU | 609 | S. aureus | CTCGG |
| chr14 | 22923086 | 22923091 | 10419_13_57 | 10419 | - | CUCUUCCUCCAAGCUGUACA | 610 | S. aureus | CTCAT |
| chr14 | 22923134 | 22923139 | 10419_13_62 | 10419 | - | UGAUGGUGUGAGCAUCCCCG | 611 | S. aureus | CTCCC |
| chr14 | 22923135 | 22923140 | 10419_13_63 | 10419 | - | AUGAUGGUGUGAGCAUCCCC | 612 | S. aureus | TCCCC |
| chr14 | 22923136 | 22923141 | 10419_13_64 | 10419 | - | GAUGAUGGUGUGAGCAUCCC | 613 | S. aureus | CCCCG |
| chr14 | 22923137 | 22923142 | 10419_13_67 | 10419 | - | AGAUGAUGGUGUGAGCAUCC | 614 | S. aureus | CCCGG |
| chr14 | 22923147 | 22923152 | 10419_13_69 | 10419 | - | CCUGCUGUGCAGAUGAUGGU | 615 | S. aureus | CTCAC |
| chr14 | 22923991 | 22924011 | 10419_12_1 | 10419 | + | CCCAACCUGGGGCACCUUUU | 616 | S. aureus | TAGGA |
| chr14 | 22923992 | 22924012 | 10419_12_3 | 10419 | + | CCAACCUGGGGCACCUUUUU | 617 | S. aureus | AGGAA |
| chr14 | 22924000 | 22924020 | 10419_12_4 | 10419 | + | GGGGCACCUUUUUAGGAAGUG | 618 | S. aureus | CTGGG |
| chr14 | 22924044 | 22924064 | 10419_12_12 | 10419 | + | CGACAAUUCAUUGUCAGCAA | 619 | S. aureus | ATGAG |
| chr14 | 22924051 | 22924071 | 10419_12_14 | 10419 | + | UCAUUGUCAGCAAAUGAGCC | 620 | S. aureus | CAGAA |
| chr14 | 22924083 | 22924103 | 10419_12_16 | 10419 | + | GACAAUGAUGUCUGCUUUCU | 621 | S. aureus | CTGGA |
| chr14 | 22924084 | 22924104 | 10419_12_18 | 10419 | + | ACAAUGAUGUCUGCUUUCUC | 622 | S. aureus | TGGAG |
| chr14 | 22924110 | 22924130 | 10419_12_21 | 10419 | + | CACCCAUUCCCUCAUGUCUG | 623 | S. aureus | ATGAG |
| chr14 | 22924163 | 22924183 | 10419_12_29 | 10419 | + | CAAACUGCCAGUUCUCUAGC | 624 | S. aureus | CTGAA |
| chr14 | 22924169 | 22924189 | 10419_12_30 | 10419 | + | GCCAGUUCUCUAGCCUGAAA | 625 | S. aureus | CAGAG |
| chr14 | 22923990 | 22923995 | 10419_12_34 | 10419 | - | CCUAAAAAGGUGCCCCCAGGU | 626 | S. aureus | CCCCA |
| chr14 | 22923991 | 22923996 | 10419_12_37 | 10419 | - | UCCUAAAAGGUGCCCCCAGG | 627 | S. aureus | CCCAA |
| chr14 | 22924025 | 22924030 | 10419_12_42 | 10419 | - | UUGUCGCCUGAGUGCCUGGA | 628 | S. aureus | CTCCA |
| chr14 | 22924026 | 22924031 | 10419_12_43 | 10419 | - | AUUGUCGCCUGAGUGCCUGG | 629 | S. aureus | TCCAT |
| chr14 | 22924030 | 22924035 | 10419_12_45 | 10419 | - | AUGAAUUGUCGCCUGAGUGC | 630 | S. aureus | TCCAG |
| chr14 | 22924038 | 22924043 | 10419_12_48 | 10419 | - | UGCUGACAAUGAAUUGUCGC | 631 | S. aureus | CTCAG |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22924050 | 22924055 | 10419_12_51 | 10419 | - | UCUGGGCUCAUUUGCUGACA | 632 | S. aureus | TTCAT |
| chr14 | 22924069 | 22924074 | 10419_12_54 | 10419 | - | ACAUCAUUGUCAGUGAGCUU | 633 | S. aureus | CCCAG |
| chr14 | 22924077 | 22924082 | 10419_12_56 | 10419 | - | GAAAGCAGACACCAUUGUCA | 634 | S. aureus | CTCAC |
| chr14 | 22924099 | 22924104 | 10419_12_57 | 10419 | - | UGAGGGAAUGGGUGGCUCCA | 635 | S. aureus | TTCTC |
| chr14 | 22924101 | 22924106 | 10419_12_58 | 10419 | - | CAUGAGGGAAUGGGUGGCUC | 636 | S. aureus | CTCTG |
| chr14 | 22924112 | 22924117 | 10419_12_61 | 10419 | - | GUCUCAUCAGACAUGAGGGA | 637 | S. aureus | CCCAT |
| chr14 | 22924116 | 22924121 | 10419_12_63 | 10419 | - | CGUAGUCUCAUCAGACAUGA | 638 | S. aureus | TTCCC |
| chr14 | 22924117 | 22924122 | 10419_12_64 | 10419 | - | CCCUAGUCUCAUCAGACAUG | 639 | S. aureus | TCCCT |
| chr14 | 22924118 | 22924123 | 10419_12_66 | 10419 | - | ACCGUAGUCUCAUCAGACAU | 640 | S. aureus | CCCTC |
| chr14 | 22924120 | 22924125 | 10419_12_68 | 10419 | - | UGACCGUAGUCUCAUCAGAC | 641 | S. aureus | CTCAT |
| chr14 | 22924151 | 22924156 | 10419_12_71 | 10419 | - | AACUGGCAGUUUGAAGAAUG | 642 | S. aureus | TTCCC |
| chr14 | 22924152 | 22924157 | 10419_12_72 | 10419 | - | GAACUGGCAGUUUGAAGAAU | 643 | S. aureus | TCCCC |
| chr14 | 22924153 | 22924158 | 10419_12_74 | 10419 | - | AGAACUGGCAGUUUGAAGAA | 644 | S. aureus | CCCCA |
| chr14 | 22924154 | 22924159 | 10419_12_75 | 10419 | - | GAGAACUGGCAGUUUGAAGA | 645 | S. aureus | CCCAT |
| chr14 | 22924158 | 22924163 | 10419_12_78 | 10419 | - | GCUAGAGAACUGGCAGUUUG | 646 | S. aureus | TTCTT |
| chr14 | 22924161 | 22924166 | 10419_12_79 | 10419 | - | CAGGCUAGAGAACUGGCAGU | 647 | S. aureus | TTCAA |
| chr14 | 22924174 | 22924179 | 10419_12_85 | 10419 | - | AUUGUCUCUGUUUCAGGCUA | 648 | S. aureus | TTCTC |
| chr14 | 22924176 | 22924181 | 10419_12_87 | 10419 | - | UUAUUGUCUCUGUUUCAGGC | 649 | S. aureus | CTCTA |
| chr14 | 22924262 | 22924282 | 10419_11_3 | 10419 | + | UACUCACGUCACCACGGCAU | 650 | S. aureus | TTGGG |
| chr14 | 22924320 | 22924340 | 10419_11_17 | 10419 | + | UCGGCCUGCCUUGGCUGCCCG | 651 | S. aureus | CAGGG |
| chr14 | 22924321 | 22924341 | 10419_11_19 | 10419 | + | CGGCCUGCCUUGGCUGCCGC | 652 | S. aureus | AGGGA |
| chr14 | 22924322 | 22924342 | 10419_11_20 | 10419 | + | GGCCUGCUUGGCUGCCCGCA | 653 | S. aureus | GGGAA |
| chr14 | 22924335 | 22924355 | 10419_11_23 | 10419 | + | GCCCGCGACUUGGAAGCGUUCAC | 654 | S. aureus | CAGGG |
| chr14 | 22924336 | 22924356 | 10419_11_24 | 10419 | + | CCCGCAGGGAAGCGUUCACC | 655 | S. aureus | AGGGG |

TABLE 2-continued

PRMT5-targeting sequences

| Chromo-some | Start | Stop | ID | Gene_ID | PRMT5-Targeting Sequence | SEQ ID NO | System | Strand | Pam |
|---|---|---|---|---|---|---|---|---|---|
| chr14 | 22924374 | 22924394 | 10419_11_30 | 10419 | CCCAGCACCAUCAGUAGUACCCU | 656 | S. aureus | + | AAGAA |
| chr14 | 22924378 | 22924398 | 10419_11_32 | 10419 | GCACCAUCAGUACCCUAAGA | 657 | S. aureus | + | AAGAA |
| chr14 | 22924382 | 22924402 | 10419_11_33 | 10419 | CAUCAGUACCCUAAGAAAGA | 658 | S. aureus | + | AAGGG |
| chr14 | 22924383 | 22924403 | 10419_11_35 | 10419 | AUCAGUACCCUAAGAAAGAA | 659 | S. aureus | + | AGGGA |
| chr14 | 22924384 | 22924404 | 10419_11_36 | 10419 | UCAGUACCCUAAGAAAGAAA | 660 | S. aureus | + | GGGAA |
| chr14 | 22924387 | 22924407 | 10419_11_38 | 10419 | GUACCCUAAGAAAGAAAGGG | 661 | S. aureus | + | AAGAG |
| chr14 | 22924264 | 22924269 | 10419_11_39 | 10419 | AACCCAAAUGCCCUGGUGAC | 662 | S. aureus | - | CTCAC |
| chr14 | 22924290 | 22924295 | 10419_11_41 | 10419 | GGAUAAAGCCUGUAUGCUGUG | 663 | S. aureus | - | TTCTC |
| chr14 | 22924292 | 22924297 | 10419_11_42 | 10419 | GCGGAUAAAGCUGUAUGCUG | 664 | S. aureus | - | CTCCA |
| chr14 | 22924293 | 22924298 | 10419_11_43 | 10419 | GGCGGAUAAAGCUGUAUGCU | 665 | S. aureus | - | TCCAC |
| chr14 | 22924312 | 22924317 | 10419_11_45 | 10419 | GCAGCCAAGCAGGCCGACCG | 666 | S. aureus | - | TCCGC |
| chr14 | 22924336 | 22924341 | 10419_11_51 | 10419 | CCCCUGGUGAACGCCUUCCCU | 667 | S. aureus | - | CCCGC |
| chr14 | 22924350 | 22924355 | 10419_11_53 | 10419 | GAGCAGGACGGGGACCCCUG | 668 | S. aureus | - | TTCAC |
| chr14 | 22924361 | 22924366 | 10419_11_55 | 10419 | GAUGGUGCUGGGAGCAGGAC | 669 | S. aureus | - | TCCCC |
| chr14 | 22924362 | 22924367 | 10419_11_56 | 10419 | UGAUGGUGCUGGGAGCAGGA | 670 | S. aureus | - | CCCCG |
| chr14 | 22924363 | 22924368 | 10419_11_59 | 10419 | CUGAUGGUGCUGGGAGCAGG | 671 | S. aureus | - | CCCGT |
| chr14 | 22924367 | 22924372 | 10419_11_61 | 10419 | GGUACUGAUGGUGCUGGGAG | 672 | S. aureus | - | TCCTG |
| chr14 | 22924372 | 22924377 | 10419_11_64 | 10419 | CUUAGGGUACUGAUGGUGCU | 673 | S. aureus | - | CTCCC |
| chr14 | 22924373 | 22924378 | 10419_11_66 | 10419 | UCUUAGGGUACUGAUGGUGC | 674 | S. aureus | - | TCCCA |
| chr14 | 22924374 | 22924379 | 10419_11_67 | 10419 | UUCUUAGGGUACUGAUGGUG | 675 | S. aureus | - | CCCAG |
| chr14 | 22924517 | 22924537 | 10419_10_10 | 10419 | AGCAGACAUUUAUAGAUGGC | 676 | S. aureus | + | CTGGA |
| chr14 | 22924518 | 22924538 | 10419_10_11 | 10419 | GCAGACAUUUAUAGAUGGCC | 677 | S. aureus | + | TGGAG |
| chr14 | 22924520 | 22924540 | 10419_10_13 | 10419 | AGACAUUUAUAGAUGGCCUG | 678 | S. aureus | + | GAGGG |
| chr14 | 22924521 | 22924541 | 10419_10_14 | 10419 | GACAUUUAUAGAUGGCCUGG | 679 | S. aureus | + | AGGGA |

TABLE 2-continued

| Chromo-some | Start | Stop | ID | Gene_ID | PRMT5-Targeting Sequence | SEQ ID NO | System | Strand | Pam |
|---|---|---|---|---|---|---|---|---|---|
| chr14 | 22924522 | 22924542 | 10419_10_16 | 10419 | ACAUUUAUAGAUGGCCUGGA | 680 | S. aureus | + | GGGAG |
| chr14 | 22924524 | 22924544 | 10419_10_18 | 10419 | AUUUAUAGAUGGCCUGGAGG | 681 | S. aureus | + | GAGGA |
| chr14 | 22924525 | 22924545 | 10419_10_19 | 10419 | UUUAUAGAUGGCCUGGAGGG | 682 | S. aureus | + | AGGAG |
| chr14 | 22924527 | 22924547 | 10419_10_23 | 10419 | UAUAGAUGGCCUGGAGGGAG | 683 | S. aureus | + | GAGAG |
| chr14 | 22924529 | 22924549 | 10419_10_25 | 10419 | UAGAUGGCCUGGAGGGAGGA | 684 | S. aureus | + | GAGAA |
| chr14 | 22924473 | 22924478 | 10419_10_26 | 10419 | GAGAAGGAUACCAAUGUCCA | 685 | S. aureus | - | CTCAC |
| chr14 | 22924490 | 22924495 | 10419_10_27 | 10419 | ACCGAGUACCAGAAGAGGAG | 686 | S. aureus | - | TCCTT |
| chr14 | 22924493 | 22924498 | 10419_10_30 | 10419 | UAGACCGAGUACCAGAAGAG | 687 | S. aureus | - | TTCTC |
| chr14 | 22924495 | 22924500 | 10419_10_31 | 10419 | GCUAGACCGAGUACCAGAAG | 688 | S. aureus | - | CTCCT |
| chr14 | 22924496 | 22924501 | 10419_10_32 | 10419 | UGCUAGACCGAGUACCAGAA | 689 | S. aureus | - | TCCTC |
| chr14 | 22924498 | 22924503 | 10419_10_34 | 10419 | UCUGCUAGACCGAGUACCAG | 690 | S. aureus | - | CTCTT |
| chr14 | 22924501 | 22924506 | 10419_10_36 | 10419 | AUGUCUGCUAGACCGAGUAC | 691 | S. aureus | - | TTCTG |
| chr14 | 22924509 | 22924514 | 10419_10_37 | 10419 | AUCUAUAAAUGUCUGCUAGA | 692 | S. aureus | - | CTCGG |
| chr14 | 22924620 | 22924640 | 10419_9_2 | 10419 | CCACACAGUACCUGCUGGUA | 693 | S. aureus | + | CTGAG |
| chr14 | 22924622 | 22924642 | 10419_9_3 | 10419 | ACACAGUACCUGCUGGUACU | 694 | S. aureus | + | GAGAG |
| chr14 | 22924633 | 22924653 | 10419_9_4 | 10419 | GCUGGUACUGAGAGUAUUUG | 695 | S. aureus | + | ATGGG |
| chr14 | 22924634 | 22924654 | 10419_9_5 | 10419 | CUGGUACUGAGAGUAUUUGA | 696 | S. aureus | + | TGGGG |
| chr14 | 22924662 | 22924682 | 10419_9_12 | 10419 | UUUUCAAACACUUCAUAUGU | 697 | S. aureus | + | CTGAG |
| chr14 | 22924692 | 22924712 | 10419_9_18 | 10419 | AGAUGUCCAUCAGUGGCUG | 698 | S. aureus | + | ATGAA |
| chr14 | 22924696 | 22924716 | 10419_9_20 | 10419 | UGUCCAUCAGUGGCUGAUGA | 699 | S. aureus | + | ATGAG |
| chr14 | 22924698 | 22924718 | 10419_9_21 | 10419 | UCCAUCAGUGGCUGAUGAAU | 700 | S. aureus | + | GAGGA |
| chr14 | 22924699 | 22924719 | 10419_9_22 | 10419 | CCAUCAGUGGCUGAUGAAUG | 701 | S. aureus | + | AGGAA |
| chr14 | 22924704 | 22924724 | 10419_9_24 | 10419 | AGUGGCUGAUGAAUGAGGAA | 702 | S. aureus | + | AAGGA |
| chr14 | 22924611 | 22924616 | 10419_9_26 | 10419 | AGCAGGUACUGUGUGGUGCC | 703 | S. aureus | - | CCCTG |

TABLE 2-continued

PRMT5-Targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22924659 | 22924664 | 10419_9_33 | 10419 | - | AGACAUAUGAAGUGUUUGAA | 704 | S. aureus | TCCTT |
| chr14 | 22924664 | 22924669 | 10419_9_35 | 10419 | - | AUCUCAGACAUAUGAAGUGU | 705 | S. aureus | TTCAA |
| chr14 | 22924673 | 22924678 | 10419_9_36 | 10419 | - | CAAUCUGGAAUCUCAGACAU | 706 | S. aureus | TTCAT |
| chr14 | 22924688 | 22924693 | 10419_9_37 | 10419 | - | UCAGCCACUGAUGGACAAUC | 707 | S. aureus | TTCCA |
| chr14 | 22924689 | 22924694 | 10419_9_38 | 10419 | - | AUCAGCCACUGAUGGACAAU | 708 | S. aureus | TCCAG |
| chr14 | 22924698 | 22924703 | 10419_9_42 | 10419 | - | UCCUCAUUCAUCAGCCACUG | 709 | S. aureus | TCCAT |
| chr14 | 22924858 | 22924878 | 10419_8_1 | 10419 | + | UAAGUGCACUCCAGACCCAC | 710 | S. aureus | CTGAA |
| chr14 | 22924863 | 22924883 | 10419_8_2 | 10419 | + | GCACUCCAGACCCACCUGAA | 711 | S. aureus | GCGGG |
| chr14 | 22924864 | 22924884 | 10419_8_3 | 10419 | + | CACUCCAGACCCACCUGAAG | 712 | S. aureus | CGGGG |
| chr14 | 22924865 | 22924885 | 10419_8_6 | 10419 | + | ACUCCAGACCCACCUGAAGC | 713 | S. aureus | GGGGA |
| chr14 | 22924898 | 22924918 | 10419_8_9 | 10419 | + | AGUCUUCAUAGCCCUUGGCA | 714 | S. aureus | AAGAG |
| chr14 | 22924917 | 22924937 | 10419_8_14 | 10419 | + | AAAGAGUUCAUAGGCAUUAG | 715 | S. aureus | GTGGA |
| chr14 | 22924918 | 22924938 | 10419_8_16 | 10419 | + | AAGAGUUCAUAGGCAUUAGG | 716 | S. aureus | TGGAG |
| chr14 | 22924920 | 22924940 | 10419_8_17 | 10419 | + | GAGUUCAUAGGCAUUAGGUG | 717 | S. aureus | GAGGA |
| chr14 | 22924951 | 22924971 | 10419_8_25 | 10419 | + | UGGCUUAAGUAUUCCAGGUA | 718 | S. aureus | TTGGA |
| chr14 | 22924952 | 22924972 | 10419_8_26 | 10419 | + | GGCUUAAGUAUUCCAGGUAU | 719 | S. aureus | TGGAG |
| chr14 | 22924958 | 22924978 | 10419_8_30 | 10419 | + | AGUAUUCCAGGUAUUGGAGG | 720 | S. aureus | TAGGA |
| chr14 | 22924959 | 22924979 | 10419_8_31 | 10419 | + | GUAUUCCAGGUAUUGGAGGU | 721 | S. aureus | AGGAG |
| chr14 | 22924964 | 22924984 | 10419_8_34 | 10419 | + | CCAGGUAUUGGAGGUAGGAG | 722 | S. aureus | CAGAA |
| chr14 | 22924977 | 22924997 | 10419_8_36 | 10419 | + | GUAGGAGCAGAACUCCUUCU | 723 | S. aureus | CTGAG |
| chr14 | 22925003 | 22925023 | 10419_8_41 | 10419 | + | GGUGGUUGGUGCCUGUGUAUG | 724 | S. aureus | ATGAA |
| chr14 | 22925022 | 22925042 | 10419_8_43 | 10419 | + | GAUGAACUGCACUCCAACU | 725 | S. aureus | GTGAG |
| chr14 | 22925024 | 22925044 | 10419_8_45 | 10419 | + | UGAACUGCACCUCCAACUGU | 726 | S. aureus | GAGAA |
| chr14 | 22924866 | 22924871 | 10419_8_46 | 10419 | - | GUCCCCGCUUCGAGGUGGUC | 727 | S. aureus | CTCCA |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22924867 | 22924872 | 10419_8_47 | 10419 | - | AGUCCCGCCUUCAGGUGGGU | 728 | S. aureus | TCCAG |
| chr14 | 22924873 | 22924878 | 10419_8_50 | 10419 | - | AUCUGCAGUCCCCGCUUCAG | 729 | S. aureus | CCCAC |
| chr14 | 22924902 | 22924907 | 10419_8_55 | 10419 | - | UGAACUCUUUGCCAAGGGCU | 730 | S. aureus | TTCAT |
| chr14 | 22924909 | 22924914 | 10419_8_57 | 10419 | - | AUGCCUAUGAACUCUUUGCC | 731 | S. aureus | CCCTT |
| chr14 | 22924923 | 22924928 | 10419_8_59 | 10419 | - | CCGCUCCACCUAAUGCCU | 732 | S. aureus | TTCAT |
| chr14 | 22924948 | 22924953 | 10419_8_62 | 10419 | - | AAUACCUGAAUACUUAAGC | 733 | S. aureus | TTCTG |
| chr14 | 22924962 | 22924967 | 10419_8_63 | 10419 | - | CUGCUCCUACCUCCAAUACC | 734 | S. aureus | TTCCA |
| chr14 | 22924963 | 22924968 | 10419_8_64 | 10419 | - | UCUGCUCCUACCUCCAAUAC | 735 | S. aureus | TCCAG |
| chr14 | 22924989 | 22924994 | 10419_8_67 | 10419 | - | CACCAACCACCACUCAGAGA | 736 | S. aureus | CTCCT |
| chr14 | 22924990 | 22924995 | 10419_8_68 | 10419 | - | GCACCAACCACCACUCAGAG | 737 | S. aureus | TCCTT |
| chr14 | 22924993 | 22924998 | 10419_8_71 | 10419 | - | CAGGCACCAACCACCACUCA | 738 | S. aureus | TTCTC |
| chr14 | 22924995 | 22925000 | 10419_8_72 | 10419 | - | CACAGGCACCAACCACCACU | 739 | S. aureus | CTCTG |
| chr14 | 22925034 | 22925039 | 10419_8_80 | 10419 | - | GGUCUGACUUUUCUCAGU | 740 | S. aureus | CTCCA |
| chr14 | 22925035 | 22925040 | 10419_8_81 | 10419 | - | UGGUCUGACUUUUCUCACAG | 741 | S. aureus | TCCAA |
| chr14 | 22926113 | 22926133 | 10419_7_1 | 10419 | + | GAACCUCCUACCACCACC | 742 | S. aureus | TTGAG |
| chr14 | 22926115 | 22926135 | 10419_7_2 | 10419 | + | ACCUCCUACCACCACCUU | 743 | S. aureus | GAGGA |
| chr14 | 22926116 | 22926136 | 10419_7_4 | 10419 | + | CCCUCCUACCACCACCUUG | 744 | S. aureus | AGGAG |
| chr14 | 22926121 | 22926141 | 10419_7_5 | 10419 | + | CUACCACCACCUUGAGAG | 745 | S. aureus | CCGGA |
| chr14 | 22926122 | 22926142 | 10419_7_7 | 10419 | + | UACCACCACCUUGAGGAGC | 746 | S. aureus | CGGAA |
| chr14 | 22926128 | 22926148 | 10419_7_8 | 10419 | + | UCACCUUGAGGAGCCGGAAG | 747 | S. aureus | ATGAG |
| chr14 | 22926147 | 22926167 | 10419_7_12 | 10419 | + | GAUGAGCCUCUGGUGCAUCU | 748 | S. aureus | TAGAA |
| chr14 | 22926151 | 22926171 | 10419_7_13 | 10419 | + | AGCCUCUGGUGCAUCUUAGA | 749 | S. aureus | AAGAA |
| chr14 | 22926156 | 22926176 | 10419_7_14 | 10419 | + | CUGGUGCAUCUUAGAAAGAA | 750 | S. aureus | CAGGA |
| chr14 | 22926157 | 22926177 | 10419_7_15 | 10419 | + | UGGUGCAUCUUAGAAAGAAC | 751 | S. aureus | AGGAA |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22926178 | 22926198 | 10419_7_19 | 10419 | + | GGAAAUCCCUUCUAUGGAU | 752 | S. aureus | CAGGA |
| chr14 | 22926179 | 22926199 | 10419_7_20 | 10419 | + | GAAAUCCCUUCUAUAUGGUC | 753 | S. aureus | AGGAA |
| chr14 | 22926191 | 22926211 | 10419_7_24 | 10419 | + | UAUUGGUCAGGAAAAUGCUA | 754 | S. aureus | GTGGG |
| chr14 | 22926192 | 22926212 | 10419_7_25 | 10419 | + | AUUGGUCAGGAAAAUGCUAG | 755 | S. aureus | TGGGG |
| chr14 | 22926193 | 22926213 | 10419_7_28 | 10419 | + | UUGGUCAGGAAAAUGCUAGU | 756 | S. aureus | GGGGA |
| chr14 | 22926194 | 22926214 | 10419_7_31 | 10419 | + | UGGUCAGGAAAAUGCUAGUG | 757 | S. aureus | GGGAG |
| chr14 | 22926196 | 22926216 | 10419_7_33 | 10419 | + | GUCAGGAAAAUGCUAGUGGG | 758 | S. aureus | GAGAA |
| chr14 | 22926212 | 22926232 | 10419_7_35 | 10419 | + | UGGGGAGAAUGGCUGCUUUG | 759 | S. aureus | ATGGG |
| chr14 | 22926249 | 22926269 | 10419_7_40 | 10419 | + | GCGAUCAAUGACAUGAUUAG | 760 | S. aureus | ATGGG |
| chr14 | 22926250 | 22926270 | 10419_7_41 | 10419 | + | CGAUCAAUGACAUGAUUAGA | 761 | S. aureus | TGGGA |
| chr14 | 22926251 | 22926271 | 10419_7_44 | 10419 | + | GAUCAAUGACAUGAUUAGAU | 762 | S. aureus | GGGAG |
| chr14 | 22926271 | 22926291 | 10419_7_47 | 10419 | + | GGGGAGUUCAGCCCCAAUUUC | 763 | S. aureus | AAGAG |
| chr14 | 22926280 | 22926300 | 10419_7_48 | 10419 | + | GCCCCAAUUUCAAGAGCUAC | 764 | S. aureus | ATGAG |
| chr14 | 22926289 | 22926309 | 10419_7_53 | 10419 | + | UCAAGAGCUACAUGAGGCAA | 765 | S. aureus | AAGAA |
| chr14 | 22926116 | 22926121 | 10419_7_55 | 10419 | - | CUCCUCAAGGUGAGUGGUAG | 766 | S. aureus | CCCTC |
| chr14 | 22926118 | 22926123 | 10419_7_57 | 10419 | - | GGCUCCUCAAGGUGAGUGGU | 767 | S. aureus | CTCCT |
| chr14 | 22926119 | 22926124 | 10419_7_58 | 10419 | - | CGGCUCCUCAAGGUGAGUGG | 768 | S. aureus | TCCTA |
| chr14 | 22926127 | 22926132 | 10419_7_62 | 10419 | - | UCAUCUCCGGCUCCUCAAG | 769 | S. aureus | CTCAC |
| chr14 | 22926154 | 22926159 | 10419_7_69 | 10419 | - | CUGUUCUUUCUAAGAUGCAC | 770 | S. aureus | CTCTG |
| chr14 | 22926183 | 22926188 | 10419_7_75 | 10419 | - | CAUUUUCCUGACCAAUAAGA | 771 | S. aureus | TCCCT |
| chr14 | 22926184 | 22926189 | 10419_7_77 | 10419 | - | GCAUUUUCCUGACCAAUAAG | 772 | S. aureus | CCCTT |
| chr14 | 22926187 | 22926192 | 10419_7_80 | 10419 | - | CUAGCAUUUUCCUGACCAAU | 773 | S. aureus | TTCTT |
| chr14 | 22926237 | 22926242 | 10419_7_84 | 10419 | - | UGUCAUUUGAUCGCUGGCUUG | 774 | S. aureus | CTCCC |
| chr14 | 22926238 | 22926243 | 10419_7_85 | 10419 | - | AUGUCAUUGAUCGCUGGCUU | 775 | S. aureus | TCCCC |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22926239 | 22926244 | 10419_7_86 | 10419 | - | CAUGUCAUUGAUCGCUGGCU | 776 | S. aureus | CCCCA |
| chr14 | 22926240 | 22926245 | 10419_7_88 | 10419 | - | UCAUGUCAUUGAUCGCUGGC | 777 | S. aureus | CCCAA |
| chr14 | 22926281 | 22926286 | 10419_7_95 | 10419 | - | CCUCAUGUAGCUCUUGAAAU | 778 | S. aureus | CCCCA |
| chr14 | 22926282 | 22926287 | 10419_7_97 | 10419 | - | GCCUCAUGUAGCUCUUGAAA | 779 | S. aureus | CCCAA |
| chr14 | 22926288 | 22926293 | 10419_7_102 | 10419 | - | UCUUUUGCCUCAUGUAGCUC | 780 | S. aureus | TTCAA |
| chr14 | 22926519 | 22926539 | 10419_6_2 | 10419 | + | UUACUAUAGUCACACAAAGU | 781 | S. aureus | CCGGA |
| chr14 | 22926520 | 22926540 | 10419_6_5 | 10419 | + | UACUAUAGUCACACAAAGUC | 782 | S. aureus | CGGAA |
| chr14 | 22926550 | 22926570 | 10419_6_7 | 10419 | + | GCCACCUGUUCACAGUCAAUA | 783 | S. aureus | CAGAA |
| chr14 | 22926490 | 22926495 | 10419_6_9 | 10419 | - | AUUGCAGUGGGUGAGUCCAU | 784 | S. aureus | TTCTC |
| chr14 | 22926492 | 22926497 | 10419_6_10 | 10419 | - | GGAUUGCAGUGGGUGAGUCC | 785 | S. aureus | CTCAT |
| chr14 | 22926500 | 22926505 | 10419_6_11 | 10419 | - | UAGUAAGAGGAUUGCAGUGG | 786 | S. aureus | CTCAC |
| chr14 | 22926504 | 22926509 | 10419_6_13 | 10419 | - | ACUAUAGUAAGAGGAUUGCA | 787 | S. aureus | CCCAC |
| chr14 | 22926514 | 22926519 | 10419_6_17 | 10419 | - | ACUUUGUGUGACUAUAGUAA | 788 | S. aureus | TCCTC |
| chr14 | 22926516 | 22926521 | 10419_6_19 | 10419 | - | GGACUUUGUGUGACUAUAGU | 789 | S. aureus | CTCTT |
| chr14 | 22926538 | 22926543 | 10419_6_21 | 10419 | - | CUGAACAGGUGGCACACUU | 790 | S. aureus | TCCGG |
| chr14 | 22926774 | 22926794 | 10419_5_10 | 10419 | + | UCAGGUCCUCUGUGCCACC | 791 | S. aureus | AAGGG |
| chr14 | 22926789 | 22926809 | 10419_5_13 | 10419 | + | CCACCAAGGGUACCCGCAUC | 792 | S. aureus | CAGAA |
| chr14 | 22926800 | 22926820 | 10419_5_14 | 10419 | + | ACCCGCAUCCAGAACUGCAC | 793 | S. aureus | ATGAA |
| chr14 | 22926705 | 22926710 | 10419_5_16 | 10419 | - | UACAGUGGGAGGAGAAAAC | 794 | S. aureus | TCCAC |
| chr14 | 22926713 | 22926718 | 10419_5_18 | 10419 | - | CAGAGAGUACAGUGGGGAG | 795 | S. aureus | TTCTC |
| chr14 | 22926715 | 22926720 | 10419_5_19 | 10419 | - | CACAGAGAGUACAGUGGGG | 796 | S. aureus | CTCCT |
| chr14 | 22926716 | 22926721 | 10419_5_20 | 10419 | - | ACACAGAGAGUACAGUGGG | 797 | S. aureus | TCCTC |
| chr14 | 22926718 | 22926723 | 10419_5_22 | 10419 | - | ACACACAGAGAGUACAGUG | 798 | S. aureus | CTCCC |
| chr14 | 22926719 | 22926724 | 10419_5_23 | 10419 | - | CACACACAGAGAGUACAGU | 799 | S. aureus | TCCCC |

TABLE 2-continued

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22926720 | 22926725 | 10419_5_25 | 10419 | - | ACACACACAGAGAGAGUACAG | 800 | S. aureus | CCCCA |
| chr14 | 22926721 | 22926726 | 10419_5_27 | 10419 | - | UACACACACAGAGAGGAGUACA | 801 | S. aureus | CCCAC |
| chr14 | 22926730 | 22926735 | 10419_5_29 | 10419 | - | UGCACCAACUACACACACAG | 802 | S. aureus | CTCCT |
| chr14 | 22926731 | 22926736 | 10419_5_30 | 10419 | - | AUGCACCAACUACACACACA | 803 | S. aureus | TCCCT |
| chr14 | 22926733 | 22926738 | 10419_5_32 | 10419 | - | GAAUGCACCAACUACACACA | 804 | S. aureus | CTCTG |
| chr14 | 22926755 | 22926760 | 10419_5_34 | 10419 | - | ACCUGAGAGAUGAUAUAAUU | 805 | S. aureus | TTCTC |
| chr14 | 22926757 | 22926762 | 10419_5_35 | 10419 | - | GGACCUGAGAGAUGAUAUAA | 806 | S. aureus | CTCAA |
| chr14 | 22926771 | 22926776 | 10419_5_37 | 10419 | - | UUGGUGGCACCAGAGGACCU | 807 | S. aureus | CTCTC |
| chr14 | 22926773 | 22926778 | 10419_5_38 | 10419 | - | CCUUGGUGGCACCAGAGGAC | 808 | S. aureus | CTCAG |
| chr14 | 22926779 | 22926784 | 10419_5_39 | 10419 | - | GGGUACCCUUGGUGGCACCA | 809 | S. aureus | TCCTC |
| chr14 | 22926781 | 22926786 | 10419_5_41 | 10419 | - | GCGGGUACCCUUGGUGGCAC | 810 | S. aureus | CTCTG |
| chr14 | 22926801 | 22926806 | 10419_5_47 | 10419 | - | GUUCAUGUGCAGUCUGGAU | 811 | S. aureus | CCCGC |
| chr14 | 22926807 | 22926812 | 10419_5_49 | 10419 | - | GUGACUGUUCAUGUGCAGUU | 812 | S. aureus | TCCAG |
| chr14 | 22927506 | 22927526 | 10419_4_1 | 10419 | + | AGGAGCCCCUCAGCUAUACC | 813 | S. aureus | ATGGA |
| chr14 | 22927507 | 22927527 | 10419_4_3 | 10419 | + | GGAGCCCCUCAGCUAUACCA | 814 | S. aureus | TGGAA |
| chr14 | 22927510 | 22927530 | 10419_4_4 | 10419 | + | GCCCUCAGCUAUACCAUGG | 815 | S. aureus | AAGAG |
| chr14 | 22927526 | 22927546 | 10419_4_6 | 10419 | + | AUGGAAGAGUGAUGGCCAGU | 816 | S. aureus | GTGGA |
| chr14 | 22927577 | 22927597 | 10419_4_14 | 10419 | + | UUGGUGUUAUCUUCCUGAUU | 817 | S. aureus | AAGGG |
| chr14 | 22927578 | 22927598 | 10419_4_17 | 10419 | + | UGGUGUUAUCUUCCUGAUUA | 818 | S. aureus | AGGGG |
| chr14 | 22927586 | 22927606 | 10419_4_21 | 10419 | + | UCUUCCUGAUUAAGGGGCAG | 819 | S. aureus | CAGGA |
| chr14 | 22927587 | 22927607 | 10419_4_22 | 10419 | + | CUUCCUGAUUAAGGGGCAGC | 820 | S. aureus | AGGAA |
| chr14 | 22927594 | 22927614 | 10419_4_25 | 10419 | + | AUUAAGGGGCAGCAGGAAAG | 821 | S. aureus | CTGGA |
| chr14 | 22927595 | 22927615 | 10419_4_28 | 10419 | + | UUAAGGGGCAGCAGGAAAGC | 822 | S. aureus | TGGAA |
| chr14 | 22927640 | 22927660 | 10419_4_31 | 10419 | + | UUCAGCUCCUGUAACAUGGC | 823 | S. aureus | CTGGA |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22927641 | 22927661 | 10419_4_33 | 10419 | + | UCAGCUCCUGUAACAUGGCC | 824 | S. aureus | TGGAA |
| chr14 | 22927645 | 22927665 | 10419_4_34 | 10419 | + | CUCCUGUAACAUGGCCUGGA | 825 | S. aureus | ACGGA |
| chr14 | 22927646 | 22927666 | 10419_4_35 | 10419 | + | UCCUGUAACAUGGCCUGGAA | 826 | S. aureus | CGGAG |
| chr14 | 22927651 | 22927671 | 10419_4_37 | 10419 | + | UAACAUGGCCUGGAACGGAG | 827 | S. aureus | ATGAA |
| chr14 | 22927654 | 22927674 | 10419_4_38 | 10419 | + | CAUGGCCUGGAACGGAGAUG | 828 | S. aureus | AAGAG |
| chr14 | 22927511 | 22927516 | 10419_4_42 | 10419 | - | ACUCUUCCAUGGUAUAGCUG | 829 | S. aureus | CCCCT |
| chr14 | 22927512 | 22927517 | 10419_4_43 | 10419 | - | CACUCUUCCAUGGUAUAGCU | 830 | S. aureus | CCCTC |
| chr14 | 22927514 | 22927519 | 10419_4_46 | 10419 | - | AUCACUCUUCCAUGGUAUAG | 831 | S. aureus | CTCAG |
| chr14 | 22927566 | 22927571 | 10419_4_52 | 10419 | - | GAAGAUAACACCAACCUGGC | 832 | S. aureus | CTCTG |
| chr14 | 22927588 | 22927593 | 10419_4_57 | 10419 | - | UUUCCUGCUGCCCCUUAAUC | 833 | S. aureus | TTCCT |
| chr14 | 22927589 | 22927594 | 10419_4_58 | 10419 | - | CUUUCCUGCUGCCCCUUAAU | 834 | S. aureus | TCCTG |
| chr14 | 22927622 | 22927627 | 10419_4_66 | 10419 | - | AGUGAAUUUGGUGCAUAU | 835 | S. aureus | CCCAA |
| chr14 | 22927640 | 22927645 | 10419_4_72 | 10419 | - | UCCAGGCCAUGUUACAGAG | 836 | S. aureus | TTCAG |
| chr14 | 22927645 | 22927650 | 10419_4_73 | 10419 | - | UCCGUUCCAGGCCAUGUUAC | 837 | S. aureus | CTCCT |
| chr14 | 22927646 | 22927651 | 10419_4_74 | 10419 | - | CUCCGUUCCAGGCCAUGUUA | 838 | S. aureus | TCCTG |
| chr14 | 22928109 | 22928129 | 10419_3_1 | 10419 | + | AGUCAAACAGUCUUACCGCC | 839 | S. aureus | TCGGA |
| chr14 | 22928110 | 22928130 | 10419_3_3 | 10419 | + | GUCAAACAGUCUUACCGCCU | 840 | S. aureus | CGGAG |
| chr14 | 22928120 | 22928140 | 10419_3_4 | 10419 | + | CUUACCGCCUCCGAGUCCU | 841 | S. aureus | GCGAA |
| chr14 | 22928137 | 22928157 | 10419_3_7 | 10419 | + | CCUGCGAAUCUCUCCACUU | 842 | S. aureus | TTGAG |
| chr14 | 22928143 | 22928163 | 10419_3_8 | 10419 | + | AAUCUUCCACUUUUGAGAGU | 843 | S. aureus | CTGAA |
| chr14 | 22928147 | 22928167 | 10419_3_10 | 10419 | + | UUCUCCACUUUUGAGUCUGG | 844 | S. aureus | ACGAA |
| chr14 | 22928155 | 22928175 | 10419_3_12 | 10419 | + | UUUUGAGUCUGGACGAAUCC | 845 | S. aureus | ATGGA |
| chr14 | 22928156 | 22928176 | 10419_3_16 | 10419 | + | UUUGAGUCUGGACGAAUCCA | 846 | S. aureus | TGGAG |
| chr14 | 22928158 | 22928178 | 10419_3_19 | 10419 | + | UGAGUCUGGACGAAUCCAUG | 847 | S. aureus | GAGAA |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22928128 | 22928133 | 10419_3_27 | 10419 | - | GGAGAAGAUUCGCAGGAACU | 848 | S. aureus | CTCGG |
| chr14 | 22928135 | 22928140 | 10419_3_28 | 10419 | - | CAAAAGUGGAGAAGAUUCGC | 849 | S. aureus | TTCCT |
| chr14 | 22928136 | 22928141 | 10419_3_29 | 10419 | - | UCAAAAGUGGAGAAGAUUCG | 850 | S. aureus | TCCTG |
| chr14 | 22928147 | 22928152 | 10419_3_33 | 10419 | - | UUCGUCCAGACUCAAAAGUG | 851 | S. aureus | TTCTC |
| chr14 | 22928149 | 22928154 | 10419_3_34 | 10419 | - | GAUUCGUCCAGACUCAAAAG | 852 | S. aureus | CTCCA |
| chr14 | 22928150 | 22928155 | 10419_3_35 | 10419 | - | GGAUUCGUCCAGACUCAAAA | 853 | S. aureus | TCCAC |
| chr14 | 22928172 | 22928177 | 10419_3_40 | 10419 | - | AUUGUGGAAAGCUUUCUCC | 854 | S. aureus | TCCAT |
| chr14 | 22928187 | 22928192 | 10419_3_42 | 10419 | - | GACUGGAAUACGCUAAUUGU | 855 | S. aureus | TTCCC |
| chr14 | 22928188 | 22928193 | 10419_3_43 | 10419 | - | AGACUGGAAUACGCUAAUUG | 856 | S. aureus | TCCCA |
| chr14 | 22928189 | 22928194 | 10419_3_45 | 10419 | - | CAGACUGGAAUACGCUAAUU | 857 | S. aureus | CCCAC |
| chr14 | 22928204 | 22928209 | 10419_3_48 | 10419 | - | UUGGGUGGGGGAGUGCAGAC | 858 | S. aureus | TTCCA |
| chr14 | 22928205 | 22928210 | 10419_3_49 | 10419 | - | CUUGGGUGGGGGAGUGCAGA | 859 | S. aureus | TCCAG |
| chr14 | 22928507 | 22928527 | 10419_2_3 | 10419 | + | AGCAGUAGGUCUGAUCGUGU | 860 | S. aureus | CTGGG |
| chr14 | 22928508 | 22928528 | 10419_2_5 | 10419 | + | GCAGUAGGUCUGAUCGUGUC | 861 | S. aureus | TGGGG |
| chr14 | 22928509 | 22928529 | 10419_2_7 | 10419 | + | CAGUAGGUCUGAUCGUGUCU | 862 | S. aureus | GGGGA |
| chr14 | 22928514 | 22928534 | 10419_2_9 | 10419 | + | GGUCUGAUCGUGUCUGGGGA | 863 | S. aureus | CCGGG |
| chr14 | 22928537 | 22928557 | 10419_2_13 | 10419 | + | GGCCGAUUCUUAGCAGGUUC | 864 | S. aureus | CTGAA |
| chr14 | 22928541 | 22928561 | 10419_2_14 | 10419 | + | GAUUCUUAGCAGGUUCCUGA | 865 | S. aureus | ATGAA |
| chr14 | 22928553 | 22928573 | 10419_2_17 | 10419 | + | GUUCCUGAAUGAACUCCCUC | 866 | S. aureus | TTGAA |
| chr14 | 22928560 | 22928580 | 10419_2_19 | 10419 | + | AAUGAACUCCCUCUUGAAAC | 867 | S. aureus | GCGGA |
| chr14 | 22928564 | 22928584 | 10419_2_21 | 10419 | + | AACUCCCUCUUGAAACGCGG | 868 | S. aureus | ATGGA |
| chr14 | 22928565 | 22928585 | 10419_2_23 | 10419 | + | ACUCCCUCUUGAAACGCGGA | 869 | S. aureus | TGGAA |
| chr14 | 22928580 | 22928600 | 10419_2_26 | 10419 | + | GCGGAUGGAAGACAGGCAUG | 870 | S. aureus | CAGAG |
| chr14 | 22928582 | 22928602 | 10419_2_27 | 10419 | + | GGAUGGAAGACAGGCAUGCA | 871 | S. aureus | GAGGA |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22928583 | 22928603 | 10419_2_29 | 10419 | + | GAUGGAAGACAGGCAUGCAG | 872 | S. aureus | AGGAA |
| chr14 | 22928489 | 22928494 | 10419_2_30 | 10419 | - | UACUGCUGUCAGGAAGGGGU | 873 | S. aureus | TCCCT |
| chr14 | 22928490 | 22928495 | 10419_2_31 | 10419 | - | CUACUGCUGUCAGGAAGGGG | 874 | S. aureus | CCCTA |
| chr14 | 22928495 | 22928500 | 10419_2_35 | 10419 | - | CAGACCUACUGCUGUCAGGA | 875 | S. aureus | CCCCT |
| chr14 | 22928496 | 22928501 | 10419_2_37 | 10419 | - | UCAGACCUACUGCUGUCAGG | 876 | S. aureus | CCCTT |
| chr14 | 22928499 | 22928504 | 10419_2_39 | 10419 | - | CGAUCAGACCUACUGCUGUC | 877 | S. aureus | TTCCT |
| chr14 | 22928500 | 22928505 | 10419_2_40 | 10419 | - | ACCGAUCAGACCUACUGCUGU | 878 | S. aureus | TCCTG |
| chr14 | 22928543 | 22928548 | 10419_2_46 | 10419 | - | AGUUCAUUCAGGAACCUGCU | 879 | S. aureus | TTCTT |
| chr14 | 22928554 | 22928559 | 10419_2_49 | 10419 | - | UUUCAAGAGGGAGUUCAUUC | 880 | S. aureus | TTCCT |
| chr14 | 22928555 | 22928560 | 10419_2_50 | 10419 | - | GUUUCAAGAGGGAGUUCAUU | 881 | S. aureus | TCCTG |
| chr14 | 22928566 | 22928571 | 10419_2_53 | 10419 | - | CUUCCAUCCGCGUUUCAAGA | 882 | S. aureus | CTCCC |
| chr14 | 22928567 | 22928572 | 10419_2_54 | 10419 | - | UCUUCCAUCCGCGUUUCAAG | 883 | S. aureus | TCCCT |
| chr14 | 22928568 | 22928573 | 10419_2_56 | 10419 | - | GUCUUCCAUCCGCGUUUCAA | 884 | S. aureus | CCCTC |
| chr14 | 22928570 | 22928575 | 10419_2_58 | 10419 | - | CUGUCUUCCAUCCGCGUUUC | 885 | S. aureus | CTCTT |
| chr14 | 22929156 | 22929176 | 10419_1_1 | 10419 | + | ACCCCCCACCCCUGCUCUCU | 886 | S. aureus | CCGGG |
| chr14 | 22929157 | 22929177 | 10419_1_3 | 10419 | + | CCCCCUCACCCCUGCUCUC | 887 | S. aureus | CGGAG |
| chr14 | 22929186 | 22929206 | 10419_1_6 | 10419 | + | UAGUCUGCCCUUCGUCCCGUCC | 888 | S. aureus | CCGAG |
| chr14 | 22929192 | 22929212 | 10419_1_7 | 10419 | + | GCCCUUCCGUCCCCGAGU | 889 | S. aureus | TCGGA |
| chr14 | 22929212 | 22929232 | 10419_1_11 | 10419 | + | UCGGACCCCGCAUUCCGCUC | 890 | S. aureus | GTGGA |
| chr14 | 22929213 | 22929233 | 10419_1_13 | 10419 | + | CGGACCCCGCAUUCCGCUCG | 891 | S. aureus | TGGAG |
| chr14 | 22929267 | 22929287 | 10419_1_19 | 10419 | + | CCCUAGUGUGUCAGCUAUU | 892 | S. aureus | TCGGG |
| chr14 | 22929268 | 22929288 | 10419_1_20 | 10419 | + | CCCUAGUGUGUCAGCUAUUU | 893 | S. aureus | CGGGG |
| chr14 | 22929269 | 22929289 | 10419_1_23 | 10419 | + | CCUAGUGUGUCAGCUAUUUC | 894 | S. aureus | GGGGA |
| chr14 | 22929294 | 22929314 | 10419_1_28 | 10419 | + | CGCAAUUCAGGUCCCCCCG | 895 | S. aureus | CTGGA |

TABLE 2-continued

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22929363 | 22929383 | 10419_1_34 | 10419 | + | UUCUCCUCGCGCUGUCCACG | 896 | S. aureus | CCGGG |
| chr14 | 22929364 | 22929384 | 10419_1_36 | 10419 | + | UCUCCUCGCGCUGUCCACGC | 897 | S. aureus | CGGGA |
| chr14 | 22929412 | 22929432 | 10419_1_40 | 10419 | + | ACAAAGUCAAACUAGUGCCC | 898 | S. aureus | CAGAA |
| chr14 | 22929418 | 22929438 | 10419_1_42 | 10419 | + | UCAAACUAGUGCCCCAGAAG | 899 | S. aureus | GCGGG |
| chr14 | 22929419 | 22929439 | 10419_1_43 | 10419 | + | CAAACUAGUGCCCCAGAAGG | 900 | S. aureus | CGGGA |
| chr14 | 22929423 | 22929443 | 10419_1_46 | 10419 | + | CUAGUGCCCCAGAAGGCCGG | 901 | S. aureus | ACGAG |
| chr14 | 22929441 | 22929461 | 10419_1_47 | 10419 | + | GGACGAGUCGCCUUAACAAC | 902 | S. aureus | CAGAG |
| chr14 | 22929461 | 22929481 | 10419_1_49 | 10419 | + | CAGAGCCGUCUGCCACAGCUC | 903 | S. aureus | CCGAA |
| chr14 | 22929466 | 22929486 | 10419_1_50 | 10419 | + | CGUCUGCCACAGCUCCCGAA | 904 | S. aureus | CAGGA |
| chr14 | 22929467 | 22929487 | 10419_1_52 | 10419 | + | GUCUGCCACAGCUCCCGAAC | 905 | S. aureus | AGGAG |
| chr14 | 22929469 | 22929489 | 10419_1_53 | 10419 | + | CUGCCACAGCUCCCGAACAG | 906 | S. aureus | GAGGG |
| chr14 | 22929470 | 22929490 | 10419_1_55 | 10419 | + | UGCCACAGCUCCCGAACAGG | 907 | S. aureus | AGGGA |
| chr14 | 22929474 | 22929494 | 10419_1_57 | 10419 | + | ACAGCUCCCGAACAGGAGGG | 908 | S. aureus | ATGGG |
| chr14 | 22929475 | 22929495 | 10419_1_59 | 10419 | + | CAGCUCCCGAACAGGAGGGA | 909 | S. aureus | TGGGG |
| chr14 | 22929476 | 22929496 | 10419_1_60 | 10419 | + | AGCUCCCGAACAGGAGGGAU | 910 | S. aureus | GGGGA |
| chr14 | 22929477 | 22929497 | 10419_1_63 | 10419 | + | GCUCCCGAACAGGAGGGAUG | 911 | S. aureus | GGGAG |
| chr14 | 22929501 | 22929521 | 10419_1_65 | 10419 | + | GUGGCUUUUCCUGCCAAUCC | 912 | S. aureus | GCGGG |
| chr14 | 22929525 | 22929545 | 10419_1_73 | 10419 | + | GCUGCAGUGGCGUACGGC | 913 | S. aureus | ATGGA |
| chr14 | 22929541 | 22929561 | 10419_1_75 | 10419 | + | CGGCAUGGAUCCACCAAUCU | 914 | S. aureus | CAGGG |
| chr14 | 22929557 | 22929577 | 10419_1_79 | 10419 | + | AUCUCAGGGUCUGGUUCCUG | 915 | S. aureus | ACGAA |
| chr14 | 22929573 | 22929593 | 10419_1_82 | 10419 | + | CCUGACCGAACUUCAAUCUCC | 916 | S. aureus | CAGAA |
| chr14 | 22929147 | 22929152 | 10419_1_83 | 10419 | - | GCAGGGGUGAGGGGGUCGGC | 917 | S. aureus | TCCTA |
| chr14 | 22929157 | 22929162 | 10419_1_87 | 10419 | - | UCCCGGAGAAGCAGGGUGA | 918 | S. aureus | CCCCC |
| chr14 | 22929158 | 22929163 | 10419_1_89 | 10419 | - | AUCCCGGAGAAGCAGGGGUG | 919 | S. aureus | CCCCT |

TABLE 2-continued

PRMT5-targeting sequences

| Chromosome | Start | Stop | ID | Gene_ID | PRMT5-Targeting Sequence | SEQ ID NO | System | Strand | Pam |
|---|---|---|---|---|---|---|---|---|---|
| chr14 | 22929159 | 22929164 | 10419_1_91 | 10419 | CAUCCCGGAGAAGCAGGGGU | 920 | S. aureus | - | CCCTC |
| chr14 | 22929161 | 22929166 | 10419_1_93 | 10419 | GUCAUCCCGGAGAAGCAGGG | 921 | S. aureus | - | CTCAC |
| chr14 | 22929165 | 22929170 | 10419_1_94 | 10419 | ACUAGUCAUCCCGGAGAAGC | 922 | S. aureus | - | CCCCT |
| chr14 | 22929166 | 22929171 | 10419_1_97 | 10419 | GACUAGUCAUCCCGGAGAAG | 923 | S. aureus | - | CCCTG |
| chr14 | 22929172 | 22929177 | 10419_1_100 | 10419 | AGGGCAGACUAGUCAUCCCG | 924 | S. aureus | - | TTCTC |
| chr14 | 22929174 | 22929179 | 10419_1_101 | 10419 | GAAGGGCAGACUAGUCAUCC | 925 | S. aureus | - | CTCCG |
| chr14 | 22929175 | 22929180 | 10419_1_102 | 10419 | AGAAGGGCAGACUAGUCAUC | 926 | S. aureus | - | TCCGG |
| chr14 | 22929193 | 22929198 | 10419_1_104 | 10419 | GUCCGAACUCGGGGACGAG | 927 | S. aureus | - | CCCTT |
| chr14 | 22929196 | 22929201 | 10419_1_108 | 10419 | GGGGUCCGAACUCGGGGACG | 928 | S. aureus | - | TTCTC |
| chr14 | 22929198 | 22929203 | 10419_1_109 | 10419 | GCGGGGUCCGAACUCGGGGA | 929 | S. aureus | - | CTCCG |
| chr14 | 22929199 | 22929204 | 10419_1_110 | 10419 | UGCGGGGUCCGAACUCGGGG | 930 | S. aureus | - | TCCGT |
| chr14 | 22929203 | 22929208 | 10419_1_112 | 10419 | GGAAUGCGGGGUCCGAACUC | 931 | S. aureus | - | TCCCC |
| chr14 | 22929204 | 22929209 | 10419_1_113 | 10419 | CGGAAUGCGGGGUCCGAACU | 932 | S. aureus | - | CCCCG |
| chr14 | 22929205 | 22929210 | 10419_1_115 | 10419 | GCGGAAUGCGGGGUCCGAAC | 933 | S. aureus | - | CCCGA |
| chr14 | 22929211 | 22929216 | 10419_1_118 | 10419 | CCACGAGCGGAAUGCGGGGU | 934 | S. aureus | - | TTCGG |
| chr14 | 22929217 | 22929222 | 10419_1_119 | 10419 | GGACCUCCACGAGCGGAAUG | 935 | S. aureus | - | CCCCG |
| chr14 | 22929218 | 22929223 | 10419_1_122 | 10419 | CGGACCUCCACGAGCGGAAU | 936 | S. aureus | - | CCCGC |
| chr14 | 22929224 | 22929229 | 10419_1_124 | 10419 | GAGGGCCGGACCUCCACGAG | 937 | S. aureus | - | TTCCG |
| chr14 | 22929225 | 22929230 | 10419_1_125 | 10419 | UGAGGGCCGGACCUCCACGA | 938 | S. aureus | - | TCCGC |
| chr14 | 22929229 | 22929234 | 10419_1_127 | 10419 | GGGGUGAGGGCCGGACCUCC | 939 | S. aureus | - | CTCGT |
| chr14 | 22929239 | 22929244 | 10419_1_128 | 10419 | UGGCCAAGCAGGGGUGAGGG | 940 | S. aureus | - | TCCGG |
| chr14 | 22929244 | 22929249 | 10419_1_130 | 10419 | GGCUGUGGCCAAGCAGGGGU | 941 | S. aureus | - | CCCTC |
| chr14 | 22929246 | 22929251 | 10419_1_133 | 10419 | GGGGCUGUGGCCAAGCAGGG | 942 | S. aureus | - | CTCAC |
| chr14 | 22929250 | 22929255 | 10419_1_134 | 10419 | ACUAGGGGCUGUGGCCAAGC | 943 | S. aureus | - | CCCCT |

TABLE 2-continued

| Chromosome | Start | Stop | ID | Gene_ID | PRMT5-Targeting Sequence | SEQ ID NO | System | Strand | Pam |
|---|---|---|---|---|---|---|---|---|---|
| chr14 | 22929251 | 22929256 | 10419_1_136 | 10419 | CACUAGGGGCUGUGGCCAAG | 944 | S. aureus | - | CCCTG |
| chr14 | 22929267 | 22929272 | 10419_1_140 | 10419 | CCCGAAAUAGCUGACACACU | 945 | S. aureus | - | CCCCT |
| chr14 | 22929268 | 22929273 | 10419_1_143 | 10419 | CCCCGAAAUAGCUGACACAC | 946 | S. aureus | - | CCCTA |
| chr14 | 22929286 | 22929291 | 10419_1_146 | 10419 | GAGGGACCUGAAUUGCGUCC | 947 | S. aureus | - | TTCGG |
| chr14 | 22929299 | 22929304 | 10419_1_147 | 10419 | GCCUGUCCAGCGGGAGGGAC | 948 | S. aureus | - | TTCAG |
| chr14 | 22929305 | 22929310 | 10419_1_148 | 10419 | GGAGCCCGCGUGUCCAGCGG | 949 | S. aureus | - | TCCCT |
| chr14 | 22929306 | 22929311 | 10419_1_150 | 10419 | GGGAGCCCGCGUGUCCAGCG | 950 | S. aureus | - | CCCTC |
| chr14 | 22929308 | 22929313 | 10419_1_152 | 10419 | GUGGGAGCCCGCGUGUCCAG | 951 | S. aureus | - | CTCCC |
| chr14 | 22929309 | 22929314 | 10419_1_153 | 10419 | GGUGGGAGCCCGCGUGUCC | 952 | S. aureus | - | TCCCG |
| chr14 | 22929310 | 22929315 | 10419_1_155 | 10419 | UGGUGGGAGCCCGCGUGUCCA | 953 | S. aureus | - | CCCGC |
| chr14 | 22929326 | 22929331 | 10419_1_157 | 10419 | UGGCGGUCGGGGGUGCUGGU | 954 | S. aureus | - | CTCCC |
| chr14 | 22929327 | 22929332 | 10419_1_158 | 10419 | AUGGCGGUCGGGGGUGCUGG | 955 | S. aureus | - | TCCCA |
| chr14 | 22929328 | 22929333 | 10419_1_160 | 10419 | GAUGGCCGUCGGGGGUGCUG | 956 | S. aureus | - | CCCAC |
| chr14 | 22929338 | 22929343 | 10419_1_163 | 10419 | AGAUGGCGGCGAUGGGCGGUC | 957 | S. aureus | - | CCCCC |
| chr14 | 22929339 | 22929344 | 10419_1_166 | 10419 | AAGAUGGCGGCGAUGGCGGU | 958 | S. aureus | - | CCCCG |
| chr14 | 22929340 | 22929345 | 10419_1_167 | 10419 | AAAGAUGGCGGCGAUGGCGG | 959 | S. aureus | - | CCCGA |
| chr14 | 22929363 | 22929368 | 10419_1_174 | 10419 | CCCGGCGUGGACAGCGCGAG | 960 | S. aureus | - | TTCTC |
| chr14 | 22929365 | 22929370 | 10419_1_175 | 10419 | AUCCCGGCGUGGACAGCGCG | 961 | S. aureus | - | CTCCT |
| chr14 | 22929366 | 22929371 | 10419_1_176 | 10419 | AAUCCCGGCGUGGACAGCGC | 962 | S. aureus | - | TCCTC |
| chr14 | 22929368 | 22929373 | 10419_1_178 | 10419 | GGAAUCCCGGCGUGGACAGC | 963 | S. aureus | - | CTCGC |
| chr14 | 22929377 | 22929382 | 10419_1_179 | 10419 | UAGUAUCAAGGAAUCCCGGC | 964 | S. aureus | - | TCCAC |
| chr14 | 22929389 | 22929394 | 10419_1_183 | 10419 | GUGAUUGGCUACUAGUAUCA | 965 | S. aureus | - | TTCCT |
| chr14 | 22929390 | 22929395 | 10419_1_184 | 10419 | UGUGAUUGGCUACUAGUAUC | 966 | S. aureus | - | TCCTT |
| chr14 | 22929429 | 22929434 | 10419_1_192 | 10419 | AGGCGACUCGUCCCGCCUUC | 967 | S. aureus | - | CCCCA |

TABLE 2-continued

PRMT5-targeting sequences

| Chromosome | Start | Stop | ID | Gene_ID | PRMT5-Targeting Sequence | SEQ ID NO | Strand | System | Pam |
|---|---|---|---|---|---|---|---|---|---|
| chr14 | 22929430 | 22929435 | 10419_1_194 | 10419 | AAGGCGACUCGUCCGCCUU | 968 | - | S. aureus | CCCAG |
| chr14 | 22929478 | 22929483 | 10419_1_203 | 10419 | ACUCCCCAUCCUCCUGUUC | 969 | - | S. aureus | CTCCC |
| chr14 | 22929479 | 22929484 | 10419_1_204 | 10419 | CACUCCCCAUCCUCCUGUU | 970 | - | S. aureus | TCCCG |
| chr14 | 22929480 | 22929485 | 10419_1_205 | 10419 | CCACUCCCCAUCCUCCUGU | 971 | - | S. aureus | CCCGA |
| chr14 | 22929508 | 22929513 | 10419_1_209 | 10419 | UGUGCAGCCCGCGGAUGGC | 972 | - | S. aureus | TTCCT |
| chr14 | 22929509 | 22929514 | 10419_1_210 | 10419 | CUGUGCAGCCCGCGGAUUGG | 973 | - | S. aureus | TCCTG |
| chr14 | 22929518 | 22929523 | 10419_1_213 | 10419 | CGUACGCCACUGUGCAGCCC | 974 | - | S. aureus | TCCGC |
| chr14 | 22929550 | 22929555 | 10419_1_216 | 10419 | GGAACCAGACCCUGAGAUUG | 975 | - | S. aureus | TCCAC |
| chr14 | 22929559 | 22929564 | 10419_1_220 | 10419 | AGUUCGUCAGGAACCAGACC | 976 | - | S. aureus | CTCAG |
| chr14 | 22929571 | 22929576 | 10419_1_222 | 10419 | CUGGGAGAUUGAAGUUCUC | 977 | - | S. aureus | TTCCT |
| chr14 | 22929572 | 22929577 | 10419_1_224 | 10419 | UCUGGGAGAUUGAAGUUCGU | 978 | - | S. aureus | TCCTG |
| chr14 | 22920491 | 22920511 | 10419_17_3 | 10419 | AGUGUGGGAAAAUAGUGGC | 979 | + | S. pyogenes | AGG |
| chr14 | 22920492 | 22920512 | 10419_17_4 | 10419 | GGUGUGGGAAAAUAGUGGCA | 980 | + | S. pyogenes | GGG |
| chr14 | 22920493 | 22920513 | 10419_17_6 | 10419 | GUGUGGGAAAAUAGUGGCAG | 981 | + | S. pyogenes | GGG |
| chr14 | 22920494 | 22920514 | 10419_17_7 | 10419 | UGUGGGAAAAUAGUGGGCAGG | 982 | + | S. pyogenes | GGG |
| chr14 | 22920502 | 22920522 | 10419_17_8 | 10419 | AAUAGUGGCAGGGGCAGCA | 983 | + | S. pyogenes | TGG |
| chr14 | 22920516 | 22920536 | 10419_17_10 | 10419 | GCAGCAUGGUCGUGCAGUAA | 984 | + | S. pyogenes | AGG |
| chr14 | 22920517 | 22920537 | 10419_17_11 | 10419 | CAGCAUGGUCGUGCAGUAAA | 985 | + | S. pyogenes | GGG |
| chr14 | 22920576 | 22920596 | 10419_17_22 | 10419 | AUCAAAAACAAGAACAGAAAA | 986 | + | S. pyogenes | AGG |
| chr14 | 22920608 | 22920628 | 10419_17_25 | 10419 | CGUUCAAACCCCAUGGGUCUC | 987 | + | S. pyogenes | AGG |
| chr14 | 22920609 | 22920629 | 10419_17_27 | 10419 | GUUCAAACCCCAUGUUCUCA | 988 | + | S. pyogenes | GGG |
| chr14 | 22920619 | 22920639 | 10419_17_30 | 10419 | CAUGUUCUCAGGGAUAUUCC | 989 | + | S. pyogenes | AGG |
| chr14 | 22920620 | 22920640 | 10419_17_33 | 10419 | AUGUUCUCAGGGAUAUUCCA | 990 | + | S. pyogenes | GGG |
| chr14 | 22920631 | 22920651 | 10419_17_36 | 10419 | GAUAUUCCAGGGAGUUCUUG | 991 | + | S. pyogenes | AGG |

TABLE 2-continued

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22920676 | 22920696 | 10419_17_42 | 10419 | + | AGCACUAAUUCCUCACCCCC | 992 | S. pyogenes | TGG |
| chr14 | 22920683 | 22920703 | 10419_17_44 | 10419 | + | AUUCCUCACCCCCUGGCCUG | 993 | S. pyogenes | AGG |
| chr14 | 22920697 | 22920717 | 10419_17_46 | 10419 | + | GGCCUGAGGUCUUCAUAGAU | 994 | S. pyogenes | TGG |
| chr14 | 22920700 | 22920720 | 10419_17_47 | 10419 | + | CUGAGGUCUUCAUAGAUUGG | 995 | S. pyogenes | TGG |
| chr14 | 22920748 | 22920768 | 10419_17_54 | 10419 | + | CCCUGCCCACCUUGAUGUA | 996 | S. pyogenes | AGG |
| chr14 | 22920752 | 22920772 | 10419_17_58 | 10419 | + | UGCCCACCUUGAUGUAAGGC | 997 | S. pyogenes | AGG |
| chr14 | 22920782 | 22920802 | 10419_17_62 | 10419 | + | AUUGAAAUGCUCUCUCUGA | 998 | S. pyogenes | TGG |
| chr14 | 22920783 | 22920803 | 10419_17_63 | 10419 | + | UUGAAAUGCUCUCUCUCUGAU | 999 | S. pyogenes | GGG |
| chr14 | 22920788 | 22920808 | 10419_17_67 | 10419 | + | AUGCUCUCUCUGAUGGGCA | 1000 | S. pyogenes | AGG |
| chr14 | 22920789 | 22920809 | 10419_17_69 | 10419 | + | UGCUCUCUCUCUGAUGGGCAA | 1001 | S. pyogenes | GGG |
| chr14 | 22920790 | 22920810 | 10419_17_71 | 10419 | + | GCUCCUCUCUGAUGGGCAAG | 1002 | S. pyogenes | GGG |
| chr14 | 22920831 | 22920851 | 10419_17_73 | 10419 | + | UACUGCACCUUCUGUACUAC | 1003 | S. pyogenes | AGG |
| chr14 | 22920857 | 22920877 | 10419_17_78 | 10419 | + | AGAACCUGAAGCUGCUUCCA | 1004 | S. pyogenes | AGG |
| chr14 | 22920863 | 22920883 | 10419_17_80 | 10419 | + | UGAAGCUGCUUCCAAGGCUC | 1005 | S. pyogenes | TGG |
| chr14 | 22920871 | 22920891 | 10419_17_81 | 10419 | + | CUUCCAAGGCUCUGGACACU | 1006 | S. pyogenes | TGG |
| chr14 | 22920879 | 22920899 | 10419_17_84 | 10419 | + | GCUCUGGACACUUGGCACGC | 1007 | S. pyogenes | AGG |
| chr14 | 22920880 | 22920900 | 10419_17_85 | 10419 | + | CUCUGGACACUUGGCACGCA | 1008 | S. pyogenes | GGG |
| chr14 | 22920887 | 22920907 | 10419_17_87 | 10419 | + | CACUUGGCACGCAGGGCUAG | 1009 | S. pyogenes | AGG |
| chr14 | 22920894 | 22920914 | 10419_17_89 | 10419 | + | CACGCAGGGCUAGAGGCCAA | 1010 | S. pyogenes | TGG |
| chr14 | 22920905 | 22920925 | 10419_17_91 | 10419 | + | AGAGGCCAAUGGUAUAUGAG | 1011 | S. pyogenes | AGG |
| chr14 | 22920912 | 22920932 | 10419_17_94 | 10419 | + | AAUGGUAUAUGAGCGGCCUG | 1012 | S. pyogenes | TGG |
| chr14 | 22920913 | 22920933 | 10419_17_95 | 10419 | + | AUGGUAUAUGAGCGGCCUGU | 1013 | S. pyogenes | CGG |
| chr14 | 22920914 | 22920934 | 10419_17_96 | 10419 | + | UGGUAUAUGAGCGGCCUGUG | 1014 | S. pyogenes | GGG |
| chr14 | 22920937 | 22920957 | 10419_17_100 | 10419 | + | UUAUGAAUAGCAGAACAGAC | 1015 | S. pyogenes | TGG |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22920972 | 22920992 | 10419_17_103 | 10419 | + | CCACUCAUACCACCACCUCU | 1016 | S. pyogenes | TGG |
| chr14 | 22921005 | 22921025 | 10419_17_109 | 10419 | + | UCGCCAGAAACGCACACAGA | 1017 | S. pyogenes | TGG |
| chr14 | 22921010 | 22921030 | 10419_17_110 | 10419 | + | AGAAACGCACACAGAUGGUU | 1018 | S. pyogenes | TGG |
| chr14 | 22921029 | 22921049 | 10419_17_114 | 10419 | + | UUGGCCUUCACGUACCGUUA | 1019 | S. pyogenes | TGG |
| chr14 | 22921030 | 22921050 | 10419_17_115 | 10419 | + | UGGCCUUCACGUACCGUUAU | 1020 | S. pyogenes | GGG |
| chr14 | 22921052 | 22921072 | 10419_17_122 | 10419 | + | GCUGCUGUAAGAAGAAAGAC | 1021 | S. pyogenes | AGG |
| chr14 | 22920560 | 22920563 | 10419_17_134 | 10419 | - | UUUUGAUGGUUUUGUGUAAG | 1022 | S. pyogenes | CCT |
| chr14 | 22920574 | 22920577 | 10419_17_142 | 10419 | - | UUUUUCGUUCUGUCUUGUUUUGA | 1023 | S. pyogenes | CCA |
| chr14 | 22920607 | 22920610 | 10419_17_149 | 10419 | - | CUGAGAACAUGGGGUUUGAA | 1024 | S. pyogenes | CCG |
| chr14 | 22920616 | 22920619 | 10419_17_152 | 10419 | - | GGAUAUCCCUGAGAACAUG | 1025 | S. pyogenes | CCC |
| chr14 | 22920617 | 22920620 | 10419_17_153 | 10419 | - | UGGAUAUCCCUGAGAACAU | 1026 | S. pyogenes | CCC |
| chr14 | 22920618 | 22920621 | 10419_17_155 | 10419 | - | CUGGAUAUCCCUGAGAACA | 1027 | S. pyogenes | CCA |
| chr14 | 22920637 | 22920640 | 10419_17_161 | 10419 | - | ACUCAGCCUCAAGAACUCCC | 1028 | S. pyogenes | CCA |
| chr14 | 22920674 | 22920677 | 10419_17_169 | 10419 | - | AGGGGGUGAGGAAUUAGUGC | 1029 | S. pyogenes | CCA |
| chr14 | 22920686 | 22920689 | 10419_17_172 | 10419 | - | AGACCUCAGGCCAGGGGGUG | 1030 | S. pyogenes | CCT |
| chr14 | 22920691 | 22920694 | 10419_17_175 | 10419 | - | UAUGAAGACCUCAGGCCAGG | 1031 | S. pyogenes | CCC |
| chr14 | 22920692 | 22920695 | 10419_17_176 | 10419 | - | CUAUGAAGACCUCAGGCCAG | 1032 | S. pyogenes | CCC |
| chr14 | 22920693 | 22920696 | 10419_17_178 | 10419 | - | UCUAUGAAGACCUCAGGCCA | 1033 | S. pyogenes | CCC |
| chr14 | 22920694 | 22920697 | 10419_17_180 | 10419 | - | AUCUAUGAAGACCUCAGGCC | 1034 | S. pyogenes | CCT |
| chr14 | 22920699 | 22920702 | 10419_17_181 | 10419 | - | CACCAAUCUAUGAAGACCUC | 1035 | S. pyogenes | CCC |
| chr14 | 22920729 | 22920732 | 10419_17_187 | 10419 | - | AGGGAUUAUAAUUAAUGCA | 1036 | S. pyogenes | CCC |
| chr14 | 22920730 | 22920733 | 10419_17_188 | 10419 | - | AAGGGAUUAUAAUUAAUUGC | 1037 | S. pyogenes | CCT |
| chr14 | 22920748 | 22920751 | 10419_17_192 | 10419 | - | CCUUACAUCAAGGUGGGCAA | 1038 | S. pyogenes | CCC |
| chr14 | 22920749 | 22920752 | 10419_17_193 | 10419 | - | GCCUUACAUCAAGGUGGGCA | 1039 | S. pyogenes | CCT |

TABLE 2-continued

PRMT5-targeting sequences

| Chromosome | Start | Stop | ID | Gene_ID | PRMT5-Targeting Sequence | SEQ ID NO | System | Strand | Pam |
|---|---|---|---|---|---|---|---|---|---|
| chr14 | 22920754 | 22920757 | 10419_17_197 | 10419 | UUCCUGCCUUACAUCAAGGU | 1040 | S. pyogenes | - | CCC |
| chr14 | 22920755 | 22920758 | 10419_17_198 | 10419 | UUUCCUGCCUUACAUCAAGG | 1041 | S. pyogenes | - | CCA |
| chr14 | 22920758 | 22920761 | 10419_17_199 | 10419 | UGCUUUCCUGCCUUACAUCA | 1042 | S. pyogenes | - | CCT |
| chr14 | 22920793 | 22920796 | 10419_17_206 | 10419 | AUUCCCCUUGCCCAUCAGAG | 1043 | S. pyogenes | - | CCT |
| chr14 | 22920821 | 22920824 | 10419_17_209 | 10419 | AGAAGGUGCAGUACAUCUAU | 1044 | S. pyogenes | - | CCC |
| chr14 | 22920822 | 22920825 | 10419_17_211 | 10419 | CAGAAGGUGCAGUACAUCUA | 1045 | S. pyogenes | - | CCA |
| chr14 | 22920838 | 22920841 | 10419_17_213 | 10419 | UUCUGCUCCUGUAGUACAGA | 1046 | S. pyogenes | - | CCT |
| chr14 | 22920861 | 22920864 | 10419_17_218 | 10419 | AGAGCCUUGGAAGCAGCUUC | 1047 | S. pyogenes | - | CCT |
| chr14 | 22920874 | 22920877 | 10419_17_221 | 10419 | GUGCCAAGUGUCCAGAGCCU | 1048 | S. pyogenes | - | CCA |
| chr14 | 22920910 | 22920913 | 10419_17_224 | 10419 | ACAGGCCCCUCAUAUACCAU | 1049 | S. pyogenes | - | CCA |
| chr14 | 22920928 | 22920931 | 10419_17_227 | 10419 | UCUGCUAUUCAUAUACCCAC | 1050 | S. pyogenes | - | CCT |
| chr14 | 22920971 | 22920974 | 10419_17_228 | 10419 | CAAGAAGUGUGGUAUGAGU | 1051 | S. pyogenes | - | CCC |
| chr14 | 22920972 | 22920975 | 10419_17_231 | 10419 | CCAAGAAGGUGUGGUAUGAG | 1052 | S. pyogenes | - | CCA |
| chr14 | 22920981 | 22920984 | 10419_17_233 | 10419 | GCAGCAAUUCCAAGAAGGUG | 1053 | S. pyogenes | - | CCA |
| chr14 | 22920986 | 22920989 | 10419_17_234 | 10419 | GCGAUGCAGCAAUUCCAAGA | 1054 | S. pyogenes | - | CCT |
| chr14 | 22921008 | 22921011 | 10419_17_239 | 10419 | AAACCAUCUGUGUGCGUUUC | 1055 | S. pyogenes | - | CCA |
| chr14 | 22921033 | 22921036 | 10419_17_240 | 10419 | CAGCCCAUAACGUACGUGA | 1056 | S. pyogenes | - | CCT |
| chr14 | 22921043 | 22921046 | 10419_17_246 | 10419 | CUUCUUACAGCAGCCCAUAA | 1057 | S. pyogenes | - | CCG |
| chr14 | 22922161 | 22922181 | 10419_16_3 | 10419 | AAAGCAGUUCCUACCUUAAU | 1058 | S. pyogenes | + | AGG |
| chr14 | 22922162 | 22922182 | 10419_16_6 | 10419 | AAGCAGUUCCUACCUUAAUA | 1059 | S. pyogenes | + | GGG |
| chr14 | 22922168 | 22922188 | 10419_16_10 | 10419 | UUCCUACCUUAAUAGGAAG | 1060 | S. pyogenes | + | AGG |
| chr14 | 22922172 | 22922192 | 10419_16_13 | 10419 | UACCUUAAUAGGGAAGAGGA | 1061 | S. pyogenes | + | TGG |
| chr14 | 22922173 | 22922193 | 10419_16_15 | 10419 | ACCUUAAUAGGGAAGAGGAU | 1062 | S. pyogenes | + | GGG |
| chr14 | 22922194 | 22922214 | 10419_16_20 | 10419 | GGAAACCAUGAGAACAUCCC | 1063 | S. pyogenes | + | AGG |

TABLE 2-continued

PRMT5-targeting sequences

| Chromosome | Start | Stop | ID | Gene_ID | PRMT5-Targeting Sequence | SEQ ID NO | System | Strand | Pam |
|---|---|---|---|---|---|---|---|---|---|
| chr14 | 22922209 | 22922229 | 10419_16_25 | 10419 | AUCCCAGGAGAGUGAGUCUC | 1064 | S. pyogenes | + | TGG |
| chr14 | 22922213 | 22922233 | 10419_16_27 | 10419 | CAGGAGAGUGAGUCUCUGGA | 1065 | S. pyogenes | + | CGG |
| chr14 | 22922225 | 22922245 | 10419_16_29 | 10419 | UCUCUGGACGGAUACCUGUG | 1066 | S. pyogenes | + | TGG |
| chr14 | 22922170 | 22922173 | 10419_16_33 | 10419 | AUCCUCUUCCCUAUUAAGGU | 1067 | S. pyogenes | − | CCT |
| chr14 | 22922174 | 22922177 | 10419_16_36 | 10419 | UCCCAUCCUCUUCCCUAUUA | 1068 | S. pyogenes | − | CCT |
| chr14 | 22922199 | 22922202 | 10419_16_38 | 10419 | ACUCUCCUGGGAUGUUCUCA | 1069 | S. pyogenes | − | CCA |
| chr14 | 22922211 | 22922214 | 10419_16_41 | 10419 | GUCCAGAGACUCACUCCCU | 1070 | S. pyogenes | − | CCC |
| chr14 | 22922212 | 22922215 | 10419_16_42 | 10419 | CGUCCAGAGACUCACUCCC | 1071 | S. pyogenes | − | CCA |
| chr14 | 22922461 | 22922481 | 10419_15_2 | 10419 | AAGCACACUGUCUCAAAGUAGC | 1072 | S. pyogenes | + | CGG |
| chr14 | 22922495 | 22922515 | 10419_15_4 | 10419 | AGUACUGUGUUCACCUCCAC | 1073 | S. pyogenes | + | AGG |
| chr14 | 22922506 | 22922526 | 10419_15_7 | 10419 | CACCUCCACAGGAAAUUCCA | 1074 | S. pyogenes | + | AGG |
| chr14 | 22922517 | 22922537 | 10419_15_8 | 10419 | GAAAUUCCAAGGUGCAAUAG | 1075 | S. pyogenes | + | CGG |
| chr14 | 22922534 | 22922554 | 10419_15_11 | 10419 | UAGCGGUUGUUGUUCAAUCAU | 1076 | S. pyogenes | + | AGG |
| chr14 | 22922544 | 22922564 | 10419_15_16 | 10419 | UGUCAAUCAUAGAGGAUCUGUC | 1077 | S. pyogenes | + | AGG |
| chr14 | 22922428 | 22922431 | 10419_15_17 | 10419 | UCACUCUGAGUGAGUGUCUA | 1078 | S. pyogenes | − | CCA |
| chr14 | 22922454 | 22922457 | 10419_15_25 | 10419 | CUUUGAGACUGUGCUUUAUC | 1079 | S. pyogenes | − | CCT |
| chr14 | 22922480 | 22922483 | 10419_15_29 | 10419 | ACAGUACUACAUGGCUUUGC | 1080 | S. pyogenes | − | CCG |
| chr14 | 22922489 | 22922492 | 10419_15_30 | 10419 | GAGGUGAACACAGUACUACA | 1081 | S. pyogenes | − | CCA |
| chr14 | 22922508 | 22922511 | 10419_15_36 | 10419 | CACCUUGGAAUUCCUGUGG | 1082 | S. pyogenes | − | CCT |
| chr14 | 22922511 | 22922514 | 10419_15_39 | 10419 | UUGCACCUUGGAAUUCCUG | 1083 | S. pyogenes | − | CCA |
| chr14 | 22922523 | 22922526 | 10419_15_42 | 10419 | CAACAACCGCUAUUGCACCU | 1084 | S. pyogenes | − | CCA |
| chr14 | 22922727 | 22922747 | 10419_14_2 | 10419 | AUAAAAGAACCUACCUCUGU | 1085 | S. pyogenes | + | TGG |
| chr14 | 22922728 | 22922748 | 10419_14_4 | 10419 | UAAAAGAACCUACCUCUGUU | 1086 | S. pyogenes | + | GGG |
| chr14 | 22922732 | 22922752 | 10419_14_5 | 10419 | AGAACCUACCUCUGUUGGGA | 1087 | S. pyogenes | + | TGG |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22922739 | 22922759 | 10419_14_7 | 10419 | + | ACCUCUGUUGGAUGGCUGA | 1088 | S. pyogenes | AGG |
| chr14 | 22922748 | 22922768 | 10419_14_11 | 10419 | + | GGGAUGGCUGAAGGUGAAAC | 1089 | S. pyogenes | AGG |
| chr14 | 22922749 | 22922769 | 10419_14_12 | 10419 | + | GGAUGGCUGAAGGUGAAACA | 1090 | S. pyogenes | GGG |
| chr14 | 22922753 | 22922773 | 10419_14_15 | 10419 | + | GGCUGAAGGUGAAACAGGGC | 1091 | S. pyogenes | TGG |
| chr14 | 22922754 | 22922774 | 10419_14_16 | 10419 | + | GCUGAAGGUGAAACAGGGCU | 1092 | S. pyogenes | GGG |
| chr14 | 22922755 | 22922775 | 10419_14_17 | 10419 | + | CUGAAGGUGAAACAGGGCUG | 1093 | S. pyogenes | GGG |
| chr14 | 22922768 | 22922788 | 10419_14_20 | 10419 | + | AGGGCUGGGGUGCAGAGAGC | 1094 | S. pyogenes | TGG |
| chr14 | 22922771 | 22922791 | 10419_14_23 | 10419 | + | GCUGGGGUGCAGAGAGCUGG | 1095 | S. pyogenes | TGG |
| chr14 | 22922797 | 22922817 | 10419_14_24 | 10419 | + | UUGUGCAGCCGUACCACAUA | 1096 | S. pyogenes | AGG |
| chr14 | 22922810 | 22922830 | 10419_14_27 | 10419 | + | CCACAUAAGGCAUCUCAAAC | 1097 | S. pyogenes | TGG |
| chr14 | 22922811 | 22922831 | 10419_14_28 | 10419 | + | CACAUAAGGCAUCUCAAACU | 1098 | S. pyogenes | GGG |
| chr14 | 22922725 | 22922728 | 10419_14_29 | 10419 | - | AACAGAGUAGGUUCUUUUA | 1099 | S. pyogenes | CCA |
| chr14 | 22922736 | 22922739 | 10419_14_31 | 10419 | - | UCAGCCAUCCCAACAGAGGU | 1100 | S. pyogenes | CCT |
| chr14 | 22922740 | 22922743 | 10419_14_32 | 10419 | - | ACCUUCAGCCAUCCCAACAG | 1101 | S. pyogenes | CCT |
| chr14 | 22922805 | 22922808 | 10419_14_40 | 10419 | - | UUGAGAUGCCCUUAUGUGUA | 1102 | S. pyogenes | CCG |
| chr14 | 22922810 | 22922813 | 10419_14_41 | 10419 | + | CCAGUUUGAGAUGCCUUAUG | 1103 | S. pyogenes | CCA |
| chr14 | 22923033 | 22923053 | 10419_13_2 | 10419 | + | AGAGAGUGGUUCUUUACCUC | 1104 | S. pyogenes | AGG |
| chr14 | 22923034 | 22923054 | 10419_13_3 | 10419 | + | GAGAGUGGUUCUUUACCUCA | 1105 | S. pyogenes | GGG |
| chr14 | 22923040 | 22923060 | 10419_13_4 | 10419 | + | GGUUCUUUACCUCCAGGGUCA | 1106 | S. pyogenes | GGG |
| chr14 | 22923056 | 22923076 | 10419_13_8 | 10419 | + | GUCACGGUCCCUUCUCCCUAC | 1107 | S. pyogenes | AGG |
| chr14 | 22923061 | 22923081 | 10419_13_10 | 10419 | + | GGUCCUUCUCCCUACAGGCU | 1108 | S. pyogenes | CGG |
| chr14 | 22923080 | 22923100 | 10419_13_14 | 10419 | + | UCGGACCUCAUUGUACAGCU | 1109 | S. pyogenes | GGG |
| chr14 | 22923083 | 22923103 | 10419_13_17 | 10419 | + | GACCUCAUUGUACAGCUUGG | 1110 | S. pyogenes | AGG |
| chr14 | 22923092 | 22923112 | 10419_13_22 | 10419 | + | GUACAGCUUGGAGGAAGAGA | 1111 | S. pyogenes | TGG |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22923093 | 22923113 | 10419_13_23 | 10419 | + | UACAGCUUGGAGGAAGAGAU | 1112 | S. pyogenes | GGG |
| chr14 | 22923104 | 22923124 | 10419_13_29 | 10419 | + | GGAAGAGAUGGAGCCAGAA | 1113 | S. pyogenes | AGG |
| chr14 | 22923119 | 22923139 | 10419_13_33 | 10419 | + | CAGAAAGGAAGUGUACUCCC | 1114 | S. pyogenes | CGG |
| chr14 | 22923120 | 22923140 | 10419_13_35 | 10419 | + | AGAAAGGAAGUGUACUCCCC | 1115 | S. pyogenes | GGG |
| chr14 | 22923121 | 22923141 | 10419_13_36 | 10419 | + | GAAAGGAAGUGUACUCCCCG | 1116 | S. pyogenes | GGG |
| chr14 | 22923149 | 22923169 | 10419_13_39 | 10419 | + | CACACCAUCAUCUGCACAGC | 1117 | S. pyogenes | AGG |
| chr14 | 22923049 | 22923052 | 10419_13_43 | 10419 | - | GGAGAAGGACCGUGACCCUG | 1118 | S. pyogenes | CCT |
| chr14 | 22923064 | 22923067 | 10419_13_46 | 10419 | - | GGUCCGACCCUGUAGGGAGA | 1119 | S. pyogenes | CCT |
| chr14 | 22923070 | 22923073 | 10419_13_52 | 10419 | - | CAAUGAGGUCCGAGCCUGUA | 1120 | S. pyogenes | CCC |
| chr14 | 22923071 | 22923074 | 10419_13_53 | 10419 | - | ACAAUGAGGUCCGAGCCUGU | 1121 | S. pyogenes | CCT |
| chr14 | 22923085 | 22923088 | 10419_13_56 | 10419 | - | UUCCUCCAAGCUGUACAAUG | 1122 | S. pyogenes | CCT |
| chr14 | 22923118 | 22923121 | 10419_13_61 | 10419 | - | CGGGGAGUACACUUCCUUUC | 1123 | S. pyogenes | CCA |
| chr14 | 22923136 | 22923139 | 10419_13_65 | 10419 | - | UGAUGGUGAGCAUCCCCG | 1124 | S. pyogenes | CCC |
| chr14 | 22923137 | 22923140 | 10419_13_66 | 10419 | - | AUGAUGGUGAGCAUCCCC | 1125 | S. pyogenes | CCC |
| chr14 | 22923138 | 22923141 | 10419_13_68 | 10419 | - | GAUGAUGGUGAGCAUCCC | 1126 | S. pyogenes | CCG |
| chr14 | 22923153 | 22923156 | 10419_13_70 | 10419 | - | CUCUCCUGCUGUGCAGAUGA | 1127 | S. pyogenes | CCA |
| chr14 | 22923992 | 22924012 | 10419_12_2 | 10419 | + | CCAACCUGGGGCACCUUUU | 1128 | S. pyogenes | AGG |
| chr14 | 22924001 | 22924021 | 10419_12_5 | 10419 | + | GGGCACCUUUUAGGAAGUGC | 1129 | S. pyogenes | TGG |
| chr14 | 22924002 | 22924022 | 10419_12_6 | 10419 | + | GGCACCUUUUAGGAAGUGCU | 1130 | S. pyogenes | GGG |
| chr14 | 22924013 | 22924033 | 10419_12_10 | 10419 | + | GGAAGUGCUGGGCUCCAUCC | 1131 | S. pyogenes | AGG |
| chr14 | 22924021 | 22924041 | 10419_12_11 | 10419 | + | UGGGCUCCAUCCAGGCACUC | 1132 | S. pyogenes | AGG |
| chr14 | 22924084 | 22924104 | 10419_12_17 | 10419 | + | ACAAUGAUGCUGCUUUCUC | 1133 | S. pyogenes | TGG |
| chr14 | 22924119 | 22924139 | 10419_12_23 | 10419 | + | CCUCAUGUCUGAUGAGACUA | 1134 | S. pyogenes | CGG |
| chr14 | 22924127 | 22924147 | 10419_12_24 | 10419 | + | CUGAUGAGACUACGGUCACU | 1135 | S. pyogenes | TGG |

TABLE 2-continued

PRMT5-targeting sequences

| Chromosome | Start | Stop | ID | Gene_ID | PRMT5-Targeting Sequence | Strand | SEQ ID NO | System | Pam |
|---|---|---|---|---|---|---|---|---|---|
| chr14 | 22924180 | 22924200 | 10419_12_32 | 10419 | AGCCUGAAACAGAGACAAUA | + | 1136 | S. pyogenes | AGG |
| chr14 | 22923990 | 22923993 | 10419_12_33 | 10419 | UAAAAGGUGCCCCCAGGUUG | - | 1137 | S. pyogenes | CCC |
| chr14 | 22923991 | 22923994 | 10419_12_36 | 10419 | CUAAAAGGUGCCCCCAGGUU | - | 1138 | S. pyogenes | CCC |
| chr14 | 22923992 | 22923995 | 10419_12_38 | 10419 | CCUAAAAGGUGCCCCCAGGU | - | 1139 | S. pyogenes | CCA |
| chr14 | 22923996 | 22923999 | 10419_12_39 | 10419 | ACUUCCUAAAAGGUGCCCCC | - | 1140 | S. pyogenes | CCT |
| chr14 | 22924006 | 22924009 | 10419_12_40 | 10419 | GGAGCCCAGCACUUCCUAAA | - | 1141 | S. pyogenes | CCT |
| chr14 | 22924027 | 22924030 | 10419_12_44 | 10419 | UUGUCGCCUGAGUGCCUGA | - | 1142 | S. pyogenes | CCA |
| chr14 | 22924031 | 22924034 | 10419_12_46 | 10419 | UGAAUUGUCGCCUGAGUGCC | - | 1143 | S. pyogenes | CCA |
| chr14 | 22924069 | 22924072 | 10419_12_53 | 10419 | AUCCAUUGUCAGUGAGCUUCU | - | 1144 | S. pyogenes | CCC |
| chr14 | 22924070 | 22924073 | 10419_12_55 | 10419 | CAUCAUUGUCAGUGAGCUUC | - | 1145 | S. pyogenes | CCA |
| chr14 | 22924109 | 22924112 | 10419_12_59 | 10419 | AUCAGACAUGAGGAAUGGG | - | 1146 | S. pyogenes | CCA |
| chr14 | 22924112 | 22924115 | 10419_12_60 | 10419 | CUCAUGACAUCAGAGGAAU | - | 1147 | S. pyogenes | CCC |
| chr14 | 22924113 | 22924116 | 10419_12_62 | 10419 | UCUCAUCAGACAUGAGGAA | - | 1148 | S. pyogenes | CCA |
| chr14 | 22924118 | 22924121 | 10419_12_65 | 10419 | CGUAGUCUCAUCAGACAUGA | - | 1149 | S. pyogenes | CCC |
| chr14 | 22924119 | 22924122 | 10419_12_67 | 10419 | CCGUAGUCUCAUCAGACAUG | - | 1150 | S. pyogenes | CCT |
| chr14 | 22924153 | 22924156 | 10419_12_73 | 10419 | AACUGGCAGUUUGAAGAAUG | - | 1151 | S. pyogenes | CCC |
| chr14 | 22924154 | 22924157 | 10419_12_76 | 10419 | GAACUGGCAGUUUGAAGAAU | - | 1152 | S. pyogenes | CCC |
| chr14 | 22924155 | 22924158 | 10419_12_77 | 10419 | AGAACUGGCAGUUUGAAGAA | - | 1153 | S. pyogenes | CCA |
| chr14 | 22924170 | 22924173 | 10419_12_82 | 10419 | UCUGUUUCAGGCUAGAGAAC | - | 1154 | S. pyogenes | CCA |
| chr14 | 22924256 | 22924276 | 10419_11_1 | 10419 | GGUUGCUACUCACGUCACCA | + | 1155 | S. pyogenes | CGG |
| chr14 | 22924263 | 22924283 | 10419_11_4 | 10419 | ACUCACGUCACCACGGCAUU | + | 1156 | S. pyogenes | TGG |
| chr14 | 22924264 | 22924284 | 10419_11_5 | 10419 | CUCACGUCACCACGGCAUUU | + | 1157 | S. pyogenes | GGG |
| chr14 | 22924297 | 22924317 | 10419_11_12 | 10419 | CAGCAUACAGCUUUAUCCGC | + | 1158 | S. pyogenes | CGG |
| chr14 | 22924301 | 22924321 | 10419_11_13 | 10419 | AUACAGCUUUAUCCGCCGGU | + | 1159 | S. pyogenes | CGG |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22924310 | 22924330 | 10419_11_16 | 10419 | + | UAUCCGCCGGUCGGCCUGCU | 1160 | S. pyogenes | TGG |
| chr14 | 22924321 | 22924341 | 10419_11_18 | 10419 | + | CGGCCUGCUUGGCUGCCCGC | 1161 | S. pyogenes | AGG |
| chr14 | 22924322 | 22924342 | 10419_11_21 | 10419 | + | GGCCUGCUUGGCUGCCCGCA | 1162 | S. pyogenes | GGG |
| chr14 | 22924336 | 22924356 | 10419_11_25 | 10419 | + | CCCGCAGGGAAGCGUUCACC | 1163 | S. pyogenes | AGG |
| chr14 | 22924337 | 22924357 | 10419_11_26 | 10419 | + | CCGCAGGGAAGCGUUCACCA | 1164 | S. pyogenes | GGG |
| chr14 | 22924338 | 22924358 | 10419_11_27 | 10419 | + | CGCAGGGAAGCGUUCACCAG | 1165 | S. pyogenes | GGG |
| chr14 | 22924383 | 22924403 | 10419_11_34 | 10419 | + | AUCAGUACCCUAAGAAAGAA | 1166 | S. pyogenes | AGG |
| chr14 | 22924384 | 22924404 | 10419_11_37 | 10419 | + | UCAGUACCCUAAGAAAGAAA | 1167 | S. pyogenes | GGG |
| chr14 | 22924273 | 22924276 | 10419_11_40 | 10419 | - | GGAGAAAACCCAAAUGCCG | 1168 | S. pyogenes | CCA |
| chr14 | 22924294 | 22924297 | 10419_11_44 | 10419 | - | GCGGAUAAAGCUGUAUGCUG | 1169 | S. pyogenes | CCA |
| chr14 | 22924313 | 22924316 | 10419_11_46 | 10419 | - | CAGCCAAGCAGGCCGACGG | 1170 | S. pyogenes | CCG |
| chr14 | 22924316 | 22924319 | 10419_11_47 | 10419 | - | GGGCAGCCAAGCAGGCCGAC | 1171 | S. pyogenes | CCG |
| chr14 | 22924324 | 22924327 | 10419_11_49 | 10419 | - | UUCCCUGCGGGCAGCCAAGC | 1172 | S. pyogenes | CCT |
| chr14 | 22924336 | 22924339 | 10419_11_50 | 10419 | - | CCUGGUGAACGCUUCCCUGC | 1173 | S. pyogenes | CCC |
| chr14 | 22924337 | 22924340 | 10419_11_52 | 10419 | - | CCUGGUGAACGCUUCCCUG | 1174 | S. pyogenes | CCG |
| chr14 | 22924354 | 22924357 | 10419_11_54 | 10419 | - | GGGAGCAGGACGGGGACCCC | 1175 | S. pyogenes | CCA |
| chr14 | 22924362 | 22924365 | 10419_11_57 | 10419 | - | AUGGUGCUGGGAGCAGGACG | 1176 | S. pyogenes | CCC |
| chr14 | 22924363 | 22924366 | 10419_11_58 | 10419 | - | GAUGGUGCUGGGAGCAGGAC | 1177 | S. pyogenes | CCC |
| chr14 | 22924364 | 22924367 | 10419_11_60 | 10419 | - | UGAUGGUGCUGGGAGCAGGA | 1178 | S. pyogenes | CCG |
| chr14 | 22924368 | 22924371 | 10419_11_62 | 10419 | - | GUACUGAUGGUGCUGGGAGC | 1179 | S. pyogenes | CCT |
| chr14 | 22924374 | 22924377 | 10419_11_68 | 10419 | - | CUUAGGGUACUGAUGGUGCU | 1180 | S. pyogenes | CCC |
| chr14 | 22924375 | 22924378 | 10419_11_70 | 10419 | - | UCUUAGGGUACUGAUGGUGC | 1181 | S. pyogenes | CCA |
| chr14 | 22924381 | 22924384 | 10419_11_73 | 10419 | - | UUUCUUUCUUAGGGUACUGA | 1182 | S. pyogenes | CCA |
| chr14 | 22924458 | 22924478 | 10419_10_1 | 10419 | + | AUUGAGGGAAAGCACUCAC | 1183 | S. pyogenes | TGG |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22924465 | 22924485 | 10419_10_3 | 10419 | + | GGAAAGCACUCACUGGACAU | 1184 | S. pyogenes | TGG |
| chr14 | 22924484 | 22924504 | 10419_10_5 | 10419 | + | UUGGUAUCCUUCUCCCUUC | 1185 | S. pyogenes | TGG |
| chr14 | 22924491 | 22924511 | 10419_10_6 | 10419 | + | CCUUCUCCUCUUCUGGUACU | 1186 | S. pyogenes | CGG |
| chr14 | 22924513 | 22924533 | 10419_10_9 | 10419 | + | GUCUAGCAGACAUUUAUAGA | 1187 | S. pyogenes | TGG |
| chr14 | 22924518 | 22924538 | 10419_10_12 | 10419 | + | GCAGACAUUUAUAGAUGGCC | 1188 | S. pyogenes | TGG |
| chr14 | 22924521 | 22924541 | 10419_10_15 | 10419 | + | GACAUUUAUAGAUGGCCUGG | 1189 | S. pyogenes | AGG |
| chr14 | 22924522 | 22924542 | 10419_10_17 | 10419 | + | ACAUUUAUAGAUGGCCUGGA | 1190 | S. pyogenes | GGG |
| chr14 | 22924525 | 22924545 | 10419_10_21 | 10419 | + | UUUAUAGAUGGCCUGGAGGG | 1191 | S. pyogenes | AGG |
| chr14 | 22924491 | 22924494 | 10419_10_28 | 10419 | - | CCGAGUACCAGAGAGAGAGA | 1192 | S. pyogenes | CCT |
| chr14 | 22924497 | 22924500 | 10419_10_33 | 10419 | - | GCUAGACCGAGUACCAGAAG | 1193 | S. pyogenes | CCT |
| chr14 | 22924615 | 22924635 | 10419_9_1 | 10419 | + | GGGCACCACACAGUACCUGC | 1194 | S. pyogenes | TGG |
| chr14 | 22924634 | 22924654 | 10419_9_6 | 10419 | + | CUGGUACUGAGAGAGUAUUGA | 1195 | S. pyogenes | TGG |
| chr14 | 22924635 | 22924655 | 10419_9_7 | 10419 | + | UGGUACUGAGAGAGUAUUGAU | 1196 | S. pyogenes | GGG |
| chr14 | 22924636 | 22924656 | 10419_9_8 | 10419 | + | GGUACUGAGAGAGUAUUUGAUG | 1197 | S. pyogenes | GGG |
| chr14 | 22924686 | 22924706 | 10419_9_16 | 10419 | + | GAUUCCAGAUUGUCCAUCAG | 1198 | S. pyogenes | TGG |
| chr14 | 22924699 | 22924719 | 10419_9_23 | 10419 | + | CCAUCAGUGGCUGAUGAAUG | 1199 | S. pyogenes | AGG |
| chr14 | 22924705 | 22924725 | 10419_9_25 | 10419 | + | GUGGCUGAUGAUGAGAGAAA | 1200 | S. pyogenes | AGG |
| chr14 | 22924611 | 22924614 | 10419_9_27 | 10419 | - | CAGGUACUGUGUGGUGCCCA | 1201 | S. pyogenes | CCC |
| chr14 | 22924612 | 22924615 | 10419_9_28 | 10419 | - | GCAGGUACUGUGUGGUGCCC | 1202 | S. pyogenes | CCT |
| chr14 | 22924620 | 22924623 | 10419_9_29 | 10419 | - | CAGUACCAGCAGUACUGUG | 1203 | S. pyogenes | CCA |
| chr14 | 22924630 | 22924633 | 10419_9_30 | 10419 | - | CAAAUACUCUCACUACCAGC | 1204 | S. pyogenes | CCT |
| chr14 | 22924660 | 22924663 | 10419_9_34 | 10419 | - | GACAUAUGAAGUGUUUGAAA | 1205 | S. pyogenes | CCT |
| chr14 | 22924690 | 22924693 | 10419_9_39 | 10419 | - | UCAGCCACUGAUGGACAAUC | 1206 | S. pyogenes | CCA |
| chr14 | 22924699 | 22924702 | 10419_9_43 | 10419 | - | CCUCAUUCAUCAGCCACUGA | 1207 | S. pyogenes | CCA |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22924864 | 22924884 | 10419_8_4 | 10419 | + | CACUCCAGACCCACCUGAAG | 1208 | S. pyogenes | CGG |
| chr14 | 22924865 | 22924885 | 10419_8_5 | 10419 | + | ACUCCAGACCCACCUGAAGC | 1209 | S. pyogenes | GGG |
| chr14 | 22924866 | 22924886 | 10419_8_7 | 10419 | + | CUCCAGACCCACCUGAAGCG | 1210 | S. pyogenes | GGG |
| chr14 | 22924893 | 22924913 | 10419_8_8 | 10419 | + | CAGAUAGUCUUCAUAGCCCU | 1211 | S. pyogenes | TGG |
| chr14 | 22924908 | 22924928 | 10419_8_11 | 10419 | + | GCCCUUGGCAAAGAGUUCAU | 1212 | S. pyogenes | AGG |
| chr14 | 22924915 | 22924935 | 10419_8_13 | 10419 | + | GCAAAGAGUUCAUAGGCAUU | 1213 | S. pyogenes | AGG |
| chr14 | 22924918 | 22924938 | 10419_8_15 | 10419 | + | AAGAGUUCAUAGGCAUUAGG | 1214 | S. pyogenes | TGG |
| chr14 | 22924921 | 22924941 | 10419_8_18 | 10419 | + | AGUUCAUAGGCAUUAGGUGG | 1215 | S. pyogenes | AGG |
| chr14 | 22924925 | 22924945 | 10419_8_20 | 10419 | + | CAUAGGCAUUAGGUGGAGGA | 1216 | S. pyogenes | CGG |
| chr14 | 22924931 | 22924951 | 10419_8_21 | 10419 | + | CAUUAGGUGGAGGACGGUUC | 1217 | S. pyogenes | TGG |
| chr14 | 22924946 | 22924966 | 10419_8_23 | 10419 | + | GGUUCUGGCUUAAGUAAUCC | 1218 | S. pyogenes | AGG |
| chr14 | 22924952 | 22924972 | 10419_8_27 | 10419 | + | GGCUUAAGUAAUUCCAGGUAU | 1219 | S. pyogenes | TGG |
| chr14 | 22924955 | 22924975 | 10419_8_28 | 10419 | + | UUAAGUAUUCCAGGUAUUGG | 1220 | S. pyogenes | AGG |
| chr14 | 22924959 | 22924979 | 10419_8_32 | 10419 | + | GUAUUCCAGGUAUUGGAGGU | 1221 | S. pyogenes | AGG |
| chr14 | 22924982 | 22925002 | 10419_8_37 | 10419 | + | AGCAGAACUCCUUCUCUGAG | 1222 | S. pyogenes | TGG |
| chr14 | 22924985 | 22925005 | 10419_8_38 | 10419 | + | AGAACUCCUUCUCUGAGUGG | 1223 | S. pyogenes | TGG |
| chr14 | 22924989 | 22925009 | 10419_8_39 | 10419 | + | CUCCUUCUCUGAGUGGGUGGU | 1224 | S. pyogenes | TGG |
| chr14 | 22924868 | 22924871 | 10419_8_48 | 10419 | – | GUCCCCGCUUCAGGUGGGUC | 1225 | S. pyogenes | CCA |
| chr14 | 22924873 | 22924876 | 10419_8_49 | 10419 | – | CUGCAGUCCCCGCUUCAGGU | 1226 | S. pyogenes | CCC |
| chr14 | 22924874 | 22924877 | 10419_8_51 | 10419 | – | UCUGCAGUCCCCGCUUCAGG | 1227 | S. pyogenes | CCA |
| chr14 | 22924877 | 22924880 | 10419_8_52 | 10419 | – | CUAUCUGCAGUCCCCGCUUC | 1228 | S. pyogenes | CCT |
| chr14 | 22924909 | 22924912 | 10419_8_56 | 10419 | – | GCCUAUGAACUCUUUGCCAA | 1229 | S. pyogenes | CCC |
| chr14 | 22924910 | 22924913 | 10419_8_58 | 10419 | – | UGCCUAUGAACUCUUUGCCA | 1230 | S. pyogenes | CCT |
| chr14 | 22924964 | 22924967 | 10419_8_66 | 10419 | – | CUGCUCCUACCUCCAAUACC | 1231 | S. pyogenes | CCA |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22924991 | 22924994 | 10419_8_69 | 10419 | - | CACCAACCACCACUCAGAGA | 1232 | S. pyogenes | CCT |
| chr14 | 22925014 | 22925017 | 10419_8_74 | 10419 | - | GAGGUGCAGUUCAUCAUCAC | 1233 | S. pyogenes | CCT |
| chr14 | 22925033 | 22925036 | 10419_8_79 | 10419 | - | CUGACUUUCUCACAGUUGG | 1234 | S. pyogenes | CCT |
| chr14 | 22925036 | 22925039 | 10419_8_82 | 10419 | - | GGUCUGACUUUUCUCACAGU | 1235 | S. pyogenes | CCA |
| chr14 | 22926116 | 22926136 | 10419_7_3 | 10419 | + | CCCUCCUACCACUCACCUUG | 1236 | S. pyogenes | AGG |
| chr14 | 22926122 | 22926142 | 10419_7_6 | 10419 | + | UACCACUCACCUUGAGGAGC | 1237 | S. pyogenes | CGG |
| chr14 | 22926137 | 22926157 | 10419_7_10 | 10419 | + | GGAGCCGGAAGAGAGCCUC | 1238 | S. pyogenes | TGG |
| chr14 | 22926157 | 22926177 | 10419_7_16 | 10419 | + | UGGUGCAUCUUAGAAAGAAC | 1239 | S. pyogenes | AGG |
| chr14 | 22926174 | 22926194 | 10419_7_18 | 10419 | + | AACAGGAAAUCCCUUCUUAU | 1240 | S. pyogenes | TGG |
| chr14 | 22926179 | 22926199 | 10419_7_21 | 10419 | + | GAAAUCCCUUCUUAUUGGUC | 1241 | S. pyogenes | AGG |
| chr14 | 22926192 | 22926212 | 10419_7_26 | 10419 | + | AUUGGUCAGGAGAAAUGCUAG | 1242 | S. pyogenes | TGG |
| chr14 | 22926193 | 22926213 | 10419_7_29 | 10419 | + | UUGGUCAGGAAAUGCUAGU | 1243 | S. pyogenes | GGG |
| chr14 | 22926194 | 22926214 | 10419_7_30 | 10419 | + | UGGUCAGGAAAUGCUAGUG | 1244 | S. pyogenes | GGG |
| chr14 | 22926201 | 22926221 | 10419_7_34 | 10419 | + | GAAAUGCUAGUGGGGAGAA | 1245 | S. pyogenes | TGG |
| chr14 | 22926213 | 22926233 | 10419_7_36 | 10419 | + | GGGGAGAAUGGCUGCUUUGA | 1246 | S. pyogenes | TGG |
| chr14 | 22926214 | 22926234 | 10419_7_37 | 10419 | + | GGGAGAAUGGCUGCUUUGAU | 1247 | S. pyogenes | GGG |
| chr14 | 22926250 | 22926270 | 10419_7_42 | 10419 | + | CGAUCAAUGACAUGAUUAGA | 1248 | S. pyogenes | TGG |
| chr14 | 22926251 | 22926271 | 10419_7_43 | 10419 | + | GAUCAAUGACAUGAUUAGAU | 1249 | S. pyogenes | GGG |
| chr14 | 22926254 | 22926274 | 10419_7_45 | 10419 | + | CAAUGACAUGAUUAGAUGGG | 1250 | S. pyogenes | AGG |
| chr14 | 22926283 | 22926303 | 10419_7_49 | 10419 | + | CCAAUUUCAAGAGAGCUACAUG | 1251 | S. pyogenes | AGG |
| chr14 | 22926116 | 22926119 | 10419_7_54 | 10419 | - | CCUCAAGGUGAGUGGUAGGA | 1252 | S. pyogenes | CCC |
| chr14 | 22926117 | 22926120 | 10419_7_56 | 10419 | - | UCCUCAAGGUGAGUGGUAGG | 1253 | S. pyogenes | CCT |
| chr14 | 22926120 | 22926123 | 10419_7_59 | 10419 | - | GGCUCCUCAAGGUGAGUGGU | 1254 | S. pyogenes | CCT |
| chr14 | 22926124 | 22926127 | 10419_7_61 | 10419 | - | UUCCGGCUCCUCAAGGUGAG | 1255 | S. pyogenes | CCA |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22926131 | 22926134 | 10419_7_63 | 10419 | - | GCUCAUCUUCCGGCUCUCA | 1256 | S. pyogenes | CCT |
| chr14 | 22926141 | 22926144 | 10419_7_64 | 10419 | - | UGCACCAGAGGCUCAUCUUC | 1257 | S. pyogenes | CCG |
| chr14 | 22926153 | 22926156 | 10419_7_68 | 10419 | - | UUCUUUCUAAGAUGCACCAG | 1258 | S. pyogenes | CCT |
| chr14 | 22926184 | 22926187 | 10419_7_76 | 10419 | - | AUUUUCCUGACCAAUAAGAA | 1259 | S. pyogenes | CCC |
| chr14 | 22926185 | 22926188 | 10419_7_78 | 10419 | - | CAUUUUCCUGACCAAUAAGA | 1260 | S. pyogenes | CCT |
| chr14 | 22926239 | 22926242 | 10419_7_87 | 10419 | - | UGUCAUUGAUCGCUGGCUUG | 1261 | S. pyogenes | CCC |
| chr14 | 22926240 | 22926243 | 10419_7_89 | 10419 | - | AUGUCAUUGAUCGCUGGCUU | 1262 | S. pyogenes | CCC |
| chr14 | 22926241 | 22926244 | 10419_7_90 | 10419 | - | CAUGUCAUUGAUCGCUGGCU | 1263 | S. pyogenes | CCA |
| chr14 | 22926246 | 22926249 | 10419_7_91 | 10419 | - | CUAAUCAUGUCAUUGAUCGC | 1264 | S. pyogenes | CCA |
| chr14 | 22926281 | 22926284 | 10419_7_94 | 10419 | - | UCAUGUAGCUCUCUUGAAAUG | 1265 | S. pyogenes | CCC |
| chr14 | 22926282 | 22926285 | 10419_7_96 | 10419 | - | CUCAUGUAGCUCUUGAAAU | 1266 | S. pyogenes | CCC |
| chr14 | 22926283 | 22926286 | 10419_7_99 | 10419 | - | CCUCAUGUAGCUCUUGAAAU | 1267 | S. pyogenes | CCA |
| chr14 | 22926520 | 22926540 | 10419_6_4 | 10419 | + | UACUAUAUGUCACACAAAGUC | 1268 | S. pyogenes | CGG |
| chr14 | 22926504 | 22926507 | 10419_6_12 | 10419 | - | UAUAGUAAGAGGAUUGCAGU | 1269 | S. pyogenes | CCC |
| chr14 | 22926505 | 22926508 | 10419_6_14 | 10419 | - | CUAUAGUAAGAGGAUUGCAG | 1270 | S. pyogenes | CCA |
| chr14 | 22926515 | 22926518 | 10419_6_18 | 10419 | - | CUUUGUGUGACUAUAGUAAG | 1271 | S. pyogenes | CCT |
| chr14 | 22926539 | 22926542 | 10419_6_22 | 10419 | - | UGAACAGGUGGCACAACUUC | 1272 | S. pyogenes | CCG |
| chr14 | 22926551 | 22926554 | 10419_6_26 | 10419 | - | UCUGUAUUUGACUGAACAGG | 1273 | S. pyogenes | CCA |
| chr14 | 22926728 | 22926748 | 10419_5_4 | 10419 | + | UACUCCCUGUGUGUGUAGU | 1274 | S. pyogenes | TGG |
| chr14 | 22926756 | 22926776 | 10419_5_7 | 10419 | + | UCUCAAUUAUAUCAUCUCUC | 1275 | S. pyogenes | AGG |
| chr14 | 22926764 | 22926784 | 10419_5_9 | 10419 | + | AUAUCAUCUCUCAGGUCCUC | 1276 | S. pyogenes | TGG |
| chr14 | 22926775 | 22926795 | 10419_5_11 | 10419 | + | CAGGUCCUCUGGUGCCACCA | 1277 | S. pyogenes | AGG |
| chr14 | 22926776 | 22926796 | 10419_5_12 | 10419 | + | AGGUCCUCUGGUGCCACCAA | 1278 | S. pyogenes | GGG |
| chr14 | 22926700 | 22926703 | 10419_5_15 | 10419 | - | GGGAGGAGAAACGUGGAUG | 1279 | S. pyogenes | CCA |

TABLE 2-continued

| Chromosome | Start | Stop | ID | Gene_ID | PRMT5-targeting sequences Strand | PRMT5-Targeting Sequence | SEQ ID NO | System | Pam |
|---|---|---|---|---|---|---|---|---|---|
| chr14 | 22926706 | 22926709 | 10419_5_17 | 10419 | - | ACAGUGGGAGGAGAGAAAACG | 1280 | S. pyogenes | CCA |
| chr14 | 22926717 | 22926720 | 10419_5_21 | 10419 | - | CACAGAGGAGUACAGUGGGG | 1281 | S. pyogenes | CCT |
| chr14 | 22926720 | 22926723 | 10419_5_24 | 10419 | - | ACACACAGAGGAGUACAGUG | 1282 | S. pyogenes | CCC |
| chr14 | 22926721 | 22926724 | 10419_5_26 | 10419 | - | CACACACAGAGGAGUACAGU | 1283 | S. pyogenes | CCC |
| chr14 | 22926722 | 22926725 | 10419_5_28 | 10419 | - | ACACACACAGAGGAGUACAG | 1284 | S. pyogenes | CCA |
| chr14 | 22926732 | 22926735 | 10419_5_31 | 10419 | - | UGCACCAACUACACACACAG | 1285 | S. pyogenes | CCT |
| chr14 | 22926780 | 22926783 | 10419_5_40 | 10419 | - | GGUACCCUUGGUGGCACCAG | 1286 | S. pyogenes | CCT |
| chr14 | 22926789 | 22926792 | 10419_5_43 | 10419 | - | CUGGAUGCGGGUACCCUUGG | 1287 | S. pyogenes | CCA |
| chr14 | 22926792 | 22926795 | 10419_5_44 | 10419 | - | GUUCUGGAUGCGGGUACCCU | 1288 | S. pyogenes | CCA |
| chr14 | 22926801 | 22926804 | 10419_5_46 | 10419 | - | UCAUGUGCAGUUCUGGAUGC | 1289 | S. pyogenes | CCC |
| chr14 | 22926802 | 22926805 | 10419_5_48 | 10419 | - | UUCAUGUGCAGUUCUGGAUG | 1290 | S. pyogenes | CCG |
| chr14 | 22926808 | 22926811 | 10419_5_50 | 10419 | - | UGACUGUUCAUGUGCAGUUC | 1291 | S. pyogenes | CCA |
| chr14 | 22927507 | 22927527 | 10419_4_2 | 10419 | + | GGAGCCCCUCAGCUAUACCA | 1292 | S. pyogenes | TGG |
| chr14 | 22927518 | 22927538 | 10419_4_5 | 10419 | + | GCUAUACCAUGGAAGAGUGA | 1293 | S. pyogenes | TGG |
| chr14 | 22927527 | 22927547 | 10419_4_7 | 10419 | + | UGGAAGAGUGAUGGCCAGUG | 1294 | S. pyogenes | TGG |
| chr14 | 22927533 | 22927553 | 10419_4_8 | 10419 | + | AGUGAUGGCCAGUGUGGAUG | 1295 | S. pyogenes | TGG |
| chr14 | 22927537 | 22927557 | 10419_4_9 | 10419 | + | AUGGCCAGUGUGGAUGUGGU | 1296 | S. pyogenes | TGG |
| chr14 | 22927549 | 22927569 | 10419_4_10 | 10419 | + | GAUGUGGUUGGUCAAAACUC | 1297 | S. pyogenes | TGG |
| chr14 | 22927554 | 22927574 | 10419_4_11 | 10419 | + | GGUUGGUCAAAACUCUGGCC | 1298 | S. pyogenes | TGG |
| chr14 | 22927558 | 22927578 | 10419_4_13 | 10419 | + | GGUCAAAACUCUGGCCAGGU | 1299 | S. pyogenes | TGG |
| chr14 | 22927578 | 22927598 | 10419_4_16 | 10419 | + | UGGUGUUAUCUUCCUGAUUA | 1300 | S. pyogenes | AGG |
| chr14 | 22927579 | 22927599 | 10419_4_18 | 10419 | + | GGUUGUUAUCUUCCUGAUUAA | 1301 | S. pyogenes | AGG |
| chr14 | 22927580 | 22927600 | 10419_4_19 | 10419 | + | GUGUUAUCUUCCUGAUUAAG | 1302 | S. pyogenes | GGG |
| chr14 | 22927587 | 22927607 | 10419_4_23 | 10419 | + | CUUCCUGAUUAAGGGGCAGC | 1303 | S. pyogenes | AGG |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22927595 | 22927615 | 10419_4_27 | 10419 | + | UUAAGGGGCAGCAGGAAAGC | 1304 | S. pyogenes | TGG |
| chr14 | 22927636 | 22927656 | 10419_4_29 | 10419 | + | AAAAUUCAGCUCCUGUAACA | 1305 | S. pyogenes | TGG |
| chr14 | 22927641 | 22927661 | 10419_4_32 | 10419 | + | UCAGCUCCUGUAACAUGGCC | 1306 | S. pyogenes | TGG |
| chr14 | 22927646 | 22927666 | 10419_4_36 | 10419 | + | UCCUGUAACAUGGCCUGGAA | 1307 | S. pyogenes | CGG |
| chr14 | 22927657 | 22927677 | 10419_4_39 | 10419 | + | GGCCUGGAACGGAGAUGAAG | 1308 | S. pyogenes | AGG |
| chr14 | 22927511 | 22927514 | 10419_4_41 | 10419 | - | UCUUCCAUGGUAUAGCUGAG | 1309 | S. pyogenes | CCC |
| chr14 | 22927512 | 22927515 | 10419_4_44 | 10419 | - | CUCUUCCAUGGUAUAGCUGA | 1310 | S. pyogenes | CCC |
| chr14 | 22927513 | 22927516 | 10419_4_45 | 10419 | - | ACUCUUCCAUGGUAUAGCUG | 1311 | S. pyogenes | CCT |
| chr14 | 22927524 | 22927527 | 10419_4_47 | 10419 | - | CACUGGCCAUCAUCCACUCCA | 1312 | S. pyogenes | CCA |
| chr14 | 22927541 | 22927544 | 10419_4_51 | 10419 | - | UUGACCAACCACCACCACCACC | 1313 | S. pyogenes | CCA |
| chr14 | 22927572 | 22927575 | 10419_4_53 | 10419 | - | UCAGGAAGAUAACACCACC | 1314 | S. pyogenes | CCA |
| chr14 | 22927590 | 22927593 | 10419_4_59 | 10419 | - | UUUCCUGCUGCCCCUUAAUC | 1315 | S. pyogenes | CCT |
| chr14 | 22927622 | 22927625 | 10419_4_67 | 10419 | - | CUGAAUUUUGGUGCAUAUUU | 1316 | S. pyogenes | CCC |
| chr14 | 22927623 | 22927626 | 10419_4_68 | 10419 | - | GCUGAAUUUUGGUGCAUAUU | 1317 | S. pyogenes | CCA |
| chr14 | 22927634 | 22927637 | 10419_4_70 | 10419 | - | AUGUUACAGGAGCUGAUUU | 1318 | S. pyogenes | CCA |
| chr14 | 22927647 | 22927650 | 10419_4_75 | 10419 | - | UCCGUUCCAGGCCAUGUUAC | 1319 | S. pyogenes | CCT |
| chr14 | 22928110 | 22928130 | 10419_3_2 | 10419 | + | GUCAAACAGUCUUACCGCCU | 1320 | S. pyogenes | CGG |
| chr14 | 22928144 | 22928164 | 10419_3_9 | 10419 | + | AUCUUCUCCACUUUUGAGUC | 1321 | S. pyogenes | TGG |
| chr14 | 22928156 | 22928176 | 10419_3_15 | 10419 | + | UUUGAGUCUGGACGAAUCCA | 1322 | S. pyogenes | TGG |
| chr14 | 22928124 | 22928127 | 10419_3_25 | 10419 | - | GAUUCGCAGGAACUCCGAGG | 1323 | S. pyogenes | CCG |
| chr14 | 22928127 | 22928130 | 10419_3_26 | 10419 | - | GAAGAUUCGCAGGAACUCCG | 1324 | S. pyogenes | CCT |
| chr14 | 22928137 | 22928140 | 10419_3_30 | 10419 | - | CAAAAGUGGAGAAGAUUCGC | 1325 | S. pyogenes | CCT |
| chr14 | 22928151 | 22928154 | 10419_3_36 | 10419 | - | GAUUCGUCCAGACUCAAAAG | 1326 | S. pyogenes | CCA |
| chr14 | 22928173 | 22928176 | 10419_3_41 | 10419 | - | UUGUGGGAAAGCUUUCUCCA | 1327 | S. pyogenes | CCA |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22928189 | 22928192 | 10419_3_44 | 10419 | - | GACUGGAAUACGCUAAUUGU | 1328 | S. pyogenes | CCC |
| chr14 | 22928190 | 22928193 | 10419_3_46 | 10419 | - | AGACUGGAAUACGCUAAUUG | 1329 | S. pyogenes | CCA |
| chr14 | 22928206 | 22928209 | 10419_3_50 | 10419 | - | UUGGGUGGGGAGUGCAGAC | 1330 | S. pyogenes | CCA |
| chr14 | 22928493 | 22928513 | 10419_2_1 | 10419 | + | UACCCCUUCCUGACAGCAGU | 1331 | S. pyogenes | AGG |
| chr14 | 22928508 | 22928528 | 10419_2_4 | 10419 | + | GCAGUAGGUCUGAUCGUGUC | 1332 | S. pyogenes | TGG |
| chr14 | 22928509 | 22928529 | 10419_2_6 | 10419 | + | CAGUAGGUCUGAUCGUGUCU | 1333 | S. pyogenes | GGG |
| chr14 | 22928510 | 22928530 | 10419_2_8 | 10419 | + | AGUAGGUCUGAUCGUGUCUG | 1334 | S. pyogenes | GGG |
| chr14 | 22928515 | 22928535 | 10419_2_10 | 10419 | + | GUCUGAUCGUGUCUGGGGAC | 1335 | S. pyogenes | CGG |
| chr14 | 22928516 | 22928536 | 10419_2_11 | 10419 | + | UCUGAUCGUGUCUGGGGACC | 1336 | S. pyogenes | GGG |
| chr14 | 22928531 | 22928551 | 10419_2_12 | 10419 | + | GGACCGGGCCGAUUCUUAGC | 1337 | S. pyogenes | AGG |
| chr14 | 22928561 | 22928581 | 10419_2_20 | 10419 | + | AUGAACUCCCUCUUGAAACG | 1338 | S. pyogenes | CGG |
| chr14 | 22928565 | 22928585 | 10419_2_22 | 10419 | + | ACUCCCUCUUGAAACGCGGA | 1339 | S. pyogenes | TGG |
| chr14 | 22928573 | 22928593 | 10419_2_24 | 10419 | + | UUGAAACGCGGAUGGAAGAC | 1340 | S. pyogenes | AGG |
| chr14 | 22928583 | 22928603 | 10419_2_28 | 10419 | + | GAUGGAAGACAGGCAUGCAG | 1341 | S. pyogenes | AGG |
| chr14 | 22928490 | 22928493 | 10419_2_32 | 10419 | - | ACUGCUGUCAGGAAGGGGUA | 1342 | S. pyogenes | CCC |
| chr14 | 22928491 | 22928494 | 10419_2_33 | 10419 | - | UACUGCUGUCAGGAAGGGGU | 1343 | S. pyogenes | CCT |
| chr14 | 22928495 | 22928498 | 10419_2_34 | 10419 | - | GACCUACUGCUGUCAGGAAG | 1344 | S. pyogenes | CCC |
| chr14 | 22928496 | 22928499 | 10419_2_36 | 10419 | - | AGACCUACUGCUGUCAGGAA | 1345 | S. pyogenes | CCC |
| chr14 | 22928497 | 22928500 | 10419_2_38 | 10419 | - | CAGACCUACUGCUGUCAGGA | 1346 | S. pyogenes | CCT |
| chr14 | 22928501 | 22928504 | 10419_2_41 | 10419 | - | CGAUCAGACCUACUGCUGUC | 1347 | S. pyogenes | CCT |
| chr14 | 22928534 | 22928537 | 10419_2_42 | 10419 | - | GAACCUGCUAAGAAUCGCCC | 1348 | S. pyogenes | CCG |
| chr14 | 22928539 | 22928542 | 10419_2_44 | 10419 | - | UUCAGGAACCUGCUAAGAAU | 1349 | S. pyogenes | CCG |
| chr14 | 22928556 | 22928559 | 10419_2_51 | 10419 | - | UUUCAAGAGGGAGUUCAUUC | 1350 | S. pyogenes | CCT |
| chr14 | 22928568 | 22928571 | 10419_2_55 | 10419 | - | CUUCCAUCCGCGUUUCAAGA | 1351 | S. pyogenes | CCC |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22928569 | 22928572 | 10419_2_57 | 10419 | - | UCUUCCAUCCGCGUUUCAAG | 1352 | S. pyogenes | CCT |
| chr14 | 22929157 | 22929177 | 10419_1_2 | 10419 | + | CCCCCUCACCCCUGCUUCUC | 1353 | S. pyogenes | CGG |
| chr14 | 22929158 | 22929178 | 10419_1_4 | 10419 | + | CCCCUCACCCCUGCUUCUCC | 1354 | S. pyogenes | GGG |
| chr14 | 22929193 | 22929213 | 10419_1_8 | 10419 | + | CCCUUCCGUCCCCGAGUU | 1355 | S. pyogenes | CGG |
| chr14 | 22929213 | 22929233 | 10419_1_12 | 10419 | + | CGGACCCCGCAUUCCGUCG | 1356 | S. pyogenes | TGG |
| chr14 | 22929216 | 22929236 | 10419_1_14 | 10419 | + | ACCCCGCAUUCCGCUCGUGG | 1357 | S. pyogenes | AGG |
| chr14 | 22929221 | 22929241 | 10419_1_15 | 10419 | + | GCAUUCCGCUCGUGGAGGUC | 1358 | S. pyogenes | CGG |
| chr14 | 22929238 | 22929258 | 10419_1_17 | 10419 | + | GUCCGGCCCUCACCCCUGCU | 1359 | S. pyogenes | TGG |
| chr14 | 22929268 | 22929288 | 10419_1_21 | 10419 | + | CCCUAGUGUGUCAGCUAUUU | 1360 | S. pyogenes | CGG |
| chr14 | 22929269 | 22929289 | 10419_1_22 | 10419 | + | CCUAGUGUGUCAGCUAUUUC | 1361 | S. pyogenes | GGG |
| chr14 | 22929270 | 22929290 | 10419_1_24 | 10419 | + | CUAUUUCGGGGACGCAAUUC | 1362 | S. pyogenes | GGG |
| chr14 | 22929282 | 22929302 | 10419_1_25 | 10419 | + | CUAUUUCGGGGACGCAAUUC | 1363 | S. pyogenes | AGG |
| chr14 | 22929295 | 22929315 | 10419_1_29 | 10419 | + | GCAAUUCAGGGUCCCCCGC | 1364 | S. pyogenes | TGG |
| chr14 | 22929303 | 22929323 | 10419_1_31 | 10419 | + | GGUCCCCCGCUGGACACG | 1365 | S. pyogenes | CGG |
| chr14 | 22929364 | 22929384 | 10419_1_35 | 10419 | + | UCUCCUCGCGCUGUCCACGC | 1366 | S. pyogenes | CGG |
| chr14 | 22929365 | 22929385 | 10419_1_37 | 10419 | + | CUCCUCGCGCUGUCCACGCC | 1367 | S. pyogenes | GGG |
| chr14 | 22929416 | 22929436 | 10419_1_41 | 10419 | + | AGUCAAACUAGUGCCCCAGA | 1368 | S. pyogenes | AGG |
| chr14 | 22929419 | 22929439 | 10419_1_44 | 10419 | + | CAAACUAGUGCCCCAGAGG | 1369 | S. pyogenes | CGG |
| chr14 | 22929420 | 22929440 | 10419_1_45 | 10419 | + | AAACUAGUGCCCCAGAGGC | 1370 | S. pyogenes | GGG |
| chr14 | 22929467 | 22929487 | 10419_1_51 | 10419 | + | GUCUGCCACAGCUCCCGAAC | 1371 | S. pyogenes | AGG |
| chr14 | 22929470 | 22929490 | 10419_1_54 | 10419 | + | UGCCACAGCUCCCGAACAGG | 1372 | S. pyogenes | AGG |
| chr14 | 22929471 | 22929491 | 10419_1_56 | 10419 | + | GCCACAGCUCCCGAACAGGA | 1373 | S. pyogenes | GGG |
| chr14 | 22929475 | 22929495 | 10419_1_58 | 10419 | + | CAGCUCCCGAACAGGAGGA | 1374 | S. pyogenes | TGG |
| chr14 | 22929476 | 22929496 | 10419_1_61 | 10419 | + | AGCUCCCGAACAGGAGGAU | 1375 | S. pyogenes | GGG |

TABLE 2-continued

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22929477 | 22929497 | 10419_1_62 | 10419 | + | GCUCCCGAACAGGAGGAUG | 1376 | S. pyogenes | GGG |
| chr14 | 22929482 | 22929502 | 10419_1_64 | 10419 | + | CGAACAGGAGGAUGGGGAG | 1377 | S. pyogenes | TGG |
| chr14 | 22929502 | 22929522 | 10419_1_66 | 10419 | + | UGGCUUUUCCUGCCAAUCCG | 1378 | S. pyogenes | CGG |
| chr14 | 22929503 | 22929523 | 10419_1_67 | 10419 | + | GGCUUUUCCUGCCAAUCCGC | 1379 | S. pyogenes | GGG |
| chr14 | 22929514 | 22929534 | 10419_1_71 | 10419 | + | CCAAUCCGCGGGCUGCACAG | 1380 | S. pyogenes | TGG |
| chr14 | 22929521 | 22929541 | 10419_1_72 | 10419 | + | GCGGGCUGCACAGUGGCCUA | 1381 | S. pyogenes | CGG |
| chr14 | 22929526 | 22929546 | 10419_1_74 | 10419 | + | CUGCACAGUGGCCUACGGCA | 1382 | S. pyogenes | TGG |
| chr14 | 22929542 | 22929562 | 10419_1_76 | 10419 | + | GGCAUGGAUCCACCAAUCUC | 1383 | S. pyogenes | AGG |
| chr14 | 22929543 | 22929563 | 10419_1_77 | 10419 | + | GCAUGGAUCCACCAAUCUCA | 1384 | S. pyogenes | GGG |
| chr14 | 22929548 | 22929568 | 10419_1_78 | 10419 | + | GAUCCACCAAUCUCAGGGUC | 1385 | S. pyogenes | TGG |
| chr14 | 22929148 | 22929151 | 10419_1_84 | 10419 | - | CAGGGGUGAGGGGUCGCU | 1386 | S. pyogenes | CCT |
| chr14 | 22929153 | 22929156 | 10419_1_85 | 10419 | - | AGAAGCAGGGGUGAGGGGGU | 1387 | S. pyogenes | CCG |
| chr14 | 22929157 | 22929160 | 10419_1_86 | 10419 | - | CCGGAGAAGCAGGGGUGAGG | 1388 | S. pyogenes | CCC |
| chr14 | 22929158 | 22929161 | 10419_1_88 | 10419 | - | CCCGGAGAAGCAGGGGUGAG | 1389 | S. pyogenes | CCC |
| chr14 | 22929159 | 22929162 | 10419_1_90 | 10419 | - | UCCCGGAGAAGCAGGGGUGA | 1390 | S. pyogenes | CCT |
| chr14 | 22929160 | 22929163 | 10419_1_92 | 10419 | - | AUCCCGGAGAAGCAGGGGUG | 1391 | S. pyogenes | CCC |
| chr14 | 22929165 | 22929168 | 10419_1_95 | 10419 | - | UAGUCAUCCCGGAGAAGCAG | 1392 | S. pyogenes | CCT |
| chr14 | 22929166 | 22929169 | 10419_1_96 | 10419 | - | CUAGUCAUCCCGGAGAAGCA | 1393 | S. pyogenes | CCC |
| chr14 | 22929167 | 22929170 | 10419_1_98 | 10419 | - | ACUAGUCAUCCCGGAGAAGC | 1394 | S. pyogenes | CCT |
| chr14 | 22929176 | 22929179 | 10419_1_103 | 10419 | - | GAAGGGCAGACUAGUCAUCC | 1395 | S. pyogenes | CCG |
| chr14 | 22929193 | 22929196 | 10419_1_105 | 10419 | - | CCGAACUCGGGGACGGAGAA | 1396 | S. pyogenes | CCC |
| chr14 | 22929194 | 22929197 | 10419_1_106 | 10419 | - | UCCGAACUCGGGGACGGAGA | 1397 | S. pyogenes | CCT |
| chr14 | 22929200 | 22929203 | 10419_1_111 | 10419 | - | GCGGGGUCCGAACUCGGGGA | 1398 | S. pyogenes | CCG |
| chr14 | 22929204 | 22929207 | 10419_1_114 | 10419 | - | GAAUGCCGGGGUCCGAACUCG | 1399 | S. pyogenes | CCC |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22929205 | 22929208 | 10419_1_116 | 10419 | - | GGAAUGCGGGGUCCGAACUC | 1400 | S. pyogenes | CCC |
| chr14 | 22929206 | 22929209 | 10419_1_117 | 10419 | - | CGGAAUGCGGGGUCCGAACU | 1401 | S. pyogenes | CCG |
| chr14 | 22929217 | 22929220 | 10419_1_120 | 10419 | - | ACCUCCACGAGCGGAAUGCG | 1402 | S. pyogenes | CCC |
| chr14 | 22929218 | 22929221 | 10419_1_121 | 10419 | - | GACCUCCACGAGCGGAAUGC | 1403 | S. pyogenes | CCC |
| chr14 | 22929219 | 22929222 | 10419_1_123 | 10419 | - | GGACCUCCACGAGCGGAAUG | 1404 | S. pyogenes | CCG |
| chr14 | 22929226 | 22929229 | 10419_1_126 | 10419 | - | GAGGGCCCGACCUCCACCAG | 1405 | S. pyogenes | CCG |
| chr14 | 22929240 | 22929243 | 10419_1_129 | 10419 | - | GGCCAAGCAGGGGUGAGGGC | 1406 | S. pyogenes | CCG |
| chr14 | 22929244 | 22929247 | 10419_1_131 | 10419 | - | CUGUGGCCAAGCAGGGGUGA | 1407 | S. pyogenes | CCC |
| chr14 | 22929245 | 22929248 | 10419_1_132 | 10419 | - | GCUGUGGCCAAGCAGGGGUG | 1408 | S. pyogenes | CCT |
| chr14 | 22929250 | 22929253 | 10419_1_135 | 10419 | - | UAGGGGCUGUGGCCAAGCAG | 1409 | S. pyogenes | CCC |
| chr14 | 22929251 | 22929254 | 10419_1_137 | 10419 | - | CUAGGGGCUGUGGCCAAGCA | 1410 | S. pyogenes | CCC |
| chr14 | 22929252 | 22929255 | 10419_1_138 | 10419 | - | ACUAGGGGCUGUGGCCAAGC | 1411 | S. pyogenes | CCT |
| chr14 | 22929261 | 22929264 | 10419_1_139 | 10419 | - | AGCUGACACUAGGGGCUG | 1412 | S. pyogenes | CCA |
| chr14 | 22929267 | 22929270 | 10419_1_141 | 10419 | - | CGAAAUAGCUGACACUAG | 1413 | S. pyogenes | CCC |
| chr14 | 22929268 | 22929271 | 10419_1_142 | 10419 | - | CCGAAAUAGCUGACACACUA | 1414 | S. pyogenes | CCC |
| chr14 | 22929269 | 22929272 | 10419_1_144 | 10419 | - | CCCGAAAUAGCUGACACACU | 1415 | S. pyogenes | CCT |
| chr14 | 22929306 | 22929309 | 10419_1_149 | 10419 | - | GAGCCGCGUGUCCAGCGGA | 1416 | S. pyogenes | CCC |
| chr14 | 22929307 | 22929310 | 10419_1_151 | 10419 | - | GGAGCCGCGUGUCCAGCGG | 1417 | S. pyogenes | CCT |
| chr14 | 22929310 | 22929313 | 10419_1_154 | 10419 | - | GUGGGAGCCGCGUGUCCAGC | 1418 | S. pyogenes | CCC |
| chr14 | 22929311 | 22929314 | 10419_1_156 | 10419 | - | GGUGGGAGCCGCGUGUCCAG | 1419 | S. pyogenes | CCG |
| chr14 | 22929328 | 22929331 | 10419_1_159 | 10419 | - | UGGCGGUCGGGGGUGCUGGU | 1420 | S. pyogenes | CCC |
| chr14 | 22929329 | 22929332 | 10419_1_161 | 10419 | - | AUGGCGGUCGGGGGUGCUGG | 1421 | S. pyogenes | CCA |
| chr14 | 22929332 | 22929335 | 10419_1_162 | 10419 | - | GCGAUGGCGGUCGGGGGUGC | 1422 | S. pyogenes | CCA |
| chr14 | 22929338 | 22929341 | 10419_1_164 | 10419 | - | AUGGCGGCGAUGGCGGUCGG | 1423 | S. pyogenes | CCC |

TABLE 2-continued

PRMT5-targeting sequences

| Chromo-some | Start | Stop | ID | Gene_ID | Strand | PRMT5-Targeting Sequence | SEQ ID NO | System | Pam |
|---|---|---|---|---|---|---|---|---|---|
| chr14 | 22929339 | 22929342 | 10419_1_165 | 10419 | - | GAUGGCGGCGAUGGCGGUCG | 1424 | S. pyogenes | CCC |
| chr14 | 22929340 | 22929343 | 10419_1_168 | 10419 | - | AGAUGGCGGCGAUGGCGGUC | 1425 | S. pyogenes | CCC |
| chr14 | 22929341 | 22929344 | 10419_1_169 | 10419 | - | AAGAUGGCGGCGAUGGCGGU | 1426 | S. pyogenes | CCG |
| chr14 | 22929345 | 22929348 | 10419_1_170 | 10419 | - | GAGAAAGAUGGCGGCGAUGG | 1427 | S. pyogenes | CCG |
| chr14 | 22929348 | 22929351 | 10419_1_171 | 10419 | - | GAGGAGAAAGAUGGCGGCGA | 1428 | S. pyogenes | CCA |
| chr14 | 22929354 | 22929357 | 10419_1_172 | 10419 | - | CAGCGCGAGGAGAAAGAUGG | 1429 | S. pyogenes | CCG |
| chr14 | 22929357 | 22929360 | 10419_1_173 | 10419 | - | GGACAGCCGCGAGGAGAAAGA | 1430 | S. pyogenes | CCA |
| chr14 | 22929367 | 22929370 | 10419_1_177 | 10419 | - | AUCCCGGCGUGGACAGCCGCG | 1431 | S. pyogenes | CCT |
| chr14 | 22929378 | 22929381 | 10419_1_180 | 10419 | - | AGUAUCAAGGAAUCCCGGCG | 1432 | S. pyogenes | CCA |
| chr14 | 22929383 | 22929386 | 10419_1_181 | 10419 | - | CUACUAGUAUCAAGGAAUCC | 1433 | S. pyogenes | CCG |
| chr14 | 22929391 | 22929394 | 10419_1_187 | 10419 | - | GUGAUUGGCUACUAGUAUCA | 1434 | S. pyogenes | CCT |
| chr14 | 22929406 | 22929409 | 10419_1_190 | 10419 | - | CACUAGUUUGACUUUGUGAU | 1435 | S. pyogenes | CCA |
| chr14 | 22929429 | 22929432 | 10419_1_193 | 10419 | - | GCGACUCGUCCCGCCUUCUG | 1436 | S. pyogenes | CCC |
| chr14 | 22929430 | 22929433 | 10419_1_195 | 10419 | - | GGCGACUCGUCCCGCCUUCU | 1437 | S. pyogenes | CCC |
| chr14 | 22929431 | 22929434 | 10419_1_197 | 10419 | - | AGGCGACUCGUCCCGCCUUC | 1438 | S. pyogenes | CCA |
| chr14 | 22929451 | 22929454 | 10419_1_199 | 10419 | - | GGCAGAGCGCUCUGGUUGUUA | 1439 | S. pyogenes | CCT |
| chr14 | 22929460 | 22929463 | 10419_1_200 | 10419 | - | GGGAGCUGUGGGCAGACGCUC | 1440 | S. pyogenes | CCA |
| chr14 | 22929472 | 22929475 | 10419_1_202 | 10419 | - | UCCCUCCUGUUCGGGAGCUG | 1441 | S. pyogenes | CCA |
| chr14 | 22929480 | 22929483 | 10419_1_206 | 10419 | - | ACUCCCCAUCCUCCCUGUUC | 1442 | S. pyogenes | CCC |
| chr14 | 22929481 | 22929484 | 10419_1_207 | 10419 | - | CACUCCCCAUCCUCCCUGUU | 1443 | S. pyogenes | CCG |
| chr14 | 22929510 | 22929513 | 10419_1_211 | 10419 | - | UGUGCAGCCCGCGGAUUGGC | 1444 | S. pyogenes | CCT |
| chr14 | 22929514 | 22929517 | 10419_1_212 | 10419 | - | CCACUGUGCAGCCCGCGGAU | 1445 | S. pyogenes | CCA |
| chr14 | 22929519 | 22929522 | 10419_1_214 | 10419 | - | GUACGCCACUGUGCAGCCCG | 1446 | S. pyogenes | CCG |
| chr14 | 22929551 | 22929554 | 10419_1_217 | 10419 | - | GAACCAGACCCUGAGAUUGG | 1447 | S. pyogenes | CCA |

TABLE 2-continued

PRMT5-targeting sequences

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22929554 | 22929557 | 10419_1_218 | 10419 | - | CAGGAACCAGACCCUGAGAU | 1448 | S. pyogenes | CCA |
| chr14 | 22929573 | 22929576 | 10419_1_225 | 10419 | - | CUGGGAGAUUGAAGUCCGUC | 1449 | S. pyogenes | CCT |
| chr14 | 22920568 | 22920588 | 10419_17_20 | 10419 | + | ACAAAACCAUCAAAACAAGA | 1450 | S. thermophilis | ACAGAAA |
| chr14 | 22920988 | 22921008 | 10419_17_104 | 10419 | + | UUCUUGGAAUUGCUGCAUCG | 1451 | S. thermophilis | CCAGAAA |
| chr14 | 22921042 | 22921062 | 10419_17_118 | 10419 | + | ACCGUUAUGGGCUGCUGUAA | 1452 | S. thermophilis | GAAGAAA |
| chr14 | 22920622 | 22920629 | 10419_17_156 | 10419 | - | AGAACUCCCUGGAAUAUCCC | 1453 | S. thermophilis | GUUCUCA |
| chr14 | 22920644 | 22920651 | 10419_17_162 | 10419 | - | UGAAGCUACGCACUCAGCCU | 1454 | S. thermophilis | GUUCUUG |
| chr14 | 22920839 | 22920846 | 10419_17_214 | 10419 | - | UCAGGUUCUGCUCCUGUAGU | 1455 | S. thermophilis | CUUCUGU |
| chr14 | 22920987 | 22920994 | 10419_17_235 | 10419 | + | UUCUGGGCGAUGCAGCAAUUC | 1456 | S. thermophilis | CUUCUUG |
| chr14 | 22923098 | 22923118 | 10419_13_25 | 10419 | + | CUUGGAGAAGAGAUGGGAG | 1457 | S. thermophilis | CCAGAAA |
| chr14 | 22923041 | 22923048 | 10419_13_41 | 10419 | - | AAGGACCGUGACCCUGAGGU | 1458 | S. thermophilis | GUUCUUU |
| chr14 | 22923065 | 22923072 | 10419_13_47 | 10419 | - | AAUGAGGUCCGAGCCUGUAG | 1459 | S. thermophilis | CUUCUCU |
| chr14 | 22924173 | 22924180 | 10419_12_84 | 10419 | - | UAUUGUCUCUGUUUCAGGCU | 1460 | S. thermophilis | GUUCUCT |
| chr14 | 22924373 | 22924393 | 10419_11_29 | 10419 | + | UCCCAGCACCAUCAGUACCC | 1461 | S. thermophilis | TAAGAAA |
| chr14 | 22924377 | 22924397 | 10419_11_31 | 10419 | + | AGCACCAUCAGUACCCUAAG | 1462 | S. thermophilis | AAAGAAA |
| chr14 | 22924528 | 22924548 | 10419_10_24 | 10419 | + | AUAGAUGGCCUGGAGGGAGG | 1463 | S. thermophilis | AGAGAAT |
| chr14 | 22924492 | 22924499 | 10419_10_29 | 10419 | - | CUAGACCGAGUACCAGAAGA | 1464 | S. thermophilis | CUUCUCC |
| chr14 | 22924500 | 22924507 | 10419_10_35 | 10419 | - | AAUGUCUGCUAGACCGAGUA | 1465 | S. thermophilis | CUUCUGG |
| chr14 | 22925023 | 22925043 | 10419_8_44 | 10419 | + | AUGAACUGCACCUCCAACUG | 1466 | S. thermophilis | TGAGAAA |
| chr14 | 22924947 | 22924954 | 10419_8_61 | 10419 | - | CAAUACCUGGAAUACUUAAG | 1467 | S. thermophilis | GUUCUGG |
| chr14 | 22924992 | 22924999 | 10419_8_70 | 10419 | - | ACAGGCACCAACCACCACUC | 1468 | S. thermophilis | CUUCUCT |
| chr14 | 22926146 | 22926166 | 10419_7_11 | 10419 | + | AGAUGAGCCCUGGUGCAUC | 1469 | S. thermophilis | TTAGAAA |
| chr14 | 22926195 | 22926215 | 10419_7_32 | 10419 | + | GGUCAGGAAAAUGCUAGUGG | 1470 | S. thermophilis | GGAGAAT |
| chr14 | 22926288 | 22926308 | 10419_7_52 | 10419 | + | UUCAAGAGCUACAUGAGGCA | 1471 | S. thermophilis | AAAGAAA |

TABLE 2-continued

| Chromosome | Start | Stop | ID | Gene_ID | Strand | PRMT5-Targeting Sequence | SEQ ID NO | System | Pam |
|---|---|---|---|---|---|---|---|---|---|
| chr14 | 22926186 | 22926193 | 10419_7_79 | 10419 | - | ACUAGCAUUUCCUGACCAA | 1472 | S. thermophilis | CTTCTTA |
| chr14 | 22928157 | 22928177 | 10419_3_17 | 10419 | + | UUGAGUCUGGACGAAUCCAU | 1473 | S. thermophilis | GGAGAAA |
| chr14 | 22928146 | 22928153 | 10419_3_32 | 10419 | - | AUUCGUCCAGACUCAAAAGU | 1474 | S. thermophilis | CTTCTCC |
| chr14 | 22929572 | 22929592 | 10419_1_81 | 10419 | + | UCCUGACGAACUUCAAUCUC | 1475 | S. thermophilis | CCAGAAT |
| chr14 | 22929171 | 22929178 | 10419_1_99 | 10419 | - | AAGGGCAGACUAGUCAUCCC | 1476 | S. thermophilis | CTTCTCC |
| chr14 | 22929195 | 22929202 | 10419_1_107 | 10419 | - | CGGGGUCCGAACUCGGGGAC | 1477 | S. thermophilis | CTTCTCC |

TALEN to Inhibit PRMT5

By "TALEN" or "TALEN to PRMT5" or "TALEN to inhibit PRMT5" and the like is meant a transcription activator-like effector nuclease, an artificial nuclease which can be used to edit the PRMT5 gene.

TALENs are produced artificially by fusing a TAL effector DNA binding domain to a DNA cleavage domain. Transcription activator-like effects (TALEs) can be engineered to bind any desired DNA sequence, including a portion of the PRMT5 gene. By combining an engineered TALE with a DNA cleavage domain, a restriction enzyme can be produced which is specific to any desired DNA sequence, including a PRMT5 sequence. These can then be introduced into a cell, wherein they can be used for genome editing. Boch 2011 Nature Biotech. 29: 135-6; and Boch et al. 2009 Science 326: 1509-12; Moscou et al. 2009 Science 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. 2011 Nucl. Acids Res. 39: e82; Miller et al. 2011 Nature Biotech. 29: 143-8; Hockemeyer et al. 2011 Nature Biotech. 29: 731-734; Wood et al. 2011 Science 333: 307; Doyon et al. 2010 Nature Methods 8: 74-79; Szczepek et al. 2007 Nature Biotech. 25: 786-793; and Guo et al. 2010 J. Mol. Biol. 200: 96.

The Fold domain functions as a dimer, requiring two constructs with unique DNA binding domains for sites in the target genome with proper orientation and spacing. Both the number of amino acid residues between the TALE DNA binding domain and the Fold cleavage domain and the number of bases between the two individual TALEN binding sites appear to be important parameters for achieving high levels of activity. Miller et al. 2011 Nature Biotech. 29: 143-8.

A PRMT5 TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the PRMT5 gene or introduce such a defect into a wt PRMT5 gene, thus decreasing expression of PRMT5.

TALENs specific to sequences in PRMT5 can be constructed using any method known in the art, including various schemes using modular components. Zhang et al. 2011 Nature Biotech. 29: 149-53; Geibler et al. 2011 PLoS ONE 6: e19509.

Zinc Finger Nuclease to Inhibit PRMT5

By "ZFN" or "Zinc Finger Nuclease" or "ZFN to PRMT5" or "ZFN to inhibit PRMT5" and the like is meant a zinc finger nuclease, an artificial nuclease which can be used to edit the PRMT5 gene.

Like a TALEN, a ZFN comprises a FokI nuclease domain (or derivative thereof) fused to a DNA-binding domain. In the case of a ZFN, the DNA-binding domain comprises one or more zinc fingers. Carroll et al. 2011. Genetics Society of America 188: 773-782; and Kim et al. Proc. Natl. Acad. Sci. USA 93: 1156-1160.

A zinc finger is a small protein structural motif stabilized by one or more zinc ions. A zinc finger can comprise, for example, $Cys_2His_2$, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. 1998 Proc. Natl. Acad. Sci. USA 95: 10570-5.

Also like a TALEN, a ZFN can create a double-stranded break in the DNA, which can create a frame-shift mutation if improperly repaired, leading to a decrease in the expression and level and/or activity of PRMT5 in a cell. ZFNs can also be used with homologous recombination to mutate, or repair defects, in the PRMT5 gene.

ZFNs specific to sequences in PRMT5 can be constructed using any method known in the art. Cathomen et al. Mol. Ther. 16: 1200-7; and Guo et al. 2010. J. Mol. Biol. 400: 96.

Low Molecular Weight Compounds to Inhibit PRMT5

Many small molecules have been found which have inhibitory properties against PRMT5.

Examples of inhibitors to PRMT5 activity include, but are not limited to, those known in the art. Exemplary PRMT5 inhibitors include, as non-limiting examples:

PRMT inhibitors disclosed by Cheng, et al. in a publication J. Biol. Chem., 2004, 279, 23, 23892-23899;

Sinefungin (5'-Deoxy-5'-(1,4-diamino-4-carboxybutyl) adenosine), which inhibits PRMT5 activity, methylating the substrate E2-F-1, as disclosed in the Declaration of La Thangue, dated Apr. 23, 2014, in U.S. Patent Application Publ. No. 20130011497 (U.S. patent application Ser. No. 13/518,200), and a publication by Antonysamy et al. 2012 Proc. Natl. Acad. Sci. U.S.A. 109: 17960-17965, and has the molecular structure

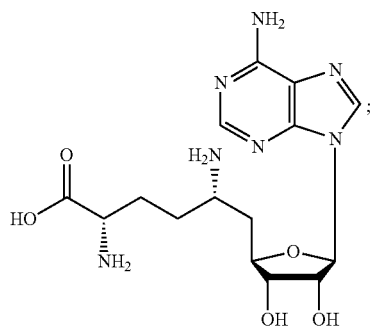

PRMT5 inhibitors CMP5, HLCL7 and CMP12, as disclosed in a publication by Roach et al. 2013 Blood 122 (21);

PRMT5 inhibitors BLL-1 and BLL-3, as disclosed in a publication by Parekh et al., 2011 Sem. Cancer Biol. 21: 335-346, and Yan et al. 2013 Cancer Res. 73 (8), Supp. 1, which describe;

PRMT5 inhibitors selected from: compound CMP5 (BLL1) and various derivatives thereof, including BLL2-BLL8 and BLL36, as disclosed in U.S. Pat. Appl. Publ. No. US20130059892 and International Pat. Publ. No. WO 2011/079236 to Baiocchi et al.;

PRMT5 inhibitors CMP5 and BLL54, as disclosed in a publication by Gordon, 2012, Targeting Protein Arginine Methyltransferase 5 (PRMT5) Overexpression by Use of Small Molecule PRMT5 Inhibitors in Glioblastoma Multiforme (GBM), Honors Research Thesis, Ohio State University;

A cell line study disclosing that inhibition of PRMT5 induces lymphoma cell death in different non-Hodgkin lymphoma cell lines through reactivation of the retinoblastoma tumor pathway and polycomb repressor complex 2 (PRC2) silencing in a publication by Chung et al. 2013 J. Biol. Chem. 288: 35534-47;

Lysine and arginine protein methyltransferase inhibitors of Formulas I, II and III:

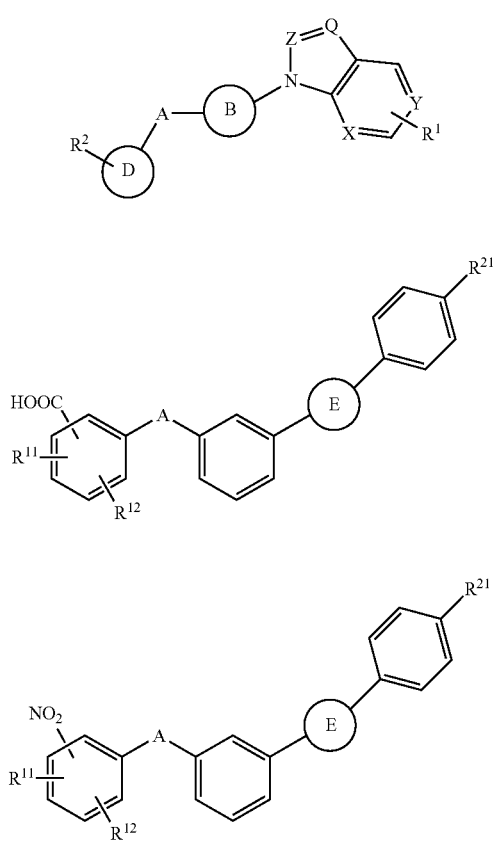

Wherein:
Q is chosen from —CH— and —N—;
X is chosen from —CH— and —N—;
Y is chosen from —CR$^1$— and —N—;
Z is chosen from —CH— and —N—;
R$^1$ is chosen from (C$_1$-C$_4$)alkyl, halogen and optionally substituted aryl;
B is chosen from
(a) aryl optionally substituted with from one to three substituents chosen independently from halogen, OH, —NR$^5$R$^9$, (C$_1$-C$_4$)alkyl, (C$_1$-C$_4$)alkoxy, —COOR$^5$, —NH(C=O)R$^5$, —NH(C=O)NR$^5$R$^9$, —NH(C=O)OR$^7$, —O(C=O)NR$^5$R$^9$ and —NHSO$_2$R$^7$;

(b) heteroaryl, optionally substituted with from one to three substituents chosen independently from halogen, OH, —NR$^5$R$^9$, (C$_1$-C$_4$)alkyl, (C$_1$-C$_4$)alkoxy, —COOR$^5$, NH(C=O)R$^5$, —NH(C=O)NR$^5$R$^9$, —NH(C=O)OR$^7$, —O(C=O)NR$^5$R$^9$ and —NHSO$_2$R$^7$; and (c) non-aromatic heterocyclyl;

A is (C$_2$-C$_7$)-alkylene in which one or more —CH$_2$— may be replaced by a radical chosen from —CH(OH)—, —CH (NH$_2$)—, CHF, CF$_2$, —C(=O)—, —CH(O-loweralkyl)-, —CH(NH-loweralkyl)-, —O—, —S—, —SO—, —SO$_2$—, —NH— and —N[(C$_1$-C$_4$)alkyl]-; or two adjacent —CH$_2$— may be replaced by —CH=CH—;

D is chosen from a (C$_4$-C$_{12}$)carbocycle, a 4- to 7-membered monocyclic heterocycle and a 7- to 12-membered bicyclic heterocycle;

R$^2$ represents from one to three substituents each independently chosen from hydrogen, COOH, OH, SO$_2$NH-Het, SO$_2$(C$_1$-C$_4$)alkyl, acylsulfonamide, NO$_2$, halogen, (C$_1$-C$_4$) alkyl, (C$_1$-C$_4$)alkoxy, halo(C$_1$-C$_4$)alkyl, halo(C$_1$-C$_4$)alkoxy, cyano, phenyl, substituted phenyl, heterocyclyl, —CHO, —CH(R$^5$)NR$^5$R$^9$ and —NR$^5$R$^9$, with the proviso that at least one instance of R$^2$ must be other than hydrogen;

Het is an optionally substituted heteroaryl;

R$^5$ is chosen independently in each occurrence from hydrogen, (C$_1$-C$_4$)alkyl, aryl and heteroaryl;

R$^7$ is chosen independently in each occurrence from (C$_1$-C$_4$)alkyl and aryl; and R$^9$ is chosen from hydrogen, (C$_1$-C$_4$)alkyl, aryl and heteroaryl, or, R$^5$ and R$^9$ taken together with the nitrogen to which they are attached, form a 5-8-membered nitrogen heterocycle;

E is chosen from
(a) aryl, optionally substituted with from one to three substituents chosen independently from halogen, OH, —NR$^5$R$^9$, (C$_1$-C$_4$)alkyl, (C$_1$-C$_4$)alkoxy, halo(C$_1$-C$_4$)alkyl, halo(C$_1$-C$_4$)alkoxy;

(b) heteroaryl, optionally substituted with from one to three substituents chosen independently from halogen, OH, —NR$^5$R$^9$, (C$_1$-C$_4$)alkyl, (C$_1$-C$_4$)alkoxy, halo(C$_1$-C$_4$)alkyl, halo(C$_1$-C$_4$)alkoxy;

(c) non-aromatic heterocyclyl, optionally substituted with from one to three substituents chosen independently from halogen, OH, —NR$^5$R$^9$, (C$_1$-C$_4$)alkyl, (C$_1$-C$_4$)alkoxy, halo (C$_1$-C$_4$)alkyl, and halo(C$_1$-C$_4$)alkoxy;

R$^1$ is one or two substituents chosen from H, (C$_1$-C$_4$)alkyl and halo(C$_1$-C$_4$)alkyl;

R$^5$ is chosen independently in each occurrence from hydrogen, (C$_1$-C$_4$)alkyl, aryl and heteroaryl;

R$^7$ is chosen from (C$_1$-C$_4$)alkyl and aryl; and

R$^9$ is chosen from hydrogen, (C$_1$-C$_4$)alkyl, aryl and heteroaryl, or, R$^5$ and R$^9$ taken together with the nitrogen to which they are attached, form a 5-8-membered nitrogen heterocycle;

R$^{11}$ and R$^{12}$ are chosen independently from H, CH$_3$, OH, CF$_3$, halogen and (C$_1$-C$_4$)alkoxy; and R$^{21}$ is one or two substituents chosen from hydrogen, (C$_1$-C$_4$)alkyl, halo(C$_1$-C$_4$)alkyl, cyano, NO$_2$, halogen, (C$_1$-C$_4$)acyl and (C$_1$-C$_4$)alkoxycarbonyl, as disclosed in WO 2011/082098;

PRMT inhibitors of Formulas IV, V and VI:

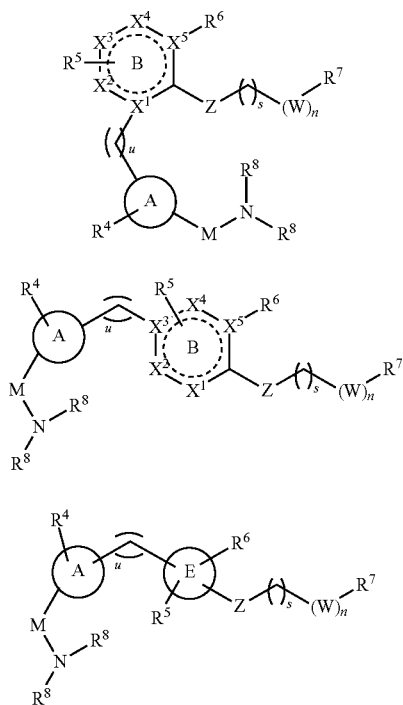

(IV)

(V)

(VI)

and N-oxides, hydrates, solvates, pharmaceutically acceptable salts, prodrugs and complexes thereof and racemic mixtures, diastereomers, enantiomers and tautomers thereof, wherein A is a cycloalkyl ring, a heterocyclic ring, a heteroaryl ring, or an aryl ring; B is selected from the group consisting of phenyl, and a 5- or 6-membered heteroaryl, wherein when B is a 5-membered heteroaryl, $X^4$ is a bond, and $X^1$, $X^2$, $X^3$ and $X^5$ are each independently selected from the group consisting of C, N, O and S, provided that at least one of $X^1$, $X^2$, $X^3$ and $X^5$ is N, O or S, and provided that for Formula (IV), $X^1$ is not O or S, and for Formula (V), $X^3$ is not O or S; and when B is a 6-membered heteroaryl, each of $X^1$, $X^2$, $X^3$, $X^4$ and $X^5$ are independently C or N, provided that at least one of $X^1$, $X^2$, $X^3$, $X^4$ and $X^5$ are N; E is a 5 to 10-membered heterocycle, preferably a 9-membered heterocycle; M is selected from the group consisting of

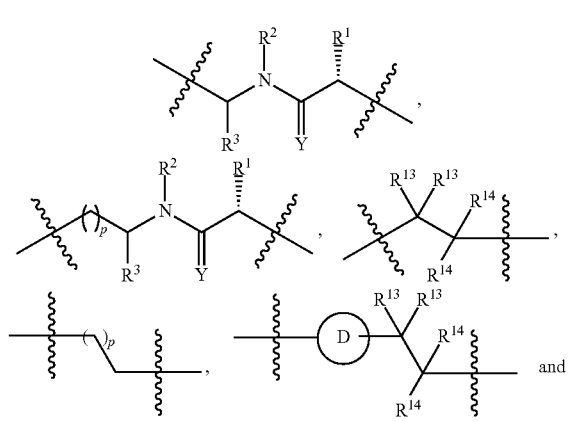

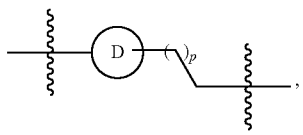

or M is selected from the group consisting of

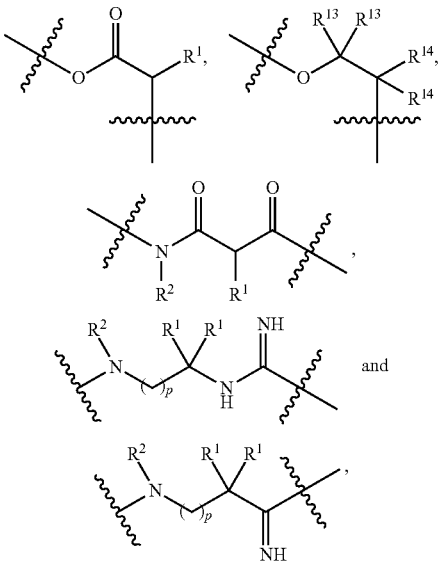

or M is selected from the group consisting of

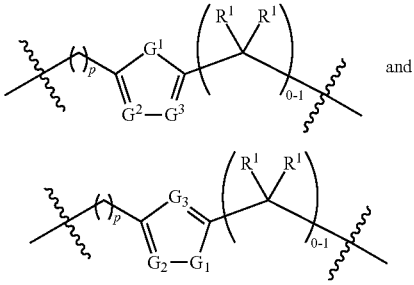

or M is selected from the group consisting of

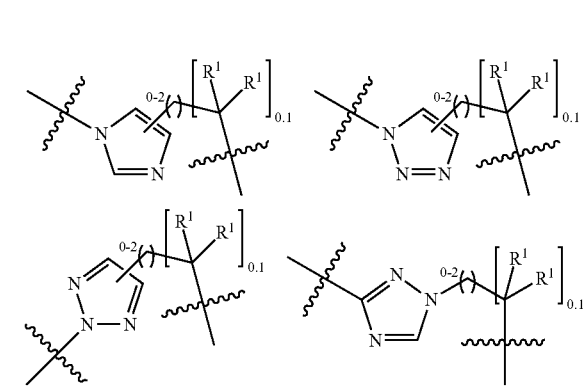

-continued

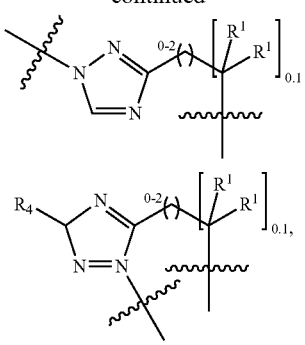

wherein p is 1, 2 or 3; each $R^{13}$ is independently selected from the group consisting of H and $C_1$-$C_4$alkyl; each $R^{14}$ is independently selected from the group consisting of H and $C_1$-$C_4$alkyl; or alternatively, $R^8$ and $R^{14}$ may join to form a 4, 5- or 6-membered saturated ring containing one N atom; and ring D is a heterocycle, preferably selected from the group consisting of -continued

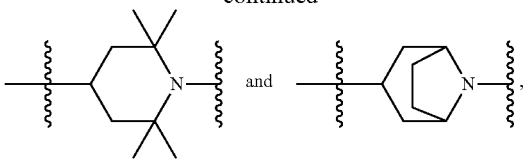

wherein the left side of ring D as shown is attached to ring A; and wherein Q is selected from the group consisting of —N($R^{15}$)—, O and S; and $R^{15}$ is $C_1$-$C_6$alkyl; and each $R^1$ is independently selected from the group consisting of H, —OH, —$CF_3$, —$CHF_2$, —$CH_2F$, halo, —CN, alkyl, alkenyl, alkynyl, aryl, heteroaryl, alkoxy, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$aryl, —O-heteroaryl, —S(O)$_{0-1}$-heteroaryl, -alkyl-cycloalkyl, -alkyl-heterocyclyl, -alkyl-aryl, -alkyl-heteroaryl and =O ($R^1$ is preferably H, Me, Et, propyl, iso-propyl, —$CF_3$, $CH_2Ph$, OH or OPh; $R^2$ is selected from the group consisting of H, alkyl, aryl, heteroaryl, cycloalkyl, heterocyclyl, -alkyl-aryl, -alkyl-heteroaryl, -alkyl-cycloalkyl and -alkyl-heterocycle, each of which is optionally substituted (preferably $R^2$ is H, Me or Et); or $R^1$ and $R^2$ together form a 5-, 6- or 7-membered heterocycle, each of which is optionally substituted; or $R^2$ optionally bonds with Ring A to form a 5 or 6 membered heterocycle fused to ring A; $R^3$ is selected from the group consisting of H, —OH, —$CF_3$, —$CHF_2$, —$CH_2F$, halo, —CN, alkyl, alkenyl, alkynyl, aryl, heteroaryl, alkoxy, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$-aryl, —O-heteroaryl, —S(O)$_{0-1}$-heteroaryl, -alkyl-cycloalkyl, -alkyl-heterocyclyl, -alkyl-aryl, -alkyl-heteroaryl and =O (preferably $R^3$ is H or $C_1$-$C_4$ alkyl); or $R^2$ together with $R^3$ optionally form a 4-, 5-, 6- or 7-membered heterocycle, each of which is optionally substituted; $R^4$ is selected from the group consisting of H, —OH, halo, —CN, alkyl, alkenyl, alkynyl, aryl, heteroaryl, alkoxy, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$aryl, —O-heteroaryl, —S(O)$_{0-1}$-heteroaryl, -alkyl-cycloalkyl, -alkyl-heterocyclyl, -alkyl-aryl, -alkyl-heteroaryl and =O, each of which is optionally substituted, (preferably $R^4$ is selected from the group consisting of H, halogen, CN, alkyl, substituted alkyl, —O—($C_1$-$C_4$alkyl), —S—($C_1$-$C_4$alkyl) and —S(O)$_2$—($C_1$-$C_4$alkyl)); $R^5$ is selected from the group consisting of H, —$NO_2$, halo, —CN, —$CF_3$, —$CHF_2$, —$CH_2F$, —OH, —SH, $C_1$-$C_6$alkyl, $C_2$-$C_6$alkenyl, $C_2$-$C_6$alkynyl, alkoxy, cycloalkyl, heterocyclyl, aryl, heteroaryl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, =O, —O-aryl, —S(O)$_{0-1}$-aryl, —O-heteroaryl, —S(O)$_{0-1}$-heteroaryl, —O—C(O)—N($R^2$)$_2$, —N($R^2$)—C(O)—O—$R^2$, —C(O)—NH2, —C(O)—O—$R^2$, —C(O)—N($R^2$)$_2$, (preferably $R^5$ is selected from the group consisting of H, Me, Et, propyl, iso-propyl, OMe, OEt, SMe, $SO_2Me$, $CF_3$ and $OCF_3$); $R^6$ is selected from the group consisting of H, —CN, alkyl, alkenyl, alkynyl, halo, —OH, —SH, =O, —$CF_3$, —$CHF_2$, —$CHF_2$, alkoxy, aryl, heteroaryl, cycloalkyl, heterocyclyl, —O— alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$-aryl, —O-heteroaryl and —S(O)$_{0-1}$-heteroaryl, (preferably $R^6$ is selected from the group consisting of H, Me, Et, —$NH_2$, —$CF_3$ and —$NO_2$); $R^7$ is selected from the group consisting of cycloalkyl, substituted cycloalkyl, heterocycle, substituted heterocycle, aryl, substituted aryl, heteroaryl and substituted heteroaryl, alkyl, optionally substituted alkyl; each $R^8$ is independently selected from the group consisting of H and $C_1$-$C_4$alkyl; Y is nil (i.e., =Y is —H), O, S or —N($R^8$); $G^1$ is O, S or $NR^8$; $G^2$ is N or CH; and $G^3$ is N or CH; and Z is a moiety selected from the group consisting of a bond, —O—, —N($R^9$)—, —S—, —C(O)—, optionally substituted aryl, optionally substituted heteroaryl, optionally substituted -aryl-N($R^2$)—, optionally substituted -heteroaryl-N($R^2$)—, —C(=O)N($R^{10}$)—, —N($R^{10}$)C(=O)—, —N($R^{10}$)C(=O)—N($R^{10}$)—, —N($R^{10}$)C(=O)O—, —C(=S)N($R^{10}$)—, —N($R^{10}$)C(=S)—, —N($R^{10}$)C(=S)—N($R^{10}$)—, —N($R^{10}$)C(=S)O—, —N($R^{10}$)—S(O)$_2$—, —S(O)$_2$—N($R^{10}$)—, —O—C(O)—N(R.s-up.10)- and —N($R^{10}$)—C(O)—O—; wherein $R^{10}$ is selected from the group consisting of H, alkyl, aryl, heteroaryl, cycloalkyl, heterocyclyl, -alkyl-aryl, -alkyl-heteroaryl, -alkyl-cycloalkyl and -alkyl-heterocycle, each of which is optionally substituted (preferably $R^{10}$ is H, or Me); W is selected from the group consisting of a bond, an optionally substituted $C_1$-$C_4$alkyl, —O—, —S(O)$_{0-2}$—, —N($R^{10}$), —O—C(O)—N($R^{10}$)—, —N($R^{10}$)—C(O)—O—, —O—C(S)—N($R^{10}$), —N($R^{10}$)—C(S)—O—, —N($R^{10}$)—S(O)$_2$—, —S(O)$_2$—N($R^{10}$)—, —C(O)—, —C(S)—, —O—C(O)— and —C(O)—O—; or $R^6$ together with W optionally form a 5- or 6-membered heterocycle; or W together with $R^7$ optionally form a 5- or 6-membered heterocycle, wherein the heterocycle is optionally substituted; or $R^6$ together with Z form an optionally substituted heteroaryl; u is 0 or 1; s is 0, 1, 2 or 3; and n is 0 or 1; or —Z—(CH$_2$)$_s$—(W)$_n$—$R^7$ is an optionally substituted —C(O)-heterocycle or an optionally substituted 5- to 10-membered heteroaryl, preferably selected from the group consisting of

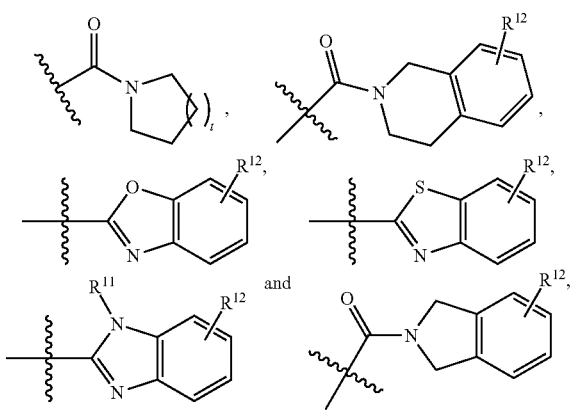

wherein t is 1, 3 or 4; and $R^{12}$ is selected from the group consisting of hydrogen, halogen, haloalkyl, cyano, nitro, alkyl, cycloalkyl, alkenyl, cycloalkenyl, alkynyl, heterocycle, aryl, heteroaryl, —OR, —SR, —S(=O)R, —S(=O)$_2$R, —P(=O)$_2$R, —S(=O)$_2$OR, —P(=O)$_2$OR, —N(R)(R), —N(R)S(=O)$_2$R, —S(=O)$_2$N(R)(R), —N(R)P(=O)$_2$R, —P(=O)$_2$N(R)(R), —C(=O)OR, —C(=O)R, —C(=O)N(R)(R), —C(=S)N(R)(R), —OC(=O)R, —OC(=O)N(R)(R), —OC(=S)N(R)(R), —N(R)C(=O)OR, —N(R)C(=S)OR, —N(R)C(=O)N(R)(R), —N(R)C(=S)N(R)(R), —N(R)S(=O)$_2$N(R)(R), —N(R)P(=O)$_2$N(R)(R), —N(R)C(=O)R, —N(R)C(=S)R and —N(R)P(=O)$_2$R, wherein each R is independently selected from the group consisting of hydrogen, alkyl, cycloalkyl, alkenyl, cycloalkenyl, alkynyl, heterocycle, aryl and heteroaryl; provided that —Z—(CH$_2$)$_s$—(W)$_n$— is not —O—O— or —O—CH$_2$—O—; and provided that Formula (IV) excludes those compounds wherein (1) M is

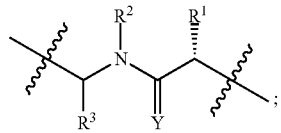

$R^8$ are both H; Y is O; $R^3$ is H or $C_1$-$C_4$alkyl; A is phenyl; u is 0; Z is a moiety selected from the group consisting of

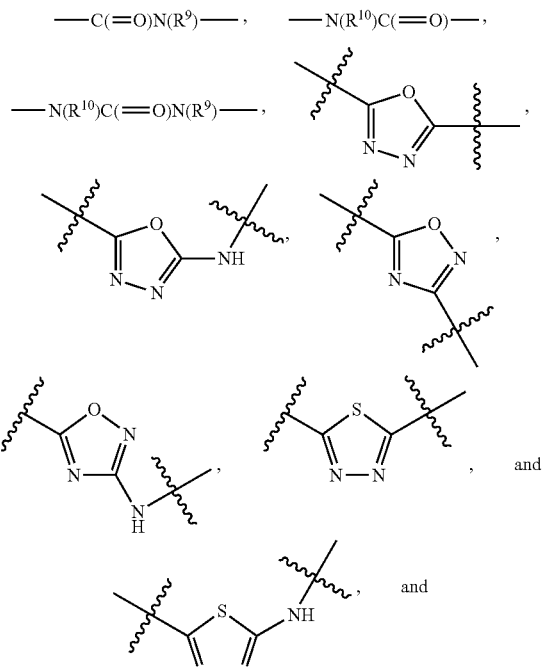

W is O; or (2) M is

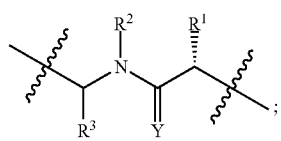

$R^8$ are both H; Y is O; $R^3$ is H or $C_1$-$C_4$alkyl; A is phenyl; u is 0; and —Z—(CH$_2$)$_m$—(W)$_n$—$R^7$ is selected from the group consisting of

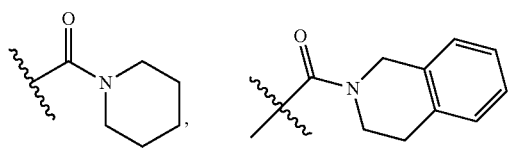

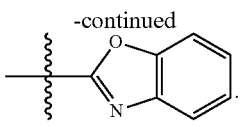

as disclosed in U.S. Pat. No. 8,338,437 and WO 2008/104077;

PRMT5 inhibitors SAM, MTA, AMI-1, -6, -9 and compounds 1-5 disclosed by Bonham et al, in a publication FEBS, 2010, 277, 2096-2108;

inhibitors of protein arginine methyl transferases of Formula VII and VIId:

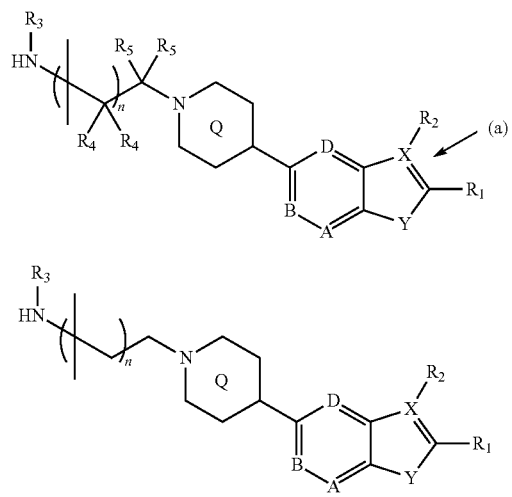

wherein:
Ring Q is

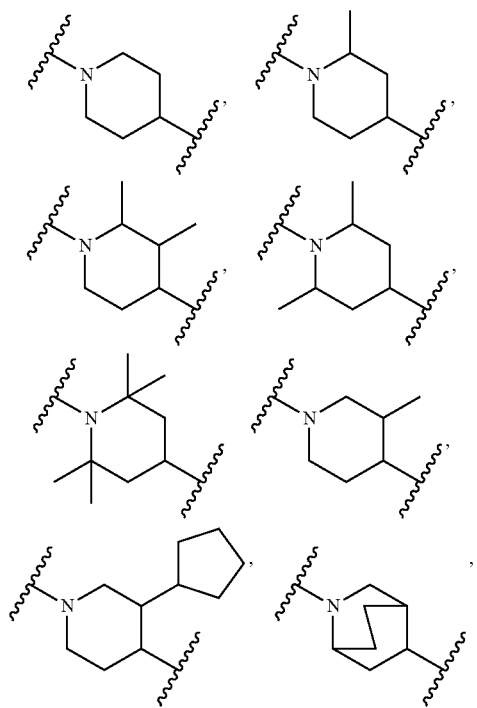

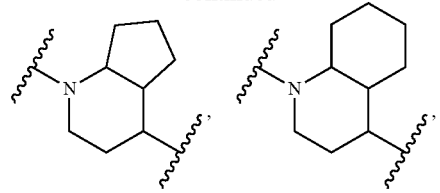

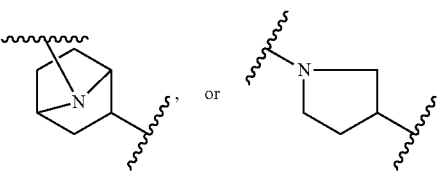

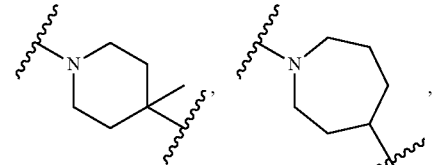

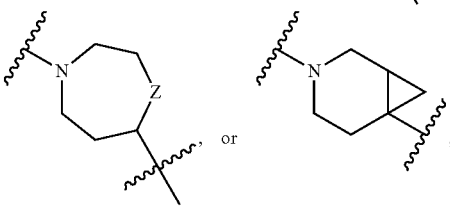

bond (a) is an optional double or single bond;

X is C (i.e., carbon) or N (i.e., nitrogen);

Y is NH, N-Me, or CH;

Z is N—$R_6$, O, or S, where $R_6$ is $C_1$-$C_6$ alkyl;

wherein when bond (a) is a single bond, X is —CR—, R is independently H or $C_{1-4}$ alkyl and $CR_2$ is H or $C_{1-4}$ alkyl; alternatively, $R_2$ and R may join to form a 3-6 membered cycloalkyl ring;

A, B and D are each independently N or C, in which C may be optionally substituted with H, Me, Et, halogen, CN, $NO_2$, OMe, OEt, SMe, $SO_2$Me, $CF_3$, or $OCF_3$;

$R_1$ is aryl, substituted aryl, heterocycle, or substituted heterocycle;

$R_2$ is H, Me, Et, halogen, CN, $NO_2$, OMe, OEt, SMe, $SO_2$Me, $CF_3$, or $OCF_3$, provided that when X is N, $R_2$ is nil;

$R_3$ is H or $C_1$-$C_4$ alkyl; and $R_4$ is independently H or $C_{1-4}$ alkyl;

$R_5$ is independently H, $C_{1-4}$ alkyl; alternatively, R5 and R3 may join to form a 4, 5, or 6 membered saturated ring containing one N; and n is 1, 2, or 3, as disclosed in WO 2006/113458;

PRMT5 inhibitors of formula (I)

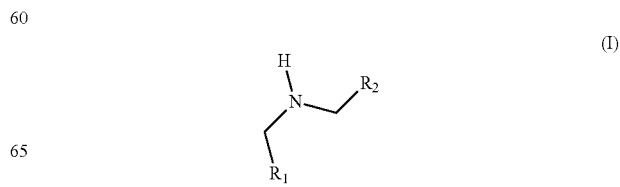

wherein
R₁ is

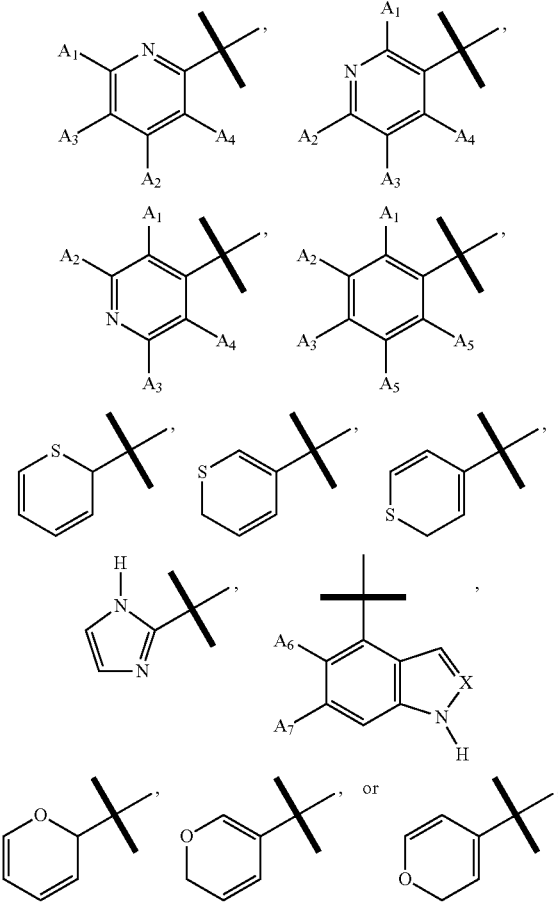

R₂ is

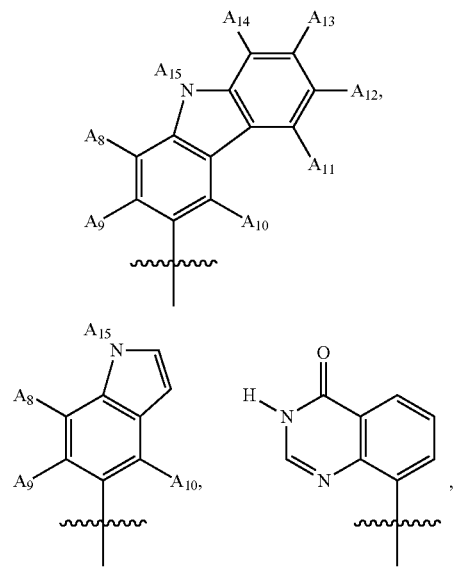

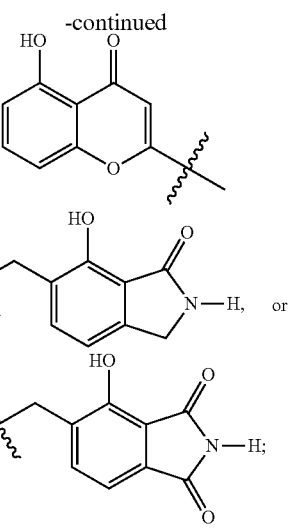

$A_i$, $A_2$, $A_3$, $A_4$, and $A_5$ are each individually hydrogen, halo, alkyl, alkoxyl, acetoxyl, alkylacetoxyl, —OH, trihalomethyl, —NH₂ or —NO₂;

$A_6$ and $A_7$ are each individually hydrogen, OH or NH₂;

$A_8$, $A_9$, $A_{10}$, $A_{11}$, $A_{12}$, $A_{13}$ and $A_{14}$ are each individually hydrogen, halo, alkyl, alkoxyl, acetoxyl, alkylacetoxyl, —OH, trihalomethyl, —NH₂ or —NO₂; and $A_{15}$ is alkyl (1-6 carbons in length); or a salt thereof;

PRMT5 inhibitors of formula:

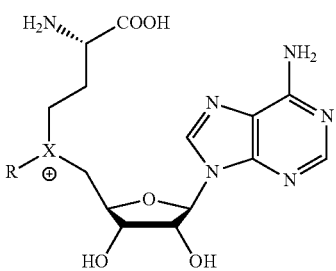

X: S, Se

As disclosed in a publication by Bothwell, et al in a publication Org. Lett., 2014, 16, 3056-3059;

PRMT5 inhibitors disclosed by Mai et al in a publication J. Med. Chem., 2008, 51, 2279-2290;

PRMT5 inhibitors disclosed in U.S. Pat. Appl. Publ. No. 2010/0151506;

PRMT5 inhibitors disclosed by Bothwell, et al in a publication Org. Lett., 2014, S1-S46;

PRMT5 inhibitors of Formula VIII:

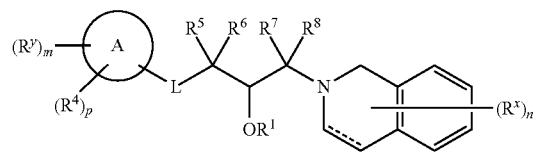

(VIII)

wherein:

===== represents a single or double bond;

$R^1$ is hydrogen, IV, or —C(O)$R^z$, wherein $R^z$ is optionally substituted $C_{1-6}$ alkyl;

L is —O—, —N(R)—, —C($R^2$)($R^3$)—, —O—C$R^2R^3$, —N(R)—C$R^2R^3$—, —O—C$R^2R^3$—O—, —N(R)—C$R^2R^3$—O, —N(R)—C$R^2R^3$—N(R)—, —O—C$R^2R^3$—N(R)—, —C$R^2R^3$—O—, —C$R^2R^3$—N(R)—, —O—C$R^2R^3$—C$R^9R^{10}$—, —N(R)—C$R^2R^3$—C$R^9R^{10}$—, —C$R^2R^3$—C$R^9R^{10}$—O—, —C$R^2R^3$—C$R^9R^{10}$—N(R)—, or —C$R^2R^3$—C$R^9R^{10}$—;

each R is independently hydrogen or optionally substituted $C_{1-6}$ aliphatic;

$R^2$ and $R^3$ are independently selected from the group consisting of hydrogen, halo, —CN, —NO$_2$, optionally substituted aliphatic, optionally substituted carbocyclyl; optionally substituted phenyl, optionally substituted heterocyclyl, optionally substituted heteroaryl, —O$R^A$, —N($R^B$)$_2$, —S$R^A$, —C(=O)$R^A$, —C(O)O$R^A$, —C(O)S$R^A$, —C(O)N($R^B$)$_2$, —C(O)N($R^B$)N($R^B$)$_2$, —OC(O)$R^A$, —OC(O)N($R^B$)$_2$, —N$R^B$C(O)$R^A$, —N$R^B$C(O)N($R^B$)$_2$, —N$R^B$C(O)N($R^B$)N($R^B$)$_2$, —N$R^B$C(O)O$R^A$, —SC(O)$R^A$, —C(=N$R^B$)$R^A$, —C(=NN$R^B$)$R^A$, —C(=NO$R^A$)$R^A$, —C(=N$R^B$)N($R^B$)$_2$, —N$R^B$C(=N$R^B$)$R^B$, —C(=S)$R^A$, —C(=S)N($R^B$)$_2$, —N$R^B$C(=S)$R^A$, —S(O)$R^A$, —OS(O)$_2R^A$, —SO$_2R^A$, —NR B SO$_2$R A, and —SO$_2$N(R B)$_2$; or R 2 and R 3 are taken together with their intervening atoms to form an optionally substituted carbocyclic or heterocyclic ring;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two R groups are taken together with their intervening atoms to form an optionally substituted heterocyclic ring;

Ring A is a monocyclic or bicyclic, saturated, partially unsaturated, or aromatic ring having 0-4 heteroatoms independently selected from nitrogen, oxygen, and sulfur;

$R^4$ is -Li-Cy;

$L_1$ is a bond, —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$— —SO$_2$N(R)—, —N(R)SO$_2$— —OC(O)—, —C(O)O—, or an optionally substituted, straight or branched, C1-6 aliphatic chain wherein one, two, or three methylene units of hi are optionally and independently replaced by —O—, —S—, —N(R)—, —C(O)—, —C(O)N(R)—, —N(R)C(O)N(R)—, —N(R)C(O)—, —N(R)C(O)O— —OC(O)N(R)—, —SO$_2$—, —SO$_2$N(R)—, —N(R)SO$_2$— —OC(O)—, or —C(O)O—;

Cy is an optionally substituted, monocyclic, bicyclic or tricyclic, saturated, partially unsaturated, or aromatic ring having 0-4 heteroatoms independently selected from nitrogen, oxygen, and sulfur;

$R^5$, $R^6$, $R^7$, and $R^8$ are independently hydrogen, halo, or optionally substituted aliphatic;

$R^9$ and $R^{10}$ are independently selected from the group consisting of hydrogen, halo, —CN, —NO$_2$, optionally substituted aliphatic, optionally substituted carbocyclyl; optionally substituted phenyl, optionally substituted heterocyclyl, optionally substituted heteroaryl, —O$R^A$, —N($R^B$)$_2$, —S$R^A$, —C(=0)$R^A$, —C(O)O$R^A$, —C(O)S$R^A$, —C(O)N($R^B$)$_2$, —C(O)N($R^B$)N($R^B$)$_2$, —OC(O)$R^A$, —OC(O)N($R^B$)$_2$, —N$R^B$C(O)$R^A$, —N$R^B$C(O)N($R^B$)$_2$, —N$R^B$C(O)N($R^B$)N($R^B$)$_2$, —N$R^B$C(O)O$R^A$, —SC(O)$R^A$, —C(=N$R^B$)$R^A$, —C(=NN$R^B$)$R^A$, —C(=NO$R^A$)$R^A$, —C(=N$R^B$)N($R^B$)$_2$, —N$R^B$C(=N$R^B$)$R^B$, —C(=S)$R^A$, —C(=S)N($R^B$)$_2$, —N$R^B$C(=S)$R^A$, —S(O)$R^A$, —OS(O)$_2R^A$, —SO$_2R^A$, —N$R^B$SO$_2R^A$, and —SO$_2$N($R^B$)$_2$; or $R^9$ and $R^{10}$ are taken together with their intervening atoms to form an optionally substituted carbocyclic or heterocyclic ring;

each $R^y$ is independently selected from the group consisting of halo, —CN, —NO$_2$, optionally substituted aliphatic, optionally substituted carbocyclyl; optionally substituted aryl, optionally substituted heterocyclyl, optionally substituted heteroaryl, —O$R^A$, —N($R^B$)$_2$, —S$R^A$, —C(=0)$R^A$, —C(O)O$R^A$, —C(O)S$R^A$, —C(O)N($R^B$)$_2$, —C(O)N($R^B$)N($R^B$)$_2$, —OC(O)$R^A$, —OC(O)N($R^B$)$_2$, —N$R^B$C(O)$R^A$, —N$R^B$C(O)N($R^B$)$_2$, —N$R^B$C(O)N($R^B$)N($R^B$)$_2$, —N$R^B$C(O)O$R^A$, —SC(O)$R^A$, —C(=N$R^B$)$R^A$, —C(=NN$R^B$)$R^A$, —C(=NO$R^A$)$R^A$, —C(=N$R^B$)N($R^B$)$_2$, —N$R^B$C(=N$R^B$)$R^B$, —C(=S)$R^A$, —C(=S)N($R^B$)$_2$, —N$R^B$C(=S)$R^A$, —S(O)$R^A$, —OS(O)$_2R^A$, —SO$_2R^A$, —N$R^B$SO$_2R^A$, and —SO$_2$N($R^B$)$_2$;

each $R^x$ is independently selected from the group consisting of halo, —CN, optionally substituted aliphatic, —OR, and —N(R")$_2$;

R' is hydrogen or optionally substituted aliphatic; each R" is independently hydrogen or optionally substituted aliphatic, or two R" are taken together with their intervening atoms to form a heterocyclic ring;

n is 0, 1, 2, 3, 4, 5, 6, 7, 8, 9, or 10, as valency permits;

m is 0, 1, 2, 3, 4, 5, 6, 7, or 8, as valency permits; and p is 0 or 1;

wherein, and unless otherwise specified, heterocyclyl or heterocyclic refers to a radical of a 3-10 membered non-aromatic ring system having ring carbon atoms and 1-4 ring heteroatoms, wherein each heteroatom is independently selected from nitrogen, oxygen, and sulfur;

carbocyclyl or carbocyclic refers to a radical of a non-aromatic cyclic hydrocarbon group having from 3 to 10 ring carbon atoms and zero heteroatoms in the non-aromatic ring system;

aryl refers to a radical of a monocyclic or polycyclic aromatic ring system having 6-14 ring carbon atoms and zero heteroatoms provided in the aromatic ring system; and heteroaryl refers to a radical of a 5-10 membered monocyclic or bicyclic aromatic ring system having ring carbon atoms and 1-4 ring heteroatoms provided in the aromatic ring system, wherein each heteroatom is independently selected from nitrogen, oxygen and sulfur;

provided that when L is —O— and Ring A is phenyl, p is 1; and provided that the compound is not one of the following:
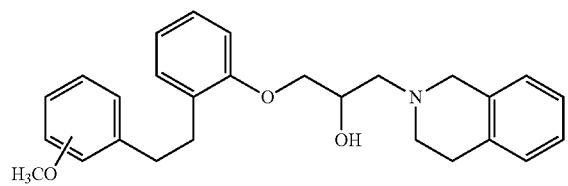
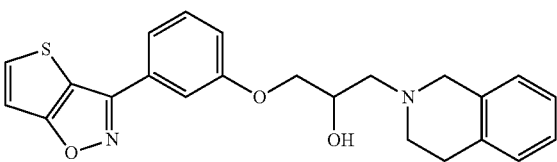
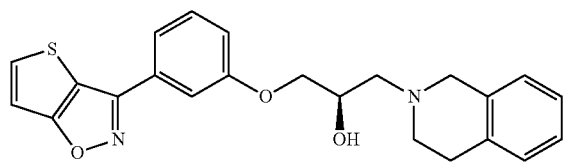
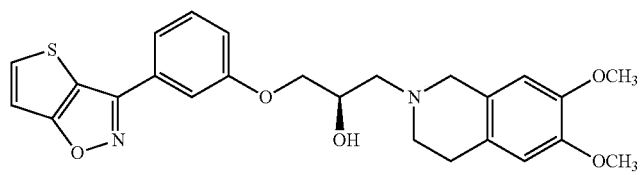
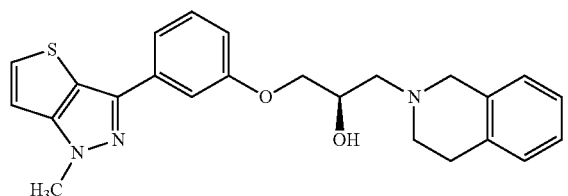
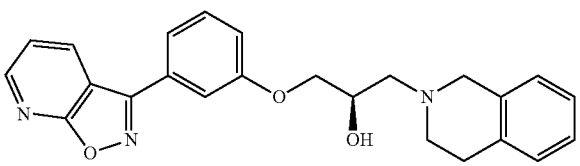
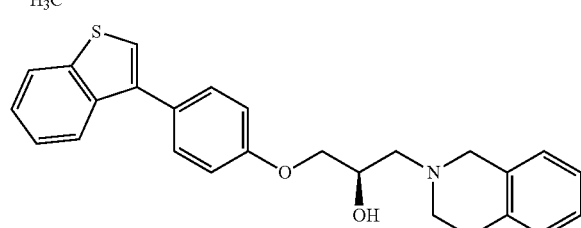
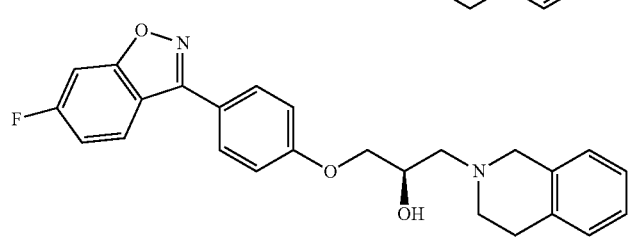
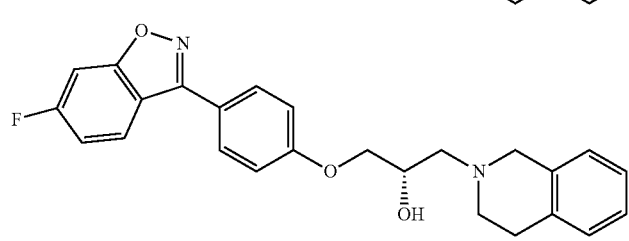
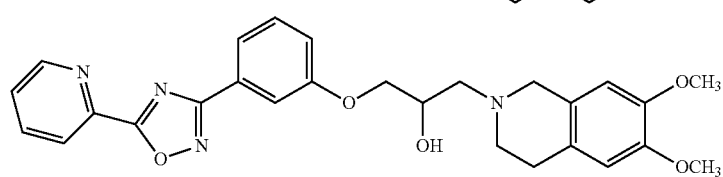

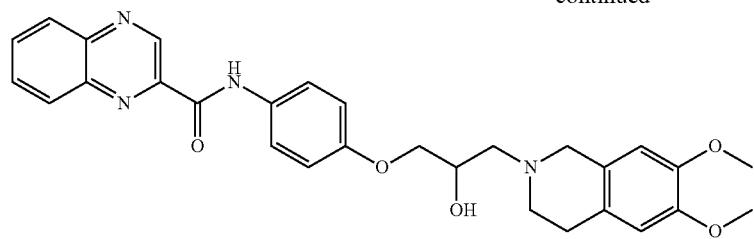
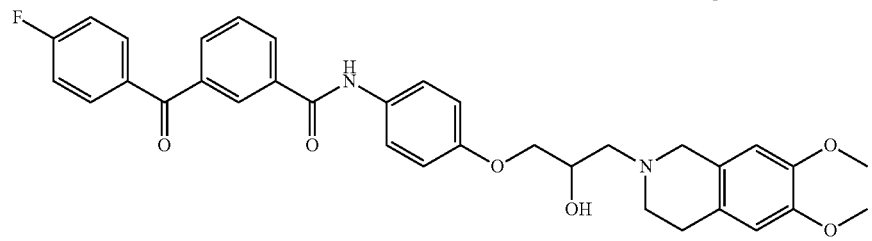
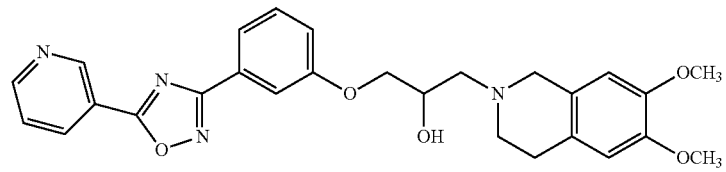
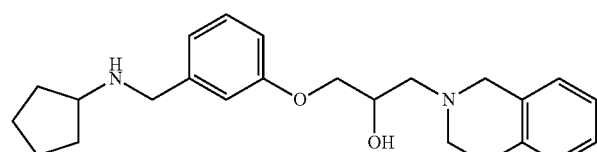
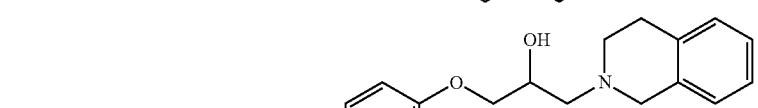
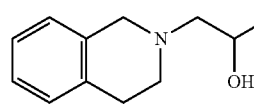
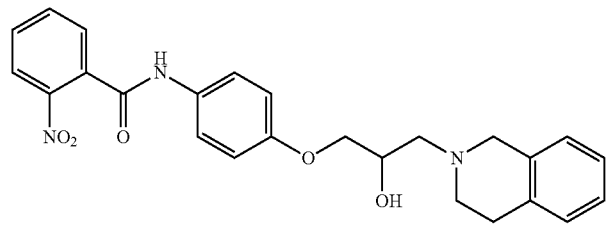
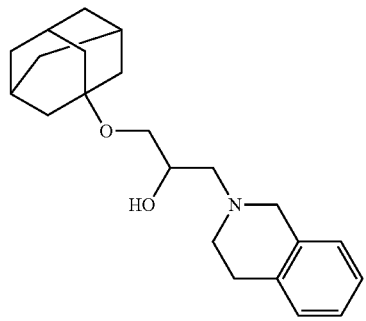
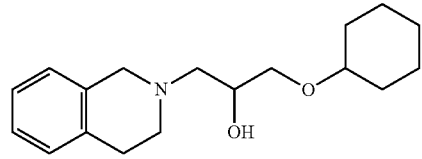
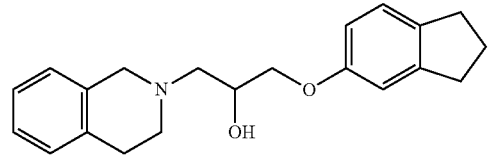
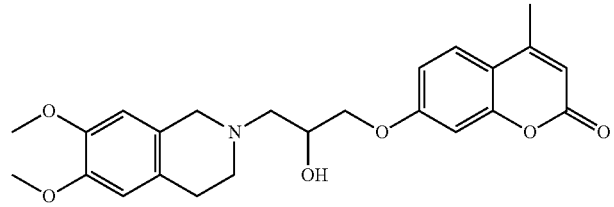
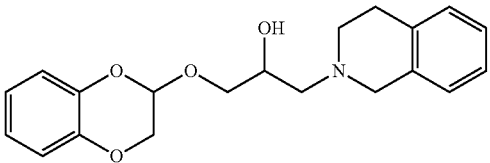

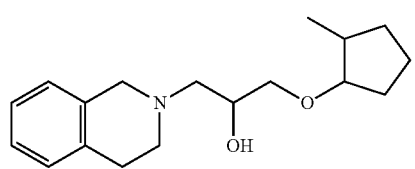
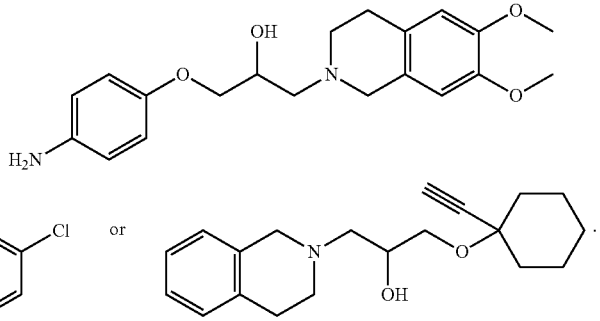
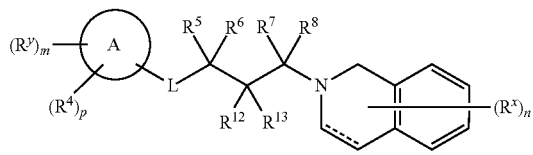

as disclosed in WO 2014/100695, WO 2014/100716, WO 2014/100719, WO 2014/100730, WO 2014/100734, and WO 2014/100764;

inhibitors of PRMT5 of Formula (A):

A or a pharmaceutically acceptable salt thereof,
wherein
represents a single or double bond;
R 12 is hydrogen, halogen, or optionally substituted $C_{1-3}$ alkyl;
$R^{13}$ is hydrogen, halogen, optionally substituted $C_{1-3}$alkyl, —$NR^{41}R^{42}$, or —$OR^1$;
$R^{41}$ and $R^{42}$ are each independently hydrogen, optionally substituted $C_{1-3}$ alkyl, a nitrogen protecting group, or $R^{41}$ and $R^{42}$ are taken together with the intervening nitrogen atom to form an optionally substituted 3-6 membered heterocyclic ring;
$R^1$ is hydrogen, $R^z$, or —$C(0)R^z$, wherein $R^z$ is optionally substituted $C_{1-6}$ alkyl;
L is -O-, —N(R)—, —C($R^2$)($R^3$)—, -O-$CR^2R^3$, —N(R)—$CR^2R^3$—, -O-$CR^2R^3$-O-, —N(R)—$CR^2R^3$-O, —N(R)—$CR^2R^3$—N(R)—, -O-$CR^2R^3$—N(R)—, —$CR^2R^3$-O-, —$CR^2R^3$—N(R)—, -O-$CR^2R^3$—$CR^9R^{10}$—, —N(R)—$CR^2R^3$—$CR^9R^{10}$—, —$CR^2R^3$—$CR^9R^{10}$—O—, —$CR^2R^3$—$CR^9R^{10}$—N(R)—, or —$CR^2R^3$—$CR^9R^{10}$—;
each R is independently hydrogen or optionally substituted $C_{1-6}$ aliphatic;
$R^2$ and $R^3$ are independently selected from the group consisting of hydrogen, halo, —CN, —$NO_2$, optionally substituted aliphatic, optionally substituted carbocyclyl; optionally substituted phenyl, optionally substituted heterocyclyl, optionally substituted heteroaryl, —$OR^A$, —$N(R^B)_2$, —$SR^A$, —C(=O)$R^A$, —C(0)$OR^A$, —C(0)$SR^A$, —C(0)N($R^B$)$_2$, —C(0)N($R^B$)N($R^B$)$_2$, —OC(0)$R^A$, —OC(0)N($R^B$)$_2$, —$NR^BC(0)R^A$, —$NR^BC(0)N(R^B)_2$, —$NR^BC(0)N(R^B)N(R^B)_2$, —$NR^BC(0)OR^A$, —SC(0)$R^A$, —C(=$NR^B$)$R^A$, —C(=NN$R^B$)$R^A$, —C(=$NOR^A$)$R^A$, —C(=$NR^B$)N($R^B$)$_2$, —$NR^BC$(=$NR^B$)$R^B$, —C(=S)$R^A$, —C(=S)N($R^B$)$_2$, —$NR^BC$(=S)$R^A$, —S(0)$R^A$, —OS(0)$_2R^A$, —$SO_2R^A$, —NR B $SO_2R$ A, and —$SO_2N(R$ B$)_2$; or $R^2$ and $R^3$ are taken together with their intervening atoms to form an optionally substituted carbocyclic or heterocyclic ring; or $R^2$ and $R^3$ are taken together with their intervening atoms to form an optionally substituted carbocyclic or heterocyclic ring;

each R is independently selected from the group consisting of hydrogen, optionally substituted aliphatic, optionally substituted carbocyclyl, optionally substituted heterocyclyl, optionally substituted aryl, and optionally substituted heteroaryl;

each R is independently selected from the group consisting of hydrogen, optionally substituted aliphatic, optionally substituted carbocyclyl, optionally substituted heterocyclyl, optionally substituted aryl, and optionally substituted heteroaryl, or two R groups are taken together with their intervening atoms to form an optionally substituted heterocyclic ring;

Ring A is a monocyclic or bicyclic, saturated, partially unsaturated, or aromatic ring having 0-4 heteroatoms independently selected from nitrogen, oxygen, and sulfur;
$R^4$ is -L Cy;
U is a bond, -O-, —S—, —N(R)—, —C(O)—, —C(0)N(R)—, —N(R)C(0)N(R)—, —N(R)C(0)-, —N(R)C(0)0-, —OC(0)N(R)—, —$SO_2$- —$SO_2N(R)$—, —N(R)$SO_2$- —OC(O)—, —C(0)0-, or an optionally substituted, straight or branched, $C_{i-6}$ aliphatic chain wherein one, two, or three methylene units of hi are optionally and independently replaced by -O-, —S—, —N(R)—, —C(O)—, —C(0)N(R)—, —N(R)C(0)N(R)—, —N(R)C(0)-, —N(R)C(0)0-, —OC(0)N(R)—, —$SO_2$- —$SO_2N(R)$—, —N(R)$SO_2$- —OC(O)—, or —C(0)0-;
Cy is an optionally substituted, monocyclic, bicyclic or tricyclic, saturated, partially unsaturated, or aromatic ring having 0-4 heteroatoms independently selected from nitrogen, oxygen, and sulfur;
$R^5$, $R^6$, $R^7$, and $R^8$ are each independently hydrogen, halo, or optionally substituted aliphatic;
$R^9$ and $R^{10}$ are each independently selected from the group consisting of hydrogen, halo, —CN, —$NO_2$, optionally substituted aliphatic, optionally substituted carbocyclyl; optionally substituted phenyl, optionally substituted heterocyclyl, optionally substituted heteroaryl, —$OR^A$, —$N(R^B)_2$, —$SR^A$, —C(=O)$R^A$, —C(0)$OR^A$, —C(0)$SR^A$, —C(0)N($R^B$)$_2$, —C(0)N($R^B$)N($R^B$)$_2$, —OC(0)$R^A$, —OC(0)N($R^B$)$_2$, —$NR^BC(0)R^A$, —$NR^BC(0)N(R^B)_2$, —$NR^BC(0)N(R^B)N(R^B)_2$, —$NR^BC(0)OR^A$, —SC(0)$R^A$, —C(=$NR^B$)$R^A$, —C(=NN$R^B$)$R^A$, —C(=$NOR^A$)$R^A$, —C(=$NR^B$)N($R^B$)$_2$, —$NR^BC$(=$NR^B$)$R^B$, —C(=S)$R^A$, —C(=S)N($R^B$)$_2$, —$NR^BC$(=S)$R^A$, —S(0)$R^A$, —OS(0)$_2R^A$, —$SO_2R^A$, —$NR^BSO_2R^A$, and —$SO_2N(R^B)_2$; or $R^9$ and $R^{10}$ are taken together with their intervening atoms to form an optionally substituted carbocyclic or heterocyclic ring;

each $R^y$ is independently selected from the group consisting of halo, —CN, —$NO_2$, optionally substituted aliphatic, optionally substituted carbocyclyl; optionally substituted phenyl, optionally substituted heterocyclyl, optionally substituted heteroaryl, —OR, —N(R)$_2$, —SR, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, and —SO$_2$N(R$^B$)$_2$;
each R$^x$ is independently selected from the group consisting of halo, —CN, optionally substituted aliphatic, —OR, and —N(R")$_2$;
R' is hydrogen or optionally substituted aliphatic;
each R" is independently hydrogen or optionally substituted aliphatic, or two R" are taken together with their intervening atoms to form a heterocyclic ring;
n is 0, 1, 2, 3, 4, 5, 6, 7, 8, 9, or 10, as valency permits;
m is 0, 1, 2, 3, 4, 5, 6, 7, or 8, as valency permits; and
p is 0 or 1, as disclosed in WO 2014/14100695;

inhibitors of PRMT5 of Formula I:

I or a pharmaceutically acceptable salt thereof,
wherein
R$^1$ is hydrogen, R$^z$, or —C(O)R$^z$, wherein R$^z$ is optionally substituted C$_{1-6}$ alkyl;
L$_z$ is a linker;
Ring Z is an optionally substituted, monocyclic or bicyclic, saturated, partially unsaturated, or aromatic ring having 0-4 heteroatoms independently selected from nitrogen, oxygen, and sulfur;
R 21, R 22, R 23, and R 2^4 are independently hydrogen, halo, or optionally substituted aliphatic:
each R$^x$ is independently selected from the group consisting of halo, —CN, optionally substituted aliphatic, and —OR';
R' is hydrogen or optionally substituted aliphatic; and
n is 0, 1, 2, 3, 4, 5, 6, 7, or 8;
wherein, and unless otherwise specified.
heterocyclyl or heterocyclic refers to a radical of a 3-10 membered non-aromatic ring system having ring carbon atoms and 1-4 ring heteroatoms, wherein each heteroatom is independently selected from nitrogen, oxygen, and sulfur;
carbocyclyl or carbocyclic refers to a radical of a non-aromatic cyclic hydrocarbon group having from 3 to 10 ring carbon atoms and zero heteroatoms in the non-aromatic ring system;
aryl refers to a radical of a monocyclic or polycyclic aromatic ring system having 6-14 ring carbon atoms and zero heteroatoms provided in the aromatic ring system; and
heteroaryl refers to a radical of a 5-10 membered monocyclic or bicyclic aromatic ring system having ring carbon atoms and 1-4 ring heteroatoms provided in the aromatic ring system, wherein each heteroatom is independently selected from nitrogen, oxygen and sulfur, as disclosed in WO 2014/100734;

inhibitors of PRMT5 of Formula I:

(I)

or a pharmaceutically acceptable salt thereof,
wherein
represents a single or double bond;
R$^1$ is hydrogen, R$^z$, or —C(O)R$^z$, wherein R$^z$ is optionally substituted C$_{1-6}$ alkyl;
X is a bond, -O-, —N(R)—, —CR$^4$R$^5$—, -O-CR$^4$R$^5$, —N(R)—CR$^4$R$^5$—, -O-CR$^4$R$^5$-O-, —N(R)—CR$^4$R$^5$-O, —N(R)—CR$^4$R—N(R)—, -O-CR$^4$R$^5$—N(R)—, —CR$^4$R$^5$-O-, —CR$^4$R—N(R)—, -O-CR$^4$R$^5$—CR$^6$R$^7$—, —N(R)—CR$^4$R$^5$—CR$^6$R$^7$—, —CR$^6$R$^7$—CR$^4$R$^5$-O-, —CR$^6$R$^7$—CR$^4$R$^5$—N(R)—, or —CR$^6$R$^7$—CR$^4$R$^5$— each R is independently hydrogen or optionally substituted C$_{1-6}$ aliphatic;
R$^2$ and R$^3$ are independently selected from the group consisting of hydrogen, halo, —CN, —NO$_2$, optionally substituted aliphatic, optionally substituted carbocyclyl, optionally substituted phenyl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R A, and —SO$_2$N(R$^B$)$_2$; or R$^2$ and R$^3$ are taken together with their intervening atoms to form an optionally substituted carbocyclic or heterocyclic ring;
R$^4$ and R$^5$ are independently selected from the group consisting of hydrogen, halo, —CN, —NO$_2$, optionally substituted aliphatic, optionally substituted carbocyclyl, optionally substituted phenyl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, and —SO$_2$N(R$^B$)$_2$; or R$^4$ and R$^5$ are taken together with their intervening atoms to form an optionally substituted carbocyclic or heterocyclic ring: R$^6$ and R$^7$ are independently selected from the group consisting of hydrogen, halo, —CN, —NO$_2$, optionally substituted aliphatic, optionally substituted carbocyclyl, optionally substituted phenyl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, — OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, and —SO$_2$N(R$^B$)$_2$; or R$^6$ and R$^7$ are taken together with their intervening atoms to form an optionally substituted carbocyclic or heterocyclic ring;
each R$^A$ is independently selected from the group consisting of hydrogen, optionally substituted aliphatic, optionally substituted carbocyclyl, optionally substituted heterocyclyl, optionally substituted aryl, and optionally substituted heteroaryl;
each R is independently selected from the group consisting of hydrogen, optionally substituted aliphatic, optionally substituted carbocyclyl, optionally substituted heterocyclyl, optionally substituted aryl, and optionally substituted heteroaryl, or two R groups are taken together with their intervening atoms to form an optionally substituted heterocyclic ring;
R$^8$, R$^9$, R$^{10}$, and R$^{11}$ are independently hydrogen, halo, or optionally substituted aliphatic;
Cy is a monocyclic or bicyclic, saturated, partially unsaturated, or aromatic ring having 0-4 heteroatoms independently selected from nitrogen, oxygen, and sulfur, wherein Cy is substituted with 0, 1, 2, 3, or 4 R$^y$ groups;
each R$^y$ is independently selected from the group consisting of halo, —CN, —NO$_2$, optionally substituted aliphatic, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, and —SO$_2$N(R$^B$)$_2$; or an R$^y$ group may be optionally taken together with R$^2$ or R$^3$ to form an optionally substituted 5- to 6-membered carbocyclic or heterocyclic ring fused to Cy;
each R$^x$ is independently selected from the group consisting of halo, —CN, optionally substituted aliphatic, —OR', and —N(R")$_2$;
R' is hydrogen or optionally substituted aliphatic; each R" is independently hydrogen or optionally substituted aliphatic, or two R" are taken together with their intervening atoms to form an optionally substituted heterocyclic ring having 1-2 heteroatoms independently selected from nitrogen, oxygen, and sulfur; and
n is 0, 1, 2, 3, 4, 5, 6, 7, 8, 9, or 10, as valency permits;
wherein, and unless otherwise specified,
heterocyclyl or heterocyclic refers to a radical of a 3-10 membered non-aromatic ring system having ring carbon atoms and 1-4 ring heteroatoms, wherein each heteroatom is independently selected from nitrogen, oxygen, and sulfur;
carbocyclyl or carbocyclic refers to a radical of a non-aromatic cyclic hydrocarbon group having from 3 to 10 ring carbon atoms and zero heteroatoms in the non-aromatic ring system;
aryl refers to a radical of a monocyclic or polycyclic aromatic ring system having 6-14 ring carbon atoms and zero heteroatoms provided in the aromatic ring system; and
heteroaryl refers to a radical of a 5-10 membered monocyclic or bicyclic aromatic ring system having ring carbon atoms and 1-4 ring heteroatoms provided in the aromatic ring system, wherein each heteroatom is independently selected from nitrogen, oxygen and sulfur, as disclosed in WO 2014/100730;

inhibitors of PRMT5 of Formula (I):

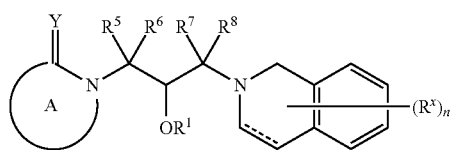

or a pharmaceutically acceptable salt thereof,
wherein
represents a single or double bond;
Ring A is an optionally substituted, 5- to 12-membered, monocyclic or bicyclic, heterocyclyl or heteroaryl having 1-4 heteroatoms independently selected from nitrogen, oxygen, and sulfur;
R$^1$ is hydrogen, R$^z$, or —C(O)R$^z$, wherein R$^z$ is optionally substituted C$_{1-6}$ alkyl;
Y is O or S;
R$^5$, R$^6$, R$^7$, and R$^8$ are independently hydrogen, halo, or optionally substituted aliphatic; each R$^x$ is independently selected from the group consisting of halo, —CN, optionally substituted aliphatic, —OR', and —N(R")$_2$;
R' is hydrogen or optionally substituted aliphatic;
each R" is independently hydrogen or optionally substituted aliphatic, or two R" are taken together with their intervening atoms to form a heterocyclic ring; and
n is 0, 1, 2, 3, 4, 5, 6, 7, 8, 9, or 10, as valency permits;
wherein, and unless otherwise specified,
heterocyclyl or heterocyclic refers to a radical of a 3-10 membered non-aromatic ring system having ring carbon atoms and 1-4 ring heteroatoms, wherein each heteroatom is independently selected from nitrogen, oxygen, and sulfur;
carbocyclyl or carbocyclic refers to a radical of a non-aromatic cyclic hydrocarbon group having from 3 to 10 ring carbon atoms and zero heteroatoms in the non-aromatic ring system;
aryl refers to a radical of a monocyclic or polycyclic aromatic ring system having 6-14 ring carbon atoms and zero heteroatoms provided in the aromatic ring system; and
heteroaryl refers to a radical of a 5-10 membered monocyclic or bicyclic aromatic ring system having ring carbon atoms and 1-4 ring heteroatoms provided in the aromatic ring system, wherein each heteroatom is independently selected from nitrogen, oxygen and sulfur, as disclosed in WO 2014/100716:

inhibitors of PRMT5 inhibitors of Formula (I):

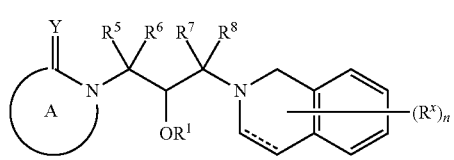

or a pharmaceutically acceptable salt thereof,
wherein
represents a single or double bond;
Ring A is an optionally substituted, 5- to 12-membered, monocyclic or bicyclic, heterocyclyl or heteroaryl having 1-4 heteroatoms independently selected from nitrogen, oxygen, and sulfur;
R$^1$ is hydrogen, R$^z$, or —C(O)R$^z$, wherein R$^z$ is optionally substituted C$_{1-6}$ alkyl;
Y is O or S;

R⁵, R⁶, R⁷, and R⁸ are independently hydrogen, halo, or optionally substituted aliphatic;
each $R^x$ is independently selected from the group consisting of halo, —CN, optionally substituted aliphatic, —OR', and —N(R")₂;
R' is hydrogen or optionally substituted aliphatic;
each R" is independently hydrogen or optionally substituted aliphatic, or two R" are taken together with their intervening atoms to form a heterocyclic ring; and
n is 0, 1, 2, 3, 4, 5, 6, 7, 8, 9, or 10, as valency permits;
wherein, and unless otherwise specified,
heterocyclyl or heterocyclic refers to a radical of a 3-10 membered non-aromatic ring system having ring carbon atoms and 1-4 ring heteroatoms, wherein each heteroatom is independently selected from nitrogen, oxygen, and sulfur;
carbocyclyl or carbocyclic refers to a radical of a non-aromatic cyclic hydrocarbon group having from 3 to 10 ring carbon atoms and zero heteroatoms in the non-aromatic ring system; and
aryl refers to a radical of a monocyclic or polycyclic aromatic ring system having 6-14 ring carbon atoms and zero heteroatoms provided in the aromatic ring system; and
heteroaryl refers to a radical of a 5-10 membered monocyclic or bicyclic aromatic ring system having ring carbon atoms and 1-4 ring heteroatoms provided in the aromatic ring system, wherein each heteroatom is independently selected from nitrogen, oxygen and sulfur, as disclosed in WO 2014/100764.

In some embodiments, the PRMT5 inhibitor is sinefungin, HLCL7, CMP12, BLL-1, BLL-3, any of BLL2-BLL8, BLL36, CMP5 (BLL1), CMP5 derivatives, BLL54, or any of the compounds designated herein as Formulas I-VIII (including VIId); any of these can use used in any of the methods disclosed herein, wherein in the case of a discrepancy between the document incorporated by reference and this disclosure in regards to chemical structures, the document incorporated by reference controls in regards to chemical structures.

In other embodiments, the PRMT5 inhibitor is selected from:

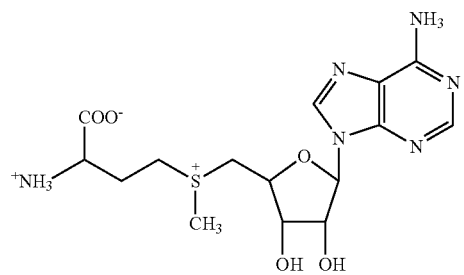

S-adenosylmethionine

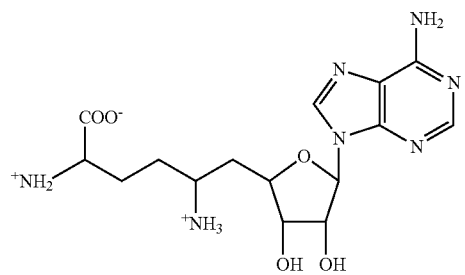

Sinefungin

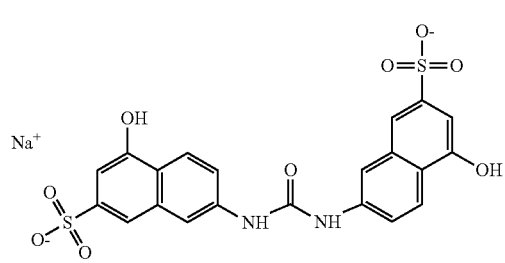

AMI-1

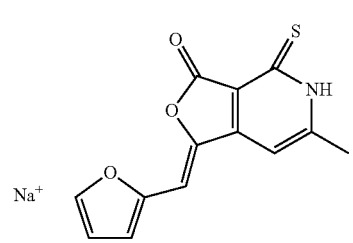

AMI-2

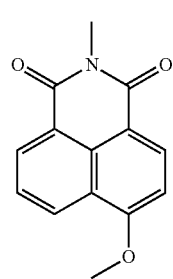

AMI-3

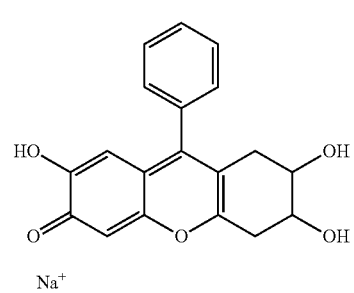

AMI-4

-continued
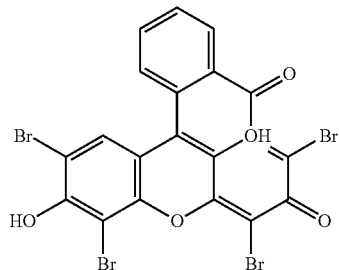
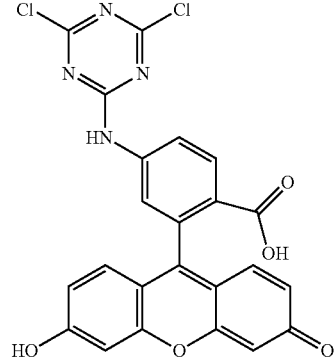
AMI-5
AMI-6
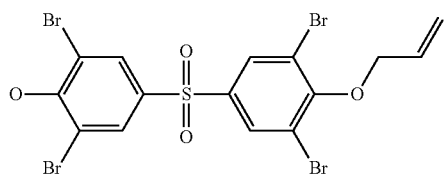
AMI-7
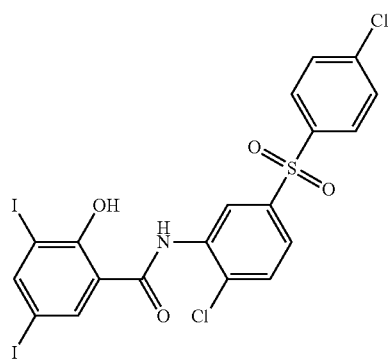
AMI-8
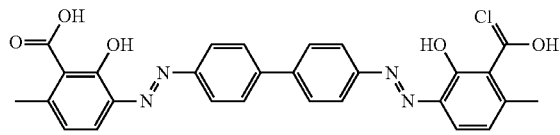
AMI-9
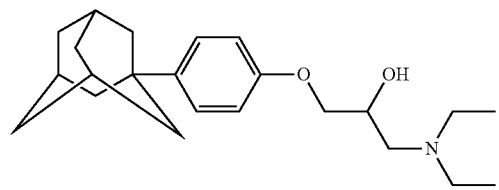
AMA-1
HCl
AMA-2
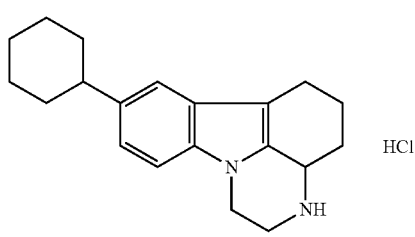
HCl

Eosin (AMI-5), curcumin, resveratrol, GW5074,
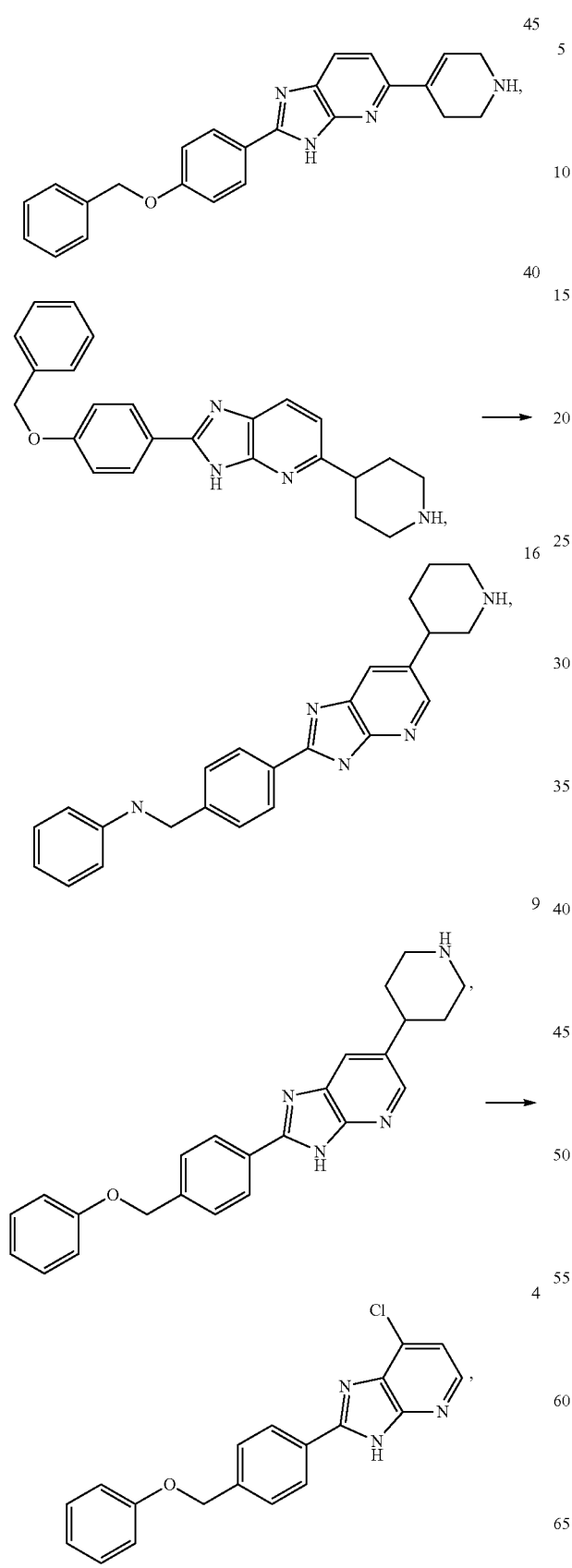
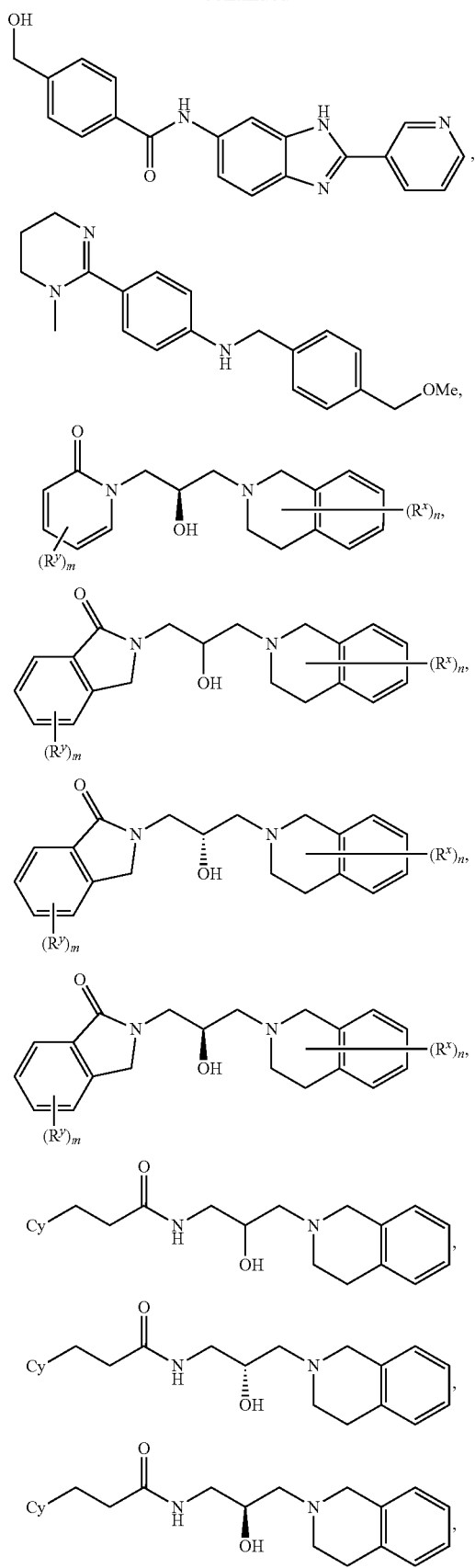

207
-continued
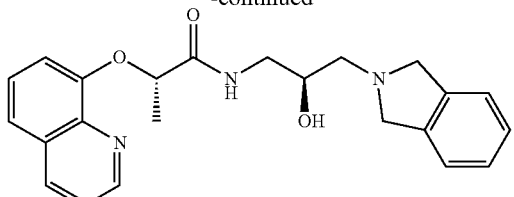
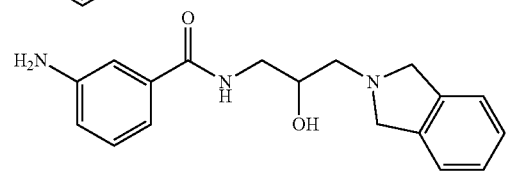
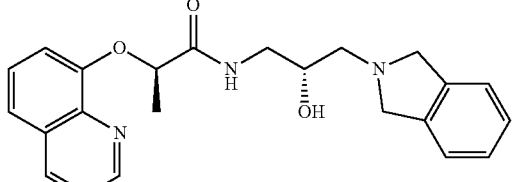
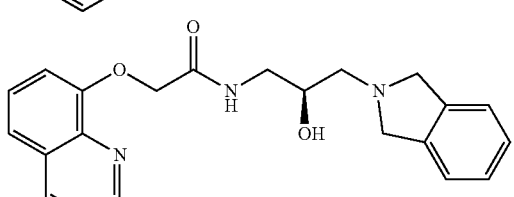
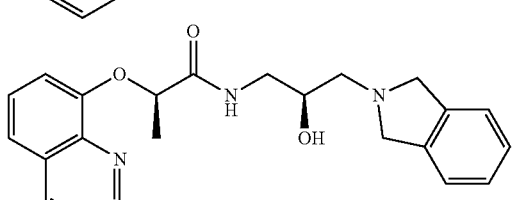
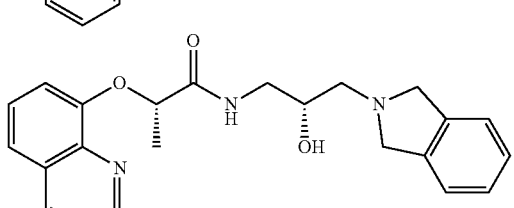
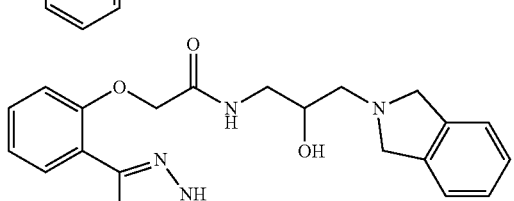
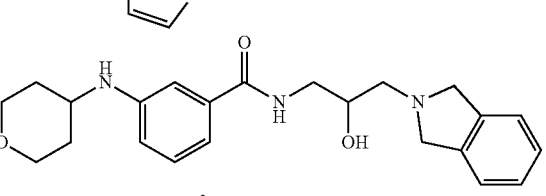
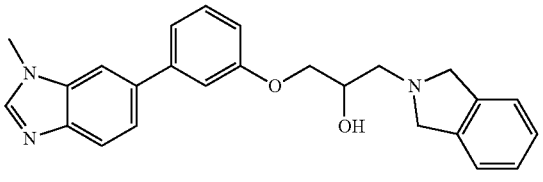
208
-continued
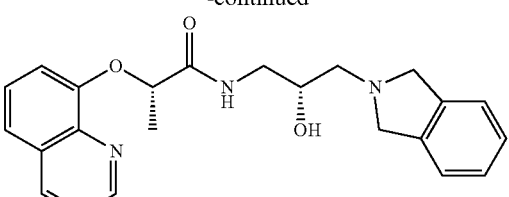
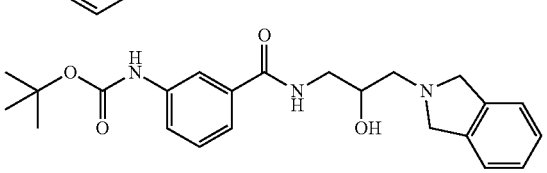
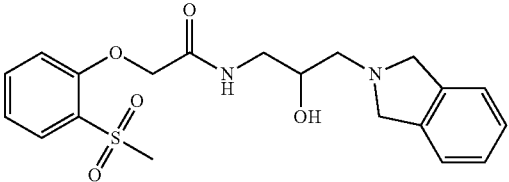
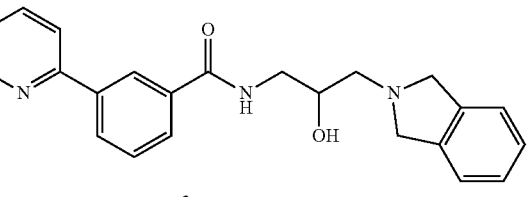
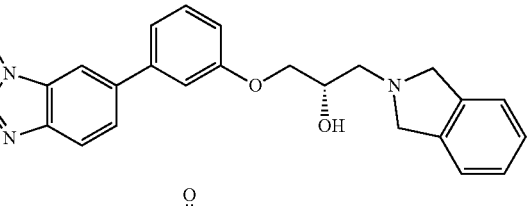
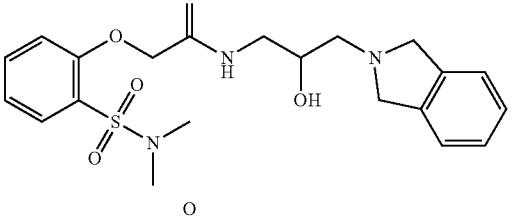
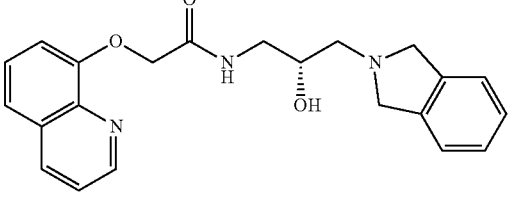
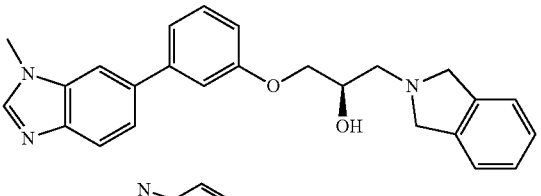
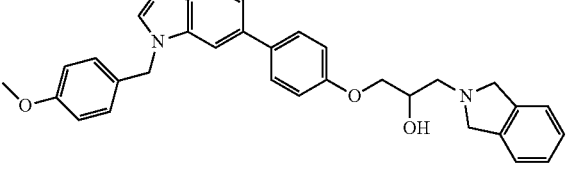

209
-continued
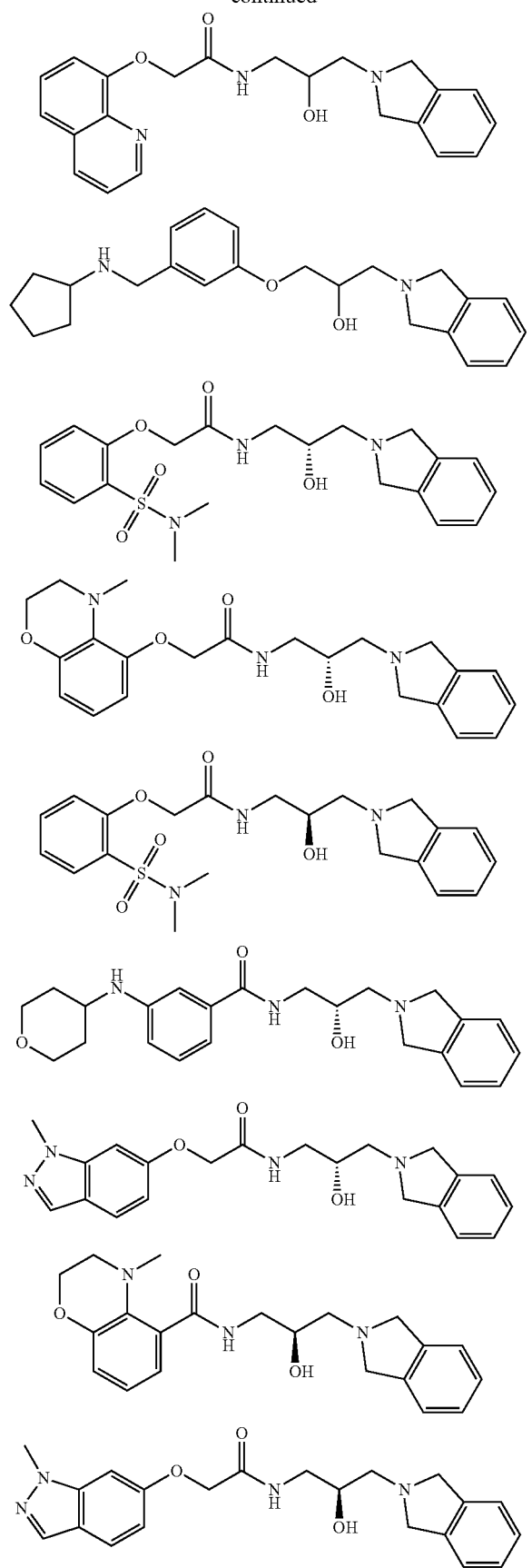
210
-continued
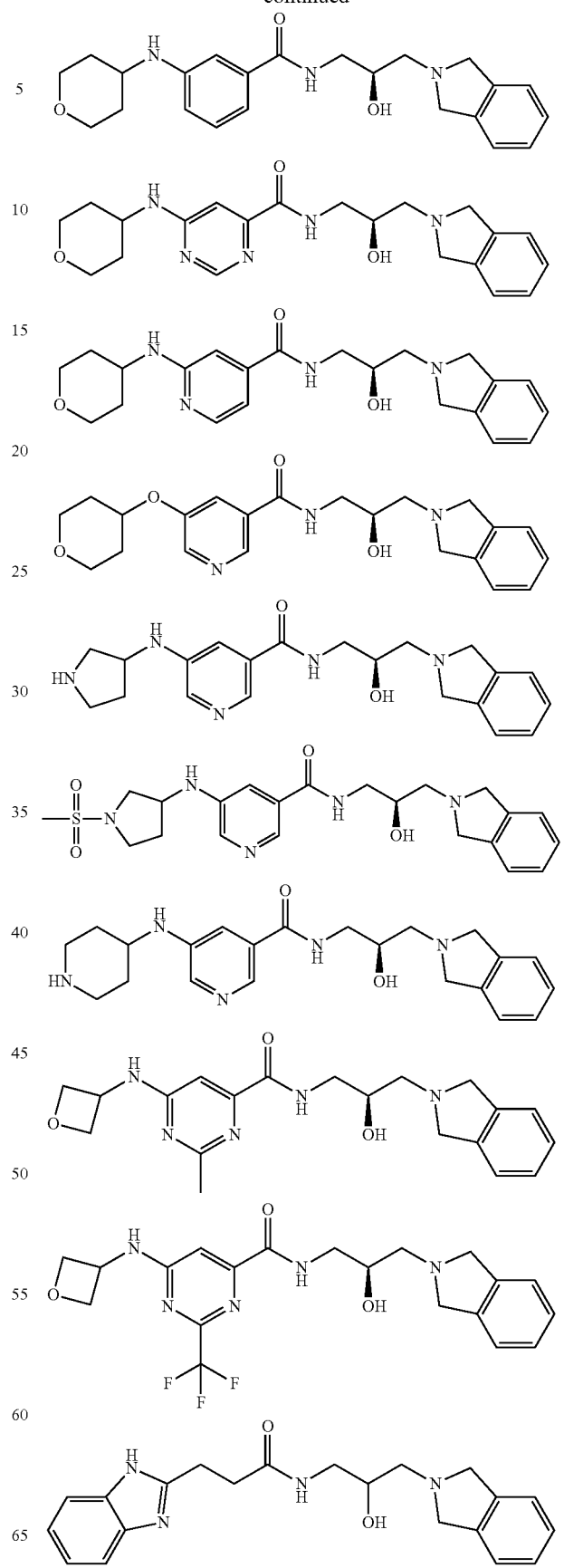

211
-continued
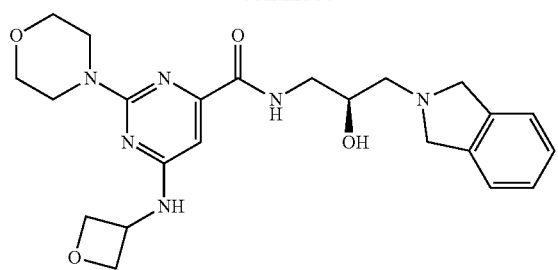
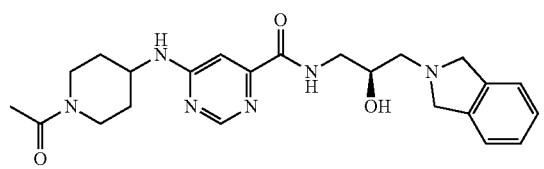
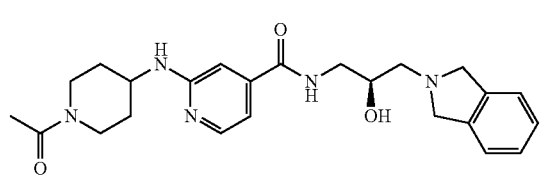
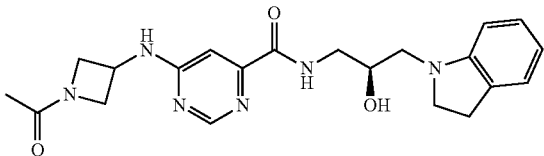
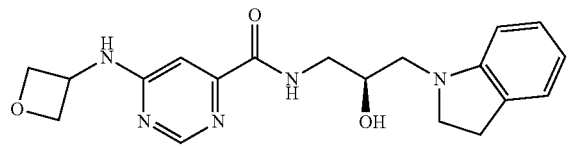
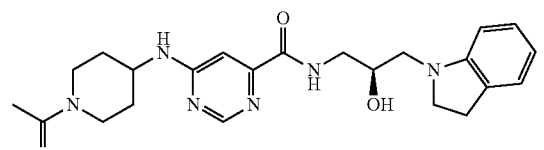
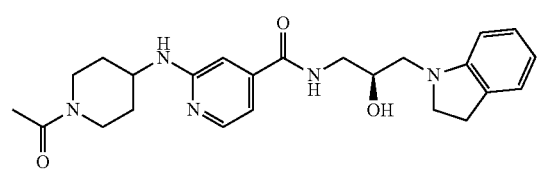
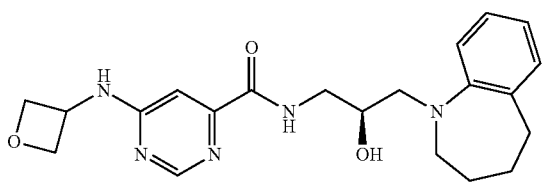
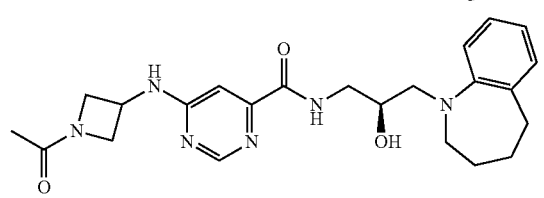
212
-continued
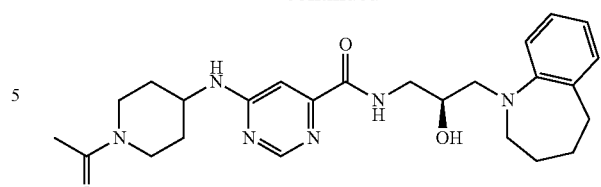
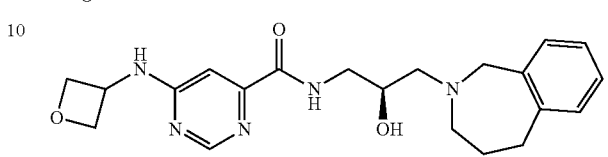
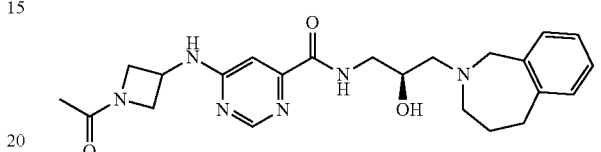
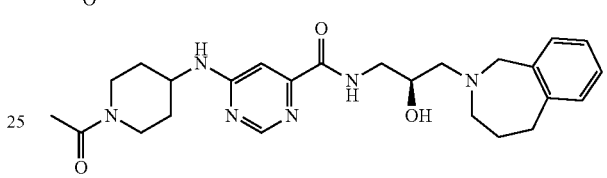
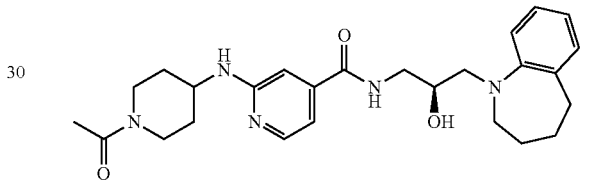
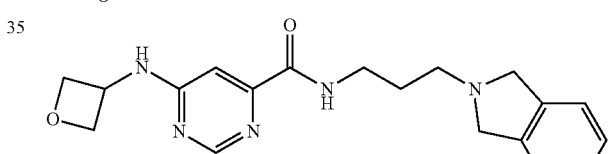
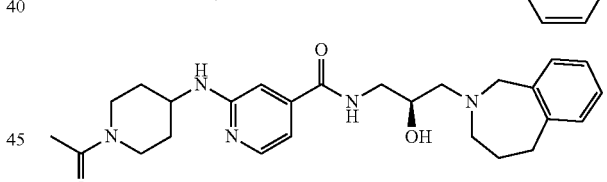
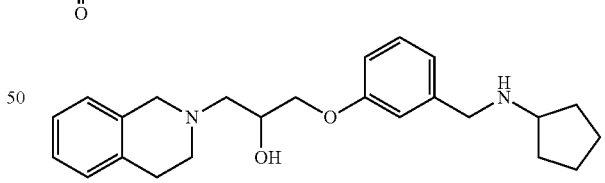
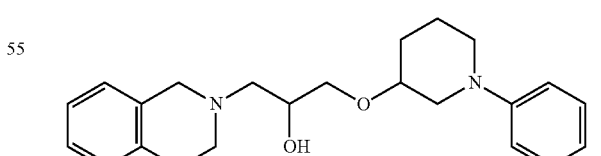
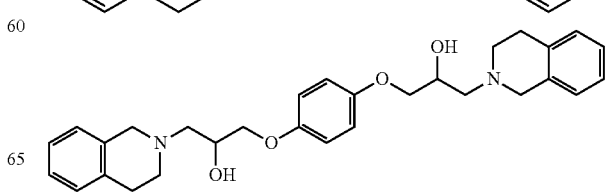

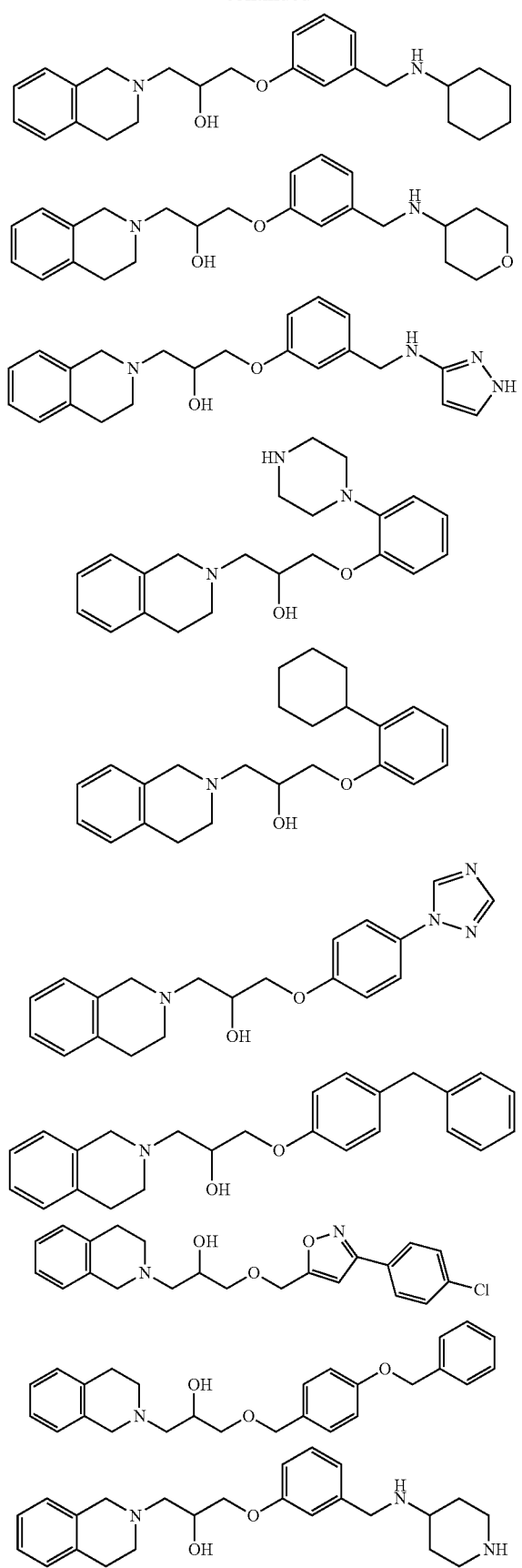
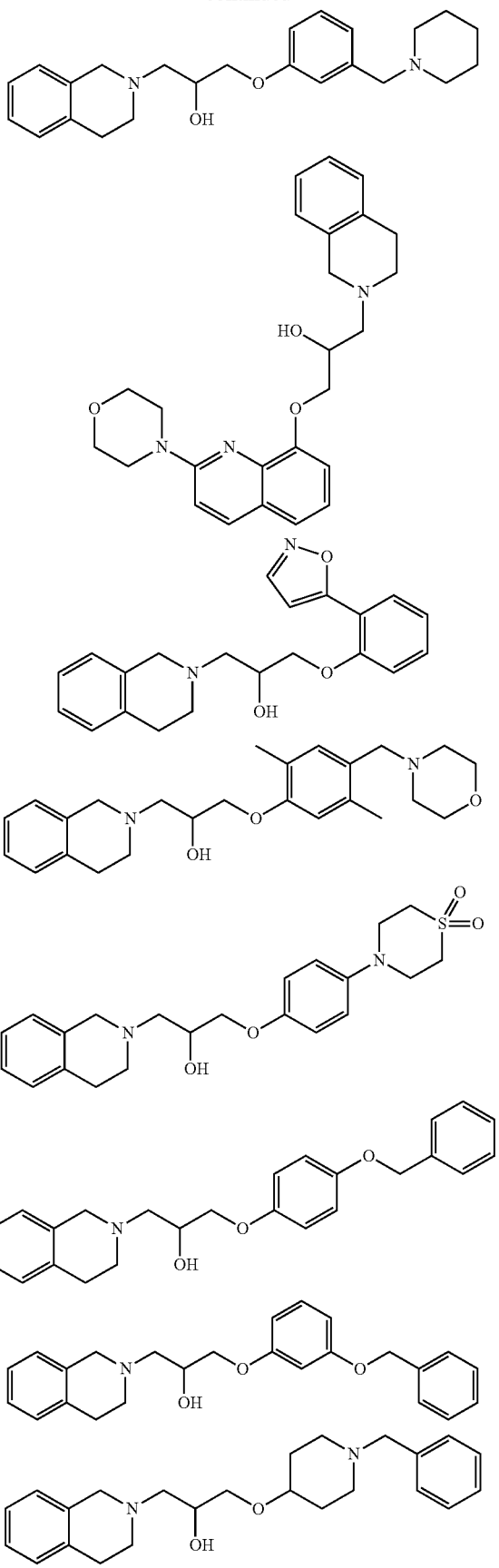

-continued
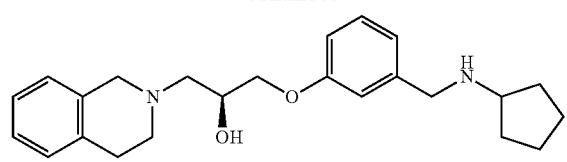
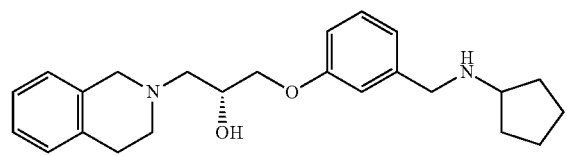
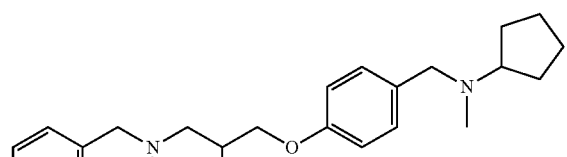
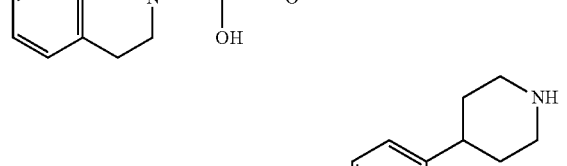
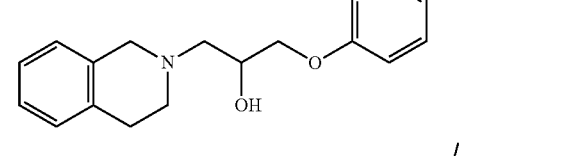
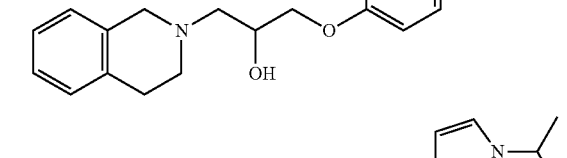
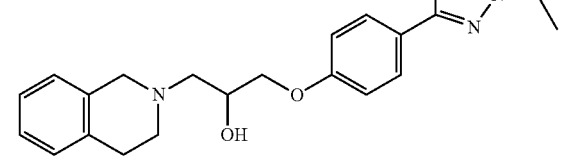
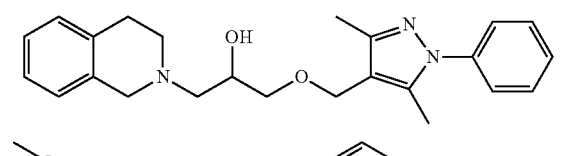
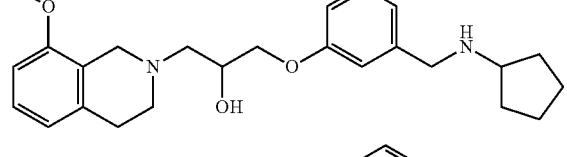
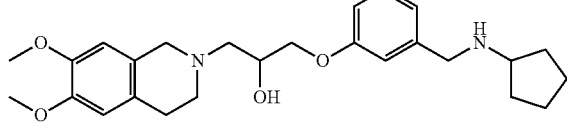
-continued
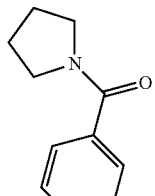
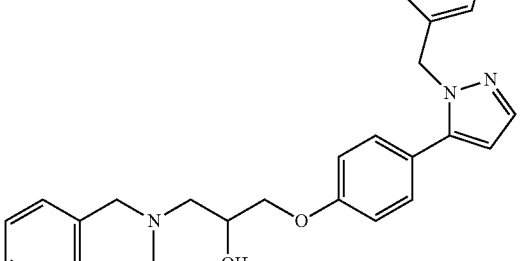
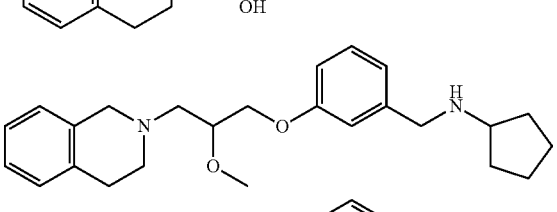
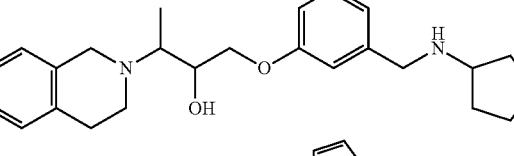
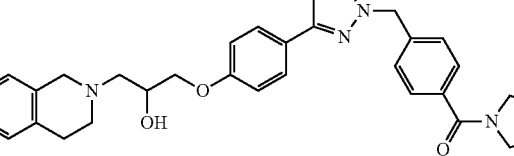
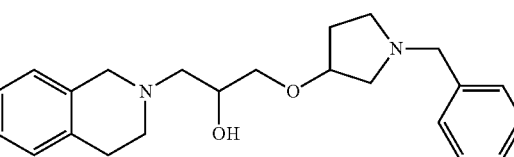
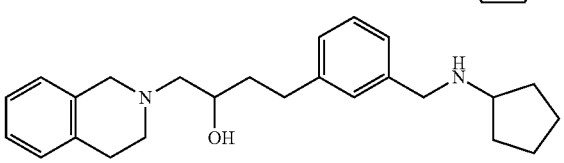
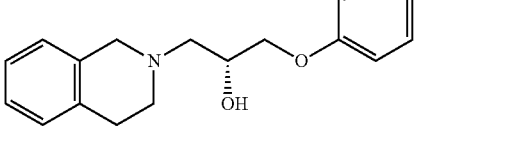

217
-continued
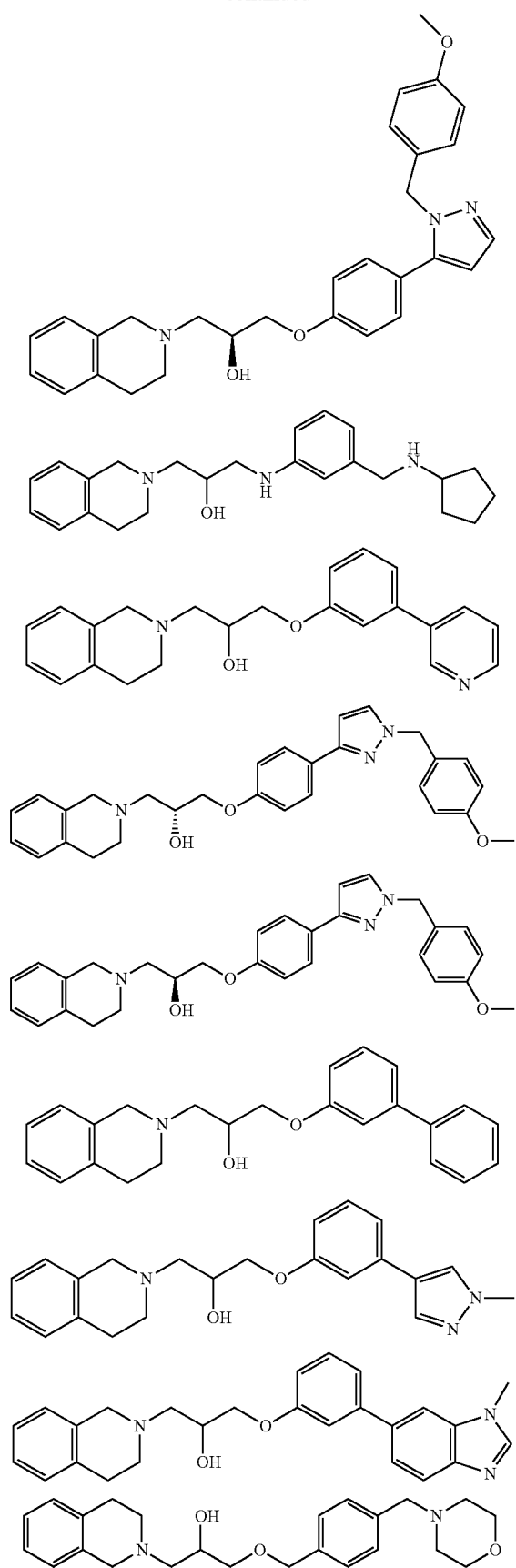
218
-continued
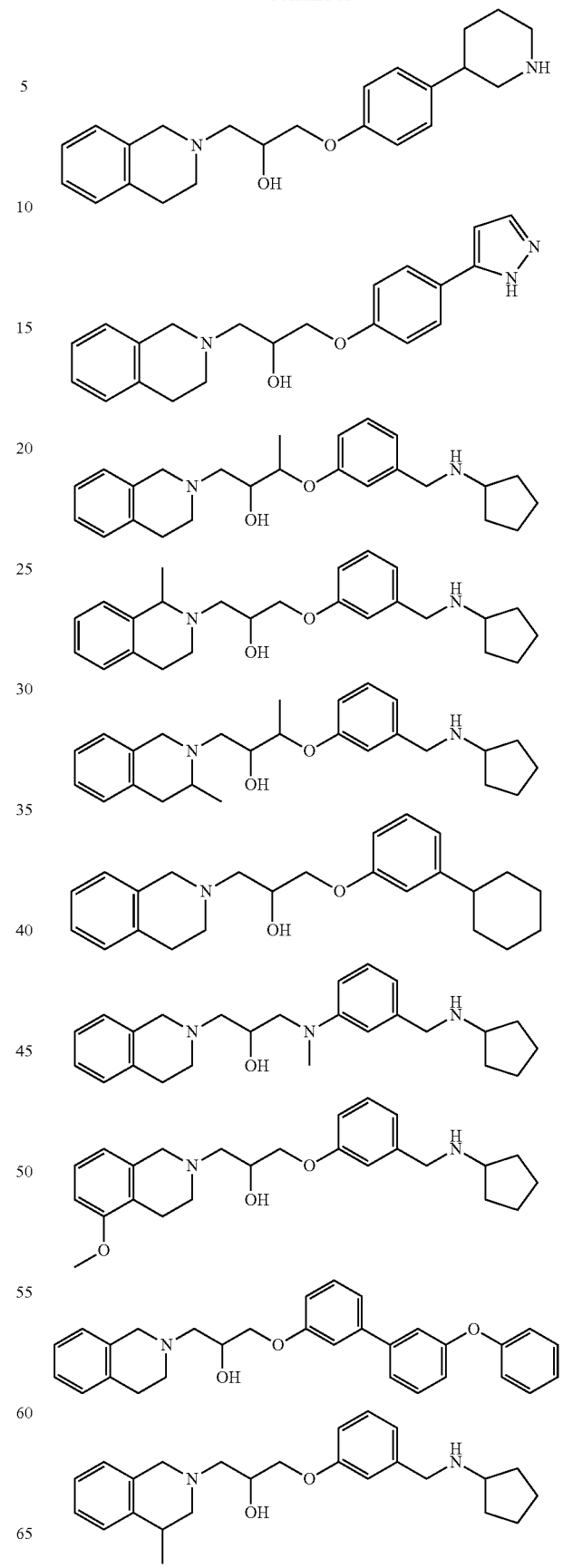

219
-continued
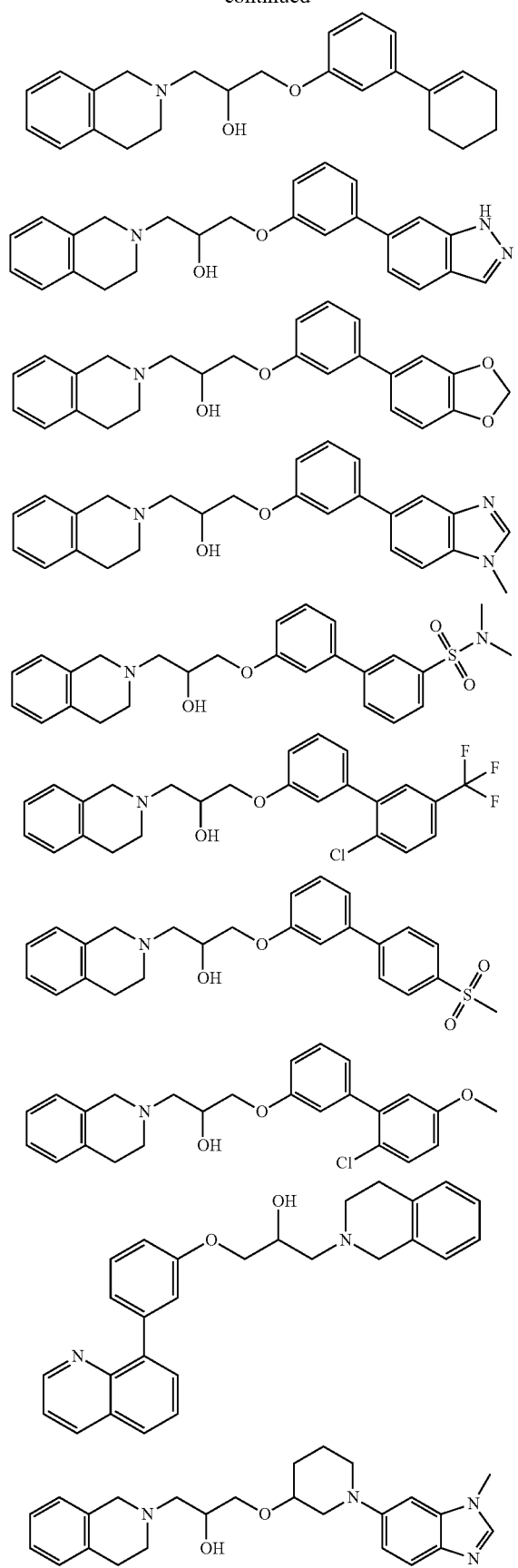
220
-continued
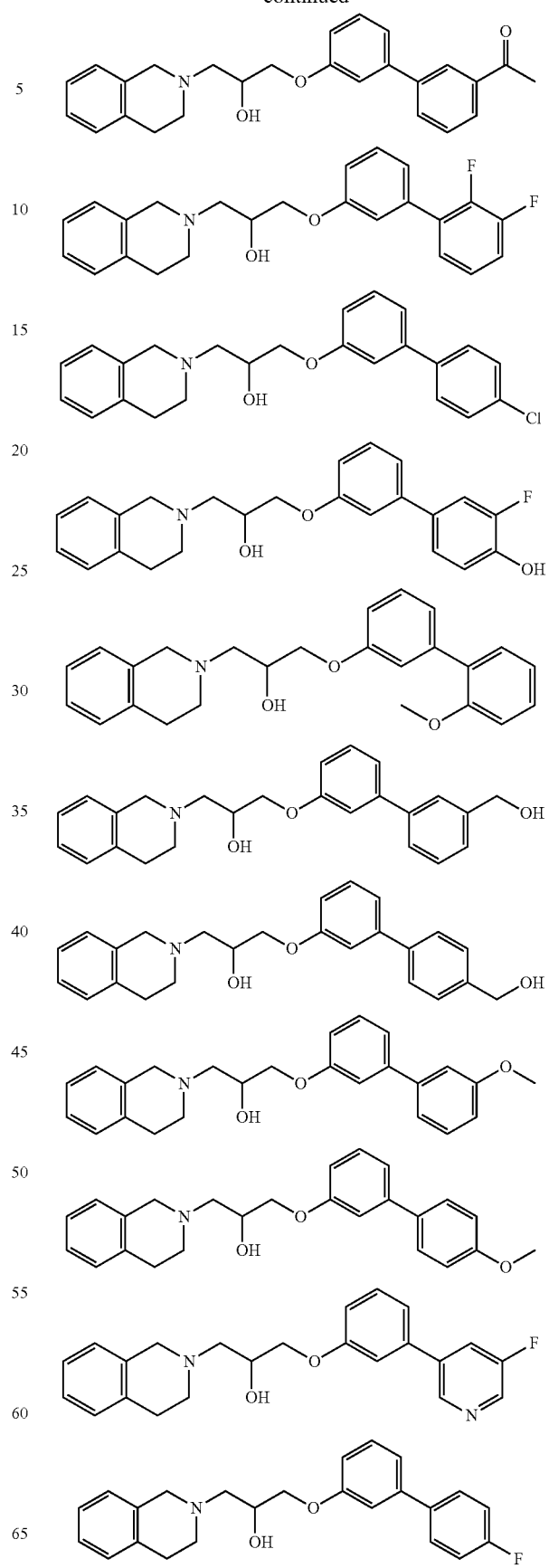

221
-continued
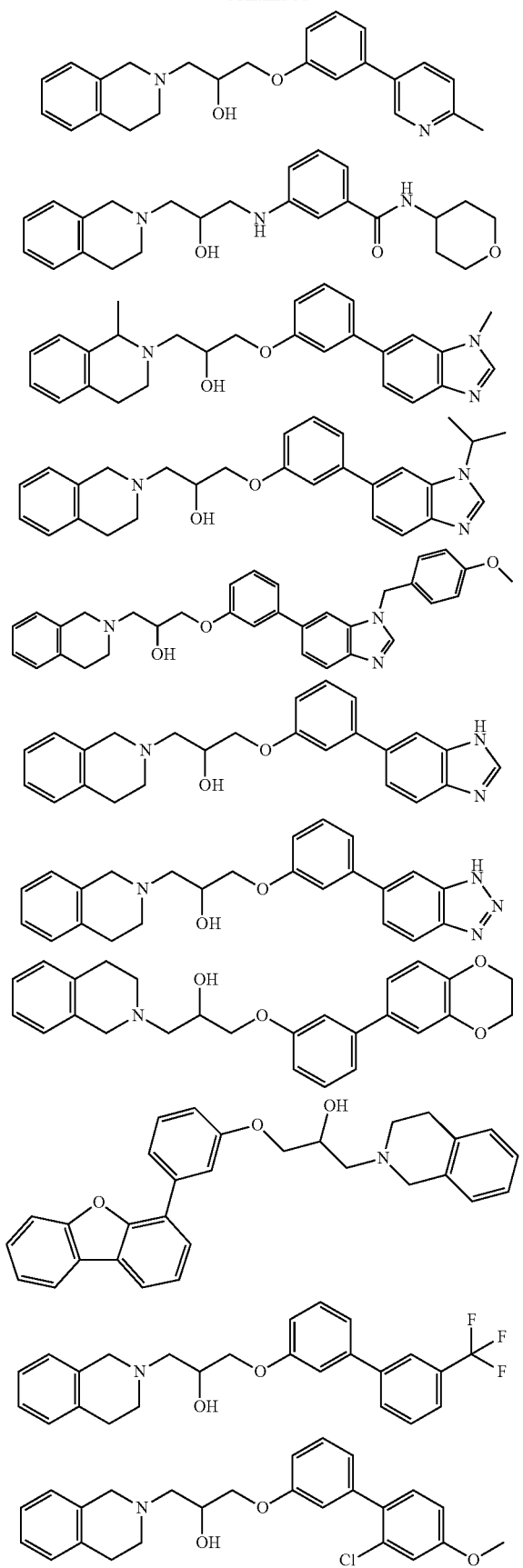
222
-continued
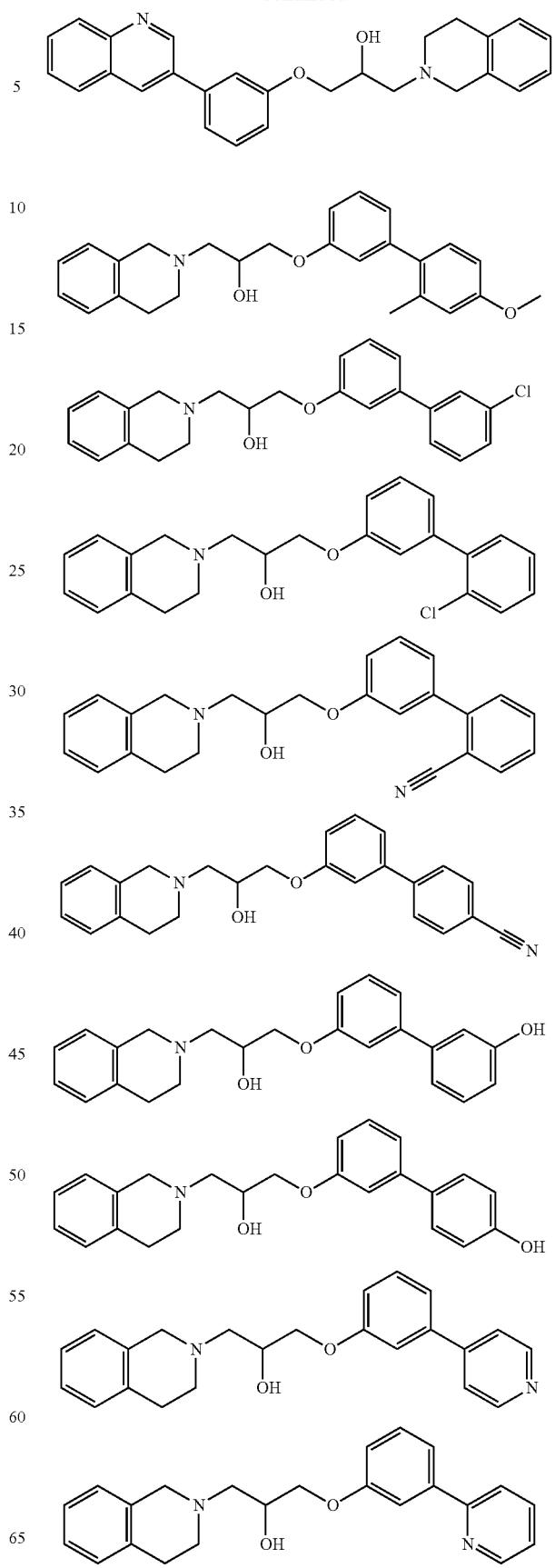

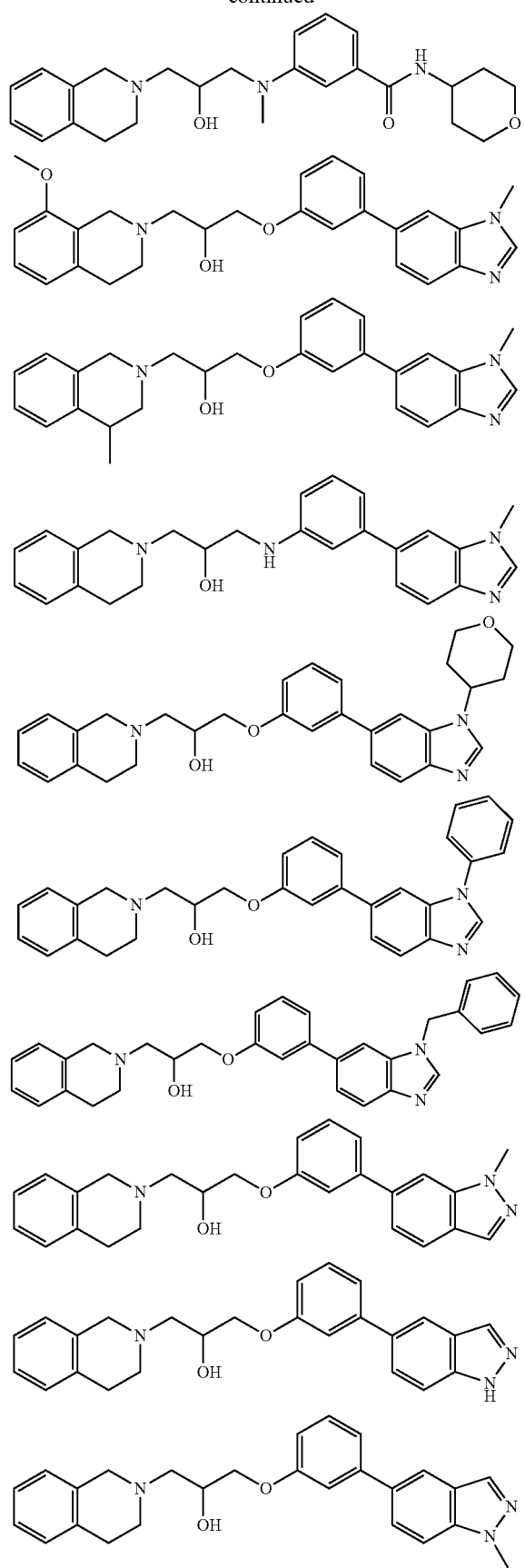
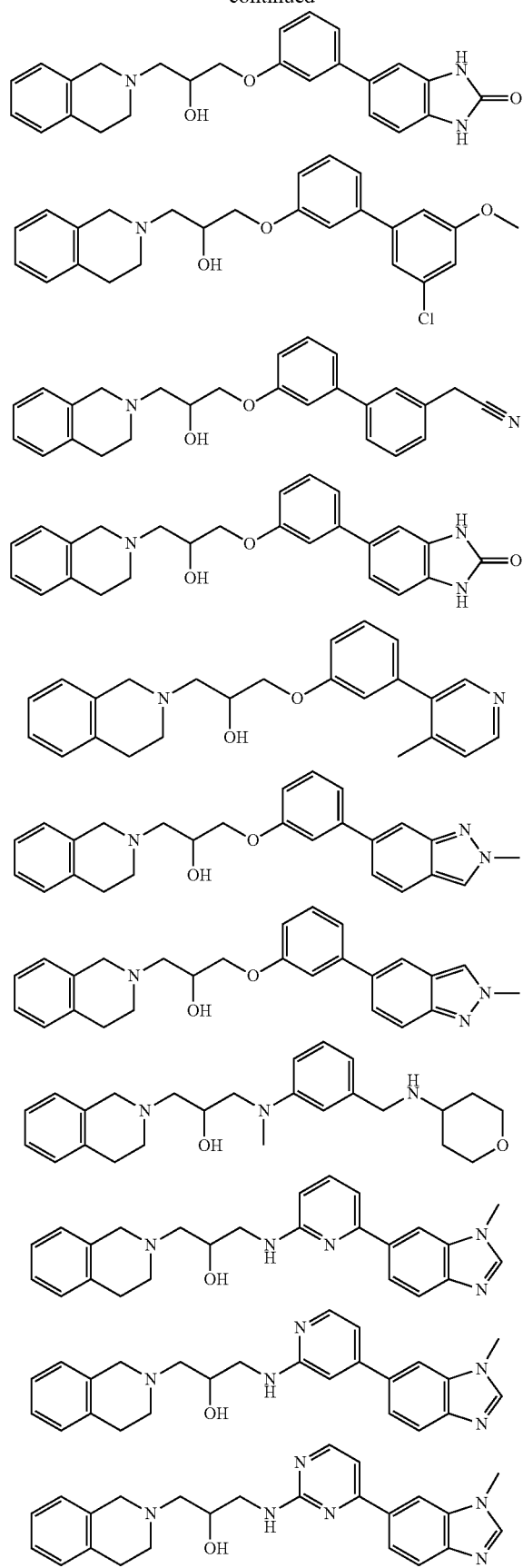

-continued

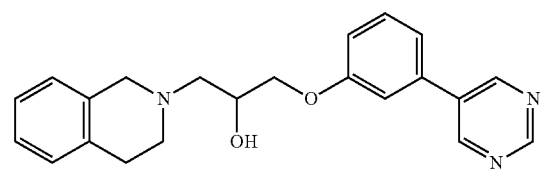
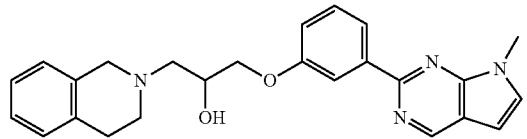
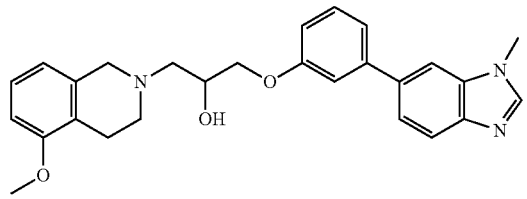
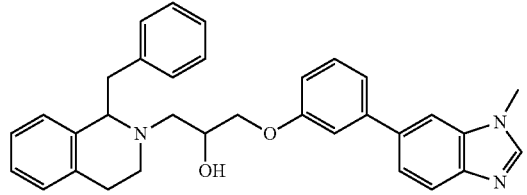
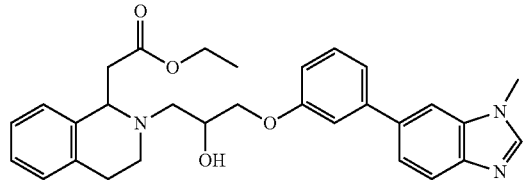
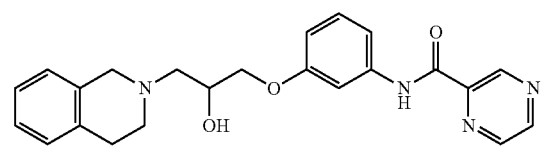
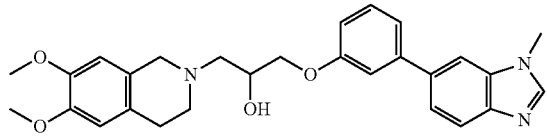
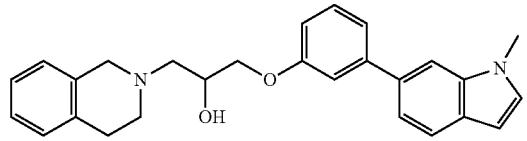
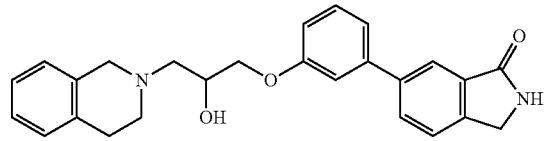
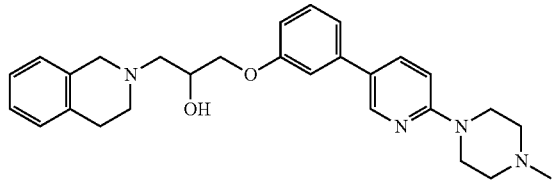
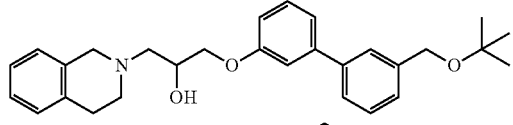
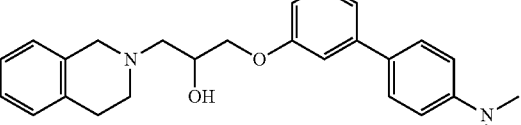
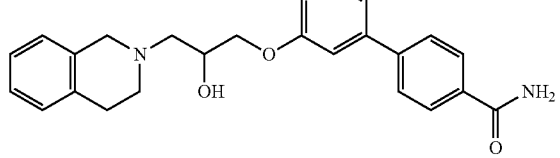
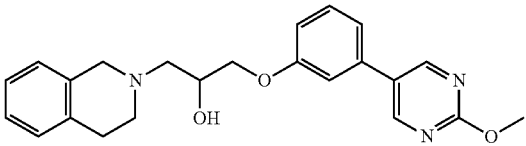
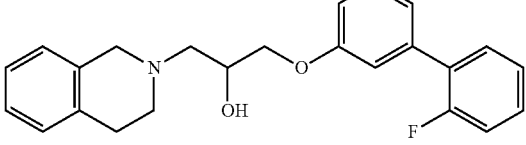
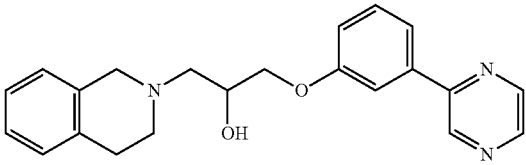
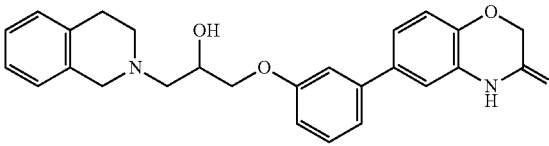
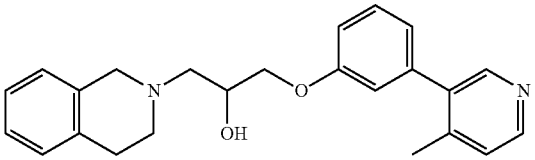
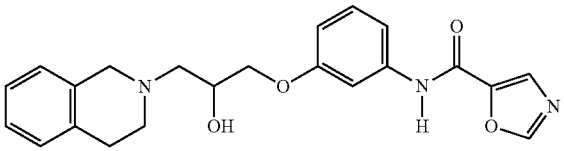
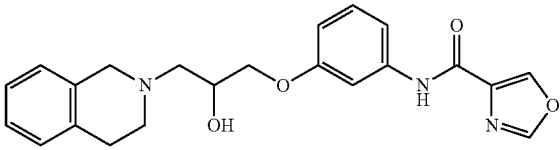
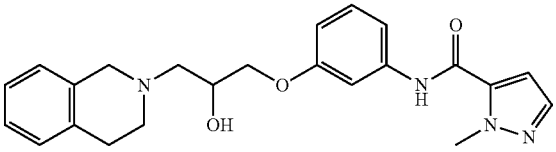

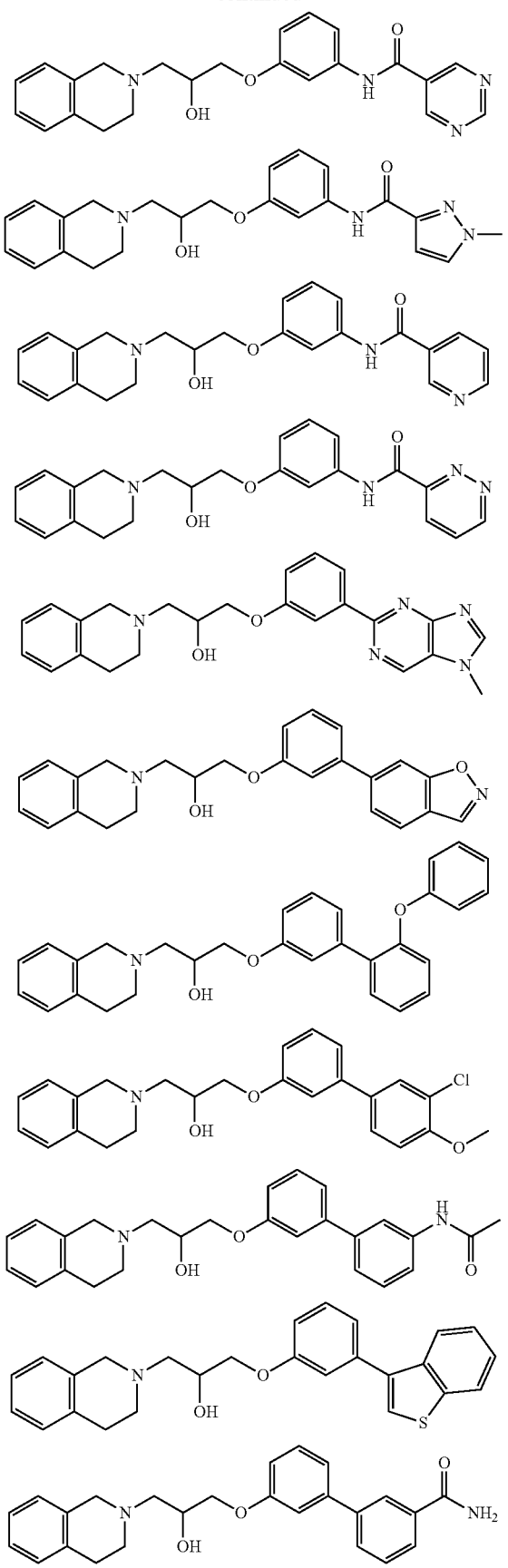
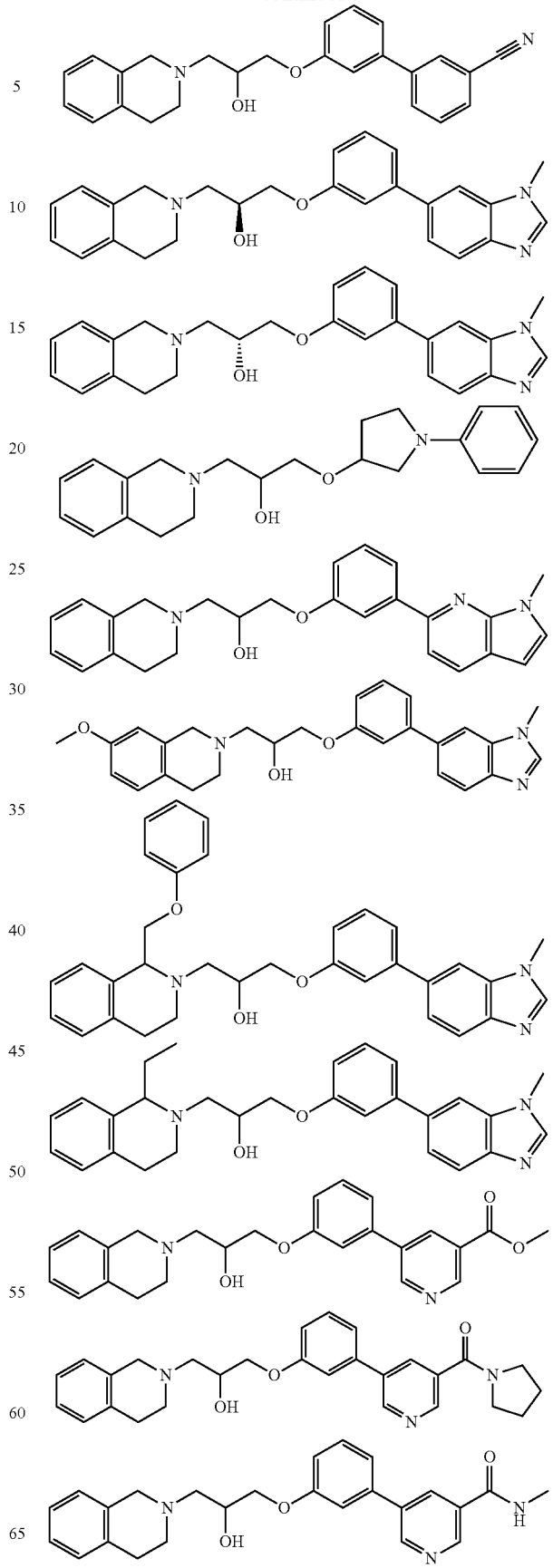

231
-continued
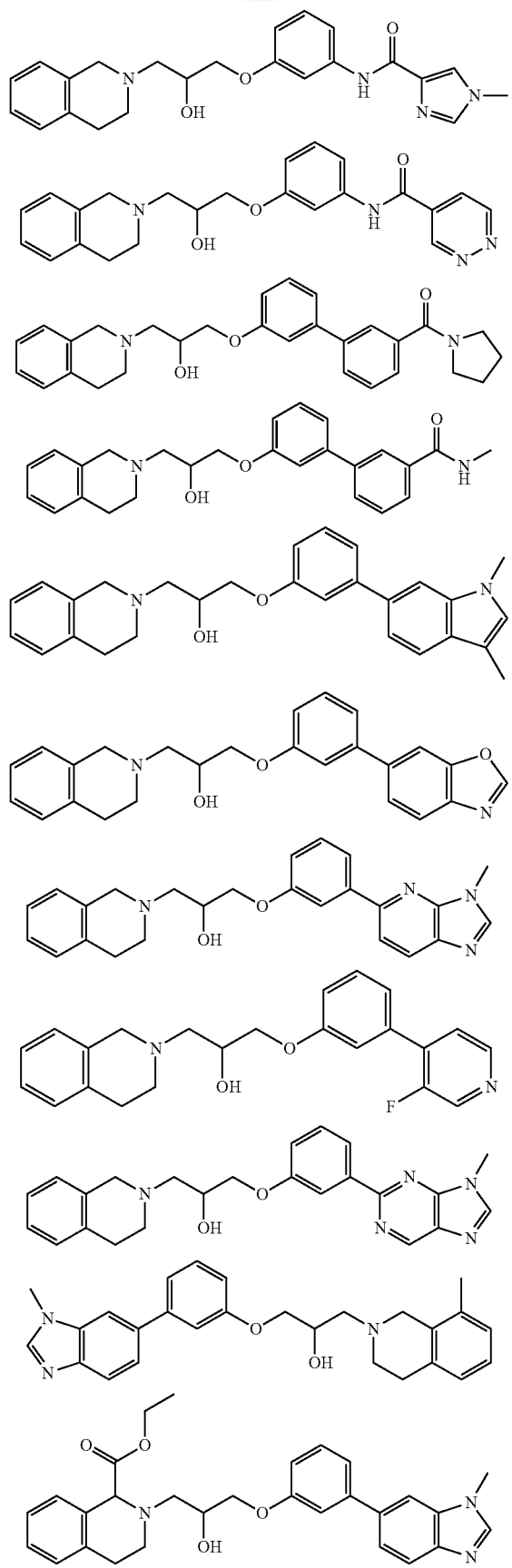
232
-continued
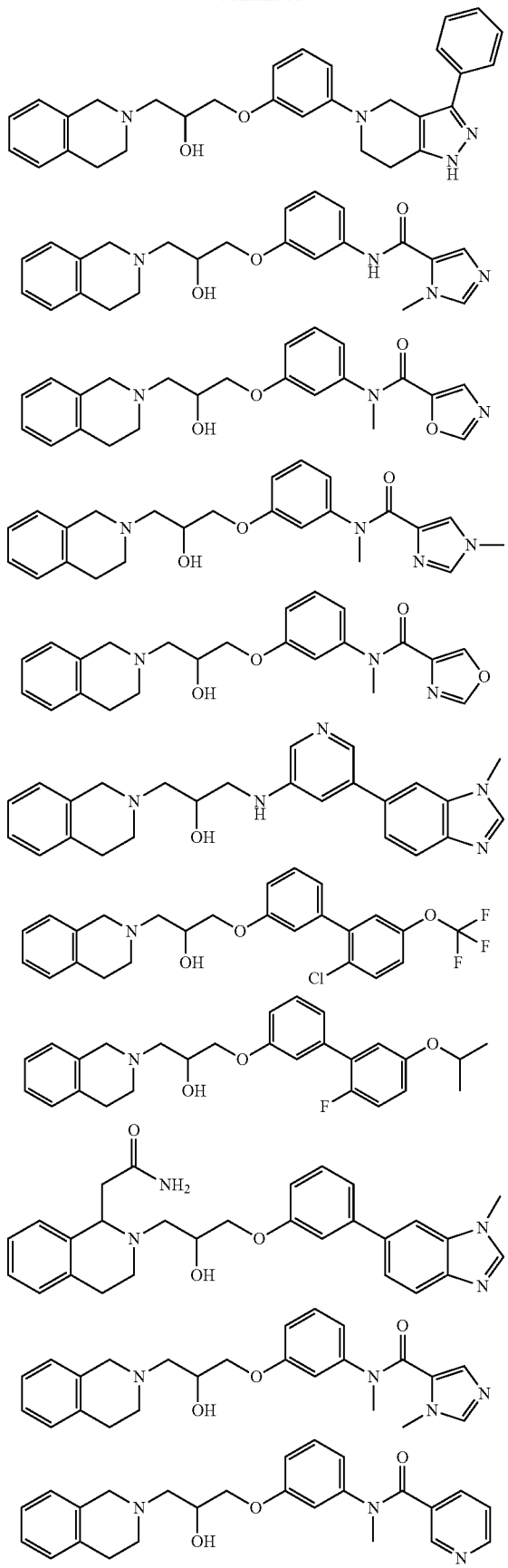

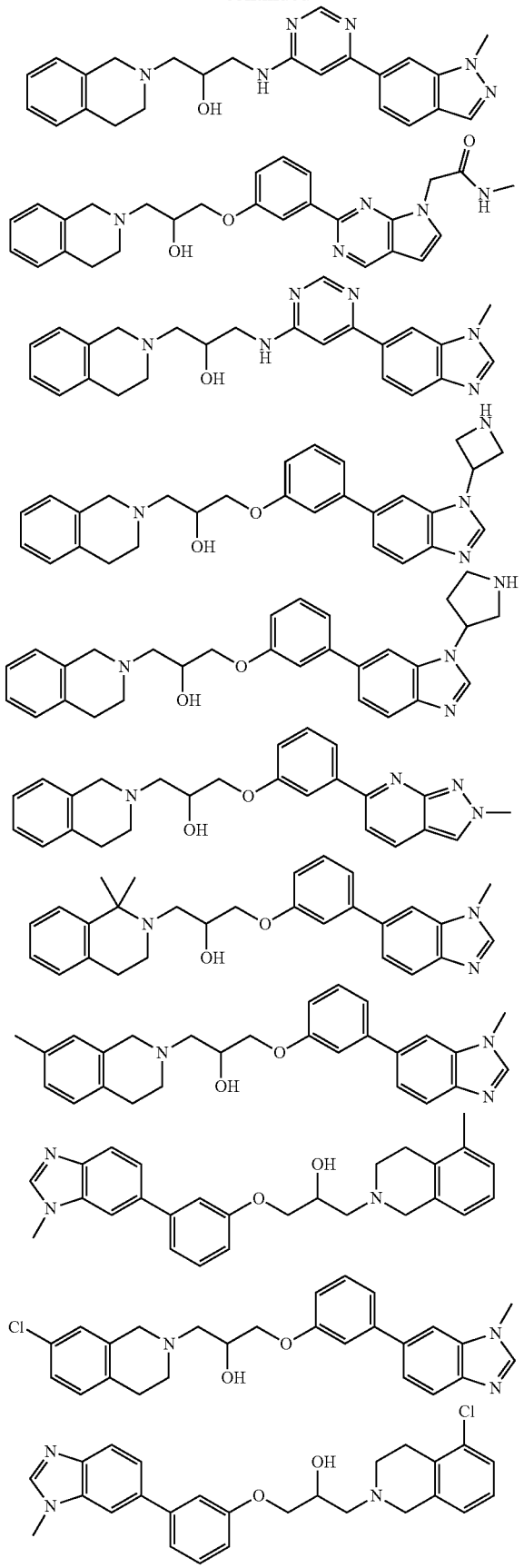
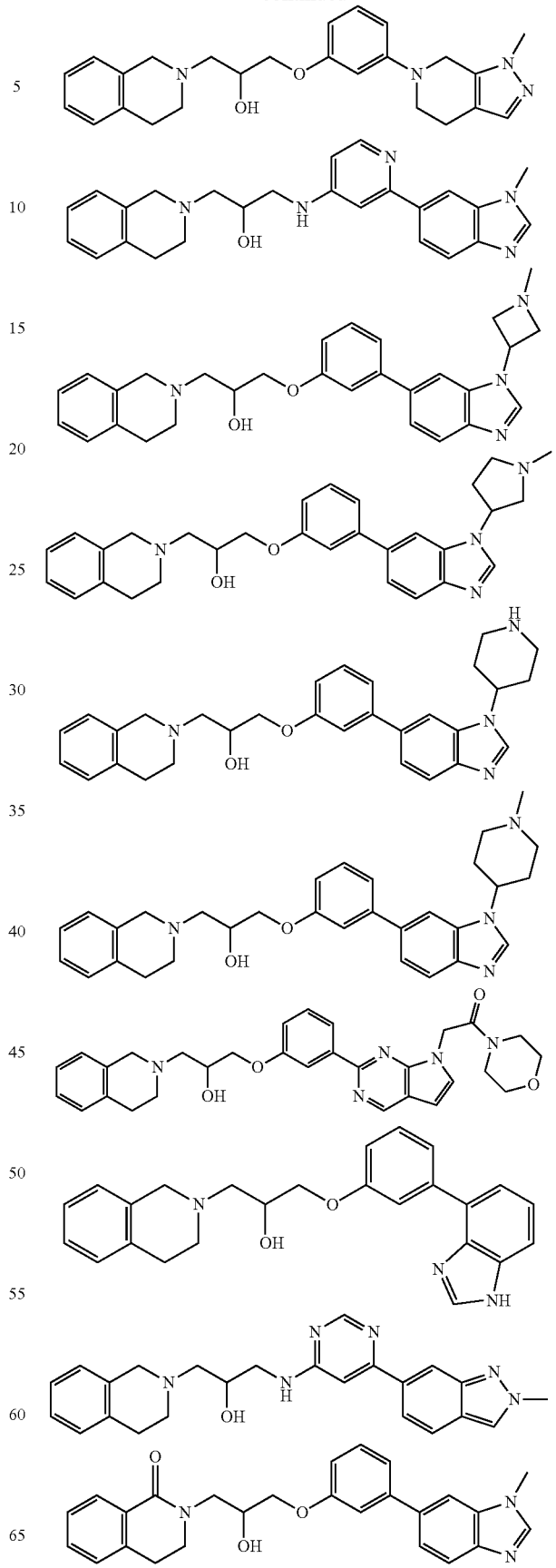

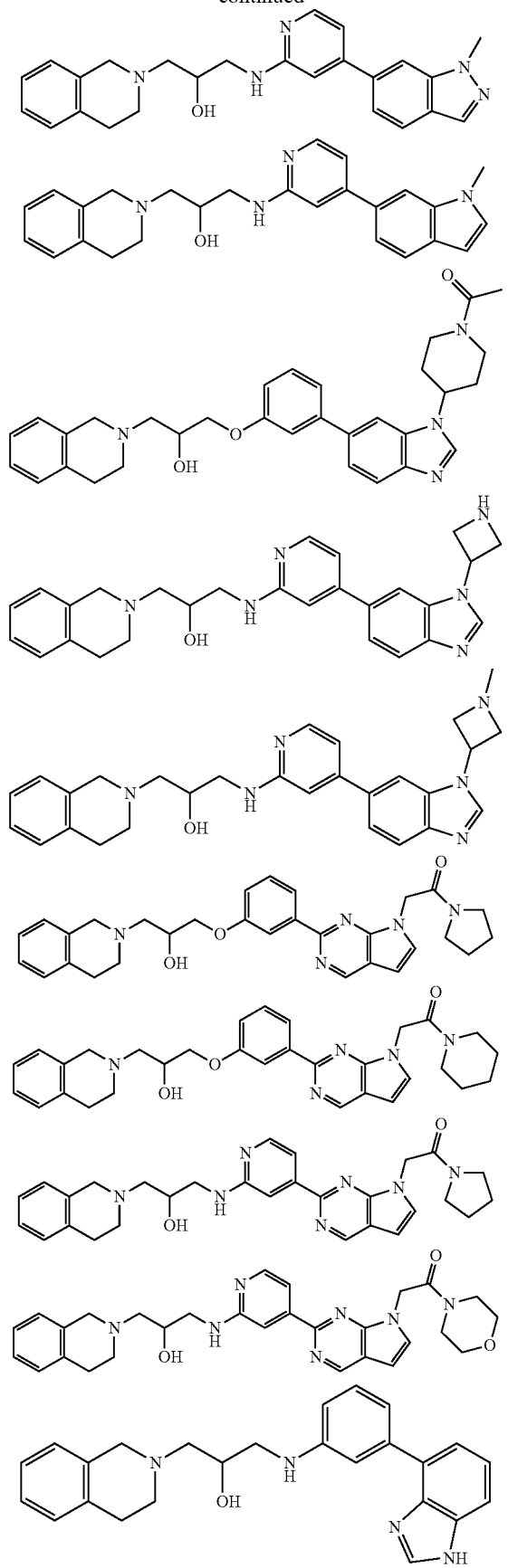
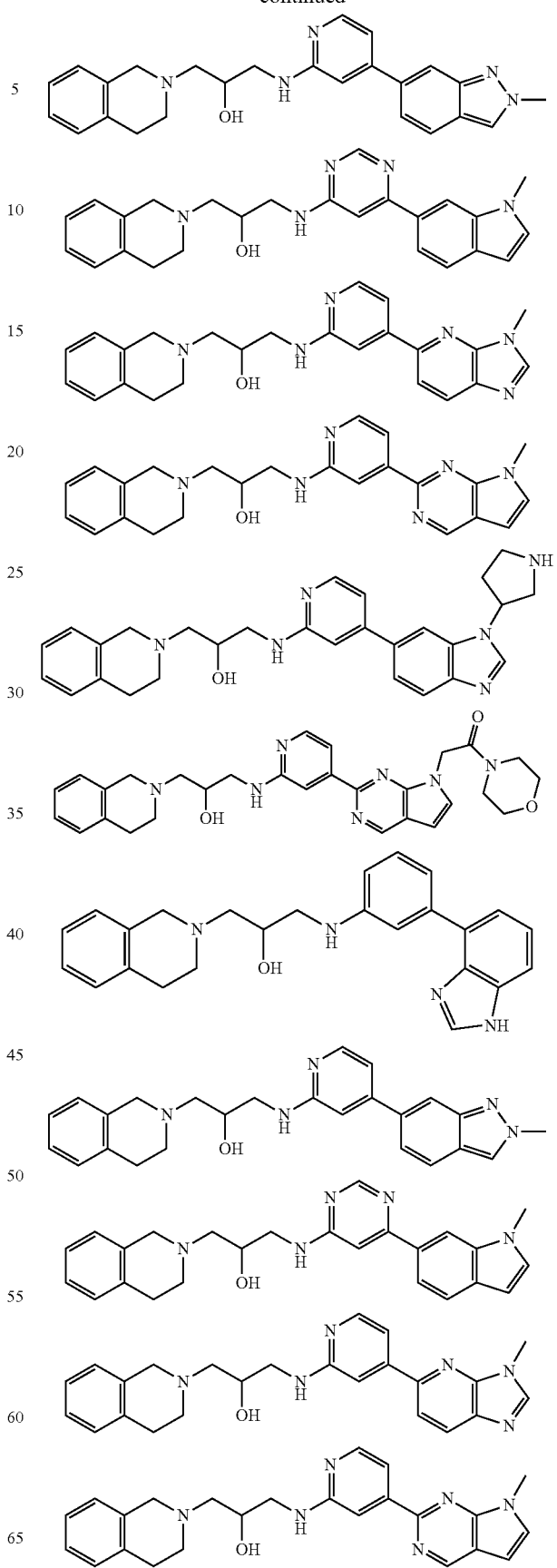

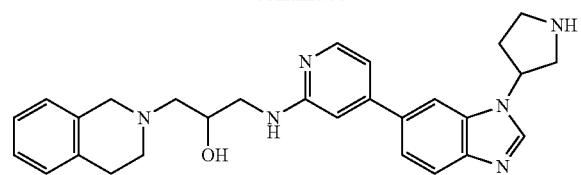
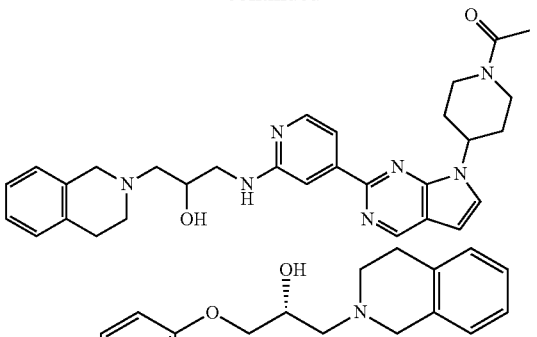
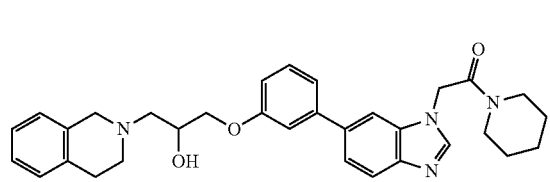
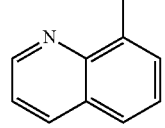
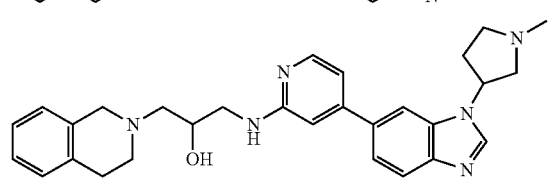
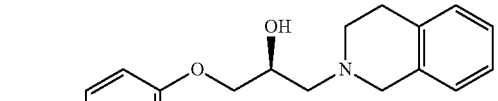
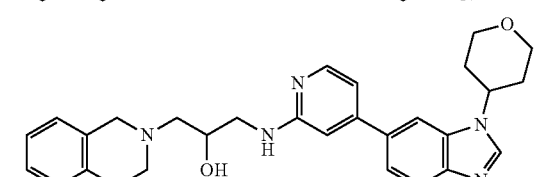
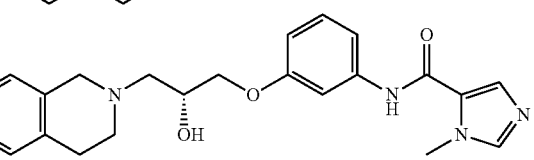
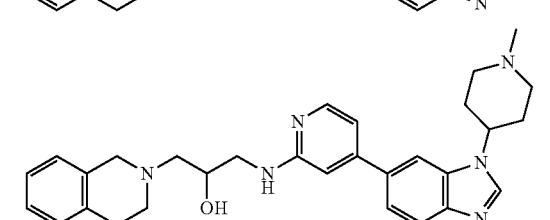
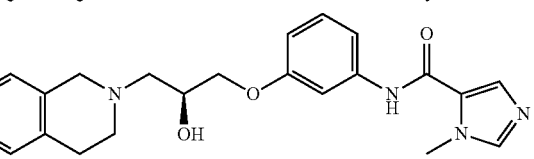
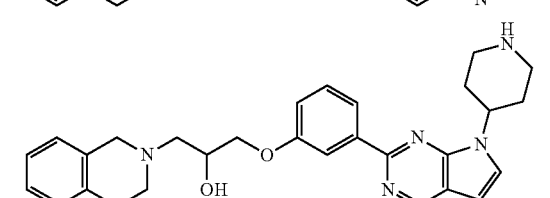
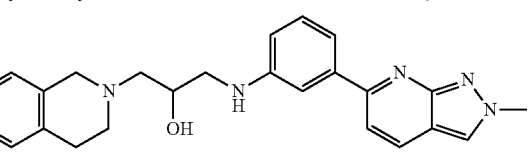
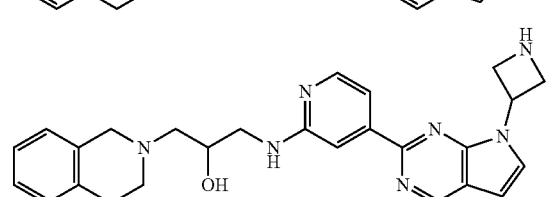
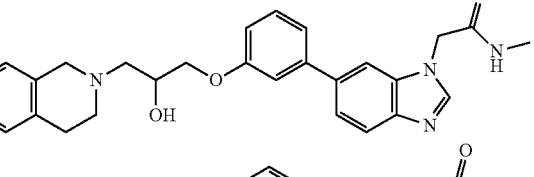
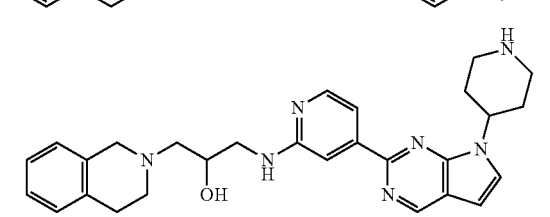
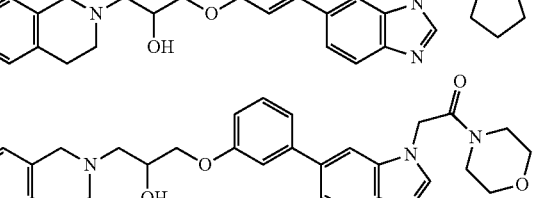

239
-continued
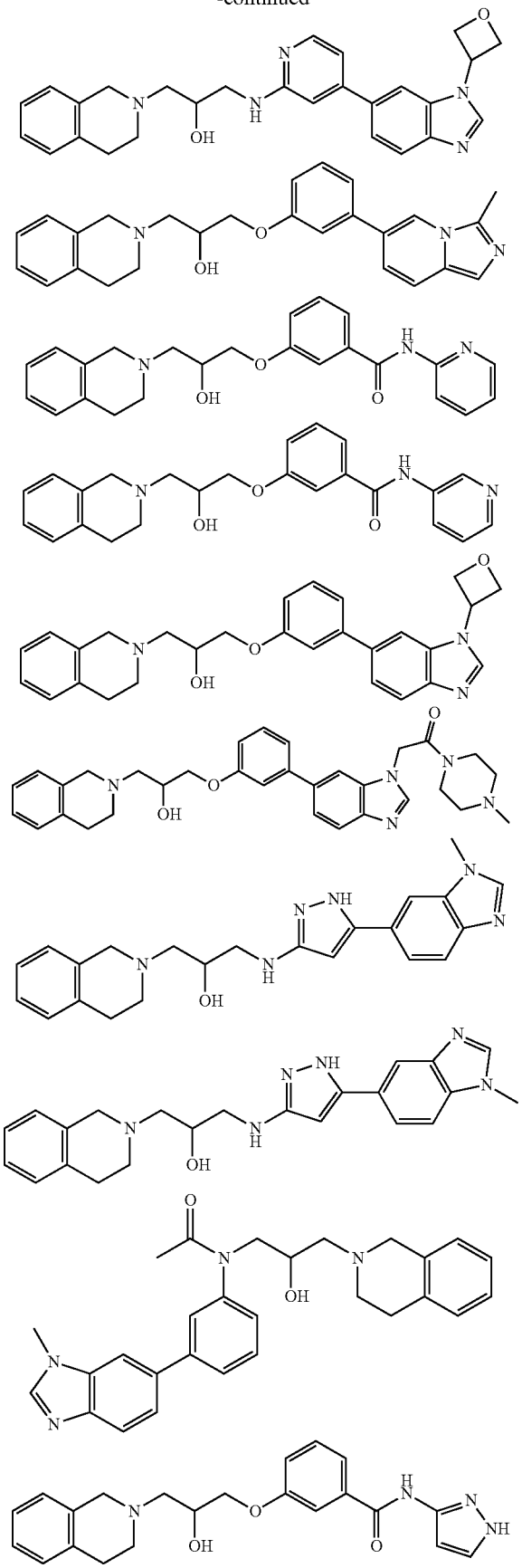
240
-continued
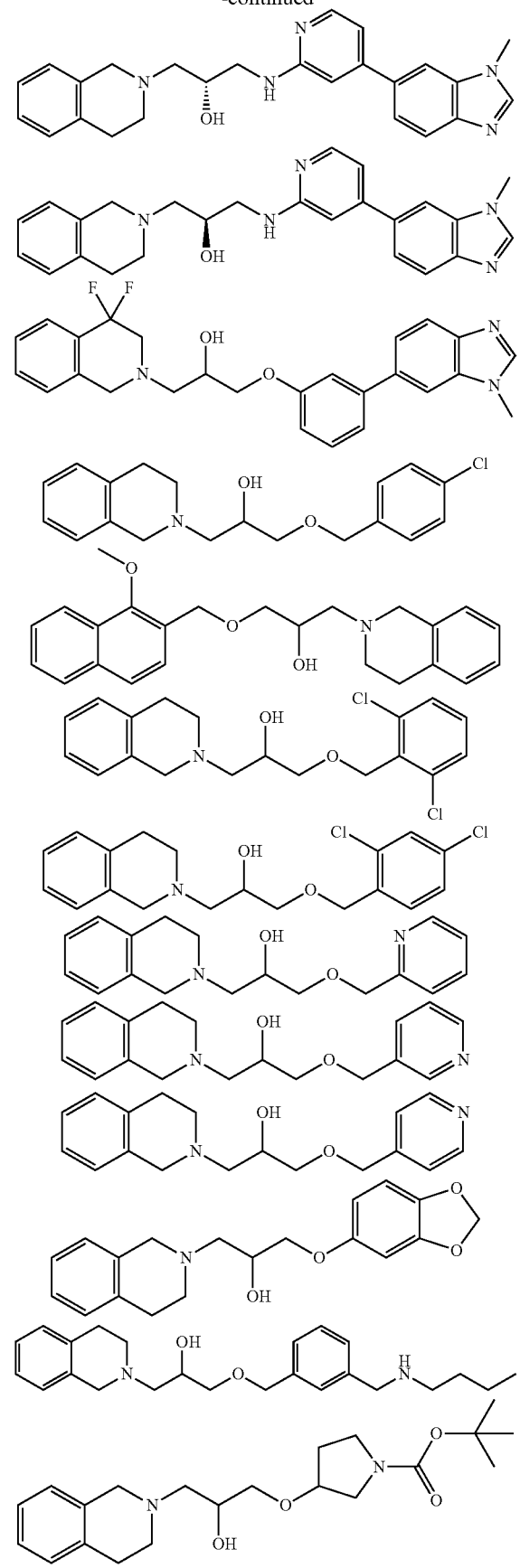

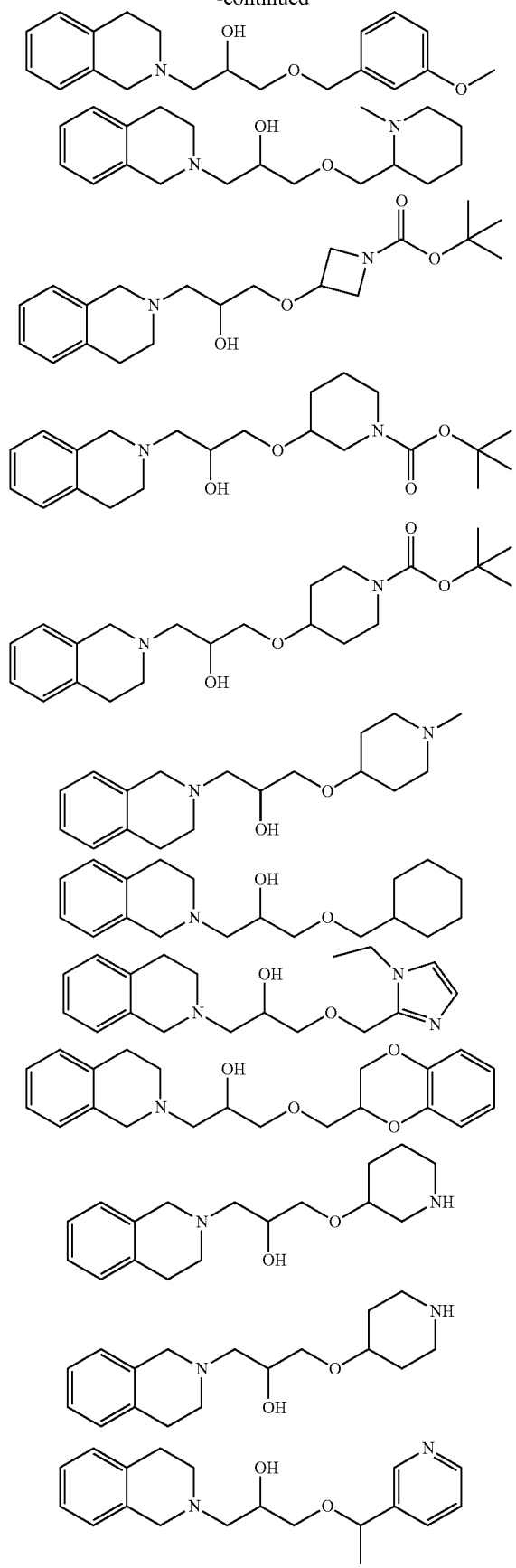
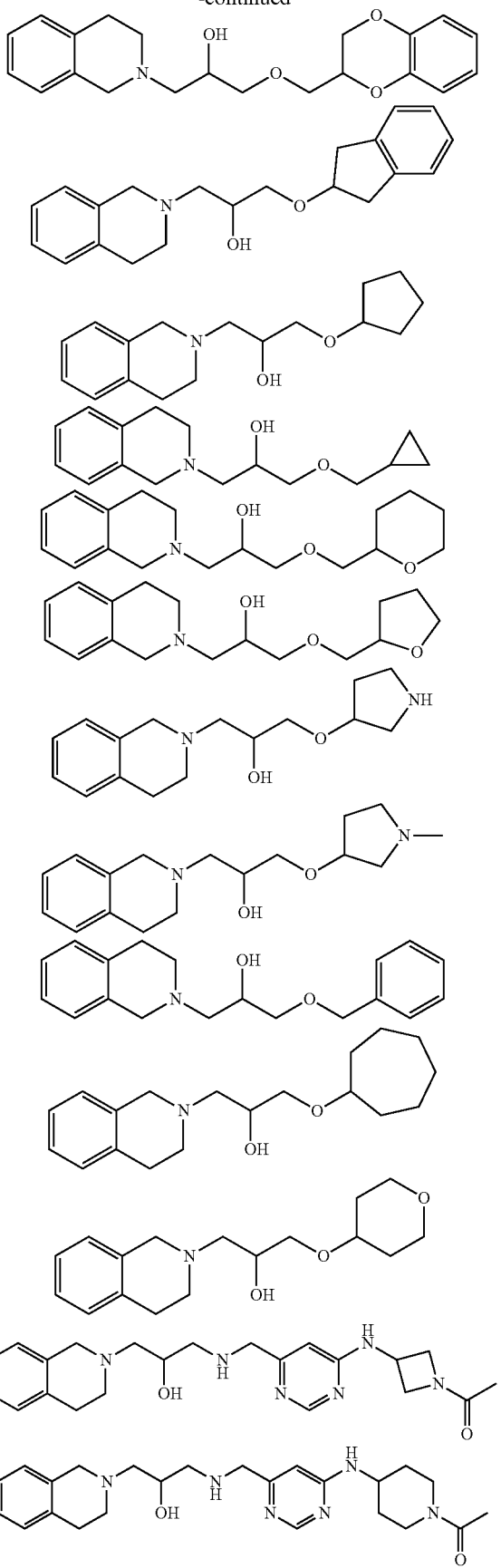

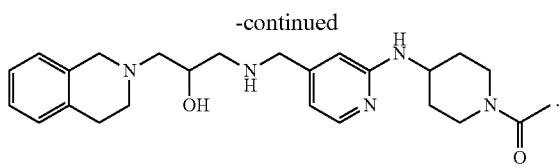

Any of the PRMT5 inhibitors described herein or known in the art can be used in the methods described herein. For example, the PRMT5 inhibitors described herein can be used in a method of inhibiting proliferation of TMPRSS2:ERG positive prostate cancer cells in a subject in need thereof, the method comprising the step of: administering to the subject, a PRMT5 inhibitor in an amount that is effective to inhibit proliferation of the TMPRSS2:ERG positive prostate cancer cells.

The PRMT5 inhibitors disclosed herein and in the art can be used in the methods of the present disclosure, wherein the proliferation and/or viability of a TMPRSS2:ERG positive prostate cancer cell can be decreased by administration of a PRMT5 inhibitor or a combination of PRMT5 inhibitors or a PRMT5 inhibitor and an anti-cancer agent selected from an Androgen Receptor antagonist, abiraterone, enzalutamide, bicalutamide, flutamide, HDAC inhibitor, a mTor inhibitor, and a PI3K inhibitor.

Combination Therapies

Many potential combination partners exist for treatment with PRMT5 inhibition. The treatment could be partnered with current standards of care in the cancer types to be treated, as well as potential future drugs that might be approved.

PRMT5 inhibitors of the instant disclosure can be used as part of a combination with other therapies. The term "Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a subject as separate entities either simultaneously, concurrently or sequentially with no specific time limits, wherein such administration provides therapeutically effective levels of the two compounds in the body of the subject. The latter also applies to cocktail therapy, e.g. the administration of three or more therapeutic agent.

By "combination", there is meant either a fixed combination in one dosage unit form, or a combined administration where a compound of the present invention and a combination partner may be administered independently at the same time or separately within time intervals that especially allow that the combination partners show a cooperative, e.g. synergistic effect. The single components may be packaged together in a kit or separately. One or both of the components (e.g., powders or liquids) may be reconstituted or diluted to a desired dose prior to administration.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

In some embodiments, PRMT5 inhibitors can be combined with other therapeutic agent(s), including, but not limited to, other anti-cancer agents, anti-allergic agents, anti-nausea agents (or anti-emetics), pain relievers, cytoprotective agents, and combinations thereof.

In some embodiments, PRMT5 inhibitors can be combined with other therapy and/or therapeutic agent(s) used against prostate cancer cells. Therapies and therapeutic agent(s) used against prostate cancer cells include, as non-limiting examples, surgery (i.e. radical prostatectomy), radiation therapy including brachytherapy (prostate brachytherapy) and external beam radiation therapy, high-intensity focused ultrasound (HIFU), chemotherapy, oral chemotherapeutic drugs (Temozolomide/TMZ), cryosurgery, hormonal therapy, or some combination thereof. These and additional therapies and therapeutic agents for prostate cancer are known in the art.

In some embodiments, PRMT5 inhibitors can be combined with other therapeutic agent(s), including, but not limited to, general chemotherapeutic agents. General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the compounds of the present invention include:

Some subjects may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, including, but not limited to, dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some subjects may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl(Kytril®), lorazepam (Ativan®), dexamethasone (Decadron®), prochlorperazine (Compazine®), casopitant (Rezonic® and Zunrisa®), and combinations thereof.

Medication to alleviate the pain experienced during the treatment period is often prescribed to make the subject more comfortable. Common over-the-counter analgesics, such Tylenol®, are often used. However, opioid analgesic drugs including, but not limited to, hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

The above-mentioned compounds, which can be used in combination with a compound of the present invention, can be prepared and administered as described in the art, including, but not limited to, in the documents cited above.

In one embodiment, the present invention provides pharmaceutical compositions comprising at least one compound of the present invention (e.g., a compound of the present invention) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects suffering from a cellular proliferative disease, including, but not limited to, cancer. The present invention provides methods of treating a human or animal subject in need of such treatment, comprising administering to the subject a therapeutically effective amount of a compound of the present invention (e.g., a compound of the present invention) or a pharmaceutically acceptable salt thereof, either alone or in combination with other anti-cancer agents.

In particular, compositions will either be formulated together as a combination therapeutic or administered separately.

In combination therapy, the compound of the present invention and other anti-cancer agent(s) may be administered either simultaneously, concurrently or sequentially with no specific time limits, wherein such administration provides therapeutically effective levels of the two compounds in the body of the subject.

In a preferred embodiment, the compound of the present invention and the other anti-cancer agent(s) is generally administered sequentially in any order by infusion or orally. The dosing regimen may vary depending upon the stage of the disease, physical fitness of the subject, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

A compound of the present invention may also be used to advantage in combination with known therapeutic processes, for example, the administration of hormones or especially radiation. A compound of the present invention may in particular be used as a radiosensitizer, especially for the treatment of tumors which exhibit poor sensitivity to radiotherapy.

In certain instances, compounds of the present invention are combined with other therapeutic agents, including, but not limited to, other anti-cancer agents, anti-allergic agents, anti-nausea agents (or anti-emetics), pain relievers, cytoprotective agents, and combinations thereof.

Specific compounds and classes of compounds acting via a specific mechanism have been identified to be particularly effective in conjunction with PRMT5 inhibitors. For example, PRMT5 is known to associate with SWI/SNF chromatin remodeling complexes along with other co-repressor molecules like HDAC2. PRMT5 activity on target H4R3 and H3R8 is enhanced when lysine residues become deacetylated by HDAC enzymes Thus, HDAC inhibitors have been tested and found to be effective when used in conjunction with PRMT5 inhibitors. The combination of a PRMT5 inhibitor, a HDAC inhibitor and a DNA methyltransferase inhibitor was synergistic. WO 011/079236.

A PRMT5 inhibitor can also be administered or co-administered in any order with an inhibitor of a protein which interacts with or is required for PRMT5 function, including, but not limited to, pICIN, WDR77 or RIOK1.

Thus, PRMT5 inhibitors of the present disclosure can be used in combination with other compounds, for example: HDAC inhibitor or DNA methyltransferase inhibitor. In some embodiments, the HDAC inhibitor is Trichostatin A. In some embodiments, the DNA methyltransferase inhibitor is 5-azacytidine. Any of the compounds can be used in combination with any PRMT5 inhibitor described herein or known in the art, in any method described herein.

A PRMT5 inhibitor can be administered in combination with a HDM2 inhibitor and/or with 5-FU. A PRMT5 inhibitor can be administered or co-administered in any order with any one or more of the following: a HDM2 inhibitor, 5-FU, a purine analogue, 6-thioguanine, 6-mercaptopurine, CDK4 inhibitor, or LEE011, or inhibitors of HDM2i, PI3K/mTOR-I, MAPKi, RTKi, EGFRi, FGFRi, METi, IGFiRi, JAKi, or WNTi.

Additional combination therapies are provided below:

(A) Combination of a PRMT5 inhibitor with 5-FU and analogues thereof; and purine analogues (e.g. 6-thioguanine, mercaptopurine and others).

(B) Combination of a PRMT5 inhibitor with targeted treatments contingent on the dependency of individual target tumors on relevant pathways as determined by suitable predictive markers, including but not limited to: inhibitors of HDM2i, PI3K/mTOR-I, MAPKi, RTKi, EGFRi, FGFRi, METi, IGFiRi, JAKi, and WNTi.

(C) Combination of a PRMT5 inhibitor with immunotherapy (D) Combination of a PRMT5 inhibitor with disease-specific huMABs (e.g., an anti-HER3 huMAB)

(E) Combination of a PRMT5 inhibitor with ADCs/ADCCs contingent on the expression of relevant surface targets on target tumors of interest (F) Combination of a PRMT5 inhibitor with prostate cancer-specific and established 1st/2nd line Gold-Standard treatments.

A PRMT5 inhibitor can be administered or co-administered in any order with any known chemotherapeutic or therapeutic agent in a combination therapy.

Anti-cancer agents of particular interest for combinations with the compounds of the present invention include fluorouracil (5-FU) and irinotecan.

Further compounds of particular interest for combinations with the compounds of the present invention include: EGFR-inhibitors, such as cetuximab, panitumimab, erlotinib, gefitinib and EGFRi NOS; MAPK-pathway inhibitors, such as BRAFi, panRAFi, MEKi, ERKi; PI3K-mTOR pathway inhibitors, such as alpha-specific PI3Ki, pan-class I PI3Ki, mTOR/PI3Ki), particularly also evirolimus and analogues thereof.

Some subjects may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some subjects may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl(Kytril®), lorazepam (Ativan®, dexamethasone (Decadron®), prochlorperazine (Compazine®), casopitant (Rezonic® and Zunrisa®), and combinations thereof.

Medication to alleviate the pain experienced during the treatment period is often prescribed to make the subject more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

The above-mentioned compounds, which can be used in combination with a compound of the present invention, can be prepared and administered as described in the art, such as in the documents cited above.

In one embodiment, the present invention provides pharmaceutical compositions comprising at least one compound of the present invention (e.g., a compound of the present invention) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a compound of the present invention (e.g., a compound of the present invention) or a pharmaceutically acceptable salt thereof, either alone or in combination with other anti-cancer agents.

In particular, compositions will either be formulated together as a combination therapeutic or administered separately.

In combination therapy, the compound of the present invention and other anti-cancer agent(s) may be administered either simultaneously, concurrently or sequentially with no specific time limits, wherein such administration provides therapeutically effective levels of the two compounds in the body of the subject.

In a preferred embodiment, the compound of the present invention and the other anti-cancer agent(s) is generally administered sequentially in any order by infusion or orally. The dosing regimen may vary depending upon the stage of the disease, physical fitness of the subject, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

A compound of the present invention may also be used to advantage in combination with known therapeutic processes, for example, the administration of hormones or especially radiation. A compound of the present invention may in particular be used as a radiosensitizer, especially for the treatment of tumors which exhibit poor sensitivity to radiotherapy.

Any of the PRMT5 inhibitors described herein or known in the art can be used in a method of inhibiting proliferation of TMPRSS2:ERG positive prostate cancer cells in a subject in need thereof, the method comprising the step of administering to the subject, a PRMT5 inhibitor in an amount that is effective to inhibit proliferation of the TMPRSS2:ERG positive prostate cancer cells. The disclosure also encompasses method of detecting TMPRSS2:ERG-positive cells, including but not limited to prostate cancer cells, and methods of preparing samples (e.g., of cells, tissues, tumors, etc.) for evaluating the samples for TMPRSS2:ERG positivity.

Sample Preparation

The invention provides, among other things, an assay for the determination of TMPRSS2:ERG positivity or negativity.

The method can include detecting TMPRSS2:ERG in a body fluid such as prostate tissue, blood (e.g., serum or plasma) bone marrow, cerebral spinal fluid, peritoneal/pleural fluid, lymph fluid, ascite, serous fluid, sputum, lacrimal fluid, stool, and urine, or in a tissue such as a tumor tissue. The tumor tissue can be fresh tissue or paraffin-embedded tissue.

As used herein, a "subject" refers to a human or animal, including all mammals such as primates (particularly higher primates), sheep, dog, rodents (e.g., mouse or rat), guinea pig, goat, pig, cat, rabbit, and cow. In a preferred embodiment, the subject is a human. In another embodiment, the subject is an experimental animal or animal suitable as a disease model.

Body fluid samples can be obtained from a subject using any of the methods known in the art. Methods for extracting cellular DNA from body fluid samples are well known in the art. Typically, cells are lysed with detergents. After cell lysis, proteins are removed from DNA using various proteases. DNA is then extracted with phenol, precipitated in alcohol, and dissolved in an aqueous solution. Methods for extracting acellular DNA from body fluid samples are also known in the art. Commonly, a cellular DNA in a body fluid sample is separated from cells, precipitated in alcohol, and dissolved in an aqueous solution.

Generally, a solid tumor sample can be a test sample of cells or tissue that are obtained from a subject with cancer by biopsy or surgical resection. A sample of cells or tissue can be removed by needle aspiration biopsy. For this, a fine needle attached to a syringe is inserted through the skin and into the tissue of interest. The needle is typically guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue can also be removed by incisional or core biopsy. For this, a cone, a cylinder, or a tiny bit of tissue is removed from the region of interest. CT imaging, ultrasound, or an endoscope is generally used to guide this type of biopsy. More particularly, the entire cancerous lesion may be removed by excisional biopsy or surgical resection. In the present invention, the test sample is typically a sample of cells removed as part of surgical resection.

The test sample of, for example tissue, may also be stored in, e.g., RNAlater (Ambion; Austin Tex.) or flash frozen and stored at −80° C. for later use. The biopsied tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. RNA or protein may also be extracted from a fixed or wax-embedded tissue sample.

Diseases amenable for treatment according to the present invention include TMPRSS2:ERG positive prostate cancer.

This disclosure notes that a subset of PRMT5 inhibitors may be neurotoxic. Potential PRMT5 inhibitors thus should be evaluated for this and other toxicities. Neurotoxic PRMT5 inhibitors can be modified to prevent transit across the blood-brain barrier, thus increasing their usefulness for treating TMPRSS2:ERG positive prostate cancer.

Detection of PRMT5 Sensibility

The determination of TMPRSS2:ERG positivity or negativity can be done by any number of ways, for example: FISH, RACE, DNA sequencing, PCR based methods, including RT-PCR, microarray analysis, Southern blotting, Northern blotting, Next Generation Sequencing, and dip stick analysis. In some embodiments, TMPRSS2:ERG positivity or negativity is evaluated by any technique known in the art, for example, immunohistochemistry utilizing an anti-TMPRSS2:ERG antibody (e.g., a combination of antibodies which recognize TMPRSS2 and/or ERG, or one or more antibodies which recognize the fusion protein) or derivative thereof, and/or genomic sequencing, or nucleic acid hybridization or amplification utilizing at least one probe or primer comprising a sequence of at least 12 contiguous nucleotides (nt) of the sequence of a TMPRSS2:ERG fusion (e.g., as described in Perner et al. 2006 Cancer Res. 66: 8337-8341), wherein the primer is no longer than about 30 nt. Various methods of detection of TMPRSS2-ERG are known in the art. These include but are limited to those described in Perner et al. 2006 Cancer Res. 66: 8337-8341; and Demichelis et al. 2007 Oncogene 26: 4596-4599.

The polymerase chain reaction (PCR) can be used to amplify and identify TMPRSS2:ERG from either genomic DNA or RNA extracted from tumor tissue. PCR is well known in the art and is described in detail in Saiki et al., Science 1988, 239:487 and in U.S. Pat. Nos. 4,683,195 and 4,683,203.

Methods of detecting TMPRSS2:ERG positivity by hybridization are provided. The method comprises identifying TMPRSS2:ERG positivity or negativity in a sample by its ability or inability, respectively, to hybridize to a TMPRSS2:ERG nucleic acid. The nucleic acid probe is detectably labeled with a label such as a radioisotope, a fluorescent agent or a chromogenic agent. Radioisotopes can include without limitation; 3H, 32P, 33P and 35S etc. Fluorescent agents can include without limitation: FITC, texas red, rhodamine, etc.

The probe used in detection that is capable of hybridizing to TMPRSS2:ERG nucleic acid can be from about 8 nucleotides to about 100 nucleotides, from about 10 nucleotides to about 75 nucleotides, from about 15 nucleotides to about 50 nucleotides, or about 20 to about 30 nucleotides. The kit can also provide instructions for analysis of subject cancer samples, wherein TMPRSS2:ERG positivity or negativity indicates if the subject is sensitive or insensitive to treatment with a PRMT5 inhibitor.

Single stranded conformational polymorphism (SSCP) can also be used to determine TMPRSS2:ERG positivity or negativity. This technique is well described in Orita et al., PNAS 1989, 86:2766-2770.

Measurement of Gene Expression

Evaluation of TMPRSS2:ERG positivity and measurement of TMPRSS2:ERG gene expression, and measurement of PRMT5 gene expression can be performed using any method or reagent known in the art.

Detection of gene expression can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. For example, using Affymetrix™ U133 microarray chips.

In one aspect, gene expression is detected and quantitated by hybridization to a probe that specifically hybridizes to the appropriate probe for that biomarker. The probes also can be attached to a solid support for use in high throughput screening assays using methods known in the art. WO 97/10365 and U.S. Pat. Nos. 5,405,783, 5,412,087 and 5,445,934, for example, disclose the construction of high density oligonucleotide chips which can contain one or more of the sequences disclosed herein. Using the methods disclosed in U.S. Pat. Nos. 5,405,783, 5,412,087 and 5,445,934, the probes of this invention are synthesized on a derivatized glass surface. Photoprotected nucleoside phosphoramidites are coupled to the glass surface, selectively deprotected by photolysis through a photolithographic mask, and reacted with a second protected nucleoside phosphoramidite. The coupling/deprotection process is repeated until the desired probe is complete.

In one aspect, the expression level of a gene is determined through exposure of a nucleic acid sample to the probe-modified chip. Extracted nucleic acid is labeled, for example, with a fluorescent tag, preferably during an amplification step. Hybridization of the labeled sample is performed at an appropriate stringency level. The degree of probe-nucleic acid hybridization is quantitatively measured using a detection device. See U.S. Pat. Nos. 5,578,832 and 5,631,734.

Alternatively any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). However, PCR conditions used for each application reaction are empirically determined. A number of parameters influence the success of a reaction. Among them are annealing temperature and time, extension time, Mg 2+ and/or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination.

In one embodiment, the hybridized nucleic acids are detected by detecting one or more labels attached to the sample nucleic acids. The labels can be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g. fluorescein-labeled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3H, 125I, 35S, 14C, or 32P) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Detection of labels is well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the coloured label.

The detectable label may be added to the target (sample) nucleic acid(s) prior to, or after the hybridization, such as described in WO 97/10365. These detectable labels are directly attached to or incorporated into the target (sample) nucleic acid prior to hybridization. In contrast, "indirect labels" are joined to the hybrid duplex after hybridization. Generally, the indirect label is attached to a binding moiety that has been attached to the target nucleic acid prior to the hybridization. For example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization with Nucleic Acid Probes, P. Tijssen, ed. Elsevier, N.Y. (1993).

Detection of Polypeptides

Expression level of TMPRSS2:ERG can be determined by examining protein expression or the protein product. Determining the protein level involves measuring the amount of any immunospecific binding that occurs between an antibody that selectively recognizes and binds to the polypeptide of the biomarker in a sample obtained from a subject and comparing this to the amount of immunospecific binding of at least one biomarker in a control sample.

A variety of techniques are available in the art for protein analysis. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), Western blot analysis, immunoprecipitation assays, immunofluorescent assays, flow cytometry, immunohistochemistry, HPLC, mass spectrometry, confocal microscopy, enzymatic assays, surface plasmon resonance and PAGE-SDS.

Assaying for Biomarkers and PRMT5 Inhibitor Treatment

A number of patient (subject) stratification strategies could be employed to find prostate cancer patients likely to be sensitive to PRMT5 depletion, including but not limited to, testing for TMPRSS2:ERG positivity. Methods of testing for TMPRSS2-ERG positivity (detecting the presence of TMPRSS2-ERG gene and/or its gene product) are described herein and/or known in the art, e.g., Perner et al. 2006 Cancer Res. 66: 8337-8341; and Demichelis et al. 2007 Oncogene 26: 4596-4599.

Once a subject has been assayed for TMPRSS2:ERG positivity and predicted to be sensitive to treatment with a PRMT5 inhibitor, administration of any PRMT5 inhibitor to a subject can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents may be empirically adjusted.

Survival of TMPRSS2:ERG positive prostate cancer cells or tumors can be assayed for after PRMT5 inhibitor administration in order to determine if the subject remains sensitive to the PRMT5 inhibitor treatment. In addition, survival can be assayed for in multiple timepoints after a single administration of a PRMT5 inhibitor. For example, after an initial bolus of an PRMT5 inhibitor is administered, survival can be assayed for at 1 hour, 2 hours, 3 hours, 4 hours, 8 hours, 16 hours, 24 hours, 48 hours, 3 days, 1 week or 1 month or several months after the first treatment.

Survival can be assayed for after each PRMT5 inhibitor administration, so if there are multiple PRMT5 inhibitor administrations, then assaying for survival for after each administration can determine continued subject sensitivity. The subject could undergo multiple PRMT5 inhibitor administrations and then assayed for survival at different timepoints. For example, a course of treatment may require administration of an initial dose of PRMT5 inhibitor, a second dose a specified time period later, and still a third dose hours after the second dose. Survival can be assayed for at 1 hour, 2 hours, 3 hours, 4 hours, 8 hours, 16 hours, 24 hours, 48 hours, 3 days, 1 week or 1 month or several months after administration of each dose of a PRMT5 inhibitor.

Finally, different PRMT5 inhibitors can be administered and followed by assaying for survival of TMPRSS2:ERG positive prostate cancer cells. In this embodiment, more than one PRMT5 inhibitor is chosen and administered to the subject. Survival can then be assayed for after administration of each different PRMT5 inhibitor. This assay can also be done at multiple timepoints after administration of the different WNR inhibitor. For example, a first PRMT5 inhibitor could be administered to the subject and survival assayed for at 1 hour, 2 hours, 3 hours, 4 hours, 8 hours, 16 hours, 24 hours, 48 hours, 3 days, 1 week or 1 month or several months after administration. A second PRMT5 inhibitor could then be administered and survival can be assayed for again at 1 hour, 2 hours, 3 hours, 4 hours, 8 hours, 16 hours, 24 hours, 48 hours, 3 days, 1 week or 1 month or several months after administration of the second PRMT5 inhibitor.

Kits for assessing the activity of any PRMT5 inhibitor can be made. For example, a kit comprising nucleic acid primers for PCR or for microarray hybridization can be used for assessing PRMT5 inhibitor sensitivity (i.e., amenability to treatment with one or more PRMT5 inhibitors).

It is well known in the art that cancers can become resistant to chemotherapeutic treatment, especially when that treatment is prolonged. Assaying for TMPRSS2:ERG positivity can be done after prolonged treatment with any chemotherapeutic to determine if the cancer would be sensitive to the PRMT5 inhibitor. If the subject has been previously treated with another chemotherapeutic or another PRMT5 inhibitor, it is useful to assay for TMPRSS2:ERG positivity to determine if the tumor is sensitive to a PRMT5 inhibitor. This assay can be especially beneficial to the subject if the cancer goes into remission and then re-grows or has metastasized to a different site.

Kits

In some embodiments kits related to methods of the invention are provided.

In one embodiment, a for predicting the sensitivity of a subject afflicted with prostate cancer for treatment with a PRMT5 inhibitor is provided. The kit comprises: i) reagents capable of detecting TMPRSS2:ERG positive prostate cancer cells; and ii) instructions for how to use said kit.

One skilled in the art will recognize many methods and materials similar or equivalent to those described herein, which could be used in the practice of the present invention. Indeed, the present invention is in no way limited to the methods and materials described.

EXAMPLES

Figure 1B:
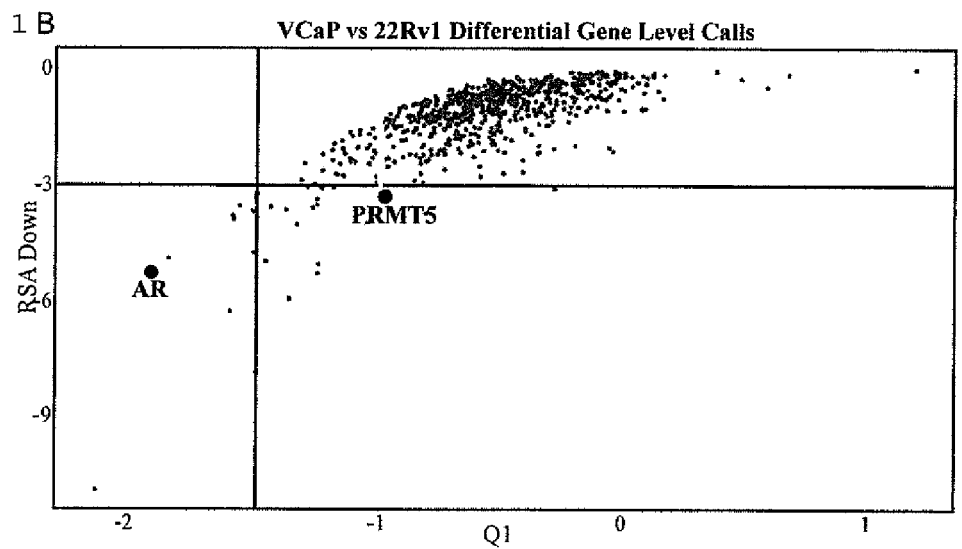

Example 1: TMPRSS2:ERG Fusion as a Biomarker for Sensitivity to PRMT5 Inhibition in Prostate Cancer ERG is required for the proliferation of TMPRSS2:ERG positive prostate cancer cells. Mounir et al. 2014 Oncogene. To better understand the mechanism of ERG function in TMPRSS2:ERG-positive prostate cancer (PC), we aimed to identify ERG protein interactors that are also necessary to maintain the proliferation of TMPRSS2:ERG-positive PC. We used a proteomics approach to identify protein interactors following an endogenous ERG pulldown from TMPRSS2:ERG-positive VCaP cells (FIG. 1A). Our data shows all peptides identified by mass spectrometry and plotted based on peptide specificity (x-axis) and abundance (y-axis). The ERG protein interactor AR is detected at high abundance and specificity as expected considering that ERG and AR have been shown to interact (FIG. 1A). In parallel, to identify targets necessary for TMPRSS2:ERG-positive PC proliferation, we used an shRNA screening approach to compare the TMPRSS2:ERG-positive VCaP cells to the TMPRSS2:ERG-negative 22Rv1 cells (FIG. 1B). Our data shows all VCaP-specific hits which scored solely in the VCaP shRNA screen and not in the 22Rv1 screen (FIG. 1B). Our positive control, AR, is necessary for the survival of VCaP cells and scored as one of the top hits in the VCaP screen. To determine which ERG protein interactors were also required to maintain ERG-positive PC proliferation, we compared the p values obtained from both the proteomics (x-axis) and shRNA screening (y-axis) studies. Based on the p values obtained, PRMT5 seemed to be the best target for follow-up as it was a strong ERG interactor with proliferation effects in ERG-positive PC. We first validated the protein interactions with ERG by overexpression and observed that PRMT5 does interact with ERG (FIG. 2A). We next investigated whether shRNA knockdown of PRMT5 would show specific proliferative effects in TMPRSS2:ERG-positive PC. Three independent doxycycline (Dox)-inducible shRNA sequences were used to deplete PRMT5 from either TMPRSS2:ERG positive VCaP cells, or TMPRSS2:ERG negative control 22Rv1 or LNCaP cells. This led to robust PRMT5 knockdown at the protein level in all cell lines (FIGS. 2B, 2C and 2D). PRMT5 knockdown with either shRNA inhibited the proliferation of VCaP cells while no effect was observed with a non-targeting control (NTC) shRNA (FIG. 2B). PRMT5 knockdown had no effect on the proliferation of TMPRSS2:ERG-negative 22Rv1 and LNCaP cells indicating that the proliferative effects of PRMT5 are specific to ERG-positive PC (FIG. 2C, 2D). Based on these results, the ERG-dependent proliferative effects of PRMT5 in PC suggest it may play an important role in regulating ERG biology.

Figures 3A, 3B, 3C:
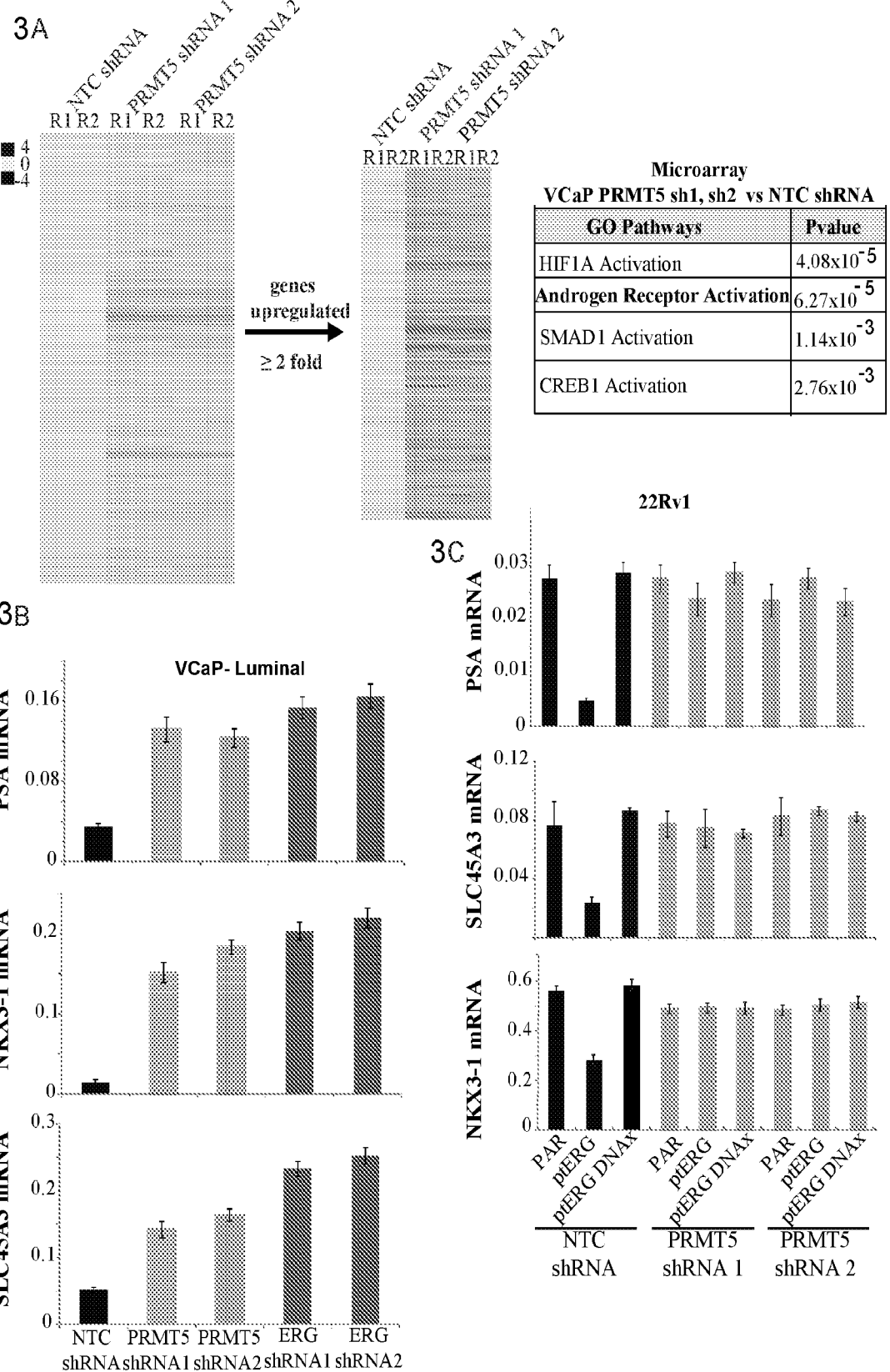
FIGS. 3A to 3C show that PRMT5 is an ERG-dependent inhibitor of AR signaling.

We next investigated the transcriptional effects of PRMT5 in ERG-positive PC cells following knockdown in VCaP cells. In line with literature findings, PRMT5 mainly functioned as an inhibitor of gene expression, considering that most genes were upregulated following PRMT5 knockdown (FIG. 3A). Analysis of pathways altered following PRMT5 knockdown in VCaP cells identified HIF1A activation, androgen receptor activation, SMAD1 activation and CREB1 activation as significantly repressed pathways by PRMT5 (FIG. 3A). This is consistent with previous studies reporting a role for PRMT5 in regulating HIF1A, CREB1 and SMAD pathways in various TMPRSS2:ERG-negative cell lines. Lim et al. 2012 Biochem. Biophys. Res. Comm. 418: 254-259; Tsai et al. 2013 Proc. Natl. Acad. Sci. USA 110: 8870-8875; and Tabata et al. 2009 Genes Cells 14: 17-28. Interestingly, the regulation of androgen receptor signaling was the only significantly altered pathway commonly modulated by ERG and PRMT5 in ERG-positive VCaP cells suggesting that ERG and PRMT5 might function in unison to regulate AR function. Mounir et al. 2014 Oncogene.

Because ERG is a repressor of AR function [Mounir et al. 2014 Oncogene; Yu et al. 2010 Cancer Cell. 17: 443-454; and Baena et al. 2013 Genes Dev. 27: 683-698], its knockdown results in the upregulation of AR target genes PSA, NKX3-1, and SLC45A3 [Mounir et al. 2014 Oncogene]. To further validate that PRMT5 knockdown has a similar effect on AR target gene expression, we used quantitative PCR of reverse transcribed RNA (qRT-PCR) to assess the expression of the AR-regulated genes PSA, NKX3-1 and SLC45A3. Expression of all three genes was increased following PRMT5 knockdown, similar to ERG knockdown (FIG. 3B).

To further investigate whether PRMT5 is necessary for ERG's inhibitory functions on luminal gene expression, we used a previously established ERG expression cell system (1) in which ERG cDNA is expressed in the TMPRSS2:ERG-negative 22Rv1 cells. Expression of ptERG, but not the transcription-defective mutant ptERG DNAx, resulted in decreased expression of the AR-dependent luminal target genes PSA, NKX3-1 and SLC45A3 (FIG. 3C). Interestingly, in the absence of PRMT5, ERG lost its ability to block luminal gene expression (FIG. 3C).

Figure 4A:
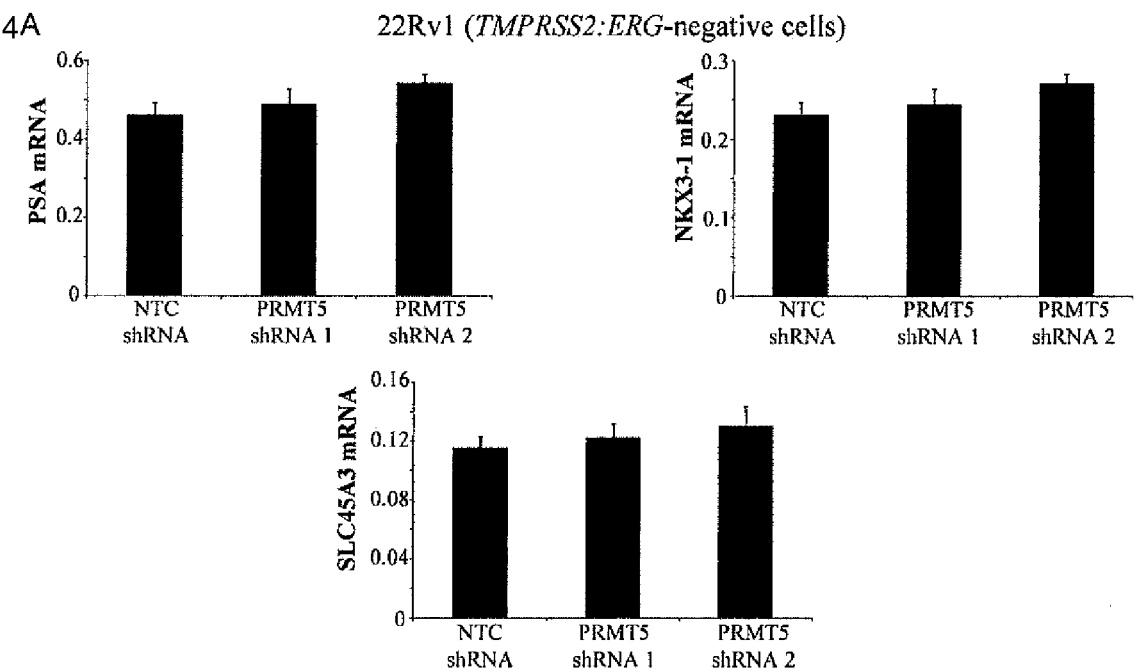
FIGS. 4A and 4B show that PRMT5 does not inhibit AR transcriptional functions in an ERG-negative prostate cancer cell line.
Figure 4B:
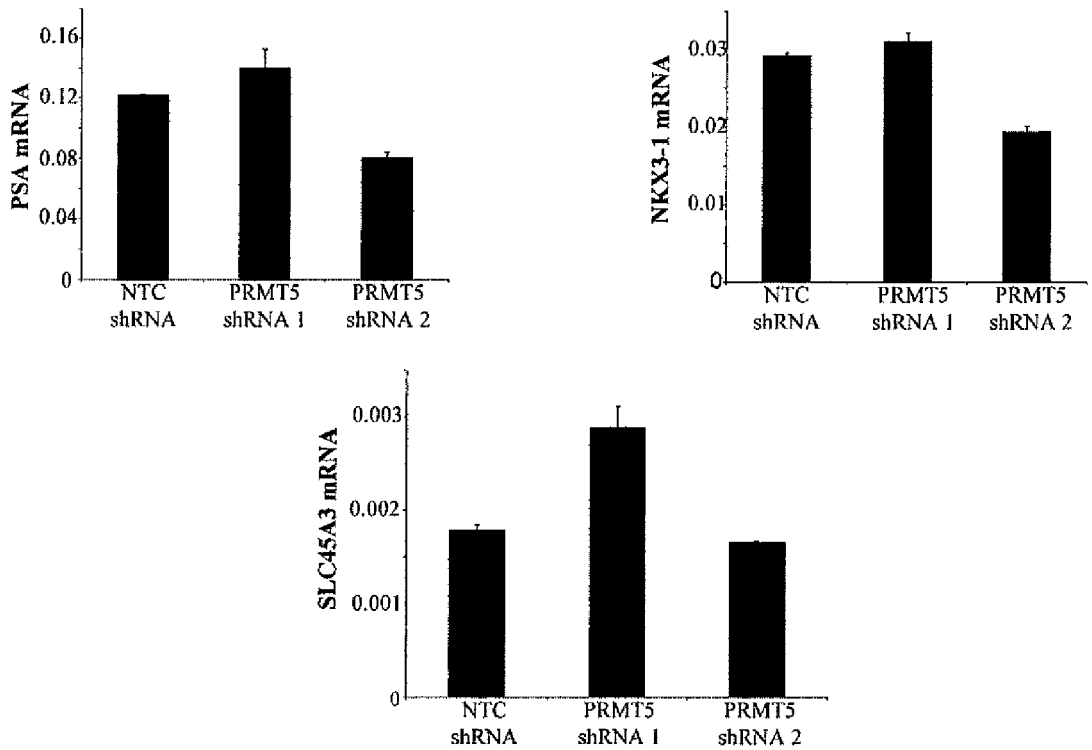

To determine whether the transcriptional effects of PRMT5 are specific to TMPRSS2:ERG-positive PC cells or whether this is a general effect on all PC cell lines, gene expression changes were evaluated in TMPRSS2:ERG-negative 22Rv1 and LNCaP PC cells following PRMT5 knockdown (FIGS. 4A and 4B). PRMT5 knockdown in either 22Rv1 and LNCaP cells failed to induce luminal gene expression as observed in VCaP cells (FIGS. 4A and 4B). These findings suggest that the inhibitory effects of PRMT5 on luminal gene expression are solely mediated in TMPRSS2:ERG-positive PC cells and could be modulated downstream of ERG. These results suggest that PRMT5 may function as an ERG corepressor that is required to block luminal gene expression, and that the observed effects of PRMT5 on AR target gene expression are dependent upon ERG DNA binding function.

Figure 5A:
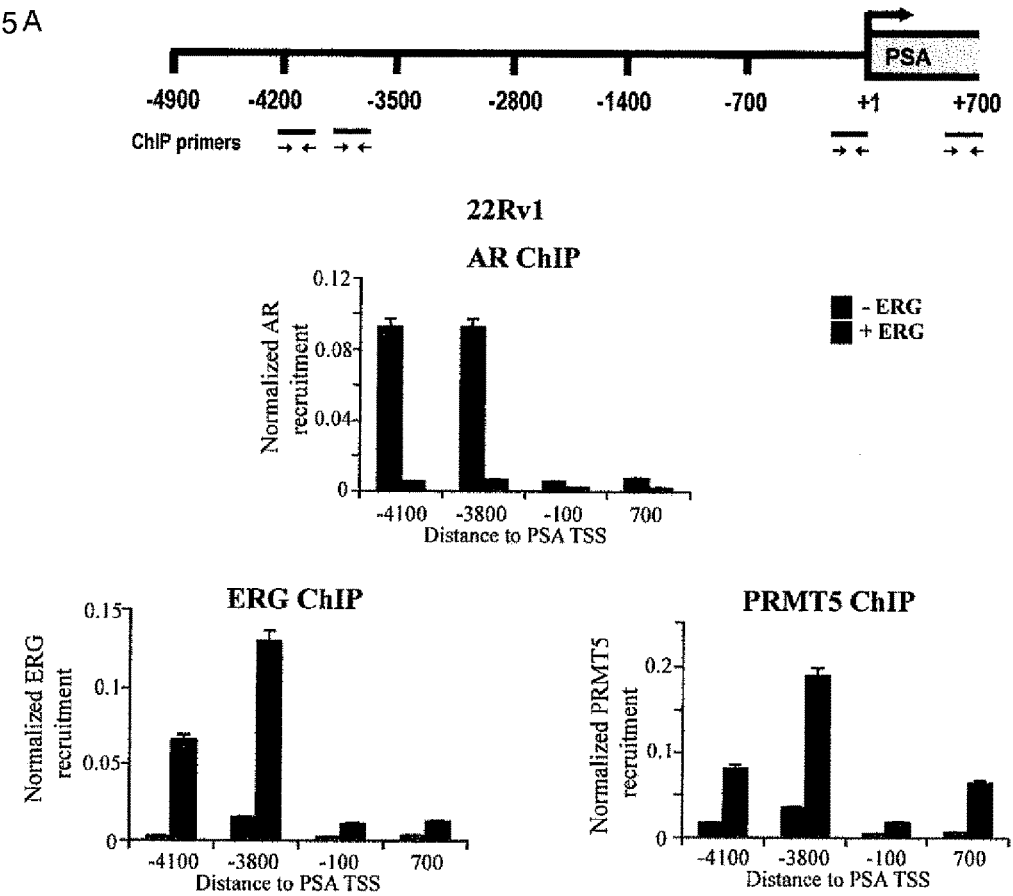
FIGS. 5A and 5B show that PRMT5 is an ERG corepressor recruited to block AR transcriptional function.

Given that PRMT5 is necessary for ERG's ability to block luminal gene expression, we investigated whether it is also co-recruited with ERG to directly regulate luminal genes. Using the 22Rv1 cell system in which we induce ERG expression, we looked at AR, ERG and PRMT5 recruitment by chromatin immunoprecipitation (ChIP) to the enhancer regions of PSA at 4100 and 3800 bp upstream of the transcription start site (TSS), the proximal promoter region 100 bp upstream of the TSS and to an internal negative control region 700 bp downstream of the TSS (FIG. 5A). We observe that AR is recruited to the enhancer regions of PSA in the absence of ERG and that its recruitment is abolished upon ERG expression and recruitment to the same enhancers (FIG. 5A). Interestingly, PRMT5 is also recruited to the enhancer regions of PSA but only in ERG-expressing cells and not in the absence of ERG (FIG. 5A).

Figure 5B:
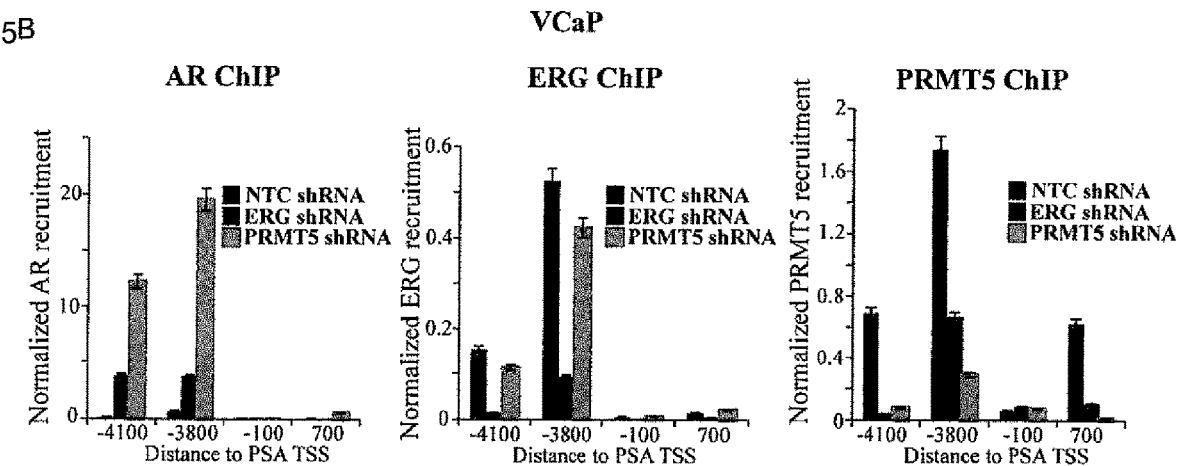

To better understand the order of recruitment events, we investigated AR and PRMT5 recruitment by ChIP to PSA following ERG knockdown as well as ERG and AR recruitment following PRMT5 knockdown. Given that ERG has been shown to compete with AR for binding to luminal target genes, ERG knockdown in VCaP cells increased AR recruitment to the enhancer regions of PSA (FIG. 5B). Interestingly, PRMT5 knockdown dramatically increased AR recruitment to PSA which confirms that not only ERG and PRMT5 knockdown have similar effects on luminal target gene expression but also on AR recruitment to its targets. These findings suggest that ERG and PRMT5 may act in collaboration to inhibit AR recruitment and transcriptional functions. Interestingly, ERG recruitment to the enhancers of PSA was not affected by PRMT5 knockdown which indicates that ERG is recruited first to PSA and is then followed by PRMT5 (FIG. 5B). In line with these findings, PRMT5 recruitment to PSA was reduced following ERG knockdown which confirms that PRMT5 recruitment to PSA is dependent and downstream of ERG (FIG. 5B). Collectively, these findings suggest that PRMT5 may function as an ERG corepressor recruited to AR target genes to block AR binding and transcriptional functions in an ERG-dependent fashion.

Figure 6A:
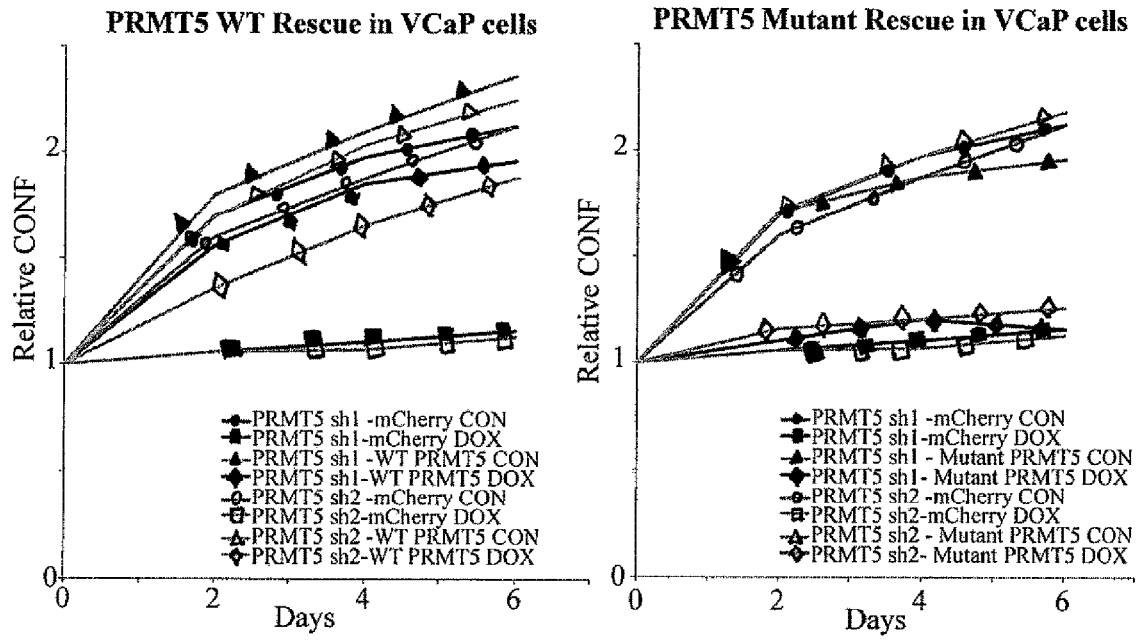
FIGS. 6A and 6B show that PRMT5 mediates its ERG-dependent corepressor functions through its methyltransferase activity.
Figure 6B:
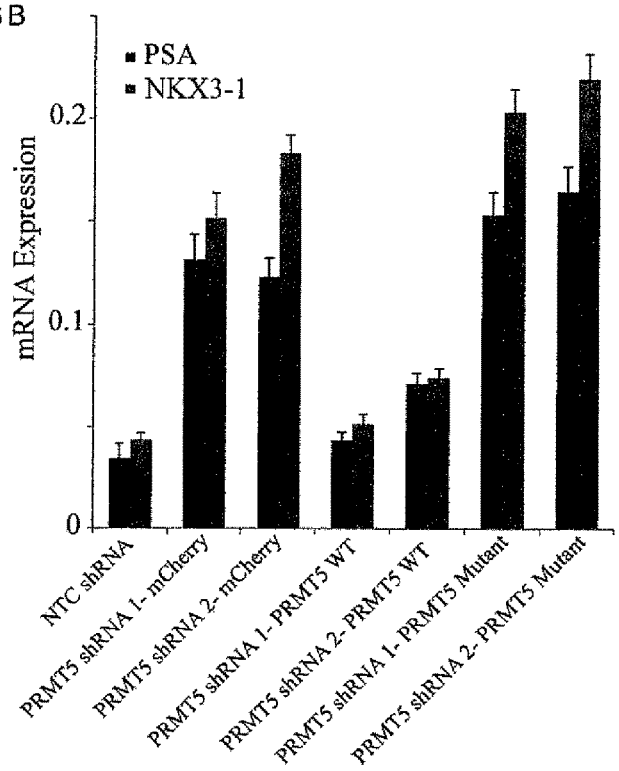

To determine whether the effects of PRMT5 on ERG-dependent inhibition of AR functions are mediated through its catalytic activity, we performed an experiment to rescue the effects of PRMT5 knockdown on VCaP cell proliferation and luminal gene expression using either wild-type or catalytic dead PRMT5. We observed that only expression of wild-type PRMT5 can rescue the effects of PRMT5 knockdown on VCaP cell proliferation and luminal gene expression (FIGS. 6A and B). The catalytic dead PRMT5 (R365A/R368A) failed to rescue the effects of PRMT5 knockdown on VCaP cell proliferation and luminal gene expression (FIGS. 6A and B). These findings suggest that PRMT5 mediates its ERG-dependent effects on proliferation and luminal gene expression through its methyltransferase functions.

Considering that the most well characterized catalytic functions of PRMT5 are mediated through histone arginine methylation and regulation of chromatin functions, we verified whether PRMT5 or ERG knockdown have any effects on global symmetric methylation levels of arginine 3 on histone 4 (H4R3). Analysis of histones extracted from VCaP cells following either PRMT5 or ERG knockdown did not show any effect on global symmetric methylation levels of H4R3 (data not shown). We also investigated the possible effects of ERG expression on global methylation levels of H4R3 and did not observe any difference in symmetric methylation levels following ERG expression in 22Rv1 cells (data not shown). To investigate the possibility that PRMT5 might regulate histone arginine methylation on a specific set of target genes which could be missed by global analysis of histone methylation, we analyzed H4R3 symmetric methylation levels by ChIP at the PSA and NKX3-1 loci (data not shown). We did not observe any difference in the H4R3 symmetric methylation levels at the PSA and NKX3-1 loci following ERG expression in 22Rv1 cells (data not shown). These findings suggest that while the catalytic functions of PRMT5 are required for its ability to regulate AR function, its mechanism of action does not involve histone methylation.

Alongside histone arginine symmetric methylation, PRMT5 has also been shown to directly methylate and regulate the activity of various transcription factors including p53, E2F1 and HIF1A [Lim et al. 2012 Biochem. Biophys. Res. Comm. 418: 254-159; Jansson et al. 2008 Nat. Cell. Biol. 10: 1431-1439; Cho et al. 2012 EMBO J. 31: 1785-1797]. Considering that histone arginine symmetric methylation was not identified as the mechanism of regulation used by PRMT5 to modulate AR transcriptional functions, we hypothesized that perhaps PRMT5 might methylate and regulate either ERG or AR activity directly.

To test whether ERG is a substrate of PRMT5, we used 22Rv1 cells to express and immunoprecipitate ERG in the presence and absence of PRMT5. Using a recently generated antibody specific for symmetric dimethyl arginine modification, we verified ERG arginine methylation levels and only observed a faint band which was not altered following PRMT5 knockdown (data not shown). To confirm these findings, we performed in vitro biochemical assays in which we incubated increasing amounts of commercial PRMT5/MEP50 enzyme complex with the methyl donor S-Adenosyl-Methionine (SAM) and either the pointed (PNT) domain or ETS domain of ERG as possible substrates of PRMT5. As a measure of PRMT5 catalytic activity and usage of the methyl donor SAM for substrate methylation, we evaluated and quantified by mass spectrometry the amount of S-Adenosyl-Homocysteine (SAH) produced (data not shown). We did not observe any SAH production with either the PNT or ETS domain of ERG further confirming that ERG is not a direct substrate of PRMT5 (data not shown).

Figures 7A, 7B, 7C, 7D:
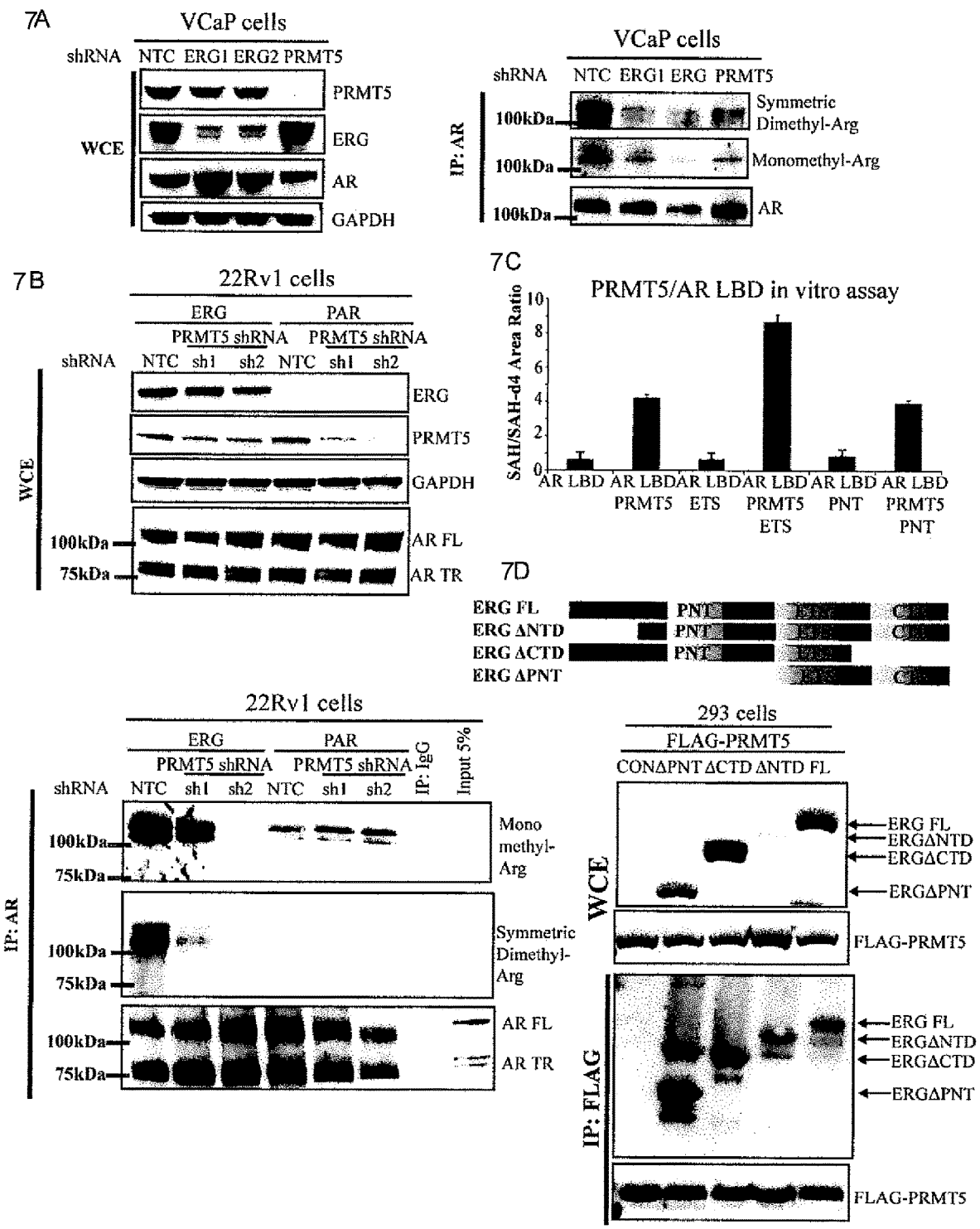
FIGS. 7A to 7D shows that PRMT5 methylates AR on its ligand binding domain.

We next evaluated whether AR is a direct substrate of PRMT5 by immunoprecipitation from VCaP cells and analysis of arginine methylation levels (FIG. 7A). Using the symmetric dimethyl arginine antibody we observed that AR is methylated at basal levels and that methylation is reduced following either ERG or PRMT5 knockdown (FIG. 7A). Analysis of AR arginine mono-methylation levels showed similar basal methylation that is also reduced by ERG or PRMT5 knockdown (FIG. 7A). To confirm these findings, we used the ERG expression system in 22Rv1 cells to immunoprecipitate AR in the presence or absence of ERG (FIG. 7B). While the parental cells lacking ERG showed low AR arginine mono-methylation which was not modulated by PRMT5 knockdown; these cells did not show any symmetric dimethylation of AR (FIG. 7B). Only ERG-expressing cells showed an elevated basal mono and symmetric dimethylation of AR, both of which were reduced following PRMT5 knockdown (FIG. 7B). Interestingly, the PRMT5-dependent arginine methylation of AR was only detected in the full-length form of AR (~110 kDa) and not in the truncated isoform of AR lacking its ligand-binding domain (~80 kDa) [Dehm et al. 2008 Cancer Res. 68: 5469-5477], both of which are expressed in 22Rv1 cells (FIG. 7B). These findings indicate that PRMT5 methylates AR on its ligand-binding domain in an ERG-dependent fashion.

To investigate whether the ligand binding domain (LBD) of AR is a direct substrate of PRMT5, we performed a series of in vitro biochemical assays in which we incubated the PRMT5/MEP50 enzyme complex with the methyl donor S-Adenosyl-Methionine (SAM) and purified AR LBD. Mass spectrometry analysis shows an increase in SAH production when PRMT5 is incubated with AR LBD which is indicative of direct AR methylation by PRMT5 (FIG. 7C). Considering that ERG domain deletion studies have shown that PRMT5 interacts with the ETS domain of ERG (FIG. 7D; deletion of any domain but the ETS domain of ERG maintained interaction with PRMT5), we investigated whether the addition of the ERG ETS domain to the PRMT5/AR LBD reaction would further increase AR methylation. Interestingly, the addition of the ERG ETS domain to the reaction increased SAH production while addition of the ERG PNT domain showed no effect (FIG. 7C). These findings indicate that the interaction between PRMT5 and the ETS domain of ERG promotes AR arginine methylation (FIG. 7C). Interestingly, treatment of the AR LBD/PRMT5 and AR LBD/PRMT5/ETS reactions with the pan-PRMT inhibitor AMI-1 [Cheng et al. 2004 J. Biol. Chem. 279: 23892-23899] completely blocked SAH production in all reactions as measured by mass spectrometry (FIG. 8A) and AR mono-methylation levels detected using the arginine mono-methyl antibody (FIG. 8B). These results suggest that the SAH production measured by mass spectrometry in our reactions is driven by the methyltransferase functions of PRMT5.

Figure 9A:
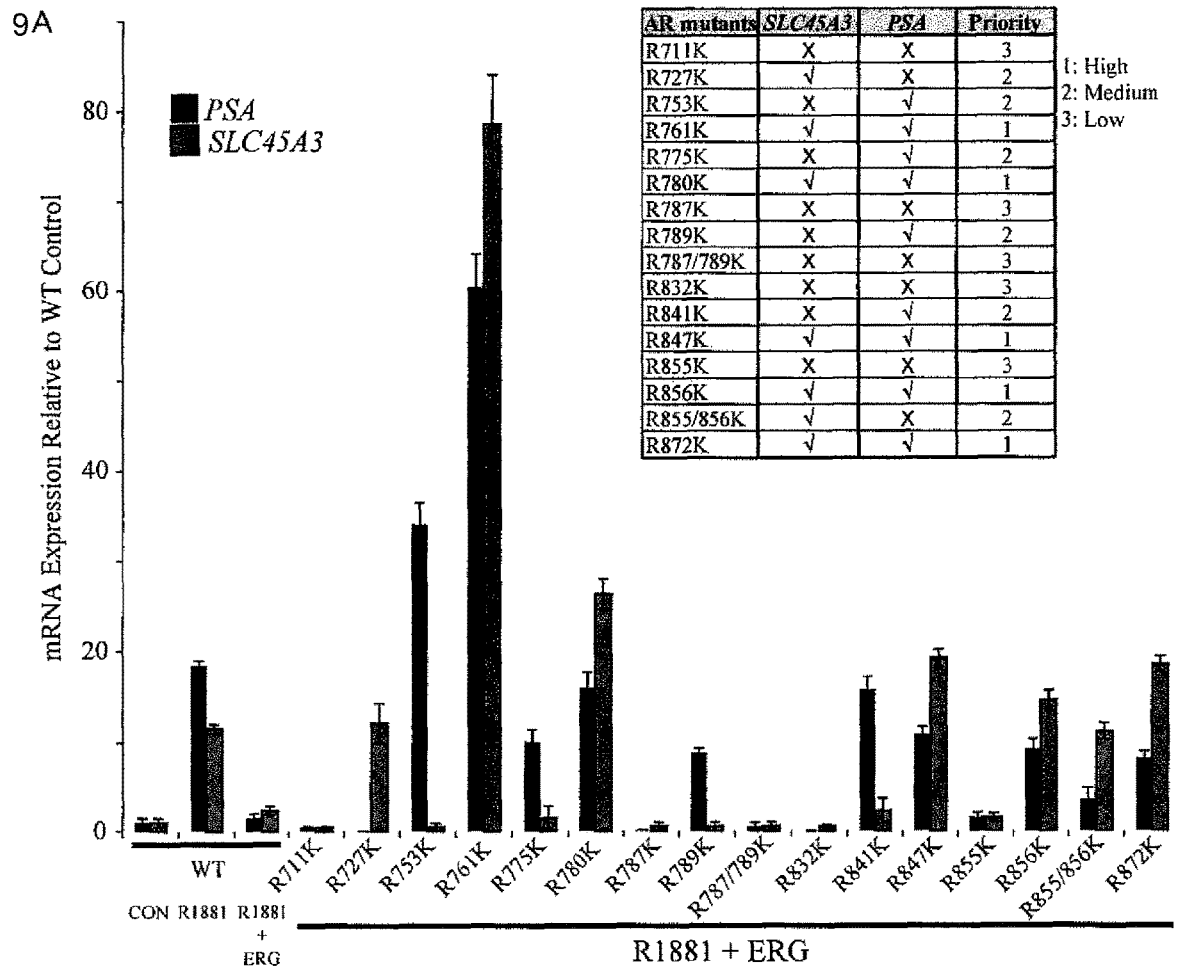
FIGS. 9A and 9B show that AR methylation by PRMT5 is a mechanism of inhibition of AR function.
Figure 9B:
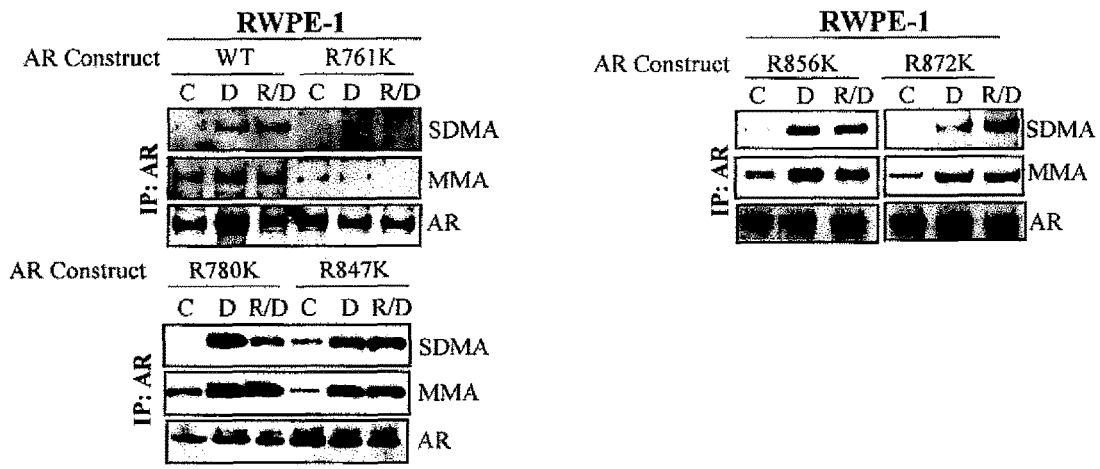

To identify the PRMT5-dependent arginine methylation site on the LBD of AR, we opted for a directed mutagenesis approach to evaluate the "methylation loss" on each arginine present in the LBD, especially that we are still unable to detect arginine methylation by mass spectrometry. To express and evaluate the effect of each AR LBD arginine mutant, we used the AR and ERG-negative immortalized prostate cell line RWPE-1 in which we can recapitulate AR and ERG functions following androgen stimulation. In this system, androgen treatment of RWPE-1 cells stably expressing AR can induce luminal gene expression, which is then repressed following ERG expression (FIG. 8C). Similarly to VCaP and 22Rv1 cells, we observed that AR arginine methylation both mono- and dimethyl is induced in this system following ERG expression (FIG. 8C). Looking at the amino acid sequence of the AR LBD, we found 14 arginine residues which were mutated to lysine in order to preserve the amino acid charge and stably expressed in RWPE-1 cells containing an ERG-inducible vector (FIG. 8D). All mutants were expressed at the protein level (FIG. 8D) and their transcriptional effects were evaluated based on ERG's ability to repress AR-dependent gene expression (FIG. 9A). We hypothesized that if AR arginine methylation is the mechanism used by ERG to repress AR transcriptional activity, then the mutant "losing" this methylation-driven inhibitory mechanism would maintain maximal transcriptional activity even following ERG expression. Expression levels of PSA and SLC45A3, two AR-driven luminal genes were induced by androgen (R1881) stimulation of AR wild-type (WT) expressing cells and reduced following ERG expression (R1881+ERG) (FIG. 9A). All arginine mutants were characterized based on their ability to be repressed by ERG, as measured by reduction PSA and SLC45A3 expression (FIG. 9A). Several mutants that could not mediate ERG function (R761K, R780K, R847K, R856K and R872K) were then immunoprecipitated to evaluate their methylation levels. Interestingly, although all five arginine mutants maintained their transcriptional functions in the presence of ERG, only one mutant, R761K, showed a lack of arginine methylation both dimethyl and mono-methyl in the presence of ERG, which indicates that R761 is primary arginine residue on AR methylated by PRMT5 in an ERG-dependent fashion (FIG. 9B).

Using an independent immunofluorescence-based assay, we were able to detect AR arginine methylation by proximity ligation assay through the use of an AR antibody and an antibody against symmetric di-methyl arginine. In this assay a signal is observed only when both antibodies are in close proximity leading the PLA probes conjugated to the secondary antibodies to ligate, creating a circular template amplified by rolling-circle amplification. A non-limiting example of a proximity ligation assay is DuoLink, Sigma Aldrich, which comprises commercially available antibodies in a commercially available kit. We only observed arginine methylation of wild-type AR following ERG expression in RWPE-1 cells and no methylation in the absence of ERG (data not shown). Interestingly, the AR R761K mutant did not show any methylation whether expressed alone or along with ERG (data not shown). These findings confirm in an independent assay that AR methylation on arginine 761 by PRMT5 is dependent on ERG.

In summary, our findings suggest that a key mechanism used by ERG to repress AR transcriptional functions in TMPRSS2:ERG-positive prostate cancer is the recruitment of PRMT5 to AR transcriptional complexes. ERG-mediated PRMT5 recruitment leads to mono- and symmetric di-methylation of AR at arginine 761, which then blocks AR binding to its target genes and transcriptional activity. This inhibitory function of PRMT5 on AR is dependent on ERG expression and DNA binding function, and is highly selective to TMPRSS2:ERG-positive prostate cancers. ERG promotes the proliferation of prostate cancer [Mounir et al. 2014 Oncogene; Tomlins et al. 2008 Neoplasia 10: 177-188; Carmichael et al. Proc. Natl. Acad. Sci. USA 109: 15437-15442], but the nature of this protein makes it a challenging target for therapeutics development. As PRMT5 enzymatic function is required for ERG-dependent AR inhibition and cell proliferation in prostate cancer, our findings suggest that TMPRSS2:ERG is a biomarker that predicts sensitivity to PRMT5 inhibition. In addition, detection of AR arginine 761 methylation may provide a biomarker tool to assess ERG activity in prostate cancer samples, rather than solely looking and relying on ERG mRNA or protein expression levels. Our data suggest that AR methylation on arginine 761 could be used as a diagnostic tool to differentiate among all TMPRSS2:ERG-positive prostate cancers. This tool could be used to stratify ERG-positive prostate cancers with "active" ERG from those with "inactive" ERG based on the levels of AR arginine methylation which would be high or low, respectively. This stratification based on ERG activity would provide a more accurate of analysis of AR activity status and transcriptional functions which can have both diagnostic and predictive value of tumor response to anti-androgen therapy.

Example 2: Predicted HLA Presented PRMT5 Peptides

We predicted the PRMT5 peptide sequences that are likely to be presented by HLA, using the method described in Stabilized Matrix Method, Tenzer S et al, 2005, PMID 15868101, which takes a regularized regression approach to modeling these processes. Further, it allows for higher order, non-additive contributions from some residues. After model training, the input to the method is a file of protein sequences (such as a fasta formatted file). For a defined peptide length (e.g., 9 amino acids), it scans through the protein and reports a score for each peptide related to how well the method predicts the peptide to be processed by the proteasome, carried by the transporter proteins, and bound to a particular MHC allele, as well as an overall score representing the entire process. High scoring peptide sequences can then be chosen for downstream analyses. For instance, the PRMT5 wildtype protein sequence contains a number of peptides predicted to be well-processed and high-affinity MHC binders as listed in TABLE 3.

TABLE 3

PRMT5 peptides predicted to be high-affinity MHC binders

| C-terminal position | 9-mer-sequence | Total score | Proteasome score | TAP score | MHC score | SEQ ID NO: |
|---|---|---|---|---|---|---|
| 98 | MLQELNFGA | 4.19 | 1.12 | -0.15 | 3.22 | 1481 |
| 566 | GMFSWFPIL | 4.01 | 1.1 | 0.38 | 2.53 | 1482 |
| 177 | WMWWHNFRT | 3.81 | 0.89 | -0.19 | 3.11 | 1483 |
| 489 | FEMPYVVRL | 3.78 | 1.19 | 0.32 | 2.26 | 1484 |
| 600 | KKVWYEWAV | 3.59 | 0.93 | 0.26 | 2.4 | 1485 |
| 109 | GLPAFLLPL | 3.5 | 0.99 | 0.36 | 2.14 | 1486 |
| 380 | YAVEKNPNA | 3.39 | 0.96 | -0.16 | 2.59 | 1487 |
| 107 | YLGLPAFLL | 3.34 | 1.19 | 0.41 | 1.74 | 1488 |
| 298 | YLQSPLQPL | 3.31 | 1.19 | 0.34 | 1.77 | 1489 |
| 447 | FLKDDGVSI | 3.26 | 1.03 | 0.19 | 2.04 | 1490 |
| 140 | SMFWMRVPL | 3.23 | 0.94 | 0.56 | 1.72 | 1491 |
| 220 | AILPTSIFL | 3.22 | 1.14 | 0.61 | 1.46 | 1492 |
| 604 | YEWAVTAPV | 3.19 | 0.77 | 0.12 | 2.31 | 1493 |
| 487 | AQFEMPYVV | 3.14 | 1.28 | 0.21 | 1.65 | 1494 |
| 270 | SYLQYLEYL | 3.12 | 1.08 | 0.56 | 1.48 | 1495 |
| 569 | SWFPILFPI | 3.11 | 0.83 | 0.36 | 1.92 | 1496 |
| 567 | MFSWFPILF | 3.09 | 1.02 | 1.18 | 0.9 | 1497 |
| 141 | MFWMRVPLV | 3 | 0.98 | 0.33 | 1.7 | 1498 |
| 309 | NLESQTYEV | 2.95 | 0.99 | 0.04 | 1.92 | 1499 |
| 495 | VRLHNFHQL | 2.83 | 1.15 | 0.56 | 1.12 | 1500 |
| 440 | CLDGAQHFL | 2.82 | 1.23 | 0.26 | 1.32 | 1501 |
| 185 | TLCDYSKRI | 2.81 | 1.12 | 0.29 | 1.39 | 1502 |
| 178 | MWWHNFRTL | 2.8 | 1.35 | 0.59 | 0.85 | 1503 |
| 541 | GFAGYFETV | 2.8 | 1.02 | 0.13 | 1.65 | 1504 |
| 455 | IPGEYTSFL | 2.78 | 1.15 | 0.25 | 1.39 | 1505 |
| 527 | CTLEFPVEV | 2.76 | 1.08 | 0.09 | 1.58 | 1506 |
| 538 | VLHGFAGYF | 2.76 | 0.87 | 1.15 | 0.74 | 1507 |
| 105 | GAYLGLPAF | 2.74 | 1 | 1.08 | 0.66 | 1508 |
| 248 | LLKLEVQFI | 2.71 | 0.93 | 0.3 | 1.49 | 1509 |
| 239 | KMHQRLIFR | 2.54 | 1.02 | 0.78 | 0.73 | 1510 |
| 176 | TWMWWHNFR | 2.52 | 1.04 | 0.81 | 0.66 | 1511 |
| 249 | LKLEVQFII | 2.52 | 0.89 | 0.28 | 1.34 | 1512 |
| 550 | LYQDITLSI | 2.51 | 1 | 0.35 | 1.15 | 1513 |
| 106 | AYLGLPAFL | 2.5 | 1.04 | 0.59 | 0.87 | 1514 |
| 470 | KLYNEVRAC | 2.49 | 0.91 | 0.17 | 1.41 | 1515 |
| 175 | KTWMWWHNF | 2.46 | 1.03 | 1.14 | 0.29 | 1516 |
| 537 | TVLHGFAGY | 2.46 | 1.02 | 1.39 | 0.05 | 1517 |
| 100 | QELNFGAYL | 2.45 | 1.11 | 0.39 | 0.95 | 1518 |
| 602 | VWYEWAVTA | 2.33 | 1.13 | 0.03 | 1.17 | 1519 |
| 33 | CMPVFHPRF | 2.32 | 0.96 | 1.15 | 0.2 | 1520 |
| 247 | RLLKLEVQF | 2.28 | 1 | 1.18 | 0.1 | 1521 |
| 573 | ILFPIKQPI | 2.28 | 0.77 | 0.24 | 1.28 | 1522 |
| 608 | VTAPVCSAI | 2.25 | 0.84 | 0.32 | 1.09 | 1523 |
| 29 | FDFLCMPVF | 2.24 | 1.01 | 0.96 | 0.26 | 1524 |
| 525 | RYCTLEFPV | 2.23 | 0.83 | 0.42 | 0.97 | 1525 |
| 96 | AAMLQELNF | 2.23 | 0.94 | 1.14 | 0.15 | 1526 |
| 221 | ILPTSIFLT | 2.22 | 0.72 | -0.23 | 1.72 | 1527 |
| 462 | FLAPISSSK | 2.18 | 0.68 | 0.2 | 1.3 | 1528 |
| 195 | VALEIGADL | 2.15 | 0.95 | 0.54 | 0.66 | 1529 |
| 201 | ADLPSNHVI | 2.14 | 1.01 | 0.16 | 0.98 | 1530 |
| 240 | MHQRLIFRL | 2.14 | 0.98 | 0.47 | 0.69 | 1531 |
| 31 | FLCMPVFHP | 2.13 | 0.88 | -0.04 | 1.3 | 1532 |
| 384 | KNPNAVVTL | 2.11 | 1.17 | 0.32 | 0.62 | 1533 |
| 236 | VLSKMHQRL | 2.1 | 1.08 | 0.39 | 0.63 | 1534 |
| 543 | AGYFETVLY | 2.09 | 1.12 | 1.25 | -0.28 | 1535 |
| 542 | FAGYFETVL | 2.06 | 1.25 | 0.31 | 0.5 | 1536 |
| 66 | GRDWNTLIV | 2.05 | 0.88 | 0.09 | 1.08 | 1537 |
| 63 | LLSGRDWNT | 2 | 0.85 | -0.28 | 1.43 | 1538 |

Unless indicated otherwise, all methods, steps, techniques and manipulations that are not specifically described in detail can be performed and/or have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of various materials and methods is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

The invention claimed is:

1. A method of determining if a subject afflicted with prostate cancer will respond to therapeutic treatment with a PRMT5 inhibitor comprising
   (a) evaluating a test sample obtained from the subject for TMPRSS2:ERG positivity by at least detecting of the methylation of R761 of the Androgen Receptor, wherein TMPRSS2:ERG positivity indicates that the subject will respond to therapeutic treatment with a PRMT5 inhibitor;
   (b) determining the level and/or activity of PRMT5 in the subject, wherein (a) and (b) can be performed in any order; and (c) administering a therapeutically effective amount of a PRMT5 inhibitor to the subject, wherein the PRMT5 inhibitor is selected from the group consisting of a RNAi agent, a CRISPR, a TALEN, a zinc finger nuclease, an mRNA, an antibody or derivative thereof, an antibody-drug conjugate, a chimeric antigen receptor T cell (CART) or a low molecular weight compound.

2. The method of claim 1, wherein the PRMT5 inhibitor is a RNAi agent.

3. The method of claim 1, wherein the method further comprises the step of administering to a subject a second therapeutic agent.

4. The method of claim 3, wherein the second therapeutic agent is an anti-cancer agent, anti-allergic agent, anti-nausea agent or anti-emetic agent, pain reliever, cytoprotective agent.

5. The method of claim 3, wherein the second therapeutic agent is an anti-cancer agent selected from the list consisting of: an Androgen Receptor antagonist, abiraterone, enzalutamide, bicalutamide, flutamide, HDAC inhibitor, fluorouracil (5-FU) irinotecan, a HDM2 inhibitor, a purine analogue, 6-thioguanine, 6-mercaptopurine, a CDK4 inhibitor, and LEE011, and inhibitors of HDM2i, PI3K/mTOR-I, MAPKi, RTKi, EGFRi, FGFRi, METi, IGFiRi, JAKi, and WNTi.

6. The method of claim 1, further comprising determining the level and/or activity of PRMT5 in the subject following step (c), wherein a decrease in the level and/or activity of PRMT5 is correlated with the inhibition of the proliferation of the cancer.

7. The method of claim 1, wherein methylation of R761 of the Androgen Receptor is monomethylation.

8. The method of claim 1, wherein methylation of R761 of the Androgen Receptor is dimethylation.

9. The method of claim 1, wherein the Androgen Receptor comprises an amino acid sequence of SEQ ID NO: 1478.

10. The method of claim 1, further comprising administering a therapeutically effective amount of a ERG inhibitor.

* * * * *

SEQUENCE LISTING

<160> NUMBER OF SEQ ID NOS: 1539

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
cccatcctct tccctattaa g                                              21

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
gtcctccacc taatgcctat g                                              21

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
gaatgcacca actacacaca c                                              21

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
gcgtttcaag agggagttca t                                              21

<210> SEQ ID NO 5
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ggctcaagcc accaatctat g                                        21

<210> SEQ ID NO 6
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
cgctagagaa ctggcagttt g                                        21

<210> SEQ ID NO 7
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gtctgttctg ctattcataa c                                        21

<210> SEQ ID NO 8
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gccatcccaa cagagatcct a                                        21

<210> SEQ ID NO 9
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
cgtggatgtg gtggcacaac t                                        21

<210> SEQ ID NO 10
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
```
ccagaagagg agaaggatac c                                       21

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
gcggataaag ctgtatgctg t                                       21

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
gacctcccat ctaatcatgt c                                       21

<210> SEQ ID NO 13
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gaagaggaga aggataccaa t                                       21

<210> SEQ ID NO 14
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ccagaggacc tgagagatga t                                       21

<210> SEQ ID NO 15
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gccaagtgac cgtagtctca t                                       21

<210> SEQ ID NO 16
<211> LENGTH: 21
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 16
agggactgga atacgctaat t                                              21

<210> SEQ ID NO 17
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
cctggaatac ttaagccaga a                                              21

<210> SEQ ID NO 18
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
gactcactct cctgggatgt t                                              21

<210> SEQ ID NO 19
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ggcaccaacc accactcaga g                                              21

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
cggctgcaca acttccacca g                                              21

<210> SEQ ID NO 21
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ccctgaggcc cagtttgaga t                                              21

<210> SEQ ID NO 22
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
cgcactcagc ctcaagaact c                                              21

<210> SEQ ID NO 23
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
ctggccatca ctcttccatg t                                              21

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
caggccatct ataaatgtct g                                              21

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
cccgaaatag ctgacacact a                                              21

<210> SEQ ID NO 26
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
gcccataacg gtacgtgaag g                                              21

<210> SEQ ID NO 27
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
```
cgcgtttcaa gagggagttc a                                              21

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ccggcggata aagctgtatg c                                              21

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
ggagcatttc aatctgcttt c                                              21

<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
cctcaagaac tccctggaat a                                              21

<210> SEQ ID NO 31
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
ctgacctccc atctaatcat g                                              21

<210> SEQ ID NO 32
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
gagatcctat gattgacaac a                                              21

<210> SEQ ID NO 33
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 33
gcccagtttg agatgcctta t                                              21

<210> SEQ ID NO 34
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
ctgctcctac ctccaatacc t                                              21

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
cactggccat cactcttcca t                                              21

<210> SEQ ID NO 36
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
cuccuuacca uuaaacug                                                  18

<210> SEQ ID NO 37
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 37
gagaaggaug acauucugut t                                              21

<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 38
acagaauguc auccuucuct t                                          21

<210> SEQ ID NO 39
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="phospho-Tyr"
<220> FEATURE:
<221> NAME/KEY: VARIANT
<222> LOCATION: (13)..(13)
<223> OTHER INFORMATION: /replace="phospho-Tyr"
<220> FEATURE:
<221> NAME/KEY: VARIANT
<222> LOCATION: (16)..(16)
<223> OTHER INFORMATION: /replace="phospho-Tyr"
<220> FEATURE:
<221> NAME/KEY: misc_feature
<222> LOCATION: (1)..(21)
<223> OTHER INFORMATION: /note="Variant residues given in the sequence
      have no preference with respect to those in the annotations
      for variant positions"

<400> SEQUENCE: 39

Cys Pro Pro Asn Ala Tyr Glu Leu Phe Ala Lys Gly Tyr Glu Asp Tyr
1               5                   10                  15

Leu Gln Ser Pro Leu
            20

<210> SEQ ID NO 40
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Lys Asn Arg Pro Gly Pro Gln Thr Arg Ser Asp Leu Leu Leu Ser Gly
1               5                   10                  15

Arg Asp Trp Asn
            20

<210> SEQ ID NO 41
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
aagagggagu ucauucagga a                                          21

<210> SEQ ID NO 42
<211> LENGTH: 21
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 42
gggacuggaa uacgcuaaut t                                              21

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 43
auuagcguau uccaguccct t                                              21

<210> SEQ ID NO 44
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 44
ggaccugaga gaugauauat t                                              21

<210> SEQ ID NO 45
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 45
uauaucaucu cucaggucct t                                              21

<210> SEQ ID NO 46
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
```

```
cctcaagaac tccctggaat a                                              21

<210> SEQ ID NO 47
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
ggacaaucug gaaucucaga cauau                                          25

<210> SEQ ID NO 48
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
ggcuccagag aaagcagaca ucauu                                          25

<210> SEQ ID NO 49
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
gcggccaugu uacaggagcu gaauu                                          25

<210> SEQ ID NO 50
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
gatcccgccc agtttgagat gccttatgtg tgctgtccat aaggcatctc aaactgggct    60
ttttggaaa                                                            69

<210> SEQ ID NO 51
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
agcttttcca aaaagcccag tttgagatgc cttatggaca gcacacataa ggcatctcaa    60
actgggcgg                                                            69

<210> SEQ ID NO 52
```

```
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
aaaaacactt catatgtctg agacctgtct c                                     31

<210> SEQ ID NO 53
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
aatctcagac atatgaagtg tttcctgtct c                                     31

<210> SEQ ID NO 54
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
ggccaucuau aaaugucug                                                   19

<210> SEQ ID NO 55
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
gagggagttc attcaggaa                                                   19

<210> SEQ ID NO 56
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
ggatgtggtg gcataactt                                                   19

<210> SEQ ID NO 57
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
```

-continued ggataaagct gtatgctgt                                              19

<210> SEQ ID NO 58
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
ggataaagct gtatgctgt                                              19

<210> SEQ ID NO 59
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
ctcttgtgaa tgcgtctctt                                             20

<210> SEQ ID NO 60
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
agctctgagt tctcttccta                                             20

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
gagggaguuc auucaggaau u                                           21

<210> SEQ ID NO 62
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ggccatctat aaatgtctg                                              19

<210> SEQ ID NO 63
<211> LENGTH: 19
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 63
cagacattta tagatggcc                                               19

<210> SEQ ID NO 64
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
gagcacagca cuuccugaaa gauga                                        25

<210> SEQ ID NO 65
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65 agacugguu gugguggcau aacuu                                         25

<210> SEQ ID NO 66
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
ccaucccaac cgagauccua ugauu                                        25

<210> SEQ ID NO 67
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
ccgcuauugc accuugaa                                                18

<210> SEQ ID NO 68
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
cagccacuga uggacaaucu ggaau                                        25
```

```
<210> SEQ ID NO 69
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
ccggcuacuu ugagacugug cuuua                                            25

<210> SEQ ID NO 70
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
ccgcuauugc accuuggaa                                                   19

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
attgcgtccc cgaaatagct                                                  20

<210> SEQ ID NO 72
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
gcggatggaa gacaggcat                                                   19

<210> SEQ ID NO 73
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
accgctattg caccttgga                                                   19

<210> SEQ ID NO 74
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 74
tccaaggtgc aatagcggt                                                                19

<210> SEQ ID NO 75
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
accgctattg caccttgga                                                                19

<210> SEQ ID NO 76
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
tccaaggtgc aatagcggt                                                                19

<210> SEQ ID NO 77
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
ccgctattgc accttggaa                                                                19

<210> SEQ ID NO 78
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
cagccactga tggacaatct ggaat                                                         25

<210> SEQ ID NO 79
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
ccggctactt tgagactgtg cttta                                                         25

<210> SEQ ID NO 80
<211> LENGTH: 60
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 80
gatccccggt tgatttcct ctgcatttca agagaatgca gaggaaatca aacctttta      60

<210> SEQ ID NO 81
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
gatccccgga ctggaatacg ctaattttca agagaaatta gcgtattcca gtcctttta      60

<210> SEQ ID NO 82
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
gatccccggt cttccagctt tcctatttca agagaatagg aaagctggaa gaccttttta     60

<210> SEQ ID NO 83
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
gatccccgcc accactcttc catgttttca agagaaacat ggaagagtgg tggcttttta     60

<210> SEQ ID NO 84
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
ggtttgattt cctctgcat                                                  19

<210> SEQ ID NO 85
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
atgcagagga aatcaaacc                                                  19
```

```
<210> SEQ ID NO 86
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
ggactggaat acgctaat                                                    18

<210> SEQ ID NO 87
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
aattagcgta ttccagtcc                                                   19

<210> SEQ ID NO 88
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
ggtcttccag ctttcctat                                                   19

<210> SEQ ID NO 89
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
ataggaaagc tggaagacc                                                   19

<210> SEQ ID NO 90
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
gccaccactc ttccatgtt                                                   19

<210> SEQ ID NO 91
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 91
aacatggaag agtggtggc                                            19

<210> SEQ ID NO 92
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
ataaggcatc tcaaactggg c                                         21

<210> SEQ ID NO 93
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
ccgcuauugc accuuggaau u                                         21

<210> SEQ ID NO 94
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
acacuucaua ugucugaga                                            19

<210> SEQ ID NO 95
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
ucucagacau augaagugu                                            19

<210> SEQ ID NO 96
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
ggacctgaga gatgatata                                            19

<210> SEQ ID NO 97
<211> LENGTH: 19
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
gaggattgca gtggctctt                                               19

<210> SEQ ID NO 98
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
accgagggac tggaatacgc taattctcga gaattagcgt attccagtcc cttt        54

<210> SEQ ID NO 99
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
cgaaaaaagg gactggaata cgctaattct cgagaattag cgtattccag tccct       55

<210> SEQ ID NO 100
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
accgagggac tggaatacgt taattgttaa tattcatagc aattagcgta ttccagtccc  60
tttt                                                              64

<210> SEQ ID NO 101
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
cgaaaaaagg gactggaata cgctaattgc tatgaatatt aacaattaac gtattccagt  60
ccct                                                              64

<210> SEQ ID NO 102
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 102

```
accggcggat aaagttgtat gttgtgttaa tattcatagc acagcataca gctttatccg    60
cttt                                                                 64
```

<210> SEQ ID NO 103
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103

```
cgaaaaagcg gataaagctg tatgctgtgc tatgaatatt aacacaacat acaactttat    60
ccgc                                                                 64
```

<210> SEQ ID NO 104
<211> LENGTH: 246
<212> TYPE: PRT
<213> ORGANISM: Homo sapiens

<400> SEQUENCE: 104

```
Ile Phe Leu Asn Val Leu Glu Ala Ile Glu Pro Gly Val Val Cys Ala
1               5                   10                  15

Gly His Asp Asn Asn Gln Pro Asp Ser Phe Ala Ala Leu Leu Ser Ser
            20                  25                  30

Leu Asn Glu Leu Gly Glu Arg Gln Leu Val His Val Val Lys Trp Ala
        35                  40                  45

Lys Ala Leu Pro Gly Phe Arg Asn Leu His Val Asp Asp Gln Met Ala
    50                  55                  60

Val Ile Gln Tyr Ser Trp Met Gly Leu Met Val Phe Ala Met Gly Trp
65                  70                  75                  80

Arg Ser Phe Thr Asn Val Asn Ser Arg Met Leu Tyr Phe Ala Pro Asp
                85                  90                  95

Leu Val Phe Asn Glu Tyr Arg Met His Lys Ser Arg Met Tyr Ser Gln
            100                 105                 110

Cys Val Arg Met Arg His Leu Ser Gln Glu Phe Gly Trp Leu Gln Ile
        115                 120                 125

Thr Pro Gln Glu Phe Leu Cys Met Lys Ala Leu Leu Leu Phe Ser Ile
    130                 135                 140

Ile Pro Val Asp Gly Leu Lys Asn Gln Lys Phe Phe Asp Glu Leu Arg
145                 150                 155                 160

Met Asn Tyr Ile Lys Glu Leu Asp Arg Ile Ile Ala Cys Lys Arg Lys
                165                 170                 175

Asn Pro Thr Ser Cys Ser Arg Arg Phe Tyr Gln Leu Thr Lys Leu Leu
            180                 185                 190

Asp Ser Val Gln Pro Ile Ala Arg Glu Leu His Gln Phe Thr Phe Asp
        195                 200                 205

Leu Leu Ile Lys Ser His Met Val Ser Val Asp Phe Pro Glu Met Met
    210                 215                 220

Ala Glu Ile Ile Ser Val Gln Val Pro Lys Ile Leu Ser Gly Lys Val
225                 230                 235                 240

Lys Pro Ile Tyr Phe His
                245
```

<210> SEQ ID NO 105
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
auuuguauuu ccucuuacac aaa                                                23

<210> SEQ ID NO 106
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
uuuguauuuc cucuuacaca aaa                                                23

<210> SEQ ID NO 107
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
guauuuccuc uuacacaaaa cca                                                23

<210> SEQ ID NO 108
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108 uauuccucu uacacaaaac cau                                                 23

<210> SEQ ID NO 109
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
ccucuuacac aaaaccauca aaa                                                23

<210> SEQ ID NO 110
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 110
cucuuacaca aaaccaucaa aac                                          23

<210> SEQ ID NO 111
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
cacaaaacca ucaaaacaag aac                                          23

<210> SEQ ID NO 112
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
aaaccccaug uucucaggga uau                                          23

<210> SEQ ID NO 113
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
ucagggauau uccagggagu ucu                                          23

<210> SEQ ID NO 114
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
cagggaguuc uugaggcuga gug                                          23

<210> SEQ ID NO 115
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
uugaggcuga gugcguagcu uca                                          23

<210> SEQ ID NO 116
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
aggcugagug cguagcuuca aau                                              23

<210> SEQ ID NO 117
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
aaauccagca cuaauccuc acc                                               23

<210> SEQ ID NO 118
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118 cucaccccu ggccugaggu cuu                                               23

<210> SEQ ID NO 119
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
auagauuggu ggcuugagcc cug                                              23

<210> SEQ ID NO 120
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
guggcuugag cccugcaauu aau                                              23

<210> SEQ ID NO 121
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
agcccugcaa uuaauuauaa ucc                                              23
```

<210> SEQ ID NO 122
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
auuauaaucc cuugcccacc uug                                            23

<210> SEQ ID NO 123
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
uaaucccuug cccaccuuga ugu                                            23

<210> SEQ ID NO 124
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
cccaccuuga uguaaggcag gaa                                            23

<210> SEQ ID NO 125
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
auguaaggca ggaaagcaga uug                                            23

<210> SEQ ID NO 126
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
aaaugcuccu cucugauggg caa                                            23

<210> SEQ ID NO 127
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 127
uguacuacag gagcagaacc uga                                              23

<210> SEQ ID NO 128
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
caaggcucug gacacuuggc acg                                              23

<210> SEQ ID NO 129
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
gcacgcaggg cuagaggcca aug                                              23

<210> SEQ ID NO 130
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
ugaauagcag aacagacugg ugc                                              23

<210> SEQ ID NO 131
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
uuggaauugc ugcaucgcca gaa                                              23

<210> SEQ ID NO 132
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gaauugcugc aucgccagaa acg                                              23

<210> SEQ ID NO 133
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
cugcaucgcc agaaacgcac aca                                              23

<210> SEQ ID NO 134
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
ggccuucacg uaccguuaug ggc                                              23

<210> SEQ ID NO 135
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
gccuucacgu accguuaugg gcu                                              23

<210> SEQ ID NO 136
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
acguaccguu augggcugcu gua                                              23

<210> SEQ ID NO 137
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
ugggcugcug uaagaagaaa gac                                              23

<210> SEQ ID NO 138
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
```
cugcacgacc augcugcccc cug                                          23

<210> SEQ ID NO 139
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
acugcacgac caugcugccc ccu                                          23

<210> SEQ ID NO 140
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
uagcccuuua cugcacgacc aug                                          23

<210> SEQ ID NO 141
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
uguaagagga aauacaaaua aag                                          23

<210> SEQ ID NO 142
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
guguaagagg aaaucaaaau aaa                                          23

<210> SEQ ID NO 143
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
uguguaagag gaaauacaaa uaa                                          23

<210> SEQ ID NO 144
<211> LENGTH: 23
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 144
augguuuugu guaagaggaa aua                                              23

<210> SEQ ID NO 145
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
gaugguuuug uguaagagga aau                                              23

<210> SEQ ID NO 146
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
ugaugguuuu guguaagagg aaa                                              23

<210> SEQ ID NO 147
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
uuuugauggu uuuguguaag agg                                              23

<210> SEQ ID NO 148
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
uuguuuugau gguuuugugu aag                                              23

<210> SEQ ID NO 149
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
uguucuuguu uugauggu uu ugu                                             23

<210> SEQ ID NO 150
```

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 150
cuguucuugu uuugaugguu uug                                                23

<210> SEQ ID NO 151
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 151
ucuguucuug uuugauggu uuu                                                 23

<210> SEQ ID NO 152
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 152
uucuguucuu guuugaugg uuu                                                 23

<210> SEQ ID NO 153
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 153
agccuuuuuc uguucuuguu uug                                                23

<210> SEQ ID NO 154
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 154
cagccuuuuu cuguucuugu uuu                                                23

<210> SEQ ID NO 155
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 155
ucagccuuuu ucuguucuug uuu                                                    23

<210> SEQ ID NO 156
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
aacggauuuu cagccuuuuu cug                                                    23

<210> SEQ ID NO 157
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
gaacggauuu ucagccuuuu ucu                                                    23

<210> SEQ ID NO 158
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
aagcuacgca cucagccuca aga                                                    23

<210> SEQ ID NO 159
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
gaagcuacgc acucagccuc aag                                                    23

<210> SEQ ID NO 160
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
gugcuggauu ugaagcuacg cac                                                    23

<210> SEQ ID NO 161
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 161
cagggcucaa gccaccaauc uau                                           23

<210> SEQ ID NO 162
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
auugcagggc ucaagccacc aau                                           23

<210> SEQ ID NO 163
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
uaauuaauug cagggcucaa gcc                                           23

<210> SEQ ID NO 164
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
caucaaggug ggcaagggau uau                                           23

<210> SEQ ID NO 165
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
cugccuuaca ucaaggnggg caa                                           23

<210> SEQ ID NO 166
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
ccugccuuac aucaaggugg gca                                           23
```

```
<210> SEQ ID NO 167
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
aaucugcuuu ccugccuuac auc                                                 23

<210> SEQ ID NO 168
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
caaucugcuu uccugccuua cau                                                 23

<210> SEQ ID NO 169
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
cccaucagag aggagcauuu caa                                                 23

<210> SEQ ID NO 170
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
cccuugccca ucagagagga gca                                                 23

<210> SEQ ID NO 171
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
ugcuccugua guacagaagg ugc                                                 23

<210> SEQ ID NO 172
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 172
agguucugcu ccuguaguac aga                                              23

<210> SEQ ID NO 173
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
gaagcagcuu cagguucugc ucc                                              23

<210> SEQ ID NO 174
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
gccucuagcc cugcgugcca agu                                              23

<210> SEQ ID NO 175
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
auaaccccac aggccgcuca uau                                              23

<210> SEQ ID NO 176
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
ugcuauucau aaccccacag gcc                                              23

<210> SEQ ID NO 177
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
caagaaggug ugguaugagu ggg                                              23

<210> SEQ ID NO 178
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 178
uggcgaugca gcaauuccaa gaa                                          23

<210> SEQ ID NO 179
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
cuggcgaugc agcaauucca aga                                          23

<210> SEQ ID NO 180
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
cagcagccca uaacgguacg uga                                          23

<210> SEQ ID NO 181
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
uuacagcagc ccauaacggu acg                                          23

<210> SEQ ID NO 182
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
uucuuacagc agcccauaac ggu                                          23

<210> SEQ ID NO 183
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
cuucuuacag cagcccauaa cgg                                          23
```

<210> SEQ ID NO 184
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
aaagcaguuc cuaccuuaau agg                                               23

<210> SEQ ID NO 185
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
cuaccuuaau agggaagagg aug                                               23

<210> SEQ ID NO 186
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
auagggaaga ggaugggaaa cca                                               23

<210> SEQ ID NO 187
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
ccuauuaagg uaggaacugc uuu                                               23

<210> SEQ ID NO 188
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
ccauccucuu cccauuaag gua                                                23

<210> SEQ ID NO 189
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 189
cccauccucu ucccuauuaa ggu                                              23

<210> SEQ ID NO 190
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
ucaugguuuc ccauccucuu ccc                                              23

<210> SEQ ID NO 191
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
uccacacagg uauccgucca gag                                              23

<210> SEQ ID NO 192
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
guccacacag guauccgucc aga                                              23

<210> SEQ ID NO 193
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
uguccacaca gguauccguc cag                                              23

<210> SEQ ID NO 194
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
uuuuguccac acagguaucc guc                                              23

<210> SEQ ID NO 195
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
accuccacag gaaauuccaa ggu                                              23

<210> SEQ ID NO 196
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
caaggugcaa uagcgguugu ugu                                              23

<210> SEQ ID NO 197
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
uugucaauca uaggaucugu cag                                              23

<210> SEQ ID NO 198
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
ucaaucauag gaucugucag gaa                                              23

<210> SEQ ID NO 199
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
ucaggacauc acucugagug agu                                              23

<210> SEQ ID NO 200
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
aucaggacau cacucugagu gag                                              23
```

<210> SEQ ID NO 201
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
agacugugcu uuaucaggac auc                                              23

<210> SEQ ID NO 202
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
gagacugugc uuuaucagga cau                                              23

<210> SEQ ID NO 203
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
ccggcuacuu ugagacugug cuu                                              23

<210> SEQ ID NO 204
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
gccggcuacu uugagacugu gcu                                              23

<210> SEQ ID NO 205
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
cuguggaggu gaacacagua cua                                              23

<210> SEQ ID NO 206
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 206
ccuguggagg ugaacacagu acu                                          23

<210> SEQ ID NO 207
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
gaauuuccug uggaggugaa cac                                          23

<210> SEQ ID NO 208
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
caccuuggaa uuccugugg agg                                           23

<210> SEQ ID NO 209
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
acaacaaccg cuauugcacc uug                                          23

<210> SEQ ID NO 210
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
cugacagauc cuaugauuga caa                                          23

<210> SEQ ID NO 211
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
ccugacagau ccuaugauug aca                                          23

<210> SEQ ID NO 212
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
uuuccugaca gauccuauga uug                                              23

<210> SEQ ID NO 213
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
ggauggcuga aggugaaaca ggg                                              23

<210> SEQ ID NO 214
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
ugcagccgua ccacauaagg cau                                              23

<210> SEQ ID NO 215
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
agccauccca acagagguag guu                                              23

<210> SEQ ID NO 216
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
accuucagcc aucccaacag agg                                              23

<210> SEQ ID NO 217
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
```
caccuucagc caucccaaca gag                                              23

<210> SEQ ID NO 218
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
caccagcucu cugcacccca gcc                                              23

<210> SEQ ID NO 219
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
ugugguacgg cugcacaacu ucc                                              23

<210> SEQ ID NO 220
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
agaugccuua ugugguacgg cug                                              23

<210> SEQ ID NO 221
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
gagaugccuu augugguacg gcu                                              23

<210> SEQ ID NO 222
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
uuuaccucag ggucacgguc cuu                                              23

<210> SEQ ID NO 223
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 223
accucagggu cacguccuu cuc                                              23

<210> SEQ ID NO 224
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
ccucaggguc acguccuuc ucc                                              23

<210> SEQ ID NO 225
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
ucccuacagg cucggaccuc auu                                             23

<210> SEQ ID NO 226
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
uacagcuugg aggaagagau ggg                                             23

<210> SEQ ID NO 227
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
gaggaagaga ugggagccag aaa                                             23

<210> SEQ ID NO 228
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
cuccaagcug uacaaugagg ucc                                             23

<210> SEQ ID NO 229
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
uggcucccau cucuuccucc aag                                          23

<210> SEQ ID NO 230
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230 cuggcucccca ucucuuccuc caa                                         23

<210> SEQ ID NO 231
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
cuuucuggcu cccaucucuu ccu                                          23

<210> SEQ ID NO 232
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
acucuccugc ugugcagaug aug                                          23

<210> SEQ ID NO 233
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
uaggaagugc ugggcuccau cca                                          23

<210> SEQ ID NO 234
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
```

```
aggaagugcu gggcuccauc cag                                          23

<210> SEQ ID NO 235
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
ggaagugcug ggcuccaucc agg                                          23

<210> SEQ ID NO 236
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
auugucagca aaugagccca gaa                                          23

<210> SEQ ID NO 237
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
ucagcaaaug agcccagaag cuc                                          23

<210> SEQ ID NO 238
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
cucuggagcc acccauuccc uca                                          23

<210> SEQ ID NO 239
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
ucuggagcca cccauucccu cau                                          23

<210> SEQ ID NO 240
<211> LENGTH: 23
<212> TYPE: RNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 240
ccucaugucu gaugagacua cgg                                              23

<210> SEQ ID NO 241
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
gcuuccccau ucuucaaacu gcc                                              23

<210> SEQ ID NO 242
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
cccauucuuc aaacugccag uuc                                              23

<210> SEQ ID NO 243
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
uucaaacugc caguucucua gcc                                              23

<210> SEQ ID NO 244
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
aaacugccag uucucuagcc uga                                              23

<210> SEQ ID NO 245
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
ucuagccuga aacagagaca aua                                              23

```
<210> SEQ ID NO 246
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
cuaaaaggug cccccagguu ggg                                              23

<210> SEQ ID NO 247
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
ucgccugagu gccuggaugg agc                                              23

<210> SEQ ID NO 248
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
cugacaauga auugucgccu gag                                              23

<210> SEQ ID NO 249
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
gcugacaaug aaugucgcc uga                                               23

<210> SEQ ID NO 250
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
ugggcucauu ugcugacaau gaa                                              23

<210> SEQ ID NO 251
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 251
ucagugagcu ucugggcuca uuu                                            23

<210> SEQ ID NO 252
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
aagaaugggg aagccaagug acc                                            23

<210> SEQ ID NO 253
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253 gaagaaugggg gaagccaagu gac                                           23

<210> SEQ ID NO 254
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
aggcuagaga acuggcaguu uga                                            23

<210> SEQ ID NO 255
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
caggcuagag aacuggcagu uug                                            23

<210> SEQ ID NO 256
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
ucucuguuuc aggcuagaga acu                                            23

<210> SEQ ID NO 257
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 257
uugucucugu uucaggcuag aga                                          23

<210> SEQ ID NO 258
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
cuacucacgu caccacggca uuu                                          23

<210> SEQ ID NO 259
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
ggguuuuucu ccacagcaua cag                                          23

<210> SEQ ID NO 260
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
gguuuuucuc cacagcauac agc                                          23

<210> SEQ ID NO 261
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
uucuccacag cauacagcuu uau                                          23

<210> SEQ ID NO 262
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
ucuccacagc auacagcuuu auc                                          23
```

<210> SEQ ID NO 263
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
cuccacagca uacagcuuua ucc                                              23

<210> SEQ ID NO 264
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
uccacagcau acagcuuuau ccg                                              23

<210> SEQ ID NO 265
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
auccgccggu cggccugcuu ggc                                              23

<210> SEQ ID NO 266
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
uccgccgguc ggccugcuug gcu                                              23

<210> SEQ ID NO 267
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
gcugcccgca gggaagcguu cac                                              23

<210> SEQ ID NO 268
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 268
accagggguc cccguccugc ucc                          23

<210> SEQ ID NO 269
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
ccugcgggca gccaagcagg ccg                          23

<210> SEQ ID NO 270
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
ggguacugau ggugcuggga gca                          23

<210> SEQ ID NO 271
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
uuaggguacu gauggugcug gga                          23

<210> SEQ ID NO 272
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
cuuaggguac ugauggugcu ggg                          23

<210> SEQ ID NO 273
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
uuucuuaggg uacugauggu gcu                          23

<210> SEQ ID NO 274
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
cuuucuuagg guacugaugg ugc                                           23

<210> SEQ ID NO 275
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
ccuuucuuuc uuaggguacu gau                                           23

<210> SEQ ID NO 276
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
aggggaaagc acucacugga cau                                           23

<210> SEQ ID NO 277
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
guauccuucu ccucuucugg uac                                           23

<210> SEQ ID NO 278
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
uccucuucug guacucgguc uag                                           23

<210> SEQ ID NO 279
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
ugguacucgg ucuagcagac auu                                           23

```
<210> SEQ ID NO 280
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
auagauggcc uggagggagg aga                                              23

<210> SEQ ID NO 281
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
uagauggccu ggagggagga gag                                              23

<210> SEQ ID NO 282
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
ucuccucccu ccaggccauc uau                                              23

<210> SEQ ID NO 283
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283 gaugggqucc uuuucaaaca cuu                                              23

<210> SEQ ID NO 284
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
augggguccu uuucaaacac uuc                                              23

<210> SEQ ID NO 285
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 285
ucaaacacuu cauaugucug aga					23

<210> SEQ ID NO 286
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
caaacacuuc auaugucuga gau					23

<210> SEQ ID NO 287
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
aaacacuuca uaugucugag auu					23

<210> SEQ ID NO 288
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
auaugucuga gauuccagau ugu					23

<210> SEQ ID NO 289
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
cagauugucc aucaguggcu gau					23

<210> SEQ ID NO 290
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
uccaucagug gcugaugaau gag					23

<210> SEQ ID NO 291
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
aaaaggaccc caucaaauac ucu                                              23

<210> SEQ ID NO 292
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
gaaaaggacc ccaucaaaua cuc                                              23

<210> SEQ ID NO 293
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
aucagccacu gauggacaau cug                                              23

<210> SEQ ID NO 294
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
cucauucauc agccacugau gga                                              23

<210> SEQ ID NO 295
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
ccucauucau cagccacuga ugg                                              23

<210> SEQ ID NO 296
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
```
uccucauuca ucagccacug aug                                          23

<210> SEQ ID NO 297
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
auagcccuug gcaaagaguu cau                                          23

<210> SEQ ID NO 298
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
gcaaagaguu cauaggcauu agg                                          23

<210> SEQ ID NO 299
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
auaggcauua gguggaggac ggu                                          23

<210> SEQ ID NO 300
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
gguggaggac gguucuggcu uaa                                          23

<210> SEQ ID NO 301
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
uggcuuaagu auuccaggua uug                                          23

<210> SEQ ID NO 302
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 302
aguauuccag guauuggagg uag                                         23

<210> SEQ ID NO 303
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
cagguauugg agguaggagc aga                                         23

<210> SEQ ID NO 304
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
gagguaggag cagaacuccu ucu                                         23

<210> SEQ ID NO 305
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
ucugaguggu gguuggugcc ugu                                         23

<210> SEQ ID NO 306
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
gugccuguga ugaugaacug cac                                         23

<210> SEQ ID NO 307
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
ccaagggcua ugaagacuau cug                                         23

<210> SEQ ID NO 308
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
gccaagggcu augaagacua ucu                                            23

<210> SEQ ID NO 309
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
agccagaacc guccuccacc uaa                                            23

<210> SEQ ID NO 310
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
ugcuccuacc uccaauaccu gga                                            23

<210> SEQ ID NO 311
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
aucaucacag gcaccaacca cca                                            23

<210> SEQ ID NO 312
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
gaggugcagu ucaucaucac agg                                            23

<210> SEQ ID NO 313
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
```
ucacaguugg aggugcaguu cau                                              23

<210> SEQ ID NO 314
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
cucacaguug gaggugcagu uca                                              23

<210> SEQ ID NO 315
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
ucucacaguu ggaggugcag uuc                                              23

<210> SEQ ID NO 316
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
aggagccgga agaugagccu cug                                              23

<210> SEQ ID NO 317
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
gaaagaacag gaaaucccuu cuu                                              23

<210> SEQ ID NO 318
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
uuauugguca ggaaaaugcu agu                                              23

<210> SEQ ID NO 319
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 319
uuggucagga aaaugcuagu ggg                                              23

<210> SEQ ID NO 320
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
gucaggaaaa ugcuaguggg gag                                              23

<210> SEQ ID NO 321
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
gaugggcucc ccaagccagc gau                                              23

<210> SEQ ID NO 322
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
augggcuccc caagccagcg auc                                              23

<210> SEQ ID NO 323
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
gaugggaggu cagccccaau uuc                                              23

<210> SEQ ID NO 324
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
caagagcuac augaggcaaa aga                                              23

```
<210> SEQ ID NO 325
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
aagagcuaca ugaggcaaaa gaa                                            23

<210> SEQ ID NO 326
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
cggcuccuca aggugagugg uag                                            23

<210> SEQ ID NO 327
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
uaagaugcac cagaggcuca ucu                                            23

<210> SEQ ID NO 328
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
cuaagaugca ccagaggcuc auc                                            23

<210> SEQ ID NO 329
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
uuucuaagau gcaccagagg cuc                                            23

<210> SEQ ID NO 330
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 330 cguucuuuc uaagaugcac cag                                              23

<210> SEQ ID NO 331
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
ccuguucuuu cuaagaugca cca                                             23

<210> SEQ ID NO 332
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
cugaccaaua agaaggggauu ucc                                            23

<210> SEQ ID NO 333
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
ccugaccaau aagaaggggau uuc                                            23

<210> SEQ ID NO 334
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
uccugaccaa uaagaaggga uuu                                             23

<210> SEQ ID NO 335
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
uccccacuag cauuuccug acc                                              23

<210> SEQ ID NO 336
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 336
gggagcccau caaagcagcc auu                                            23

<210> SEQ ID NO 337
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
aucgcuggcu uggggagccc auc                                            23

<210> SEQ ID NO 338
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
gggcugaccu cccaucuaau cau                                            23

<210> SEQ ID NO 339
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
aaauuggggc ugaccuccca ucu                                            23

<210> SEQ ID NO 340
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
ccucauguag cucuugaaau ugg                                            23

<210> SEQ ID NO 341
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
gccucaugua gcucuugaaa uug                                            23
```

```
<210> SEQ ID NO 342
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
ugccucaugu agcucuugaa auu                                              23

<210> SEQ ID NO 343
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
uuuugccuca uguagcucuu gaa                                              23

<210> SEQ ID NO 344
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
cuuuugccuc auguagcucu uga                                              23

<210> SEQ ID NO 345
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
ucuuuugccu cauguagcuc uug                                              23

<210> SEQ ID NO 346
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
ucauggacuc acccacugca auc                                              23

<210> SEQ ID NO 347
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 347
cuauagucac acaaaguccg gaa                                              23

<210> SEQ ID NO 348
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
ugccaccugu ucagucaaau aca                                              23

<210> SEQ ID NO 349
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
caguggguga guccaugaga auc                                              23

<210> SEQ ID NO 350
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
ugugacuaua guaagaggau ugc                                              23

<210> SEQ ID NO 351
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
gugugacuau aguaagagga uug                                              23

<210> SEQ ID NO 352
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
cggacuuugu gugacuauag uaa                                              23

<210> SEQ ID NO 353
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
acugaacagg uggcacaacu ucc                                            23

<210> SEQ ID NO 354
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
gacugaacag guggcacaac uuc                                            23

<210> SEQ ID NO 355
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
uguauuugac ugaacaggug gca                                            23

<210> SEQ ID NO 356
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
ucuccucccc acuguacucc ucu                                            23

<210> SEQ ID NO 357
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357 cuccuccca cuguacuccu cug                                             23

<210> SEQ ID NO 358
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
uccuccccac uguacuccuc ugu                                            23
```

```
<210> SEQ ID NO 359
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
gugcauucuc aauuauauca ucu                                         23

<210> SEQ ID NO 360
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
ucaauuauau caucucucag guc                                         23

<210> SEQ ID NO 361
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
uaucaucucu cagguccucu ggu                                         23

<210> SEQ ID NO 362
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
agaaugcacc aacuacacac aca                                         23

<210> SEQ ID NO 363
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
guggcaccag aggaccugag aga                                         23

<210> SEQ ID NO 364
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

```
                      Synthetic oligonucleotide"

<400> SEQUENCE: 364
uggaugcggg uacccuuggu ggc                                              23

<210> SEQ ID NO 365
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
augugcaguu cuggaugcgg gua                                              23

<210> SEQ ID NO 366
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
gucaaaacuc uggccagguu ggu                                              23

<210> SEQ ID NO 367
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
guguuaucuu ccugauuaag ggg                                              23

<210> SEQ ID NO 368
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
ucuuccugau uaaggggcag cag                                              23

<210> SEQ ID NO 369
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
cugauuaagg ggcagcagga aag                                              23

<210> SEQ ID NO 370
<211> LENGTH: 23
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
aggggcagca ggaaagcugg aag                                       23

<210> SEQ ID NO 371
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
agcuccugua acauggccug gaa                                       23

<210> SEQ ID NO 372
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
caugguauag cugaggggcu ccu                                       23

<210> SEQ ID NO 373
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
accaaccaca uccacacugg cca                                       23

<210> SEQ ID NO 374
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
gaccaaccac auccacacug gcc                                       23

<210> SEQ ID NO 375
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
```
ugaccaacca cauccacacu ggc                                           23

<210> SEQ ID NO 376
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
aucaggaaga uaacaccaac cug                                           23

<210> SEQ ID NO 377
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
cugcugcccc uuaaucagga aga                                           23

<210> SEQ ID NO 378
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
ccugcugccc cuuaaucagg aag                                           23

<210> SEQ ID NO 379
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
cagcuuuccu gcugccccuu aau                                           23

<210> SEQ ID NO 380
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
ggucuuccag cuuccugcu gcc                                            23

<210> SEQ ID NO 381
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 381
gggucuucca gcuuccugc ugc                                              23

<210> SEQ ID NO 382
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
gugcauauuu gggucuucca gcu                                             23

<210> SEQ ID NO 383
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
ggugcauauu ugggucuucc agc                                             23

<210> SEQ ID NO 384
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
uggugcauau uugggucuuc cag                                             23

<210> SEQ ID NO 385
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
caggagcuga auuuggugc aua                                              23

<210> SEQ ID NO 386
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
caggccaugu uacaggagcu gaa                                             23

<210> SEQ ID NO 387
```

-continued

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
aucuccguuc caggccaugu uac                                           23

<210> SEQ ID NO 388
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
ccgccucgga guuccugcga auc                                           23

<210> SEQ ID NO 389
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
cugcgaaucu ucuccacuuu uga                                           23

<210> SEQ ID NO 390
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
uccacuuuug agucuggacg aau                                           23

<210> SEQ ID NO 391
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
ugagucugga cgaauccaug gag                                           23

<210> SEQ ID NO 392
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
```

```
gagucuggac gaauccaugg aga                                            23
```

<210> SEQ ID NO 393
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393

```
agucuggacg aauccaugga gaa                                            23
```

<210> SEQ ID NO 394
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394

```
cccacaauua gcguauucca guc                                            23
```

<210> SEQ ID NO 395
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395

```
ccacaauuag cguauuccag ucu                                            23
```

<210> SEQ ID NO 396
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396

```
gcguauucca gucugcacuc ccc                                            23
```

<210> SEQ ID NO 397
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397

```
cagucugcac uccccaccc aag                                             23
```

<210> SEQ ID NO 398
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 398
gcaggaacuc cgaggcggua aga                                                23

<210> SEQ ID NO 399
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
guccagacuc aaaaguggag aag                                                23

<210> SEQ ID NO 400
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
uccauggauu cguccagacu caa                                                23

<210> SEQ ID NO 401
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligoneotide"

<400> SEQUENCE: 401
cuccauggau ucguccagac uca                                                23

<210> SEQ ID NO 402
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
ugggaaagcu uucuccaugg auu                                                23

<210> SEQ ID NO 403
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
gguggggagg ugcagacugg aau                                                23
```

```
<210> SEQ ID NO 404
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
cugacagcag uaggucugau cgu                                             23

<210> SEQ ID NO 405
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
uuagcagguu ccugaaugaa cuc                                             23

<210> SEQ ID NO 406
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
gcagguuccu gaaugaacuc ccu                                             23

<210> SEQ ID NO 407
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
cugaaugaac ucccucuuga aac                                             23

<210> SEQ ID NO 408
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
aaacgcggau ggaagacagg cau                                             23

<210> SEQ ID NO 409
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 409
aggaaccugc uaagaaucgg ccc                                            23

<210> SEQ ID NO 410
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
auucaggaac cugcuaagaa ucg                                            23

<210> SEQ ID NO 411
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
aagagggagu ucauucagga acc                                            23

<210> SEQ ID NO 412
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
caagagggag uucauucagg aac                                            23

<210> SEQ ID NO 413
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
cauccgcguu ucaagaggga guu                                            23

<210> SEQ ID NO 414
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
cucugcaugc cugucuucca ucc                                            23

<210> SEQ ID NO 415
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 415
ccucugcaug ccugucuucc auc                                              23

<210> SEQ ID NO 416
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416 auuccucug caugccuguc uuc                                               23

<210> SEQ ID NO 417
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417 gauuccucu gcaugccugu cuu                                               23

<210> SEQ ID NO 418
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
uagguuugau uccucugca ugc                                               23

<210> SEQ ID NO 419
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
uccgggauga cuagucugcc cuu                                              23

<210> SEQ ID NO 420
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420 uccgucccg aguucggacc ccg                                               23
```

<210> SEQ ID NO 421
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 421
ggaccccgca uuccgcucgu gga                                          23

<210> SEQ ID NO 422
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 422
cgcucgugga gguccggccc uca                                          23

<210> SEQ ID NO 423
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 423
gccacagccc cuaguguguc agc                                          23

<210> SEQ ID NO 424
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 424
cggggacgca auucaggucc cuc                                          23

<210> SEQ ID NO 425
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 425
ggggacgcaa uucagguccc ucc                                          23

<210> SEQ ID NO 426
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 426 agucccucc cgcuggacac gcg                                           23

<210> SEQ ID NO 427
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
cuccucgcgc uguccacgcc ggg                                          23

<210> SEQ ID NO 428
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
uccucgcgcu guccacgccg gga                                          23

<210> SEQ ID NO 429
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
cuugauacua guagccaauc aca                                          23

<210> SEQ ID NO 430
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
auacuaguag ccaaucacaa agu                                          23

<210> SEQ ID NO 431
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
acaaccagag cgucugccac agc                                          23

<210> SEQ ID NO 432
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
uccugccaau ccgcgggcug cac                                              23

<210> SEQ ID NO 433
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
ccugccaauc cgcgggcugc aca                                              23

<210> SEQ ID NO 434
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
cugccaaucc gcgggcugca cag                                              23

<210> SEQ ID NO 435
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
cugacgaacu ucaaucuccc aga                                              23

<210> SEQ ID NO 436
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
cguccccgaa auagcugaca cac                                              23

<210> SEQ ID NO 437
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
gcuacuagua ucaaggaauc ccg                                              23
```

-continued

<210> SEQ ID NO 438
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
ugauuggcua cuaguaucaa gga                                               23

<210> SEQ ID NO 439
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
gugauuggcu acuaguauca agg                                               23

<210> SEQ ID NO 440
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
acuuugugau uggcuacuag uau                                               23

<210> SEQ ID NO 441
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
gacuuuguga uuggcuacua gua                                               23

<210> SEQ ID NO 442
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442 ugggggcacua guuugacuuu gug                                              23

<210> SEQ ID NO 443
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 443
aggcgacucg ucccgccuuc ugg                                            23

<210> SEQ ID NO 444
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
uuaaggcgac ucgucccgcc uuc                                            23

<210> SEQ ID NO 445
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
gggagcugug gcagacgcuc ugg                                            23

<210> SEQ ID NO 446
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
gcaggaaaag ccacuccccca ucc                                           23

<210> SEQ ID NO 447
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
guggauccau gccguacgcc acu                                            23

<210> SEQ ID NO 448
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
gucaggaacc agacccugag auu                                            23

<210> SEQ ID NO 449
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
aaguucguca ggaaccagac ccu                                            23

<210> SEQ ID NO 450
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
ugggagauug aaguucguca gga                                            23

<210> SEQ ID NO 451
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
gagguguggg aaaauagugg                                                20

<210> SEQ ID NO 452
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
agguguggga aaauaguggc                                                20

<210> SEQ ID NO 453
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453 gguguggaa aauaguggca                                                 20

<210> SEQ ID NO 454
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
```
ggcagcaugg ucgugcagua                                              20

<210> SEQ ID NO 455
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
uuacacaaaa ccaucaaaac                                              20

<210> SEQ ID NO 456
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
caaaaccauc aaaacaagaa                                              20

<210> SEQ ID NO 457
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
aaaacaagaa cagaaaaagg                                              20

<210> SEQ ID NO 458
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
ccguucaaac cccauguucu                                              20

<210> SEQ ID NO 459
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
cguucaaacc ccauguucuc                                              20

<210> SEQ ID NO 460
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 460
ccauguucuc agggauauuc                                                 20

<210> SEQ ID NO 461
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
cauguucuca gggauauucc                                                 20

<210> SEQ ID NO 462
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
auguucucag ggauauucca                                                 20

<210> SEQ ID NO 463
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
agggauauuc cagggaguuc                                                 20

<210> SEQ ID NO 464
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
auuccaggga guucuugagg                                                 20

<210> SEQ ID NO 465
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
cuaauuccuc accccuggc                                                  20

<210> SEQ ID NO 466
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
ggucuucaua gauugguggc                                               20

<210> SEQ ID NO 467
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
uugcccaccu ugauguaagg                                               20

<210> SEQ ID NO 468
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
ugcccaccuu gauguaaggc                                               20

<210> SEQ ID NO 469
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
auguaaggca ggaaagcaga                                               20

<210> SEQ ID NO 470
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
gauugaaaug cuccucucug                                               20

<210> SEQ ID NO 471
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
```

```
aaugcuccuc ucgaugggc                                               20

<210> SEQ ID NO 472
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
augcuccucu cugaugggca                                              20

<210> SEQ ID NO 473
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
ugcuccucuc ugaugggcaa                                              20

<210> SEQ ID NO 474
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
gcuccucucu gaugggcaag                                              20

<210> SEQ ID NO 475
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
guacugcacc uucuguacua                                              20

<210> SEQ ID NO 476
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
uacugcaccu ucuguacuac                                              20

<210> SEQ ID NO 477
<211> LENGTH: 20
<212> TYPE: RNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 477
caccuucugu acuacaggag                                               20

<210> SEQ ID NO 478
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
cuguacuaca ggagcagaac                                               20

<210> SEQ ID NO 479
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
cugaagcugc uuccaaggcu                                               20

<210> SEQ ID NO 480
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
ggcucuggac acuuggcacg                                               20

<210> SEQ ID NO 481
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
ggacacuugg cacgcagggc                                               20

<210> SEQ ID NO 482
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
gggcuagagg ccaaugguau                                               20

```
<210> SEQ ID NO 483
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
caaugguaua ugagcggccu                                               20

<210> SEQ ID NO 484
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
aaugguauau gagcggccug                                               20

<210> SEQ ID NO 485
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
uaugagcggc cugugggguu                                               20

<210> SEQ ID NO 486
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
gccugugggg uuaugaauag                                               20

<210> SEQ ID NO 487
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
cccacucaua ccacaccuuc                                               20

<210> SEQ ID NO 488
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 488
ccacucauac cacaccuucu                                               20

<210> SEQ ID NO 489
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
ucuuggaauu gcugcaucgc                                               20

<210> SEQ ID NO 490
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
uuuggccuuc acguaccguu                                               20

<210> SEQ ID NO 491
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
guaccguuau gggcugcugu                                               20

<210> SEQ ID NO 492
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
ccguuauggg cugcuguaag                                               20

<210> SEQ ID NO 493
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
ggcugcugua agaagaaaga                                               20

<210> SEQ ID NO 494
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 494
uuuugauggu uuuguguaag                                              20

<210> SEQ ID NO 495
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
guuuugaugg uuuuguguaa                                              20

<210> SEQ ID NO 496
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
uuguuuugau gguuuugugu                                              20

<210> SEQ ID NO 497
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
ccugagaaca uggguuuga                                               20

<210> SEQ ID NO 498
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
uaucccugag aacauggggu                                              20

<210> SEQ ID NO 499
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
cuggaauauc ccugagaaca                                              20
```

```
<210> SEQ ID NO 500
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
ccuggaauau cccugagaac                                               20

<210> SEQ ID NO 501
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
gaacucccug gaauaucccu                                               20

<210> SEQ ID NO 502
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
aagaacuccc uggaauaucc                                               20

<210> SEQ ID NO 503
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
acucagccuc aagaacuccc                                               20

<210> SEQ ID NO 504
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
cacucagccu caagaacucc                                               20

<210> SEQ ID NO 505
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 505
gaagcuacgc acucagccuc                                              20

<210> SEQ ID NO 506
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
gugaggaauu agugcuggau                                              20

<210> SEQ ID NO 507
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
caggggguga ggaauuagug                                              20

<210> SEQ ID NO 508
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
agaccucagg ccaggggguq                                              20

<210> SEQ ID NO 509
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
aagaccucag gccaggggu                                               20

<210> SEQ ID NO 510
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
ugaagaccuc aggccagggg                                              20

<210> SEQ ID NO 511
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
ucuaugaaga ccucaggcca                                           20

<210> SEQ ID NO 512
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
aucuaugaag accucaggcc                                           20

<210> SEQ ID NO 513
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
aaucuaugaa gaccucaggc                                           20

<210> SEQ ID NO 514
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
agggcucaag ccaccaaucu                                           20

<210> SEQ ID NO 515
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
caagggauua uaauuaauug                                           20

<210> SEQ ID NO 516
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
gccuuacauc aagugggca                                            20
```

```
<210> SEQ ID NO 517
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
ugccuuacau caaggugggc                                                    20

<210> SEQ ID NO 518
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
cuuuccugcc uuacaucaag                                                    20

<210> SEQ ID NO 519
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
auuccccuug cccaucagag                                                    20

<210> SEQ ID NO 520
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
gauuccccuu gcccaucaga                                                    20

<210> SEQ ID NO 521
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
gugauucccc uugcccauca                                                    20

<210> SEQ ID NO 522
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 522
cugugauucc ccuugcccau					20

<210> SEQ ID NO 523
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
acagaaggug caguacaucu					20

<210> SEQ ID NO 524
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
cagguucugc uccuguagua					20

<210> SEQ ID NO 525
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
gugccaagug uccagagccu					20

<210> SEQ ID NO 526
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
cgugccaagu guccagagcc					20

<210> SEQ ID NO 527
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
agcccugcgu gccaaguguc					20

<210> SEQ ID NO 528
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
uccaagaagg ugugguauga                                                20

<210> SEQ ID NO 529
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
caauuccaag aagguguggu                                                20

<210> SEQ ID NO 530
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
ucuggcgaug cagcaauucc                                                20

<210> SEQ ID NO 531
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
acagcagccc auaacgguac                                                20

<210> SEQ ID NO 532
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
aaaagcaguu ccuaccuuaa                                                20

<210> SEQ ID NO 533
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
```
aaagcaguuc cuaccuuaau 20

<210> SEQ ID NO 534
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
aagcaguucc uaccuuaaua 20

<210> SEQ ID NO 535
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535 caguccuac cuuaauaggg 20

<210> SEQ ID NO 536
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
guuccuaccu uaauagggaa 20

<210> SEQ ID NO 537
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
cuaccuuaau agggaagagg 20

<210> SEQ ID NO 538
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
uaccuuaaua gggaagagga 20

<210> SEQ ID NO 539
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 539
accuuaauag ggaagaggau                                                    20

<210> SEQ ID NO 540
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
agggaagagg augggaaacc                                                    20

<210> SEQ ID NO 541
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
ggaagaggau gggaaaccau                                                    20

<210> SEQ ID NO 542
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
gggaaaccau gagaacaucc                                                    20

<210> SEQ ID NO 543
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
ggaaaccaug agaacauccc                                                    20

<210> SEQ ID NO 544
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
aaaccaugag aacaucccag                                                    20

<210> SEQ ID NO 545
```

-continued

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
caugagaaca ucccaggaga                                                      20

<210> SEQ ID NO 546
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
caucccagga gagugagucu                                                      20

<210> SEQ ID NO 547
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
ccaggagagu gagucucugg                                                      20

<210> SEQ ID NO 548
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
gucucuggac ggauaccugu                                                      20

<210> SEQ ID NO 549
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
auccucuucc cuauuaaggu                                                      20

<210> SEQ ID NO 550
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
```
cauccucuuc ccuauuaagg                                              20

<210> SEQ ID NO 551
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
cguccagaga cucacucucc                                              20

<210> SEQ ID NO 552
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
ccguccagag acucacucuc                                              20

<210> SEQ ID NO 553
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
uguccacaca gguauccguc                                              20

<210> SEQ ID NO 554
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
uacugccaua gacacucacu                                              20

<210> SEQ ID NO 555
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
uaguacugug uucaccucca                                              20

<210> SEQ ID NO 556
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 556
aguacugugu ucaccuccac                                                    20

<210> SEQ ID NO 557
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
auagcgguug uugucaauca                                                    20

<210> SEQ ID NO 558
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
uugucaauca uaggaucugu                                                    20

<210> SEQ ID NO 559
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
ugucaaucau aggaucuguc                                                    20

<210> SEQ ID NO 560
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
uuaucaggac aucacucuga                                                    20

<210> SEQ ID NO 561
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
ugcuuuauca ggacaucacu                                                    20
```

```
<210> SEQ ID NO 562
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
acuuugagac ugugcuuuau                                               20

<210> SEQ ID NO 563
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
acauggcuuu gccggcuacu                                               20

<210> SEQ ID NO 564
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
ccuuggaauu uccuguggag                                               20

<210> SEQ ID NO 565
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
uugcaccuug gaauuuccug                                               20

<210> SEQ ID NO 566
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
auugcaccuu ggaauuuccu                                               20

<210> SEQ ID NO 567
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 567
caacaaccgc uauugcaccu                                                    20

<210> SEQ ID NO 568
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
acaacaaccg cuauugcacc                                                    20

<210> SEQ ID NO 569
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569 cauaaagaa ccuaccucug                                                     20

<210> SEQ ID NO 570
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
auaaaagaac cuaccucugu                                                    20

<210> SEQ ID NO 571
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
accuaccucu guugggaugg                                                    20

<210> SEQ ID NO 572
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
cucuguuggg auggcugaag                                                    20

<210> SEQ ID NO 573
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 573
ugggauggcu gaaggugaaa                                              20

<210> SEQ ID NO 574
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
uggcugaagg ugaaacaggg                                              20

<210> SEQ ID NO 575
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
ggcugaaggu gaaacagggc                                              20

<210> SEQ ID NO 576
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
ggugaaacag ggcuggggug                                              20

<210> SEQ ID NO 577
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
ugaaacaggg cuggggugca                                              20

<210> SEQ ID NO 578
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
ggcuggggug cagagagcug                                              20
```

```
<210> SEQ ID NO 579
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
gcuggggugc agagagcugg                                              20

<210> SEQ ID NO 580
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
accacauaag gcaucucaaa                                              20

<210> SEQ ID NO 581
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
uucaccuuca gccaucccaa                                              20

<210> SEQ ID NO 582
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
gacagagaga caggcccagu                                              20

<210> SEQ ID NO 583
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
gagagagugg uucuuuaccu                                              20

<210> SEQ ID NO 584
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 584
cgguccuucu cccuacaggc                                                      20

<210> SEQ ID NO 585
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
cucggaccuc auuguacagc                                                      20

<210> SEQ ID NO 586
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
ucggaccuca uuguacagcu                                                      20

<210> SEQ ID NO 587
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
ggaccucauu guacagcuug                                                      20

<210> SEQ ID NO 588
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
gaccucauug uacagcuugg                                                      20

<210> SEQ ID NO 589
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
cucauuguac agcuuggagg                                                      20

<210> SEQ ID NO 590
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
uguacagcuu ggaggaagag                                              20

<210> SEQ ID NO 591
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
guacagcuug gaggaagaga                                              20

<210> SEQ ID NO 592
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
uacagcuugg aggaagagau                                              20

<210> SEQ ID NO 593
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
uuggaggaag agaugggagc                                              20

<210> SEQ ID NO 594
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
aggaagagau gggagccaga                                              20

<210> SEQ ID NO 595
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
ggaagagaug ggagccagaa                                              20
```

```
<210> SEQ ID NO 596
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
ccagaaagga aguguacucc                                                    20

<210> SEQ ID NO 597
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
cagaaaggaa guguacuccc                                                    20

<210> SEQ ID NO 598
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
agaaaggaag uguacucccc                                                    20

<210> SEQ ID NO 599
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
ucacaccauc aucugcacag                                                    20

<210> SEQ ID NO 600
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
cacaccauca ucugcacagc                                                    20

<210> SEQ ID NO 601
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 601
caccaucauc ugcacagcag                                              20

<210> SEQ ID NO 602
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
aggaccguga cccugaggua                                              20

<210> SEQ ID NO 603
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
uagggagaag gaccgugacc                                              20

<210> SEQ ID NO 604
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
agguccgagc cguagggag                                               20

<210> SEQ ID NO 605
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
augagguccg agccuguagg                                              20

<210> SEQ ID NO 606
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
caaugagguc cgagccugua                                              20

<210> SEQ ID NO 607
<211> LENGTH: 20

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
acaaugaggu ccgagccugu                                               20

<210> SEQ ID NO 608
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
uacaaugagg uccgagccug                                               20

<210> SEQ ID NO 609
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
uccaagcugu acaaugaggu                                               20

<210> SEQ ID NO 610
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
cucuuccucc aagcuguaca                                               20

<210> SEQ ID NO 611
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
ugauggugug agcauccccg                                               20

<210> SEQ ID NO 612
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
```
augauggugu gagcaucccc                                            20

<210> SEQ ID NO 613
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
gaugauggug ugagcauccc                                            20

<210> SEQ ID NO 614
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
agaugauggu gugagcaucc                                            20

<210> SEQ ID NO 615
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
ccugcugugc agaugauggu                                            20

<210> SEQ ID NO 616
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
cccaaccugg gggcaccuuu                                            20

<210> SEQ ID NO 617
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
ccaaccuggg ggcaccuuuu                                            20

<210> SEQ ID NO 618
<211> LENGTH: 20
<212> TYPE: RNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 618
ggggcaccuu uuaggaagug                                              20

<210> SEQ ID NO 619
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
cgacaauuca uugucagcaa                                              20

<210> SEQ ID NO 620
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
ucauugucag caaaugagcc                                              20

<210> SEQ ID NO 621
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
gacaaugaug ucugcuuucu                                              20

<210> SEQ ID NO 622
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
acaaugaugu cugcuuucuc                                              20

<210> SEQ ID NO 623
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
cacccauucc cucaugucug                                              20

<210> SEQ ID NO 624

-continued

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
caaacugcca guucucuagc                                                   20

<210> SEQ ID NO 625
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
gccaguucuc uagccugaaa                                                   20

<210> SEQ ID NO 626
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
ccuaaaaggu gcccccaggu                                                   20

<210> SEQ ID NO 627
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
uccuaaaagg ugcccccagg                                                   20

<210> SEQ ID NO 628
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
uugucgccug agugccugga                                                   20

<210> SEQ ID NO 629
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
```
auugucgccu gagugccugg                          20

<210> SEQ ID NO 630
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
augaauuguc gccugagugc                          20

<210> SEQ ID NO 631
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
ugcugacaau gaauugucgc                          20

<210> SEQ ID NO 632
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
ucugggcuca uuugcugaca                          20

<210> SEQ ID NO 633
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
acaucauugu cagugagcuu                          20

<210> SEQ ID NO 634
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
gaaagcagac aucauuguca                          20

<210> SEQ ID NO 635
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 635
ugagggaaug gguggcucca                                              20

<210> SEQ ID NO 636
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
caugagggaa uggguggcuc                                              20

<210> SEQ ID NO 637
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
gucucaucag acaugaggga                                              20

<210> SEQ ID NO 638
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
cguagucuca ucagacauga                                              20

<210> SEQ ID NO 639
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
ccguagucuc aucagacaug                                              20

<210> SEQ ID NO 640
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
accguagucu caucagacau                                              20
```

```
<210> SEQ ID NO 641
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
ugaccguagu cucaucagac                                               20

<210> SEQ ID NO 642
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
aacuggcagu uugaagaaug                                               20

<210> SEQ ID NO 643
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
gaacuggcag uuugaagaau                                               20

<210> SEQ ID NO 644
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
agaacuggca guuugaagaa                                               20

<210> SEQ ID NO 645
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
gagaacuggc aguuugaaga                                               20

<210> SEQ ID NO 646
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 646
gcuagagaac uggcaguuug                                              20

<210> SEQ ID NO 647
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
caggcuagag aacuggcagu                                              20

<210> SEQ ID NO 648
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
auugucucug uuucaggcua                                              20

<210> SEQ ID NO 649
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
uuauugucuc uguuucaggc                                              20

<210> SEQ ID NO 650
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
uacucacguc accacggcau                                              20

<210> SEQ ID NO 651
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
ucggccugcu uggcugcccg                                              20

<210> SEQ ID NO 652
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 652
cggccugcuu ggcugcccgc                                              20

<210> SEQ ID NO 653
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
ggccugcuug gcugcccgca                                              20

<210> SEQ ID NO 654
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
gcccgcaggg aagcguucac                                              20

<210> SEQ ID NO 655
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
cccgcaggga agcguucacc                                              20

<210> SEQ ID NO 656
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
cccagcacca ucaguacccu                                              20

<210> SEQ ID NO 657
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
gcaccaucag uacccuaaga                                              20
```

```
<210> SEQ ID NO 658
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
caucaguacc cuaagaaaga                                               20

<210> SEQ ID NO 659
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
aucaguaccc uaagaaagaa                                               20

<210> SEQ ID NO 660
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
ucaguacccu aagaaagaaa                                               20

<210> SEQ ID NO 661
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
guacccuaag aaagaaaggg                                               20

<210> SEQ ID NO 662
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
aacccaaaug ccguggugac                                               20

<210> SEQ ID NO 663
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 663
ggauaaagcu guaugcugug                                              20

<210> SEQ ID NO 664
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
gcggauaaag cuguaugcug                                              20

<210> SEQ ID NO 665
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
ggcggauaaa gcuguaugcu                                              20

<210> SEQ ID NO 666
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
gcagccaagc aggccgaccg                                              20

<210> SEQ ID NO 667
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
ccccugguga acgcuucccu                                              20

<210> SEQ ID NO 668
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
gagcaggacg gggaccccug                                              20

<210> SEQ ID NO 669
<211> LENGTH: 20
<212> TYPE: RNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
gauggugcug ggagcaggac                                              20

<210> SEQ ID NO 670
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
ugauggugcu gggagcagga                                              20

<210> SEQ ID NO 671
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
cugauggugc ugggagcagg                                              20

<210> SEQ ID NO 672
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
gguacugaug gugcugggag                                              20

<210> SEQ ID NO 673
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
cuuaggguac ugauggugcu                                              20

<210> SEQ ID NO 674
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
ucuuagggua cugauggugc                                              20

```
<210> SEQ ID NO 675
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
uucuuagggu acugauggug                                               20

<210> SEQ ID NO 676
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
agcagacauu uauagauggc                                               20

<210> SEQ ID NO 677
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
gcagacauuu auagauggcc                                               20

<210> SEQ ID NO 678
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678
agacauuuau agauggccug                                               20

<210> SEQ ID NO 679
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
gacauuuaua gauggccugg                                               20

<210> SEQ ID NO 680
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 680
acauuuauag auggccugga                                       20

<210> SEQ ID NO 681
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 681
auuuauagau ggccuggagg                                       20

<210> SEQ ID NO 682
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
uuuauagaug gccuggaggg                                       20

<210> SEQ ID NO 683
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
uauagauggc cuggagggag                                       20

<210> SEQ ID NO 684
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 684
uagauggccu ggagggagga                                       20

<210> SEQ ID NO 685
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
gagaaggaua ccaaugucca                                       20

<210> SEQ ID NO 686
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
accgaguacc agaagaggag                                                    20

<210> SEQ ID NO 687
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
uagaccgagu accagaagag                                                    20

<210> SEQ ID NO 688
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
gcuagaccga guaccagaag                                                    20

<210> SEQ ID NO 689
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 689
ugcuagaccg aguaccagaa                                                    20

<210> SEQ ID NO 690
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
ucugcuagac cgaguaccag                                                    20

<210> SEQ ID NO 691
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
```
augucugcua gaccgaguac                                                  20

<210> SEQ ID NO 692
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 692
aucuauaaau gucugcuaga                                                  20

<210> SEQ ID NO 693
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 693
ccacacagua ccugcuggua                                                  20

<210> SEQ ID NO 694
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694
acacaguacc ugcugguacu                                                  20

<210> SEQ ID NO 695
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
gcugguacug agaguauuug                                                  20

<210> SEQ ID NO 696
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696
cugguacuga gaguauuuga                                                  20

<210> SEQ ID NO 697
<211> LENGTH: 20
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 697
uuuucaaaca cuucauaugu                                              20

<210> SEQ ID NO 698
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698
agauugucca ucaguggcug                                              20

<210> SEQ ID NO 699
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
uguccaucag uggcugauga                                              20

<210> SEQ ID NO 700
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700
uccaucagug gcugaugaau                                              20

<210> SEQ ID NO 701
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 701
ccaucagugg cugaugaaug                                              20

<210> SEQ ID NO 702
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
aguggcugau gaaugaggaa                                              20

<210> SEQ ID NO 703
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
agcagguacu gugguguggugcc                                              20

<210> SEQ ID NO 704
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
agacauauga aguguuugaa                                                 20

<210> SEQ ID NO 705
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
aucucagaca uaugaagugu                                                 20

<210> SEQ ID NO 706
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
caaucuggaa ucucagacau                                                 20

<210> SEQ ID NO 707
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
ucagccacug auggacaauc                                                 20

<210> SEQ ID NO 708
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
```
aucagccacu gauggacaau                                              20

<210> SEQ ID NO 709
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
uccucauuca ucagccacug                                              20

<210> SEQ ID NO 710
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
uaagugcacu ccagacccac                                              20

<210> SEQ ID NO 711
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
gcacuccaga cccaccugaa                                              20

<210> SEQ ID NO 712
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
cacuccagac ccaccugaag                                              20

<210> SEQ ID NO 713
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
acuccagacc caccugaagc                                              20

<210> SEQ ID NO 714
<211> LENGTH: 20
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 714
agucuucaua gcccuuggca                                                     20

<210> SEQ ID NO 715
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 715
aaagaguuca uaggcauuag                                                     20

<210> SEQ ID NO 716
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716
aagaguucau aggcauuagg                                                     20

<210> SEQ ID NO 717
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717
gaguucauag gcauuaggug                                                     20

<210> SEQ ID NO 718
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 718
uggcuuaagu auuccaggua                                                     20

<210> SEQ ID NO 719
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 719
ggcuuaagua uuccagguau                                                     20

```
-continued

<210> SEQ ID NO 720
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 720
aguauuccag guauuggagg                                              20

<210> SEQ ID NO 721
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
guauuccagg uauuggaggu                                              20

<210> SEQ ID NO 722
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
ccagguauug gagguaggag                                              20

<210> SEQ ID NO 723
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 723
guaggagcag aacuccuucu                                              20

<210> SEQ ID NO 724
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
ggugguuggu gccugugaug                                              20

<210> SEQ ID NO 725
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 725
gaugaacugc accuccaacu                                              20

<210> SEQ ID NO 726
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
ugaacugcac cuccaacugu                                              20

<210> SEQ ID NO 727
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 727 gucccgcuu caggugggue                                               20

<210> SEQ ID NO 728
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
aguccccgcu ucagguqggu                                              20

<210> SEQ ID NO 729
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
aucugcaguc cccgcuucag                                              20

<210> SEQ ID NO 730
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
ugaacucuuu gccaagggcu                                              20

<210> SEQ ID NO 731
<211> LENGTH: 20
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 731
augccuauga acucuuugcc                                              20

<210> SEQ ID NO 732
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 732
ccguccucca ccuaaugccu                                              20

<210> SEQ ID NO 733
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
aauaccugga auacuuaagc                                              20

<210> SEQ ID NO 734
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 734
cugcuccuac cuccaauacc                                              20

<210> SEQ ID NO 735
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 735
ucugcuccua ccuccaauac                                              20

<210> SEQ ID NO 736
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 736
caccaaccac cacucagaga                                              20
```

<210> SEQ ID NO 737
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 737
gcaccaacca ccacucagag                                               20

<210> SEQ ID NO 738
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 738
caggcaccaa ccaccacuca                                               20

<210> SEQ ID NO 739
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 739
cacaggcacc aaccaccacu                                               20

<210> SEQ ID NO 740
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 740
ggucugacuu uucucacagu                                               20

<210> SEQ ID NO 741
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 741
uggucugacu uuucucacag                                               20

<210> SEQ ID NO 742
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 742
gaacccuccu accacucacc                                             20

<210> SEQ ID NO 743
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
acccuccuac cacucaccuu                                             20

<210> SEQ ID NO 744
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
cccuccuacc acucaccuug                                             20

<210> SEQ ID NO 745
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
cuaccacuca ccuugaggag                                             20

<210> SEQ ID NO 746
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 746
uaccacucac cuugaggagc                                             20

<210> SEQ ID NO 747
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
ucaccuugag gagccggaag                                             20

<210> SEQ ID NO 748
<211> LENGTH: 20
<212> TYPE: RNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
gaugagccuc uggugcaucu                                           20

<210> SEQ ID NO 749
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
agccucuggu gcaucuuaga                                           20

<210> SEQ ID NO 750
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750
cuggugcauc uuagaaagaa                                           20

<210> SEQ ID NO 751
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751
uggugcaucu uagaaagaac                                           20

<210> SEQ ID NO 752
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 752 ggaaucccu ucuuauuggu                                            20

<210> SEQ ID NO 753
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 753 gaaauccuu cuuauugguc                                            20

<210> SEQ ID NO 754
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 754
uauuggucag gaaaaugcua                                              20

<210> SEQ ID NO 755
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 755
auuggucagg aaaaugcuag                                              20

<210> SEQ ID NO 756
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 756
uuggucagga aaaugcuagu                                              20

<210> SEQ ID NO 757
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 757
uggucaggaa aaugcuagug                                              20

<210> SEQ ID NO 758
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758
gucaggaaaa ugcuagaggg                                              20

<210> SEQ ID NO 759
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 759 ugggagaau ggcugcuuug                    20

<210> SEQ ID NO 760
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
gcgaucaaug acaugauuag                    20

<210> SEQ ID NO 761
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
cgaucaauga caugauuaga                    20

<210> SEQ ID NO 762
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
gaucaaugac augauuagau                    20

<210> SEQ ID NO 763
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 763
gggaggucag ccccaauuuc                    20

<210> SEQ ID NO 764
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
gccccaauuu caagagcuac                    20

<210> SEQ ID NO 765
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 765
ucaagagcua caugaggcaa                                                   20

<210> SEQ ID NO 766
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
cuccucaagg ugagugguag                                                   20

<210> SEQ ID NO 767
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 767
ggcuccucaa ggugaguggu                                                   20

<210> SEQ ID NO 768
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
cggcuccuca aggugagugg                                                   20

<210> SEQ ID NO 769
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 769
ucaucuuccg gcuccucaag                                                   20

<210> SEQ ID NO 770
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 770
```
cuguucuuuc uaagaugcac                          20

<210> SEQ ID NO 771
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 771
cauuuuccug accaauaaga                          20

<210> SEQ ID NO 772
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 772
gcauuuuccu gaccaauaag                          20

<210> SEQ ID NO 773
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 773
cuagcauuuu ccugaccaau                          20

<210> SEQ ID NO 774
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 774
ugucauugau cgcuggcuug                          20

<210> SEQ ID NO 775
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 775
augucauuga ucgcuggcuu                          20

<210> SEQ ID NO 776
<211> LENGTH: 20
<212> TYPE: RNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 776
caugucauug aucgcuggcu                                              20

<210> SEQ ID NO 777
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 777
ucaugucauu gaucgcuggc                                              20

<210> SEQ ID NO 778
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 778
ccucauguag cucuugaaau                                              20

<210> SEQ ID NO 779
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
gccucaugua gcucuugaaa                                              20

<210> SEQ ID NO 780
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 780
ucuuuugccu cauguagcuc                                              20

<210> SEQ ID NO 781
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 781
uuacuauagu cacacaaagu                                              20

<210> SEQ ID NO 782

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 782
uacuauaguc acacaaaguc                                                    20

<210> SEQ ID NO 783
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
gccaccuguu cagucaaaua                                                    20

<210> SEQ ID NO 784
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 784
auugcagugg gugaguccau                                                    20

<210> SEQ ID NO 785
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 785
ggauugcagu gggugagucc                                                    20

<210> SEQ ID NO 786
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
uaguaagagg auugcagugg                                                    20

<210> SEQ ID NO 787
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
```
acuauaguaa gaggauugca                                               20

<210> SEQ ID NO 788
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 788 acuugugug acuauaguaa                                                20

<210> SEQ ID NO 789
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 789
ggacuuugug ugacuauagu                                               20

<210> SEQ ID NO 790
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 790
cugaacaggu ggcacaacuu                                               20

<210> SEQ ID NO 791
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 791
ucagguccuc uggugccacc                                               20

<210> SEQ ID NO 792
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 792
ccaccaaggg uacccgcauc                                               20

<210> SEQ ID NO 793
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 793
acccgcaucc agaacugcac                                                  20

<210> SEQ ID NO 794
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 794
uacagugggg aggagaaaac                                                  20

<210> SEQ ID NO 795
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 795
cagaggagua cagugggag                                                   20

<210> SEQ ID NO 796
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 796
cacagaggag uacagugggg                                                  20

<210> SEQ ID NO 797
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 797
acacagagga guacaguggg                                                  20

<210> SEQ ID NO 798
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 798
acacacagag gaguacagug                                                  20
```

```
<210> SEQ ID NO 799
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 799
cacacacaga ggaguacagu                                                    20

<210> SEQ ID NO 800
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800
acacacacag aggaguacag                                                    20

<210> SEQ ID NO 801
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801
uacacacaca gaggaguaca                                                    20

<210> SEQ ID NO 802
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 802
ugcaccaacu acacacacag                                                    20

<210> SEQ ID NO 803
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 803
augcaccaac uacacacaca                                                    20

<210> SEQ ID NO 804
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 804
gaaugcacca acuacacaca                                              20

<210> SEQ ID NO 805
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 805
accugagaga ugauauaauu                                              20

<210> SEQ ID NO 806
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 806
ggaccugaga gaugauauaa                                              20

<210> SEQ ID NO 807
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 807 uuggugcac cagaggaccu                                               20

<210> SEQ ID NO 808
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 808
ccuugguggc accagaggac                                              20

<210> SEQ ID NO 809
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 809
ggguacccuu gguggcacca                                              20

<210> SEQ ID NO 810
<211> LENGTH: 20
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 810 gcgggguaccc uuggguggcac                                              20

<210> SEQ ID NO 811
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811
guucaugugc aguucuggau                                                20

<210> SEQ ID NO 812
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 812
gugacuguuc augugcaguu                                                20

<210> SEQ ID NO 813
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
aggagccccu cagcuauacc                                                20

<210> SEQ ID NO 814
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 814
ggagccccuc agcuauacca                                                20

<210> SEQ ID NO 815
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 815
gccccucagc uauaccaugg                                                20
```

<210> SEQ ID NO 816
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 816
auggaagagu gauggccagu                                          20

<210> SEQ ID NO 817
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 817
uugguguuau cuuccugauu                                          20

<210> SEQ ID NO 818
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 818
ugguguuauc uuccugauua                                          20

<210> SEQ ID NO 819
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 819
ucuuccugau uaaggggcag                                          20

<210> SEQ ID NO 820
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 820
cuuccugauu aagggcagc                                           20

<210> SEQ ID NO 821
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
auuaaggggc agcaggaaag                                            20

<210> SEQ ID NO 822
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
uuaaggggca gcaggaaagc                                            20

<210> SEQ ID NO 823
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 823
uucagcuccu guaacauggc                                            20

<210> SEQ ID NO 824
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
ucagcuccug uaacauggcc                                            20

<210> SEQ ID NO 825
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 825
cuccuguaac auggccugga                                            20

<210> SEQ ID NO 826
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 826
uccuguaaca uggccuggaa                                            20

<210> SEQ ID NO 827
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
uaacauggcc uggaacggag                                              20

<210> SEQ ID NO 828
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
cauggccugg aacggagaug                                              20

<210> SEQ ID NO 829
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
acucuuccau gguauagcug                                              20

<210> SEQ ID NO 830
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
cacucuucca ugguauagcu                                              20

<210> SEQ ID NO 831
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
aucacucuuc caugguauag                                              20

<210> SEQ ID NO 832
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 832
gaagauaaca ccaaccuggc                                              20
```

<210> SEQ ID NO 833
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
uuuccugcug ccccuuaauc                                                    20

<210> SEQ ID NO 834
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 834
cuuuccugcu gccccuuaau                                                    20

<210> SEQ ID NO 835
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835
agcugaauuu uggugcauau                                                    20

<210> SEQ ID NO 836
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 836
uccaggccau guuacaggag                                                    20

<210> SEQ ID NO 837
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 837
uccguuccag gccauguuac                                                    20

<210> SEQ ID NO 838
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 838
cuccguucca ggccauguua                                           20

<210> SEQ ID NO 839
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 839
agucaaacag ucuuaccgcc                                           20

<210> SEQ ID NO 840
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 840
gucaaacagu cuuaccgccu                                           20

<210> SEQ ID NO 841
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841
cuuaccgccu cggaguuccu                                           20

<210> SEQ ID NO 842
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842
ccugcgaauc uucuccacuu                                           20

<210> SEQ ID NO 843
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
aaucuucucc acuuuugagu                                           20

<210> SEQ ID NO 844
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 844
uucuccacuu uugagucugg                                              20

<210> SEQ ID NO 845
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
uuuugagucu ggacgaaucc                                              20

<210> SEQ ID NO 846
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846
uuugagucug gacgaaucca                                              20

<210> SEQ ID NO 847
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 847
ugagucugga cgaauccaug                                              20

<210> SEQ ID NO 848
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 848
ggagaagauu cgcaggaacu                                              20

<210> SEQ ID NO 849
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 849
```

-continued caaaagugga gaagauucgc                                              20

<210> SEQ ID NO 850
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 850
ucaaaagugg agaagauucg                                              20

<210> SEQ ID NO 851
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 851
uucguccaga cucaaaagug                                              20

<210> SEQ ID NO 852
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 852
gauucgucca gacucaaaag                                              20

<210> SEQ ID NO 853
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 853
ggauucgucc agacucaaaa                                              20

<210> SEQ ID NO 854
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 854
auugugggaa agcuuucucc                                              20

<210> SEQ ID NO 855
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 855
gacuggaaua cgcuaauugu					20

<210> SEQ ID NO 856
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 856
agacuggaau acgcuaauug					20

<210> SEQ ID NO 857
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
cagacuggaa uacgcuaauu					20

<210> SEQ ID NO 858
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 858
uugggugggg gagugcagac					20

<210> SEQ ID NO 859
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 859
cuuggguggg ggagugcaga					20

<210> SEQ ID NO 860
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 860
agcaguaggu cugaucgugu					20

<210> SEQ ID NO 861

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 861
gcaguagguc ugaucguguc                                               20

<210> SEQ ID NO 862
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 862
caguaggucu gaucgugucu                                               20

<210> SEQ ID NO 863
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 863
ggucugaucg ugucugggga                                               20

<210> SEQ ID NO 864
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 864
ggccgauucu uagcagguuc                                               20

<210> SEQ ID NO 865
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 865
gauucuuagc agguuccuga                                               20

<210> SEQ ID NO 866
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 866
```

```
guuccugaau gaacucccuc                                            20

<210> SEQ ID NO 867
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 867
aaugaacucc cucuugaaac                                            20

<210> SEQ ID NO 868
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 868
aacucccucu ugaaacgcgg                                            20

<210> SEQ ID NO 869
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 869
acucccucuu gaaacgcgga                                            20

<210> SEQ ID NO 870
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 870
gcggauggaa gacaggcaug                                            20

<210> SEQ ID NO 871
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 871
ggauggaaga caggcaugca                                            20

<210> SEQ ID NO 872
<211> LENGTH: 20
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 872
gauggaagac aggcaugcag                                              20

<210> SEQ ID NO 873
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 873
uacugcuguc aggaaggggu                                              20

<210> SEQ ID NO 874
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 874
cuacugcugu caggaagggg                                              20

<210> SEQ ID NO 875
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 875
cagaccuacu gcugucagga                                              20

<210> SEQ ID NO 876
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 876
ucagaccuac ugcugucagg                                              20

<210> SEQ ID NO 877
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
cgaucagacc uacugcuguc                                              20
```

```
<210> SEQ ID NO 878
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 878
acgaucagac cuacugcugu                                            20

<210> SEQ ID NO 879
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879
aguucauuca ggaaccugcu                                            20

<210> SEQ ID NO 880
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 880
uuucaagagg gaguucauuc                                            20

<210> SEQ ID NO 881
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881
guuucaagag ggaguucauu                                            20

<210> SEQ ID NO 882
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882
cuuccauccg cguuucaaga                                            20

<210> SEQ ID NO 883
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 883
ucuuccaucc gcguuucaag                                              20

<210> SEQ ID NO 884
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 884
gucuuccauc cgcguuucaa                                              20

<210> SEQ ID NO 885
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 885
cugucuucca uccgcguuuc                                              20

<210> SEQ ID NO 886
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 886
acccccucac cccugcuucu                                              20

<210> SEQ ID NO 887
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 887
cccccucacc ccugcuucuc                                              20

<210> SEQ ID NO 888
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
uagucugccc uucuccgucc                                              20

<210> SEQ ID NO 889
<211> LENGTH: 20
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 889
gcccuucucc gucccgagu                                              20

<210> SEQ ID NO 890
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 890
ucggaccccg cauuccgcuc                                             20

<210> SEQ ID NO 891
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 891
cggaccccgc auuccgcucg                                             20

<210> SEQ ID NO 892
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 892
ccccuagugu gucagcuauu                                             20

<210> SEQ ID NO 893
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893
cccuagugug ucagcuauuu                                             20

<210> SEQ ID NO 894
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 894
ccuagugugu cagcuauuuc                                             20
```

```
<210> SEQ ID NO 895
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 895
cgcaauucag gucccucccg                                                   20

<210> SEQ ID NO 896
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 896
uucuccucgc gcuguccacg                                                   20

<210> SEQ ID NO 897
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 897
ucuccucgcg cuguccacgc                                                   20

<210> SEQ ID NO 898
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 898
acaaagucaa acuagugccc                                                   20

<210> SEQ ID NO 899
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 899
ucaaacuagu gccccagaag                                                   20

<210> SEQ ID NO 900
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 900
caaacuagug ccccagaagg                                                      20

<210> SEQ ID NO 901
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 901
cuagugcccc agaaggcggg                                                      20

<210> SEQ ID NO 902
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 902
ggacgagucg ccuuaacaac                                                      20

<210> SEQ ID NO 903
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 903
cagagcgucu gccacagcuc                                                      20

<210> SEQ ID NO 904
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 904
cgucugccac agcucccgaa                                                      20

<210> SEQ ID NO 905
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 905
gucugccaca gcucccgaac                                                      20

<210> SEQ ID NO 906
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 906
cugccacagc ucccgaacag                                                 20

<210> SEQ ID NO 907
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 907
ugccacagcu cccgaacagg                                                 20

<210> SEQ ID NO 908
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908
acagcucccg aacaggaggg                                                 20

<210> SEQ ID NO 909
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 909
cagcucccga acaggaggga                                                 20

<210> SEQ ID NO 910
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910
agcucccgaa caggagggau                                                 20

<210> SEQ ID NO 911
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 911
gcucccgaac aggagggaug                                                 20
```

```
<210> SEQ ID NO 912
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 912
guggcuuuuc cugccaaucc                                                    20

<210> SEQ ID NO 913
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 913
gcugcacagu ggcguacggc                                                    20

<210> SEQ ID NO 914
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 914
cggcauggau ccaccaaucu                                                    20

<210> SEQ ID NO 915
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 915
aucucagggu cugguuccug                                                    20

<210> SEQ ID NO 916
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 916
ccugacgaac uucaaucucc                                                    20

<210> SEQ ID NO 917
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 917
gcaggggtga ggggucggc                                                   20

<210> SEQ ID NO 918
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 918
ucccggagaa gcaggggtga                                                  20

<210> SEQ ID NO 919
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 919
aucccggaga agcaggggtg                                                  20

<210> SEQ ID NO 920
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
caucccggag aagcaggggu                                                  20

<210> SEQ ID NO 921
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 921
gucaucccgg agaagcaggg                                                  20

<210> SEQ ID NO 922
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 922
acuagucauc ccggagaagc                                                  20

<210> SEQ ID NO 923
<211> LENGTH: 20

-continued

<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 923
gacuagucau cccggagaag                                            20

<210> SEQ ID NO 924
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 924
agggcagacu agucaucccg                                            20

<210> SEQ ID NO 925
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 925
gaagggcaga cuagucaucc                                            20

<210> SEQ ID NO 926
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 926
agaagggcag acuagucauc                                            20

<210> SEQ ID NO 927
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 927
guccgaacuc ggggacggag                                            20

<210> SEQ ID NO 928
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928 ggggguccgaa cucggggacg                                              20

<210> SEQ ID NO 929
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 929 gcggggguccg aacucgggga                                              20

<210> SEQ ID NO 930
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 930
ugcggggucc gaacucgggg                                               20

<210> SEQ ID NO 931
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931
ggaaugcggg guccgaacuc                                               20

<210> SEQ ID NO 932
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 932
cggaaugcgg gguccgaacu                                               20

<210> SEQ ID NO 933
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
gcggaaugcg ggguccgaac                                               20

<210> SEQ ID NO 934
<211> LENGTH: 20
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 934
ccacgagcgg aaugcggggu                                               20

<210> SEQ ID NO 935
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 935
ggaccuccac gagcggaaug                                               20

<210> SEQ ID NO 936
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 936
cggaccucca cgagcggaau                                               20

<210> SEQ ID NO 937
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 937
gagggccgga ccuccacgag                                               20

<210> SEQ ID NO 938
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 938
ugagggccgg accuccacga                                               20

<210> SEQ ID NO 939
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 939
ggggugaggg ccggaccucc                                               20

<210> SEQ ID NO 940
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 940
uggccaagca ggggugaggg                                           20

<210> SEQ ID NO 941
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 941
ggcuguggcc aagcaggggu                                           20

<210> SEQ ID NO 942
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 942
ggggcugugg ccaagcaggg                                           20

<210> SEQ ID NO 943
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 943
acuaggggcu guggccaagc                                           20

<210> SEQ ID NO 944
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 944
cacuaggggc uguggccaag                                           20

<210> SEQ ID NO 945
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 945
```
cccgaaauag cugacacacu                                                   20

<210> SEQ ID NO 946
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 946
ccccgaaaua gcugacacac                                                   20

<210> SEQ ID NO 947
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 947
gagggaccug aauugcgucc                                                   20

<210> SEQ ID NO 948
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 948
gcguguccag cgggagggac                                                   20

<210> SEQ ID NO 949
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 949
ggagccgcgu guccagcggg                                                   20

<210> SEQ ID NO 950
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 950
gggagccgcg uguccagcgg                                                   20

<210> SEQ ID NO 951
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 951
gugggagccg cguguccagc                                              20

<210> SEQ ID NO 952
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 952
ggugggagcc gcguguccag                                              20

<210> SEQ ID NO 953
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 953
uggugggagc cgcgugucca                                              20

<210> SEQ ID NO 954
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 954
uggcggucgg gggugcuggu                                              20

<210> SEQ ID NO 955
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 955
auggcggucg ggggugcugg                                              20

<210> SEQ ID NO 956
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 956
gauggcgguc ggggugcug                                               20
```

```
<210> SEQ ID NO 957
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 957
agauggcggc gauggcgguc                                                    20

<210> SEQ ID NO 958
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 958
aagauggcgg cgauggcggu                                                    20

<210> SEQ ID NO 959
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 959
aaagauggcg gcgauggcgg                                                    20

<210> SEQ ID NO 960
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 960
cccggcgugg acagcgcgag                                                    20

<210> SEQ ID NO 961
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 961
aucccggcgu ggacagcgcg                                                    20

<210> SEQ ID NO 962
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 962
aaucccggcg uggacagcgc                                               20

<210> SEQ ID NO 963
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 963
ggaaucccgg cguggacagc                                               20

<210> SEQ ID NO 964
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 964
uaguaucaag gaaucccggc                                               20

<210> SEQ ID NO 965
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 965
gugauuggcu acuaguauca                                               20

<210> SEQ ID NO 966
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 966
ugugauuggc uacuaguauc                                               20

<210> SEQ ID NO 967
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 967
aggcgacucg ucccgccuuc                                               20

<210> SEQ ID NO 968
<211> LENGTH: 20
<212> TYPE: RNA
<213> ORGANISM: Artificial Sequence
```

<220> FEATURE:
<221> NAME/KEY: source
<223> OTHER INFORMATION: /note="Description of Artificial Sequence:
      Synthetic oligonucleotide"

<400> SEQUENCE: 968
aaggcgacuc gucccgccuu                                                20

<210> SEQ ID NO 969
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 969
acuccccauc ccuccuguuc                                                20

<210> SEQ ID NO 970
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 970
cacuccccau cccuccuguu                                                20

<210> SEQ ID NO 971
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 971
ccacucccca ucccuccugu                                                20

<210> SEQ ID NO 972
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 972
ugugcagccc gcggauuggc                                                20

<210> SEQ ID NO 973
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 973
cugugcagcc cgcggauugg                                                20

<210> SEQ ID NO 974
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 974
cguacgccac ugugcagccc                                          20

<210> SEQ ID NO 975
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 975
ggaaccagac ccugagauug                                          20

<210> SEQ ID NO 976
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 976
aguucgucag gaaccagacc                                          20

<210> SEQ ID NO 977
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 977
cugggagauu gaaguucguc                                          20

<210> SEQ ID NO 978
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 978
ucugggagau ugaaguucgu                                          20

<210> SEQ ID NO 979
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 979
aggugugggu aaauaguggc                                        20

<210> SEQ ID NO 980
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 980
ggugugggaa aauaguggca                                        20

<210> SEQ ID NO 981
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 981 guguqggaaa auaguggcag                                        20

<210> SEQ ID NO 982
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 982
ugugggaaaa uaguggcagg                                        20

<210> SEQ ID NO 983
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 983
aauaguggca gggggcagca                                        20

<210> SEQ ID NO 984
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 984
gcagcauggu cgugcaguaa                                        20

<210> SEQ ID NO 985
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 985
cagcaugguc gugcaguaaa                                                    20

<210> SEQ ID NO 986
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 986
aucaaaacaa gaacagaaaa                                                    20

<210> SEQ ID NO 987
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 987
cguucaaacc ccauguucuc                                                    20

<210> SEQ ID NO 988
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 988
guucaaaccc cauguucuca                                                    20

<210> SEQ ID NO 989
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 989
cauguucuca gggauauucc                                                    20

<210> SEQ ID NO 990
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 990
auguucucag ggauauucca                                                    20
```

-continued

```
<210> SEQ ID NO 991
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 991
gauauuccag ggaguucuug                                                      20

<210> SEQ ID NO 992
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 992
agcacuaauu ccucacccccc                                                     20

<210> SEQ ID NO 993
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 993
auuccucacc cccuggccug                                                      20

<210> SEQ ID NO 994
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 994
ggccugaggu cuucauagau                                                      20

<210> SEQ ID NO 995
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 995
cugaggucuu cauagauugg                                                      20

<210> SEQ ID NO 996
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 996
cccuugccca ccuugaugua                                               20

<210> SEQ ID NO 997
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 997
ugcccaccuu gauguaaggc                                               20

<210> SEQ ID NO 998
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 998
auugaaaugc uccucucuga                                               20

<210> SEQ ID NO 999
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 999
uugaaaugcu ccucucugau                                               20

<210> SEQ ID NO 1000
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1000
augcuccucu cugaugggca                                               20

<210> SEQ ID NO 1001
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1001
ugcuccucuc ugaugggcaa                                               20

<210> SEQ ID NO 1002
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1002
gcuccucucu gaugggcaag                                                 20

<210> SEQ ID NO 1003
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1003
uacugcaccu ucuguacuac                                                 20

<210> SEQ ID NO 1004
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1004
agaaccugaa gcugcuucca                                                 20

<210> SEQ ID NO 1005
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1005
ugaagcugcu uccaaggcuc                                                 20

<210> SEQ ID NO 1006
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1006
cuuccaaggc ucuggacacu                                                 20

<210> SEQ ID NO 1007
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1007
```
gcucuggaca cuuggcacgc                                              20

<210> SEQ ID NO 1008
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1008
cucuggacac uuggcacgca                                              20

<210> SEQ ID NO 1009
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1009
cacuuggcac gcagggcuag                                              20

<210> SEQ ID NO 1010
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1010
cacgcagggc uagaggccaa                                              20

<210> SEQ ID NO 1011
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1011
agaggccaau gguauaugag                                              20

<210> SEQ ID NO 1012
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1012
aaugguauau gagcggccug                                              20

<210> SEQ ID NO 1013
<211> LENGTH: 20
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 1013
augguauaug agcggccugu                                                  20

<210> SEQ ID NO 1014
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1014
ugguauauga gcggccugug                                                  20

<210> SEQ ID NO 1015
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1015
uuaugaauag cagaacagac                                                  20

<210> SEQ ID NO 1016
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1016
ccacucauac cacaccuucu                                                  20

<210> SEQ ID NO 1017
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1017
ucgccagaaa cgcacacaga                                                  20

<210> SEQ ID NO 1018
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1018
agaaacgcac acagaugguu                                                  20

<210> SEQ ID NO 1019
```

-continued

<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1019
uuggccuuca cguaccguua                                                   20

<210> SEQ ID NO 1020
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1020
uggccuucac guaccguuau                                                   20

<210> SEQ ID NO 1021
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1021
gcugcuguaa gaagaaagac                                                   20

<210> SEQ ID NO 1022
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1022
uuuugauggu uuguguaag                                                    20

<210> SEQ ID NO 1023
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1023
uuuuucuguu cuuguuuuga                                                   20

<210> SEQ ID NO 1024
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1024
cugagaacau gggguuugaa                                               20

<210> SEQ ID NO 1025
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1025
ggaauauccc ugagaacaug                                               20

<210> SEQ ID NO 1026
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1026
uggaauaucc cugagaacau                                               20

<210> SEQ ID NO 1027
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1027
cuggaauauc ccugagaaca                                               20

<210> SEQ ID NO 1028
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1028
acucagccuc aagaacuccc                                               20

<210> SEQ ID NO 1029
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1029
agggggugag gaauuagugc                                               20

<210> SEQ ID NO 1030
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1030
agaccucagg ccaggggug                                                  20

<210> SEQ ID NO 1031
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1031
uaugaagacc ucaggccagg                                                 20

<210> SEQ ID NO 1032
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1032
cuaugaagac cucaggccag                                                 20

<210> SEQ ID NO 1033
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1033
ucuaugaaga ccucaggcca                                                 20

<210> SEQ ID NO 1034
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1034
aucuaugaag accucaggcc                                                 20

<210> SEQ ID NO 1035
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1035
caccaaucua ugaagaccuc                                                 20
```

-continued

```
<210> SEQ ID NO 1036
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1036
agggauuaua auuaauugca                                                    20

<210> SEQ ID NO 1037
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1037
aagggauuau aauuaauugc                                                    20

<210> SEQ ID NO 1038
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1038
ccuuacauca aggugggcaa                                                    20

<210> SEQ ID NO 1039
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1039
gccuuacauc aaggugggca                                                    20

<210> SEQ ID NO 1040
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1040
uuccugccuu acaucaaggu                                                    20

<210> SEQ ID NO 1041
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 1041
uuuccugccu uacaucaagg                                               20

<210> SEQ ID NO 1042
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1042
ugcuuuccug ccuuacauca                                               20

<210> SEQ ID NO 1043
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1043
auuccccuug cccaucagag                                               20

<210> SEQ ID NO 1044
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1044
agaaggugca guacaucuau                                               20

<210> SEQ ID NO 1045
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1045
cagaaggugc aguacaucua                                               20

<210> SEQ ID NO 1046
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1046
uucugcuccu guaguacaga                                               20

<210> SEQ ID NO 1047
<211> LENGTH: 20
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 1047
agagccuugg aagcagcuuc                                                   20

<210> SEQ ID NO 1048
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1048
gugccaagug uccagagccu                                                   20

<210> SEQ ID NO 1049
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1049
acaggccgcu cauauaccau                                                   20

<210> SEQ ID NO 1050
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1050
ucugcuauuc auaaccccac                                                   20

<210> SEQ ID NO 1051
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1051
caagaaggug ugguaugagu                                                   20

<210> SEQ ID NO 1052
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1052
ccaagaaggu gugguaugag                                                   20
```

```
<210> SEQ ID NO 1053
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1053
gcagcaauuc caagaaggug                                                20

<210> SEQ ID NO 1054
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1054
gcgaugcagc aauuccaaga                                                20

<210> SEQ ID NO 1055
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1055
aaaccaucug ugugcguuuc                                                20

<210> SEQ ID NO 1056
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1056
cagcccauaa cgguacguga                                                20

<210> SEQ ID NO 1057
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1057
cuucuuacag cagcccauaa                                                20

<210> SEQ ID NO 1058
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 1058
aaagcaguuc cuaccuuaau                                               20

<210> SEQ ID NO 1059
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1059
aagcaguucc uaccuuaaua                                               20

<210> SEQ ID NO 1060
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1060
uuccuaccuu aauagggaag                                               20

<210> SEQ ID NO 1061
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1061
uaccuuaaua gggaagagga                                               20

<210> SEQ ID NO 1062
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1062
accuuaauag ggaagaggau                                               20

<210> SEQ ID NO 1063
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1063
ggaaaccaug agaacauccc                                               20

<210> SEQ ID NO 1064
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1064
aucccaggag agugagucuc                                                  20

<210> SEQ ID NO 1065
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1065
caggagagug agucucugga                                                  20

<210> SEQ ID NO 1066
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1066
ucucuggacg gauaccugug                                                  20

<210> SEQ ID NO 1067
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1067
auccucuucc cuauuaaggu                                                  20

<210> SEQ ID NO 1068
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1068
ucccauccuc uucccuauua                                                  20

<210> SEQ ID NO 1069
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1069
acucuccugg gauguucuca                                                  20
```

-continued

<210> SEQ ID NO 1070
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1070
guccagagac ucacucuccu                                              20

<210> SEQ ID NO 1071
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1071
cguccagaga cucacucucc                                              20

<210> SEQ ID NO 1072
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1072
aagcacaguc ucaaaguagc                                              20

<210> SEQ ID NO 1073
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1073
aguacugugu ucaccuccac                                              20

<210> SEQ ID NO 1074
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1074
caccuccaca ggaaauucca                                              20

<210> SEQ ID NO 1075
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 1075
gaaauuccaa ggugcaauag                                              20

<210> SEQ ID NO 1076
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1076
uagcgguugu ugucaaucau                                              20

<210> SEQ ID NO 1077
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1077
ugucaaucau aggaucuguc                                              20

<210> SEQ ID NO 1078
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1078
ucacucugag ugagugucua                                              20

<210> SEQ ID NO 1079
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1079
cuuugagacu gugcuuuauc                                              20

<210> SEQ ID NO 1080
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1080
acaguacuac auggcuuugc                                              20

<210> SEQ ID NO 1081
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1081
gaggugaaca caguacuaca                                                    20

<210> SEQ ID NO 1082
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1082
caccuuggaa uuuccugugg                                                    20

<210> SEQ ID NO 1083
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1083
uugcaccuug gaauuuccug                                                    20

<210> SEQ ID NO 1084
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1084
caacaaccgc uauugcaccu                                                    20

<210> SEQ ID NO 1085
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1085
auaaaagaac cuaccucugu                                                    20

<210> SEQ ID NO 1086
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1086
```

```
uaaaagaacc uaccucuguu                                              20

<210> SEQ ID NO 1087
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1087
agaaccuacc ucuguuggga                                              20

<210> SEQ ID NO 1088
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1088
accucuguug ggauggcuga                                              20

<210> SEQ ID NO 1089
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1089
gggauggcug aaggugaaac                                              20

<210> SEQ ID NO 1090
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1090
ggauggcuga aggugaaaca                                              20

<210> SEQ ID NO 1091
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1091
ggcugaaggu gaaacagggc                                              20

<210> SEQ ID NO 1092
<211> LENGTH: 20
<212> TYPE: RNA
<213> ORGANISM: Artificial Sequence
<220> FEATURE:
<221> NAME/KEY: source
```

-continued

```
<223> OTHER INFORMATION: /note="Description of Artificial Sequence:
      Synthetic oligonucleotide"

<400> SEQUENCE: 1092
gcugaaggug aaacagggcu                                              20

<210> SEQ ID NO 1093
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1093
cugaagguga aacagggcug                                              20

<210> SEQ ID NO 1094
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1094
agggcugggg ugcagagagc                                              20

<210> SEQ ID NO 1095
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1095
gcuggggugc agagagcugg                                              20

<210> SEQ ID NO 1096
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1096
uugugcagcc guaccacaua                                              20

<210> SEQ ID NO 1097
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1097
ccacauaagg caucucaaac                                              20

<210> SEQ ID NO 1098
```

-continued

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1098
cacauaaggc aucucaaacu                                                20

<210> SEQ ID NO 1099
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1099
aacagaggua gguucuuuua                                                20

<210> SEQ ID NO 1100
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1100
ucagccaucc caacagaggu                                                20

<210> SEQ ID NO 1101
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1101
accuucagcc aucccaacag                                                20

<210> SEQ ID NO 1102
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1102
uugagaugcc uuauguggua                                                20

<210> SEQ ID NO 1103
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1103
```

```
ccaguuugag augccuuaug                                               20

<210> SEQ ID NO 1104
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1104
agagaguggu ucuuuaccuc                                               20

<210> SEQ ID NO 1105
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1105
gagagugguu cuuuaccuca                                               20

<210> SEQ ID NO 1106
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1106
gguucuuuac cucaggguca                                               20

<210> SEQ ID NO 1107
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1107
gucacggucc uucucccuac                                               20

<210> SEQ ID NO 1108
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1108
gguccuucuc ccuacaggcu                                               20

<210> SEQ ID NO 1109
<211> LENGTH: 20
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 1109
ucggaccuca uuguacagcu                                                    20

<210> SEQ ID NO 1110
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1110
gaccucauug uacagcuugg                                                    20

<210> SEQ ID NO 1111
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1111
guacagcuug gaggaagaga                                                    20

<210> SEQ ID NO 1112
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1112
uacagcuugg aggaagagau                                                    20

<210> SEQ ID NO 1113
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1113
ggaagagaug ggagccagaa                                                    20

<210> SEQ ID NO 1114
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1114
cagaaaggaa guguacuccc                                                    20
```

```
<210> SEQ ID NO 1115
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1115
agaaaggaag uguacucccc                                                  20

<210> SEQ ID NO 1116
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1116
gaaaggaagu guacuccccg                                                  20

<210> SEQ ID NO 1117
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1117
cacaccauca ucugcacagc                                                  20

<210> SEQ ID NO 1118
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1118
ggagaaggac cgugacccug                                                  20

<210> SEQ ID NO 1119
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1119
gguccgagcc uguagggaga                                                  20

<210> SEQ ID NO 1120
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 1120
caaugagguc cgagccugua                                               20

<210> SEQ ID NO 1121
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1121
acaaugaggu ccgagccugu                                               20

<210> SEQ ID NO 1122
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1122
uuccuccaag cuguacaaug                                               20

<210> SEQ ID NO 1123
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1123
cggggaguac acuuccuuuc                                               20

<210> SEQ ID NO 1124
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1124
ugauggugug agcaucccg                                                20

<210> SEQ ID NO 1125
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1125
augauggugu gagcaucccc                                               20

<210> SEQ ID NO 1126
<211> LENGTH: 20
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 1126
gaugauggug ugagcauccc                                              20

<210> SEQ ID NO 1127
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1127
cucuccugcu gugcagauga                                              20

<210> SEQ ID NO 1128
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1128
ccaaccuggg ggcaccuuuu                                              20

<210> SEQ ID NO 1129
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1129
gggcaccuuu uaggaagugc                                              20

<210> SEQ ID NO 1130
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1130
ggcaccuuuu aggaagugcu                                              20

<210> SEQ ID NO 1131
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1131
ggaagugcug ggcuccaucc                                              20
```

```
<210> SEQ ID NO 1132
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1132
ugggcuccau ccaggcacuc                                                      20

<210> SEQ ID NO 1133
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1133
acaaugaugu cugcuuucuc                                                      20

<210> SEQ ID NO 1134
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1134
ccucaugucu gaugagacua                                                      20

<210> SEQ ID NO 1135
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1135
cugaugagac uacggucacu                                                      20

<210> SEQ ID NO 1136
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1136
agccugaaac agagacaaua                                                      20

<210> SEQ ID NO 1137
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 1137
uaaaaggugc ccccagguug                                              20

<210> SEQ ID NO 1138
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1138
cuaaaaggug ccccagguu                                               20

<210> SEQ ID NO 1139
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1139
ccuaaaaggu gcccccaggu                                              20

<210> SEQ ID NO 1140
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1140
acuuccuaaa aggugccccc                                              20

<210> SEQ ID NO 1141
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1141
ggagcccagc acuuccuaaa                                              20

<210> SEQ ID NO 1142
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1142
uugucgccug agugccugga                                              20

<210> SEQ ID NO 1143
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1143
ugaauugucg ccugagugcc                                              20

<210> SEQ ID NO 1144
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1144
aucauuguca gugagcuucu                                              20

<210> SEQ ID NO 1145
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1145
caucauuguc agugagcuuc                                              20

<210> SEQ ID NO 1146
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1146
aucagacaug agggaauggg                                              20

<210> SEQ ID NO 1147
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1147
cucaucagac augagggaau                                              20

<210> SEQ ID NO 1148
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1148
ucucaucaga caugagggaa                                              20
```

```
<210> SEQ ID NO 1149
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1149
cguagucuca ucagacauga                                              20

<210> SEQ ID NO 1150
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1150
ccguagucuc aucagacaug                                              20

<210> SEQ ID NO 1151
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1151
aacuggcagu uugaagaaug                                              20

<210> SEQ ID NO 1152
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1152
gaacuggcag uuugaagaau                                              20

<210> SEQ ID NO 1153
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1153
agaacuggca guuugaagaa                                              20

<210> SEQ ID NO 1154
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

```
          Synthetic oligonucleotide"

<400> SEQUENCE: 1154
ucuguuucag gcuagagaac                                          20

<210> SEQ ID NO 1155
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1155
gguugcuacu cacgucacca                                          20

<210> SEQ ID NO 1156
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1156
acucacguca ccacggcauu                                          20

<210> SEQ ID NO 1157
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1157
cucacgucac cacggcauuu                                          20

<210> SEQ ID NO 1158
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1158
cagcauacag cuuuauccgc                                          20

<210> SEQ ID NO 1159
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1159
auacagcuuu auccgccggu                                          20

<210> SEQ ID NO 1160
<211> LENGTH: 20
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1160
uauccgccgg ucggccugcu                                                 20

<210> SEQ ID NO 1161
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1161
cggccugcuu ggcugcccgc                                                 20

<210> SEQ ID NO 1162
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1162
ggccugcuug gcugcccgca                                                 20

<210> SEQ ID NO 1163
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1163
cccgcaggga agcguucacc                                                 20

<210> SEQ ID NO 1164
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1164
ccgcagggaa gcguucacca                                                 20

<210> SEQ ID NO 1165
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1165
```
cgcagggaag cguucaccag                                              20

<210> SEQ ID NO 1166
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1166
aucaguaccc uaagaaagaa                                              20

<210> SEQ ID NO 1167
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1167
ucaguacccu aagaaagaaa                                              20

<210> SEQ ID NO 1168
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1168
ggagaaaaac ccaaaugccg                                              20

<210> SEQ ID NO 1169
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1169
gcggauaaag cuguaugcug                                              20

<210> SEQ ID NO 1170
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1170
cagccaagca ggccgaccgg                                              20

<210> SEQ ID NO 1171
<211> LENGTH: 20
<212> TYPE: RNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 1171
gggcagccaa gcaggccgac                                              20

<210> SEQ ID NO 1172
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1172
uucccugcgg gcagccaagc                                              20

<210> SEQ ID NO 1173
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1173
ccuggugaac gcuucccugc                                              20

<210> SEQ ID NO 1174
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1174
cccuggugaa cgcuucccug                                              20

<210> SEQ ID NO 1175
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1175
gggagcagga cggggacccc                                              20

<210> SEQ ID NO 1176
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1176
auggugcugg gagcaggacg                                              20

<210> SEQ ID NO 1177

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1177
gauggugcug ggagcaggac                                               20

<210> SEQ ID NO 1178
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1178
ugauggugcu gggagcagga                                               20

<210> SEQ ID NO 1179
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1179
guacugaugg ugcugggagc                                               20

<210> SEQ ID NO 1180
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1180 cuuagggguac ugauggugcu                                              20

<210> SEQ ID NO 1181
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1181
ucuuagggua cugaugggugc                                              20

<210> SEQ ID NO 1182
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1182
```
uuucuuucuu aggguacuga                                              20

<210> SEQ ID NO 1183
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1183 auugaggggga aagcacucac                                             20

<210> SEQ ID NO 1184
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1184
ggaaagcacu cacuggacau                                              20

<210> SEQ ID NO 1185
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1185
uugguauccu ucuccucuuc                                              20

<210> SEQ ID NO 1186
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1186
ccuucuccuc uucugguacu                                              20

<210> SEQ ID NO 1187
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1187
gucuagcaga cauuuauaga                                              20

<210> SEQ ID NO 1188
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1188
gcagacauuu auagauggcc                                              20

<210> SEQ ID NO 1189
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1189
gacauuuaua gauggccugg                                              20

<210> SEQ ID NO 1190
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1190
acauuuauag auggccugga                                              20

<210> SEQ ID NO 1191
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1191
uuuauagaug gccuggaggg                                              20

<210> SEQ ID NO 1192
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1192
ccgaguacca gaagaggaga                                              20

<210> SEQ ID NO 1193
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1193
gcuagaccga guaccagaag                                              20
```

```
<210> SEQ ID NO 1194
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1194
gggcaccaca caguaccugc                                                   20

<210> SEQ ID NO 1195
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1195
cugguacuga gaguauuuga                                                   20

<210> SEQ ID NO 1196
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1196
ugguacugag aguauuugau                                                   20

<210> SEQ ID NO 1197
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1197
gguacugaga guauuugaug                                                   20

<210> SEQ ID NO 1198
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1198
gauuccagau uguccaucag                                                   20

<210> SEQ ID NO 1199
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1199
ccaucagugg cugaugaaug                                           20

<210> SEQ ID NO 1200
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1200
guggcugaug aaugaggaaa                                           20

<210> SEQ ID NO 1201
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1201
cagguacugu guggugccca                                           20

<210> SEQ ID NO 1202
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1202
gcagguacug ugguggccc                                            20

<210> SEQ ID NO 1203
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1203
caguaccagc agguacugug                                           20

<210> SEQ ID NO 1204
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1204
caaauacucu caguaccagc                                           20

<210> SEQ ID NO 1205
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 1205
gacauaugaa guguuugaaa                                                    20

<210> SEQ ID NO 1206
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1206
ucagccacug auggacaauc                                                    20

<210> SEQ ID NO 1207
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1207
ccucauucau cagccacuga                                                    20

<210> SEQ ID NO 1208
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1208
cacuccagac ccaccugaag                                                    20

<210> SEQ ID NO 1209
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1209
acuccagacc caccugaagc                                                    20

<210> SEQ ID NO 1210
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1210
cuccagaccc accugaagcg                                                    20
```

```
<210> SEQ ID NO 1211
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1211
cagauagucu ucauagcccu                                                    20

<210> SEQ ID NO 1212
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1212
gcccuuggca aagaguucau                                                    20

<210> SEQ ID NO 1213
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1213
gcaaagaguu cauaggcauu                                                    20

<210> SEQ ID NO 1214
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1214
aagaguucau aggcauuagg                                                    20

<210> SEQ ID NO 1215
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1215
aguucauagg cauuaggugg                                                    20

<210> SEQ ID NO 1216
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1216
cauaggcauu agguggagga                                               20

<210> SEQ ID NO 1217
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1217
cauuaggugg aggacgguuc                                               20

<210> SEQ ID NO 1218
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1218
gguucuggcu uaaguauucc                                               20

<210> SEQ ID NO 1219
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1219
ggcuuaagua uuccagguau                                               20

<210> SEQ ID NO 1220
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1220
uuaaguauuc cagguauugg                                               20

<210> SEQ ID NO 1221
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1221
guauuccagg uauuggaggu                                               20

<210> SEQ ID NO 1222
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1222
agcagaacuc cuucucugag                                              20

<210> SEQ ID NO 1223
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1223
agaacuccuu cucugagugg                                              20

<210> SEQ ID NO 1224
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1224
cuccuucucu gaguggguggu                                             20

<210> SEQ ID NO 1225
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1225
guccccgcuu caggugggguc                                             20

<210> SEQ ID NO 1226
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1226
cugcaguccc cgcuucaggu                                              20

<210> SEQ ID NO 1227
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1227
ucugcagucc ccgcuucagg                                              20
```

<210> SEQ ID NO 1228
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1228
cuaucugcag uccccgcuuc                                            20

<210> SEQ ID NO 1229
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1229
gccuaugaac ucuuugccaa                                            20

<210> SEQ ID NO 1230
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1230
ugccuaugaa cucuuugcca                                            20

<210> SEQ ID NO 1231
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1231
cugcuccuac cuccaauacc                                            20

<210> SEQ ID NO 1232
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1232
caccaaccac cacucagaga                                            20

<210> SEQ ID NO 1233
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 1233
gaggugcagu ucaucaucac                                               20

<210> SEQ ID NO 1234
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1234
cugacuuuuc ucacaguugg                                               20

<210> SEQ ID NO 1235
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1235
ggucugacuu uucucacagu                                               20

<210> SEQ ID NO 1236
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1236
cccuccuacc acucaccuug                                               20

<210> SEQ ID NO 1237
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1237
uaccacucac cuugaggagc                                               20

<210> SEQ ID NO 1238
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1238
ggagccggaa gaugagccuc                                               20

<210> SEQ ID NO 1239
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1239
uggugcaucu uagaaagaac                                                  20

<210> SEQ ID NO 1240
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1240
aacaggaaau cccuucuuau                                                  20

<210> SEQ ID NO 1241
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1241
gaaaucccuu cuuauugguc                                                  20

<210> SEQ ID NO 1242
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1242
auuggucagg aaaaugcuag                                                  20

<210> SEQ ID NO 1243
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1243
uuggucagga aaaugcuagu                                                  20

<210> SEQ ID NO 1244
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1244
```

-continued uggucaggaa aaugcuagug                                          20

<210> SEQ ID NO 1245
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1245
gaaaaugcua gugggagaa                                           20

<210> SEQ ID NO 1246
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1246
ggggagaaug gcugcuuuga                                          20

<210> SEQ ID NO 1247
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1247
gggagaaugg cugcuuugau                                          20

<210> SEQ ID NO 1248
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1248
cgaucaauga caugauuaga                                          20

<210> SEQ ID NO 1249
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1249
gaucaaugac augauuagau                                          20

<210> SEQ ID NO 1250
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1250
caaugacaug auuagauggg                                           20

<210> SEQ ID NO 1251
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1251
ccaauuucaa gagcuacaug                                           20

<210> SEQ ID NO 1252
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1252
ccucaaggug agugguagga                                           20

<210> SEQ ID NO 1253
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1253
uccucaaggu gagugguagg                                           20

<210> SEQ ID NO 1254
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1254
ggcuccucaa ggugaguggu                                           20

<210> SEQ ID NO 1255
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1255
uuccggcucc ucaaggugag                                           20

<210> SEQ ID NO 1256

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1256
gcucaucuuc cggcuccuca                                              20

<210> SEQ ID NO 1257
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1257
ugcaccagag gcucaucuuc                                              20

<210> SEQ ID NO 1258
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1258
uucuuucuaa gaugcaccag                                              20

<210> SEQ ID NO 1259
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1259
auuuuccuga ccaauaagaa                                              20

<210> SEQ ID NO 1260
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1260 cauuuccug accaauaaga                                               20

<210> SEQ ID NO 1261
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonuceotide"

<400> SEQUENCE: 1261
```
ugucauugau cgcuggcuug                                              20

<210> SEQ ID NO 1262
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1262
augucauuga ucgcuggcuu                                              20

<210> SEQ ID NO 1263
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1263
caugucauug aucgcuggcu                                              20

<210> SEQ ID NO 1264
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1264
cuaaucaugu cauugaucgc                                              20

<210> SEQ ID NO 1265
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1265
ucauguagcu cuugaaauug                                              20

<210> SEQ ID NO 1266
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1266
cucauguagc ucuugaaauu                                              20

<210> SEQ ID NO 1267
<211> LENGTH: 20
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 1267
ccucauguag cucuugaaau                                                    20

<210> SEQ ID NO 1268
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1268
uacuauaguc acacaaaguc                                                    20

<210> SEQ ID NO 1269
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1269
uauaguaaga ggauugcagu                                                    20

<210> SEQ ID NO 1270
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1270
cuauaguaag aggauugcag                                                    20

<210> SEQ ID NO 1271
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1271
cuuuguguga cuauaguaag                                                    20

<210> SEQ ID NO 1272
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1272
ugaacaggug gcacaacuuc                                                    20

```
<210> SEQ ID NO 1273
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1273
ucuguauuug acugaacagg                                                    20

<210> SEQ ID NO 1274
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1274
uacuccucug uguguguagu                                                    20

<210> SEQ ID NO 1275
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1275
ucucaauuau aucaucucuc                                                    20

<210> SEQ ID NO 1276
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1276
auaucaucuc ucagguccuc                                                    20

<210> SEQ ID NO 1277
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1277
cagguccucu ggugccacca                                                    20

<210> SEQ ID NO 1278
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 1278
agguccucug gugccaccaa                                              20

<210> SEQ ID NO 1279
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1279
gggaggagaa aacguggaug                                              20

<210> SEQ ID NO 1280
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1280 acaguggga ggagaaaacg                                               20

<210> SEQ ID NO 1281
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1281
cacagaggag uacagugggg                                              20

<210> SEQ ID NO 1282
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1282
acacacagag gaguacagug                                              20

<210> SEQ ID NO 1283
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1283
cacacacaga ggaguacagu                                              20

<210> SEQ ID NO 1284
<211> LENGTH: 20
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 1284
acacacacag aggaguacag                                               20

<210> SEQ ID NO 1285
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1285
ugcaccaacu acacacacag                                               20

<210> SEQ ID NO 1286
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1286
gguacccuug guggcaccag                                               20

<210> SEQ ID NO 1287
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1287
cuggaugcgg guacccuugg                                               20

<210> SEQ ID NO 1288
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1288
guucuggaug cggguacccu                                               20

<210> SEQ ID NO 1289
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1289
ucaugugcag uucuggaugc                                               20
```

<210> SEQ ID NO 1290
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1290
uucaugugca guucuggaug                                             20

<210> SEQ ID NO 1291
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1291
ugacuguuca ugugcaguuc                                             20

<210> SEQ ID NO 1292
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1292 ggagcccuc agcuauacca                                              20

<210> SEQ ID NO 1293
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1293
gcuauaccau ggaagaguga                                             20

<210> SEQ ID NO 1294
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1294
uggaagagug auggccagug                                             20

<210> SEQ ID NO 1295
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 1295
agugauggcc aguguggaug                                        20

<210> SEQ ID NO 1296
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1296
auggccagug uggauguggu                                        20

<210> SEQ ID NO 1297
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1297
gaugugguug gucaaaacuc                                        20

<210> SEQ ID NO 1298
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1298
gguuggucaa aacucuggcc                                        20

<210> SEQ ID NO 1299
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1299
ggucaaaacu cuggccaggu                                        20

<210> SEQ ID NO 1300
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1300
ugguguuauc uuccugauua                                        20

<210> SEQ ID NO 1301
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1301
gguguuaucu uccugauuaa                                                 20

<210> SEQ ID NO 1302
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1302
guguuaucuu ccugauuaag                                                 20

<210> SEQ ID NO 1303
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1303
cuuccugauu aaggggcagc                                                 20

<210> SEQ ID NO 1304
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1304
uuaaggggca gcaggaaagc                                                 20

<210> SEQ ID NO 1305
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1305
aaaauucagc uccuguaaca                                                 20

<210> SEQ ID NO 1306
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1306
ucagcuccug uaacauggcc                                                 20
```

```
<210> SEQ ID NO 1307
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1307
uccuguaaca uggccuggaa                                                   20

<210> SEQ ID NO 1308
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1308
ggccuggaac ggagaugaag                                                   20

<210> SEQ ID NO 1309
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1309
ucuuccaugg uauagcugag                                                   20

<210> SEQ ID NO 1310
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1310
cucuuccaug guauagcuga                                                   20

<210> SEQ ID NO 1311
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1311
acucuuccau gguauagcug                                                   20

<210> SEQ ID NO 1312
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 1312
cacuggccau cacucuucca					20

<210> SEQ ID NO 1313
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1313
uugaccaacc acauccacac					20

<210> SEQ ID NO 1314
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1314
ucaggaagau aacaccaacc					20

<210> SEQ ID NO 1315
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1315 uuccugcug ccccuuaauc					20

<210> SEQ ID NO 1316
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1316
cugaauuuug gugcauauuu					20

<210> SEQ ID NO 1317
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1317
gcugaauuuu ggugcauauu					20

<210> SEQ ID NO 1318
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1318
auguuacagg agcugaauuu                                              20

<210> SEQ ID NO 1319
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1319
uccguuccag gccauguuac                                              20

<210> SEQ ID NO 1320
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1320
gucaaacagu cuuaccgccu                                              20

<210> SEQ ID NO 1321
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1321
aucuucucca cuuuugaguc                                              20

<210> SEQ ID NO 1322
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1322
uuugagucug gacgaaucca                                              20

<210> SEQ ID NO 1323
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1323
```

```
gauucgcagg aacuccgagg                                               20
```

<210> SEQ ID NO 1324
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1324

```
gaagauucgc aggaacuccg                                               20
```

<210> SEQ ID NO 1325
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1325

```
caaaagugga gaagauucgc                                               20
```

<210> SEQ ID NO 1326
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1326

```
gauucgucca gacucaaaag                                               20
```

<210> SEQ ID NO 1327
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1327

```
uugugggaaa gcuuucucca                                               20
```

<210> SEQ ID NO 1328
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1328

```
gacuggaaua cgcuaauugu                                               20
```

<210> SEQ ID NO 1329
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1329
agacuggaau acgcuaauug                                                    20

<210> SEQ ID NO 1330
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1330
uugggugggg gagugcagac                                                    20

<210> SEQ ID NO 1331
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1331
uaccccuucc ugacagcagu                                                    20

<210> SEQ ID NO 1332
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1332
gcaguagguc ugaucguguc                                                    20

<210> SEQ ID NO 1333
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1333
caguaggucu gaucgugucu                                                    20

<210> SEQ ID NO 1334
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1334
aguaggucug aucgugucug                                                    20

<210> SEQ ID NO 1335

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1335
gucugaucgu gucuggggac                                               20

<210> SEQ ID NO 1336
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1336
ucugaucgug ucugggacc                                                20

<210> SEQ ID NO 1337
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1337
ggaccgggcc gauucuuagc                                               20

<210> SEQ ID NO 1338
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1338
augaacuccc ucuugaaacg                                               20

<210> SEQ ID NO 1339
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1339
acucccucuu gaaacgcgga                                               20

<210> SEQ ID NO 1340
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1340
```
uugaaacgcg gauggaagac                  20

<210> SEQ ID NO 1341
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1341
gauggaagac aggcaugcag                  20

<210> SEQ ID NO 1342
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1342
acugcuguca ggaaggggua                  20

<210> SEQ ID NO 1343
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1343
uacugcuguc aggaaggggu                  20

<210> SEQ ID NO 1344
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1344
gaccuacugc ugucaggaag                  20

<210> SEQ ID NO 1345
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1345
agaccuacug cugucaggaa                  20

<210> SEQ ID NO 1346
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1346
cagaccuacu gcugucagga                                               20

<210> SEQ ID NO 1347
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1347
cgaucagacc uacugcuguc                                               20

<210> SEQ ID NO 1348
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1348
gaaccugcua agaaucggcc                                               20

<210> SEQ ID NO 1349
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1349
uucaggaacc ugcuaagaau                                               20

<210> SEQ ID NO 1350
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1350
uuucaagagg gaguucauuc                                               20

<210> SEQ ID NO 1351
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1351
cuuccauccg cguuucaaga                                               20
```

-continued

<210> SEQ ID NO 1352
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1352
ucuuccaucc gcguuucaag                                                20

<210> SEQ ID NO 1353
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1353
cccccucacc ccugcuucuc                                                20

<210> SEQ ID NO 1354
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1354
ccccucaccc cugcuucucc                                                20

<210> SEQ ID NO 1355
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1355
cccuucuccg uccccgaguu                                                20

<210> SEQ ID NO 1356
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1356
cggaccccgc auuccgcucg                                                20

<210> SEQ ID NO 1357
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 1357
accccgcauu ccgcucgugg                                           20

<210> SEQ ID NO 1358
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1358
gcauuccgcu cguggagguc                                           20

<210> SEQ ID NO 1359
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1359
guccggcccu cacccrugcu                                           20

<210> SEQ ID NO 1360
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1360
cccuagugug ucagcuauuu                                           20

<210> SEQ ID NO 1361
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1361
ccuagugugu cagcuauuuc                                           20

<210> SEQ ID NO 1362
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1362
cuaguguguc agcuauuucg                                           20

<210> SEQ ID NO 1363
<211> LENGTH: 20
<212> TYPE: RNA
<213> ORGANISM: Artificial Sequence
```

<220> FEATURE:
<221> NAME/KEY: source
<223> OTHER INFORMATION: /note="Description of Artificial Sequence:
      Synthetic oligonucleotide"

<400> SEQUENCE: 1363
cuauuucggg gacgcaauuc                                              20

<210> SEQ ID NO 1364
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1364
gcaauucagg ucccucccgc                                              20

<210> SEQ ID NO 1365
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1365
ggucccuccc gcuggacacg                                              20

<210> SEQ ID NO 1366
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1366
ucuccucgcg cuguccacgc                                              20

<210> SEQ ID NO 1367
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1367
cuccucgcgc uguccacgcc                                              20

<210> SEQ ID NO 1368
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1368
agucaaacua gugccccaga                                              20

```
<210> SEQ ID NO 1369
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1369
caaacuagug ccccagaagg                                                     20

<210> SEQ ID NO 1370
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1370
aaacuagugc cccagaaggc                                                     20

<210> SEQ ID NO 1371
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1371
gucugccaca gcucccgaac                                                     20

<210> SEQ ID NO 1372
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1372
ugccacagcu cccgaacagg                                                     20

<210> SEQ ID NO 1373
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1373
gccacagcuc ccgaacagga                                                     20

<210> SEQ ID NO 1374
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 1374
cagcucccga acaggaggga					20

<210> SEQ ID NO 1375
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1375
agcucccgaa caggagggau					20

<210> SEQ ID NO 1376
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1376
gcucccgaac aggagggaug					20

<210> SEQ ID NO 1377
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1377
cgaacaggag ggaugggag					20

<210> SEQ ID NO 1378
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1378
uggcuuuucc ugccaauccg					20

<210> SEQ ID NO 1379
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1379
ggcuuuuccu gccaauccgc					20

<210> SEQ ID NO 1380
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1380
ccaauccgcg ggcugcacag                                              20

<210> SEQ ID NO 1381
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1381
gcgggcugca caguggcgua                                              20

<210> SEQ ID NO 1382
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1382
cugcacagug gcguacggca                                              20

<210> SEQ ID NO 1383
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1383
ggcauggauc caccaaucuc                                              20

<210> SEQ ID NO 1384
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1384
gcauggaucc accaaucuca                                              20

<210> SEQ ID NO 1385
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1385
gauccaccaa ucucaggguc                                              20
```

```
<210> SEQ ID NO 1386
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1386
cagggguGAG ggggucggcu                                                  20

<210> SEQ ID NO 1387
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1387
agaagcaggg gugagggggu                                                  20

<210> SEQ ID NO 1388
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1388
ccggagaagc agggguGAGg                                                  20

<210> SEQ ID NO 1389
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1389
cccggagaag cagggguGAG                                                  20

<210> SEQ ID NO 1390
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1390
ucccggagaa gcaggggUGA                                                  20

<210> SEQ ID NO 1391
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 1391
aucccggaga agcagggggug                                          20

<210> SEQ ID NO 1392
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1392
uagucauccc ggagaagcag                                           20

<210> SEQ ID NO 1393
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1393
cuagucaucc cggagaagca                                           20

<210> SEQ ID NO 1394
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1394
acuagucauc ccggagaagc                                           20

<210> SEQ ID NO 1395
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1395
gaagggcaga cuagucaucc                                           20

<210> SEQ ID NO 1396
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1396
ccgaacucgg ggacggagaa                                           20

<210> SEQ ID NO 1397
<211> LENGTH: 20

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1397
uccgaacucg gggacggaga                                                20

<210> SEQ ID NO 1398
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1398
gcgggguccg aacucgggga                                                20

<210> SEQ ID NO 1399
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1399
gaaugcgggg uccgaacucg                                                20

<210> SEQ ID NO 1400
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1400
ggaaugcggg guccgaacuc                                                20

<210> SEQ ID NO 1401
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1401
cggaaugcgg gguccgaacu                                                20

<210> SEQ ID NO 1402
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1402
```

```
accuccacga gcggaaugcg                                               20

<210> SEQ ID NO 1403
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1403
gaccuccacg agcggaaugc                                               20

<210> SEQ ID NO 1404
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1404
ggaccuccac gagcggaaug                                               20

<210> SEQ ID NO 1405
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1405
gagggccgga ccuccacgag                                               20

<210> SEQ ID NO 1406
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1406
ggccaagcag gggugagggc                                               20

<210> SEQ ID NO 1407
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1407
cuguggccaa gcagggguga                                               20

<210> SEQ ID NO 1408
<211> LENGTH: 20
<212> TYPE: RNA
<213> ORGANISM: Artificial Sequence
<220> FEATURE:
<221> NAME/KEY: source
```

<223> OTHER INFORMATION: /note="Description of Artificial Sequence:
       Synthetic oligonucleotide"

<400> SEQUENCE: 1408
gcuguggcca agcagggguG                                                   20

<210> SEQ ID NO 1409
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 1409
uaggggcugu ggccaagcag                                                   20

<210> SEQ ID NO 1410
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 1410
cuaggggcug uggccaagca                                                   20

<210> SEQ ID NO 1411
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 1411
acuaggggcu guggccaagc                                                   20

<210> SEQ ID NO 1412
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 1412
agcugacaca cuaggggcug                                                   20

<210> SEQ ID NO 1413
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 1413
cgaaauagcu gacacacuag                                                   20

<210> SEQ ID NO 1414

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1414
ccgaaauagc ugacacacua                                                   20

<210> SEQ ID NO 1415
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1415
cccgaaauag cugacacacu                                                   20

<210> SEQ ID NO 1416
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1416
gagccgcgug uccagcggga                                                   20

<210> SEQ ID NO 1417
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1417
ggagccgcgu guccagcggg                                                   20

<210> SEQ ID NO 1418
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1418
gugggagccg cguguccagc                                                   20

<210> SEQ ID NO 1419
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1419
```

```
ggugggagcc gcguguccag                                              20

<210> SEQ ID NO 1420
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1420
uggcggucgg gggugcuggu                                              20

<210> SEQ ID NO 1421
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1421
auggcggucg ggggugcugg                                              20

<210> SEQ ID NO 1422
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1422
gcgauggcgg ucgggggugc                                              20

<210> SEQ ID NO 1423
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1423
auggcggcga uggcggucgg                                              20

<210> SEQ ID NO 1424
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1424
gauggcggcg auggcggucg                                              20

<210> SEQ ID NO 1425
<211> LENGTH: 20
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 1425
agauggcggc gauggcgguc                                              20

<210> SEQ ID NO 1426
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1426
aagauggcgg cgauggcggu                                              20

<210> SEQ ID NO 1427
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1427
gagaaagaug gcggcgaugg                                              20

<210> SEQ ID NO 1428
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1428
gaggagaaag auggcggcga                                              20

<210> SEQ ID NO 1429
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1429
cagcgcgagg agaaagaugg                                              20

<210> SEQ ID NO 1430
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1430
ggacagcgcg aggagaaaga                                              20
```

<210> SEQ ID NO 1431
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1431
aucccggcgu ggacagcgcg          20

<210> SEQ ID NO 1432
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1432
aguaucaagg aaucccggcg          20

<210> SEQ ID NO 1433
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1433
cuacuaguau caaggaaucc          20

<210> SEQ ID NO 1434
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1434
gugauuggcu acuaguauca          20

<210> SEQ ID NO 1435
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1435
cacuaguuug acuuugugau          20

<210> SEQ ID NO 1436
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1436
gcgacucguc ccgccuucug                                                    20

<210> SEQ ID NO 1437
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1437
ggcgacucgu cccgccuucu                                                    20

<210> SEQ ID NO 1438
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1438
aggcgacucg ucccgccuuc                                                    20

<210> SEQ ID NO 1439
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1439
ggcagacgcu cugguuguua                                                    20

<210> SEQ ID NO 1440
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1440
gggagcugug gcagacgcuc                                                    20

<210> SEQ ID NO 1441
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1441
ucccuccugu ucgggagcug                                                    20

<210> SEQ ID NO 1442
<211> LENGTH: 20
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 1442
acuccccauc ccuccuguuc                                              20

<210> SEQ ID NO 1443
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1443
cacuccccau cccuccuguu                                              20

<210> SEQ ID NO 1444
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1444
ugugcagccc gcggauuggc                                              20

<210> SEQ ID NO 1445
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1445
ccacugugca gcccgcggau                                              20

<210> SEQ ID NO 1446
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1446
guacgccacu gugcagcccg                                              20

<210> SEQ ID NO 1447
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1447
gaaccagacc cugagauugg                                              20
```

<210> SEQ ID NO 1448
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1448
caggaaccag acccugagau                                              20

<210> SEQ ID NO 1449
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1449
cugggagauu gaaguucguc                                              20

<210> SEQ ID NO 1450
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1450
acaaaaccau caaaacaaga                                              20

<210> SEQ ID NO 1451
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1451
uucuuggaau ugcugcaucg                                              20

<210> SEQ ID NO 1452
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1452
accguuaugg gcugcuguaa                                              20

<210> SEQ ID NO 1453
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 1453 agaacuccc ggaauauccc                                            20

<210> SEQ ID NO 1454
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1454
ugaagcuacg cacucagccu                                           20

<210> SEQ ID NO 1455
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1455
ucagguucug cuccuguagu                                           20

<210> SEQ ID NO 1456
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1456
uucuggcgau gcagcaauuc                                           20

<210> SEQ ID NO 1457
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1457
cuuggaggaa gagaugggag                                           20

<210> SEQ ID NO 1458
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1458
aaggaccgug acccugaggu                                           20

<210> SEQ ID NO 1459
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1459
aaugaggucc gagccuguag                                                    20

<210> SEQ ID NO 1460
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1460
uauugucucu guuucaggcu                                                    20

<210> SEQ ID NO 1461
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1461
ucccagcacc aucaguaccc                                                    20

<210> SEQ ID NO 1462
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1462
agcaccauca guacccuaag                                                    20

<210> SEQ ID NO 1463
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1463
auagauggcc uggagggagg                                                    20

<210> SEQ ID NO 1464
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1464
cuagaccgag uaccagaaga                                                    20
```

```
<210> SEQ ID NO 1465
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1465
aaugucugcu agaccgagua                                                    20

<210> SEQ ID NO 1466
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1466
augaacugca ccuccaacug                                                    20

<210> SEQ ID NO 1467
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1467
caauaccugg aauacuuaag                                                    20

<210> SEQ ID NO 1468
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1468
acaggcacca accaccacuc                                                    20

<210> SEQ ID NO 1469
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1469
agaugagccu cuggugcauc                                                    20

<210> SEQ ID NO 1470
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 1470
ggucaggaaa augcuagugg                                           20

<210> SEQ ID NO 1471
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1471
uucaagagcu acaugaggca                                           20

<210> SEQ ID NO 1472
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1472
acuagcauuu uccugaccaa                                           20

<210> SEQ ID NO 1473
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1473
uugagucugg acgaauccau                                           20

<210> SEQ ID NO 1474
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1474
auucguccag acucaaaagu                                           20

<210> SEQ ID NO 1475
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1475
uccugacgaa cuucaaucuc                                           20

<210> SEQ ID NO 1476
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1476
aagggcagac uagucauccc                                               20

<210> SEQ ID NO 1477
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1477
cgggguccga acucggggac                                               20

<210> SEQ ID NO 1478
<211> LENGTH: 920
<212> TYPE: PRT
<213> ORGANISM: Homo sapiens

<400> SEQUENCE: 1478
```

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His

```
                    245                 250                 255
Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Tyr Thr Lys Gly Leu
305                 310                 315                 320

Glu Gly Glu Ser Leu Gly Cys Ser Gly Ser Ala Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Tyr Asn Phe Pro
        355                 360                 365

Leu Ala Leu Ala Gly Pro Pro Pro Pro Pro Pro Pro His Pro His
    370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
        435                 440                 445

Pro Cys Gly Gly Gly Gly Gly Gly Gly Gly Gly Gly Gly Gly
    450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
        515                 520                 525

Asp Ser Tyr Ser Gly Pro Tyr Gly Asp Met Arg Leu Glu Thr Ala Arg
530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
    610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
            660                 665                 670
```

```
Ile Phe Leu Asn Val Leu Glu Ala Ile Glu Pro Gly Val Val Cys Ala
        675                 680                 685

Gly His Asp Asn Asn Gln Pro Asp Ser Phe Ala Ala Leu Leu Ser Ser
    690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
    770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
    850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920

<210> SEQ ID NO 1479
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1479
ccgcuauugc accuuggaa                                              19

<210> SEQ ID NO 1480
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1480
caacagagau ccuaugauu                                              19

<210> SEQ ID NO 1481
```

```
<210> SEQ ID NO 1481
<211> LENGTH: 9
<212> TYPE: PRT
<213> ORGANISM: Homo sapiens

<400> SEQUENCE: 1481

Met Leu Gln Glu Leu Asn Phe Gly Ala
1               5

<210> SEQ ID NO 1482
<211> LENGTH: 9
<212> TYPE: PRT
<213> ORGANISM: Homo sapiens

<400> SEQUENCE: 1482

Gly Met Phe Ser Trp Phe Pro Ile Leu
1               5

<210> SEQ ID NO 1483
<211> LENGTH: 9
<212> TYPE: PRT
<213> ORGANISM: Homo sapiens

<400> SEQUENCE: 1483

Trp Met Trp Trp His Asn Phe Arg Thr
1               5

<210> SEQ ID NO 1484
<211> LENGTH: 9
<212> TYPE: PRT
<213> ORGANISM: Homo sapiens

<400> SEQUENCE: 1484

Phe Glu Met Pro Tyr Val Val Arg Leu
1               5

<210> SEQ ID NO 1485
<211> LENGTH: 9
<212> TYPE: PRT
<213> ORGANISM: Homo sapiens

<400> SEQUENCE: 1485

Lys Lys Val Trp Tyr Glu Trp Ala Val
1               5

<210> SEQ ID NO 1486
<211> LENGTH: 9
<212> TYPE: PRT
<213> ORGANISM: Homo sapiens

<400> SEQUENCE: 1486

Gly Leu Pro Ala Phe Leu Leu Pro Leu
1               5

<210> SEQ ID NO 1487
<211> LENGTH: 9
<212> TYPE: PRT
<213> ORGANISM: Homo sapiens

<400> SEQUENCE: 1487

Tyr Ala Val Glu Lys Asn Pro Asn Ala
1               5

<210> SEQ ID NO 1488
<211> LENGTH: 9
<212> TYPE: PRT
```

<213> ORGANISM: Homo sapiens

<400> SEQUENCE: 1488

Tyr Leu Gly Leu Pro Ala Phe Leu Leu
1               5

<210> SEQ ID NO 1489
<211> LENGTH: 9
<212> TYPE: PRT
<213> ORGANISM: Homo sapiens

<400> SEQUENCE: 1489

Tyr Leu Gln Ser Pro Leu Gln Pro Leu
1               5

<210> SEQ ID NO 1490
<211> LENGTH: 9
<212> TYPE: PRT
<213> ORGANISM: Homo sapiens

<400> SEQUENCE: 1490

Phe Leu Lys Asp Asp Gly Val Ser Ile
1               5

<210> SEQ ID NO 1491
<211> LENGTH: 9
<212> TYPE: PRT
<213> ORGANISM: Homo sapiens

<400> SEQUENCE: 1491

Ser Met Phe Trp Met Arg Val Pro Leu
1               5

<210> SEQ ID NO 1492
<211> LENGTH: 9
<212> TYPE: PRT
<213> ORGANISM: Homo sapiens

<400> SEQUENCE: 1492

Ala Ile Leu Pro Thr Ser Ile Phe Leu
1               5

<210> SEQ ID NO 1493
<211> LENGTH: 9
<212> TYPE: PRT
<213> ORGANISM: Homo sapiens

<400> SEQUENCE: 1493

Tyr Glu Trp Ala Val Thr Ala Pro Val
1               5

<210> SEQ ID NO 1494
<211> LENGTH: 9
<212> TYPE: PRT
<213> ORGANISM: Homo sapiens

<400> SEQUENCE: 1494

Ala Gln Phe Glu Met Pro Tyr Val Val
1               5

<210> SEQ ID NO 1495
<211> LENGTH: 9
<212> TYPE: PRT
<213> ORGANISM: Homo sapiens

<400> SEQUENCE: 1495

Ser Tyr Leu Gln Tyr Leu Glu Tyr Leu
1               5

<210> SEQ ID NO 1496
<211> LENGTH: 9
<212> TYPE: PRT
<213> ORGANISM: Homo sapiens

<400> SEQUENCE: 1496

Ser Trp Phe Pro Ile Leu Phe Pro Ile
1               5

<210> SEQ ID NO 1497
<211> LENGTH: 9
<212> TYPE: PRT
<213> ORGANISM: Homo sapiens

<400> SEQUENCE: 1497

Met Phe Ser Trp Phe Pro Ile Leu Phe
1               5

<210> SEQ ID NO 1498
<211> LENGTH: 9
<212> TYPE: PRT
<213> ORGANISM: Homo sapiens

<400> SEQUENCE: 1498

Met Phe Trp Met Arg Val Pro Leu Val
1               5

<210> SEQ ID NO 1499
<211> LENGTH: 9
<212> TYPE: PRT
<213> ORGANISM: Homo sapiens

<400> SEQUENCE: 1499

Asn Leu Glu Ser Gln Thr Tyr Glu Val
1               5

<210> SEQ ID NO 1500
<211> LENGTH: 9
<212> TYPE: PRT
<213> ORGANISM: Homo sapiens

<400> SEQUENCE: 1500

Val Arg Leu His Asn Phe His Gln Leu
1               5

<210> SEQ ID NO 1501
<211> LENGTH: 9
<212> TYPE: PRT
<213> ORGANISM: Homo sapiens

<400> SEQUENCE: 1501

Cys Leu Asp Gly Ala Gln His Phe Leu
1               5

<210> SEQ ID NO 1502
<211> LENGTH: 9
<212> TYPE: PRT
<213> ORGANISM: Homo sapiens

<400> SEQUENCE: 1502

Thr Leu Cys Asp Tyr Ser Lys Arg Ile
1               5

<210> SEQ ID NO 1503
<211> LENGTH: 9
<212> TYPE: PRT
<213> ORGANISM: Homo sapiens

<400> SEQUENCE: 1503

Met Trp Trp His Asn Phe Arg Thr Leu
1               5

<210> SEQ ID NO 1504
<211> LENGTH: 9
<212> TYPE: PRT
<213> ORGANISM: Homo sapiens

<400> SEQUENCE: 1504

Gly Phe Ala Gly Tyr Phe Glu Thr Val
1               5

<210> SEQ ID NO 1505
<211> LENGTH: 9
<212> TYPE: PRT
<213> ORGANISM: Homo sapiens

<400> SEQUENCE: 1505

Ile Pro Gly Glu Tyr Thr Ser Phe Leu
1               5

<210> SEQ ID NO 1506
<211> LENGTH: 9
<212> TYPE: PRT
<213> ORGANISM: Homo sapiens

<400> SEQUENCE: 1506

Cys Thr Leu Glu Phe Pro Val Glu Val
1               5

<210> SEQ ID NO 1507
<211> LENGTH: 9
<212> TYPE: PRT
<213> ORGANISM: Homo sapiens

<400> SEQUENCE: 1507

Val Leu His Gly Phe Ala Gly Tyr Phe
1               5

<210> SEQ ID NO 1508
<211> LENGTH: 9
<212> TYPE: PRT
<213> ORGANISM: Homo sapiens

<400> SEQUENCE: 1508

Gly Ala Tyr Leu Gly Leu Pro Ala Phe
1               5

<210> SEQ ID NO 1509
<211> LENGTH: 9
<212> TYPE: PRT
<213> ORGANISM: Homo sapiens

<400> SEQUENCE: 1509

Leu Leu Lys Leu Glu Val Gln Phe Ile
1               5

<210> SEQ ID NO 1510
<211> LENGTH: 9
<212> TYPE: PRT
<213> ORGANISM: Homo sapiens

<400> SEQUENCE: 1510

Lys Met His Gln Arg Leu Ile Phe Arg
1               5

<210> SEQ ID NO 1511
<211> LENGTH: 9
<212> TYPE: PRT
<213> ORGANISM: Homo sapiens

<400> SEQUENCE: 1511

Thr Trp Met Trp Trp His Asn Phe Arg
1               5

<210> SEQ ID NO 1512
<211> LENGTH: 9
<212> TYPE: PRT
<213> ORGANISM: Homo sapiens

<400> SEQUENCE: 1512

Leu Lys Leu Glu Val Gln Phe Ile Ile
1               5

<210> SEQ ID NO 1513
<211> LENGTH: 9
<212> TYPE: PRT
<213> ORGANISM: Homo sapiens

<400> SEQUENCE: 1513

Leu Tyr Gln Asp Ile Thr Leu Ser Ile
1               5

<210> SEQ ID NO 1514
<211> LENGTH: 9
<212> TYPE: PRT
<213> ORGANISM: Homo sapiens

<400> SEQUENCE: 1514

Ala Tyr Leu Gly Leu Pro Ala Phe Leu
1               5

<210> SEQ ID NO 1515
<211> LENGTH: 9
<212> TYPE: PRT
<213> ORGANISM: Homo sapiens

<400> SEQUENCE: 1515

Lys Leu Tyr Asn Glu Val Arg Ala Cys
1               5

<210> SEQ ID NO 1516
<211> LENGTH: 9
<212> TYPE: PRT
<213> ORGANISM: Homo sapiens

<400> SEQUENCE: 1516

Lys Thr Trp Met Trp Trp His Asn Phe
1               5

```
<210> SEQ ID NO 1517
<211> LENGTH: 9
<212> TYPE: PRT
<213> ORGANISM: Homo sapiens

<400> SEQUENCE: 1517

Thr Val Leu His Gly Phe Ala Gly Tyr
1               5

<210> SEQ ID NO 1518
<211> LENGTH: 9
<212> TYPE: PRT
<213> ORGANISM: Homo sapiens

<400> SEQUENCE: 1518

Gln Glu Leu Asn Phe Gly Ala Tyr Leu
1               5

<210> SEQ ID NO 1519
<211> LENGTH: 9
<212> TYPE: PRT
<213> ORGANISM: Homo sapiens

<400> SEQUENCE: 1519

Val Trp Tyr Glu Trp Ala Val Thr Ala
1               5

<210> SEQ ID NO 1520
<211> LENGTH: 9
<212> TYPE: PRT
<213> ORGANISM: Homo sapiens

<400> SEQUENCE: 1520

Cys Met Pro Val Phe His Pro Arg Phe
1               5

<210> SEQ ID NO 1521
<211> LENGTH: 9
<212> TYPE: PRT
<213> ORGANISM: Homo sapiens

<400> SEQUENCE: 1521

Arg Leu Leu Lys Leu Glu Val Gln Phe
1               5

<210> SEQ ID NO 1522
<211> LENGTH: 9
<212> TYPE: PRT
<213> ORGANISM: Homo sapiens

<400> SEQUENCE: 1522

Ile Leu Phe Pro Ile Lys Gln Pro Ile
1               5

<210> SEQ ID NO 1523
<211> LENGTH: 9
<212> TYPE: PRT
<213> ORGANISM: Homo sapiens

<400> SEQUENCE: 1523

Val Thr Ala Pro Val Cys Ser Ala Ile
1               5

<210> SEQ ID NO 1524
<211> LENGTH: 9
```

<212> TYPE: PRT
<213> ORGANISM: Homo sapiens

<400> SEQUENCE: 1524

Phe Asp Phe Leu Cys Met Pro Val Phe
1               5

<210> SEQ ID NO 1525
<211> LENGTH: 9
<212> TYPE: PRT
<213> ORGANISM: Homo sapiens

<400> SEQUENCE: 1525

Arg Tyr Cys Thr Leu Glu Phe Pro Val
1               5

<210> SEQ ID NO 1526
<211> LENGTH: 9
<212> TYPE: PRT
<213> ORGANISM: Homo sapiens

<400> SEQUENCE: 1526

Ala Ala Met Leu Gln Glu Leu Asn Phe
1               5

<210> SEQ ID NO 1527
<211> LENGTH: 9
<212> TYPE: PRT
<213> ORGANISM: Homo sapiens

<400> SEQUENCE: 1527

Ile Leu Pro Thr Ser Ile Phe Leu Thr
1               5

<210> SEQ ID NO 1528
<211> LENGTH: 9
<212> TYPE: PRT
<213> ORGANISM: Homo sapiens

<400> SEQUENCE: 1528

Phe Leu Ala Pro Ile Ser Ser Ser Lys
1               5

<210> SEQ ID NO 1529
<211> LENGTH: 9
<212> TYPE: PRT
<213> ORGANISM: Homo sapiens

<400> SEQUENCE: 1529

Val Ala Leu Glu Ile Gly Ala Asp Leu
1               5

<210> SEQ ID NO 1530
<211> LENGTH: 9
<212> TYPE: PRT
<213> ORGANISM: Homo sapiens

<400> SEQUENCE: 1530

Ala Asp Leu Pro Ser Asn His Val Ile
1               5

<210> SEQ ID NO 1531
<211> LENGTH: 9
<212> TYPE: PRT
<213> ORGANISM: Homo sapiens

<400> SEQUENCE: 1531

Met His Gln Arg Leu Ile Phe Arg Leu
1               5

<210> SEQ ID NO 1532
<211> LENGTH: 9
<212> TYPE: PRT
<213> ORGANISM: Homo sapiens

<400> SEQUENCE: 1532

Phe Leu Cys Met Pro Val Phe His Pro
1               5

<210> SEQ ID NO 1533
<211> LENGTH: 9
<212> TYPE: PRT
<213> ORGANISM: Homo sapiens

<400> SEQUENCE: 1533

Lys Asn Pro Asn Ala Val Val Thr Leu
1               5

<210> SEQ ID NO 1534
<211> LENGTH: 9
<212> TYPE: PRT
<213> ORGANISM: Homo sapiens

<400> SEQUENCE: 1534

Val Leu Ser Lys Met His Gln Arg Leu
1               5

<210> SEQ ID NO 1535
<211> LENGTH: 9
<212> TYPE: PRT
<213> ORGANISM: Homo sapiens

<400> SEQUENCE: 1535

Ala Gly Tyr Phe Glu Thr Val Leu Tyr
1               5

<210> SEQ ID NO 1536
<211> LENGTH: 9
<212> TYPE: PRT
<213> ORGANISM: Homo sapiens

<400> SEQUENCE: 1536

Phe Ala Gly Tyr Phe Glu Thr Val Leu
1               5

<210> SEQ ID NO 1537
<211> LENGTH: 9
<212> TYPE: PRT
<213> ORGANISM: Homo sapiens

<400> SEQUENCE: 1537

Gly Arg Asp Trp Asn Thr Leu Ile Val
1               5

<210> SEQ ID NO 1538
<211> LENGTH: 9
<212> TYPE: PRT
<213> ORGANISM: Homo sapiens

<400> SEQUENCE: 1538

```
Leu Leu Ser Gly Arg Asp Trp Asn Thr
1               5

<210> SEQ ID NO 1539
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Orn

<400> SEQUENCE: 1539

Ser Gly Xaa Gly Lys Gly Gly Lys Gly Leu Gly Lys Gly Gly Ala Lys
1               5                   10                  15

Arg His Arg Lys Val
            20
```